(12) United States Patent
Calderwood et al.

(10) Patent No.: US 8,110,687 B2
(45) Date of Patent: Feb. 7, 2012

(54) BICYCLIC COMPOUNDS WITH KINASE INHIBITORY ACTIVITY

(75) Inventors: Emily F. Calderwood, Farmingham, MA (US); Alexandra E. Gould, Cambridge, MA (US); Paul D. Greenspan, Acton, MA (US); Robyn Scott Rowland, Swampscott, MA (US); Tricia J. Vos, Medford, MA (US); Matthew J. LaMarche, Reading, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 1044 days.

(21) Appl. No.: 11/636,609

(22) Filed: Dec. 7, 2006

(65) Prior Publication Data

US 2007/0149533 A1    Jun. 28, 2007

Related U.S. Application Data

(60) Provisional application No. 60/748,369, filed on Dec. 8, 2005.

(51) Int. Cl.
*A61K 31/53* (2006.01)
*C07D 403/00* (2006.01)
*C07D 217/00* (2006.01)

(52) U.S. Cl. .................. 546/139; 544/209; 514/241
(58) Field of Classification Search .................. 544/209; 546/139; 514/241
See application file for complete search history.

(56) References Cited

U.S. PATENT DOCUMENTS

| | | | |
|---|---|---|---|
| 2,415,554 A | 2/1947 | Friedheim | |
| 2,778,813 A | 1/1957 | Gaspar et al. | |
| 4,334,004 A | 6/1982 | Scheler | |
| 4,741,994 A | 5/1988 | Ichijima et al. | |
| 2005/0245524 A1 | 11/2005 | Noronha et al. | |
| 2005/0245536 A1 | 11/2005 | Hao et al. | |

FOREIGN PATENT DOCUMENTS

| | | |
|---|---|---|
| WO | WO 02/055014 A2 | 7/2002 |
| WO | WO 02/085857 A2 | 10/2002 |
| WO | WO 03/037871 A1 | 5/2003 |
| WO | WO 03/037872 A1 | 5/2003 |
| WO | WO 03/055848 A2 | 7/2003 |
| WO | WO 2004/026305 A1 | 4/2004 |
| WO | WO 2005/037285 A1 | 4/2005 |
| WO | WO 2005/070891 A2 | 8/2005 |
| WO | WO 2005/085202 A1 | 9/2005 |
| WO | WO 2005/120497 A2 | 12/2005 |
| WO | WO 2006/002421 A2 | 1/2006 |
| WO | WO 2006/014012 A2 | 2/2006 |
| WO | WO 2006/024034 A1 | 3/2006 |
| WO | WO 2006/059234 A2 | 6/2006 |
| WO | WO 2006/065703 A1 | 6/2006 |

OTHER PUBLICATIONS

Almaraz, M., et al., "Chiral Recognition of Lactic Acid Derivatives With Chromenone-Benzoxazole Receptors," *Journal of the American Chemical Society*, vol. 120, pp. 3516-3517 (Mar. 31, 1998).
Hernandez, J.V., et al., "Enantioselective Chromenone Benzoxazole Receptor for Glutamic Acid and Its Derivatives," *Journal of Organic Chemistry*, vol. 68, No. 19, pp. 7513-7516 (2003).
Wellbrock, Claudia, et al., "B-RAF is an Oncogene in Melanocytes," *Cancer Research*, vol. 64, pp. 2338-2342 (Apr. 1, 2004).
Wellbrock, Claudia, et al., "The RAF Proteins Take Centre Stage," *Nature Reviews/Molecular Cell Biology*, vol. 5, pp. 875-885 (Nov. 2004).
International Search Report dated Apr. 25, 2007 from PCT/US06/046097, which corresponds to U.S. Appl. No. 11/636,609.

*Primary Examiner* — Rita Desai
*Assistant Examiner* — John Mabry

(57) ABSTRACT

The present invention provides novel bicyclic compounds useful as inhibitors of protein kinases. The invention also provides pharmaceutical compositions comprising the compounds of the invention and methods of using the compositions in the treatment of various diseases.

19 Claims, No Drawings

BICYCLIC COMPOUNDS WITH KINASE INHIBITORY ACTIVITY

RELATED APPLICATIONS

This application claims priority from U.S. Provisional Patent Application No. 60/748,369, filed on Dec. 8, 2005, which is hereby incorporated by reference in its entirety.

BACKGROUND OF THE INVENTION

1. Field of the Invention

The present invention relates to protein kinase inhibitors, particularly inhibitors of Raf-kinase. The invention also provides pharmaceutical compositions comprising the compounds of the invention and methods of using the compositions in the treatment of various diseases.

2. Background of the Invention

Protein kinases constitute a large family of structurally related enzymes that effect the transfer of a phosphate group from a nucleoside triphosphate to a Ser, Thr or Tyr residue on a protein acceptor. A vast array of cellular functions, including DNA replication, cell cycle progression, energy metabolism, and cell growth and differentiation, are regulated by reversible protein phosphorylation events mediated by protein kinases. Additionally, protein kinase activity has been implicated in a number of disease states, including cancers. Of the >100 dominant oncogenes known to date, many encode receptor and cytoplasmic tyrosine kinases known to be mutated and/or over expressed in human cancers (Blume-Jensen and Hunter, *Nature*, 411:355-365 (2001)). Accordingly, protein kinase targets have attracted substantial drug discovery efforts in recent years, with several protein kinase inhibitors achieving regulatory approval (reviewed in Fischer, *Curr. Med. Chem.*, 11:1563 (2004); Dancey and Sausville, *Nature Rev. Drug Disc.*, 2:296 (2003)).

Intracellular signaling pathways activated in response to growth factor/cytokine stimulation are known to control functions such as proliferation, differentiation and cell death (Chiloeches and Marais, In *Targets for Cancer Therapy; Transcription Factors and Other Nuclear Proteins*, 179-206 (La Thangue and Bandara, eds., Totowa, Humana Press 2002)). One example is the Ras-Raf-MEK-ERK pathway which is controlled by receptor tyrosine kinase activation. Activation of Ras proteins at the cell membrane leads to phosphorylation and recruitment of accessory factors and Raf which is then activated by phosphorylation. Activation of Raf leads to downstream activation of MEK and ERK. ERK has several cytoplasmic and nuclear substrates, including ELK and Ets-family transcription factor, which regulates genes involved in cell growth, survival and migration (Marais et al., *J. Biol. Chem.*, 272:4378-4383 (1997); Peyssonnaux and Eychene, *Biol. Cell*, 93-53-62 (2001)). As a result, this pathway is an important mediator of tumor cell proliferation and angiogenesis. For instance, overexpression of constitutively active B-Raf can induce an oncogenic event in untransformed cells (Wellbrock et al., *Cancer Res.*, 64:2338-2342 (2004)). Aberrant activation of the pathway, such as by activating Ras and/or Raf mutations, is known to be associated with a malignant phenotype in a variety of tumor types (Bos, *Hematol. Pathol.*, 2:55-63 (1988); Downward, *Nature Rev. Cancer*, 3:11-22 (2003); Karasarides et al., *Oncogene*, 23:6292-6298 (2004); Tuveson, *Cancer Cell*, 4:95-98 (2003); Bos, *Cancer Res*, 49:4682-4689 (1989)). Activating mutations in B-Raf are found in 60-70% of melanomas. Melanoma cells that carry mutated B-Raf-V599E are transformed, and cell growth, ERK signaling and cell viability are dependent on mutant B-Raf function (Karasarides et al., *Oncogene*, 23:6292-6298 (2004)).

There are three Raf isoforms, A-Raf, B-Raf and C-Raf (Raf-1), all of which can act as downstream effectors of Ras. Although they show significant sequence similarities, they also exhibit distinct roles in development, in addition to significant biochemical and functional differences. In particular, the high basal kinase activity of B-Raf may explain why mutated forms of only this isoform have been found in human cancers. Nevertheless, the isoforms show redundant functions in facilitating oncogenic Ras-induced activation of the MEK-ERK signaling cascade (Wellbrock, *Cancer Res*, 64:2338-2342 (2004)). In addition to Raf signaling via the MEK-ERK pathway there is some evidence that C-Raf (and possibly B-Raf and A-Raf) may signal via alternative pathways directly involved in cell survival by interaction with the BH3 family of anti-apoptotic proteins (Wellbrock et al., *Nature Rev.: Mol. Cell Biol.* 5:875 (2004)).

Inhibitors of the Raf kinases may be expected to interrupt the Ras-Raf signaling cascade and thereby provide new methods for the treatment of proliferative disorders, such as cancer. There is thus a need for new inhibitors of Raf kinase activity.

DESCRIPTION OF THE INVENTION

The present invention provides compounds that are effective inhibitors of Raf-kinase. These compounds are useful for inhibiting kinase activity in vitro and in vivo, and are especially useful for the treatment of various cell proliferative diseases.

Compounds useful for the methods of the invention are represented by formula (I-A):

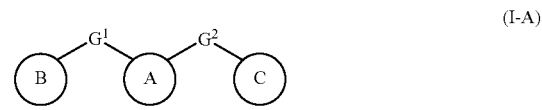

(I-A)

or a pharmaceutically acceptable salt thereof;

wherein:

$G^1$ is —C($R^e$)($R^{e'}$)—, —C(O)—, —O—, —S—, —S(O)—, —S(O)$_2$—, or —N($R^f$)—;

$G^2$ is —C(O)—NH—, —C(O)—N($C_{1-3}$ aliphatic)-, —NH—C(O)—, or —N($C_{1-3}$ aliphatic)—C(O)—, provided that $G^2$ is —C(O)—NH— or —C(O)—N($C_{1-3}$ aliphatic)— if it is connected to a ring nitrogen atom in Ring A;

Ring A is a bicyclic ring system selected from the group consisting of:

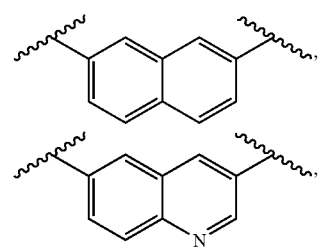

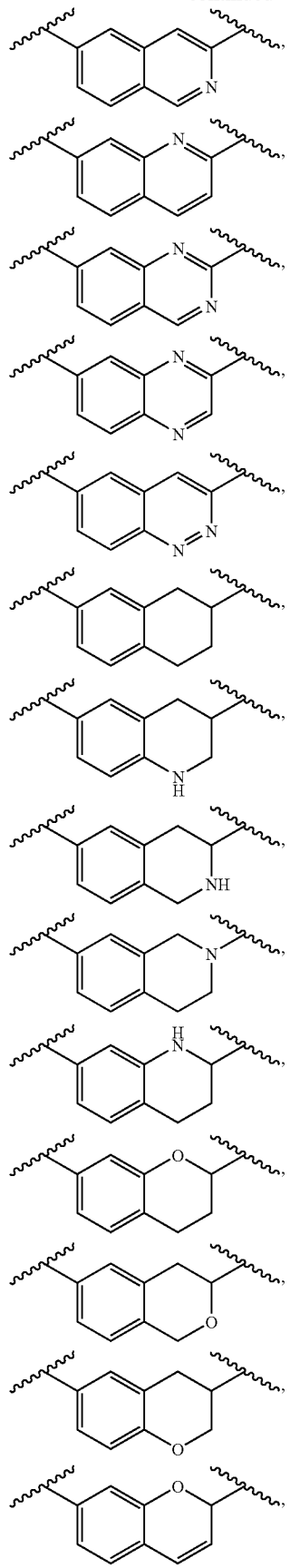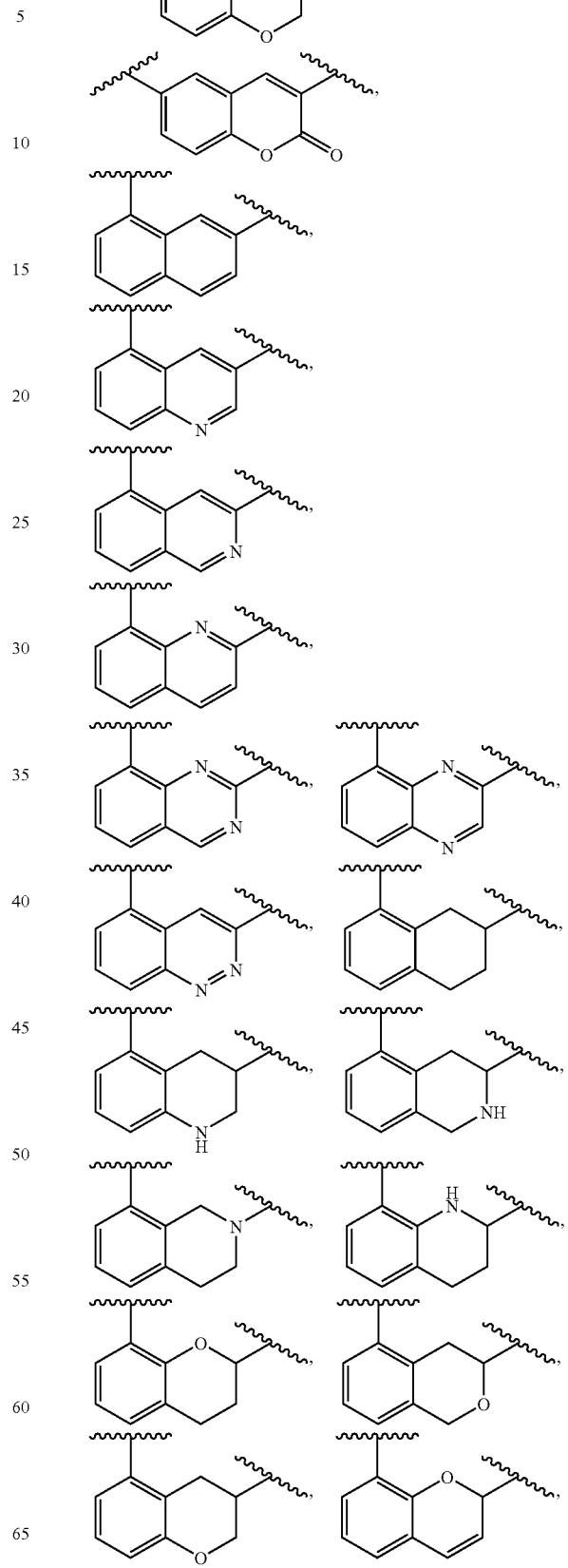

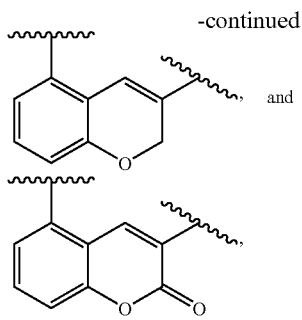

wherein Ring A is substituted with 0-2 $R^a$;

Ring B is an optionally substituted monocyclic nitrogen-containing heteroaryl; or Ring B has the formula:

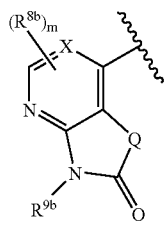

X is CH or N;

Q is —C($R^{10}$)($R^{11}$)—, —N($R^{9b}$)—, —O—, —C($R^{10}$)($R^{11}$)—C($R^{10}$)($R^{11}$)—, —C($R^{11}$)═C($R^{11}$)—, —C($R^{10}$)($R^{11}$)—N($R^{9b}$)—, —N($R^{9b}$)—C($R^{10}$)($R^{11}$)—, or —O—C($R^{10}$)($R^{11}$)—, wherein the oxygen atom of the group —O—C($R^{10}$)($R^{11}$)— is attached to the carbonyl carbon atom;

each $R^{8b}$ independently is selected from the group consisting of $C_{1-4}$ aliphatic, $C_{1-4}$ fluoroaliphatic, halo, —OH, —O($C_{1-4}$ aliphatic), —NH$_2$, —NH($C_{1-4}$ aliphatic), and —N($C_{1-4}$ aliphatic)$_2$;

$R^{9b}$ is hydrogen, $C^{1-4}$ aliphatic, or $C_{6-10}$ar($C_{1-4}$)alkyl, the aryl portion of which may be optionally substituted.

$R^{10}$ is hydrogen, fluoro, $C_{1-4}$ aliphatic, or $C_{1-4}$ fluoroaliphatic;

$R^{11}$ is hydrogen, fluoro, or a $C_{1-4}$ aliphatic or $C_{1-4}$ fluoroaliphatic group optionally substituted with one or two substituents independently selected from the group consisting of —OR$^5$, —N(R$^4$)$_2$, —CO$_2$R$^5$, or —C(O)N(R$^4$)$_2$;

Ring C is a 5- or 6-membered aryl or heteroaryl ring having 0-3 ring nitrogen atoms and optionally one additional ring heteroatom selected from oxygen and sulfur;

Ring C is substituted on its substitutable ring carbon atoms with 0-2 $R^c$ and 0-2 $R^{8c}$;

each $R^c$ independently is halo, —NO$_2$, —CN, —C(R$^5$)═C(R$^5$)$_2$, —C≡C—R$^5$, —OR$^5$, —SR$^6$, —S(O)R$^6$, —SO$_2$R$^6$, —SO$_2$N(R$^4$)$_2$, —N(R$^4$)$_2$, —NR$^4$C(O)R$^5$, —NR$^4$C(O)N(R$^4$)$_2$, —N(R$^4$)C(═NR$^4$)—N(R$^4$)$_2$, —N(R$^4$)C(═NR$^4$)—R$^6$, —NR$^4$CO$_2$R$^6$, —N(R$^4$)SO$_2$R$^6$, —N(R$^4$)SO$_2$N(R$^4$)$_2$, —O—C(O)R$^5$, —OC(O)N(R$^4$)$_2$, —C(O)R$^5$, —CO$_2$R$^5$, —C(O)N(R$^4$)$_2$, —C(O)N(R$^4$)—OR$^5$, —C(O)N(R$^4$)C(═NR$^4$)—N(R$^4$)$_2$, —N(R$^4$)C(═NR$^4$)—N(R$^4$)—C(O)R$^5$, —C(═NR$^4$)—N(R$^4$)$_2$, —C(═NR$^4$)—OR$^5$, —C(═NR$^4$)—N(R$^4$)—OR$^5$, —C(R$^6$)═N—OR$^5$, or an optionally substituted aliphatic, aryl, heteroaryl, or heterocyclyl; or two adjacent $R^c$, taken together with the intervening ring atoms, form an optionally substituted fused 5- or 6-membered aromatic or non-aromatic ring having 0-3 ring heteroatoms independently selected from the group consisting of O, N, and S;

each $R^{8c}$ independently is selected from the group consisting of $C_{1-4}$ aliphatic, $C_{1-4}$ fluoroaliphatic, —O($C_{1-4}$ aliphatic), —O($C_{1-4}$ fluoroaliphatic), and halo;

each substitutable ring nitrogen atom in Ring C is unsubstituted or is substituted with —C(O)R$^5$, —C(O)N(R$^4$)$_2$, —CO$_2$R$^6$, —SO$_2$R$^6$, —SO$_2$N(R$^4$)$_2$, an optionally substituted $C_{6-10}$ aryl, or a $C_{1-4}$ aliphatic optionally substituted with —F, —OH, —O($C_{1-4}$ aliphatic), —CN, —N(R$^4$)$_2$, —C(O)($C_{1-4}$ aliphatic), —CO$_2$H, —CO$_2$($C_{1-4}$ aliphatic), —C(O)NH$_2$, —C(O)NH($C_{1-4}$ aliphatic), or an optionally substituted $C_{6-10}$ aryl ring;

one ring nitrogen atom in Ring C optionally is oxidized;

$R^a$ is halo, —NO$_2$, —CN, —OR$^5$, —SR$^6$, —S(O)R$^6$, —SO$_2$R$^6$, —SO$_2$N(R$^4$)$_2$, —N(R$^4$)$_2$, —OC(O)R$^5$, —N(R$^4$)—C(O)R$^5$, —CO$_2$R$^5$, —C(O)N(R$^4$)$_2$, —N(R$^4$)SO$_2$R$^6$, —N(R$^4$)SO$_2$N(R$^4$)$_2$, or an optionally substituted $C_{1-4}$ aliphatic;

$R^{e'}$ is hydrogen, fluoro, $C_{1-4}$ aliphatic, $C_{1-4}$ fluoroaliphatic, —NH$_2$, —NH($C_{1-4}$ aliphatic), —N($C_{1-4}$ aliphatic)$_2$, —OH, or —O($C_{1-4}$ aliphatic);

$R^e$ is hydrogen, fluoro, $C_{1-4}$ aliphatic, $C_{1-4}$ fluoroaliphatic; or $R^{e'}$ and $R^e$, taken together with the carbon atom to which they are attached, form a 3- to 6-membered cycloaliphatic or heterocyclyl ring;

$R^f$ is —H, —C(O)R$^5$, —C(O)N(R$^4$)$_2$, —CO$_2$R$^6$, —SO$_2$R$^6$, —SO$_2$N(R$^4$)$_2$, or an optionally substituted $C_{1-6}$ aliphatic;

each $R^4$ independently is hydrogen or an optionally substituted aliphatic, aryl, heteroaryl, or heterocyclyl group; or two $R^4$ on the same nitrogen atom, taken together with the nitrogen atom, form an optionally substituted 4- to 8-membered heterocyclyl ring having, in addition to the nitrogen atom, 0-2 ring heteroatoms independently selected from N, O, and S;

each $R^5$ independently is hydrogen or an optionally substituted aliphatic, aryl, heteroaryl, or heterocyclyl group;

each $R^6$ independently is an optionally substituted aliphatic, aryl, or heteroaryl group; and m is 0 or 1.

Compounds of this invention include those described generally above, and are further illustrated by the classes, subclasses, and species disclosed herein. Terms used herein shall be accorded the following defined meanings, unless otherwise indicated.

The terms "Raf" and "Raf kinase" are used interchangeably, and unless otherwise specified refer to any member of the Raf family of kinase enzymes, including without limitation, the isoforms A-Raf, B-Raf, and C-Raf. These enzymes, and the corresponding genes, also may be referred to in the literature by variants of these terms, e.g., RAF, raf, BRAF, B-raf. The isoform C-Raf also is referred to by the terms Raf-1 and C-Raf-1.

The term "aliphatic" or "aliphatic group", as used herein, means a substituted or unsubstituted straight-chain, branched, or cyclic $C_{1-12}$ hydrocarbon, which is completely saturated or which contains one or more units of unsaturation, but which is not aromatic. For example, suitable aliphatic groups include substituted or unsubstituted linear, branched or cyclic alkyl, alkenyl, or alkynyl groups and hybrids thereof, such as (cycloalkyl)alkyl, (cycloalkenyl)alkyl or (cycloalkyl)alkenyl. In various embodiments, the aliphatic group has 1 to 12, 1 to 8, 1 to 6, 1 to 4, or 1 to 3 carbons.

The terms "alkyl", "alkenyl", and "alkynyl", used alone or as part of a larger moiety, refer to a straight or branched chain aliphatic group having from 1 to 12 carbon atoms. For purposes of the present invention, the term "alkyl" will be used when the carbon atom attaching the aliphatic group to the rest of the molecule is a saturated carbon atom. However, an alkyl group may include unsaturation at other carbon atoms. Thus, alkyl groups include, without limitation, methyl, ethyl, propyl, allyl, propargyl, butyl, pentyl, and hexyl.

For purposes of the present invention, the term "alkenyl" will be used when the carbon atom attaching the aliphatic group to the rest of the molecule forms part of a carbon-carbon double bond. Alkenyl groups include, without limitation, vinyl, 1-propenyl, 1-butenyl, 1-pentenyl, and 1-hexenyl.

For purposes of the present invention, the term "alkynyl" will be used when the carbon atom attaching the aliphatic group to the rest of the molecule forms part of a carbon-carbon triple bond. Alkynyl groups include, without limitation, ethynyl, 1-propynyl, 1-butynyl, 1-pentynyl, and 1-hexynyl.

The term "cycloaliphatic", used alone or as part of a larger moiety, refers to a saturated or partially unsaturated cyclic aliphatic ring system having from 3 to about 14 members, wherein the aliphatic ring system is optionally substituted. In some embodiments, the cycloaliphatic is a monocyclic hydrocarbon having 3-8 or 3-6 ring carbon atoms. Nonlimiting examples include cyclopropyl, cyclobutyl, cyclopentyl, cyclopentenyl, cyclohexyl, cyclohexenyl, cycloheptyl, cycloheptenyl, cyclooctyl, cyclooctenyl, and cyclooctadienyl. In some embodiments, the cycloaliphatic is a bridged or fused bicyclic hydrocarbon having 6-12, 6-10, or 6-8 ring carbon atoms, wherein any individual ring in the bicyclic ring system has 3-8 members.

In some embodiments, two adjacent substituents on the cycloaliphatic ring, taken together with the intervening ring atoms, form an optionally substituted fused 5- to 6-membered aromatic or 3- to 8-membered non-aromatic ring having 0-03 ring heteroatoms selected from the group consisting of O, N, and S. Thus, the term "cycloaliphatic" includes aliphatic rings that are fused to one or more aryl, heteroaryl, or heterocyclyl rings. Nonlimiting examples include indanyl, 5,6,7,8-tetrahydroquinoxalinyl, decahydronaphthyl, or tetrahydronaphthyl, where the radical or point of attachment is on the aliphatic ring.

The terms "aryl" and "ar-", used alone or as part of a larger moiety, e.g., "aralkyl", "aralkoxy", or "aryloxyalkyl", refer to a $C_6$ to $C_{14}$ aromatic hydrocarbon, comprising one to three rings, each of which is optionally substituted. Preferably, the aryl group is a $C_{6-10}$ aryl group. Aryl groups include, without limitation, phenyl, naphthyl, and anthracenyl. In some embodiments, two adjacent substituents on the aryl ring, taken together with the intervening ring atoms, form an optionally substituted fused 5- to 6-membered aromatic or 4 to 8-membered non-aromatic ring having 0-3 ring heteroatoms selected from the group consisting of O, N, and S. Thus, the term "aryl", as used herein, includes groups in which an aryl ring is fused to one or more heteroaryl, cycloaliphatic, or heterocyclyl rings, where the radical or point of attachment is on the aromatic ring. Nonlimiting examples of such fused ring systems include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, carbazolyl, acridinyl, phenazinyl, phenothiazinyl, phenoxazinyl, tetrahydroquinolinyl, tetrahydroisoquinolinyl, fluorenyl, indanyl, phenanthridinyl, tetrahydronaphthyl, indolinyl, phenoxazinyl, benzodioxanyl, and benzodioxolyl. An aryl group may be mono-, bi-, tri-, or polycyclic, preferably mono-, bi-, or tricyclic, more preferably mono- or bicyclic. The term "aryl" may be used interchangeably with the terms "aryl group", "aryl moiety", and "aryl ring".

An "aralkyl" or "arylalkyl" group comprises an aryl group covalently attached to an alkyl group, either of which independently is optionally substituted. Preferably, the aralkyl group is $C_{6-10}$ aryl($C_{1-6}$)alkyl, $C_{6-10}$ aryl($C_{1-4}$)alkyl, or $C_{6-10}$ aryl($C_{1-3}$)alkyl, including, without limitation, benzyl, phenethyl, and naphthylmethyl.

The terms "heteroaryl" and "heteroar-", used alone or as part of a larger moiety, e.g., heteroaralkyl, or "heteroaralkoxy", refer to groups having 5 to 14 ring atoms, preferably 5, 6, 9, or 10 ring atoms; having 6, 10, or 14 π electrons shared in a cyclic array; and having, in addition to carbon atoms, from one to four heteroatoms. The term "heteroatom" refers to nitrogen, oxygen, or sulfur, and includes any oxidized form of nitrogen or sulfur, and any quaternized form of a basic nitrogen. Thus, when used in reference to a ring atom of a heteroaryl, the term "nitrogen" includes an oxidized nitrogen (as in pyridine N-oxide). Certain nitrogen atoms of 5-membered heteroaryl groups also are substitutable, as further defined below. Heteroaryl groups include, without limitation, radicals derived from thiophene, furan, pyrrole, imidazole, pyrazole, triazole, tetrazole, oxazole, isoxazole, oxadiazole, thiazole, isothiazole, thiadiazole, pyridine, pyridazine, pyrimidine, pyrazine, indolizine, naphthyridine, pteridine, pyrrolopyridine, imidazopyridine, oxazolopyridine, thiazolopyridine, triazolopyridine, pyrrolopyrimidine, purine, and triazolopyrimidine. As used herein, the phrase "radical derived from" means a monovalent radical produced by removal of a hydrogen radical from the parent heteroaromatic ring system. The radical (i.e., the point of attachment of the heteroaryl to the rest of the molecule) may be created at any substitutable position on any ring of the parent heteroaryl ring system.

In some embodiments, two adjacent substituents on the heteroaryl, taken together with the intervening ring atoms, form an optionally substituted fused 5- to 6-membered aromatic or 4- to 8-membered non-aromatic ring having 0-3 ring heteroatoms selected from the group consisting of O, N, and S. Thus, the terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, benzoxazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolnyl, tetrahydroisoquinolinyl, and pyrido[2,3-b]-1,4-oxazin-3(4H)-one. A heteroaryl group may be mono-, bi-, tri-, or polycyclic, preferably mono-, bi-, or tricyclic, more preferably mono- or bicyclic. The term "heteroaryl" may be used interchangeably with the terms "heteroaryl ring", or "heteroaryl group", any of which terms include rings that are optionally substituted. The term "heteroaralkyl" refers to an alkyl group substituted by a heteroaryl, wherein the alkyl and heteroaryl portions independently are optionally substituted.

As used herein, the terms "aromatic ring" and "aromatic ring system" refer to an optionally substituted mono-, bi-, or tricyclic group having 0-6, preferably 0-4 ring heteroatoms, and having 6, 10, or 14 π electrons shared in a cyclic array.

Thus, the terms "aromatic ring" and "aromatic ring system" encompass both aryl and heteroaryl groups.

As used herein, the terms "heterocycle", "heterocyclyl", "heterocyclic radical", and "heterocyclic ring" are used interchangeably and refer to a stable 3- to 7-membered monocyclic, or to a fused 7- to 10-membered or bridged 6- to 10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a heterocyclyl ring having 1-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl). A heterocyclic ring can be attached to its pendant group at any heteroatom or carbon atom that results in a stable structure, and any of the ring atoms can be optionally substituted. Examples of such saturated or partially unsaturated heterocyclic radicals include, without limitation, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl.

In some embodiments, two adjacent substituents on a heterocyclic ring, taken together with the intervening ring atoms, form an optionally substituted fused 5- to 6-membered aromatic or 3- to 8-membered non-aromatic ring having 0-3 ring heteroatoms selected from the group consisting of O, N, and S. Thus, the terms "heterocycle", "heterocyclyl", "heterocyclyl ring", "heterocyclic group", "heterocyclic moiety", and "heterocyclic radical", are used interchangeably herein, and include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono-, bi-, tri-, or polycyclic, preferably mono-, bi-, or tricyclic, more preferably mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond between ring atoms. The term "partially unsaturated" is intended to encompass rings having multiple sites of unsaturation, but is not intended to include aryl or heteroaryl moieties, as herein defined.

The terms "haloaliphatic", "haloalkyl", "haloalkenyl" and "haloalkoxy" refer to an aliphatic, alkyl, alkenyl or alkoxy group, as the case may be, which is substituted with one or more halogen atoms. As used herein, the term "halogen" or "halo" means F, Cl, Br, or I. The term "fluoroaliphatic" refers to a haloaliphatic wherein the halogen is fluoro, including perfluorinated aliphatic groups. Examples of fluoroaliphatic groups include, without: limitation, fluoromethyl, difluoromethyl, trifluoromethyl, 2-fluoroethyl, 2,2,2-trifluoroethyl, 1,1,2-trifluoroethyl, 1,2,2-trifluoroethyl, and pentafluoroethyl.

The term "linker group" or "linker" means an organic moiety that connects two parts of a compound. Linkers typically comprise an atom such as oxygen or sulfur, a unit such as —NH—, —CH$_2$—, —C(O)—, —C(O)NH—, or a chain of atoms, such as an alkylene chain. The molecular mass of a linker is typically in the range of about 14 to 200, preferably in the range of 14 to 96 with a length of up to about six atoms. In some embodiments, the linker is a $C_{1-6}$ alkylene chain.

The term "alkylene" refers to a bivalent alkyl group. An "alkylene chain" is a polymethylene group, i.e., —(CH$_2$)$_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms is replaced with a substituent. Suitable substituents include those described below for a substituted aliphatic group. An alkylene chain also may be substituted at one or more positions with an aliphatic group or a substituted aliphatic group.

An alkylene chain also can be optionally interrupted by a functional group. An alkylene chain is "interrupted" by a functional group when an internal methylene unit is replaced with the functional group. Examples of suitable "interrupting functional groups" include —C(R*)=C(R*)—, —C≡C—, —O—, —S—, —S(O)—, —S(O)$_2$—, —S(O)$_2$N(R$^+$)—, —N(R*)—, —N(R$^+$)CO—, —N(R$^+$)C(O)N(R$^+$)—, —N(R$^+$)C(=NR$^+$)—N(R$^+$)—, —N(R$^+$)—C(=NR$^+$)—, —N(R$^+$)CO$_2$—, —N(R$^+$)SO$_2$—, —N(R$^+$)SO$_2$N(R$^+$)—, —OC(O)—, —OC(O)O—, —OC(O)N(R$^+$)—, —C(O)—, —CO$_2$—, —C(O)N(R$^+$)—, —C(O)—C(O)—, —C(=NR$^+$)—N(R$^+$)—, —C(NR$^+$)=N—, —C(=NR$^+$)—O—, —C(OR*)=N—, —C(R°)=N—O—, or —N(R$^+$)—N(R$^+$)—. Each R$^+$, independently, is hydrogen or an optionally substituted aliphatic, aryl, heteroaryl, or heterocyclyl group, or two R$^+$ on the same nitrogen atom, taken together with the nitrogen atom, form a 5-8 membered aromatic or non-aromatic ring having, in addition to the nitrogen atom, 0-2 ring heteroatoms selected from N, O, and S. Each R* independently is hydrogen or an optionally substituted aliphatic, aryl, heteroaryl, or heterocyclyl group.

Examples of $C_{3-6}$ alkylene chains that have been "interrupted" with —O— include —CH$_2$OCH$_2$—, —CH$_2$O(CH$_2$)$_2$—, —CH$_2$O(CH$_2$)$_3$—, —CH$_2$O(CH$_2$)$_4$—, —(CH$_2$)$_2$OCH$_2$—, —(CH$_2$)$_2$O(CH$_2$)$_2$—, —(CH$_2$)$_2$O(CH$_2$)$_3$—, —(CH$_2$)$_3$O(CH$_2$)—, —(CH$_2$)$_3$O(CH$_2$)$_2$—, and —(CH$_2$)$_4$O(CH$_2$)—. Other examples of alkylene chains that are "interrupted" with functional groups include —CH$_2$ZCH$_2$—, —CH$_2$Z(CH$_2$)$_2$—, —CH$_2$Z(CH$_2$)$_3$—, —CH$_2$Z(CH$_2$)$_4$—, —(CH$_2$)$_2$ZCH$_2$—, —(CH$_2$)$_2$Z(CH$_2$)$_2$—, —(CH$_2$)$_2$Z(CH$_2$)$_3$—, —(CH$_2$)$_3$Z(CH$_2$)—, —(CH$_2$)$_3$Z(CH$_2$)$_2$—, and —(CH$_2$)$_4$Z(CH$_2$)—, wherein Z is one of the "interrupting" functional groups listed above.

For purposes of clarity, all bivalent groups described herein, including, e.g., the alkylene chain linkers described above and the variables $G^1$, $T^1$, $T^2$, $T^3$, $V^1$, and $V^3$, are intended to be read from left to right, with a corresponding left-to-right reading of the formula or structure in which the variable appears.

One of ordinary skill in the art will recognize that when an alkylene chain having an interruption is attached to a functional group, certain combinations would not be sufficiently stable for pharmaceutical use. Similarly, certain combinations of $V^1$, $T^1$, and $R^{2b}$, and certain combinations of $V^3$, $T^3$, and $R^{2d}$ would not be sufficiently stable for pharmaceutical use. Only stable or chemically feasible compounds are within the scope of the present invention. A stable or chemically feasible compound is one in which the chemical structure is not substantially altered when kept at a temperature from about −80° C. to about +40° C., preferably −20° C. to about +40° C., in the absence of moisture or other chemically reactive conditions, for at least a week, or a compound which maintains its integrity long enough to be useful for therapeutic or prophylactic administration to a patient.

The term "substituted", as used herein, means that a hydrogen radical of the designated moiety is replaced with the radical of a specified substituent, provided that the substitution results in a stable or chemically feasible compound. The term "substitutable", when used in reference to a designated atom, means that attached to the atom is a hydrogen radical, which can be replaced with the radical of a suitable substituent.

The phrase "one or more substituents", as used herein, refers to a number of substituents that equals from one to the maximum number of substituents possible based on the number of available bonding sites, provided that the above conditions of stability and chemical feasibility are met. Unless otherwise indicated, an optionally substituted group may have a substituent at each substitutable position of the group, and the substituents may be either the same or different.

As used herein, the term "independently selected" means that the same or different values may be selected for multiple instances of a given variable in a single compound. By way of example, in a compound of formula (I), if Ring B is substituted with two substituents —$R^b$, each substituent is selected from the group of defined values for $R^b$, and the two values selected may be the same or different.

An aryl (including the aryl moiety in aralkyl, aralkoxy, aryloxyalkyl and the like) or heteroaryl (including the heteroaryl moiety in heteroaralkyl and heteroaralkoxy and the like) group may contain one or more substituents. Examples of suitable substituents on the unsaturated carbon atom of an aryl or heteroaryl group include -halo, —$NO_2$, —CN, —R*, —C(R*)=C(R*)$_2$, —C≡C—R*, —OR*, —SR°, —S(O)R°, —$SO_2R°$, —$SO_3R^*$, —$SO_2N(R^+)_2$, —$N(R^+)_2$, —$NR^+C(O)R^*$, —$NR^+C(O)N(R^+)_2$, —$N(R^+)C(=NR^+)$—$N(R^+)_2$, —$N(R^+)C(=NR)$—$R°$, —$NR^+CO_2R°$, —$NR^+SO_2R°$, —$NR^+SO_2N(R^+)_2$, —C(O)R*, —O—$CO_2R^*$, —OC(O)N(R^+)$_2$, —C(O)R*, —$CO_2R^*$, —C(O)—C(O)R*, —C(O)N(R^+)$_2$, —C(O)N(R^+)—OR*, —C(O)N(R^+)C(=NR^+)—N(R^+)$_2$, —N(R^+)C(=NR^+)—N(R^+)—C(O)R*, —C(=NR^+)—N(R^+)$_2$, —C(=NR^+)—OR*, —N(R^+)—N(R^+)$_2$, —C(=NR^+)—N(R^+)—OR*, —C(R°)=N—OR*, —P(O)(R*)$_2$, —P(O)(OR*)$_2$, —O—P(O)—OR*, and —P(O)(NR^+)—N(R^+)$_2$, wherein R° is an optionally substituted aliphatic, aryl, or heteroaryl group, and $R^+$ and R* are as defined above, or two adjacent substituents, taken together with their intervening atoms, form a 5-6 membered unsaturated or partially unsaturated ring having 0-3 ring atoms selected from the group consisting of N, O, and S.

An aliphatic group or a non-aromatic heterocyclic ring may be substituted with one or more substituents. Examples of suitable substituents on the saturated carbon of an aliphatic group or of a non-aromatic heterocyclic ring include, without limitation, those listed above for the unsaturated carbon of an aryl or heteroaryl group and the following: =O, =S, =C(R*)$_2$, =N—N(R*)$_2$, =N—OR*, =N—NHC(O)R*, =N—NHCO$_2$R°, =N—NHSO$_2$R°, or =N—R*, where each R* and R° is as defined above.

Suitable substituents on a substitutable nitrogen atom of a heteroaryl or non-aromatic heterocyclic ring include —R*, —N(R*)$_2$, —C(O)R*, —CO$_2$R*, —C(O)—C(O)R*—C(O)CH2C(O)R*, —SO$_2$R*, —SO$_2$N(R*)$_2$, —C(=S)N(R*)$_2$, —C(=NH)—N(R*)$_2$, and —NR*SO$_2$R*; wherein each R* is as defined above. A ring nitrogen atom of a heteroaryl or non-aromatic heterocyclic ring also may be oxidized to form the corresponding N-hydroxy or N-oxide compound. A non-limiting example of such a heteroaryl having an oxidized ring nitrogen atom is N-oxidopyridyl.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%.

As used herein, the term "comprises" means "includes, but is not limited to."

It will be apparent to one skilled in the art that certain compounds of this invention may exist in tautomeric forms, all such tautomeric forms of the compounds being within the scope of the invention. Unless otherwise stated, structures depicted herein are also meant to include all geometric (or conformational) isomers, i.e., (Z) and (E) double bond isomers and (Z) and (E) conformational isomers, as well as all stereochemical forms of the structure; i.e., the R and S configurations for each asymmetric center. Therefore, single stereochemical isomers as well as enantiomeric and diastereomeric mixtures of the present compounds are within the scope of the invention. When a mixture is enriched in one stereoisomer relative to another stereoisomer, the mixture may contain, for example, an enantiomeric excess of at least 50%, 75%, 90%, 99%, or 99.5%.

Unless otherwise stated, structures depicted herein are also meant to include compounds which differ only in the presence of one or more isotopically enriched atoms. For example, compounds having the present structure except for the replacement of a hydrogen atom by a deuterium or tritium, or the replacement of a carbon atom by a $^{13}$C- or $^{14}$C-enriched carbon are within the scope of the invention.

One embodiment of the invention relates to a subgenus of the compounds of formula (I-A) characterized by formula (I):

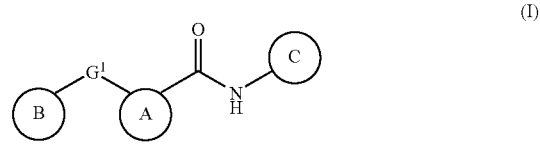

or a pharmaceutically acceptable salt thereof;
wherein:
  $G^1$ is —C(R$^d$)(R$^e$)—, —C(O)—, —O—, —S—, —S(O)—, —S(O)$_2$—, or —N(R$^f$)—;
  Ring A is a bicyclic ring system selected from the group consisting of:

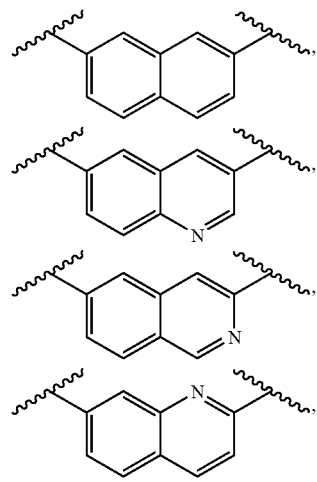

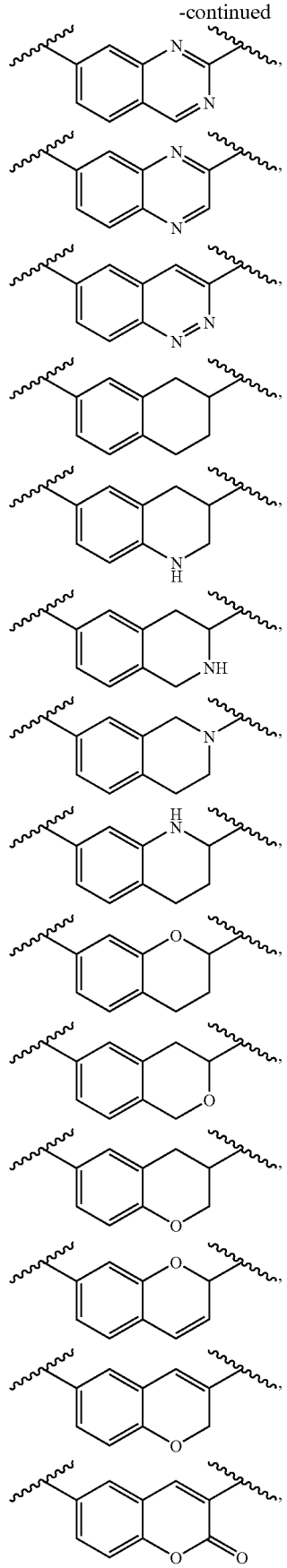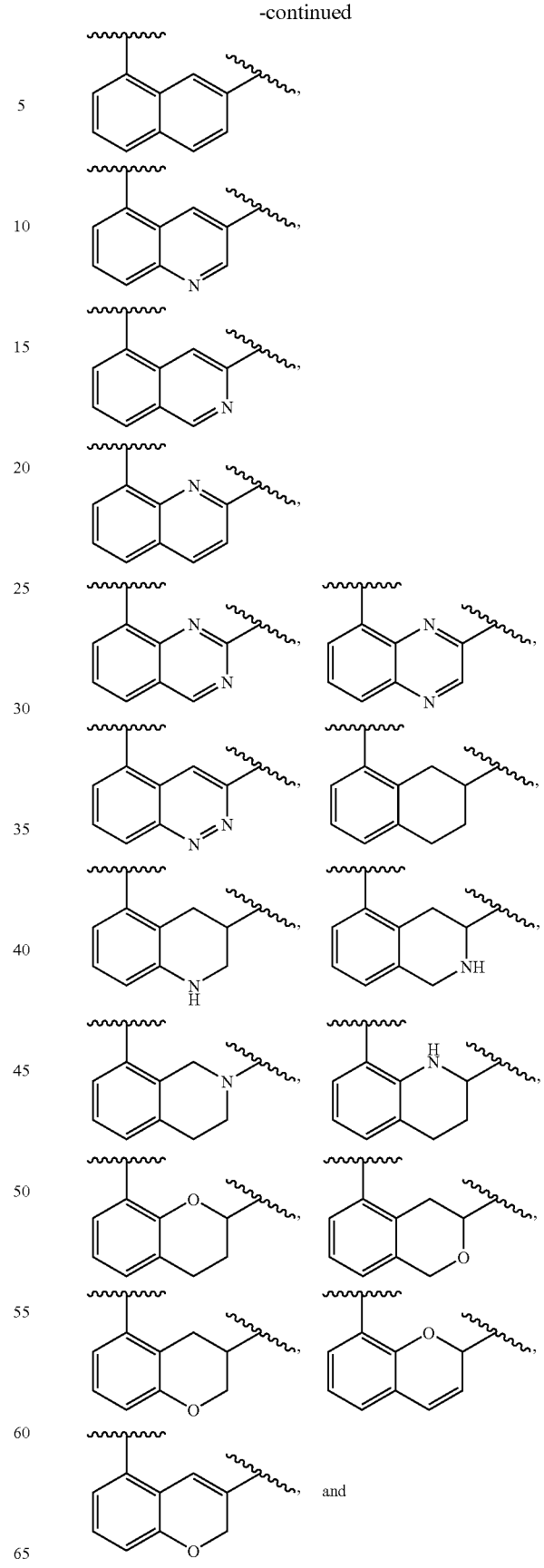

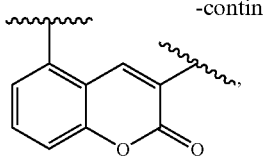

wherein Ring A is substituted with 0-2 $R^a$;

Ring B is an optionally substituted monocyclic nitrogen-containing heteroaryl;

Ring C is a 5- or 6-membered aryl or heteroaryl ring having 0-3 ring nitrogen atoms and optionally one additional ring heteroatom selected from oxygen and sulfur, wherein Ring C is substituted with 0-2 $R^c$ and 0-1 $R^{8c}$;

each $R^c$ independently is selected from the group consisting of $C_{1-4}$ aliphatic, $C_{14}$ fluoroaliphatic, halo, $-R^{2c}$ and $-T^2-R^{2c}$; or two adjacent $R^c$, taken together with the intervening ring atoms, form an optionally substituted fused 5- or 6-membered aromatic or non-aromatic ring having 0-3 ring heteroatoms independently selected from the group consisting of O, N, and S;

$T^2$ is a $C_{1-4}$ alkylene chain optionally substituted with one or two groups independently selected from -F, $C_{1-4}$ aliphatic, and $C_{14}$ fluoroaliphatic; and each $R^{2c}$ independently is $-CN$, $-C(R^5)=C(R^5)_2$, $-C\equiv C-R^5$, $-OR^5$, $-SR^6$, $-N(R^4)_2$, $-NR^4C(O)R^5$, $-NR^4C(O)N(R^4)_2$, $-NR^4CO_2R^6$, $-CO_2R^5$, or $-C(O)N(R^4)_2$;

each $R^{8c}$ independently is selected from the group consisting of $C_{1-4}$ aliphatic, $C_{1-4}$ fluoroaliphatic, $-O(C_{1-4}$ alkyl), and halo;

$R^a$ is halo, $-NO_2$, $-CN$, $-OR^5$, $-SR^6$, $-S(O)R^6$, $-SO_2R^6$, $-SO_2N(R^4)_2$, $-N(R^4)2$, $-OC(O)R^5$, $-CO_2R^5$, $-C(O)N(R^4)_2$, $-N(R^4)SO_2R^6$, $-N(R^4)SO_2N(R^4)_2$, or an optionally substituted $C^4$ aliphatic;

$R^d$ is hydrogen, fluoro, $C_{1-4}$ aliphatic, $C_{1-4}$ fluoroaliphatic, $-NH_2$, $-NH(C_{1-4}$ alkyl), $-N(C_{1-4}$ alkyl)$_2$, $-OH$, or $-O(C_{1-4}$ alkyl);

$R^e$ is hydrogen, fluoro, $C_{1-4}$ aliphatic, $C_{1-4}$ fluoroaliphatic; or $R^d$ and $R^e$, taken together with the carbon atom to which they are attached, form a 3- to 6-membered cycloaliphatic or heterocyclyl ring;

$R^f$ is $-H$, $-C(O)R^5$, $-C(O)N(R^4)_2$, $-CO_2R^6$, $-SO_2R^6$, $-SO_2N(R^4)_2$, or an optionally substituted $C_{1-6}$ aliphatic;

each $R^4$ independently is hydrogen or an optionally substituted aliphatic, aryl, heteroaryl, or heterocyclyl group; or two $R^4$ on the same nitrogen atom, taken together with the nitrogen atom, form an optionally substituted 4- to 8-membered heterocyclyl ring having, in addition to the nitrogen atom, 0-2 ring heteroatoms independently selected from N, O, and S;

each $R^5$ independently is hydrogen or an optionally substituted aliphatic, aryl, heteroaryl, or heterocyclyl group; and each $R^6$ independently is an optionally substituted aliphatic, aryl, or heteroaryl group.

In the compounds of formulae (I-A) and (I), Ring A is additionally substituted with 0, 1, or 2 substituents $R^a$, where $R^a$ is as defined above. Either or both rings of the bicyclic Ring A ring system may be substituted with $R^a$. In some embodiments, $R^a$ is selected from the group consisting of halo, $C_4$ aliphatic, $C_{1-4}$ fluoroaliphatic, $-NO_2$, $-CN$, $-CO_2H$, $-O(C_{1-4}$ alkyl), $-O(C_{1-4}$ fluoroalkyl), $-S(C_{1-4}$ alkyl), $-SO_2(C_{1-4}$ alkyl), $-NH_2$, $-NH(C_{1-4}$ alkyl), $-N(C_{1-4}$ alkyl)$_2$, $-C(O)NH_2$, $-C(O)NH(C_{1-4}$ alkyl), and $-C(O)N(C_{1-4}$ alkyl)$_2$. In some embodiments, $R^a$ is selected from the group consisting of, $-F$, $-Cl$, $-NO_2$, $-CH_3$, $-CF_3$, $-OCH_3$, $-SCH_3$, $-SO_2CH_3$, $-CN$, $-CO_2H$, $-C(O)NH_2$, $-C(O)NHCH_3$ and $-C(O)N(CH_3)_2$. In certain embodiments, $R^a$ is $-F$. In certain particular embodiments Ring A is unsubstituted or is substituted with one fluoro substituent.

In some embodiments, the invention relates to a subgenus of the compounds of formula (I-A) or formula (I), wherein Ring A is selected from the group consisting of:

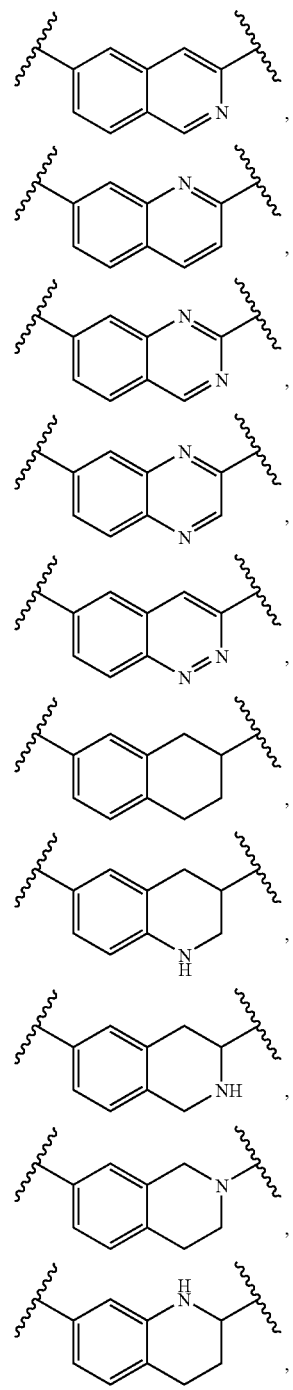

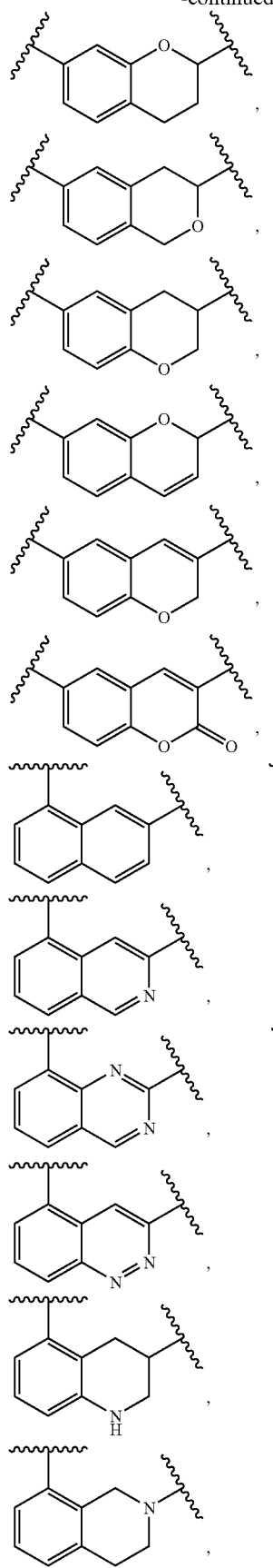
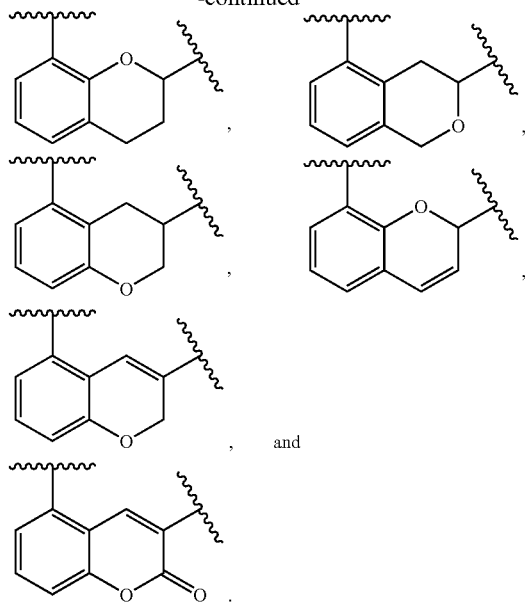
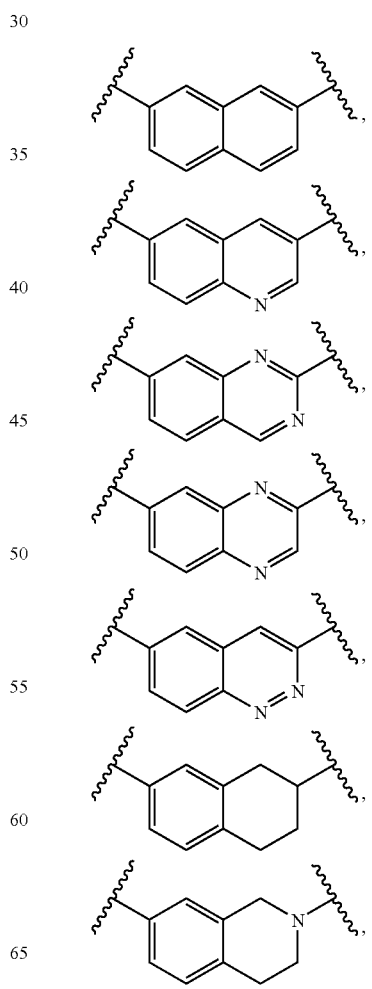
Another embodiment of the invention relates to a subgenus of the compounds of formula (I-A) or formula (I), wherein Ring A is selected from the group consisting of:

-continued

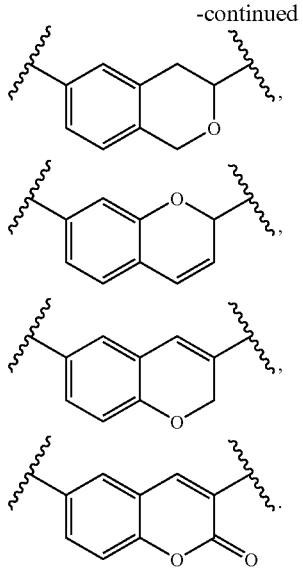

Another embodiment of the invention relates to a subgenus of the compounds of formula (I-A) of formula (I), wherein Ring A selected from the group consisting of:

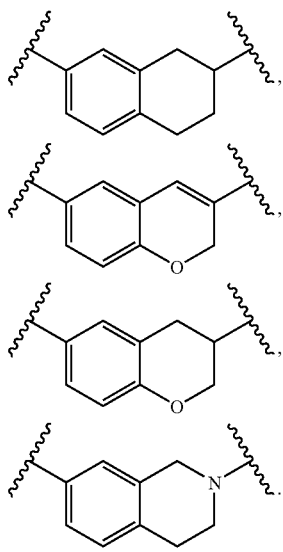

Another embodiment of the invention relates to a subgenus of the compounds of formula (I-A) or formula (1), wherein Ring A is selected from the group consisting of:

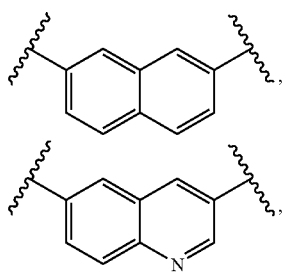

-continued

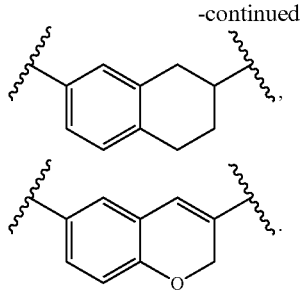
and

In certain such embodiments, Ring A is selected from the group consisting of

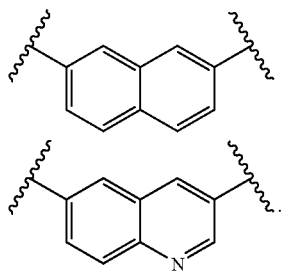
and

In certain other embodiments, Ring A is selected from the group consisting of

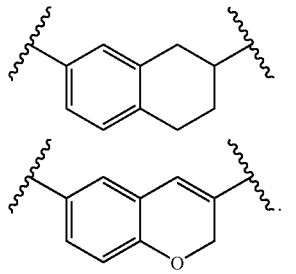
and

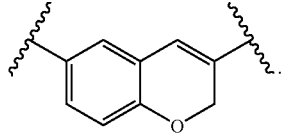

Each of the bicyclic Ring A ring systems depicted above is additionally substituted with 0-2 substituents Ra, wherein Ra has the values and preferred values described above.

The linker $G^1$ is a one-atom linker selected from the group consisting of —C($R^{e'}$)($R^e$)—, —C(O)—, —O—, —S—, —S(O)—, —S(O)$_2$—, or —N($R^f$)—, where each of $R^{e'}$, $R^e$, and $R^f$ is as defined above. When $G^1$ is a carbon linker, $R^{e'}$ and $R^e$ preferably are each independently hydrogen, fluoro, $C_{1-4}$ aliphatic, or $C_{1-4}$ fluoroaliphatic. Alternatively, $R^{e'}$, and $R^e$, taken together with the carbon atom to which they are attached, form a 3 to 6-membered cycloaliphatic or heterocyclyl ring, preferably a cyclopropyl ring. In some embodiments, each of $R^{e'}$ and $R^e$ is hydrogen. When $G^1$ is a nitrogen linker, $R^f$ preferably is hydrogen, —C(O)$R^5$, or an optionally substituted $C_{1-4}$ aliphatic. More preferably, $R^f$ is hydrogen. In certain embodiments, $G^1$ is —O— or —NH—.

The linker $G^2$ is —C(O)—NH—, —C(O)—N($C_{1-3}$ aliphatic)-, —NH—C(O)—, or —N($C_{1-3}$ aliphatic)—C(O)—, provided that $G^2$ is —C(O)—NH— or —C(O)—N($C_{1-3}$ aliphatic) - if it is connected to a ring nitrogen atom in Ring A. In some embodiments, $G^2$ is —C(O)—NH— or —NH—C(O)—. In certain particular embodiments, $G^2$ is —C(O)—NH—.

In one embodiment, the invention relates to a subgenus of the compounds of formula (I-A) characterized by formula (II-A) or (II-B):

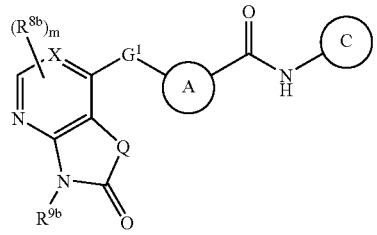

(II-A)

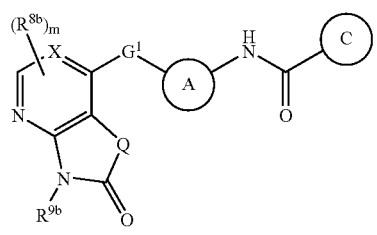

(II-B)

wherein the variables X, Q, $R^{8b}$, $R^{9b}$, and m have the values described below. Rings A and C and the variable $G^1$ have the values and preferred values described herein for formulae (I) and (I-A).

Q is —C($R^{10}$)($R^{11}$)—, —N($R^{9b}$)—, —O—, —C($R^{10}$)($R^{11}$)—C($R^{10}$)($R^{11}$)—, —C($R^{11}$)=C($R^{11}$)—, —C($R^{10}$)($R^{11}$)—N($R^{9b}$)—, —N($R^{9b}$)—C($R^{10}$)($R^{11}$)—, or —O—C($R^{10}$)($R^{11}$)—, wherein the oxygen atom of the group —O—C($R^{10}$)($R^{11}$)— is attached to the carbonyl carbon atom. In some embodiments, Q is —C($R^{10}$)($R^{11}$)—, —C($R^{10}$)($R^{11}$)—C($R^{10}$)($R^{11}$)—, or —C($R^{11}$)=C($R^{11}$)—.

Each $R^{10}$ independently is hydrogen, fluoro, $C_{1-4}$ aliphatic, or $C_{1-4}$ fluoroaliphatic.

Each $R^{11}$ independently is hydrogen, fluoro, or a $C_{1-4}$ aliphatic or $C_{1-4}$ fluoroaliphatic group optionally substituted with one or two substituents independently selected from the group consisting of —$OR^5$, —N($R^4$)$_2$, —$CO_2R^5$, or —C(O)N($R^4$)$_2$. In some embodiments, each $R^{11}$ is hydrogen, fluoro, $C_{1-4}$ aliphatic, or $C_{1-4}$ fluoroaliphatic.

Each $R^{8b}$ independently is selected from the group consisting of $C_{1-4}$ aliphatic, $C_{1-4}$ fluoroaliphatic, halo, —OH, —O($C_{1-4}$ aliphatic), —$NH_2$, —NH($C_{1-4}$ aliphatic), and —N($C_{1-4}$ aliphatic)$_2$.

$R^{9b}$ is hydrogen, $C_{1-4}$ aliphatic, or $C_{6-10}$ar($C_{1-4}$)alkyl, the aryl portion of which may be optionally substituted. In some embodiments, $R^{9b}$ is hydrogen.

The variable m is 0 or 1.

In some other embodiments, Ring B in formula (I-A) or formula (I) is an optionally substituted monocyclic nitrogen-containing heteroaryl. In such embodiments, each substitutable ring carbon atom is unsubstituted or substituted; each substitutable ring nitrogen atom in Ring B is unsubstituted or substituted, preferably with —C(O)$R^5$, —C(O)N($R^4$)$_2$, —$CO_2R^6$, —$SO_2R^6$, —$SO_2$N($R^4$)$_2$, $C_{1-4}$ aliphatic, an optionally substituted $C_{6-10}$ aryl, or a $C_{6-10}$ ar($C_{1-4}$)alkyl, the aryl portion of which is optionally substituted; and one ring nitrogen atom in Ring B optionally is oxidized. In some embodiments, the substitutable ring nitrogen atoms in Ring B all are unsubstituted, and one ring nitrogen atom optionally is oxidized.

In some embodiments, Ring B is selected from the group consisting of pyrrolyl, oxazolyl, thiazolyl, imidazolyl, pyrazolyl, isoxazolyl, isothiazolyl, oxadiazolyl, triazolyl, thiadiazolyl, pyridyl, pyridazinyl, pyrimidinyl, pyrazinyl, and triazinyl. Any such ring system optionally is substituted on any substitutable ring carbon and on any substitutable ring nitrogen atom, and one ring nitrogen atom optionally is oxidized. In some embodiments, Ring B is an optionally substituted pyrimidinyl, pyridyl, or N-oxidopyridyl. In some preferred embodiments, Ring B is an optionally substituted pyridyl or N-oxidopyridyl. In certain preferred embodiments, Ring B is an optionally substituted 4-pyridyl or N-oxido-4-pyridyl.

Substitutable ring carbon atoms in Ring B preferably are substituted with 0-2 $R^b$ and 0-2 $R^{8b}$. Each $R^{8b}$ independently is selected from the group consisting of $C_{1-4}$ aliphatic, $C_{1-4}$ fluoroaliphatic, halo, —OH, —O($C_{1-4}$ aliphatic), —$NH_2$, —NH($C_{1-4}$ aliphatic), and —N($C_{1-4}$ aliphatic)$_2$. Each $R^b$ independently is halo, —$NO_2$, —CN, —C($R^5$)=C($R^5$)$_2$, —C≡C—$R^5$, —$OR^5$, —$SR^6$, —S(O)$R^6$, —$SO_2R^6$, —$SO_2$N($R^4$)$_2$, —N($R^4$)$_2$, —$NR^4$C(O)$R^5$, —$NR^4$C(O)N($R^4$)$_2$, —N($R^4$)C(=$NR^4$)—N($R^4$)$_2$, —N($R^4$)C(=$NR^4$)—$R^6$, —$NR^4CO_2R^6$, —N($R^4$)$SO_2R^6$, —N($R^4$)$SO_2$N($R^4$)$_2$, —O—C(O)$R^5$, —OC(O)N($R^4$)$_2$, —C(O)$R^5$, —$CO_2R^5$, —C(O)N($R^4$)$_2$, —C(O)N($R^4$)—$OR^5$, —C(O)N($R^4$)C(=$NR^4$)—N($R^4$)$_2$, —N($R^4$)C(=$NR^4$)—N($R^4$)—C(O)$R^5$, —C(=$NR^4$)—N($R^4$)$_2$, —C(=$NR^4$)—$OR^5$, —C(=$NR^4$)—N($R_4$)—$OR^5$, —C($R^6$)=N—$OR^5$, or an optionally substituted aliphatic, aryl, heteroaryl, or heterocyclyl.

In some embodiments, each $R^b$ independently is selected from the group consisting of $C_{1-6}$ aliphatic, $C_{1-6}$ fluoroaliphatic, halo, —$R^{1b}$, —$R^{2b}$, —$T^1$—$R^{1b}$, —$T^1$—$R^{2b}$, —$V^1$—$T^1$—$R^{1b}$, and —$V^1$—$T^1$—$R^{2b}$. The variables $T^1$, $V^1$, $R^{1b}$, and $R^{2b}$ have the values described below.

$T^1$ is a $C_{1-6}$ alkylene chain optionally substituted with $R^{3a}$ or $R^{3b}$, wherein the alkylene chain optionally is interrupted by —C($R^5$)=C($R^5$)—, —C≡C—, —O—, —S—, —S(O)—, —S(O)$_2$—, —$SO_2$N($R^4$)—, —N($R^4$)—, —N($R^4$)C(O)—, —$NR^4$C(O)N($R^4$)—, —N($R^4$)C(=$NR^4$)—N($R^4$)—, —N($R^4$)—C(=$NR^4$)—, —N($R^4$)$CO_2$—, —N($R^4$)$SO_2$—, —N($R^4$)$SO_2$N($R^4$)—, —OC(O)—, —OC(O)N($R^4$)—, —C(O)—, —$CO_2$—, —C(O)N($R^4$)—, —C(=$NR^4$)—N($R^4$)—, —C($NR^4$)=N($R^4$)—, —C(=NR)—O—, or —C($R^6$)=N—O—, and wherein $T^1$ or a portion thereof optionally forms part of a 3-7 membered ring. In some embodiments, $T^1$ is a $C_{1-4}$ alkylene chain optionally substituted with one or two substituents independently selected from the group consisting of $C_{1-3}$ aliphatic, $C_{1-3}$ fluoroaliphatic, —F, —OH, —O($C_{1-4}$ alkyl), —$CO_2$H, —$CO_2$($C_{1-4}$ alkyl), —C(O)$NH_2$, and —C(O)NH($C_{1-4}$ alkyl), wherein the alkylene chain optionally is interrupted with —N($R^4$)—, —C(=$NR^4$)—N($R^4$)—, —C($NR^4$)=N($R^4$)—, —N($R^4$)C(=$NR^4$)—, —N($R^4$)—C(O)—, or —C(O)N($R^4$)—. In some particular embodiments, $T^1$ is a $C_{1-6}$ or $C_{1-4}$ alkylene chain optionally substituted with —F, $C_{1-3}$ alkyl, or $C_{1-3}$ fluoroalkyl, wherein the alkylene chain optionally is interrupted by —N($R^4$)—, —C(O)—N($R^4$)—, —C(=$NR^4$)—N($R^4$)—, —C($NR^4$)=N($R^4$)—, —N($R^4$)—C(O)—, or —N($R^4$)—C(=$NR^4$)—. In certain particular embodiments, $T^1$ is a $C_{1-4}$ alkylene chain optionally substituted with —F, $C_{1-3}$ alkyl, or $C_{1-3}$ fluoroalkyl.

$V^1$ is —C($R^5$)=C($R^5$)—, —C≡C—, —O—, —S—, —S(O)—, —S(O)$_2$—, —$SO_2$N($R^4$)—, —N($R^4$)—, —N($R^4$)C(O)—, —$NR^4$C(O)N($R^4$)—, —N($R^4$)C(=$NR^4$)—N($R^4$)—, —N($R^4$)C(=$NR^4$)—, —N($R^4$)$CO_2$—, —N($R^4$)$SO_2$—, —N($R^4$)$SO_2$N($R^4$)—, —OC(O)—, —OC(O)N($R^4$)—, —C(O)—, —$CO_2$—, —C(O)N($R^4$)—, —C(O)N($R^4$)—O—, —C(O)N($R^4$)C(=$NR^4$)—N($R^4$)—, —N($R^4$)C(=$NR^4$)—N($R^4$)—C(O)—, —C(=$NR^4$)—N($R^4$)—, —C($NR^4$)=N($R^4$)—, —C(=$NR^4$)—O—, or —C($R^6$)

=N—O—. In some embodiments, $V^1$ is —C($R^5$)=C($R^5$)—, —C≡C—, —O—, —N($R^4$)—, —N($R^4$)C(O)—, —C(O)N($R^4$)—, —C(=N$R^4$)—N($R^4$)—, —C(N$R^4$)=N($R^4$)—, or —N($R^4$)—C(=N$R^4$)—. In certain preferred embodiments, $V^1$ is —N($R^4$)—, —N($R^4$)—C(O)—, —C(O)N($R^4$)—, —C(=N$R^4$)N($R^4$)—, or —N($R^4$)—C(=N$R^4$)—. In certain particular embodiments, $V^1$ is —N($R^{4x}$)—, —N($R^{4x}$)—C(O)—, —C(O)N($R^{4x}$)—, —C(=N$R^{4x}$)N($R^{4x}$)—, or —N($R^{4x}$)—C(=N$R^{4x}$)—, where $R^{4x}$ is hydrogen, $C_{1-4}$ aliphatic, $C_{1-4}$ fluoroaliphatic, or $C_{6-10}$ ar($C_{1-4}$)alkyl, the aryl portion of which may be optionally substituted. In some embodiments, $V^1$ is —C(O)NH—, —NH—C(O)—, or —C(=NH)NH—.

Each $R^{1b}$ independently is an optionally substituted aryl, heteroaryl, heterocyclyl, or cycloaliphatic ring. In some embodiments, $R^{1b}$ is an optionally substituted $C_{3-6}$ cycloaliphatic or an optionally substituted phenyl, azetidinyl, pyrrolyl, imidazolyl, oxazolyl, thiazolyl, isoxazolyl, isothiazolyl, pyrazolyl, triazolyl, tetrazolyl, oxadiazolyl, thiadiazolyl, pyrrolinyl, imidazolinyl, pyrazolinyl, pyrrolidinyl, imidazolidinyl, pyrazolidinyl, piperidinyl, morpholinyl, piperazinyl, pyridyl, pyridazinyl, pyrimidinyl, pyrazinyl, or tetrahydropyrimidinyl. In certain preferred embodiments, $R^{1b}$ is an optionally substituted $C_{3-6}$ cycloaliphatic or an optionally substituted pyrrolidinyl, piperidinyl, morpholinyl, or piperazinyl ring.

Each $R^{2b}$ independently is —$NO_2$, —CN, —C($R^5$)=C($R^5$)$_2$, —C≡C—$R^5$, —$OR^5$, —$SR^6$, —S(O)$R^6$, —$SO_2R^6$, —$SO_2N(R^4)_2$, —$N(R^4)_2$, —$NR^4C(O)R^5$, —$NR^4C(O)N(R^4)_2$, —$N(R^4)C(=NR^4)$—$N(R^4)_2$, —$N(R^4)C(=NR^4)$—$R^6$, —$NR^4CO_2R^6$, —$N(R^4)SO_2R^6$, —$N(R^4)SO_2N(R^4)_2$, —O—C(O)$R^5$, —OC(O)N($R^4$)$_2$, —C(O)$R^5$, —$CO_2R^5$, —C(O)N($R^4$)$_2$, —C(O)N($R^4$)—$OR^5$, —C(O)N($R^4$)C(=N$R^4$)—N($R^4$)$_2$, —N($R^4$)C(=N$R^4$)—N($R^4$)—C(O)$R^5$, —C(=N$R^4$)—N($R^4$)$_2$, —C(=N$R^4$)—$OR^5$, —C(=N$R^4$)—N($R^4$)—OR, or —C($R^6$)=N—$OR^5$. In some embodiments, each $R^{2b}$ independently is —$NO_2$, —CN, —C($R^5$)=C($R^5$)$_2$, —C≡C—$R^5$, —$OR^5$, —$SR^6$, —S(O)$R^6$, —$SO_2R^6$, —$SO_2N(R^4)_2$, —$N(R^4)_2$, —$NR^4C(O)R^5$, —$NR^4C(O)N(R^4)_2$, —$N(R^4)C(=NR^4)$—$N(R^4)_2$, —$N(R^4)C(=NR^4)$—$R^6$, —$NR^4CO_2R^6$, —$N(R^4)SO_2R^6$, —$N(R^4)SO_2N(R^4)_2$, —C(O)$R^5$, —$CO_2R^5$, —C(O)N($R^4$)$_2$, —C(O)N($R^4$)—$OR^5$, —C(O)N($R^4$)C(=N$R^4$)—N($R^4$)$_2$, —N($R^4$)C(=N$R^4$)—N($R^4$)—C(O)$R^5$, —C(=N$R^4$)—N($R^4$)$_2$, —C(=N$R^4$)—N($R^4$)—$OR^5$, or —C($R^6$)=N—$OR^5$.

In some embodiments, each $R^{2b}$ independently is —CN, —$OR^5$, —$N(R^4)_2$, —$NR^4C(O)R^5$, —$NR^4C(O)N(R^4)_2$, —C(O)N($R^4$)—$OR^5$, —C(O)N($R^4$)$_2$, —N($R^4$)—$CO_2R^5$, —N($R^4$)—C(=NR)—$R^5$ or —C(=N$R^4$)—N($R^4$)$_2$. In some embodiments, each $R^{2b}$ independently is —$OR^5$, —$N(R^4)_2$, —$NR^4C(O)R^5$, —$NR^4C(O)N(R^4)_2$, —C(O)N($R^4$)—$OR^5$, —C(O)N($R^4$)$_2$, —N($R^4$)—$CO_2R^5$, —N($R^4$)—C(=N$R^4$)—$R^5$ or —C(=N$R^4$)—N($R^4$)$_2$. In some embodiments, each $R^{2b}$ independently is —$N(R^4)_2$, —$NR^4C(O)R^5$, —C(O)N($R^4$)$_2$, —$CO_2R^5$, or —$OR^5$. In some embodiments, each $R^{2b}$ independently is —CN, —$NR^4C(O)R^5$, —C(O)N($R^4$)$_2$, or —N($R^4$)—$CO_2R^5$.

Each $R^{3a}$ independently is selected from the group consisting of —F, —OH, —O($C_{1-4}$ alkyl), —CN, —N($R^4$)$_2$, —C(O)($C_{1-4}$ alkyl), —$CO_2H$, —$CO_2$($C_{1-4}$ alkyl), —C(O)$NH_2$, and —C(O)NH($C_{1-4}$ alkyl).

Each $R^{3b}$ independently is a $C_{1-3}$ aliphatic optionally substituted with $R^{3a}$ or $R^7$, or two substituents $R^{3b}$ on the same carbon atom, taken together with the carbon atom to which they are attached, form a 3- to 6-membered cycloaliphatic ring.

Each $R^4$ independently is hydrogen or an optionally substituted aliphatic, aryl, heteroaryl, or heterocyclyl group; or two $R^4$ on the same nitrogen atom, taken together with the nitrogen atom, form an optionally substituted 4- to 8-membered heterocyclyl ring having, in addition to the nitrogen atom, 0-2 ring heteroatoms selected from N, O, and S.

Each $R^5$ independently is hydrogen or an optionally substituted aliphatic, aryl, heteroaryl, or heterocyclyl group.

Each $R^6$ independently is an optionally substituted aliphatic, aryl, or heteroaryl group.

Each $R^7$ independently is an optionally substituted aryl or heteroaryl ring.

In some embodiments, the substitutable ring carbon atoms in Ring B are substituted with 0-1 $R^b$ and 0-2 $R^{8b}$. More preferably, the substitutable ring carbon atoms in Ring B are substituted with 0-1 $R^b$ and 0-1 $R^{8b}$. In such embodiments, $R^b$ preferably is selected from the group consisting of $C_{1-4}$ aliphatic, $C_{1-4}$ fluoroaliphatic, halo, —$R^{1b}$, —$R^{2b}$, —$T^1$—$R^{1b}$—$T^1$—$R^{2b}$, —$V^1$—$T^1$—$R^{1b}$, and —$V^1$—$T^1$—$R^{2b}$, where the variables $T^1$, $V^1$, $R^{1b}$, and $R^{2b}$ have the values and preferred values described above for formulae (I) and (I-A).

In a more particular embodiment, the invention relates to a subgenus of the compounds of formula (I), characterized by formula (III):

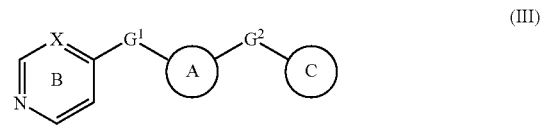

(III)

or a pharmaceutically acceptable salt thereof;
wherein:
  $G^1$ is —O— or —NH—;
  X is CH or N;
  Ring B is substituted with 0-1 $R^b$ and 0-1 $R^{8b}$, and one nitrogen atom in Ring B optionally is oxidized; and
  Ring A, Ring C, and the variables $G^1$, $R^b$, and $R^{8b}$ have the values and preferred values described above for formula (I).

In a more particular embodiment, the invention relates to a compound of formula (III-A) or (III-B):

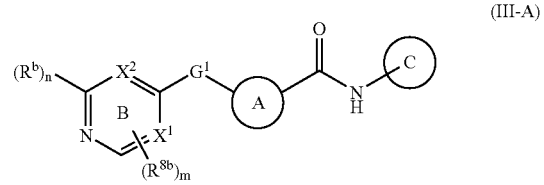

(III-A)

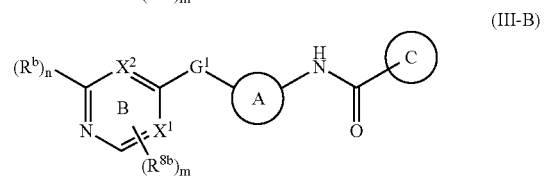

(III-B)

or a pharmaceutically acceptable salt thereof, wherein:
  $X^1$ and $X^2$ are each independently CH or N, provided that $X^1$ and $X^2$ are not both N;
  m is 0 or 1;
  n is 0 or 1; and
  Rings A and C, and the variables $G^1$, $R^b$, and $R^{8b}$ have the values and preferred values described above for formulae (I)-(II).

In some such embodiments, Ring A is selected from the group consisting of:

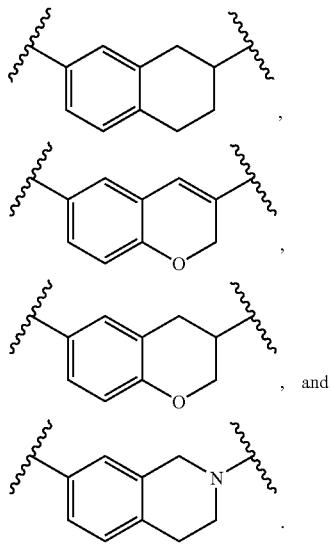

wherein Ring A is substituted with 0, 1, or 2 substituents $R^a$.

In other such embodiments, Ring A is selected from the group consisting of:

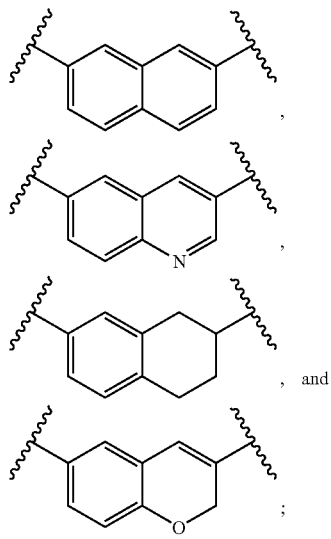

wherein Ring A is substituted with 0, 1, or 2 substituents $R^a$.

In certain such embodiments, Ring A is selected from the group consisting of:

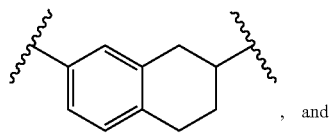

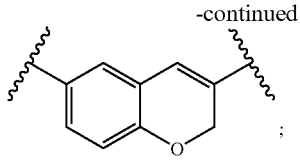

wherein Ring A is substituted with 0, 1, or 2 substituents $R^a$.

In some embodiments, the invention relates to a compound of formula (III-A) or (III-B), or a pharmaceutically acceptable salt thereof, wherein $R^b$ is selected from the group consisting of halo, —CN, —N($R^4$)$_2$, —CO$_2R^5$, —C(O)—N($R^4$)$_2$, —C(O)—N($R^4$)—OR$^5$, —N($R^4$)C(O)R$^5$, —N($R^4$)C(O)—OR$^5$, —N($R^4$)C(O)—N($R^4$)$_2$, —N($R^4$)SO$_2R^6$, —C(=NR$^4$)N($R^4$)$_2$, and —C(=NR$^4$)N($R^4$)—OR$^5$. In some embodiments, $R^b$ is —N($R^4$)C(O)R$^5$, —C(=NR$^4$)N($R^4$)$_2$, or —C(=NR$^4$)N($R^4$)—OR$^5$. In some embodiments, $R^b$ is —CN, —N($R^4$)C(O)R$^5$, —N($R^4$)C(O)OR$^5$, —C(=NR$^4$)N($R^4$)$_2$, or —C(O)N($R^4$)$_2$.

In some embodiments, $R^b$ is selected from the group consisting of halo, —CN, —N($R^{4x}$)($R^{4x}$), —CO$_2R^{5x}$, —C(O)—N($R^{4x}$)($R^{4z}$), —C(O)—N($R^{4x}$)—OR$^{5x}$, —N($R^{4x}$)C(O)R$^{5x}$, —N($R^{4x}$)C(O)—OR$^{5x}$, —N($R^{4x}$)C(O)—N($R^{4x}$)($R^{4z}$), —N($R^{4x}$)SO$_2R^{6x}$, —C(=NR$^{4x}$)N($R^{4x}$)($R^{4z}$), and —C(=NR$^{4x}$)N($R^{4x}$)—OR$^{5x}$. In certain such embodiments, $R^b$ is selected from the group consisting of halo, —CN, —NH($R^{4z}$), —N($R^{4x}$)($R^{4z}$), —CO$_2R^{5x}$, —C(O)—NH($R^{4z}$), —C(O)—N($R^{4x}$)($R^z$), —C(O)—NH—OR$^{5x}$, —NHC(O)R$^{5x}$, —NHC(O)—OR$^{5x}$, —NHC(O)—N($R^{4x}$)($R^{4z}$), —NHSO$_2R^{6x}$, —C(=NH)N($R^{4x}$)($R^{4z}$), and —C(=NH)NH—OR$^{5x}$. In certain particular embodiments, $R^b$ is —CN, —NHC(O)R$^{5x}$, —NHC(O)OR$^{5x}$, —C(=NH)N($R^{4x}$)($R^{4z}$), or —C(O)N($R^{4x}$)($R^{4z}$).

In these embodiments, each $R^{4x}$ independently is hydrogen, $C_{1-4}$ aliphatic, $C_{1-4}$ fluoroaliphatic, or $C_{6-10}$ ar($C_{1-4}$)alkyl, the aryl portion of which may be optionally substituted, and each $R^{4x}$ independently is hydrogen, $C_{1-4}$ aliphatic, $C_{1-4}$ fluoroaliphatic, $C_{6-10}$ ar($C_{1-4}$)alkyl, the aryl portion of which may be optionally substituted, or an optionally substituted 5- or 6-membered aryl, heteroaryl, or heterocyclyl ring; or $R^{4x}$ and $R^{4z}$, taken together with the nitrogen atom to which they are attached, form an optionally substituted 4-to 8-membered heterocyclyl ring having, in addition to the nitrogen atom, 0-2 ring heteroatoms independently selected from N, O, and S. In some embodiments, $R^{4x}$ and $R^{4z}$, taken together with the nitrogen atom to which they are attached, form an optionally substituted morpholinyl, piperidinyl, piperazinyl, or pyrrolidinyl ring.

Each $R^{5x}$ independently is $C_{1-4}$ aliphatic, $C_{1-4}$ fluoroaliphatic, $C_{6-10}$ ar($C_{1-4}$)alkyl, the aryl portion of which may be optionally substituted, or an optionally substituted 5- or 6-membered aryl, heteroaryl, or heterocyclyl ring.

Each $R^{6x}$ independently is $C_{1-4}$ aliphatic, $C_{1-4}$ fluoroaliphatic, $C_{6-10}$ ar($C_{1-4}$)alkyl, the aryl portion of which may be optionally substituted, or an optionally substituted 5- or 6-membered aryl, heteroaryl, or heterocyclyl ring.

In some particular embodiments, $R^b$ is —N($R^{4x}$)($R^{4z}$), —C(O)—N($R^{4x}$)($R^{4z}$), —N($R^{4x}$)C(O)R$^{5x}$ or —C(=NH)N($R^{4x}$)($R^{4z}$). In certain such embodiments, $R^{4x}$ and $R^{4z}$, taken together with the nitrogen atom to which they are attached, form a morpholinyl, piperidinyl, piperazinyl, or pyrrolidinyl ring. In certain other embodiments, $R^b$ is —N($R^{4x}$)($R^4z$) and $R^{4z}$ is hydrogen, $C_{1-4}$ aliphatic, $C_{1-4}$ fluoroaliphatic, $C_{6-10}$ ar($C_{1-4}$)alkyl, the aryl portion of which may be optionally substituted, or an optionally substituted pyrazole or imidazole ring. In certain other embodiments, $R^b$ is —C(O)—NH ($C_{1-4}$ aliphatic) or —NHC(O)($C_{1-4}$ aliphatic). In certain particular embodiments, $R^b$ is —C(O)NHCH$_3$ —C(O)NH (cyclopropyl), —NHC(O)CH$_3$, —NHC(O)(cyclopropyl).

In other embodiments, the invention relates to a compound of formula (III-A) or (III-B) or a pharmaceutically acceptable salt thereof, wherein $R^b$ is —V$^1$—T$^1$—R$^{1b}$ or —V$^1$—T$^1$—R$^{2b}$, where the variables V$^1$, T$^1$, and R$^2$b have the values described below.

V$^1$ is —N(R$^4$)—, —N(R$^4$)—C(O)—, —N(R$^4$)SO$_2$R$^6$, —N(R$^4$)C(O)—OR$^5$, —C(O)N(R$^4$)—, —C(=NR$^4$)N(R$^4$)—, or —N(R$^4$)—C(=NR$^4$)—. In some embodiments, V$^1$ is —N(R$^{4x}$)—, —N(R$^{4x}$)—C(O)—, —C(O)N(R$^{4x}$)—, —C(=NR$^{4x}$)N(R$^{4x}$)—, or —N(R$^{4x}$)—C(=NR$^{4x}$)—,. In some embodiments, V$^1$ is —C(O)—NH—, —NH—C(O)—, or —C(=NH)NH—.

T$^1$ is a $C_{1-4}$ alkylene chain optionally substituted with —F, $C_{1-3}$ alkyl, or $C_{1-3}$ fluoroalkyl.

R$^{1b}$ is an optionally substituted $C_{3-6}$ cycloaliphatic or an optionally substituted phenyl, pyrrolyl, imidazolyl, oxazolyl, thiazolyl, isoxazolyl, isothiazolyl, pyrazolyl, triazolyl, tetrazolyl, oxadiazolyl, thiadiazolyl, pyrrolinyl, imidazolinyl, pyrazolinyl, pyrrolidinyl, imidazolidinyl, pyrazolidinyl, piperidinyl, morpholinyl, piperazinyl, pyridyl, pyridazinyl, pyrimidinyl, pyrazinyl, or tetrahydropyrimidinyl ring. In some embodiments, R$^{1b}$ is an optionally substituted $C_{3-6}$ cycloaliphatic or an optionally substituted pyrrolidinyl, piperidinyl, morpholinyl, or piperazinyl ring.

R$^{2b}$ is —N(R$^4$)$_2$, —NR$^4$C(O)R$^5$, —N(R$^4$)C(O)—OR$^5$, —N(R$^4$)C(O)—N(R$^4$)$_2$, —C(O)N(R$^4$)$_2$, —CO$_2$R$^5$, or —OR$^5$. In some embodiments, R$^{2b}$ is —N(R$^{4x}$)(R$^{4z}$), —NR$^{4x}$C(O)R$^{5x}$, —C(O)N(R$^{4x}$)(R$^{4z}$), —CO$_2$R$^{5x}$, or —OR$^{5x}$.

In some particular embodiments, the invention relates to a compound of formula (III-A) or (III-B) or a pharmaceutically acceptable salt thereof, wherein $R^b$ is selected from the group consisting of:

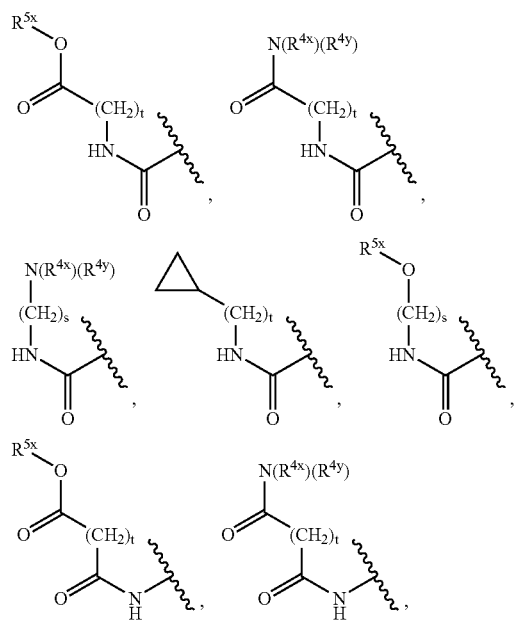

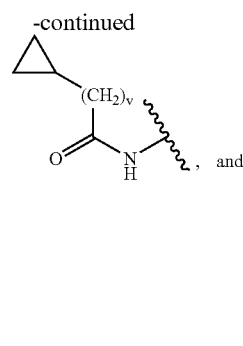

where s is 2 or 3, t is 1, 2, or 3, and v is 0, 1, 2, or 3.

In some other embodiments, the invention relates to a compound of formula (III-A) or (III-B), wherein $R^b$ is —T$^1$—R$^{1b}$ or —T$^{1b}$—R$^{2b}$. T$^1$ is a $C_{1-4}$ alkylene chain optionally substituted with —F, $C_{1-3}$ alkyl, or $C_{1-3}$ fluoroalkyl, wherein the alkylene chain optionally is interrupted by —N(R$^4$)—, —C(O)—N(R$^4$)—, —C(=NR$^4$)—N(R$^4$)—, —C(NR$^4$)=N(R$^4$)—, —N(R$^4$)—C(O)—, or —N(R$^4$)—C(=NR)—. R$^{1b}$ is an optionally substituted $C_{3-6}$ cycloaliphatic or an optionally substituted phenyl, pyrrolyl, imidazolyl, oxazolyl, thiazolyl, isoxazolyl, isothiazolyl, pyrazolyl, triazolyl, tetrazolyl, oxadiazolyl, thiadiazolyl, pyrrolinyl, imidazolinyl, pyrazolinyl, pyrrolidinyl, imidazolidinyl, pyrazolidinyl, piperidinyl, morpholinyl, piperazinyl, pyridyl, pyridazinyl, pyrimidinyl, pyrazinyl, or tetrahydropyrimidinyl ring. R$^{2b}$ is —OR$^5$, —N(R$^4$)$_2$, —NR$^4$C(O)R$^5$, —NR$^4$C(O)N(R$^4$)$_2$, —C(O)N(R$^4$)—OR$^5$, —C(O)N(R$^4$)$_2$, —N(R$^4$)—CO$_2$R$^5$, —N(R$^4$)—C(=NR$^4$)—R$^5$ or —C(=NR$^4$)—N(R$^4$)$_2$.

In some such embodiments, R$_b$ is selected from the group consisting of —(CH$_2$)$_q$—R$^{1x}$, —(CH$_2$)$_q$—R$^{2x}$, —(CH$_2$)$_q$—R$^{2y}$—(CH$_2$)$_q$—N(R$^{4x}$)—(CH$_2$)$_q$—R$^{1x}$, —(CH$_2$)$_q$—N(R$^{4x}$)—(CH$_2$)$_q$—R$^{2x}$, —(CH$_2$)$_q$,—N(R$^{4x}$)—(CH$_2$)$_s$—R$^{2y}$—-(CH$_2$)$_q$—N(R$^{4x}$)C(=NR$^{4x}$)—(CH$_2$)$_q$—R$^{1x}$, —(CH$_2$)$_q$—N(R$^{4x}$)C(=NR$^{4x}$)—(CH$_2$)$_q$—R$^{2x}$, and —(CH$_2$)$_q$—N(R$^{4x}$)C(=NR$^{4x}$)—(CH$_2$)$_q$—R$^{2y}$, wherein q at each occurrence independently is 1, 2, or 3, and s is 2 or 3. R$^{1x}$ is an optionally substituted phenyl, piperidinyl, piperazinyl, morpholinyl, or pyrrolidinyl ring. R$^{1x}$ is —C(O)N(R$^{4x}$)(R$^z$). R$^{2y}$ is —N(R$^4$x)(R$^z$), —NR$^{4x}$C(O)R$^{5x}$, —N(R$^{4x}$)—CO$_2$R$^{5x}$, —N(R$^{4x}$)—C(=NR$^{4x}$)—R$^{5x}$ or —OR$^{5x}$. R$^{4x}$ is hydrogen, $C_{1-4}$ aliphatic, $C_{1-4}$ fluoroaliphatic, or $C_{6-10}$ ar($C_{1-4}$)alkyl, the aryl portion of which may be optionally substituted; R$^{4z}$ is hydrogen, $C_{1-4}$ aliphatic, $C_4$ fluoroaliphatic, $C_{6-10}$ ar($C_{1-4}$) alkyl, the aryl portion of which may be optionally substituted, or an optionally substituted 5- or 6-membered aryl, heteroaryl, or heterocyclyl ring; or R$^{4x}$ and R$^{4z}$, taken together with the nitrogen atom to which they are attached, form an optionally substituted morpholinyl, piperidinyl, piperazinyl, or pyrrolidinyl ring. R$^{5x}$ is hydrogen, $C_{1-4}$ aliphatic, $C_{1-4}$ fluoroaliphatic, or $C_{6-10}$ ar($C_{1-4}$)alkyl, the aryl portion of which may be optionally substituted.

Another embodiment of the invention relates to a compound of formula (III-A) or (III-B) wherein $R^b$ is —R$^{1b}$. In such embodiments, the compound has formula (IV-A) or (IV-B):

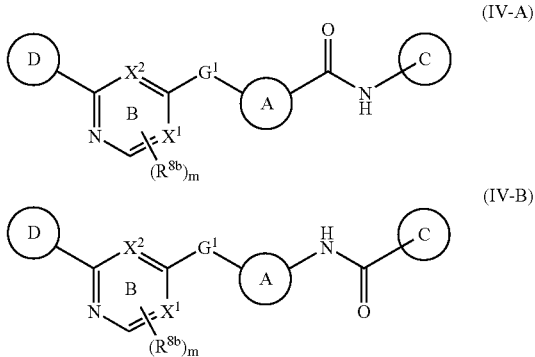

or a pharmaceutically acceptable salt thereof;
wherein:
   $X^1$ and $X^2$ are each independently CH or N, provided that $X^1$ and $X^2$ are not both N;
   Ring D is an optionally substituted aryl, heteroaryl, heterocyclyl, or cycloaliphatic ring;
   Ring A, Ring C, and the variables $R^{8b}$ and $G^1$ have the values and preferred values described above for formulae (I)-(III); and
   m is 0 or 1.

In some embodiments, $X^1$ and $X^2$ are each CH.

Each substitutable ring nitrogen atom in Ring D preferably is unsubstituted or is substituted with —C(O)$R^5$, —C(O)N($R^4$)$_2$, —CO$_2R^6$, —SO$_2R^6$, —SO$_2$(N$R^4$)$_2$, an optionally substituted $C_{6-10}$ aryl, or a $C_{1-4}$ aliphatic optionally substituted with $R^{3a}$ or $R^7$; and one ring nitrogen atom in Ring D optionally is oxidized. Each $R^{3a}$ independently is selected from the group consisting of —F, —OH, —O($C_{1-4}$ alkyl), —CN, —N($R^4$)$_2$, —C(O)($C_{1-4}$ alkyl), —CO$_2$H, —CO$_2$($C_{1-4}$ alkyl), —C(O)NH$_2$, and —C(O)NH($C_{1-4}$ alkyl). Each $R^7$ independently is an optionally substituted aryl or heteroaryl ring.

In some embodiments, Ring D is an optionally substituted heteroaryl or heterocyclyl selected from the group consisting of azetidinyl, pyrrolyl, imidazolyl, oxazolyl, thiazolyl, isoxazolyl, isothiazolyl, pyrazolyl, triazolyl, tetrazolyl, oxadiazolyl, thiadiazolyl, pyrrolinyl, imidazolinyl, oxazolinyl, pyrazolinyl, pyrrolidinyl, imidazolidinyl, oxazolidinyl, pyrazolidinyl, piperidinyl, morpholinyl, piperazinyl, pyridyl, pyridazinyl, pyrimidinyl, pyrazinyl, and tetrahydropyrimidinyl. In certain embodiments, Ring D is an optionally substituted imidazolyl, oxazolyl, thiazolyl, oxadiazolyl, thiadiazolyl, tetrazolyl, imidazolinyl, oxazolinyl, or tetrahydropyrimidinyl.

Each substitutable saturated ring carbon atom in Ring D preferably is unsubstituted or is substituted with =O, =S, =C($R^5$)$_2$, =N—O$R^5$, =N—$R^5$, or —$R^d$.

Each substitutable unsaturated ring carbon atom in Ring D preferably is unsubstituted or is substituted with —$R^d$.

Each $R^d$ independently is halo, —NO$_2$, —CN, —C($R^5$)=C($R^5$)$_2$, —C≡C—$R^5$, —O$R^5$, —S$R^6$, —S(O)$R^6$, —SO$_2R^6$, —SO$_2$N($R^4$)$_2$, —N($R^4$)$_2$, —N$R^4$C(O)$R^5$, —N$R^4$C(O)N($R^4$)$_2$, —N($R^4$)C(=N$R^4$)—N($R^4$)$_2$, —N($R^4$)C(=N$R^4$)—$R^6$, —N$R^4$CO$_2R^6$, —N($R^4$)SO$_2R^6$, —N($R^4$)SO$_2$N($R^4$)$_2$, —O—C(O)$R^5$, —OC(O)N($R^4$)$_2$, —C(O)$R^5$, —CO$_2R^5$, —C(O)N($R^4$)$_2$, —C(O)N($R^4$)—O$R^5$, —C(O)N($R^4$)C(=NR)—N($R^4$)$_2$, —N($R^4$)C(=N$R^4$)—N($R^4$)—C(O)$R^5$, —C(=N$R^4$)—N($R^4$)$_2$, —C(=N$R^4$)—O$R^5$, —C(=N$R^4$)—N($R^4$)—O$R^5$, —C($R^6$)=N—O$R^5$, or an optionally substituted aliphatic, aryl, heteroaryl, or heterocyclyl.

In some embodiments, Ring D is substituted with 0-1 $R^d$ and 0-1 $R^{8d}$. $R^{8d}$ is $C_{1-4}$ aliphatic, $C_{1-4}$ fluoroaliphatic, halo, —OH, —O($C_{1-4}$ aliphatic), —NH$_2$, —NH($C_{1-4}$ aliphatic), or —N($C_{1-4}$ aliphatic)$_2$. $R^d$ is selected from the group consisting of $C_{1-4}$ aliphatic, $C_{1-4}$ fluoroaliphatic, halo, —$R^{1d}$, —$R^{2d}$, —$T^3$—$R^{1d}$, —$T^3$—$R^{2d}$, —$V^3$—$T^3$—$R^{1d}$, and —$V^3$—$T^3$—$R^{2d}$. The variables $T^3$, $V^3$, $R^{1d}$, and $R^{2d}$ have the values described below.

$T^3$ is a $C_{1-4}$ alkylene chain optionally substituted with one or two substituents independently selected from the group consisting of $C_{1-3}$ aliphatic, $C_{1-3}$ fluoroaliphatic, —F, —OH, —O($C_{1-4}$ alkyl), —CO$_2$H, —CO$_2$($C_{1-4}$ alkyl), —C(O)NH$_2$, and —C(O)NH($C_{1-4}$ alkyl). In some embodiments, $T^3$ is —(CH$_2$)— or —(CH$_2$)$_2$—.

$V^3$ is —O—, —N($R^4$)—, —N($R^4$)C(O)—, —C(O)N($R^4$)—, —C(=N$R^4$)—N($R^4$)—, —C(N$R^4$)=N($R^4$)—, or —N($R^4$)C(=N$R^4$)—.

Each $R^{1d}$ independently is an optionally substituted aryl, heteroaryl, heterocyclyl, or cycloaliphatic ring. In some embodiments, $R^{1d}$ is an optionally substituted phenyl, pyridyl, or pyrimidinyl group.

Each $R^{2d}$ independently is —NO$_2$, —CN, —C($R^5$)=C($R^5$)$_2$, —C≡C—$R^5$, —O$R^5$, —SO$_2R^6$, —SO$_2$N($R^4$)$_2$, —N($R^4$)$_2$, —N$R^4$C(O)$R^5$, —N$R^4$C(O)N($R^4$)$_2$, —N($R^4$)C(=N$R^4$)—N($R^4$)$_2$, —N($R^4$)C(=N$R^4$)—$R^6$, —N$R^4$CO$_2R^6$, —N($R^4$)SO$_2R^6$, —N($R^4$)SO$_2$N($R^4$)$_2$, —O—C(O)$R^5$, —OC(O)N($R^4$)$_2$, —C(O)$R^5$, —CO$_2R^5$, —C(O)N($R^4$)$_2$, —C(O)N($R^4$)—O$R^5$, —C(O)N($R^4$)C(=NR)—N($R^4$)$_2$, —N($R^4$)C(=N$R^4$)—N($R^4$)—C(O)$R^5$, —C(=N$R^4$)—N($R^4$)$_2$, —C(=N$R^4$)—O$R^5$, —C(=N$R^4$)—N($R^4$)—O$R^5$, or —C($R^6$)=N—O$R^5$. In some embodiments, each $R^{2d}$ independently is selected from the group consisting of —O$R^5$, —N($R^4$)$_2$, —N$R^4$C(O)$R^5$, —N$R^4$C(O)N($R^4$)$_2$, —O—C(O)$R^5$, —CO$_2R^5$, —C(O)$R^5$, —C(O)N($R^4$)$_2$, —C(O)N($R^4$)—O$R^5$, and —C(=N$R^4$)—N($R^4$)$_2$. In some embodiments, each $R^{2d}$ is selected from the group consisting of —O$R^5$, —N($R^4$)$_2$, —CO$_2R^5$, or —C(O)N($R^4$)$_2$.

In some embodiments, Ring D is selected from the group consisting of:

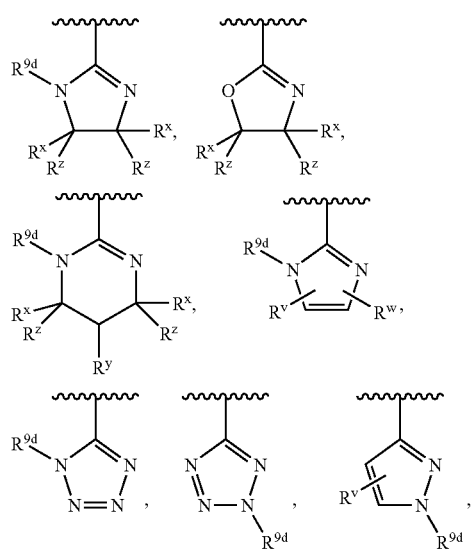

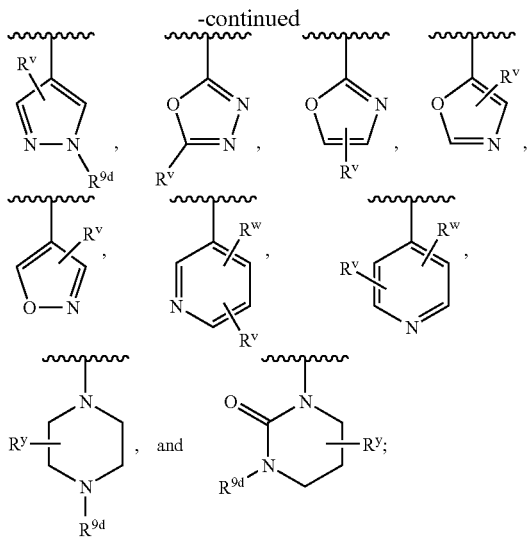

where the variables $R^{9d}$, $R^v$, $R^w$, $R^x$, $R^y$, and $R^z$ have the values and preferred values described below.

$R^v$ is hydrogen, halo, $C_{1-4}$ aliphatic, $C_{1-4}$ fluoroaliphatic, $-OR^5$, $-N(R^4)_2$, $-CO_2R^5$, $-C(O)N(R^4)_2$, $-T^3-OR^5$, $-T^3-N(R^4)_2$, $-T^3-CO_2R^5$, $-T^3-C(O)N(R^4)_2$, or an optionally substituted 5 or 6-membered aryl or heteroaryl. In certain embodiments, $R^v$ is hydrogen, an optionally substituted phenyl, pyridyl, or pyrimidinyl group, halo, $C_{1-4}$ aliphatic, $C_{1-4}$ fluoroaliphatic, $-(CH_2)_p-OR^{5x}$, $-(CH_2)_p-N(R^{4x})(R^{4z})$, $-(CH_2)_p-CO_2R^{5x}$, $-(CH_2)_p-C(O)N(R^{4x})(R^{4z})$, $-(CH_2)_q-N(R^{4x})-(CH_2)_q-R^{1x}$, $-(CH_2)_q-N(R^{4x})-(CH_2)_q-R^{2x}$, $-(CH_2)_q-N(R^{4x})-(CH_2)_s-R^{2y}$, $-(CH_2)_q-N(R^{4x})C(=NR^{4x})-(CH_2)_q-R^{1x}$, $-(CH_2)_q-N(R^{4x})C(=NR^{4x})-(CH_2)_q-R^{2x}$, or $-(CH_2)_q-N(R^{4x})C(=NR^{4x})-(CH_2)_q-R^{2y}$. In certain embodiments, $R^v$ is hydrogen, halo, $C_{1-4}$ aliphatic, $C_{1-4}$ fluoroaliphatic, $-(CH_2)_p-OR^{5x}$, $-(CH_2)_p-N(R^{4x})(R^{4z})$, $-(CH_2)_p-CO_2R^5$, $-(CH_2)_p-C(O)N(R^{4x})(R^{4z})$, or an optionally substituted phenyl, pyridyl, or pyrimidinyl group.

$R^w$ is hydrogen, halo, $C_{1-4}$ aliphatic, $C_{1-4}$ fluoroaliphatic, $-OR^5$, $-N(R^4)_2$, $-CO_2R^5$, $-C(O)N(R^4)_2$, $-T^3-OR^5$, $-T^3-N(R^4)_2$, $-T^3-CO_2R^5$, $-T^3-C(O)N(R^4)_2$, or an optionally substituted 5- or 6-membered aryl or heteroaryl. In some embodiments, $R^w$ independently is hydrogen, halo, $C_{1-4}$ aliphatic, $C_{1-4}$ fluoroaliphatic, $-(CH_2)_p-OR^{5x}$, $-(CH_2)_p-N(R^{4x})(R^{4z})$, $-(CH_2)_p-CO_2R^{5x}$, $-(CH_2)_p-C(O)N(R^{4x})(R^{4z})$, or an optionally substituted phenyl, pyridyl, or pyrimidinyl group Each $R^x$ independently is hydrogen, fluoro, $C_{1-4}$ aliphatic, $C_{1-4}$ fluoroaliphatic, $-CO_2R^5$, $-C(O)N(R^4)_2$, $-T^3-N(R^4)_2$, $-T^3-OR^5$, $-T^3-CO_2R^5$, or $-T^3-C(O)N(R^4)_2$. In certain embodiments, each $R^x$ independently is hydrogen, fluoro, $C_{1-4}$ aliphatic, $C_{1-4}$ fluoroaliphatic, $-(CH_2)_p-CO_2R^{5x}$, $-(CH_2)_p-C(O)N(R^{4x})(R^{4z})$, $-(CH_2)_r-N(R^{4x})(R^{4z})$, or $-(CH_2)_r-OR^{5x}$.

$R^y$ is hydrogen, halo, $C_{1-4}$ aliphatic, $C_{1-4}$ fluoroaliphatic, $-OR^5$, $-N(R^4)_2$, $-CO_2R^5$, $-C(O)N(R^4)_2$, $-T^3-OR^5$, $-T^3-N(R^4)_2$, $-T^3-CO_2R^5$, or $-T^3-C(O)N(R^4)_2$. In certain embodiments, $R^y$ is hydrogen, fluoro, $C_{1-4}$ aliphatic, $C_{1-4}$ fluoroaliphatic, $-(CH_2)_p-N(R^{4x})(R^{4z})$, $-(CH_2)_p-OR^{5x}$, $-(CH_2)_p-CO_2R^{5x}$, $-(CH_2)_p-C(O)N(R^{4x})(R^{4z})$.

Each $R^z$ independently is hydrogen, fluoro, $C_{1-4}$ aliphatic, or $C_{1-4}$ fluoroaliphatic.

$T^3$ is a $C_{1-4}$ alkylene chain optionally substituted with one or two substituents independently selected from the group consisting of $C_{1-3}$ aliphatic, $C_{1-3}$ fluoroaliphatic, $-F$, $-OH$, $-O(C_{1-4}$ alkyl$)$, $-CO_2H$, $-CO_2(C_{1-4}$ alkyl$)$, $-C(O)NH_2$, and $-C(O)NH(C_{1-4}$ alkyl$)$.

$R^{9d}$ is hydrogen, $-C(O)R^5$, $-C(O)N(R^4)_2$, $-CO_2R^6$, $-SO_2R^6$, $-SO_2(NR^4)_2$, an optionally substituted $C_{6-10}$ aryl, or a $C_{1-4}$ aliphatic optionally substituted with $R_{3a}$ or $R^7$. Each $R^{3a}$ independently is selected from the group consisting of $-F$, $-OH$, $-O(C_{1-4}$ alkyl$)$, $-CN$, $-N(R^4)_2$, $-C(O)(C_{1-4}$ alkyl$)$, $-CO_2H$, $-CO_2(C_{1-4}$ alkyl$)$, $-C(O)NH_2$, and $-C(O)NH(C_{1-4}$ alkyl$)$. Each $R^7$ independently is an optionally substituted aryl or heteroaryl ring.

Each $R^{1x}$ independently is an optionally substituted phenyl, piperidinyl, piperazinyl, morpholinyl, or pyrrolidinyl ring.

Each $R^{2x}$ independently is $-C(O)N(R^{4x})(R^{4z})$.

Each $R^{2y}$ independently is $-N(R^{4x})(R^{4z})$, $-NR^{4x}C(O)R^{5x}$, $-N(R^{4x})-CO_2R^{5x}$, $-N(R^{4x})-C(=NR^{4x})-R^{5x}$ or $-OR^{5x}$.

Each $R^{4x}$ independently is hydrogen, $C_{1-4}$ aliphatic, $C_{1-4}$ fluoroaliphatic, or $C_{6-10}$ ar$(C_{1-4})$alkyl, the aryl portion of which may be optionally substituted, and each $R^{4z}$ independently is hydrogen, $C_{1-4}$ aliphatic, $C_{1-4}$ fluoroaliphatic, $C_{6-10}$ ar$(C_{1-4})$alkyl, the aryl portion of which may be optionally substituted, or an optionally substituted 5- or 6-membered aryl, heteroaryl, or heterocyclyl ring; or $R^{4x}$ and $R^{4z}$, taken together with the nitrogen atom to which they are attached, form an optionally substituted 4 to 8-membered heterocyclyl ring having, in addition to the nitrogen atom, 0-2 ring heteroatoms independently selected from N, O, and S.

Each $R^{5x}$ independently is $C_{1-4}$ aliphatic, $C_{1-4}$ fluoroaliphatic, $C_{6-10}$ ar$(C_{1-4})$alkyl, the aryl portion of which may be optionally substituted, or an optionally substituted 5- or 6-membered aryl, heteroaryl, or heterocyclyl ring.

The variable p is 0, 1, or 2; q, at each occurrence independently, is 1, 2, or 3; r is 1 or 2; and s is 2 or 3.

In some particular embodiments, Ring D is selected from the group consisting of:

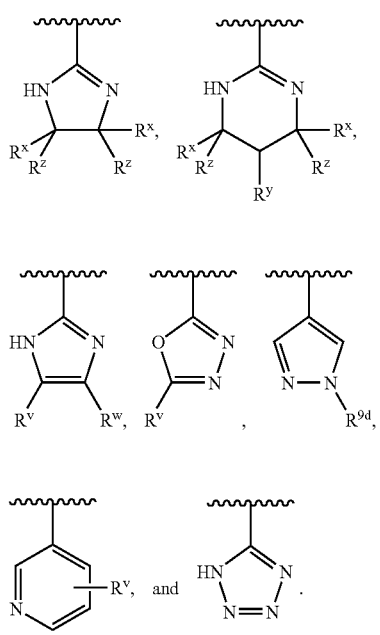

In more particular embodiments, Ring D is selected from the group consisting of:

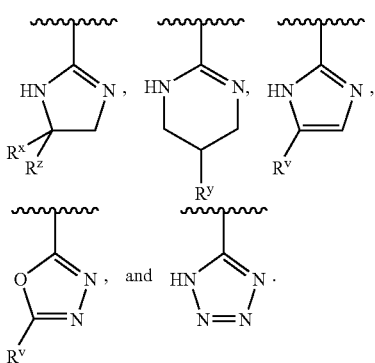

In certain particular embodiments, Ring B is selected from the group consisting of:

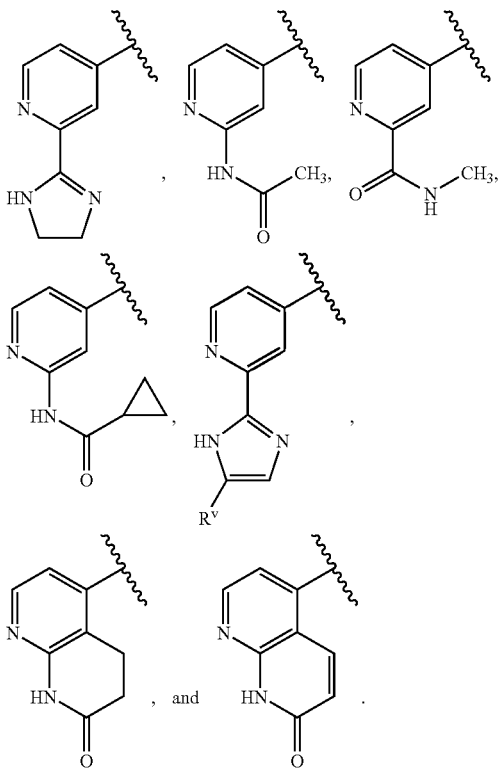

In the compounds of formula (I)-(IV), Ring C is an optionally substituted 5- or 6-membered aryl or heteroaryl ring having 0-3 ring nitrogen atoms and optionally one additional ring heteroatom selected from oxygen and sulfur. In some embodiments, two adjacent substituents on Ring C, taken together with the intervening ring atoms, form an optionally substituted fused 5- or 6-membered aromatic or non-aromatic ring having 0-3 ring heteroatoms selected from the group consisting of O, N, and S.

In some embodiments, Ring C is an optionally substituted furanyl, thienyl, pyrrolyl, oxazolyl, thiazolyl, imidazolyl, pyrazolyl, isoxazolyl, isothiazolyl, oxadiazolyl, triazolyl, thiadiazolyl, phenyl, pyridyl, pyridazinyl, pyrimidinyl, pyrazinyl, or triazinyl, wherein one ring nitrogen atom in Ring C optionally is oxidized.

Each substitutable ring nitrogen atom in Ring C is unsubstituted or is substituted with —C(O)$R^5$, —C(O)N($R^4$)$_2$, —CO$_2$$R^6$, —SO$_2$$R^6$, —SO$_2$N($R^4$)$_2$, or a $C_{1-4}$ aliphatic optionally substituted with —F, —OH, —O($C_{1-4}$ aliphatic), —CN, —N($R^4$)$_2$, —C(O)($C_{1-4}$ aliphatic), —CO$_2$H, —CO$_2$ ($C_{1-4}$ aliphatic), —C(O)NH$_2$, —C(O)NH($C_{1-4}$ aliphatic), or an optionally substituted $C_{6-10}$ aryl ring. One ring nitrogen atom in Ring C optionally is oxidized. In some embodiments, each substitutable ring nitrogen atom in Ring C is unsubstituted, and one ring nitrogen atom optionally is oxidized.

Substitutable ring carbon atoms in Ring C preferably are substituted with 0-2 $R^c$ and 0-2 $R^{8c}$. Each $R^{8c}$ independently is selected from the group consisting of $C_{1-4}$ aliphatic, $C_{1-4}$ fluoroaliphatic, —O($C_{1-4}$ aliphatic), —O($C_{1-4}$ fluoroaliphatic), and halo. In some embodiments, $R^{8c}$ is selected from the group consisting of $C_{1-4}$ aliphatic, $C_{1-4}$ fluoroalhphatic, and halo. In certain embodiments, $R^{8c}$ is selected from the group consisting of halo, methyl, trifluoromethyl, ethyl, isopropyl, cyclopropyl, tert-butyl, methoxy, and trifluoromethoxy.

Each $R^c$ independently is halo, —NO$_2$, —CN, —C($R^5$)=C($R^5$)$_2$, —C≡C—R, —O$R^5$, —S$R^6$, —S(O)$R^6$, —SO$_2$$R^6$, —SO$_2$N($R^4$)$_2$, —N($R_4$)$_2$, —N$R^4$C(O)$R^5$, —N$R^4$C(O)N($R^4$)$_2$, —N($R^4$)C(=N$R^4$)—N($R^4$)$_2$, —N($R^4$)C(=N$R^4$)—$R^6$, —N$R^4$CO$_2$$R^6$, —N($R^4$)SO$_2$$R^6$, —N($R^4$)SO$_2$N($R^4$)$_2$, —O—C(O)$R^5_1$, —OC(O)N($R^4$)$_2$, —C(O)$R^5$, —CO$_2$$R^5$, —C(O)N($R^4$)$_2$, —C(O)N($R_4$)—O$R^5$, —C(O)N($R^4$)C(=N$R^4$)—N($R^4$)$_2$, —N($R^4$)C(=N$R^4$)—N($R^4$)—C(O)$R^5$, —C(=N$R^4$)—N($R^4$)$_2$, —C(=N$R^4$)—O$R^5$, —C(=N$R^4$)—N($R^4$)—O$R^5$, —C($R^6$)=N—O$R^5$, or an optionally substituted aliphatic, aryl, heteroaryl, or heterocyclyl; or two adjacent $R^c$, taken together with the intervening ring atoms, form an optionally substituted fused 5- or 6-membered aromatic or non-aromatic ring having 0-3 ring heteroatoms independently selected from the group consisting of O, N, and S.

In some embodiments, each $R^c$ independently is selected from the group consisting of $C_{1-6}$ aliphatic, $C_{1-6}$ fluoroaliphatic, halo, —$R^{1c}$, —$R^{2c}$, —$T^2$—$R^{2c}$, and —$T^2$—$R^{1c}$; or two adjacent $R^c$, taken together with the intervening ring atoms, form an optionally substituted fused 5- or 6-membered aromatic or non-aromatic ring having 0-3 ring heteroatoms independently selected from the group consisting of O, N, and S. The variables $T^2$, $R^{1c}$, and $R^{2c}$ have the values described below.

$T^2$ is a $C_{1-6}$ alkylene chain optionally substituted with $R^{3a}$ or $R^{3b}$, wherein the alkylene chain optionally is interrupted by —C($R^5$)=C($R^5$)—, —C≡C—, —O—, —S—, —S(O)—, —S(O)$_2$—, —SO$_2$N($R^4$)—, —N($R^4$)—, —N($R^4$)C(O)—, —N$R^4$C(O)N($R^4$)—, —N($R^4$)CO$_2$—, —N($R^4$)SO$_2$—, —C(O)N($R^4$)—, —C(O)—, —CO$_2$—, —OC(O)—, or —OC(O)N($R^4$)—, and wherein $T^2$ or a portion thereof optionally forms part of a 3-7 membered ring. In some embodiments, $T^2$ is a $C_{1-4}$ or $C_{2-4}$ alkylene chain optionally substituted with $R^{3a}$ or $R^{3b}$. In some embodiments, $T^2$ is a $C_{1-4}$ alkylene chain optionally substituted with one or two groups independently selected from —F, $C_{1-4}$ aliphatic, and $C_{1-4}$ fluoroaliphatic.

Each $R^{1c}$ independently is an optionally substituted aryl, heteroaryl, heterocyclyl, or cycloaliphatic ring.

Each $R^{2c}$ independently is —NO$_2$, —CN, —C($R^5$)=C($R^5$)$_2$, —C≡C—$R^5$, —O$R^5$, —S$R^6$, —S(O)$R^6$, —SO$_2$$R^6$, —SO$_2$N($R^4$)$_2$, —N($R^4$)$_2$, —N$R^4$C(O)$R^5$, —N$R^4$C(O)N($R^4$)$_2$, —N($R^4$)C(=N$R^4$)—N($R^{4R}$)$_2$, —N($R^4$)C(=N$R^4$)—$R^6$, —N$R^4$CO$_2$$R^6$, —N($R^4$)SO$_2$$R^6$, —N($R^4$)SO$_2$N($R^4$)$_2$, —O—C(O)R$^5$, —OC(O)N(R$^4$)$_2$, —C(O)R$^5$, —CO$_2$R$^5$, —C(O)N(R$^4$)$_2$, —C(O)N(R$^4$)—OR$^5$, —C(O)N(R$^4$)C(=NR$^4$)—N(R$^4$)$_2$, —N(R$^4$)C(=NR$^4$)—N(R$^4$)—C(O)R$^5$, —C(=NR$^4$)—N(R$^4$)$_2$, —C(=NR$^4$)—OR$^5$, —C(=NR$^4$)—N(R$^4$)—OR$^5$, or —C(R$^6$)=N—OR$^5$. In some embodiments, each R$^{2c}$ independently is —CN, —C(R$^5$)=C(R$^5$)$_2$, —C≡C—R$^5$, —OR$^5$, —SR$^6$, —N(R$^4$)$_2$, —NR$^4$C(O)R$^5$, —NR$^4$C(O)N(R$^4$)$_2$, —NR$^4$CO$_2$R$^6$, —CO$_2$R$^5$, or —C(O)N(R$^4$)$_2$.

The variables R$^{3a}$, R$^{3b}$, R$^4$, R$^5$, R$^6$, and R$^7$ have the values described above for Ring B.

In some embodiments, the substitutable ring carbon atoms in Ring C are substituted with 0-2 R$^c$ and 0-1 R$^{8c}$, where:

each R$^c$ preferably is selected from the group consisting of C$_{1-4}$ aliphatic, C$_{1-4}$ fluoroaliphatic, halo, —R$^{1c}$—R$^{2c}$ and —T$^2$—R$^{2c}$; or two adjacent R$^c$, taken together with the intervening ring atoms, form an optionally substituted fused 5- or 6-membered aromatic or non-aromatic ring having 0-3 ring heteroatoms independently selected from the group consisting of O, N, and S;

T$^2$ is a C$_{1-4}$ alkylene chain optionally substituted with one or two groups independently selected from —F, C$_{1-4}$ aliphatic, and C$_{1-4}$ fluoroaliphatic;

each R$^{1c}$ independently is an optionally substituted 5- or 6-membered heteroaryl or 4- to 6-membered heterocyclyl ring having 1 to 4 ring nitrogen atoms and 0 to 1 additional ring heteroatoms selected from O and S;

each R$^{2c}$ independently is —CN, —C(R$^5$)=C(R$^5$)$_2$, —C≡C—R$^5$, —OR$^5$, —SR$^6$, —N(R$^4$)$_2$, —NR$^4$C(O)R$^5$, —NR$^4$C(O)N(R$^4$)$_2$, —NR$^4$CO$_2$R$^6$, —CO$_2$R$^5$, and —C(O)N(R$^4$)$_2$; and each R$^{8c}$ independently is selected from the group consisting of C$_{1-4}$ aliphatic, C$_{1-4}$ fluoroaliphatic, —O(C$_{1-4}$ aliphatic), —O(C$_{1-4}$ fluoroaliphatic), and halo.

In some embodiments, the substitutable ring carbon atoms in Ring C are substituted with 0-2 R$^c$ and 0-1 R$^{8c}$, where:

each R$^c$ independently is halo, —CN, —C(R$^{5x}$)=C(R$^{5x}$)(R$^{5y}$), —C≡C—R$^{5y}$, —OR$^{5y}$, —SR$^{6x}$, —N(R$^{4x}$)(R$^{4y}$), —CO$_2$R$^{5x}$, or —C(O)N(R$^{4x}$)(R$^{4y}$); or R$^c$ is a C$_{1-4}$ aliphatic or C$_{1-4}$ fluoroaliphatic optionally substituted with one or two substituents independently selected from the group consisting of —OR$^{5x}$, —N(R$^{4x}$)(R$^{4y}$), —SR$^{6x}$, —CO$_2$R$^{5x}$, or —C(O)N(R$^{4x}$)(R$^{4y}$); or R$^c$ is an optionally substituted 5- or 6-membered heteroaryl or 4- to 6-membered heterocyclyl ring having 1 to 4 ring nitrogen atoms and 0 to 1 additional ring heteroatoms selected from O and S; or two adjacent R$^c$, taken together with the intervening ring atoms, form an optionally substituted fused 5- or 6-membered aromatic or non-aromatic ring having 0-3 ring heteroatoms independently selected from the group consisting of O, N, and S;

R$^{4x}$ is hydrogen, C$_{1-4}$ aliphatic, C$_{1-4}$ fluoroaliphatic, or C$_{6-10}$ ar(C$_{1-4}$)alkyl, the aryl portion of which may be optionally substituted;

R$^{4y}$ is hydrogen, C$_{6-10}$ ar(C$_{1-4}$)alkyl, the aryl portion of which may be optionally substituted, an optionally substituted 5- or 6-membered aryl, heteroaryl, or heterocyclyl ring, or a C$_{1-4}$ aliphatic or C$_{1-4}$ fluoroaliphatic optionally substituted with one or two substituents independently selected from the group consisting of —OR$^{5x}$, —N(R$^{4x}$)$_2$, —CO$_2$R$^{5x}$, or —C(O)N(R$^{4x}$)$_2$; or R$^{4x}$ and R$^{4y}$, taken together with the nitrogen atom to which they are attached, form an optionally substituted 4- to 8-membered heterocyclyl or 5-membered heteroaryl ring having, in addition to the nitrogen atom, 0-2 ring heteroatoms independently selected from N, O, and S;

each R$^{5x}$ independently is hydrogen, C$_{1-4}$ aliphatic, C$_{1-4}$ fluoroaliphatic, or C$_{6-10}$ ar(C$_{1-4}$)alkyl, the aryl portion of which may be optionally substituted, or an optionally substituted 5- or 6-membered aryl, heteroaryl, or heterocyclyl ring;

each R$^{5y}$ independently is hydrogen, an optionally substituted monocyclic nitrogen-containing heterocyclyl, an optionally substituted C$_{6-10}$ aryl, a C$_{1-10}$ar(C$_{1-4}$)alkyl, the aryl portion of which is optionally substituted, or a C$_{1-4}$ aliphatic or C$_{1-4}$ fluoroaliphatic optionally substituted with one or two substituents independently selected from the group consisting of —OR$^{5x}$, —N(R$^{4x}$)$_2$, —CO$_2$R$^{5x}$, or —C(O)N(R$^{4x}$)$_2$; and each R$^{6x}$ independently is C$_{1-4}$ aliphatic, C$_{1-4}$ fluoroaliphatic, or C$_{6-10}$ ar(C$_{1-4}$)alkyl, the aryl portion of which may be optionally substituted.

When two adjacent R$^c$, taken together with the intervening ring atoms, form a fused 5- or 6-membered aromatic or non-aromatic ring, the fused ring preferably is unsubstituted or is substituted with 0-1 R$^c$ and 0-1 R$^{8c}$.

In some embodiments, Ring C is a 5- or 6-membered heteroaryl substituted with 0-2 R$^c$ and 0-1 R$^{8c}$. In other embodiments, Ring C is phenyl substituted with 0-2 R$^c$ and 0-1 R$^{8c}$. In still other embodiments, Ring C is phenyl substituted with 0-1 R$^c$ and 0-1 R$^{8c}$ In certain embodiments, Ring C is selected from the group consisting of:

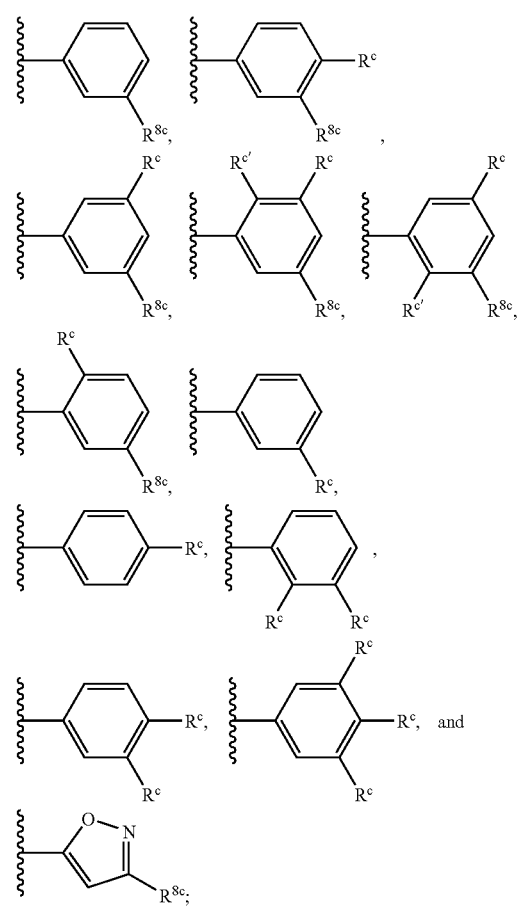

where each R$^c$ independently is halo, —CN, —C(R$^{5x}$)=C(R$^{5x}$)(R$^{5y}$), —C≡C—R$^{5y}$, —OR$^{5y}$, —SR$^{6x}$, —N(R$^{4x}$)(R$^{4y}$), —CO$_2$R$^{5x}$, —C(O)N(R$^{4x}$)(R$^{4y}$); or R$^c$ is a C$_{1-4}$ aliphatic or C$_{1-4}$ fluoroaliphatic optionally substituted with one or two substituents independently selected from the group consisting of —OR$^{5x}$, —N(R$^{4x}$)(R$^{4y}$), —SR$^{6x}$, —CO$_2$R$^{5x}$, or —C(O)N(R$^{4x}$)(R$^{4y}$); or R$^c$ is an optionally substituted pyrrolidinyl, piperidinyl, morpholinyl, or piperazinyl ring; or two adjacent R$^c$, taken together with the intervening ring atoms, form an optionally substituted fused 5- or 6-membered aromatic or non-aromatic ring having 0-3 ring heteroatoms independently selected from the group consisting of O, N, and S;

R$^{c'}$ is C$_{1-4}$ aliphatic, C$_{1-4}$ fluoroaliphatic, halo, —CN, —OH, —O(C$_{1-4}$ aliphatic), —S(C$_{1-4}$ aliphatic), —NH$_2$, —NH(C$_{1-4}$ aliphatic), or —N(C$_{1-4}$ aliphatic)$_2$;

R$^{8c}$ is C$_{1-4}$ aliphatic, C$_{1-4}$ fluoroaliphatic, —O(C$_{1-4}$ aliphatic), —O(C$_{1-4}$ fluoroaliphatic), or halo; and the variables R$^{4x}$, R$^{4y}$, R$^{5x}$, R$^{5y}$, and R$^{6x}$ have the values described above for Ring B.

In some embodiments, R$^{8c}$ is selected from the group consisting of methyl, trifluoromethyl, ethyl, isopropyl, cyclopropyl, tert-butyl, and methoxy.

In certain particular embodiments, Ring C is selected from the group consisting of:

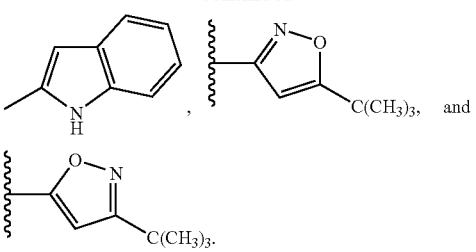

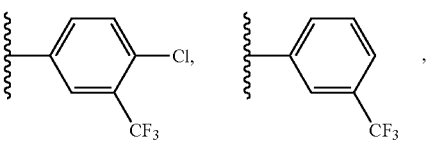

In certain other embodiments, Ring C is selected from the group consisting of:

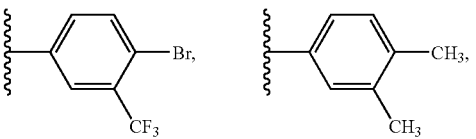

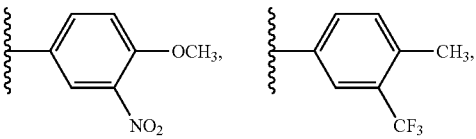

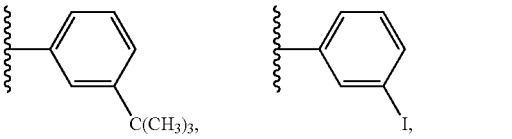

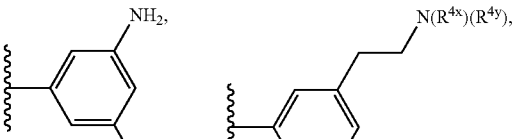

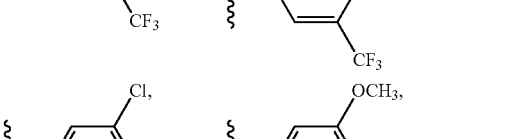

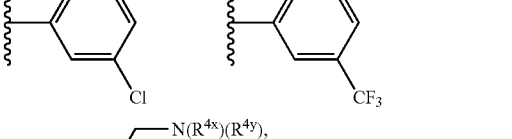

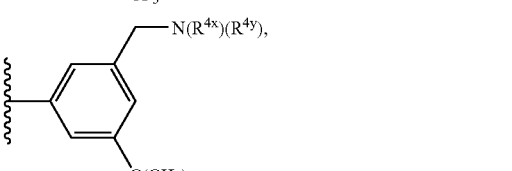

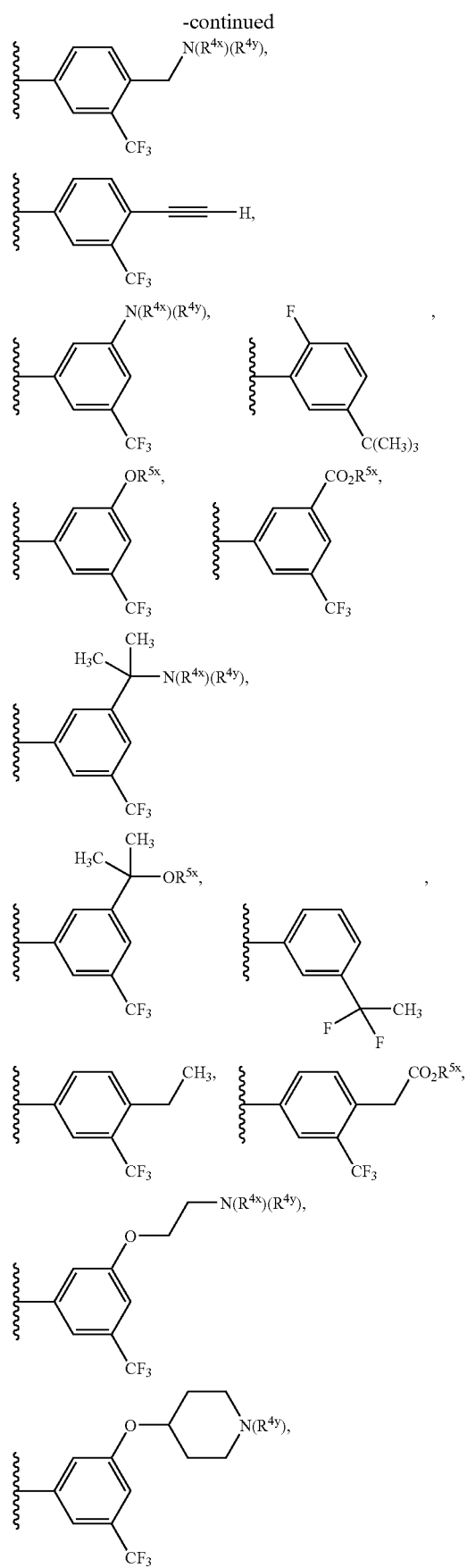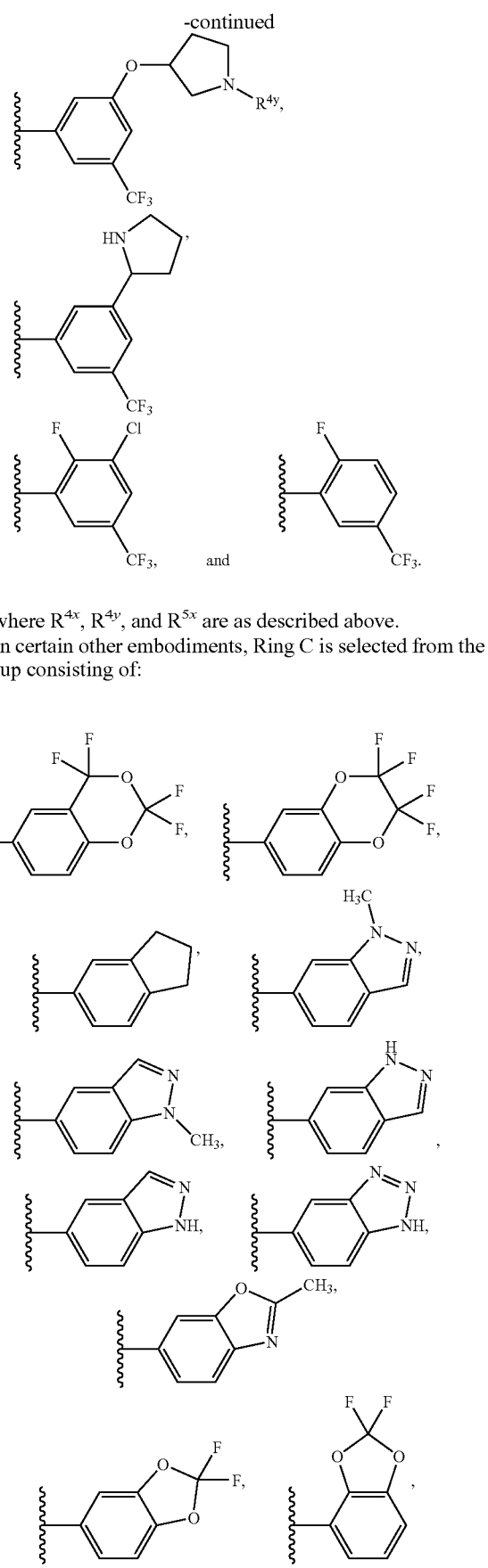
where $R^{4x}$, $R^{4y}$, and $R^{5x}$ are as described above.
In certain other embodiments, Ring C is selected from the group consisting of:

-continued

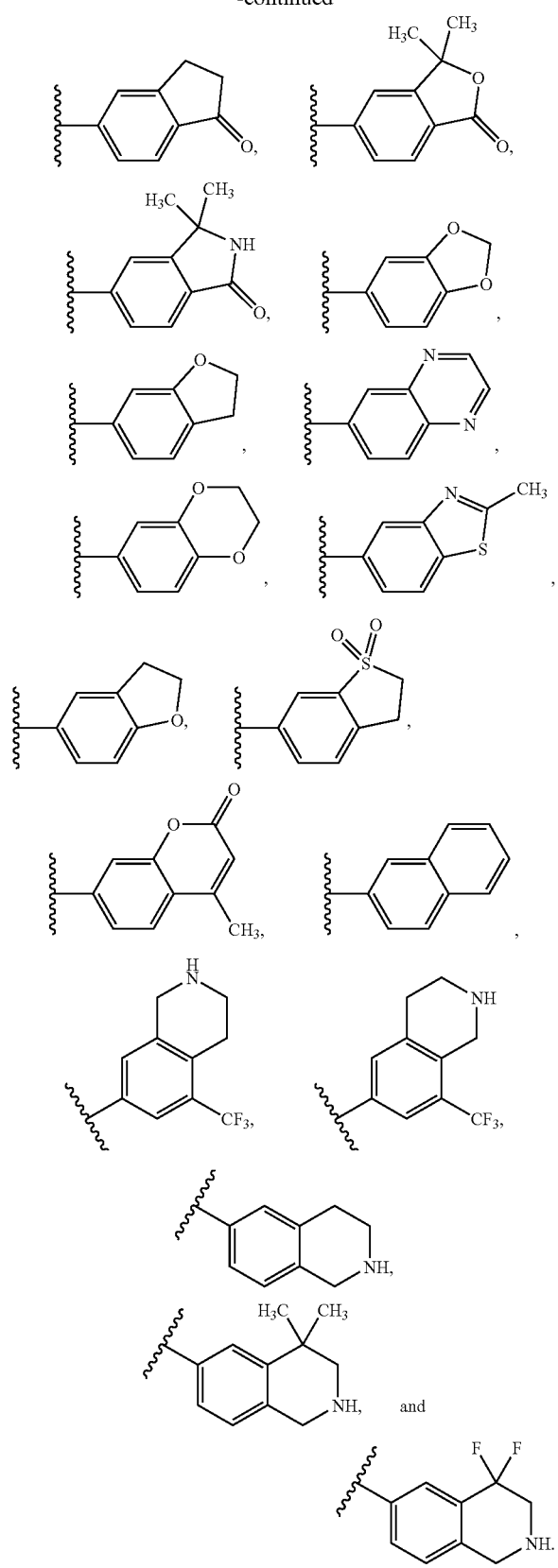

The invention also relates to a compound of formula (V-A) or (V-B):

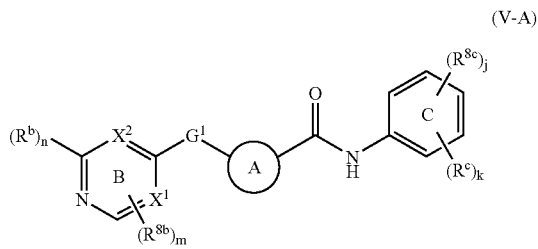

(V-A)

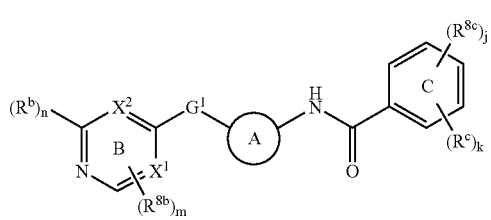

(V-B)

or a pharmaceutically acceptable salt thereof; wherein:

$G^1$ is —O— or —NH—;

$X^1$ and $X^2$ are each independently CH or N, provided that $X^1$ and $X^2$ are not both N;

one ring nitrogen atom in Ring B optionally is oxidized;

m is 0 or 1;

n is 0 or 1;

j is 0 or 1;

k is 0, 1, or 2; and

Ring A and the variables $R^b$, $R^{8b}$, $R^c$, and $R^{8c}$ have the values and preferred values described above for formulae (I)-(IV).

In some such embodiments, the compound of formula (V-A) or (V-B) is characterized by formula (VI-A) or (VI-B):

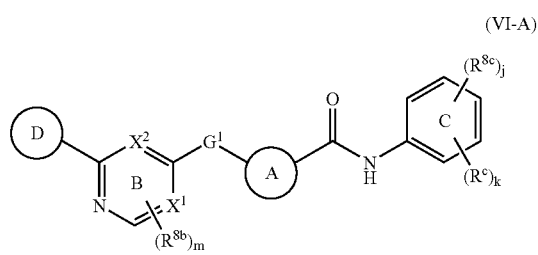

(VI-A)

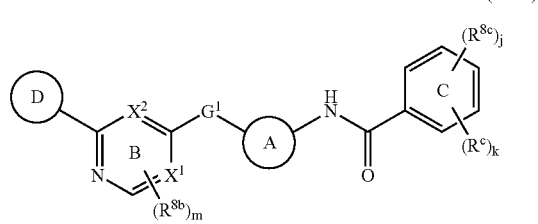

(VI-B)

or a pharmaceutically acceptable salt thereof, wherein:

Rings A and D and the variables $R^b$, $R^{8b}$, $R^c$, and $R^{8c}$ have the values and preferred values described above for formulae (I)-(V).

The invention also relates to a compound of formula (VII-A) or (VII-B)

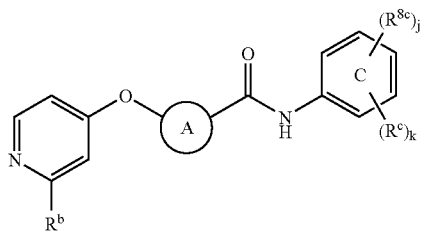

(VII-A)

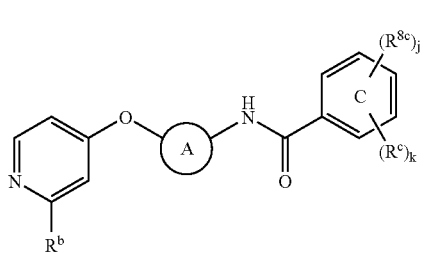

(VII-B)

or a pharmaceutically acceptable salt thereof, wherein:
j is 0 or 1;
k is 0, 1, or 2; and
Ring A the variables $R^a$, $R^b$, $R^c$, and $R^{8c}$ have the values and preferred values described above for formulae (I)-(VI).

The invention also relates to a compound of formula (VIII-A) or (VIII-B)

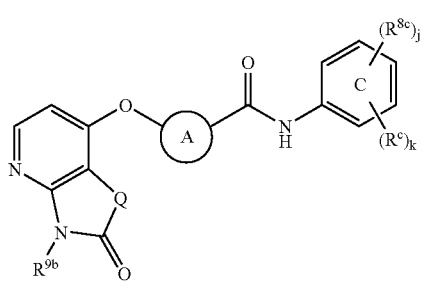

(VIII-A)

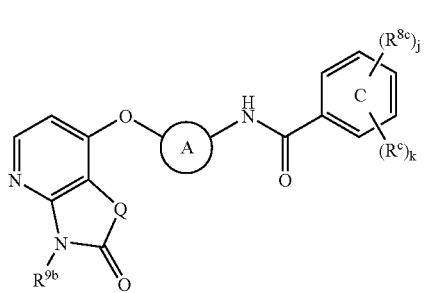

(VIII-B)

or a pharmaceutically acceptable salt thereof, wherein:
j is 0 or 1;
k is 0, 1, or 2; and
Ring A the variables Q, $R^{9b}$, $R^c$, and $R^{8c}$ have the values and preferred values described above for formulae (I)-(VII).

Specific examples of compounds of formula (I) are shown below in Table 1.

TABLE 1

Raf Kinase Inhibitors

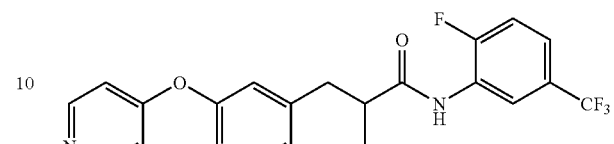

I-1

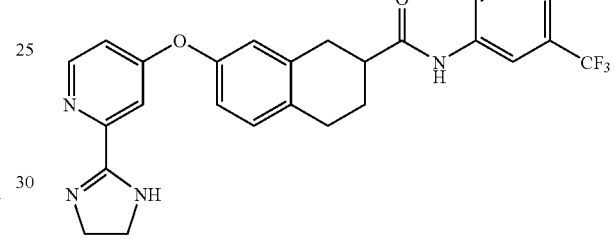

I-2

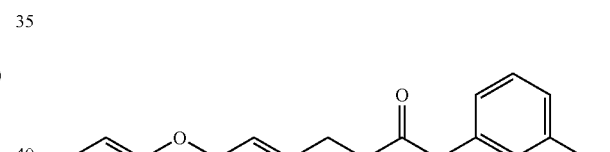

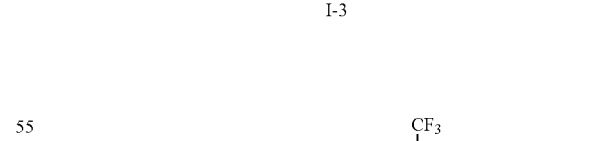

I-3

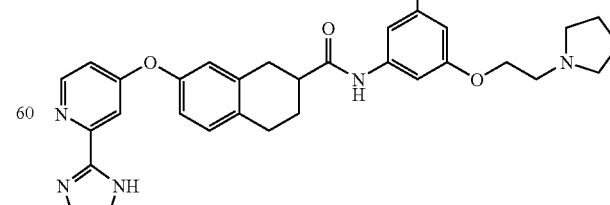

I-4

TABLE 1-continued
Raf Kinase Inhibitors
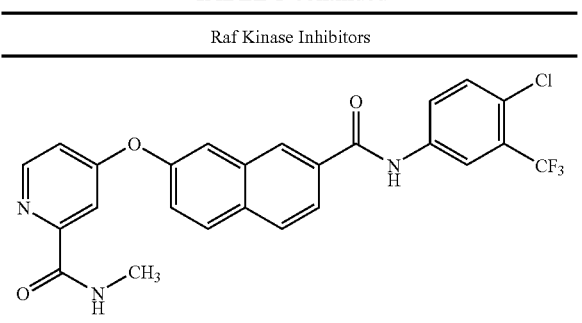
I-5
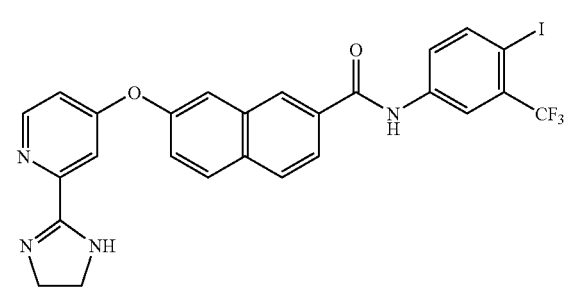
I-6
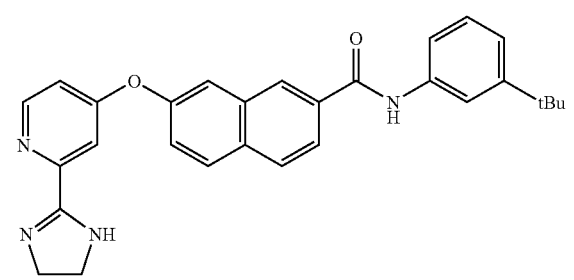
I-7
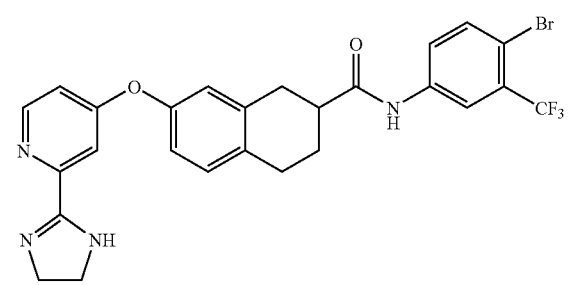
I-8
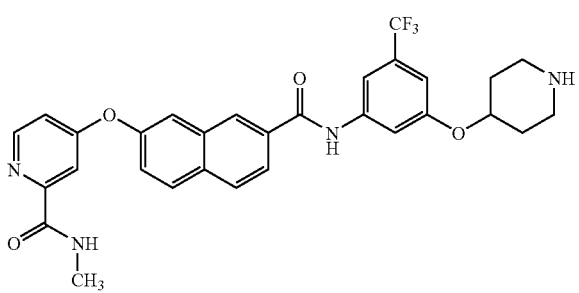
I-9
TABLE 1-continued
Raf Kinase Inhibitors
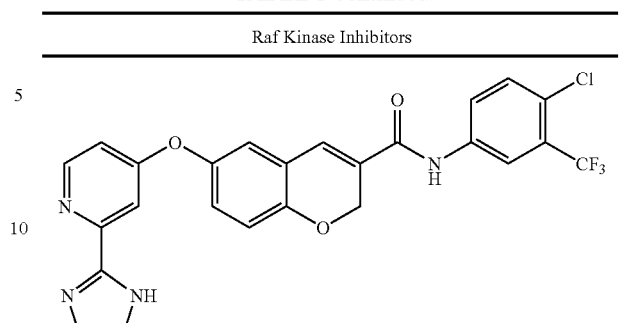
I-10
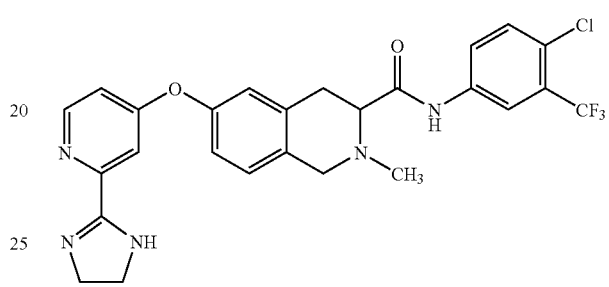
I-11
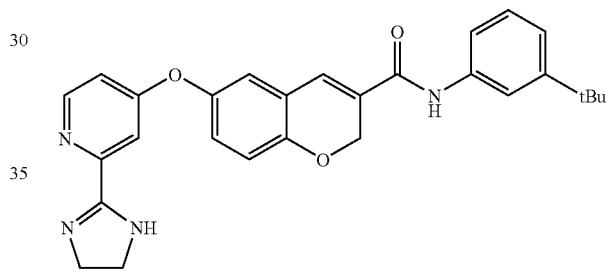
I-12
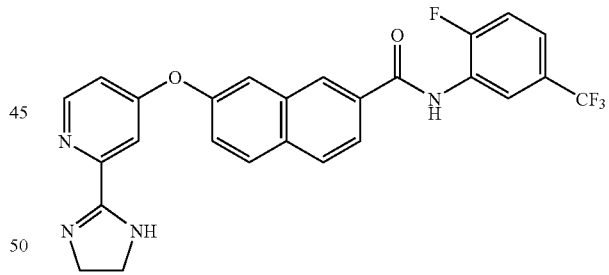
I-13
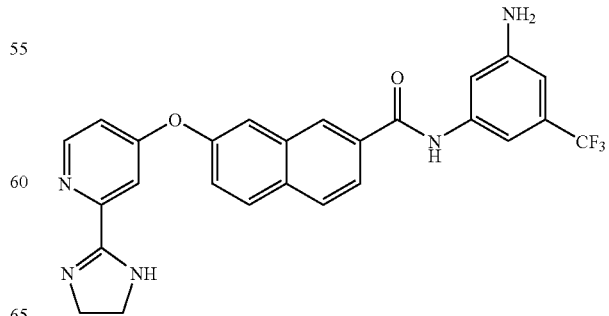
I-14

TABLE 1-continued
Raf Kinase Inhibitors
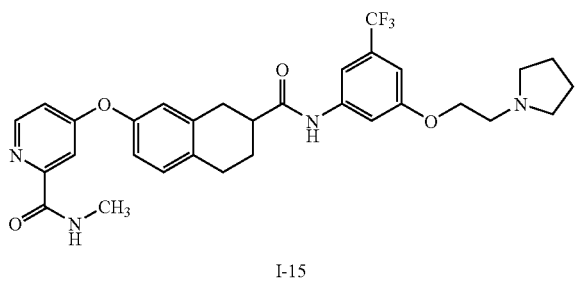
I-15
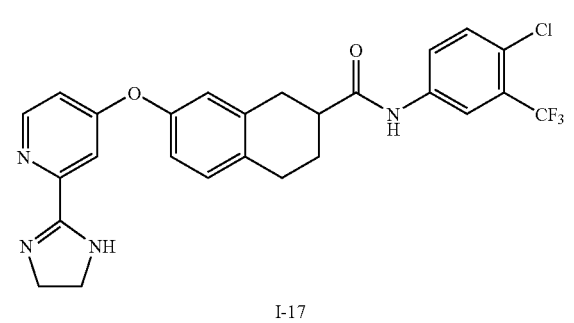
I-17
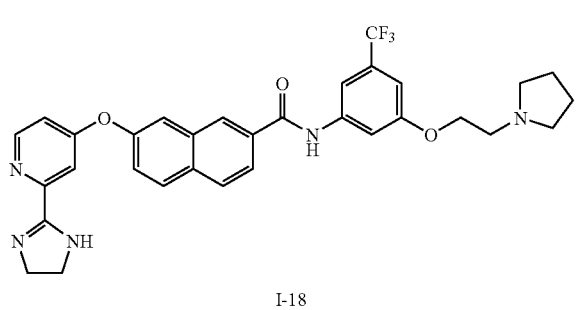
I-18
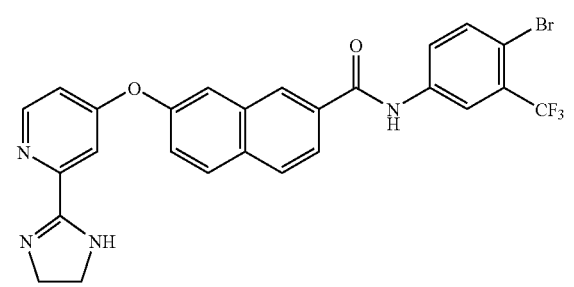
I-19
TABLE 1-continued
Raf Kinase Inhibitors
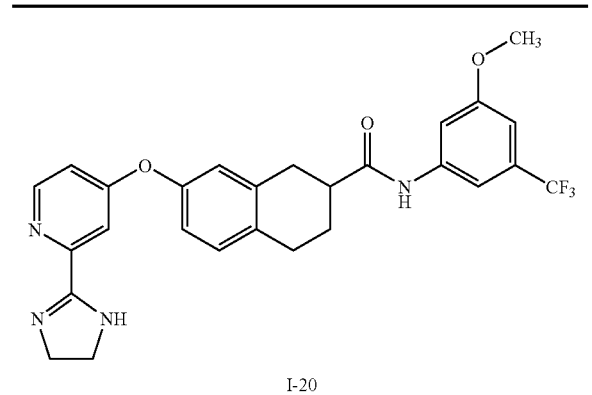
I-20
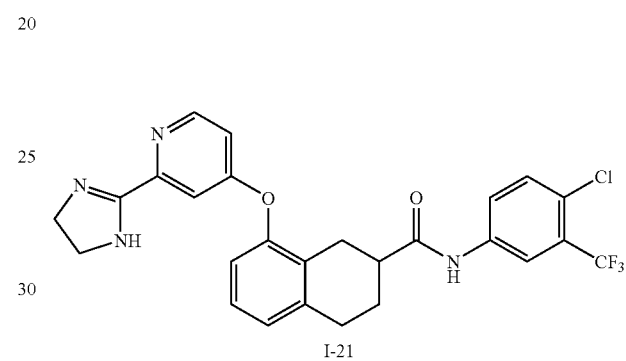
I-21
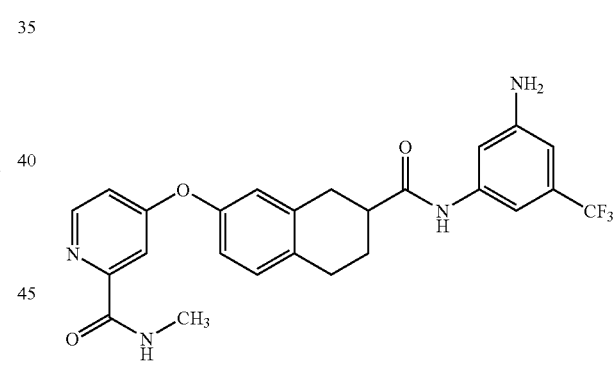
I-22
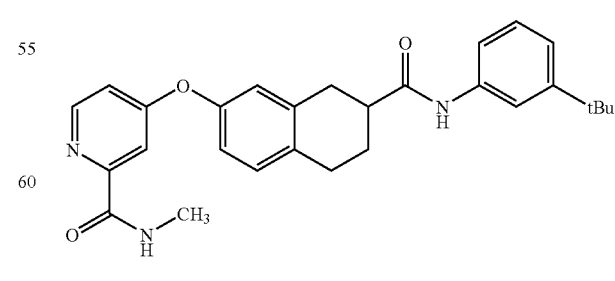
I-23

TABLE 1-continued
Raf Kinase Inhibitors
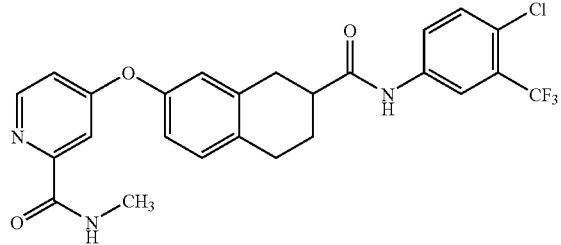
I-24
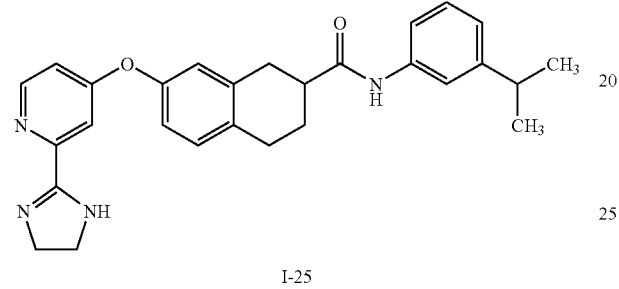
I-25
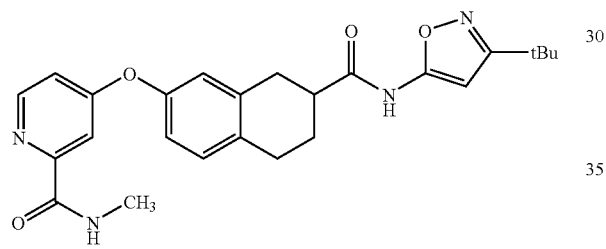
I-26
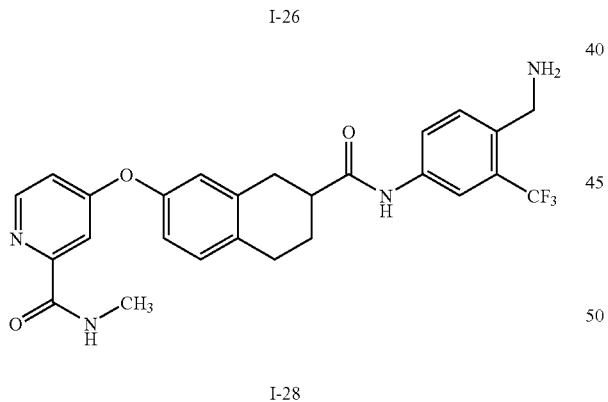
I-28
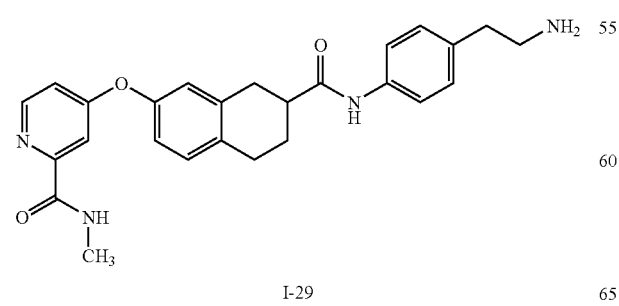
I-29
TABLE 1-continued
Raf Kinase Inhibitors
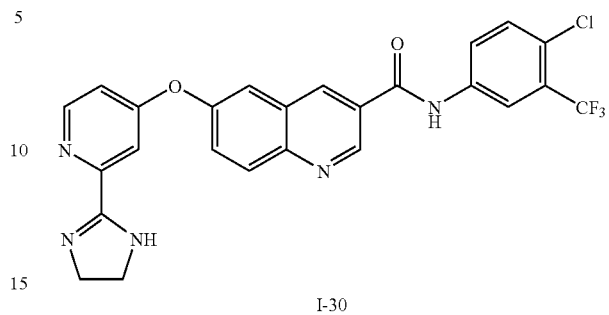
I-30
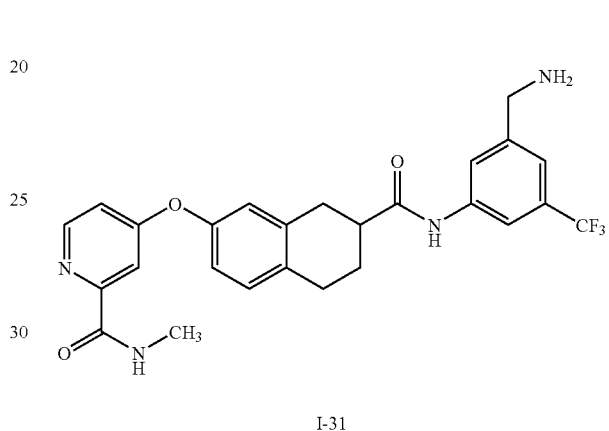
I-31
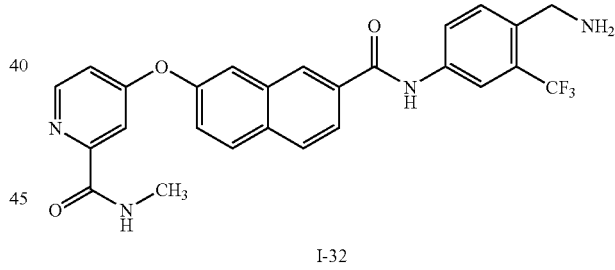
I-32
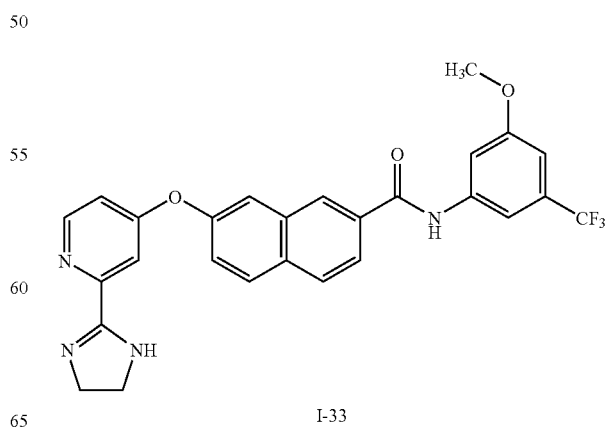
I-33

TABLE 1-continued
Raf Kinase Inhibitors
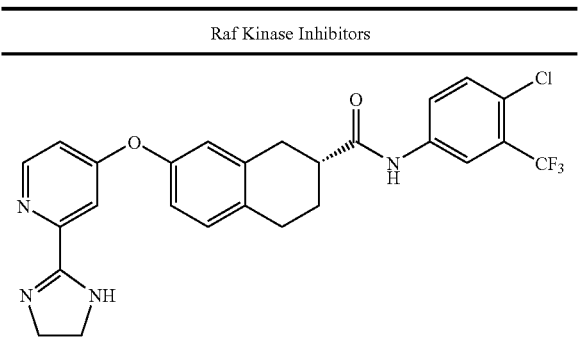
I-34
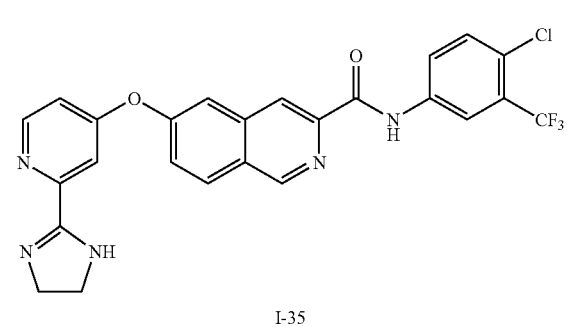
I-35
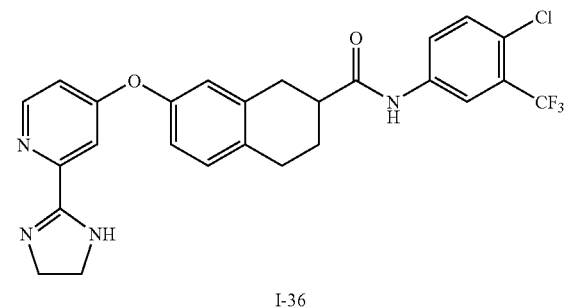
I-36
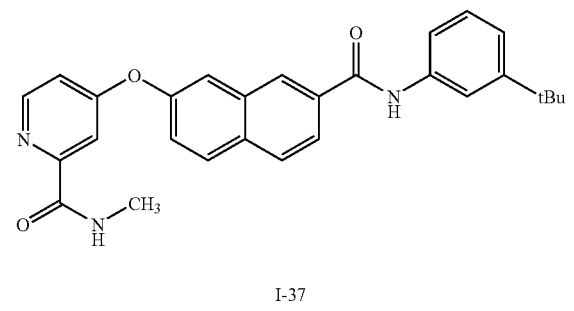
I-37
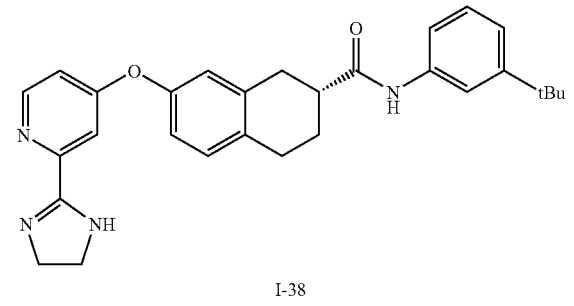
I-38
TABLE 1-continued
Raf Kinase Inhibitors
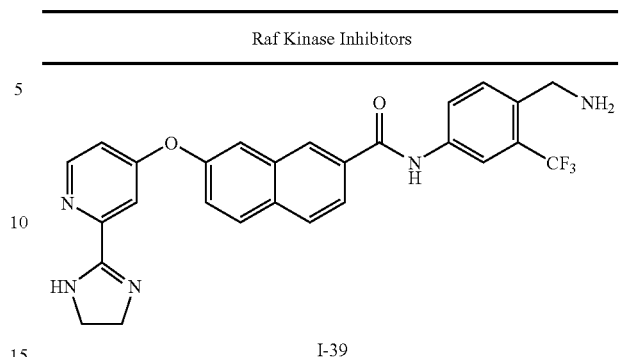
I-39
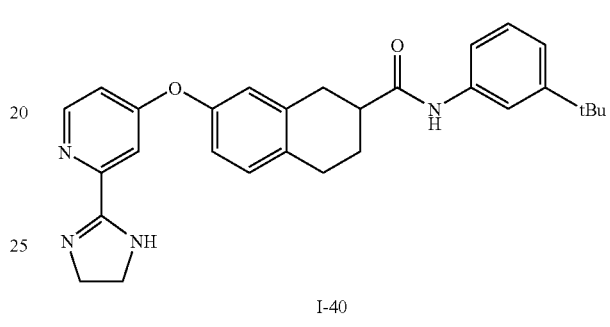
I-40
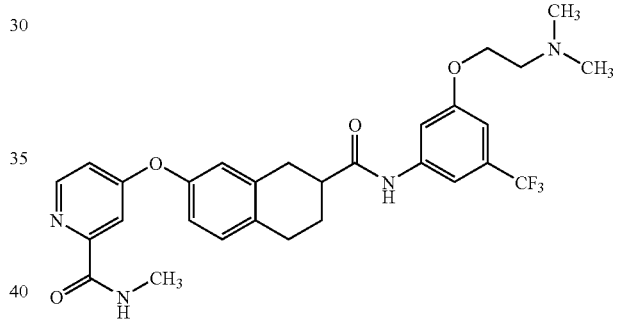
I-41
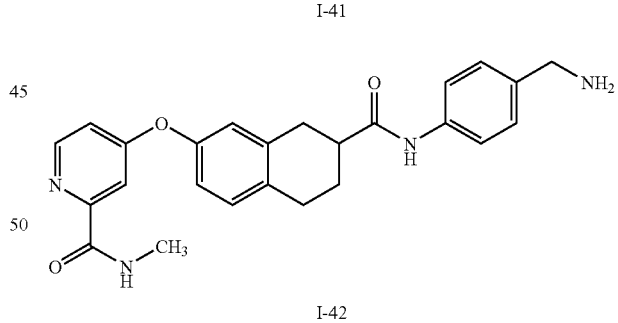
I-42
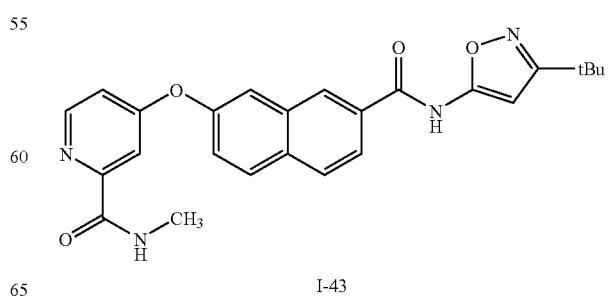
I-43

TABLE 1-continued
Raf Kinase Inhibitors
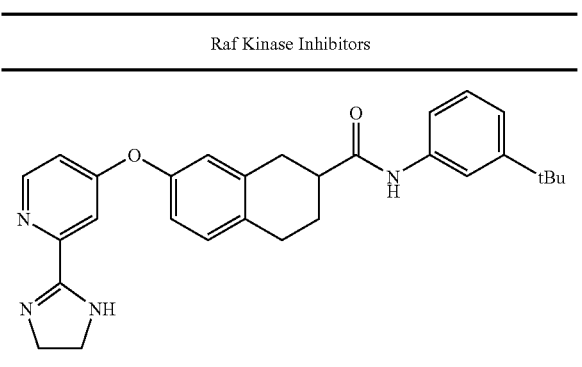
I-44
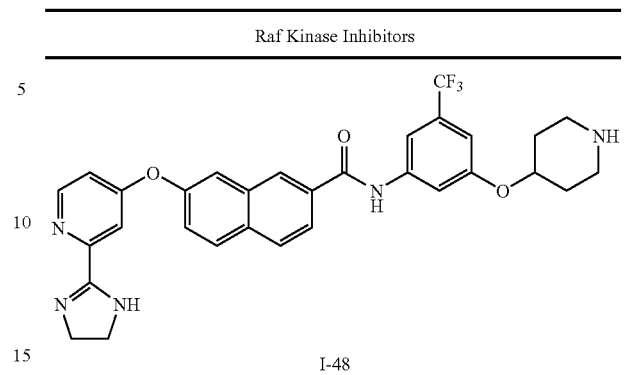
I-48
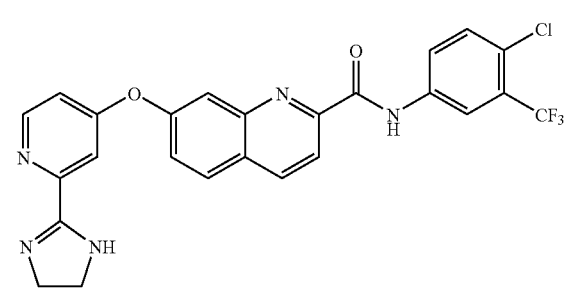
I-45
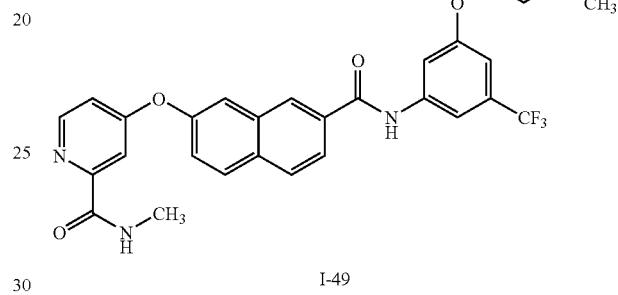
I-49
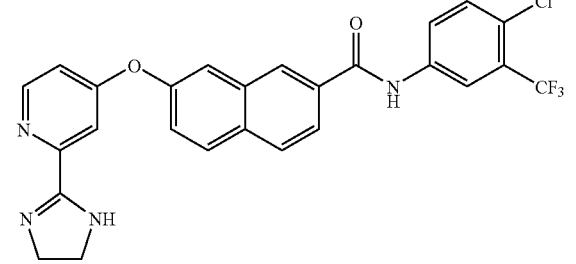
I-46
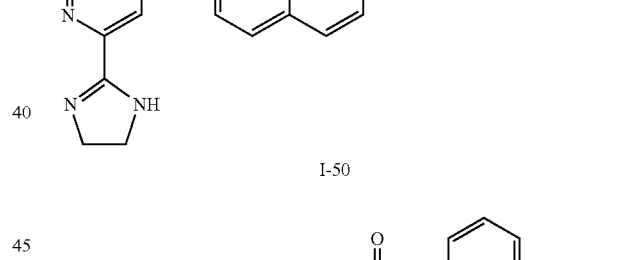
I-50
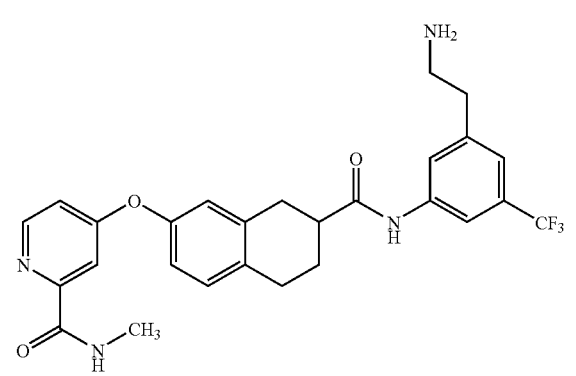
I-47
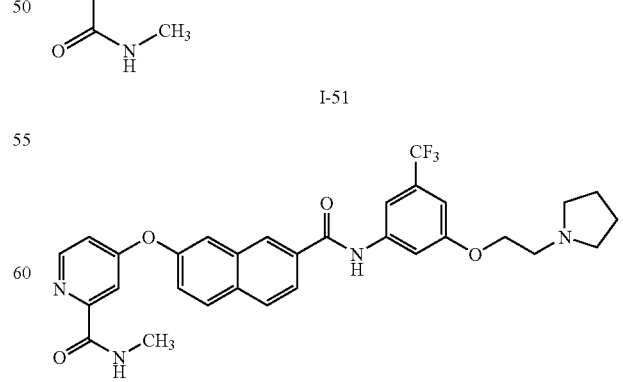
I-51
I-52

TABLE 1-continued
Raf Kinase Inhibitors
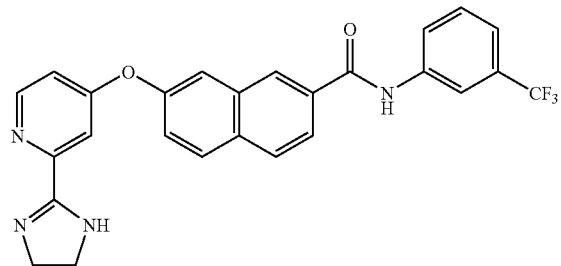
I-53
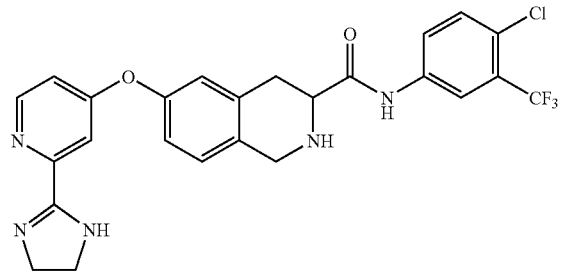
I-54
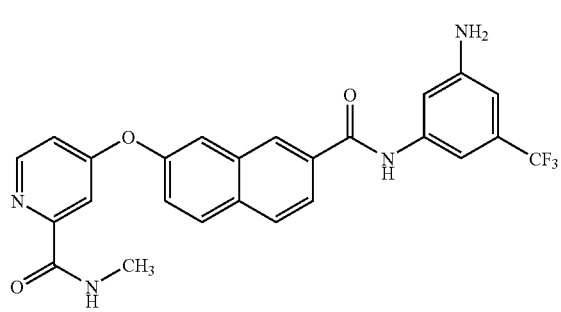
I-55
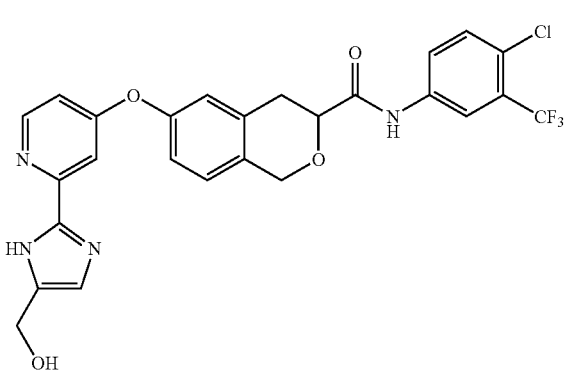
I-56
TABLE 1-continued
Raf Kinase Inhibitors
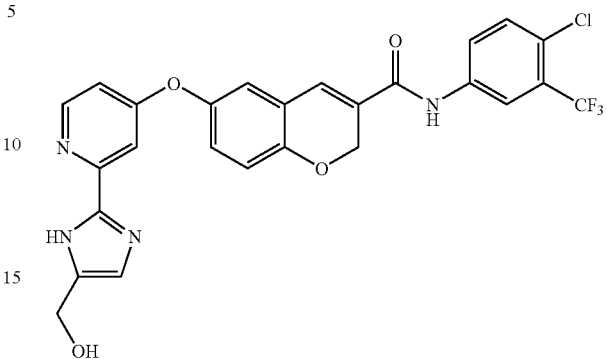
I-57
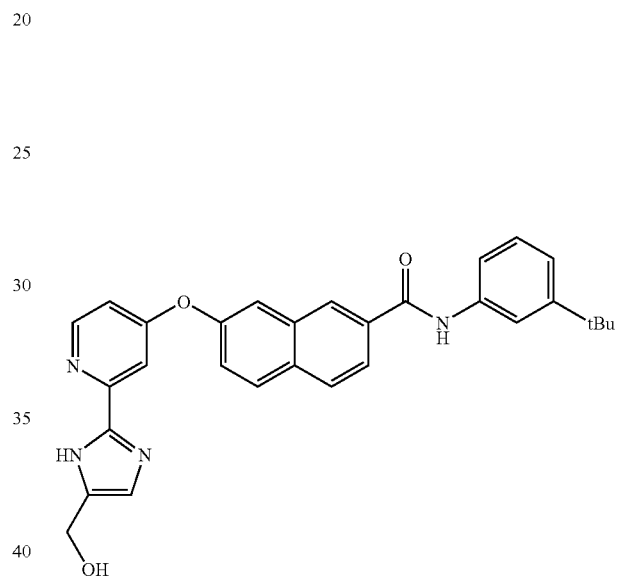
I-58
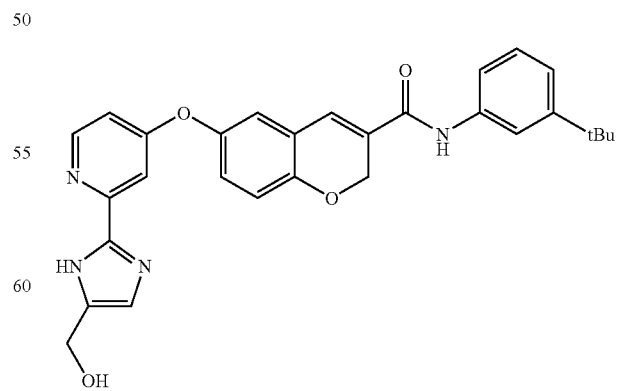
I-59

TABLE 1-continued
Raf Kinase Inhibitors
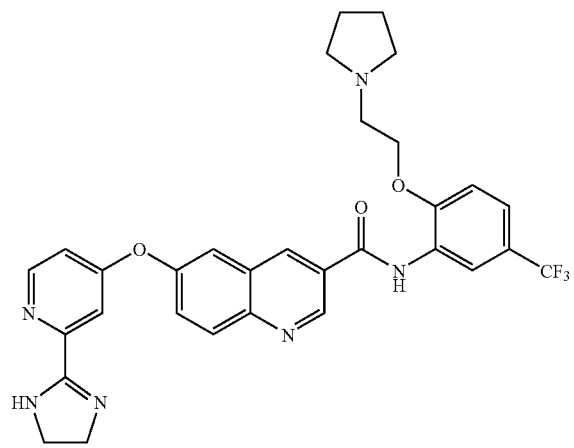
I-60
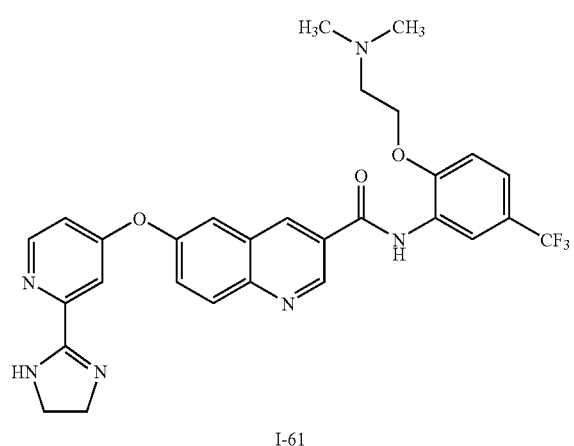
I-61
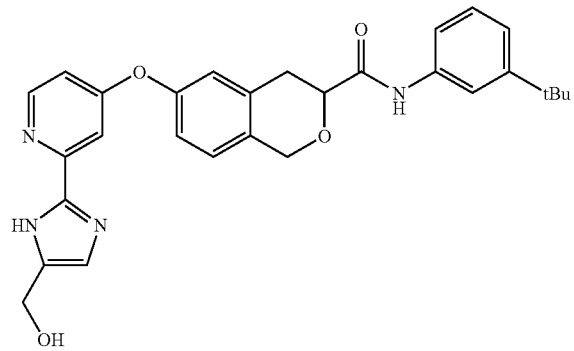
I-62
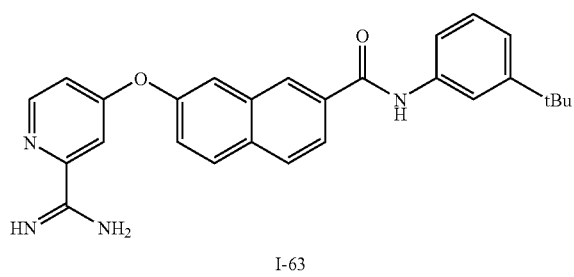
I-63
TABLE 1-continued
Raf Kinase Inhibitors
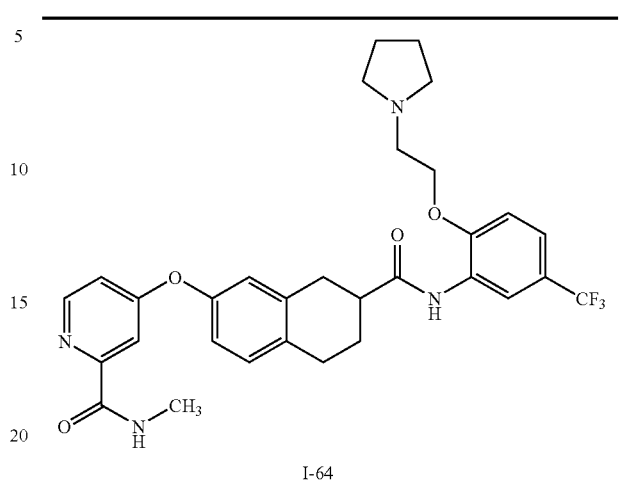
I-64
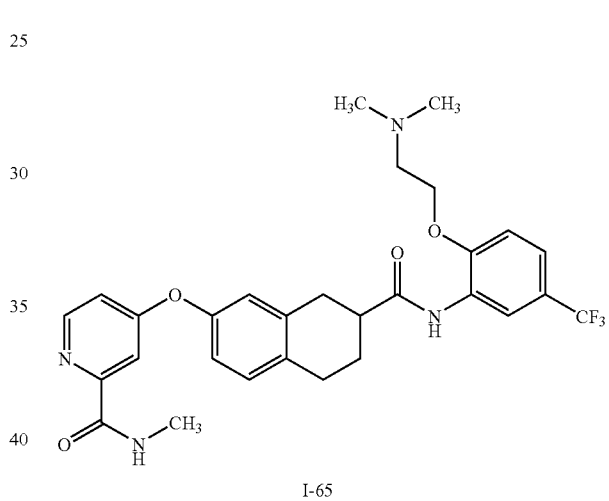
I-65
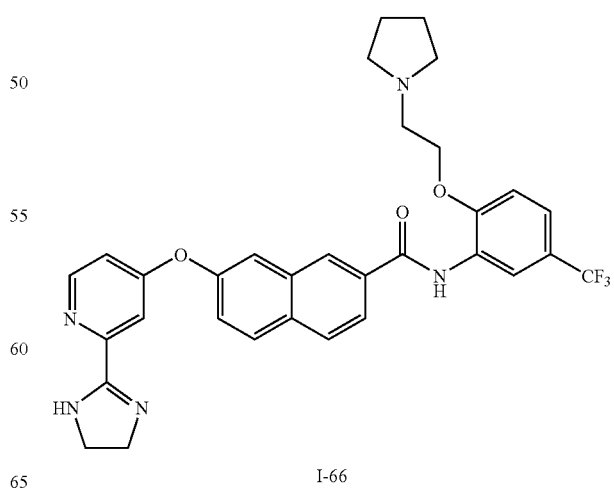
I-66

TABLE 1-continued
Raf Kinase Inhibitors
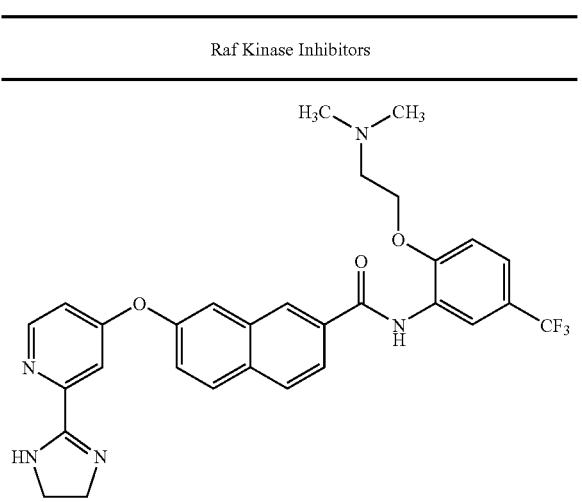
I-67
I-68
I-69
I-70
TABLE 1-continued
Raf Kinase Inhibitors
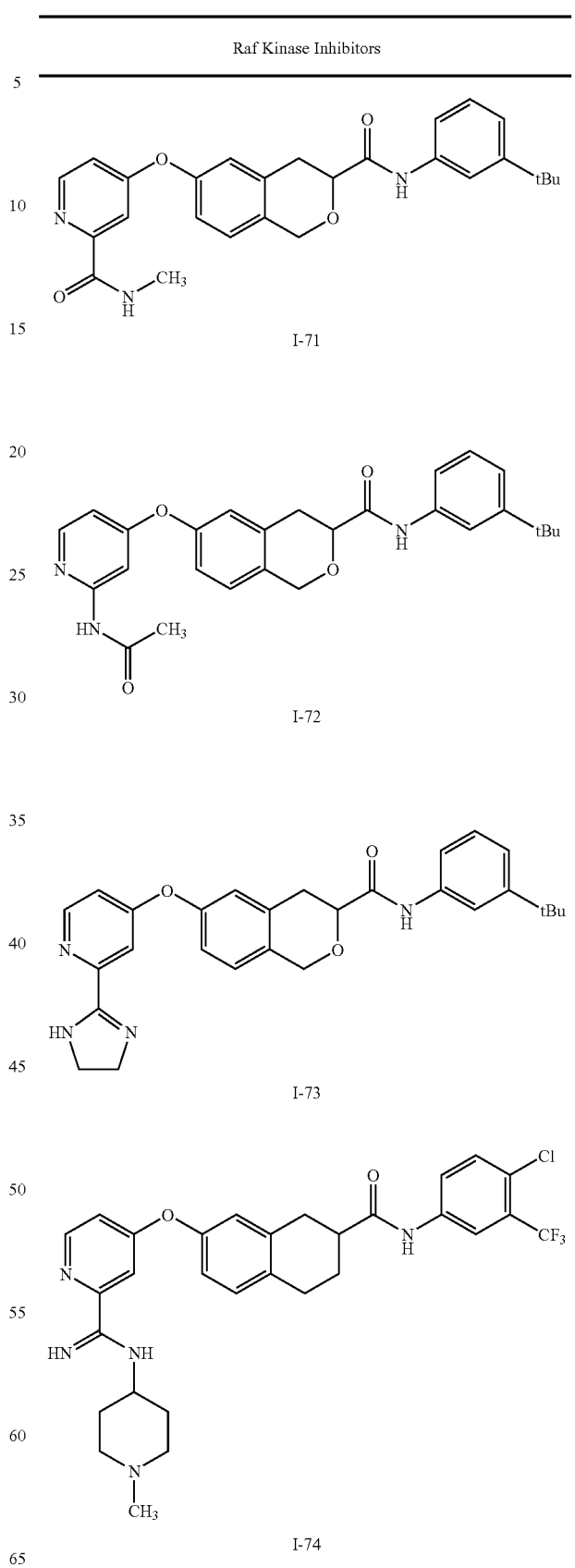
I-71
I-72
I-73
I-74

TABLE 1-continued
Raf Kinase Inhibitors
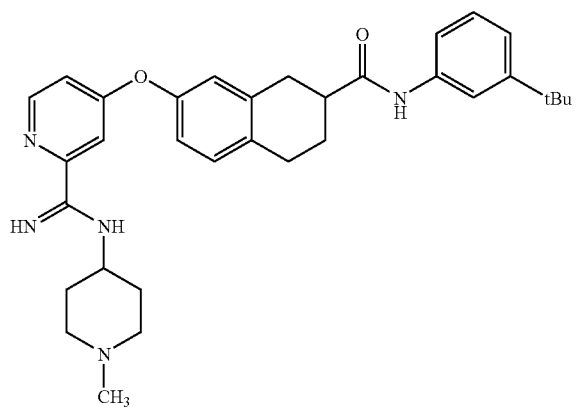
I-75
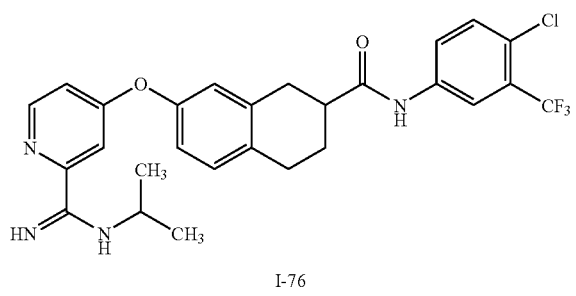
I-76
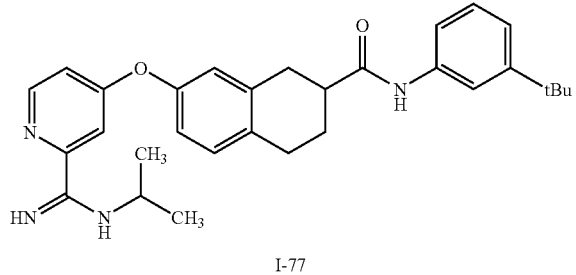
I-77
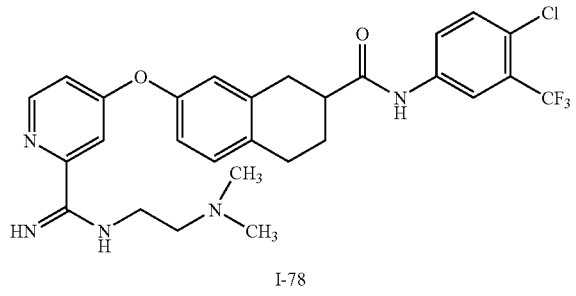
I-78
TABLE 1-continued
Raf Kinase Inhibitors
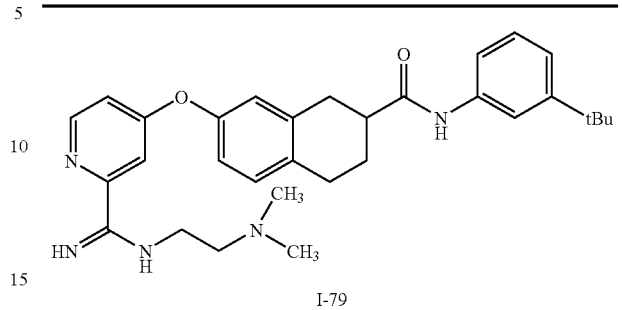
I-79
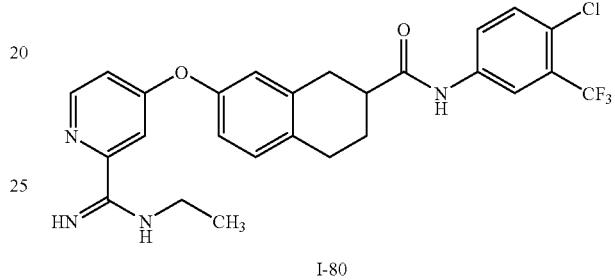
I-80
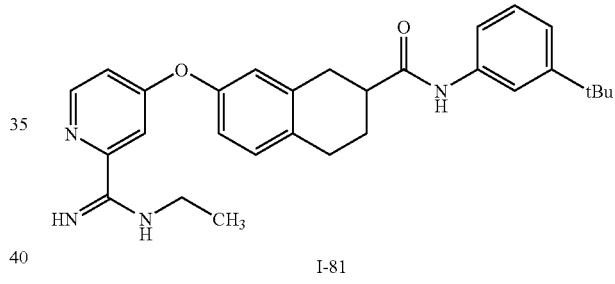
I-81
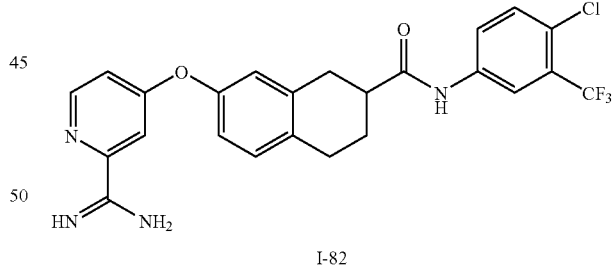
I-82
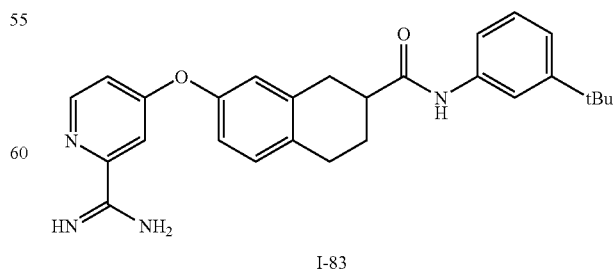
I-83

TABLE 1-continued
Raf Kinase Inhibitors
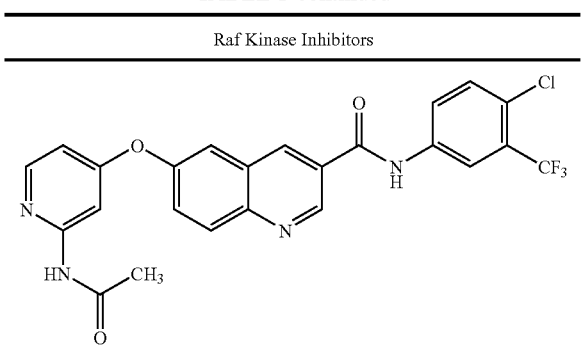
I-84
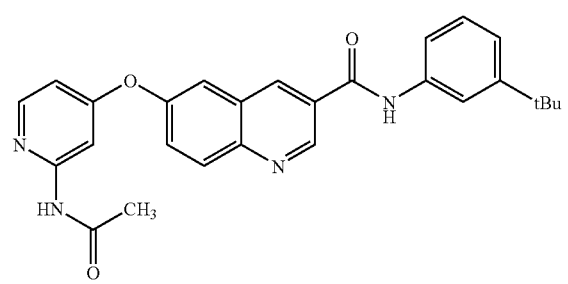
I-85
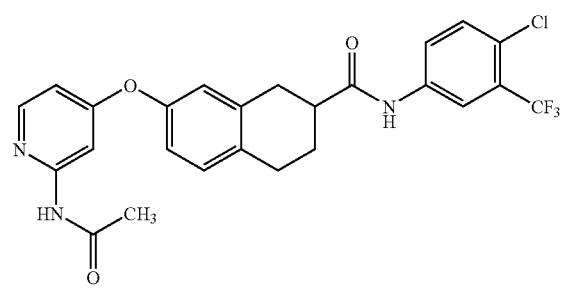
I-86
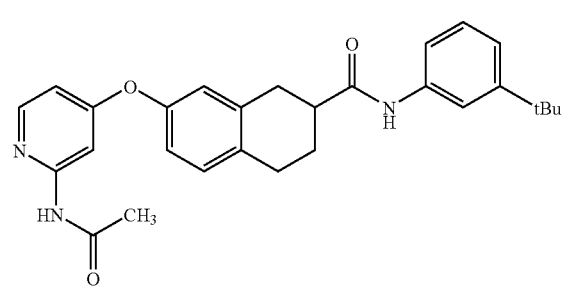
I-87
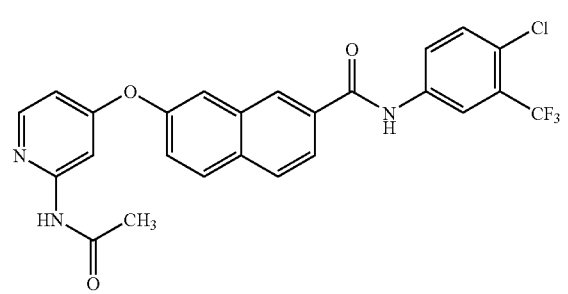
I-88
TABLE 1-continued
Raf Kinase Inhibitors
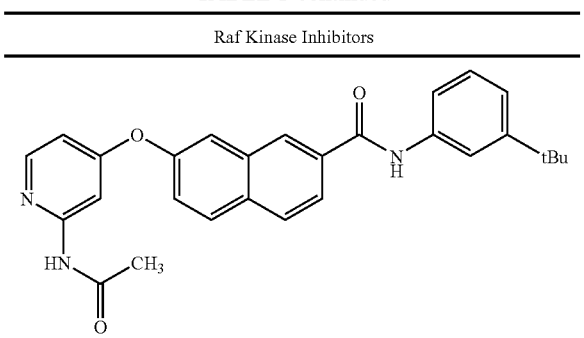
I-89
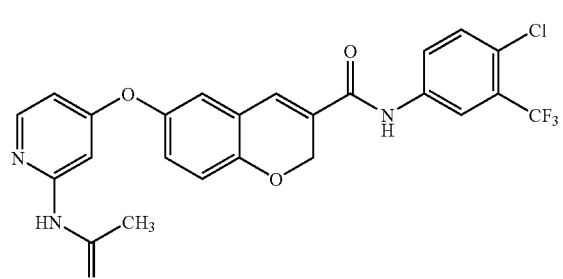
I-90
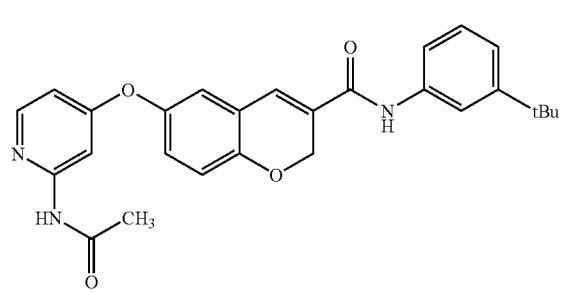
I-91
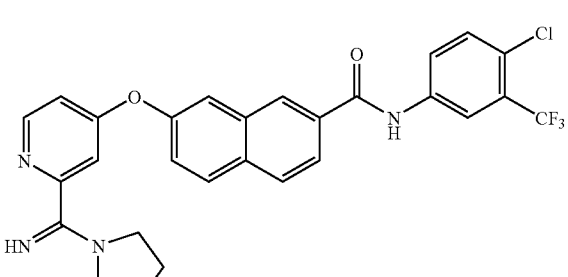
I-92
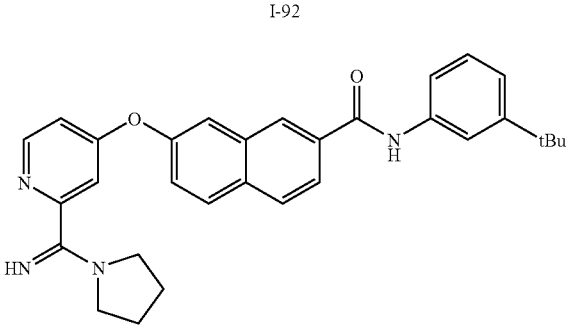
I-93

TABLE 1-continued
Raf Kinase Inhibitors
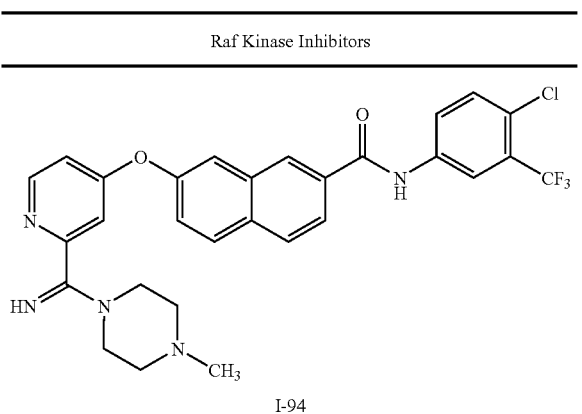
I-94
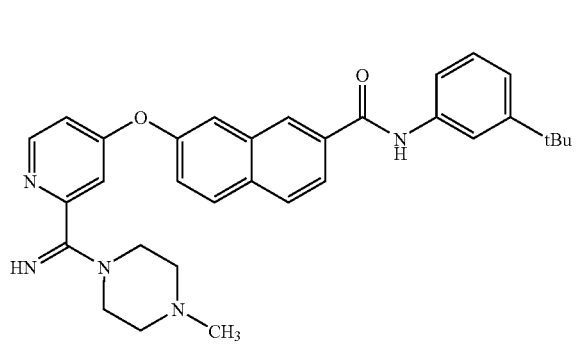
I-95
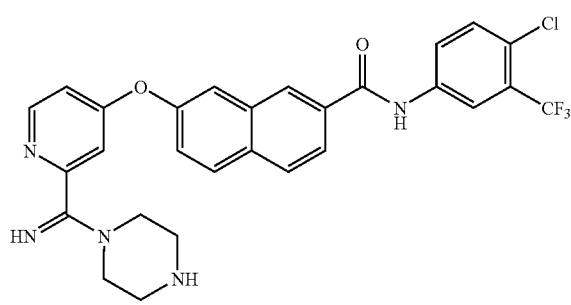
I-96
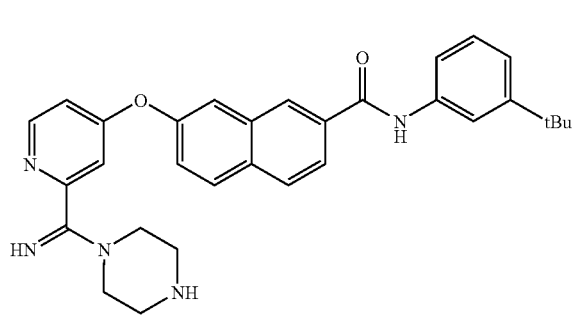
I-97
TABLE 1-continued
Raf Kinase Inhibitors
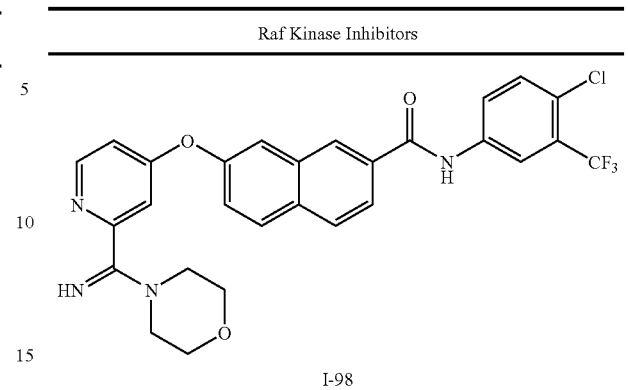
I-98
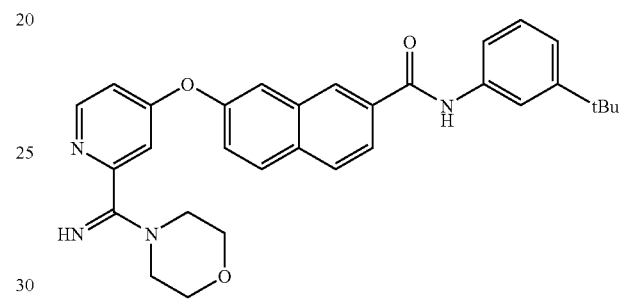
I-99
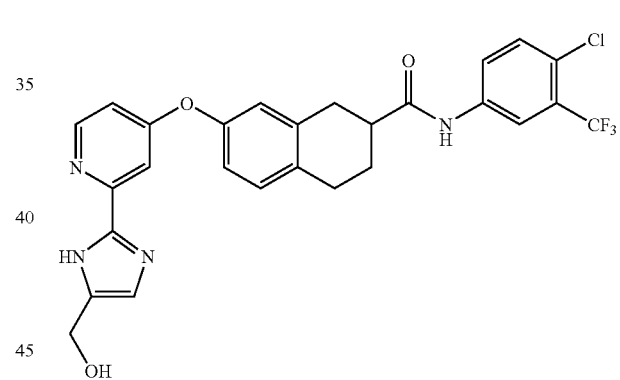
I-100
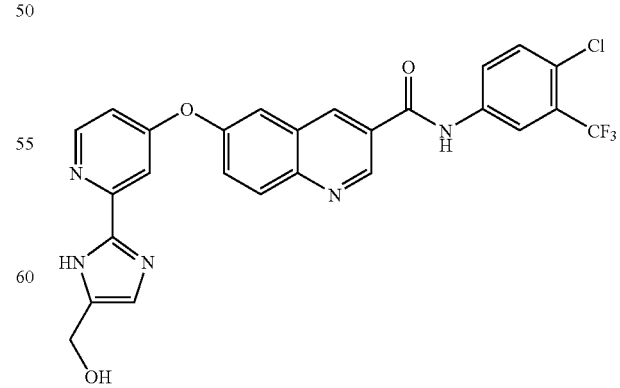
I-101

TABLE 1-continued
Raf Kinase Inhibitors
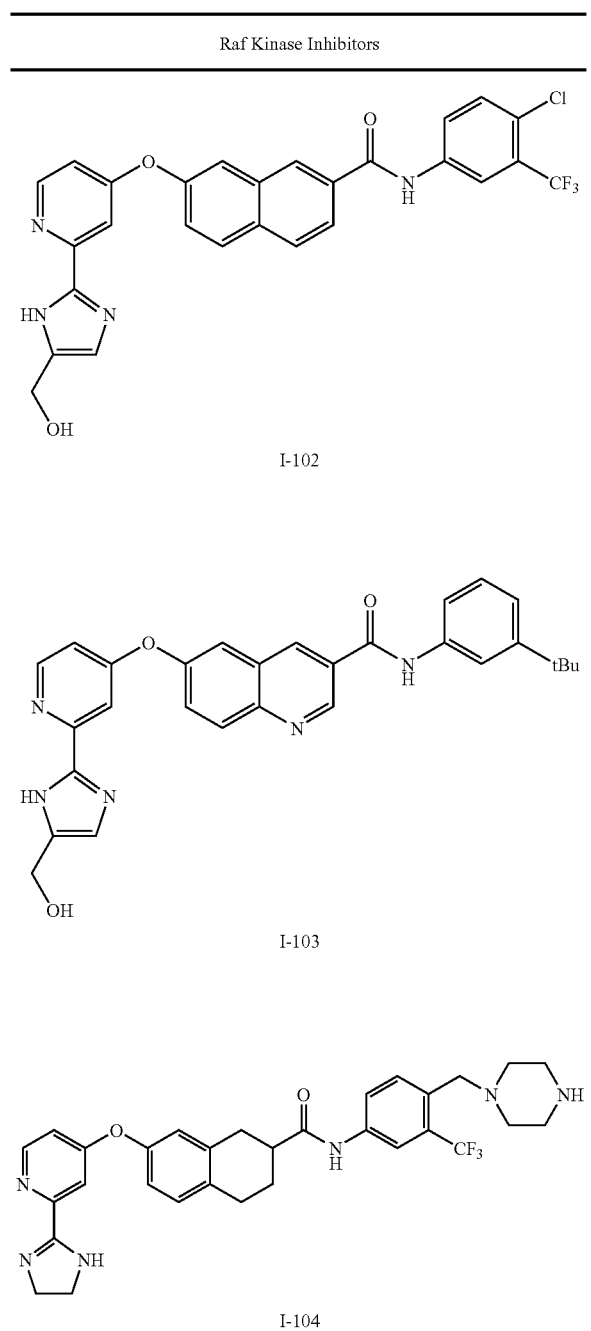
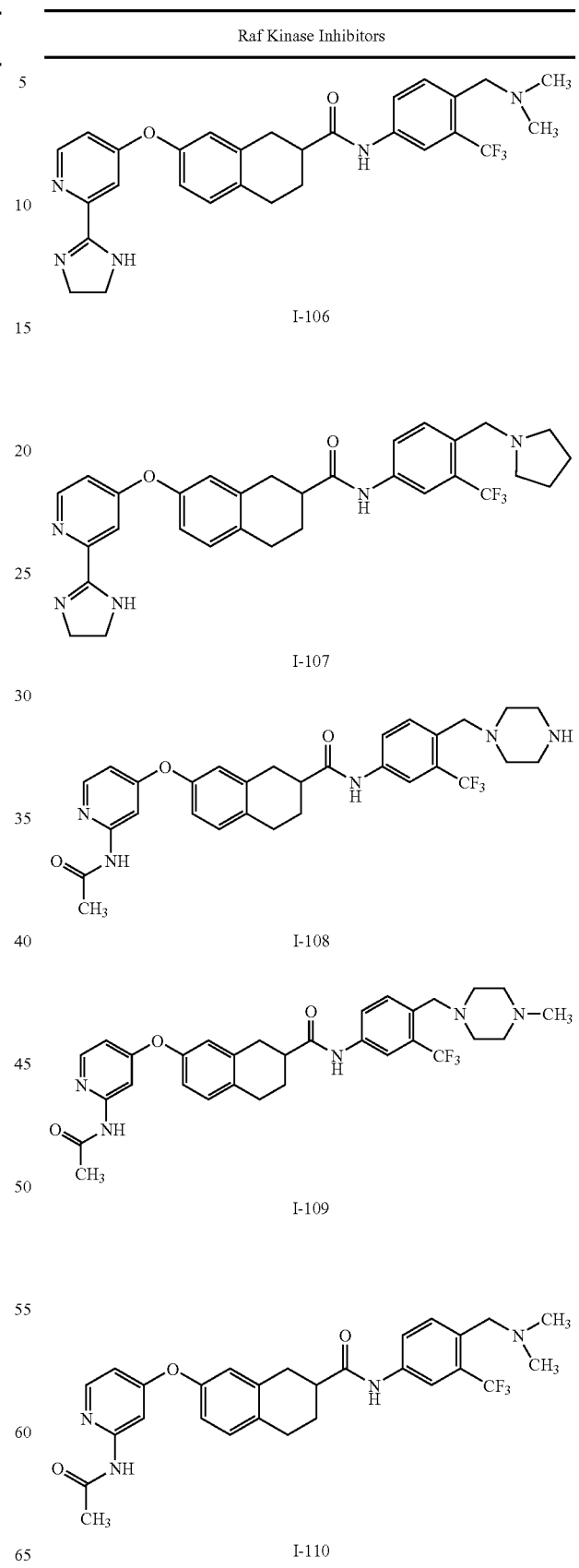

TABLE 1-continued
Raf Kinase Inhibitors
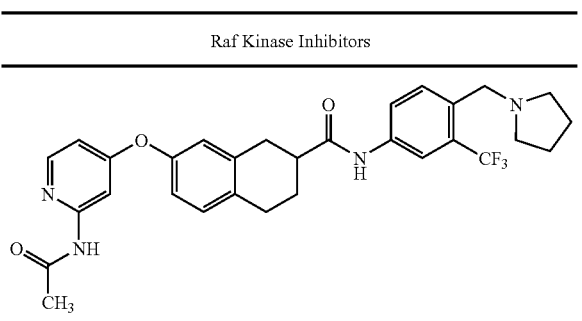
I-111
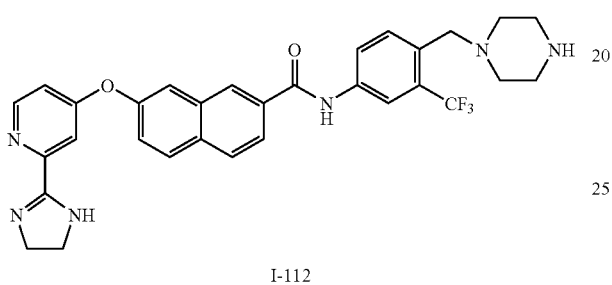
I-112
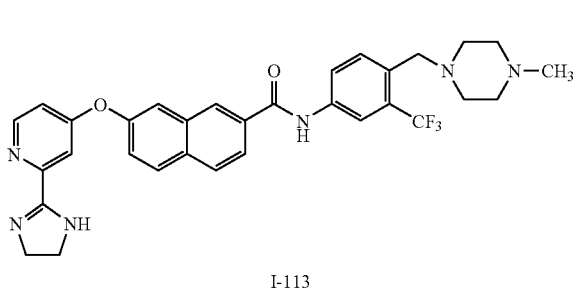
I-113
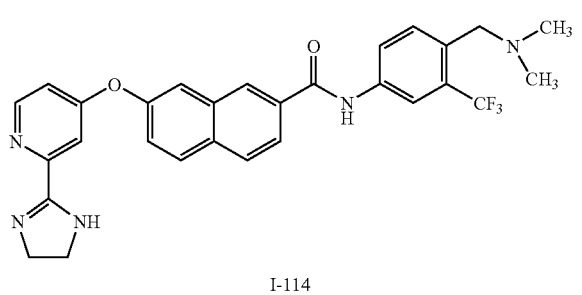
I-114
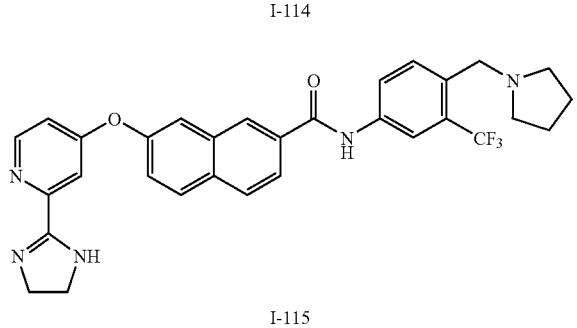
I-115
TABLE 1-continued
Raf Kinase Inhibitors
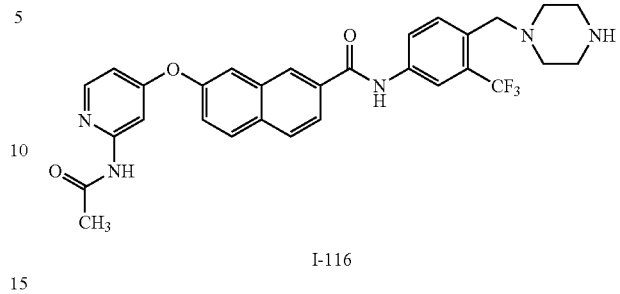
I-116
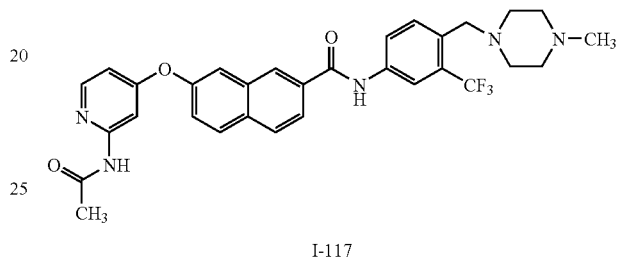
I-117
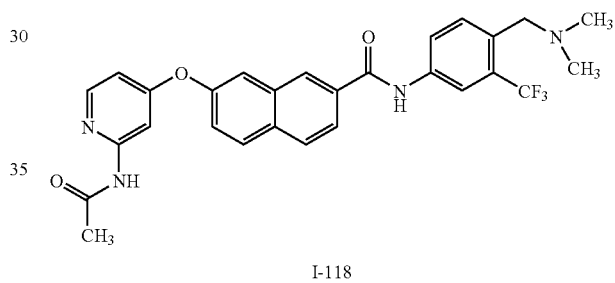
I-118
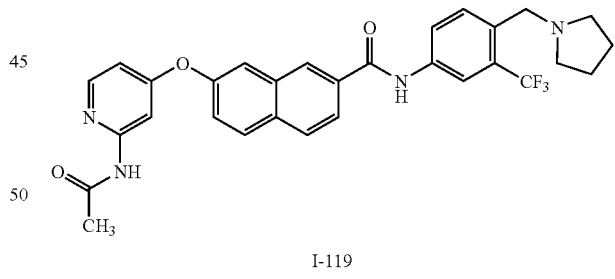
I-119
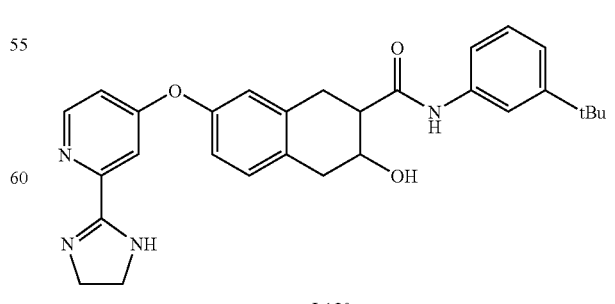
I-120

TABLE 1-continued
Raf Kinase Inhibitors
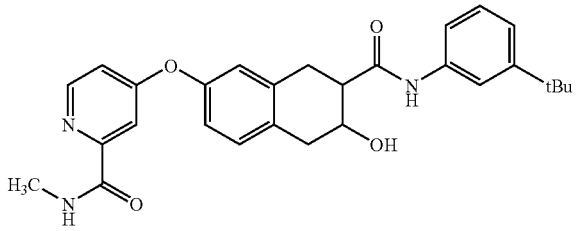
I-121
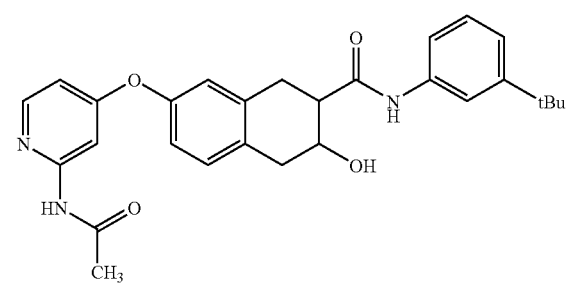
I-122
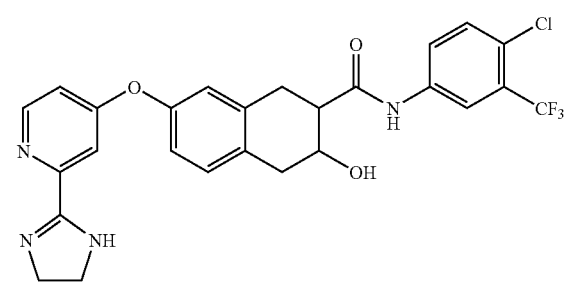
I-123
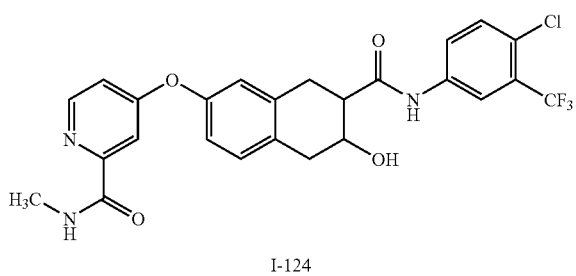
I-124
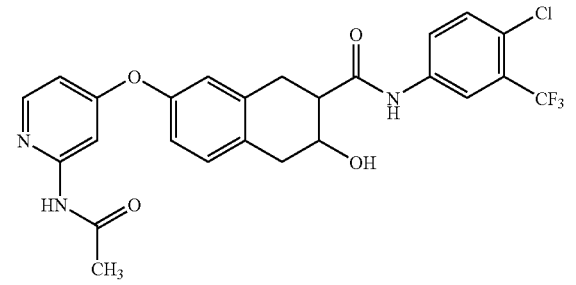
I-125
TABLE 1-continued
Raf Kinase Inhibitors
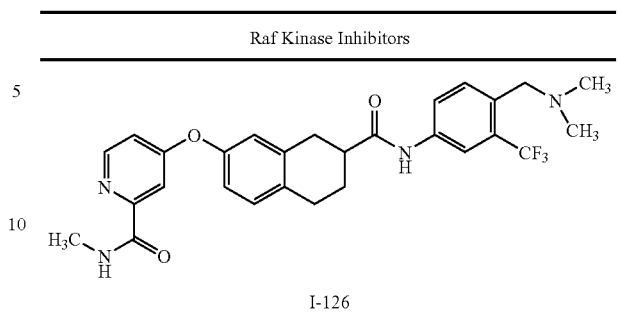
I-126
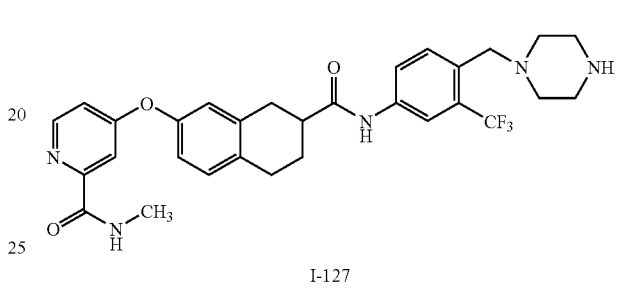
I-127
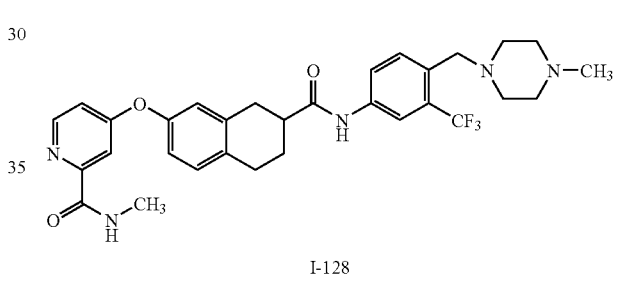
I-128
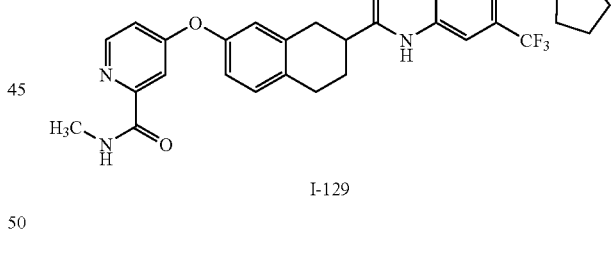
I-129
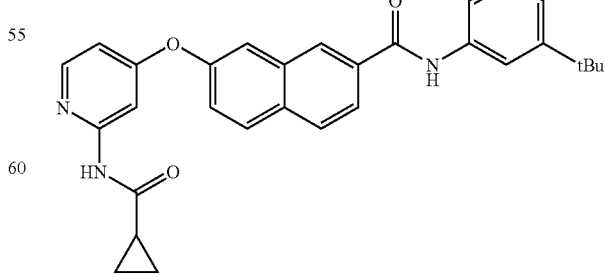
I-131

TABLE 1-continued
Raf Kinase Inhibitors
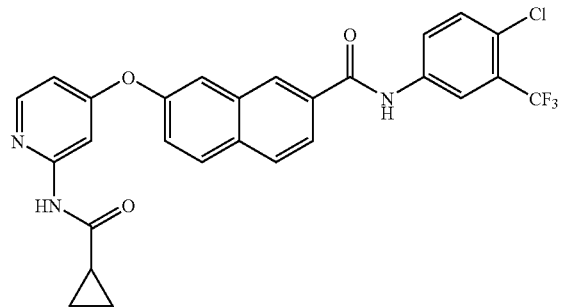
I-132
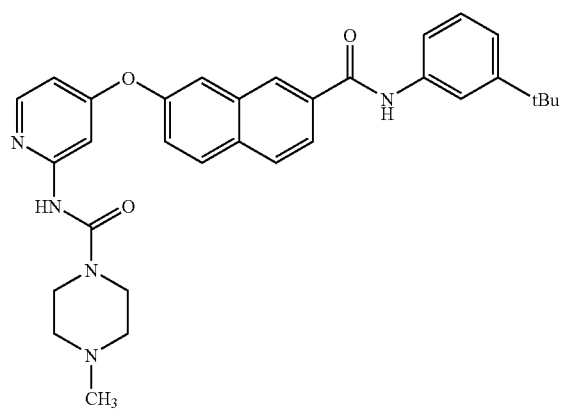
I-133
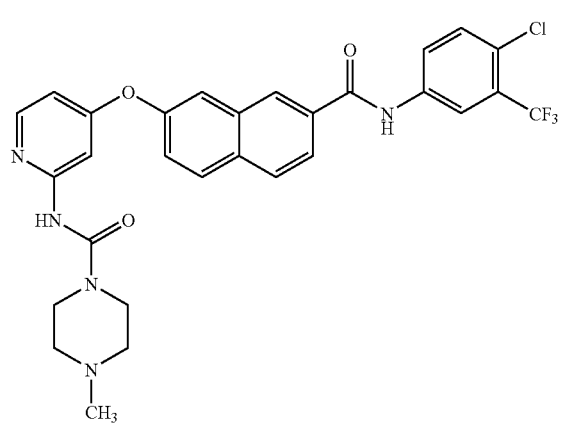
I-134
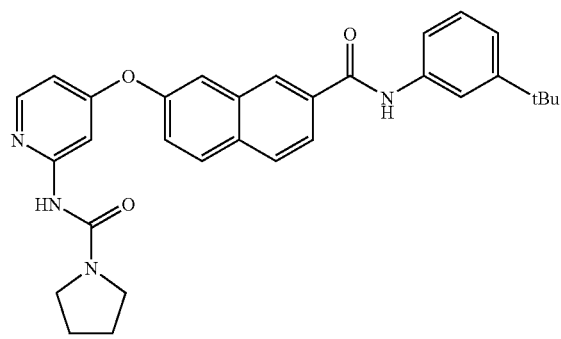
I-135
TABLE 1-continued
Raf Kinase Inhibitors
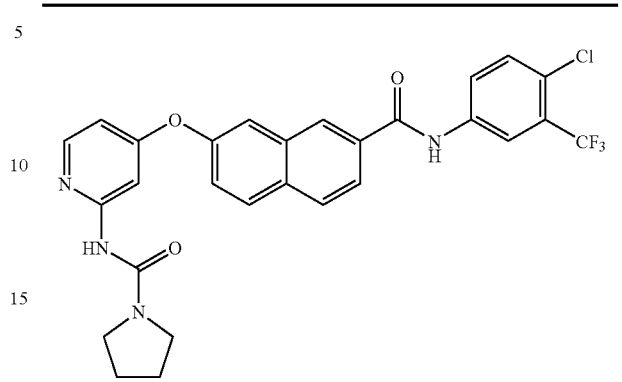
I-136
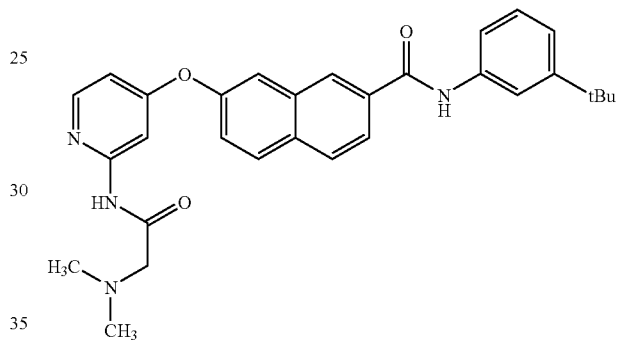
I-137
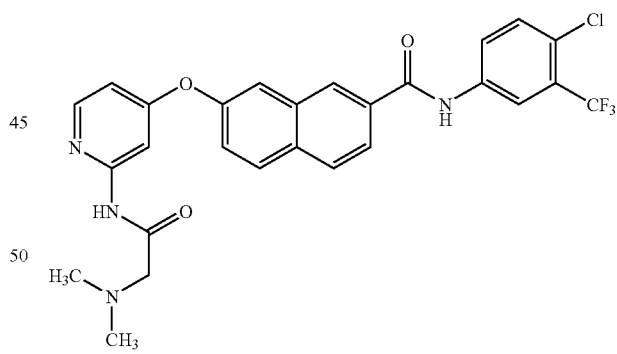
I-138
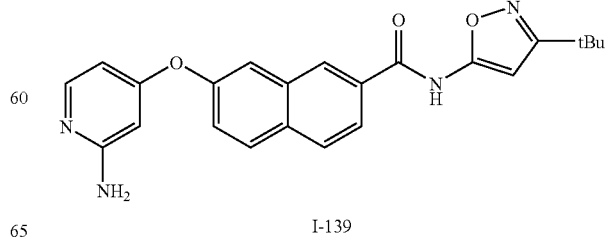
I-139

TABLE 1-continued
Raf Kinase Inhibitors
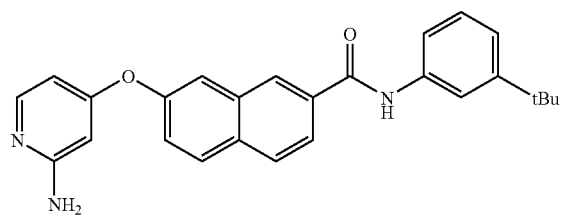
I-140
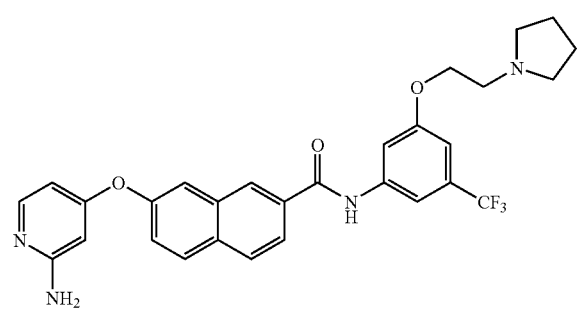
I-142
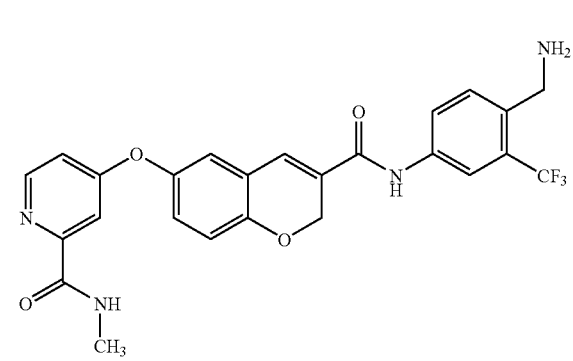
I-143
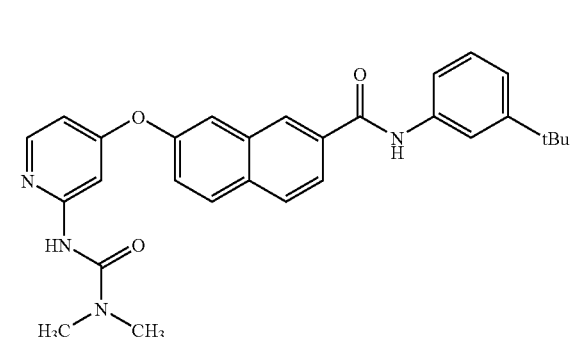
I-144
TABLE 1-continued
Raf Kinase Inhibitors
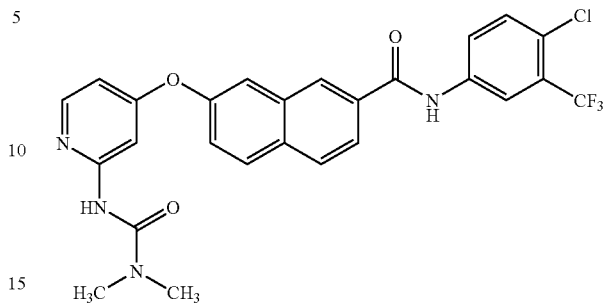
I-145
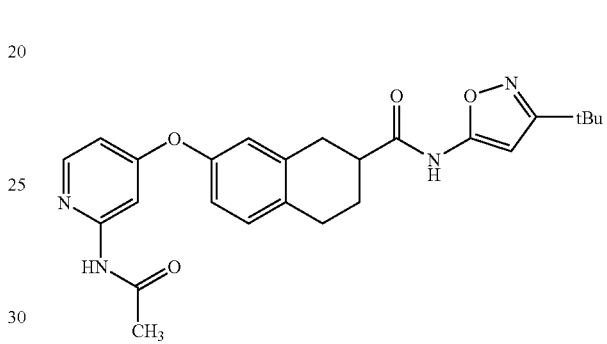
I-146
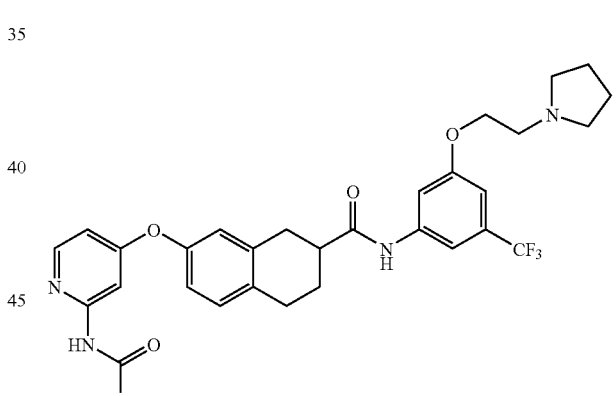
I-147
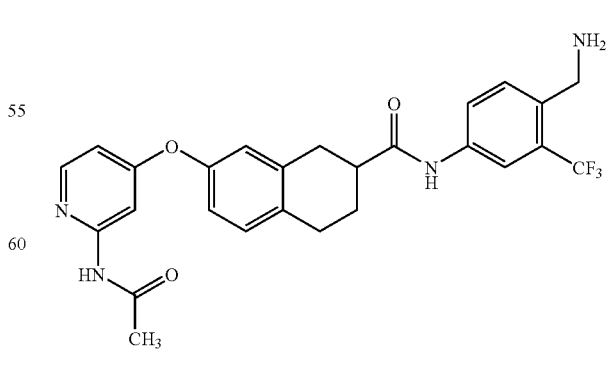
I-148

TABLE 1-continued
Raf Kinase Inhibitors
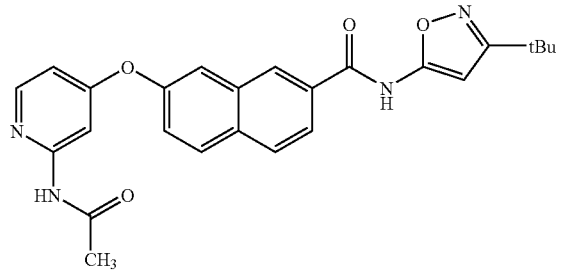
I-149
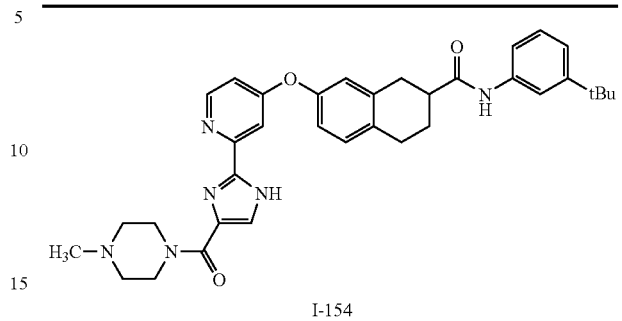
I-154
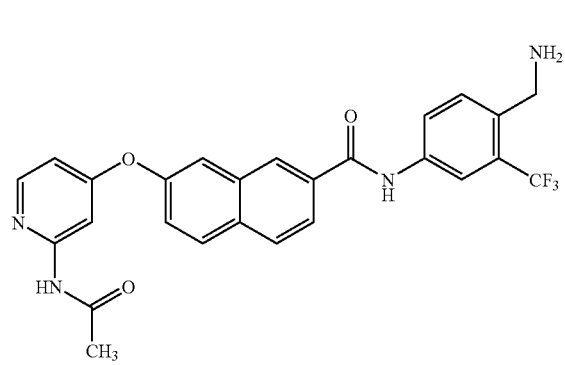
I-151
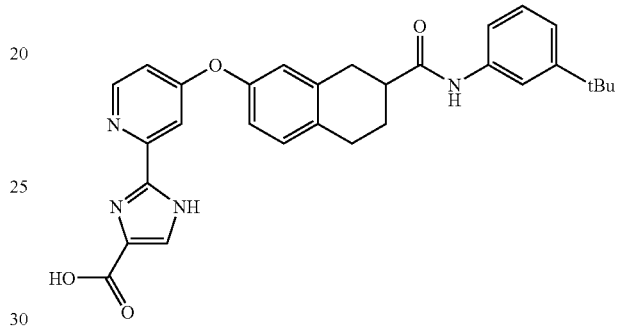
I-155
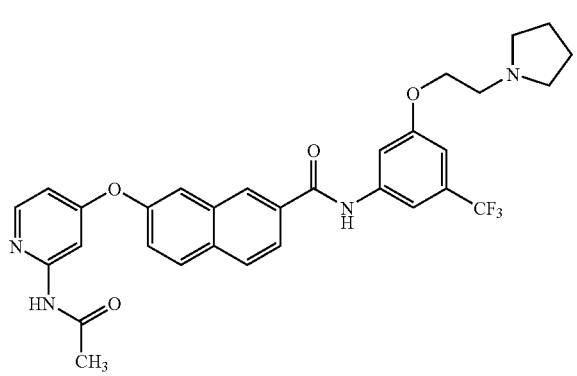
I-152
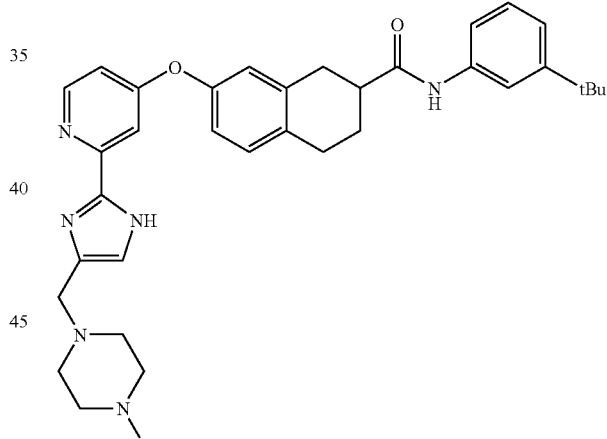
I-156
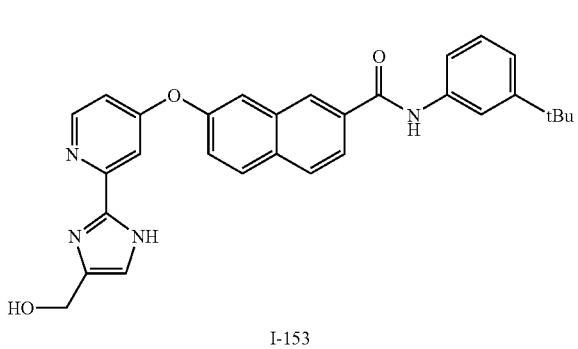
I-153
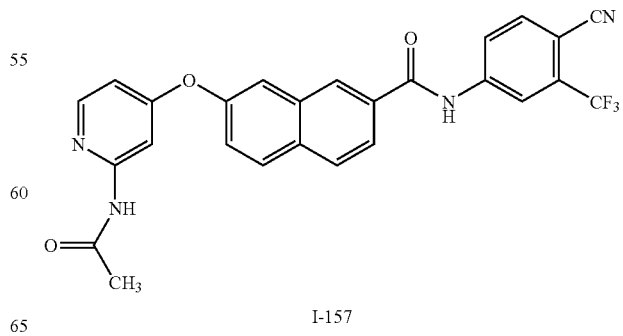
I-157

TABLE 1-continued
Raf Kinase Inhibitors
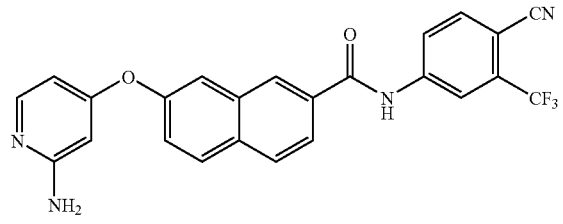
I-158
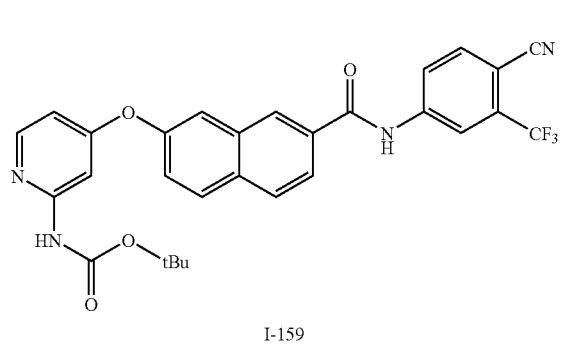
I-159
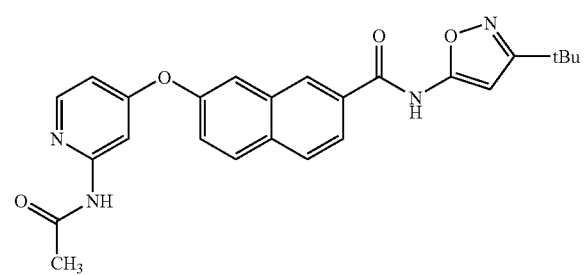
I-160
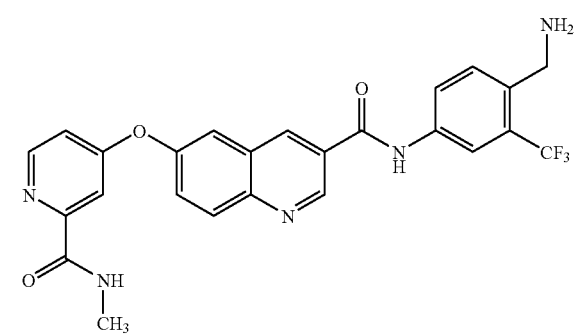
I-161
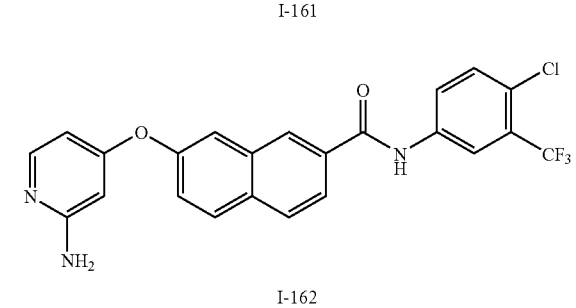
I-162
TABLE 1-continued
Raf Kinase Inhibitors
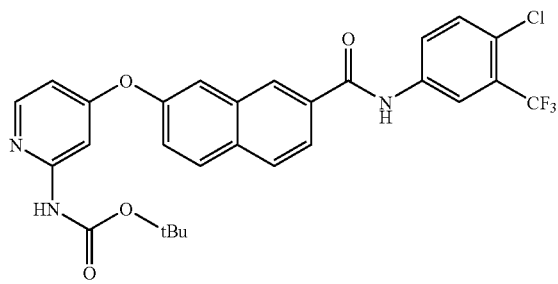
I-163
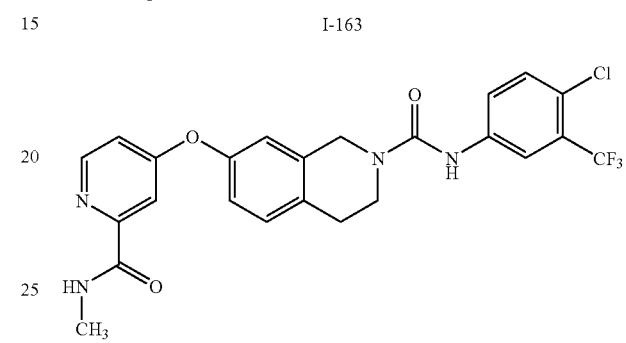
I-164
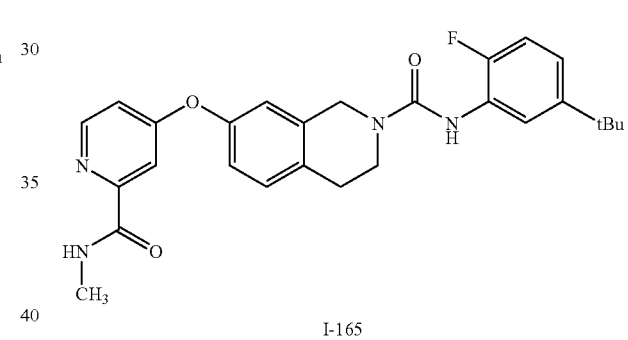
I-165
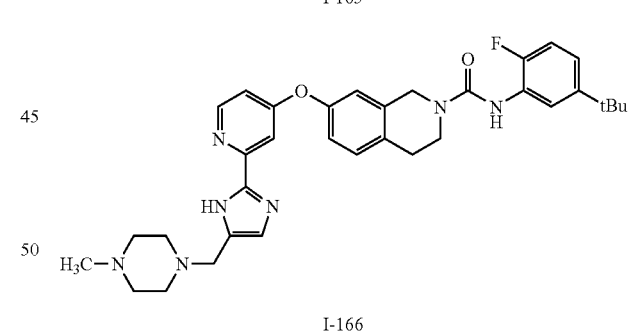
I-166
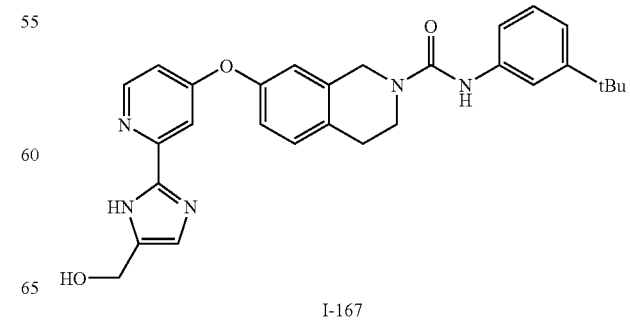
I-167

TABLE 1-continued
Raf Kinase Inhibitors
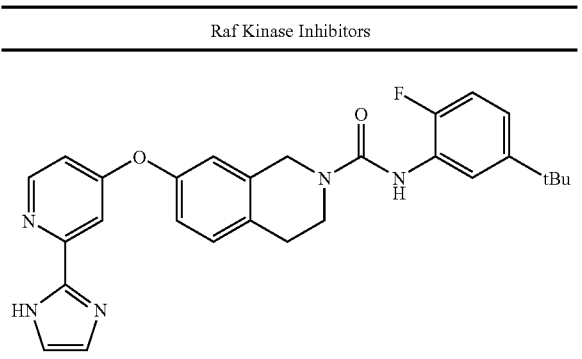
I-168
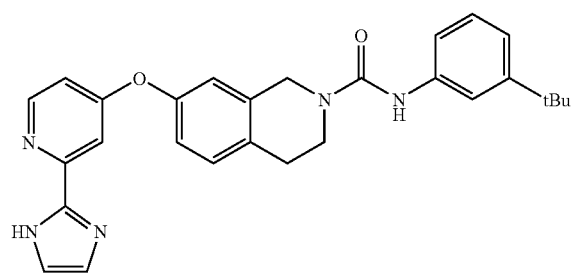
I-169
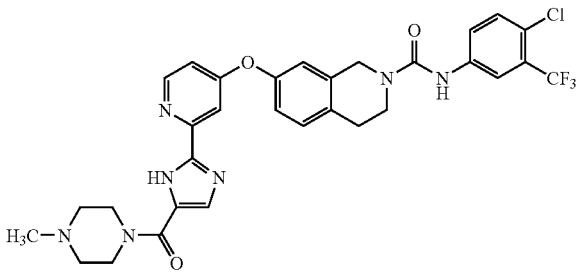
I-170
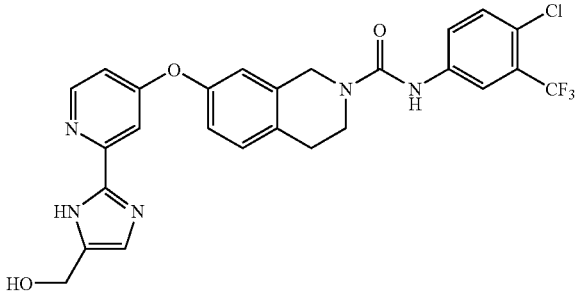
I-171
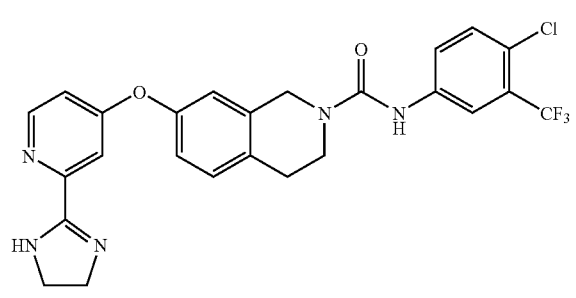
I-172
TABLE 1-continued
Raf Kinase Inhibitors
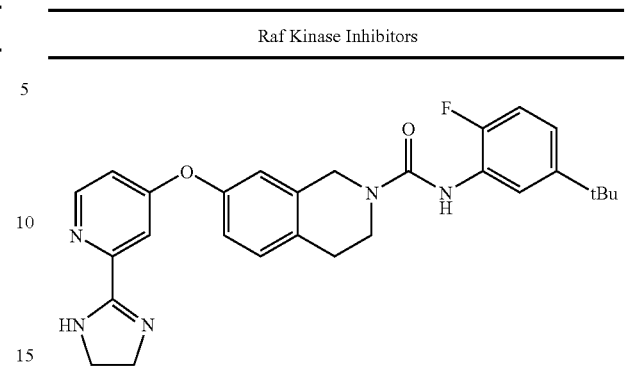
I-173
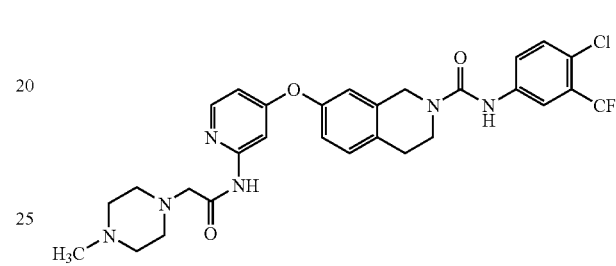
I-174
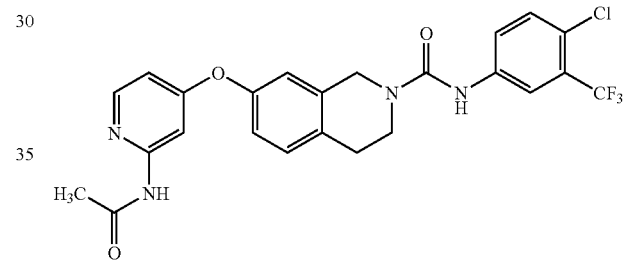
I-175
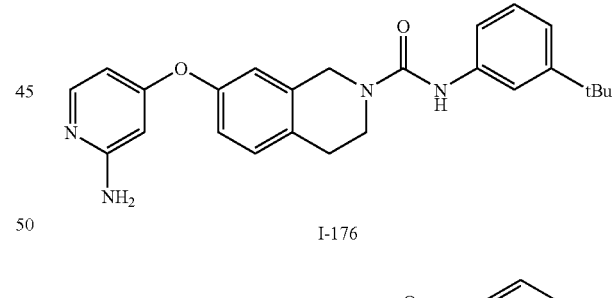
I-176
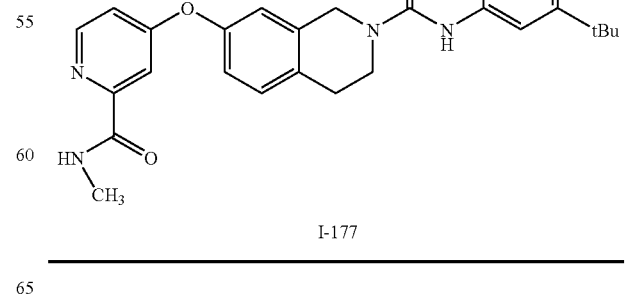
I-177
The compounds in Table 1 above also may be identified by the following chemical names:

|      | Chemical Name |
|------|---------------|
| I-1  | 7-{[2-(4,5-dihydro-1H-imidazol-2-yl)pyridin-4-yl]oxy}-N-[2-fluoro-5-(trifluoromethyl)phenyl]-1,2,3,4-tetrahydronaphthalene-2-carboxamide |
| I-2  | 7-{[2-(4,5-dihydro-1H-imidazol-2-yl)pyridin-4-yl]oxy}-N-[3-(trifluoromethyl)-phenyl]-1,2,3,4-tetrahydronaphthalene-2-carboxamide |
| I-3  | N-(3-tert-butylphenyl)-7-({2-[4-(hydroxymethyl)-1H-imidazol-2-yl]pyridin-4-yl}oxy)-1,2,3,4-tetrahydronaphthalene-2-carboxamide |
| I-4  | 7-{[2-(4,5-dihydro-1H-imidazol-2-yl)pyridin-4-yl]oxy}-N-[3-(2-pyrrolidin-1-ylethoxy)-5-(trifluoromethyl)phenyl]-1,2,3,4-tetrahydronaphthalene-2-carboxamide |
| I-5  | 4-{[7-({[4-chloro-3-(trifluoromethyl)phenyl]amino}carbonyl)-2-naphthyl]oxy}-N-methylpyridine-2-carboxamide |
| I-6  | 7-{[2-(4,5-dihydro-1H-imidazol-2-yl)pyridin-4-yl]oxy}-N-[4-iodo-3-(trifluoromethyl)phenyl]-2-naphthamide |
| I-7  | N-(3-tert-butylphenyl)-7-{[2-(4,5-dihydro-1H-imidazol-2-yl)pyridin-4-yl]oxy}-2-naphthamide |
| I-8  | N-[4-bromo-3-(trifluoromethyl)phenyl]-7-{[2-(4,5-dihydro-1H-imidazol-2-yl)-pyridin-4-yl]oxy}-1,2,3,4-tetrahydronaphthalene-2-carboxamide |
| I-9  | N-methyl-4-{[7-({[3-(piperidin-4-yloxy)-5-(trifluoromethyl)phenyl]-amino}carbonyl)-2-naphthyl]oxy}pyridine-2-carboxamide |
| I-10 | N-[4-chloro-3-(trifluoromethyl)phenyl]-6-{[2-(4,5-dihydro-1H-imidazol-2-yl)-pyridin-4-yl]oxy}-2H-chromene-3-carboxamide |
| I-11 | N-[4-chloro-3-(trifluoromethyl)phenyl]-6-{[2-(4,5-dihydro-1H-imidazol-2-yl)-pyridin-4-yl]oxy}-2-methyl-1,2,3,4-tetrahydroisoquinoline-3-carboxamide |
| I-12 | N-(3-tert-butylphenyl)-6-{[2-(4,5-dihydro-1H-imidazol-2-yl)pyridin-4-yl]oxy}-2H-chromene-3-carboxamide |
| I-13 | 7-{[2-(4,5-dihydro-1H-imidazol-2-yl)pyridin-4-yl]oxy}-N-[2-fluoro-5-(trifluoromethyl)phenyl]-2-naphthamide |
| I-14 | N-[3-amino-5-(trifluoromethyl)phenyl]-7-{[2-(4,5-dihydro-1H-imidazol-2-yl)-pyridin-4-yl]oxy}-2-naphthamide |
| I-15 | N-methyl-4-{[7-({[3-(2-pyrrolidin-1-ylethoxy)-5-(trifluoromethyl)phenyl]-amino}carbonyl)-5,6,7,8-tetrahydronaphthalen-2-yl]oxy}pyridine-2-carboxamide |
| I-17 | (2S)-N-[4-chloro-3-(trifluoromethyl)phenyl]-7-{[2-(4,5-dihydro-1H-imidazol-2-yl)pyridin-4-yl]oxy}-1,2,3,4-tetrahydronaphthalene-2-carboxamide |
| I-18 | 7-{[2-(4,5-dihydro-1H-imidazol-2-yl)pyridin-4-yl]oxy}-N-[3-(2-pyrrolidin-1-ylethoxy)-5-(trifluoromethyl)phenyl]-2-naphthamide |
| I-19 | N-[4-bromo-3-(trifluoromethyl)phenyl]-7-{[2-(4,5-dihydro-1H-imidazol-2-yl)-pyridin-4-yl]oxy}-2-naphthamide |
| I-20 | 7-{[2-(4,5-dihydro-1H-imidazol-2-yl)pyridin-4-yl]oxy}-N-[3-methoxy-5-(trifluoromethyl)phenyl]-1,2,3,4-tetrahydronaphthalene-2-carboxamide |
| I-21 | N-[4-chloro-3-(trifluoromethyl)phenyl]-8-{[2-(4,5-dihydro-1H-imidazol-2-yl)-pyridin-4-yl]oxy}-1,2,3,4-tetrahydronaphthalene-2-carboxamide |
| I-22 | 4-{[7-({[3-amino-5-(trifluoromethyl)phenyl]amino}carbonyl)-5,6,7,8-terahydronaphthalen-2-yl]oxy}-N-methylpyridine-2-carboxamide |
| I-23 | 4-[(7-{[(3-tert-butylphenyl)amino]carbonyl}-5,6,7,8-tetrahydronaphthalen-2-yl)-oxy]-N-methylpyridine-2-carboxamide |
| I-24 | 4-{[7-({[4-chloro-3-(trifluoromethyl)phenyl]amino}carbonyl)-5,6,7,8-tetrahydronaphthalen-2-yl]oxy}-N-methylpyridine-2-carboxamide |
| I-25 | 7-{[2-(4,5-dihydro-1H-imidazol-2-yl)pyridin-4-yl]oxy}-N-(3-isopropylphenyl)-1,2,3,4-tetrahydronaphthalene-2-carboxamide |
| I-26 | 4-[(7-{[(3-tert-butylisoxazol-5-yl)amino]carbonyl}-5,6,7,8-tetrahydronaphthalen-2-yl)oxy]-N-methylpyridine-2-carboxamide |
| I-28 | 4-{[7-({[4-(aminomethyl)-3-(trifluoromethyl)phenyl]amino}carbonyl)-5,6,7,8-tetrahydronaphthalen-2-yl]oxy}-N-methylpyridine-2-carboxamide |
| I-29 | 4-{[7-({[4-(2-aminoethyl)phenyl]amino}carbonyl)-5,6,7,8-tetrahydronaphthalen-2-yl]oxy}-N-methylpyridine-2-carboxamide |
| I-30 | N-[4-chloro-3-(trifluoromethyl)phenyl]-6-{[2-(4,5-dihydro-1H-imidazol-2-yl)-pyridin-4-yl]oxy}quinoline-3-carboxamide |
| I-31 | 4-{[7-({[3-(aminomethyl)-5-(trifluoromethyl)phenyl]amino}carbonyl)-5,6,7,8-tetrahydronaphthalen-2-yl]oxy}-N-methylpyridine-2-carboxamide |
| I-32 | 4-{[7-({[4-(aminomethyl)-3-(trifluoromethyl)phenyl]amino}carbonyl)-2-naphthyl]oxy}-N-methylpyridine-2-carboxamide |
| I-33 | 7-{[2-(4,5-dihydro-1H-imidazol-2-yl)pyridin-4-yl]oxy}-N-[3-methoxy-5-(trifluoromethyl)phenyl]-2-naphthamide |
| I-34 | (2R)-N-[4-chloro-3-(trifluoromethyl)phenyl]-7-{[2-(4,5-dihydro-1H-imidazol-2-yl)pyridin-4-yl]oxy}-1,2,3,4-tetrahydronaphthalene-2-carboxamide |
| I-35 | N-[4-chloro-3-(trifluoromethyl)phenyl]-6-{[2-(4,5-dihydro-1H-imidazol-2-yl)-pyridin-4-yl]oxy}isoquinoline-3-carboxamide |
| I-36 | N-[4-chloro-3-(trifluoromethyl)phenyl]-7-{[2-(4,5-dihydro-1H-imidazol-2-yl)-pyridin-4-yl]oxy}-1,2,3,4-tetrahydronaphthalene-2-carboxamide |
| I-37 | 4-[(7-{[(3-tert-butylphenyl)amino]carbonyl}-2-naphthyl)oxy]-N-methylpyridine-2-carboxamide |
| I-38 | (2R)-N-(3-tert-butylphenyl)-7-{[2-(4,5-dihydro-1H-imidazol-2-yl)pyridin-4-yl]-oxy}-1,2,3,4-tetrahydronaphthalene-2-carboxamide |
| I-39 | N-[4-(aminomethyl)-3-(trifluoromethyl)phenyl]-7-{[2-(4,5-dihydro-1H-imidazol-2-yl)pyridin-4-yl]oxy}-2-naphthamide |
| I-40 | (2S)-N-(3-tert-butylphenyl)-7-{[2-(4,5-dihydro-1H-imidazol-2-yl)pyridin-4-yl]-oxy}-1,2,3,4-tetrahydronaphthalene-2-carboxamide |

|  | Chemical Name |
|---|---|
| I-41 | 4-{[7-({[3-[2-(dimethylamino)ethoxy]-5-(trifluoromethyl)phenyl]-amino}carbonyl)-5,6,7,8-tetrahydronaphthalen-2-yl]oxy}-N-methylpyridine-2-carboxamide |
| I-42 | 4-{[7-({[4-(aminomethyl)phenyl]amino}carbonyl)-5,6,7,8-tetrahydronaphthalen-2-yl]oxy}-N-methylpyridine-2-carboxamide |
| I-43 | 4-[(7-{[(3-tert-butylisoxazol-5-yl)amino]carbonyl}-2-naphthyl)oxy]-N-methylpyridine-2-carboxamide |
| I-44 | N-(3-tert-butylphenyl)-7-{[2-(4,5-dihydro-1H-imidazol-2-yl)pyridin-4-yl]oxy}-1,2,3,4-tetrahydronaphthalene-2-carboxamide |
| I-45 | N-[4-chloro-3-(trifluoromethyl)phenyl]-7-{[2-(4,5-dihydro-1H-imidazol-2-yl)-pyridin-4-yl]oxy}quinoline-2-carboxamide |
| I-46 | N-[4-chloro-3-(trifluoromethyl)phenyl]-7-{[2-(4,5-dihydro-1H-imidazol-2-yl)-pyridin-4-yl]oxy}-2-naphthamide |
| I-47 | 4-{[7-({[3-(2-aminoethyl)-5-(trifluoromethyl)phenyl]amino}carbonyl)-5,6,7,8-tetrahydronaphthalen-2-yl]oxy}-N-methylpyridine-2-carboxamide |
| I-48 | 7-{[2-(4,5-dihydro-1H-imidazol-2-yl)pyridin-4-yl]oxy}-N-[3-(piperidin-4-yloxy)-5-(trifluoromethyl)phenyl]-2-naphthamide |
| I-49 | 4-{[7-({[3-[2-(dimethylamino)ethoxy]-5-(trifluoromethyl)phenyl]-amino}carbonyl)-2-naphthyl]oxy}-N-methylpyridine-2-carboxamide |
| I-50 | N-(3-tert-butylphenyl)-7-{[2-(4,5-dihydro-1H-imidazol-2-yl)pyridin-4-yl]-oxy}quinoline-2-carboxamide |
| I-51 | 4-{[7-({[3-(aminomethyl)phenyl]amino}carbonyl)-5,6,7,8-tetrahydronaphthalen-2-yl]oxy}-N-methylpyridine-2-carboxamide |
| I-52 | N-methyl-4-{[7-({[3-(2-pyrrolidin-1-ylethoxy)-5-(trifluoromethyl)phenyl]-amino}carbonyl)-2-naphthyl]oxy}pyridine-2-carboxamide |
| I-53 | 7-{[2-(4,5-dihydro-1H-imidazol-2-yl)pyridin-4-yl]oxy}-N-[3-(trifluoromethyl)-phenyl]-2-naphthamide |
| I-54 | N-[4-chloro-3-(trifluoromethyl)phenyl]-6-{[2-(4,5-dihydro-1H-imidazol-2-yl)-pyridin-4-yl]oxy}-1,2,3,4-tetrahydroisoquinoline-3-carboxamide |
| I-55 | 4-{[7-({[3-amino-5-(trifluoromethyl)phenyl]amino}carbonyl)-2-naphthyl]oxy}-N-methylpyridine-2-carboxamide |
| I-56 | N-[4-chloro-3-(trifluoromethyl)phenyl]-6-({2-[5-(hydroxymethyl)-1H-imidazol-2-yl]pyridin-4-yl}oxy)-3,4-dihydro-1H-isochromene-3-carboxamide |
| I-57 | N-[4-chloro-3-(trifluoromethyl)phenyl]-6-({2-[5-(hydroxymethyl)-1H-imidazol-2-yl]pyridin-4-yl}oxy)-2H-chromene-3-carboxamide |
| I-58 | N-(3-tert-butylphenyl)-7-({2-[5-(hydroxymethyl)-1H-imidazol-2-yl]pyridin-4-yl}oxy)-2-naphthamide |
| I-59 | N-(3-tert-butylphenyl)-6-({2-[5-(hydroxymethyl)-1H-imidazol-2-yl]pyridin-4-yl}oxy)-2H-chromene-3-carboxamide |
| I-60 | 6-{[2-(4,5-dihydro-1H-imidazol-2-yl)pyridin-4-yl]oxy}-N-[2-(2-pyrrolidin-1-ylethoxy)-5-(trifluoromethyl)phenyl]quinoline-3-carboxamide |
| I-61 | 6-{[2-(4,5-dihydro-1H-imidazol-2-yl)pyridin-4-yl]oxy}-N-[2-[2-(dimethylamino)-ethoxy]-5-(trifluoromethyl)phenyl]quinoline-3-carboxamide |
| I-62 | N-(3-tert-butylphenyl)-6-({2-[5-(hydroxymethyl)-1H-imidazol-2-yl]pyridin-4-yl}oxy)-3,4-dihydro-1H-isochromene-3-carboxamide |
| I-63 | 7-({2-[amino(imino)methyl]pyridin-4-yl}oxy)-N-(3-tert-butylphenyl)-2-naphthamide |
| I-64 | N-methyl-4-{[7-({[2-(2-pyrrolidin-1-ylethoxy)-5-(trifluoromethyl)phenyl]-amino}carbonyl)-5,6,7,8-tetrahydronaphthalen-2-yl]oxy}pyridine-2-carboxamide |
| I-65 | 4-{[7-({[2-[2-(dimethylamino)ethoxy]-5-(trifluoromethyl)phenyl]-amino}carbonyl)-5,6,7,8-tetrahydronaphthalen-2-yl]oxy}-N-methylpyridine-2-carboxamide |
| I-66 | 7-{[2-(4,5-dihydro-1H-imidazol-2-yl)pyridin-4-yl]oxy}-N-[2-(2-pyrrolidin-1-ylethoxy)-5-(trifluoromethyl)phenyl]-2-naphthamide |
| I-67 | 7-{[2-(4,5-dihydro-1H-imidazol-2-yl)pyridin-4-yl]oxy}-N-[2-[2-(dimethylamino)-ethoxy]-5-(trifluoromethyl)phenyl]-2-naphthamide |
| I-68 | 4-{[3-({[4-chloro-3-(trifluoromethyl)phenyl]amino}carbonyl)-3,4-dihydro-1H-isochromen-6-yl]oxy}-N-methylpyridine-2-carboxamide |
| I-69 | 6-{[2-(acetylamino)pyridin-4-yl]oxy}-N-[4-chloro-3-(trifluoromethyl)phenyl]-3,4-dihydro-1H-isochromene-3-carboxamide |
| I-70 | N-[4-chloro-3-(trifluoromethyl)phenyl]-6-{[2-(4,5-dihydro-1H-imidazol-2-yl)-pyridin-4-yl]oxy}-3,4-dihydro-1H-isochromene-3-carboxamide |
| I-71 | 4-[(3-{[(3-tert-butylphenyl)amino]carbonyl}-3,4-dihydro-1H-isochromen-6-yl)-oxy]-N-methylpyridine-2-carboxamide |
| I-72 | 6-{[2-(acetylamino)pyridin-4-yl]oxy}-N-(3-tert-butylphenyl)-3,4-dihydro-1H-isochromene-3-carboxamide |
| I-73 | N-(3-tert-butylphenyl)-6-{[2-(4,5-dihydro-1H-imidazol-2-yl)pyridin-4-yl]oxy}-3,4-dihydro-1H-isochromene-3-carboxamide |
| I-74 | N-[4-chloro-3-(trifluoromethyl)phenyl]-7-[(2-{imino[(1-methylpiperidin-4-yl)-amino]methyl}pyridin-4-yl)oxy]-1,2,3,4-tetrahydronaphthalene-2-carboxamide |
| I-75 | N-(3-tert-butylphenyl)-7-[(2-{imino[(1-methylpiperidin-4-yl)amino]methyl}-pyridin-4-yl)oxy]-1,2,3,4-tetrahydronaphthalene-2-carboxamide |
| I-76 | N-[4-chloro-3-(trifluoromethyl)phenyl]-7-({2-[imino(isopropylamino)methyl]-pyridin-4-yl}oxy)-1,2,3,4-tetrahydronaphthalene-2-carboxamide |
| I-77 | N-(3-tert-butylphenyl)-7-({2-[imino(isopropylamino)methyl]pyridin-4-yl}oxy)-1,2,3,4-tetrahydronaphthalene-2-carboxamide |

| | Chemical Name |
|---|---|
| I-78 | N-[4-chloro-3-(trifluoromethyl)phenyl]-7-({2-[{[2-(dimethylamino)ethyl]-amino}(imino)methyl]pyridin-4-yl}oxy)-1,2,3,4-tetrahydronaphthalene-2-carboxamide |
| I-79 | N-(3-tert-butylphenyl)-7-({2-[{[2-(dimethylamino)ethyl]amino}(imino)methyl]-pyridin-4-yl}oxy)-1,2,3,4-tetrahydronaphthalene-2-carboxamide |
| I-80 | N-[4-chloro-3-(trifluoromethyl)phenyl]-7-({2-[(ethylamino)(imino)methyl]-pyridin-4-yl}oxy)-1,2,3,4-tetrahydronaphthalene-2-carboxamide |
| I-81 | N-(3-tert-butylphenyl)-7-({2-[(ethylamino)(imino)methyl]pyridin-4-yl}oxy)-1,2,3,4-tetrahydronaphthalene-2-carboxamide |
| I-82 | 7-({2-[amino(imino)methyl]pyridin-4-yl}oxy)-N-[4-chloro-3-(trifluoromethyl)-phenyl]-1,2,3,4-tetrahydronaphthalene-2-carboxamide |
| I-83 | 7-({2-[amino(imino)methyl]pyridin-4-yl}oxy)-N-(3-tert-butylphenyl)-1,2,3,4-tetrahydronaphthalene-2-carboxamide |
| I-84 | 6-{[2-(acetylamino)pyridin-4-yl]oxy}-N-[4-chloro-3-(trifluoromethyl)phenyl]-quinoline-3-carboxamide |
| I-85 | 6-{[2-(acetylamino)pyridin-4-yl]oxy}-N-(3-tert-butylphenyl)quinoline-3-carboxamide |
| I-86 | 7-{[2-(acetylamino)pyridin-4-yl]oxy}-N-[4-chloro-3-(trifluoromethyl)phenyl]-1,2,3,4-tetrahydronaphthalene-2-carboxamide |
| I-87 | 7-{[2-(acetylamino)pyridin-4-yl]oxy}-N-(3-tert-butylphenyl)-1,2,3,4-tetrahydronaphthalene-2-carboxamide |
| I-88 | 7-{[2-(acetylamino)pyridin-4-yl]oxy}-N-[4-chloro-3-(trifluoromethyl)phenyl]-2-naphthamide |
| I-89 | 7-{[2-(acetylamino)pyridin-4-yl]oxy}-N-(3-tert-butylphenyl)-2-naphthamide |
| I-90 | 6-{[2-(acetylamino)pyridin-4-yl]oxy}-N-[4-chloro-3-(trifluoromethyl)phenyl]-2H-chromene-3-carboxamide |
| I-91 | 6-{[2-(acetylamino)pyridin-4-yl]oxy}-N-(3-tert-butylphenyl)-2H-chromene-3-carboxamide |
| I-92 | N-[4-chloro-3-(trifluoromethyl)phenyl]-7-({2-[imino(pyrrolidin-1-yl)methyl]-pyridin-4-yl}oxy)-2-naphthamide |
| I-93 | N-(3-tert-butylphenyl)-7-({2-[imino(pyrrolidin-1-yl)methyl]pyridin-4-yl}oxy)-2-naphthamide |
| I-94 | N-[4-chloro-3-(trifluoromethyl)phenyl]-7-({2-[imino(4-methylpiperazin-1-yl)-methyl]pyridin-4-yl}oxy)-2-naphthamide |
| I-95 | N-(3-tert-butylphenyl)-7-({2-[imino(4-methylpiperazin-1-yl)methyl]pyridin-4-yl}oxy)-2-naphthamide |
| I-96 | N-[4-chloro-3-(trifluoromethyl)phenyl]-7-({2-[imino(piperazin-1-yl)methyl]-pyridin-4-yl}oxy)-2-naphthamide |
| I-97 | N-(3-tert-butylphenyl)-7-({2-[imino(piperazin-1-yl)methyl]pyridin-4-yl}oxy)-2-naphthamide |
| I-98 | N-[4-chloro-3-(trifluoromethyl)phenyl]-7-({2-[imino(morpholin-4-yl)methyl]-pyridin-4-yl}oxy)-2-naphthamide |
| I-99 | N-(3-tert-butylphenyl)-7-({2-[imino(morpholin-4-yl)methyl]pyridin-4-yl}oxy)-2-naphthamide |
| I-100 | N-[4-chloro-3-(trifluoromethyl)phenyl]-7-({2-[5-(hydroxymethyl)-1H-imidazol-2-yl]pyridin-4-yl}oxy)-1,2,3,4-tetrahydronaphthalene-2-carboxamide |
| I-101 | N-[4-chloro-3-(trifluoromethyl)phenyl]-6-({2-[5-(hydroxymethyl)-1H-imidazol-2-yl]pyridin-4-yl}oxy)quinoline-3-carboxamide |
| I-102 | N-[4-chloro-3-(trifluoromethyl)phenyl]-7-({2-[5-(hydroxymethyl)-1H-imidazol-2-yl]pyridin-4-yl}oxy)-2-naphthamide |
| I-103 | N-(3-tert-butylphenyl)-6-({2-[5-(hydroxymethyl)-1H-imidazol-2-yl]pyridin-4-yl}oxy)quinoline-3-carboxamide |
| I-104 | 7-{[2-(4,5-dihydro-1H-imidazol-2-yl)pyridin-4-yl]oxy}-N-[4-(piperazin-1-ylmethyl)-3-(trifluoromethyl)phenyl]-1,2,3,4-tetrahydronaphthalene-2-carboxamide |
| I-105 | 7-{[2-(4,5-dihydro-1H-imidazol-2-yl)pyridin-4-yl]oxy}-N-[4-[(4-methylpiperazin-1-yl)methyl]-3-(trifluoromethyl)phenyl]-1,2,3,4-tetrahydronaphthalene-2-carboxamide |
| I-106 | 7-{[2-(4,5-dihydro-1H-imidazol-2-yl)pyridin-4-yl]oxy}-N-[4-[(dimethylamino)-methyl]-3-(trifluoromethyl)phenyl]-1,2,3,4-tetrahydronaphthalene-2-carboxamide |
| I-107 | 7-{[2-(4,5-dihydro-1H-imidazol-2-yl)pyridin-4-yl]oxy}-N-[4-(pyrrolidin-1-ylmethyl)-3-(trifluoromethyl)phenyl]-1,2,3,4-tetrahydronaphthalene-2-carboxamide |
| I-108 | 7-{[2-(acetylamino)pyridin-4-yl]oxy}-N-[4-(piperazin-1-ylmethyl)-3-(trifluoromethyl)phenyl]-1,2,3,4-tetrahydronaphthalene-2-carboxamide |
| I-109 | 7-{[2-(acetylamino)pyridin-4-yl]oxy}-N-[4-[(4-methylpiperazin-1-yl)methyl]-3-(trifluoromethyl)phenyl]-1,2,3,4-tetrahydronaphthalene-2-carboxamide |
| I-110 | 7-{[2-(acetylamino)pyridin-4-yl]oxy}-N-[4-[(dimethylamino)methyl]-3-(trifluoromethyl)phenyl]-1,2,3,4-tetrahydronaphthalene-2-carboxamide |
| I-111 | 7-{[2-(acetylamino)pyridin-4-yl]oxy}-N-[4-(pyrrolidin-1-ylmethyl)-3-(trifluoromethyl)phenyl]-1,2,3,4-tetrahydronaphthalene-2-carboxamide |
| I-112 | 7-{[2-(4,5-dihydro-1H-imidazol-2-yl)pyridin-4-yl]oxy}-N-[4-(piperazin-1-ylmethyl)-3-(trifluoromethyl)phenyl]-2-naphthamide |
| I-113 | 7-{[2-(4,5-dihydro-1H-imidazol-2-yl)pyridin-4-yl]oxy}-N-[4-[(4-methylpiperazin-1-yl)methyl]-3-(trifluoromethyl)phenyl]-2-naphthamide |
| I-114 | 7-{[2-(4,5-dihydro-1H-imidazol-2-yl)pyridin-4-yl]oxy}-N-[4-[(dimethylamino)-methyl]-3-(trifluoromethyl)phenyl]-2-naphthamide |

|   | Chemical Name |
|---|---|
| I-115 | 7-{[2-(4,5-dihydro-1H-imidazol-2-yl)pyridin-4-yl]oxy}-N-[4-(pyrrolidin-1-ylmethyl)-3-(trifluoromethyl)phenyl]-2-naphthamide |
| I-116 | 7-{[2-(acetylamino)pyridin-4-yl]oxy}-N-[4-(piperazin-1-ylmethyl)-3-(trifluoromethyl)phenyl]-2-naphthamide |
| I-117 | 7-{[2-(acetylamino)pyridin-4-yl]oxy}-N-[4-[(4-methylpiperazin-1-yl)methyl]-3-(trifluoromethyl)phenyl]-2-naphthamide |
| I-118 | 7-{[2-(acetylamino)pyridin-4-yl]oxy}-N-[4-[(dimethylamino)methyl]-3-(trifluoromethyl)phenyl]-2-naphthamide |
| I-119 | 7-{[2-(acetylamino)pyridin-4-yl]oxy}-N-[4-(pyrrolidin-1-ylmethyl)-3-(trifluoromethyl)phenyl]-2-naphthamide |
| I-120 | N-(3-tert-butylphenyl)-7-{[2-(4,5-dihydro-1H-imidazol-2-yl)pyridin-4-yl]oxy}-3-hydroxy-1,2,3,4-tetrahydronaphthalene-2-carboxamide |
| I-121 | 4-[(7-{[(3-tert-butylphenyl)amino]carbonyl}-6-hydroxy-5,6,7,8-tetrahydronaphthalen-2-yl)oxy]-N-methylpyridine-2-carboxamide |
| I-122 | 7-{[2-(acetylamino)pyridin-4-yl]oxy}-N-(3-tert-butylphenyl)-3-hydroxy-1,2,3,4-tetrahydronaphthalene-2-carboxamide |
| I-123 | N-[4-chloro-3-(trifluoromethyl)phenyl]-7-{[2-(4,5-dihydro-1H-imidazol-2-yl)-pyridin-4-yl]oxy}-3-hydroxy-1,2,3,4-tetrahydronaphthalene-2-carboxamide |
| I-124 | 4-{[7-({[4-chloro-3-(trifluoromethyl)phenyl]amino}carbonyl)-6-hydroxy-5,6,7,8-tetrahydronaphthalen-2-yl]oxy}-N-methylpyridine-2-carboxamide |
| I-125 | 7-{[2-(acetylamino)pyridin-4-yl]oxy}-N-[4-chloro-3-(trifluoromethyl)phenyl]-3-hydroxy-1,2,3,4-tetrahydronaphthalene-2-carboxamide |
| I-126 | 4-{[7-({[4-[(dimethylamino)methyl]-3-(trifluoromethyl)phenyl]amino}carbonyl)-5,6,7,8-tetrahydronaphthalen-2-yl]oxy}-N-methylpyridine-2-carboxamide |
| I-127 | N-methyl-4-{[7-({[4-(piperazin-1-ylmethyl)-3-(trifluoromethyl)phenyl]-amino}carbonyl)-5,6,7,8-tetrahydronaphthalen-2-yl]oxy}pyridine-2-carboxamide |
| I-128 | N-methyl-4-{[7-({[4-[(4-methylpiperazin-1-yl)methyl]-3-(trifluoromethyl)-phenyl]amino}carbonyl)-5,6,7,8-tetrahydronaphthalen-2-yl]oxy}pyridine-2-carboxamide |
| I-129 | N-methyl-4-{[7-({[4-(pyrrolidin-1-ylmethyl)-3-(trifluoromethyl)phenyl]-amino}carbonyl)-5,6,7,8-tetrahydronaphthalen-2-yl]oxy}pyridine-2-carboxamide |
| I-131 | N-(3-tert-butylphenyl)-7-({2-[(cyclopropylcarbonyl)amino]pyridin-4-yl}oxy)-2-naphthamide |
| I-132 | N-[4-chloro-3-(trifluoromethyl)phenyl]-7-({2-[(cyclopropylcarbonyl)-amino]pyridin-4-yl}oxy)-2-naphthamide |
| I-133 | N-{4-[(7-{[(3-tert-butylphenyl)amino]carbonyl}-2-naphthyl)oxy]pyridin-2-yl}-4-methylpiperazine-1-carboxamide |
| I-134 | N-(4-{[7-({[4-chloro-3-(trifluoromethyl)phenyl]amino}carbonyl)-2-naphthyl]-oxy}pyridin-2-yl)-4-methylpiperazine-1-carboxamide |
| I-135 | N-{4-[(7-{[(3-tert-butylphenyl)amino]carbonyl}-2-naphthyl)oxy]pyridin-2-yl}-pyrrolidine-1-carboxamide |
| I-136 | N-(4-{[7-({[4-chloro-3-(trifluoromethyl)phenyl]amino}carbonyl)-2-naphthyl]-oxy}pyridin-2-yl)pyrrolidine-1-carboxamide |
| I-137 | N-(3-tert-butylphenyl)-7-[(2-{[(dimethylamino)acetyl]amino}pyridin-4-yl)oxy]-2-naphthamide |
| I-138 | N-[4-chloro-3-(trifluoromethyl)phenyl]-7-[(2-{[(dimethylamino)acetyl]-amino}pyridin-4-yl)oxy]-2-naphthamide |
| I-139 | 7-[(2-aminopyridin-4-yl)oxy]-N-(3-tert-butylisoxazol-5-yl)-2-naphthamide |
| I-140 | 7-[(2-aminopyridin-4-yl)oxy]-N-(3-tert-butylphenyl)-2-naphthamide |
| I-141 | N-{4-[(7-{[(3-tert-butylphenyl)amino]carbonyl}-2-naphthyl)oxy]pyridin-2-yl}-4-methylpiperazine-1-carboxamide |
| I-142 | 7-[(2-aminopyridin-4-yl)oxy]-N-[3-(2-pyrrolidin-1-ylethoxy)-5-(trifluoromethyl)phenyl]-2-naphthamide |
| I-143 | 4-{[3-({[4-(aminomethyl)-3-(trifluoromethyl)phenyl]amino}carbonyl)-2H-chromen-6-yl]oxy}-N-methylpyridine-2-carboxamide |
| I-144 | N-(3-tert-butylphenyl)-7-[(2-{[(dimethylamino)carbonyl]amino}pyridin-4-yl)-oxy]-2-naphthamide |
| I-145 | N-[4-chloro-3-(trifluoromethyl)phenyl]-7-[(2-{[(dimethylamino)carbonyl]-amino}pyridin-4-yl)oxy]-2-naphthamide |
| I-146 | 7-{[2-(acetylamino)pyridin-4-yl]oxy}-N-(3-tert-butylisoxazol-5-yl)-1,2,3,4-tetrahydronaphthalene-2-carboxamide |
| I-147 | 7-{[2-(acetylamino)pyridin-4-yl]oxy}-N-[3-(2-pyrrolidin-1-ylethoxy)-5-(trifluoromethyl)phenyl]-1,2,3,4-tetrahydronaphthalene-2-carboxamide |
| I-148 | 7-{[2-(acetylamino)pyridin-4-yl]oxy}-N-[4-(aminomethyl)-3-(trifluoromethyl)-phenyl]-1,2,3,4-tetrahydronaphthalene-2-carboxamide |
| I-149 | 7-{[2-(acetylamino)pyridin-4-yl]oxy}-N-(3-tert-butylisoxazol-5-yl)-2-naphthamide |
| I-151 | 7-{[2-(acetylamino)pyridin-4-yl]oxy}-N-[4-(aminomethyl)-3-(trifluoromethyl)-phenyl]-2-naphthamide |
| I-152 | 7-{[2-(acetylamino)pyridin-4-yl]oxy}-N-[3-(2-pyrrolidin-1-ylethoxy)-5-(trifluoromethyl)phenyl]-2-naphthamide |
| I-153 | N-(3-tert-butylphenyl)-7-({2-[4-(hydroxymethyl)-1H-imidazol-2-yl]pyridin-4-yl}oxy)-2-naphthamide |
| I-154 | N-(3-tert-butylphenyl)-7-[(2-{4-[(4-methylpiperazin-1-yl)carbonyl]-1H-imidazol-2-yl}pyridin-4-yl)oxy]-1,2,3,4-tetrahydronaphthalene-2-carboxamide |

| | Chemical Name |
|---|---|
| I-155 | 2-{4-[(7-{[(3-tert-butylphenyl)amino]carbonyl}-5,6,7,8-tetrahydronaphthalen-2-yl)oxy]pyridin-2-yl}-1H-imidazole-4-carboxylic acid |
| I-156 | N-(3-tert-butylphenyl)-7-[(2-{4-[(4-methylpiperazin-1-yl)methyl]-1H-imidazol-2-yl}pyridin-4-yl)oxy]-1,2,3,4-tetrahydronaphthalene-2-carboxamide |
| I-157 | 7-{[2-(acetylamino)pyridin-4-yl]oxy}-N-[4-cyano-3-(trifluoromethyl)phenyl]-2-naphthamide |
| I-158 | 7-[(2-aminopyridin-4-yl)oxy]-N-[4-cyano-3-(trifluoromethyl)phenyl]-2-naphthamide |
| I-159 | tert-butyl (4-{[7-({[4-cyano-3-(trifluoromethyl)phenyl]amino}carbonyl)-2-naphthyl]oxy}pyridin-2-yl)carbamate |
| I-160 | 7-{[2-(acetylamino)pyridin-4-yl]oxy}-N-(3-tert-butylisoxazol-5-yl)-2-naphthamide |
| I-161 | N-[4-(aminomethyl)-3-(trifluoromethyl)phenyl]-6-({2-[(methylamino)carbonyl]pyridin-4-yl}oxy)quinoline-3-carboxamide |
| I-162 | 7-[(2-aminopyridin-4-yl)oxy]-N-[4-chloro-3-(trifluoromethyl)phenyl]-2-naphthamide |
| I-163 | tert-butyl (4-{[7-({[4-chloro-3-(trifluoromethyl)phenyl]amino}carbonyl)-2-naphthyl]oxy}pyridin-2-yl)carbamate |
| I-164 | N-[4-chloro-3-(trifluoromethyl)phenyl]-7-({2-[(methylamino)carbonyl]pyridin-4-yl}oxy)-3,4-dihydroisoquinoline-2(1H)-carboxamide |
| I-165 | N-(5-tert-butyl-2-fluorophenyl)-7-({2-[(methylamino)carbonyl]pyridin-4-yl}oxy)-3,4-dihydroisoquinoline-2(1H)-carboxamide |
| I-166 | N-(5-tert-butyl-2-fluorophenyl)-7-[(2-{5-[(4-methylpiperazin-1-yl)methyl]-1H-imidazol-2-yl}pyridin-4-yl)oxy]-3,4-dihydroisoquinoline-2(1H)-carboxamide |
| I-167 | N-(3-tert-butylphenyl)-7-({2-[5-(hydroxymethyl)-1H-imidazol-2-yl]pyridin-4-yl}oxy)-3,4-dihydroisoquinoline-2(1H)-carboxamide |
| I-168 | N-(5-tert-butyl-2-fluorophenyl)-7-{[2-(1H-imidazol-2-yl)pyridin-4-yl]oxy}-3,4-dihydroisoquinoline-2(1H)-carboxamide |
| I-169 | N-(3-tert-butylphenyl)-7-{[2-(1H-imidazol-2-yl)pyridin-4-yl]oxy}-3,4-dihydroisoquinoline-2(1H)-carboxamide |
| I-170 | N-[4-chloro-3-(trifluoromethyl)phenyl]-7-[(2-{5-[(4-methylpiperazin-1-yl)carbonyl]-1H-imidazol-2-yl}pyridin-4-yl)oxy]-3,4-dihydroisoquinoline-2(1H)-carboxamide |
| I-171 | N-[4-chloro-3-(trifluoromethyl)phenyl]-7-({2-[5-(hydroxymethyl)-1H-imidazol-2-yl]pyridin-4-yl}oxy)-3,4-dihydroisoquinoline-2(1H)-carboxamide |
| I-172 | N-[4-chloro-3-(trifluoromethyl)phenyl]-7-{[2-(4,5-dihydro-1H-imidazol-2-yl)pyridin-4-yl]oxy}-3,4-dihydroisoquinoline-2(1H)-carboxamide |
| I-173 | N-(5-tert-butyl-2-fluorophenyl)-7-{[2-(4,5-dihydro-1H-imidazol-2-yl)pyridin-4-yl]oxy}-3,4-dihydroisoquinoline-2(1H)-carboxamide |
| I-174 | N-[4-chloro-3-(trifluoromethyl)phenyl]-7-[(2-{[(4-methylpiperazin-1-yl)acetyl]amino}pyridin-4-yl)oxy]-3,4-dihydroisoquinoline-2(1H)-carboxamide |
| I-175 | 7-{[2-(acetylamino)pyridin-4-yl]oxy}-N-[4-chloro-3-(trifluoromethyl)phenyl]-3,4-dihydroisoquinoline-2(1H)-carboxamide |
| I-176 | 7-[(2-aminopyridin-4-yl)oxy]-N-(3-tert-butylphenyl)-3,4-dihydroisoquinoline-2(1H)-carboxamide |
| I-177 | N-(3-tert-butylphenyl)-7-({2-[(methylamino)carbonyl]pyridin-4-yl}oxy)-3,4-dihydroisoquinoline-2(1H)-carboxamide |

Additional examples of compounds of formula (I) are listed below.

| | Chemical Name |
|---|---|
| I-178 | N-(3-tert-butylphenyl)-7-({2-[imino(4-methylpiperazin-1-yl)methyl]pyridin-4-yl}oxy)-1,2,3,4-tetrahydronaphthalene-2-carboxamide |
| I-179 | N-(3-tert-butylphenyl)-7-({2-[(4-methoxybenzyl)(methyl)amino]pyridin-4-yl}oxy)-1,2,3,4-tetrahydronaphthalene-2-carboxamide |
| I-180 | (2S)-7-{[2-(acetylamino)pyridin-4-yl]oxy}-N-[3-(aminomethyl)-5-(trifluoromethyl)phenyl]-1,2,3,4-tetrahydronaphthalene-2-carboxamide |
| I-181 | 7-{[2-(acetylamino)pyridin-4-yl]oxy}-N-[3-[(4-ethylpiperazin-1-yl)methyl]-5-(trifluoromethyl)phenyl]-1,2,3,4-tetrahydronaphthalene-2-carboxamide |
| I-182 | N-methyl-4-{[7-({[3-[(4-methylpiperazin-1-yl)methyl]-5-(trifluoromethyl)phenyl]amino}carbonyl)-5,6,7,8-tetrahydronaphthalen-2-yl]oxy}pyridine-2-carboxamide |
| I-183 | N-[3-(aminomethyl)-5-(trifluoromethyl)phenyl]-7-(2,4'-bipyridin-4-yloxy)-1,2,3,4-tetrahydronaphthalene-2-carboxamide |
| I-184 | N-[3-(aminomethyl)-5-(trifluoromethyl)phenyl]-7-{[2-(3,5-dimethylisoxazol-4-yl)pyridin-4-yl]oxy}-1,2,3,4-tetrahydronaphthalene-2-carboxamide |
| I-185 | (2R)-7-{[2-(acetylamino)pyridin-4-yl]oxy}-N-[3-(pyrrolidin-1-ylmethyl)-5-(trifluoromethyl)phenyl]-1,2,3,4-tetrahydronaphthalene-2-carboxamide |
| I-186 | 6-({2-[(cyclopropylcarbonyl)amino]pyridin-4-yl}oxy)-N-[3-{[(3S)-3-fluoropyrrolidin-1-yl]methyl}-5-(trifluoromethyl)phenyl]-2H-chromene-3-carboxamide |

|   | Chemical Name |
|---|---|
| I-187 | N-[3-(aminomethyl)-5-(trifluoromethyl)phenyl]-7-[(7-oxo-7,8-dihydro-1,8-naphthyridin-4-yl)oxy]-1,2,3,4-tetrahydronaphthalene-2-carboxamide |
| I-189 | N-[3-(aminomethyl)-5-(trifluoromethyl)phenyl]-7-({2-[4-(pyrrolidin-1-ylmethyl)-1H-imidazol-2-yl]pyridin-4-yl}oxy)-1,2,3,4-tetrahydronaphthalene-2-carboxamide |
| I-190 | N-(3-tert-butylphenyl)-7-({2-[({[2-(dimethylamino)ethyl]amino}acetyl)-amino]pyridin-4-yl}oxy)-2-naphthamide |
| I-191 | N-[3-(aminomethyl)-5-(trifluoromethyl)phenyl]-7-[(7-oxo-5,6,7,8-tetrahydro-1,8-naphthyridin-4-yl)oxy]-1,2,3,4-tetrahydronaphthalene-2-carboxamide |
| I-192 | methyl [(4-{[7-({[3-(aminomethyl)-5-(trifluoromethyl)phenyl]amino}carbonyl)-5,6,7,8-tetrahydronaphthalen-2-yl]oxy}pyridin-2-yl)methyl]carbamate |
| I-193 | methyl (4-{[7-({[3-(aminomethyl)-5-(trifluoromethyl)phenyl]amino}carbonyl)-5,6,7,8-tetrahydronaphthalen-2-yl]oxy}pyridin-2-yl)carbamate |
| I-194 | N-(3-tert-butylphenyl)-7-({2-[imino(pyrrolidin-1-yl)methyl]pyridin-4-yl}oxy)-1,2,3,4-tetraydronaphthalene-2-carboxamide |
| I-195 | 7-({2-[(cyclopropylcarbonyl)amino]pyridin-4-yl}oxy)-N-[3-[(4-ethylpiperazin-1-yl)methyl]-5-(trifluoromethyl)phenyl]-1,2,3,4-tetrahydronaphthalene-2-carboxamide |
| I-196 | 2-pyrrolidin-1-ylethyl {4-[(7-{[(3-tert-butylphenyl)amino]carbonyl}-2-naphthyl)-oxy]pyridin-2-yl}carbamate |
| I-197 | 7-{[2-(acetylamino)pyridin-4-yl]oxy}-N-[3-(1-amino-1-methylethyl)-5-(trifluoromethyl)phenyl]-1,2,3,4-tetrahydronaphthalene-2-carboxamide |
| I-198 | 7-{[2-(acetylamino)pyridin-4-yl]oxy}-N-(3-tert-butyl-4-fluorophenyl)-1,2,3,4-tetrahydronaphthalene-2-carboxamide |
| I-199 | 7-({2-[(cyclopropylcarbonyl)amino]pyridin-4-yl}oxy)-N-[3-(2-pyrrolidin-1-ylethoxy)-5-(trifluoromethyl)phenyl]-1,2,3,4-tetrahydronaphthalene-2-carboxamide |
| I-201 | (2R)-7-{[2-(acetylamino)pyridin-4-yl]oxy}-N-[3-(aminomethyl)-5-(trifluoromethyl)phenyl]-1,2,3,4-tetrahydronaphthalene-2-carboxamide |
| I-202 | N-(3-tert-butylphenyl)-7-{[2-({[(isopropylamino)acetyl]amino}methyl)pyridin-4-yl]oxy}-1,2,3,4-tetrahydronaphthalene-2-carboxamide |
| I-203 | 7-({2-[(acetylamino)methyl]pyridin-4-yl}oxy)-N-[3-(aminomethyl)-5-(trifluoromethyl)phenyl]-1,2,3,4-tetrahydronaphthalene-2-carboxamide |
| I-204 | N-methyl-4-({7-[(1,2,3,4-tetrahydroisoquinolin-7-ylamino)carbonyl]-5,6,7,8-tetrahydronaphthalen-2-yl}oxy)pyridine-2-carboxamide |
| I-205 | N-[3-(aminomethyl)-5-(trifluoromethyl)phenyl]-7-{[2-(1H-imidazol-1-yl)-pyridin-4-yl]oxy}-1,2,3,4-tetrahydronaphthalene-2-carboxamide |
| I-206 | 7-({2-[(cyclopropylcarbonyl)amino]pyridin-4-yl}oxy)-N-[3-(hydroxymethyl)-5-(trifluoromethyl)phenyl]-1,2,3,4-tetrahydronaphthalene-2-carboxamide |
| I-207 | N-(3-tert-butylphenyl)-7-({2-[(2-pyrrolidin-1-ylpropanoyl)amino]pyridin-4-yl}-oxy)-2-naphthamide |
| I-208 | 7-{[2-(acetylamino)pyridin-4-yl]oxy}-N-(2-tert-butylpyrimidin-5-yl)-1,2,3,4-tetrahydronaphthalene-2-carboxamide |
| I-209 | 7-{[2-(acetylamino)pyridin-4-yl]oxy}-N-[3-(1-hydroxy-1-methylethyl)-5-(trifluoromethyl)phenyl]-1,2,3,4-tetrahydronaphthalene-2-carboxamide |
| I-210 | N-[3-(aminomethyl)-5-(trifluoromethyl)phenyl]-7-{[2-(1,3-oxazol-5-yl)pyridin-4-yl]oxy}-1,2,3,4-tetrahydronaphthalene-2-carboxamide |
| I-211 | 7-{[2-(acetylamino)pyridin-4-yl]oxy}-N-(4-chloro-3-methylphenyl)-1,2,3,4-tetrahydronaphthalene-2-carboxamide |
| I-212 | N-[3-(aminomethyl)-5-tert-butylphenyl]-7-({2-[(cyclopropylcarbonyl)-amino]pyridin-4-yl}oxy)-1,2,3,4-tetrahydronaphthalene-2-carboxamide |
| I-213 | 7-({2-[(2,2-dimethylpropanoyl)amino]pyridin-4-yl}oxy)-N-[3-(2-pyrrolidin-1-ylethoxy)-5-(trifluoromethyl)phenyl]-1,2,3,4-tetrahydronaphthalene-2-carboxamide |
| I-214 | 7-({2-[(cyclopropylcarbonyl)amino]pyridin-4-yl}oxy)-N-[3-(1,1-difluoroethyl)-phenyl]-1,2,3,4-tetrahydronaphthalene-2-carboxamide |
| I-215 | 7-{[2-(acetylamino)pyridin-4-yl]oxy}-N-[3-(aminomethyl)-5-(trifluoromethyl)-phenyl]-2-naphthamide |
| I-216 | N-(3-tert-butylphenyl)-7-[(2-{5-[(4-methylpiperazin-1-yl)methyl]-1H-imidazol-2-yl}pyridin-4-yl)oxy]-2-naphthamide |
| I-217 | 7-{[2-(acetylamino)pyridin-4-yl]oxy}-N-[3-(trifluoromethyl)phenyl]-1,2,3,4-tetrahydronaphthalene-2-carboxamide |
| I-218 | 6-{[2-(4-methyl-4,5-dihydro-1H-imidazol-2-yl)pyridin-4-yl]oxy}-N-[3-(2-pyrrolidin-1-ylethoxy)-5-(trifluoromethyl)phenyl]quinoline-3-carboxamide |
| I-219 | 7-{[2-(acetylamino)pyridin-4-yl]oxy}-N-[3-(piperidin-1-ylmethyl)-5-(trifluoromethyl)phenyl]-1,2,3,4-tetrahydronaphthalene-2-carboxamide |
| I-220 | methyl (4-{[(7S)-7-({[3-(aminomethyl)-5-(trifluoromethyl)phenyl]-amino}carbonyl)-5,6,7,8-tetrahydronaphthalen-2-yl]oxy}pyridin-2-yl)carbamate |
| I-222 | 6-{[2-(4,5-dihydro-1H-imidazol-2-yl)pyridin-4-yl]oxy}-N-[3-(2-pyrrolidin-1-ylethoxy)-5-(trifluoromethyl)phenyl]quinoline-3-carboxamide |
| I-223 | N-[3-tert-butyl-5-(pyrrolidin-1-ylmethyl)phenyl]-7-({2-[(cyclopropylcarbonyl)-amino]pyridin-4-yl}oxy)-1,2,3,4-tetrahydronaphthalene-2-carboxamide |
| I-224 | 7-({2-[(cyclopropylcarbonyl)amino]pyridin-4-yl}oxy)-N-[3-(2-pyrrolidin-1-ylethoxy)-5-(trifluoromethyl)phenyl]-2-naphthamide |
| I-226 | 7-({2-[(cyclopropylcarbonyl)amino]pyridin-4-yl}oxy)-N-[3-{[(2-hydroxyethyl)-amino]methyl}-5-(trifluoromethyl)phenyl]-1,2,3,4-tetrahydronaphthalene-2-carboxamide |

| | Chemical Name |
|---|---|
| I-227 | methyl (4-{[7-({[3-(2-pyrrolidin-1-ylethoxy)-5-(trifluoromethyl)phenyl]-amino}carbonyl)-5,6,7,8-tetrahydronaphthalen-2-yl]oxy}pyridin-2-yl)carbamate |
| I-229 | 4-{[7-({[3-(aminomethyl)-5-(trifluoromethyl)phenyl]amino}carbonyl)-5,6,7,8-tetrahydronaphthalen-2-yl]oxy}-N-isopropylpyridine-2-carboxamide |
| I-230 | 4-{[7-({[3-{[(3-amino-3-oxopropyl)amino]methyl}-5-(trifluoromethyl)phenyl]-amino}carbonyl)-5,6,7,8-tetrahydronaphthalen-2-yl]oxy}-N-methylpyridine-2-carboxamide |
| I-231 | N-(3-tert-butylphenyl)-7-{[2-(1H-pyrazol-3-yl)pyridin-4-yl]oxy}-1,2,3,4-tetrahydronaphthalene-2-carboxamide |
| I-232 | 7-{[2-(acetylamino)pyridin-4-yl]oxy}-N-phenyl-1,2,3,4-tetrahydronaphthalene-2-carboxamide |
| I-233 | N-(3-tert-butylphenyl)-6-[(2-{4-[(4-methylpiperazin-1-yl)methyl]-1H-imidazol-2-yl}pyridin-4-yl)oxy]quinoline-3-carboxamide |
| I-234 | 7-{[2-(acetylamino)pyridin-4-yl]oxy}-N-[3-[(4-methylpiperazin-1-yl)methyl]-5-(trifluoromethyl)phenyl]-1,2,3,4-tetrahydronaphthalene-2-carboxamide |
| I-235 | 7-[(2-aminopyridin-4-yl)oxy]-N-(3-tert-butylphenyl)-1,2,3,4-tetrahydronaphthalene-2-carboxamide |
| I-236 | 7-{[2-(acetylamino)pyridin-4-yl]oxy}-N-(5-tert-butyl-2-fluorophenyl)-1,2,3,4-tetrahydronaphthalene-2-carboxamide |
| I-237 | 7-[(2-piperan-1-ylpyridin-4-yl)oxy]-N-[3-(2-pyrrolidin-1-ylethoxy)-5-(trifluoromethyl)phenyl]-1,2,3,4-tetrahydronaphthalene-2-carboxamide |
| I-238 | N-[3-(aminomethyl)-5-(trifluoromethyl)phenyl]-7-{[2-(propionylamino)pyridin-4-yl]oxy}-1,2,3,4-tetrahydronaphthalene-2-carboxamide |
| I-239 | 2-{4-[(7-{[(3-tert-butylphenyl)amino]carbonyl}-2-naphthyl)oxy]pyridin-2-yl}-1H-imidazole-4-carboxylic acid |
| I-240 | N-[3-(aminomethyl)-5-(trifluoromethyl)phenyl]-7-({2-[(cyclobutylcarbonyl)-amino]pyridin-4-yl}oxy)-1,2,3,4-tetrahydronaphthalene-2-carboxamide |
| I-241 | methyl (4-{[7-({[3-(2-pyrrolidin-1-ylethoxy)-5-(trifluoromethyl)phenyl]-amino}carbonyl)-2-naphthyl]oxy}pyridin-2-yl)carbamate |
| I-242 | 7-{[2-(acetylamino)pyridin-4-yl]oxy}-N-[4-cyano-3-(trifluoromethyl)phenyl]-1,2,3,4-tetrahydronaphthalene-2-carboxamide |
| I-243 | 7-{[2-(acetylamino)pyridin-4-yl]oxy}-N-[3-pyrrolidin-2-yl-5-(trifluoromethyl)-phenyl]-1,2,3,4-tetrahydronaphthalene-2-carboxamide |
| I-244 | 4-{[(7R)-7-({[3-(aminomethyl)-5-(trifluoromethyl)phenyl]amino}carbonyl)-5,6,7,8-tetrahydronaphthalen-2-yl]oxy}-N-methylpyridine-2-carboxamide |
| I-245 | N-(3-tert-butylphenyl)-7-{[2-(1,4,5,6-tetrahydropyrimidin-2-yl)pyridin-4-yl]-oxy}-2-naphthamide |
| I-246 | 7-({2-[(acetylamino)methyl]pyridin-4-yl}oxy)-N-(3-tert-butylphenyl)-1,2,3,4-tetrahydronaphthalene-2-carboxamide |
| I-247 | 7-{[2-(acetylamino)pyridin-4-yl]oxy}-N-(3-isopropylphenyl)-1,2,3,4-tetrahydronaphthalene-2-carboxamide |
| I-249 | 7-({2-[(cyclopropylcarbonyl)amino]pyridin-4-yl}oxy)-N-[3-{[(3S)-3-hydroxypyrrolidin-1-yl]methyl}-5-(trifluoromethyl)phenyl]-1,2,3,4-tetrahydronaphthalene-2-carboxamide |
| I-250 | 7-({2-[(cyclopropylcarbonyl)amino]pyridin-4-yl}oxy)-N-[3-[(ethylamino)-methyl]-5-(trifluoromethyl)phenyl]-1,2,3,4-tetrahydronaphthalene-2-carboxamide |
| I-251 | N-[3-(aminomethyl)-5-(trifluoromethyl)phenyl]-7-[(2-{4-[(4-methylpiperazin-1-yl)carbonyl]-1H-imidazol-2-yl}pyridin-4-yl)oxy]-1,2,3,4-tetrahydronaphthalene-2-carboxamide |
| I-252 | N-[3-(aminomethyl)-5-(trifluoromethyl)phenyl]-7-{[2-(1H-pyrazol-4-yl)pyridin-4-yl]oxy}-1,2,3,4-tetrahydronaphthalene-2-carboxamide |
| I-253 | methyl {4-[(7-{[(3-tert-butylphenyl)amino]carbonyl}-5,6,7,8-tetrahydronaphthalen-2-yl)oxy]pyridin-2-yl}carbamate |
| I-254 | N-(3-tert-butylphenyl)-7-({2-[(methylsulfonyl)amino]pyridin-4-yl}oxy)-1,2,3,4-tetrahydronaphthalene-2-carboxamide |
| I-255 | 7-{[2-(acetylamino)pyridin-4-yl]oxy}-N-[3-[(diethylamino)methyl]-5-(trifluoromethyl)phenyl]-1,2,3,4-tetrahydronaphthalene-2-carboxamide |
| I-256 | 7-({2-[(cyclopropylcarbonyl)amino]pyridin-4-yl}oxy)-N-[3-pyrrolidin-2-yl-5-(trifluoromethyl)phenyl]-1,2,3,4-tetrahydronaphthalene-2-carboxamide |
| I-257 | 7-(2,3'-bipyridin-4-yloxy)-N-(3-tert-butylphenyl)-1,2,3,4-tetrahydronaphthalene-2-carboxamide |
| I-259 | N-[4-chloro-3-(trifluoromethyl)phenyl]-7-({2-[(cyclopropylcarbonyl)-amino]pyridin-4-yl}oxy)-3,4-dihydroisoquinoline-2(1H)-carboxamide |
| I-260 | N-(3-tert-butylphenyl)-7-({2-[(cyclopentylamino)(imino)methyl]pyridin-4-yl}-oxy)-2-naphthamide |
| I-261 | 7-{[2-(4,5-dihydro-1H-imidazol-2-yl)pyridin-4-yl]oxy}-N-[2-(2-piperazin-1-ylethoxy)-5-(trifluoromethyl)phenyl]-1,2,3,4-tetrahydronaphthalene-2-carboxamide |
| I-264 | N-(3-tert-butylphenyl)-7-[(2-{[(4-methylpiperazin-1-yl)acetyl]amino}pyridin-4-yl)oxy]-2-naphthamide |
| I-265 | N-(3-tert-butylphenyl)-7-({2-[imino(morpholin-4-yl)methyl]pyridin-4-yl}oxy)-1,2,3,4-tetrahydronaphthalene-2-carboxamide |
| I-266 | N-[4-(aminomethyl)-3-(trifluoromethyl)phenyl]-6-({2-[4-(hydroxymethyl)-1H-imidazol-2-yl]pyridin-4-yl}oxy)quinoline-3-carboxamide |
| I-267 | N-[3-(aminomethyl)-5-(trifluoromethyl)phenyl]-6-({2-[(cyclopropylcarbonyl)-amino]pyridin-4-yl}oxy)-2H-chromene-3-carboxamide |

| | Chemical Name |
|---|---|
| I-269 | 7-({2-[(cyclopropylcarbonyl)amino]pyridin-4-yl}oxy)-N-[3-(pyrrolidin-1-ylmethyl)-5-(trifluoromethyl)phenyl]-1,2,3,4-tetrahydronaphthalene-2-carboxamide |
| I-270 | (2R)-N-[3-(aminomethyl)-5-(trifluoromethyl)phenyl]-7-({2-[(cyclopropylcarbonyl)amino]pyridin-4-yl}oxy)-1,2,3,4-tetrahydronaphthalene-2-carboxamide |
| I-271 | N-[3-(aminomethyl)-5-(trifluoromethyl)phenyl]-7-[(2-aminopyridin-4-yl)oxy]-1,2,3,4-tetrahydronaphthalene-2-carboxamide |
| I-272 | (2S)-2,3-dihydroxypropyl {4-[(7-{[(3-tert-butylphenyl)amino]carbonyl}-5,6,7,8-tetrahydronaphthalen-2-yl)oxy]pyridin-2-yl}carbamate |
| I-273 | N-(3-tert-butylphenyl)-7-({2-[(pyrrolidin-1-ylacetyl)amino]pyridin-4-yl}oxy)-1,2,3,4-tetrahydronaphthalene-2-carboxamide |
| I-274 | N-methyl-4-{[7-({[3-({[(methylamino)acetyl]amino}methyl)-5-(trifluoromethyl)phenyl]amino}carbonyl)-5,6,7,8-tetrahydronaphthalen-2-yl]oxy}pyridine-2-carboxamide |
| I-275 | N-(3-tert-butylphenyl)-7-({2-[(2-pyrrolidin-1-ylpropanoyl)amino]pyridin-4-yl}oxy)-1,2,3,4-tetrahydronaphthalene-2-carboxamide |
| I-276 | 4-{[7-({[3-{[(2-hydroxyethyl)amino]methyl}-5-(trifluoromethyl)phenyl]amino}carbonyl)-5,6,7,8-tetrahydronaphthalen-2-yl]oxy}-N-methylpyridine-2-carboxamide |
| I-277 | (2R)-2,3-dihydroxypropyl {4-[(7-{[(3-tert-butylphenyl)amino]carbonyl}-5,6,7,8-tetrahydronaphthalen-2-yl)oxy]pyridin-2-yl}carbamate |
| I-278 | N-(3-tert-butylphenyl)-7-[(2-piperazin-1-ylpyridin-4-yl)oxy]-1,2,3,4-tetrahydronaphthalene-2-carboxamide |
| I-279 | 6-({2-[(cyclopropylcarbonyl)amino]pyridin-4-yl}oxy)-N-[3-[(4-methylpiperazin-1-yl)methyl]-5-(trifluoromethyl)phenyl]-2H-chromene-3-carboxamide |
| I-280 | N-(3-tert-butylphenyl)-7-({2-[imino(piperazin-1-yl)methyl]pyridin-4-yl}oxy)-1,2,3,4-tetrahydronaphthalene-2-carboxamide |
| I-281 | 7-{[2-(acetylamino)pyridin-4-yl]oxy}-N-[4-(trifluoromethyl)phenyl]-1,2,3,4-tetrahydronaphthalene-2-carboxamide |
| I-282 | 7-{[2-(acetylamino)pyridin-4-yl]oxy}-N-[4-[(methylamino)methyl]-3-(trifluoromethyl)phenyl]-1,2,3,4-tetrahydronaphthalene-2-carboxamide |
| I-283 | tert-butyl [3-({[7-({2-[(methylamino)carbonyl]pyridin-4-yl}oxy)-1,2,3,4-tetrahydronaphthalen-2-yl]carbonyl}amino)-5-(trifluoromethyl)benzyl](2-pyrrolidin-1-ylethyl)carbamate |
| I-284 | 4-{[7-({[3-({[(dimethylamino)acetyl]amino}methyl)-5-(trifluoromethyl)phenyl]amino}carbonyl)-5,6,7,8-tetrahydronaphthalen-2-yl]oxy}-N-methylpyridine-2-carboxamide |
| I-285 | 4-{[7-({[3-(aminomethyl)-5-(trifluoromethyl)phenyl]amino}carbonyl)-3-fluoro-5,6,7,8-tetrahydronaphthalen-2-yl]oxy}-N-methylpyridine-2-carboxamide |
| I-286 | 7-{[2-(acetylamino)pyridin-4-yl]oxy}-N-[3-(hydroxymethyl)-5-(trifluoromethyl)phenyl]-1,2,3,4-tetrahydronaphthalene-2-carboxamide |
| I-287 | 7-{[2-(acetylamino)pyridin-4-yl]oxy}-N-[3-(pyrrolidin-1-ylmethyl)-5-(trifluoromethyl)phenyl]-1,2,3,4-tetrahydronaphthalene-2-carboxamide |
| I-288 | 4-[(7-{[(3-tert-butylphenyl)amino]carbonyl}-2-naphthyl)oxy]-N-methylpyridine-2-carboxamide |
| I-289 | N-(3-tert-butylphenyl)-7-({2-[(2-morpholin-4-ylpropanoyl)amino]pyridin-4-yl}oxy)-2-naphthamide |
| I-290 | N-(3-tert-butylphenyl)-6-{[2-(4,5-dihydro-1H-imidazol-2-yl)pyridin-4-yl]oxy}quinoline-3-carboxamide |
| I-293 | 7-({2-[(cyclopropylcarbonyl)amino]pyridin-4-yl}oxy)-N-[3-[(4-methylpiperazin-1-yl)methyl]-5-(trifluoromethyl)phenyl]-1,2,3,4-tetrahydronaphthalene-2-carboxamide |
| I-294 | N-[3-(aminomethyl)-5-(trifluoromethyl)phenyl]-7-[(2-pyrimidin-5-ylpyridin-4-yl)oxy]-1,2,3,4-tetrahydronaphthalene-2-carboxamide |
| I-296 | N-methyl-4-{[7-({[3-[(methylamino)methyl]-5-(trifluoromethyl)phenyl]amino}carbonyl)-5,6,7,8-tetrahydronaphthalen-2-yl]oxy}pyridine-2-carboxamide |
| I-298 | N-methyl-4-{[3-({[3-(2-pyrrolidin-1-ylethoxy)-5-(trifluoromethyl)phenyl]amino}carbonyl)-2H-chromen-6-yl]oxy}pyridine-2-carboxamide |
| I-299 | N-(3-tert-butylphenyl)-6-(pyridin-4-yloxy)quinoline-3-carboxamide |
| I-300 | N-methyl-4-{[7-({[2-(2-piperazin-1-ylethoxy)-5-(trifluoromethyl)phenyl]amino}carbonyl)-5,6,7,8-tetrahydronaphthalen-2-yl]oxy}pyridine-2-carboxamide |
| I-301 | 6-({2-[(cyclopropylcarbonyl)amino]pyridin-4-yl}oxy)-N-[3-(pyrrolidin-1-ylmethyl)-5-(trifluoromethyl)phenyl]-2H-chromene-3-carboxamide |
| I-303 | 7-{[2-(acetylamino)pyridin-4-yl]oxy}-N-(4-chlorophenyl)-1,2,3,4-tetrahydronaphthalene-2-carboxamide |
| I-304 | N-[3-(aminomethyl)-5-(trifluoromethyl)phenyl]-7-{[1-oxido-2-(1H-pyrazol-1-yl)pyridin-4-yl]oxy}-1,2,3,4-tetrahydronaphthalene-2-carboxamide |
| I-305 | N-(3-tert-butylphenyl)-7-{[2-(4,5-dihydro-1,3-oxazol-2-yl)pyridin-4-yl]oxy}-1,2,3,4-tetrahydronaphthalene-2-carboxamide |
| I-306 | N-(3-tert-butylphenyl)-7-({2-[(pyrrolidin-1-ylacetyl)amino]pyridin-4-yl}oxy)-2-naphthamide |
| I-307 | 7-({2-[(cyclopropylcarbonyl)amino]pyridin-4-yl}oxy)-N-[3-[(methylamino)methyl]-5-(trifluoromethyl)phenyl]-1,2,3,4-tetrahydronaphthalene-2-carboxamide |

| | Chemical Name |
|---|---|
| I-308 | N-[3-(aminomethyl)-5-(trifluoromethyl)phenyl]-6-({2-[(methylamino)carbonyl]-pyridin-4-yl}oxy)quinoline-3-carboxamide |
| I-309 | N-(3-tert-butylphenyl)-7-[(2-{[(morpholin-4-ylacetyl)amino]methyl}pyridin-4-yl)oxy]-1,2,3,4-tetrahydronaphthalene-2-carboxamide |
| I-310 | ethyl 5-{4-[(7-{[(3-tert-butylphenyl)amino]carbonyl}-5,6,7,8-tetrahydronaphthalen-2-yl)oxy]pyridin-2-yl}-1,3,4-oxadiazole-2-carboxylate |
| I-311 | (2S)-7-{[2-(acetylamino)pyridin-4-yl]oxy}-N-[3-(pyrrolidin-1-ylmethyl)-5-(trifluoromethyl)phenyl]-1,2,3,4-tetrahydronaphthalene-2-carboxamide |
| I-312 | 7-{[2-(acetylamino)pyridin-4-yl]oxy}-N-[3-{[(3S)-3-fluoropyrrolidin-1-yl]-methyl}-5-(trifluoromethyl)phenyl]-1,2,3,4-tetrahydronaphthalene-2-carboxamide |
| I-313 | 4-{[(7S)-7-({[3-(aminomethyl)-5-(trifluoromethyl)phenyl]amino}carbonyl)-5,6,7,8-tetrahydronaphthalen-2-yl]oxy}-N-methylpyridine-2-carboxamide |
| I-314 | 4-{[7-({[3-({[(isopropylamino)carbonyl]amino}methyl)-5-(trifluoromethyl)-phenyl]amino}carbonyl)-5,6,7,8-tetrahydronaphthalen-2-yl]oxy}-N-methylpyridine-2-carboxamide |
| I-315 | N-[4-(aminomethyl)-3-(trifluoromethyl)phenyl]-6-{[2-(1H-imidazol-2-yl)-pyridin-4-yl]oxy}quinoline-3-carboxamide |
| I-316 | N-(3-tert-butylphenyl)-6-({2-[4-(hydroxymethyl)-1H-imidazol-2-yl]pyridin-4-yl}oxy)quinoline-3-carboxamide |
| I-317 | N-(3-tert-butylphenyl)-7-({2-[(ethylamino)(imino)methyl]pyridin-4-yl}oxy)-2-naphthamide |
| I-319 | 7-{[2-(acetylamino)pyridin-4-yl]oxy}-N-(3-methoxyphenyl)-1,2,3,4-tetrahydronaphthalene-2-carboxamide |
| I-321 | N-(3-tert-butylphenyl)-7-{[2-(1-methyl-1H-tetrazol-5-yl)pyridin-4-yl]oxy}-1,2,3,4-tetrahydronaphthalene-2-carboxamide |
| I-322 | 2-morpholin-4-ylethyl {4-[(7-{[(3-tert-butylphenyl)amino]carbonyl}-2-naphthyl)-oxy]pyridin-2-yl}carbamate |
| I-323 | methyl (4-{[(7R)-7-({[3-(aminomethyl)-5-(trifluoromethyl)phenyl]-amino}carbonyl)-5,6,7,8-tetrahydronaphthalen-2-yl]oxy}pyridin-2-yl)carbamate |
| I-325 | N-(3-tert-butylphenyl)-7-{[2-(1,3-oxazol-2-yl)pyridin-4-yl]oxy}-1,2,3,4-tetrahydronaphthalene-2-carboxamide |
| I-326 | 7-{[2-(acetylamino)pyridin-4-yl]oxy}-N-[3-[(methylamino)methyl]-5-(trifluoromethyl)phenyl]-1,2,3,4-tetrahydronaphthalene-2-carboxamide |
| I-328 | tert-butyl methyl[3-({[7-({2-[(methylamino)carbonyl]pyridin-4-yl}oxy)-1,2,3,4-tetrahydronaphthalen-2-yl]carbonyl}amino)-5-(trifluoromethyl)benzyl]-carbamate |
| I-329 | 7-{[2-(acetylamino)pyridin-4-yl]oxy}-N-[3-(aminomethyl)-5-(trifluoromethyl)-phenyl]-6-fluoro-1,2,3,4-tetrahydronaphthalene-2-carboxamide |
| I-330 | N-[3-(aminomethyl)-5-(trifluoromethyl)phenyl]-7-{[2-(1H-1,2,4-triazol-1-yl)-pyridin-4-yl]oxy}-1,2,3,4-tetrahydronaphthalene-2-carboxamide |
| I-331 | 7-{[2-(aminomethyl)pyridin-4-yl]oxy}-N-(3-tert-butylphenyl)-1,2,3,4-tetrahydronaphthalene-2-carboxamide |
| I-332 | N-[3-(aminomethyl)-5-(trifluoromethyl)phenyl]-7-({2-[5-(trifluoromethyl)-1H-imidazol-2-yl]pyridin-4-yl}oxy)-1,2,3,4-tetrahydronaphthalene-2-carboxamide |
| I-333 | 7-{[2-(acetylamino)pyridin-4-yl]oxy}-N-[2-fluoro-5-(trifluoromethyl)phenyl]-1,2,3,4-tetrahydronaphthalene-2-carboxamide |
| I-334 | N-(3-tert-butylphenyl)-7-{[2-(2-methyl-2H-tetrazol-5-yl)pyridin-4-yl]oxy}-1,2,3,4-tetrahydronaphthalene-2-carboxamide |
| I-335 | 6-({2-[amino(imino)methyl]pyridin-4-yl}oxy)-N-(3-tert-butylphenyl)quinoline-3-carboxamide |
| I-336 | ethyl (4-{[7-({[3-(aminomethyl)-5-(trifluoromethyl)phenyl]amino}carbonyl)-5,6,7,8-tetrahydronaphthalen-2-yl]oxy}pyridin-2-yl)carbamate |
| I-337 | 7-({2-[(cyclopropylcarbonyl)amino]pyridin-4-yl}oxy)-N-[3-{[(3R)-3-fluoropyrrolidin-1-yl]methyl}-5-(trifluoromethyl)phenyl]-1,2,3,4-tetrahydronaphthalene-2-carboxamide |
| I-338 | N-(3-tert-butylphenyl)-7-{[2-(1H-tetrazol-5-yl)pyridin-4-yl]oxy}-1,2,3,4-tetrahydronaphthalene-2-carboxamide |
| I-339 | 7-[(2-{4-[(4-methylpiperazin-1-yl)methyl]-1H-imidazol-2-yl}pyridin-4-yl)oxy]-N-[3-(2-pyrrolidin-1-ylethoxy)-5-(trifluoromethyl)phenyl]-2-naphthamide |
| I-340 | N-(3-tert-butylphenyl)-7-[(2-cyanopyridin-4-yl)oxy]-2-naphthamide |
| I-341 | 6-{[2-(1H-imidazol-2-yl)pyridin-4-yl]oxy}-N-[3-(2-pyrrolidin-1-ylethoxy)-5-(trifluoromethyl)phenyl]quinoline-3-carboxamide |
| I-342 | N-(3-tert-butylphenyl)-7-{[2-(methylamino)pyridin-4-yl]oxy}-1,2,3,4-tetrahydronaphthalene-2-carboxamide |
| I-343 | 7-{[2-(acetylamino)pyridin-4-yl]oxy}-N-[3-(2-aminoethyl)-5-(trifluoromethyl)-phenyl]-1,2,3,4-tetrahydronaphthalene-2-carboxamide |
| I-344 | 7-{[2-(1-methyl-1H-pyrazol-4-yl)pyridin-4-yl]oxy}-N-[3-(pyrrolidin-1-ylmethyl)-5-(trifluoromethyl)phenyl]-1,2,3,4-tetrahydronaphthalene-2-carboxamide |
| I-345 | 4-{[7-({[3-{[(aminoacetyl)amino]methyl}-5-(trifluoromethyl)phenyl]-amino}carbonyl)-5,6,7,8-tetrahydronaphthalen-2-yl]oxy}-N-methylpyridine-2-carboxamide |
| I-346 | N-(3-tert-butylphenyl)-6-({2-[(cyclopropylcarbonyl)amino]pyridin-4-yl}oxy)-2H-chromene-3-carboxamide |
| I-347 | N-(3-tert-butylphenyl)-7-({2-[5-(morpholin-4-ylmethyl)-1H-imidazol-2-yl]-pyridin-4-yl}oxy)-2-naphthamide |

-continued

| | Chemical Name |
|---|---|
| I-348 | N-[3-(aminomethyl)-5-(trifluoromethyl)phenyl]-7-[(2-{4-[(4-methylpiperazin-1-yl)methyl]-1H-imidazol-2-yl}pyridin-4-yl)oxy]-1,2,3,4-tetrahydronaphthalene-2-carboxamide |
| I-349 | N-(3-tert-butylphenyl)-6-{[2-(4,5-dihydro-1H-imidazol-2-yl)pyridin-4-yl]oxy}chromane-3-carboxamide |
| I-350 | methyl {4-[(3-{[(3-tert-butylphenyl)amino]carbonyl}-2H-chromen-6-yl)oxy]pyridin-2-yl}carbamate |
| I-351 | 6-(pyridin-4-yloxy)-N-[3-(2-pyrrolidin-1-ylethoxy)-5-(trifluoromethyl)phenyl]-quinoline-3-carboxamide |
| I-352 | methyl [3-({[7-({2-[(methylamino)carbonyl]pyridin-4-yl}oxy)-1,2,3,4-tetrahydronaphthalen-2-yl]carbonyl}amino)-5-(trifluoromethyl)benzyl]carbamate |
| I-353 | N-(3-tert-butylphenyl)-7-[(2-{[(4-methylpiperazin-1-yl)acetyl]amino}pyridin-4-yl)oxy]-1,2,3,4-tetrahydronaphthalene-2-carboxamide |
| I-354 | N-(3-tert-butylphenyl)-7-({2-[imino(isopropylamino)methyl]pyridin-4-yl}oxy)-2-naphthamide |
| I-355 | N-[3-(2-pyrrolidin-1-ylethoxy)-5-(trifluoromethyl)phenyl]-7-{[2-(2H-tetrazol-5-yl)pyridin-4-yl]oxy}-1,2,3,4-tetrahydronaphthalene-2-carboxamide |
| I-357 | N-[3-(aminomethyl)-5-(trifluoromethyl)phenyl]-7-(2,3'-bipyridin-4-yloxy)-1,2,3,4-tetrahydronaphthalene-2-carboxamide |
| I-359 | 7-{[2-(propionylamino)pyridin-4-yl]oxy}-N-[3-(pyrrolidin-1-ylmethyl)-5-(trifluoromethyl)phenyl]-1,2,3,4-tetrahydronaphthalene-2-carboxamide |
| I-360 | 7-({2-[(cyclopropylcarbonyl)amino]pyridin-4-yl}oxy)-N-[3-[(diethylamino)methyl]-5-(trifluoromethyl)phenyl]-1,2,3,4-tetrahydronaphthalene-2-carboxamide |
| I-361 | N-(3-tert-butylphenyl)-7-({2-[5-(trifluoromethyl)-1H-imidazol-2-yl]pyridin-4-yl}oxy)-1,2,3,4-tetrahydronaphthalene-2-carboxamide |
| I-362 | N-[3-(aminomethyl)-5-(trifluoromethyl)phenyl]-7-{[2-(pyrrolidin-1-ylcarbonyl)-pyridin-4-yl]oxy}-1,2,3,4-tetrahydronaphthalene-2-carboxamide |
| I-363 | N-[3-(aminomethyl)-5-(trifluoromethyl)phenyl]-7-({2-[(cyclopropylcarbonyl)-amino]pyridin-4-yl}oxy)-6-fluoro-1,2,3,4-tetrahydronaphthalene-2-carboxamide |
| I-364 | N-(3-tert-butylphenyl)-7-[(2-{[2-(4-methylpiperazin-1-yl)propanoyl]-amino}pyridin-4-yl)oxy]-2-naphthamide |
| I-365 | 6-({2-[(methylamino)carbonyl]pyridin-4-yl}oxy)-N-[3-(2-pyrrolidin-1-ylethoxy)-5-(trifluoromethyl)phenyl]quinoline-3-carboxamide |
| I-366 | N-(3-tert-butylphenyl)-7-{[2-(dimethylamino)pyridin-4-yl]oxy}-1,2,3,4-tetrahydronaphthalene-2-carboxamide |
| I-367 | 7-({2-[benzyl(methyl)amino]pyridin-4-yl}oxy)-N-(3-tert-butylphenyl)-1,2,3,4-tetrahydronaphthalene-2-carboxamide |
| I-369 | N-[3-(2-pyrrolidin-1-ylethoxy)-5-(trifluoromethyl)phenyl]-7-({2-[4-(pyrrolidin-1-ylmethyl)-1H-imidazol-2-yl]pyridin-4-yl}oxy)-2-naphthamide |
| I-370 | N-(3-tert-butylphenyl)-7-[(2-{[(ethylamino)carbonyl]amino}pyridin-4-yl)oxy]-1,2,3,4-tetrahydronaphthalene-2-carboxamide |
| I-371 | N-methyl-4-{[7-({[3-{[(2-pyrrolidin-1-ylethyl)amino]methyl}-5-(trifluoromethyl)-phenyl]amino}carbonyl)-5,6,7,8-tetrahydronaphthalen-2-yl]oxy}pyridine-2-carboxamide |
| I-372 | methyl (4-{[3-({[3-(pyrrolidin-1-ylmethyl)-5-(trifluoromethyl)phenyl]-amino}carbonyl)-2H-chromen-6-yl]oxy}pyridin-2-yl)carbamate |
| I-373 | N-(3-tert-butyl-4-fluorophenyl)-7-({2-[(morpholin-4-ylacetyl)amino]pyridin-4-yl}oxy)-1,2,3,4-tetrahydronaphthalene-2-carboxamide |
| I-374 | 7-{[2-(acetylamino)pyridin-4-yl]oxy}-N-(3-ethylphenyl)-1,2,3,4-tetrahydronaphthalene-2-carboxamide |
| I-375 | 7-{[2-(acetylamino)pyridin-4-yl]oxy}-N-[3-(morpholin-4-ylmethyl)-5-(trifluoromethyl)phenyl]-1,2,3,4-tetrahydronaphthalene-2-carboxamide |
| I-376 | 6-{[2-(acetylamino)pyridin-4-yl]oxy}-N-[3-(pyrrolidin-1-ylmethyl)-5-(trifluoromethyl)phenyl]-2H-chromene-3-carboxamide |
| I-377 | N-(3-tert-butylphenyl)-7-[(2-{4-[(4-methylpiperazin-1-yl)carbonyl]-1H-imidazol-2-yl}pyridin-4-yl)oxy]-2-naphthamide |
| I-378 | 7-({2-[(cyclopropylcarbonyl)amino]pyridin-4-yl}oxy)-N-[3-{[(2-methoxyethyl)-amino]methyl}-5-(trifluoromethyl)phenyl]-1,2,3,4-tetrahydronaphthalene-2-carboxamide |
| I-379 | N-methyl-4-{[7-({[3-(pyrrolidin-1-ylmethyl)-5-(trifluoromethyl)phenyl]-amino}carbonyl)-5,6,7,8-tetrahydronaphthalen-2-yl]oxy}pyridine-2-carboxamide |
| I-380 | methyl ({4-[(7-{[(3-tert-butylphenyl)amino]carbonyl}-5,6,7,8-tetrahydronaphthalen-2-yl)oxy]pyridin-2-yl}methyl)carbamate |
| I-381 | 7-({2-[amino(imino)methyl]pyridin-4-yl}oxy)-N-[4-(aminomethyl)-3-(trifluoromethyl)phenyl]-2-naphthamide |
| I-382 | 4-{[7-({[2-cyano-5-(trifluoromethyl)phenyl]amino}carbonyl)-5,6,7,8-tetrahydronaphthalen-2-yl]oxy}-N-methylpyridine-2-carboxamide |
| I-383 | N-methyl-4-{[7-({[2-(2-piperazin-1-ylethoxy)-5-(trifluoromethyl)phenyl]-amino}carbonyl)-2-naphthyl]oxy}pyridine-2-carboxamide |
| I-384 | N-(3-tert-butylphenyl)-7-({2-[(isobutyrylamino)methyl]pyridin-4-yl}oxy)-1,2,3,4-tetrahydronaphthalene-2-carboxamide |
| I-385 | 7-{[2-(acetylamino)pyridin-4-yl]oxy}-N-[3-(aminomethyl)-5-tert-butylphenyl]-1,2,3,4-tetrahydronaphthalene-2-carboxamide |

| | Chemical Name |
|---|---|
| I-386 | (2S)-N-[3-(aminomethyl)-5-(trifluoromethyl)phenyl]-7-({2-[(cyclopropylcarbonyl)amino]pyridin-4-yl}oxy)-1,2,3,4-tetrahydronaphthalene-2-carboxamide |
| I-387 | N-(3-tert-butylphenyl)-7-[(2-{[(pyrrolidin-1-ylacetyl)amino]methyl}pyridin-4-yl)oxy]-1,2,3,4-tetrahydronaphthalene-2-carboxamide |
| I-388 | N-[3-(aminomethyl)-5-(trifluoromethyl)phenyl]-6-{[2-(4,5-dihydro-1H-imidazol-2-yl)pyridin-4-yl]oxy}quinoline-3-carboxamide |
| I-389 | 7-{[2-(acetylamino)pyridin-4-yl]oxy}-N-(3-tert-butyl-5-cyanophenyl)-1,2,3,4-tetrahydronaphthalene-2-carboxamide |
| I-390 | 7-{[2-(5-{[(2-aminoethyl)amino]methyl}-1H-imidazol-2-yl)pyridin-4-yl]oxy}-N-(3-tert-butylphenyl)-2-naphthamide |
| I-392 | N-(3-tert-butylphenyl)-6-[(2-{4-[(4-methylpiperazin-1-yl)carbonyl]-1H-imidazol-2-yl}pyridin-4-yl)oxy]quinoline-3-carboxamide |
| I-393 | 7-{[2-(isobutyrylamino)pyridin-4-yl]oxy}-N-[3-(2-pyrrolidin-1-ylethoxy)-5-(trifluoromethyl)phenyl]-1,2,3,4-tetrahydronaphthalene-2-carboxamide |
| I-394 | N-(3-tert-butylphenyl)-7-({2-[(morpholin-4-ylacetyl)amino]pyridin-4-yl}oxy)-2-naphthamide |
| I-395 | 7-({2-[acetyl(methyl)amino]pyridin-4-yl}oxy)-N-(3-tert-butylphenyl)-1,2,3,4-tetrahydronaphthalene-2-carboxamide |
| I-396 | N-[4-(aminomethyl)-3-(trifluoromethyl)phenyl]-6-{[2-(4,5-dihydro-1H-imidazol-2-yl)pyridin-4-yl]oxy}quinoline-3-carboxamide |
| I-397 | 7-{[2-(aminomethyl)pyridin-4-yl]oxy}-N-(3-tert-butylphenyl)-2-naphthamide |
| I-398 | tert-butyl [3-({[6-({2-[(cyclopropylcarbonyl)amino]pyridin-4-yl}oxy)-2H-chromen-3-yl]carbonyl}amino)-5-(trifluoromethyl)benzyl]carbamate |
| I-399 | 7-{[2-(acetylamino)pyridin-4-yl]oxy}-N-[3-{[(3R)-3-hydroxypyrrolidin-1-yl]methyl}-5-(trifluoromethyl)phenyl]-1,2,3,4-tetrahydronaphthalene-2-carboxamide |
| I-400 | N-[3-(aminomethyl)-5-(trifluoromethyl)phenyl]-7-{[2-(1H-pyrazol-1-yl)pyridin-4-yl]oxy}-1,2,3,4-tetrahydronaphthalene-2-carboxamide |
| I-401 | (2S)-2,3-dihydroxypropyl {4-[(3-{[(3-tert-butylphenyl)amino]carbonyl}-2H-chromen-6-yl)oxy]pyridin-2-yl}carbamate |
| I-402 | 4-{[3-({[3-(aminomethyl)-5-(trifluoromethyl)phenyl]amino}carbonyl)-2H-chromen-6-yl]oxy}-N-methylpyridine-2-carboxamide |
| I-403 | N-[3-(aminomethyl)-5-(trifluoromethyl)phenyl]-7-({2-[4-(hydroxymethyl)-1H-imidazol-2-yl]pyridin-4-yl}oxy)-1,2,3,4-tetrahydronaphthalene-2-carboxamide |
| I-404 | 7-{[2-(acetylamino)pyridin-4-yl]oxy}-N-[3-(aminomethyl)-5-(trifluoromethyl)-phenyl]-1,2,3,4-tetrahydronaphthalene-2-carboxamide |
| I-405 | 7-({2-[(cyclopropylcarbonyl)amino]pyridin-4-yl}oxy)-N-[3-[(methylamino)-methyl]-5-(trifluoromethyl)phenyl]-3,4-dihydroisoquinoline-2(1H)-carboxamide |
| I-406 | N-[3-[(methylamino)methyl]-5-(trifluoromethyl)phenyl]-7-{[2-(propionylamino)pyridin-4-yl]oxy}-1,2,3,4-tetrahydronaphthalene-2-carboxamide |
| I-407 | 7-{[2-(acetylamino)pyridin-4-yl]oxy}-N-[3-{[(3R)-3-fluoropyrrolidin-1-yl]methyl}-5-(trifluoromethyl)phenyl]-1,2,3,4-tetrahydronaphthalene-2-carboxamide |
| I-408 | N-(3-tert-butylphenyl)-7-{[2-(2-oxotetrahydropyrimidin-1(2H)-yl)pyridin-4-yl]-oxy}-1,2,3,4-tetrahydronaphthalene-2-carboxamide |
| I-409 | 6-{[2-(4-methyl-1H-imidazol-2-yl)pyridin-4-yl]oxy}-N-[3-(2-pyrrolidin-1-ylethoxy)-5-(trifluoromethyl)phenyl]quinoline-3-carboxamide |
| I-410 | 7-{[2-(acetylamino)pyridin-4-yl]oxy}-N-[3-(piperazin-1-ylmethyl)-5-(trifluoromethyl)phenyl]-1,2,3,4-tetrahydronaphthalene-2-carboxamide |
| I-411 | N-[4-(aminomethyl)-3-(trifluoromethyl)phenyl]-7-({2-[4-(hydroxymethyl)-1H-imidazol-2-yl]pyridin-4-yl}oxy)-2-naphthamide |
| I-412 | 7-{[2-(acetylamino)pyridin-4-yl]oxy}-N-[3-{[(2R)-2,3-dihydroxypropyl]oxy}-5-(trifluoromethyl)phenyl]-1,2,3,4-tetrahydronaphthalene-2-carboxamide |
| I-413 | 7-({2-[(cyclopropylcarbonyl)amino]pyridin-4-yl}oxy)-N-[3-[(isopropylamino)-methyl]-5-(trifluoromethyl)phenyl]-1,2,3,4-tetrahydronaphthalene-2-carboxamide |
| I-414 | 7-({2-[(cyclopropylcarbonyl)amino]pyridin-4-yl}oxy)-N-[3-{[(3S)-3-fluoropyrrolidn-1-yl]methyl}-5-(trifluoromethyl)phenyl]-1,2,3,4-tetrahydronaphthalene-2-carboxamide |
| I-415 | N-(3-tert-butylphenyl)-7-{[2-(4-methylpiperazin-1-yl)pyridin-4-yl]oxy}-1,2,3,4-tetrahydronaphthalene-2-carboxamide |
| I-416 | 7-({2-[4-(hydroxymethyl)-1H-imidazol-2-yl]pyridin-4-yl}oxy)-N-[3-(2-pyrrolidn-1-ylethoxy)-5-(trifluoromethyl)phenyl]-2-naphthamide |
| I-417 | N-[3-(aminomethyl)-5-(trifluoromethyl)phenyl]-7-({2-[(cyclopropylcarbonyl)-amino]pyridin-4-yl}oxy)-1,2,3,4-tetrahydronaphthalene-2-carboxamide |
| I-418 | N-[3-(aminomethyl)-5-(trifluoromethyl)phenyl]-6-{[2-(1H-imidazol-2-yl)-pyridin-4-yl]oxy}quinoline-3-carboxamide |
| I-419 | N-(3-tert-butylphenyl)-7-({2-[(morpholin-4-ylacetyl)amino]pyridin-4-yl}oxy)-1,2,3,4-tetrahydronaphthalene-2-carboxamide |
| I-420 | 4-{[7-({3-{[[(ethylamino)carbonyl]amino}methyl)-5-(trifluoromethyl)phenyl]-amino}carbonyl)-5,6,7,8-tetrahydronaphthalen-2-yl]oxy}-N-methylpyridine-2-carboxamide |
| I-421 | N-[7-({2-[(cyclopropylcarbonyl)amino]pyridin-4-yl}oxy)-1,2,3,4-tetrahydronaphthalen-2-yl]-3-(trifluoromethyl)benzamide |

| | Chemical Name |
|---|---|
| I-422 | 7-({2-[amino(imino)methyl]pyridin-4-yl}oxy)-N-(3-tert-butylphenyl)-1,2,3,4-tetrahydronaphthalene-2-carboxamide |
| I-424 | 7-{[2-(4,5-dihydro-1H-imidazol-2-yl)pyridin-4-yl]oxy}-N-[4-[(4-methylpiperazin-1-yl)methyl]-3-(trifluoromethyl)phenyl]-1,2,3,4-tetrahydronaphthalene-2-carboxamide |
| I-425 | 3-(aminomethyl)-5-tert-butyl-N-[7-({2-[(cyclopropylcarbonyl)amino]pyridin-4-yl}oxy)-1,2,3,4-tetrahydronaphthalen-2-yl]benzamide |
| I-426 | N-(7-{[2-(acetylamino)pyridin-4-yl]oxy}-1,2,3,4-tetrahydronaphthalen-2-yl)-3-(aminomethyl)-5-tert-butylbenzamide |
| I-427 | 7-{[2-(4,5-dihydro-1H-imidazol-2-yl)pyridin-4-yl]oxy}-N-[4-(pyrrolidin-1-ylmethyl)-3-(trifluoromethyl)phenyl]-1,2,3,4-tetrahydronaphthalene-2-carboxamide |
| I-428 | N-(7-{[2-(acetylamino)pyridin-4-yl]oxy}-1,2,3,4-tetrahydronaphthalen-2-yl)-4-chloro-3-(trifluoromethyl)benzamide |
| I-429 | tert-butyl [3-({[6-({2-[(cyclopropylcarbonyl)amino]pyridin-4-yl}oxy)-2H-chromen-3-yl]carbonyl}amino)-5-(trifluoromethyl)benzyl]methylcarbamate |
| I-430 | 3-tert-butyl-5-cyano-N-[7-({2-[(cyclopropylcarbonyl)amino]pyridin-4-yl}oxy)-1,2,3,4-tetrahydronaphthalen-2-yl]benzamide |
| I-431 | N-(3-tert-butylphenyl)-7-({2-[(cyclopropylcarbonyl)amino]pyridin-4-yl}oxy)-3,4-dihydroisoquinoline-2(1H)-carboxamide |
| I-432 | N-(7-{[2-(acetylamino)pyridin-4-yl]oxy}-1,2,3,4-tetrahydronaphthalen-2-yl)-3-(trifluoromethyl)benzamide |
| I-433 | 7-{[2-(acetylamino)pyridin-4-yl]oxy}-N-[3-(2-pyrrolidin-1-ylethoxy)-5-(trifluoromethyl)phenyl]-2-naphthamide |
| I-434 | 7-{[2-(acetylamino)pyridin-4-yl]oxy}-N-(3-tert-butylphenyl)-2-naphthamide |
| I-435 | 3-tert-butyl-N-[7-({2-[(cyclopropylcarbonyl)amino]pyridin-4-yl}oxy)-1,2,3,4-tetrahydronaphthalen-2-yl]benzamide |
| I-436 | N-(7-{[2-(acetylamino)pyridin-4-yl]oxy}-1,2,3,4-tetrahydronaphthalen-2-yl)-3-tert-butylbenzamide |
| I-437 | 3-(aminomethyl)-N-[7-({2-[(cyclopropylcarbonyl)amino]pyridin-4-yl}oxy)-1,2,3,4-tetrahydronaphthalen-2-yl]-5-(trifluoromethyl)benzamide |
| I-440 | 4-chloro-N-(7-{[2-(4,5-dihydro-1H-imidazol-2-yl)pyridin-4-yl]oxy}-2-naphthyl)-3-(trifluoromethyl)benzamide |
| I-441 | N-(7-{[2-(acetylamino)pyridin-4-yl]oxy}-1,2,3,4-tetrahydronaphthalen-2-yl)-3-(aminomethyl)-5-(trifluoromethyl)benzamide |
| I-442 | 4-chloro-N-(7-{[2-(4,5-dihydro-1H-imidazol-2-yl)pyridin-4-yl]oxy}-1,2,3,4-tetrahydronaphthalen-2-yl)-3-(trifluoromethyl)benzamide |
| I-443 | 4-chloro-N-[7-({2-[(cyclopropylcarbonyl)amino]pyridin-4-yl}oxy)-1,2,3,4-tetrahydronaphthalen-2-yl]-3-(trifluoromethyl)benzamide |
| I-444 | 4-[(7-{[4-chloro-3-(trifluoromethyl)benzoyl]amino}-5,6,7,8-tetrahydronaphthalen-2-yl)oxy]-N-methylpyridine-2-carboxamide |
| I-445 | 4-chloro-N-(6-{[2-(4,5-dihydro-1H-imidazol-2-yl)pyridin-4-yl]oxy}-3,4-dihydro-2H-chromen-3-yl)-3-(trifluoromethyl)benzamide |
| I-446 | N-[3-(aminomethyl)-5-(trifluoromethyl)phenyl]-7-({2-[(cyclopropylcarbonyl)amino]pyridin-4-yl}oxy)-3,4-dihydroisoquinoline-2(1H)-carboxamide |
| I-447 | 6-({2-[(cyclopropylcarbonyl)amino]pyridin-4-yl}oxy)-N-[3-[(methylamino)methyl]-5-(trifluoromethyl)phenyl]-2H-chromene-3-carboxamide |
| I-448 | N-(3-tert-butylphenyl)-6-[(2-cyanopyridin-4-yl)oxy]quinoline-3-carboxamide |
| I-451 | N-methyl-4-{[7-({[4-(pyrrolidin-1-ylmethyl)-3-(trifluoromethyl)phenyl]amino}carbonyl)-5,6,7,8-tetrahydronaphthalen-2-yl]oxy}pyridine-2-carboxamide |
| I-452 | N-methyl-4-{[7-({[4-[(4-methylpiperazin-1-yl)methyl]-3-(trifluoromethyl)phenyl]amino}carbonyl)-5,6,7,8-tetrahydronaphthalen-2-yl]oxy}pyridine-2-carboxamide |
| I-455 | N-(3-tert-butylphenyl)-7-({2-[4-(hydroxymethyl)-1H-imidazol-2-yl]pyridin-4-yl}oxy)-2-naphthamide |
| I-456 | 7-({2-[(cyclopropylcarbonyl)amino]pyridin-4-yl}oxy)-N-[3-(4-methylpiperazin-1-yl)-5-(trifluoromethyl)phenyl]-1,2,3,4-tetrahydronaphthalene-2-carboxamide |
| I-459 | N-[3-(aminomethyl)-5-tert-butylphenyl]-7-({2-[(cyclopropylcarbonyl)amino]pyridin-4-yl}oxy)-3,4-dihydroisoquinoline-2(1H)-carboxamide |
| I-460 | 4-({7-[(3-tert-butylbenzoyl)amino]-5,6,7,8-tetrahydronaphthalen-2-yl}oxy)-N-methylpyridine-2-carboxamide |
| I-461 | tert-butyl [3-tert-butyl-5-({[6-({2-[(cyclopropylcarbonyl)amino]pyridin-4-yl}oxy)-2H-chromen-3-yl]carbonyl}amino)benzyl]carbamate |
| I-462 | 3-(aminomethyl)-N-{7-[(7-oxo-7,8-dihydro-1,8-naphthyridin-4-yl)oxy]-1,2,3,4-tetrahydronaphthalen-2-yl}-5-(trifluoromethyl)benzamide |
| I-463 | 7-[(7-oxo-5,6,7,8-tetrahydro-1,8-naphthyridin-4-yl)oxy]-N-[3-(pyrrolidin-1-ylmethyl)-5-(trifluoromethyl)phenyl]-1,2,3,4-tetrahydronaphthalene-2-carboxamide |
| I-464 | 3-tert-butyl-N-[7-({2-[(cyclopropylcarbonyl)amino]pyridin-4-yl}oxy)-1,2,3,4-tetrahydronaphthalen-2-yl]-5-[(ethylamino)methyl]benzamide |
| I-465 | N-[3-(aminomethyl)-5-(trifluoromethyl)phenyl]-7-{[2-(1H-pyrazol-3-ylamino)-pyridin-4-yl]oxy}-1,2,3,4-tetrahydronaphthalene-2-carboxamide |
| I-466 | 7-{[2-(acetylamino)pyridin-4-yl]oxy}-N-[3-(2-aminoethyl)-5-tert-butylphenyl]-1,2,3,4-tetrahydronaphthalene-2-carboxamide |
| I-467 | N-(3-tert-butylphenyl)-7-({2-[(cyclopropylcarbonyl)amino]pyridin-4-yl}oxy)-N-methyl-1,2,3,4-tetrahydronaphthalene-2-carboxamide |

| | Chemical Name |
|---|---|
| I-468 | N-{3-tert-butyl-5-[(methylamino)methyl]phenyl}-7-({2-[(cyclopropylcarbonyl)-amino]pyridin-4-yl}oxy)-1,2,3,4-tetrahydronaphthalene-2-carboxamide |
| I-469 | 7-({2-[(cyclopropylcarbonyl)amino]pyridin-4-yl}oxy)-N-[4-[(methylamino)-methyl]-3-(trifluoromethyl)phenyl]-3,4-dihydroisoquinoline-2(1H)-carboxamide |
| I-470 | (3S)-N-(4-{[7-({[3-[(methylamino)methyl]-5-(trifluoromethyl)phenyl]-amino}carbonyl)-5,6,7,8-tetrahydronaphthalen-2-yl]oxy}pyridin-2-yl)-pyrrolidine-3-carboxamide |
| I-471 | N-{3-tert-butyl-5-[(2R)-pyrrolidin-2-yl]phenyl}-7-({2-[(cyclopropylcarbonyl)-amino]pyridin-4-yl}oxy)-1,2,3,4-tetrahydronaphthalene-2-carboxamide |
| I-472 | N-{3-tert-butyl-5-[(2S)-pyrrolidin-2-yl]phenyl}-7-({2-[(cyclopropylcarbonyl)-amino]pyridin-4-yl}oxy)-1,2,3,4-tetrahydronaphthalene-2-carboxamide |
| I-473 | N-[3-(aminomethyl)-5-(trifluoromethyl)phenyl]-7-{[2-(1H-imidazol-5-yl)-pyridin-4-yl]oxy}-1,2,3,4-tetrahydronaphthalene-2-carboxamide |
| I-474 | 7-({2-[(cyclopropylcarbonyl)amino]pyridin-4-yl}oxy)-N-[3-piperazin-1-yl-5-(trifluoromethyl)phenyl]-1,2,3,4-tetrahydronaphthalene-2-carboxamide |
| I-475 | N-(7-{[2-(acetylamino)pyridin-4-yl]oxy}-1,2,3,4-tetrahydronaphthalen-2-yl)-3-tert-butyl-5-[(ethylamino)methyl]benzamide |
| I-476 | 7-{[2-(acetylamino)pyridin-4-yl]oxy}-N-[3-[(methylamino)methyl]-5-(1-methylcyclopropyl)phenyl]-1,2,3,4-tetrahydronaphthalene-2-carboxamide |
| I-477 | 3-(aminomethyl)-N-{7-[(7-oxo-5,6,7,8-tetrahydro-1,8-naphthyridin-4-yl)oxy]-1,2,3,4-tetrahydronaphthalen-2-yl}-5-(trifluoromethyl)benzamide |
| I-478 | N-[3-(2-aminoethyl)-5-(trifluoromethyl)phenyl]-7-({2-[(cyclopropylcarbonyl)-amino]pyridin-4-yl}methyl)-1,2,3,4-tetrahydronaphthalene-2-carboxamide |
| I-479 | N-[3-(2-aminoethyl)-5-(trifluoromethyl)phenyl]-7-[(7-oxo-5,6,7,8-tetrahydro-1,8-naphthyridin-4-yl)oxy]-1,2,3,4-tetrahydronaphthalene-2-carboxamide |
| I-480 | N-(4-{[7-({[3-[(methylamino)methyl]-5-(trifluoromethyl)phenyl]-amino}carbonyl)-5,6,7,8-tetrahydronaphthalen-2-yl]oxy}pyridin-2-yl)azetidine-3-carboxamide |
| I-481 | 3-tert-butyl-N-[7-({2-[(cyclopropylcarbonyl)amino]pyridin-4-yl}oxy)-1,2,3,4-tetrahydronaphthalen-2-yl]-5-[(4-methylpiperazin-1-yl)methyl]benzamide |
| I-482 | N-[3-(aminomethyl)-5-tert-butylphenyl]-7-[(7-oxo-5,6,7,8-tetrahydro-1,8-naphthyridin-4-yl)oxy]-1,2,3,4-tetrahydronaphthalene-2-carboxamide |
| I-483 | (3R)-N-(4-{[7-({[3-(aminomethyl)-5-(trifluoromethyl)phenyl]amino}carbonyl)-5,6,7,8-tetrahydronaphthalen-2-yl]oxy}pyridin-2-yl)pyrrolidine-3-carboxamide |
| I-484 | 3-[3-({[7-({2-[(cyclopropylcarbonyl)amino]pyridin-4-yl}methyl)-1,2,3,4-tetrahydronaphthalen-2-yl]carbonyl}amino)-5-(trifluoromethyl)phenyl]-propanoic acid |
| I-485 | 7-({2-[(cyclopropylcarbonyl)amino]pyridin-4-yl}oxy)-N-methyl-N-[3-[(methylamino)methyl]-5-(trifluoromethyl)phenyl]-1,2,3,4-tetrahydronaphthalene-2-carboxamide |
| I-487 | N-(7-{[2-(acetylamino)pyridin-4-yl]oxy}-1,2,3,4-tetrahydronaphthalen-2-yl)-3-tert-butyl-5-[(4-ethylpiperazin-1-yl)methyl]benzamide |
| I-488 | N-[3-[(dimethylamino)methyl]-5-(trifluoromethyl)phenyl]-7-[(7-oxo-7,8-dihydro-1,8-naphthyridin-4-yl)oxy]-1,2,3,4-tetrahydronaphthalene-2-carboxamide |
| I-489 | tert-butyl [3-tert-butyl-5-({[6-({2-[(cyclopropylcarbonyl)amino]pyridin-4-yl}oxy)-2H-chromen-3-yl]carbonyl}amino)benzyl]methylcarbamate |
| I-490 | N-(3-tert-butylphenyl)-7-{[2-(1H-imidazol-5-yl)pyridin-4-yl]oxy}-1,2,3,4-tetrahydronaphthalene-2-carboxamide |
| I-491 | N-methyl-5-{[7-({[3-[(methylamino)methyl]-5-(trifluoromethyl)phenyl]-amino}carbonyl)-5,6,7,8-tetrahydronaphthalen-2-yl]oxy}nicotinamide |
| I-492 | (2S)-7-({2-[(cyclopropylcarbonyl)amino]pyridin-4-yl}oxy)-N-[3-[(methylamino)-methyl]-5-(trifluoromethyl)phenyl]-1,2,3,4-tetrahydronaphthalene-2-carboxamide |
| I-493 | 3-[3-tert-butyl-5-({[7-({2-[(cyclopropylcarbonyl)amino]pyridin-4-yl}methyl)-1,2,3,4-tetrahydronaphthalen-2-yl]carbonyl}amino)phenyl]propanoic acid |
| I-494 | N-[3-tert-butyl-5-(hydroxymethyl)phenyl]-7-({2-[(cyclopropylcarbonyl)-amino]pyridin-4-yl}oxy)-1,2,3,4-tetrahydronaphthalene-2-carboxamide |
| I-495 | 7-({2-[(cyclopropylcarbonyl)amino]pyridin-4-yl}oxy)-N-[7-(trifluoromethyl)-2,3-dihydro-1H-isoindol-5-yl]-1,2,3,4-tetrahydronaphthalene-2-carboxamide |
| I-496 | N-(7-{[2-(acetylamino)pyridin-4-yl]oxy}-1,2,3,4-tetrahydronaphthalen-2-yl)-3-tert-butyl-5-[(4-methylpiperazin-1-yl)methyl]benzamide |
| I-497 | 7-({2-[(cyclopropylcarbonyl)amino]pyridin-4-yl}oxy)-N-[3-(2-hydroxyethyl)-5-(trifluoromethyl)phenyl]-1,2,3,4-tetrahydronaphthalene-2-carboxamide |
| I-498 | (3S)-N-(4{[7-({[3-(aminomethyl)-5-(trifluoromethyl)phenyl]amino}carbonyl)-5,6,7,8-tetrahydronaphthalen-2-yl]oxy}pyridin-2-yl)pyrrolidine-3-carboxamide |
| I-499 | N-[3-(aminomethyl)-5-tert-butylphenyl]-7-[(7-oxo-7,8-dihydro-1,8-naphthyridin-4-yl)oxy]-1,2,3,4-tetrahydronaphthalene-2-carboxamide |
| I-500 | N-[3-(2-aminoethyl)-5-(trifluoromethyl)phenyl]-7-[(7-oxo-7,8-dihydro-1,8-naphthyridin-4-yl)oxy]-1,2,3,4-tetrahydronaphthalene-2-carboxamide |
| I-501 | 7-({2-[(cyclopropylcarbonyl)amino]pyridin-4-yl}oxy)-N-(4,4-difluoro-1,2,3,4-tetrahydroisoquinolin-6-yl)-1,2,3,4-tetrahydronaphthalene-2-carboxamide |
| I-502 | N-[3-(2-aminoethyl)-5-tert-butylphenyl]-7-[(7-oxo-7,8-dihydro-1,8-naphthyridin-4-yl)oxy]-1,2,3,4-tetrahydronaphthalene-2-carboxamide |
| I-503 | [3-tert-butyl-5-({[7-({2-[(cyclopropylcarbonyl)amino]pyridin-4-yl}methyl)-1,2,3,4-tetrahydronaphthalen-2-yl]carbonyl}amino)phenyl]acetic acid |
| I-504 | N-(3-tert-butylphenyl)-7-({2-[(1-methyl-1H-pyrazol-3-yl)amino]pyridin-4-yl}-oxy)-1,2,3,4-tetrahydronaphthalene-2-carboxamide |

| | Chemical Name |
|---|---|
| I-505 | N-[3-(aminomethyl)-5-tert-butylphenyl]-6-({2-[(cyclopropylcarbonyl)-amino]pyridin-4-yl}oxy)-2H-chromene-3-carboxamide |
| I-506 | N-{4-[(7-{[(3-tert-butylphenyl)amino]carbonyl}-5,6,7,8-tetrahydronaphthalen-2-yl)oxy]pyridin-2-yl}azetidine-3-carboxamide |
| I-507 | N-(7-{[2-(acetylamino)pyridin-4-yl]oxy}-1,2,3,4-tetrahydronaphthalen-2-yl)-3-tert-butyl-5-[(diethylamino)methyl]benzamide |
| I-508 | N-[3-tert-butyl-5-(pyrrolidin-1-ylmethyl)phenyl]-7-({2-[(cyclopropylcarbonyl)-amino]pyridin-4-yl}oxy)-3,4-dihydroisoquinoline-2(1H)-carboxamide |
| I-509 | N-[3-(4-methylpiperazin-1-yl)-5-(trifluoromethyl)phenyl]-7-[(7-oxo-7,8-dihydro-1,8-naphthyridin-4-yl)oxy]-1,2,3,4-tetrahydronaphthalene-2-carboxamide |
| I-510 | N-[3-(2-aminoethyl)-5-tert-butylphenyl]-7-[(7-oxo-5,6,7,8-tetrahydro-1,8-naphthyridin-4-yl)oxy]-1,2,3,4-tetrahydronaphthalene-2-carboxamide |
| I-511 | N-{3-tert-butyl-5-[(methylamino)methyl]phenyl}-6-({2-[(cyclopropylcarbonyl)-amino]pyridin-4-yl}oxy)-2H-chromene-3-carboxamide |
| I-512 | 3-({[7-({2-[(cyclopropylcarbonyl)amino]pyridin-4-yl}methyl)-1,2,3,4-tetrahydronaphthalen-2-yl]carbonyl}amino)-5-(trifluoromethyl)benzoic acid |
| I-513 | 3-tert-butyl-N-[7-({2-[(cyclopropylcarbonyl)amino]pyridin-4-yl}oxy)-1,2,3,4-tetrahydronaphthalen-2-yl]-5-[(diethylamino)methyl]benzamide |
| I-514 | N-{4-[(7-{[(3-tert-butylphenyl)amino]carbonyl}-5,6,7,8-tetrahydronaphthalen-2-yl)oxy]pyridin-2-yl}piperidine-4-carboxamide |
| I-516 | N-(7-{[2-(acetylamino)pyridin-4-yl]oxy}-1,2,3,4-tetrahydronaphthalen-2-yl)-3-tert-butyl-5-(piperazin-1-ylmethyl)benzamide |
| I-518 | N-[3-(aminomethyl)-5-(trifluoromethyl)phenyl]-7-({2-[(1-methyl-1H-pyrazol-3-yl)amino]pyridin-4-yl}oxy)-1,2,3,4-tetrahydronaphthalene-2-carboxamide |
| I-519 | N-[3-(aminomethyl)-5-(trifluoromethyl)phenyl]-7-({2-[(methoxyacetyl)-amino]pyridin-4-yl}oxy)-1,2,3,4-tetrahydronaphthalene-2-carboxamide |
| I-520 | N-[3-(2-aminoethyl)-5-tert-butylphenyl]-7-({2-[(cyclopropylcarbonyl)-amino]pyridin-4-yl}oxy)-1,2,3,4-tetrahydronaphthalene-2-carboxamide |
| I-521 | 7-{[2-(acetylamino)pyridin-4-yl]methyl}-N-[3-[2-(methylamino)ethyl]-5-(trifluoromethyl)phenyl]-1,2,3,4-tetrahydronaphthalene-2-carboxamide |
| I-522 | (2S)-N-[3-[(methylamino)methyl]-5-(trifluoromethyl)phenyl]-7-[(7-oxo-7,8-dihydro-1,8-naphthyridin-4-yl)oxy]-1,2,3,4-tetrahydronaphthalene-2-carboxamide |
| I-523 | N-(4-{[7-({[3-[(methylamino)methyl]-5-(trifluoromethyl)phenyl]-amino}carbonyl)-5,6,7,8-tetrahydronaphthalen-2-yl]oxy}pyridin-2-yl)-piperidine-4-carboxamide |
| I-524 | 7-[(7-oxo-7,8-dihydro-1,8-naphthyridin-4-yl)oxy]-N-[3-(pyrrolidin-1-ylmethyl)-5-(trifluoromethyl)phenyl]-1,2,3,4-tetrahydronaphthalene-2-carboxamide |
| I-525 | 7-({2-[(cyclopropylcarbonyl)amino]pyridin-4-yl}oxy)-N-[3-[(methylamino)-methyl]-5-(1-methylcyclopropyl)phenyl]-1,2,3,4-tetrahydronaphthalene-2-carboxamide |
| I-527 | 7-({2-[(cyclopropylcarbonyl)amino]pyridin-4-yl}oxy)-N-[5-(trifluoromethyl)-1,2,3,4-tetrahydroisoquinolin-7-yl]-1,2,3,4-tetrahydronaphthalene-2-carboxamide |
| I-528 | 7-({2-[(cyclopropylcarbonyl)amino]pyridin-4-yl}methyl)-N-[3-[2-(methylamino)ethyl]-5-(trifluoromethyl)phenyl]-1,2,3,4-tetrahydronaphthalene-2-carboxamide |
| I-529 | (3S)-N-{4-[(7-{[(3-tert-butylphenyl)amino]carbonyl}-5,6,7,8-tetrahydronaphthalen-2-yl)oxy]pyridin-2-yl}pyrrolidine-3-carboxamide |
| I-530 | N-[3-(aminomethyl)-5-(trifluoromethyl)phenyl]-7-({2-[(cyclopropylcarbonyl)-amino]-1-oxidopyridin-4-yl}oxy)-1,2,3,4-tetrahydronaphthalene-2-carboxamide |
| I-531 | [3-({[7-({2-[(cyclopropylcarbonyl)amino]pyridin-4-yl}methyl)-1,2,3,4-tetrahydronaphthalen-2-yl]carbonyl}amino)-5-(trifluoromethyl)phenyl]acetic acid |
| I-532 | (3R)-N-(4-{[7-({[3-[(methylamino)methyl]-5-(trifluoromethyl)phenyl]-amino}carbonyl)-5,6,7,8-tetrahydronaphthalen-2-yl]oxy}pyridin-2-yl)-pyrrolidine-3-carboxamide |
| I-533 | N-[3-(2-aminoethyl)-5-(trifluoromethyl)phenyl]-7-({2-[(cyclopropylcarbonyl)-amino]pyridin-4-yl}oxy)-3,4-dihydroisoquinoline-2(1H)-carboxamide |
| I-534 | 7-{[2-(acetylamino)pyridin-4-yl]oxy}-N-{3-tert-butyl-5-[(methylamino)methyl]-phenyl}-1,2,3,4-tetrahydronaphthalene-2-carboxamide |
| I-535 | N-[3-(4-methylpiperazin-1-yl)-5-(trifluoromethyl)phenyl]-7-[(7-oxo-5,6,7,8-tetrahydro-1,8-naphthyridin-4-yl)oxy]-1,2,3,4-tetrahydronaphthalene-2-carboxamide |
| I-536 | 7-{[2-(glycoloylamino)pyridin-4-yl]oxy}-N-[3-[(methylamino)methyl]-5-(trifluoromethyl)phenyl]-1,2,3,4-tetrahydronaphthalene-2-carboxamide |
| I-537 | N-(7-{[2-(acetylamino)pyridin-4-yl]oxy}-1,2,3,4-tetrahydronaphthalen-2-yl)-3-tert-butyl-5-[(methylamino)methyl]benzamide |
| I-538 | 3-tert-butyl-N-[7-({2-[(cyclopropylcarbonyl)amino]pyridin-4-yl}oxy)-1,2,3,4-tetrahydronaphthalen-2-yl]-5-(piperazin-1-ylmethyl)benzamide |
| I-539 | N-(3-tert-butylphenyl)-7-{[2-(1H-pyrazol-3-ylamino)pyridin-4-yl]oxy}-1,2,3,4-tetrahydronaphthalene-2-carboxamide |
| I-540 | 7-({2-[(cyclopropylcarbonyl)amino]pyridin-4-yl}oxy)-N-(4,4-dimethyl-1,2,3,4-tetrahydroisoquinolin-6-yl)-1,2,3,4-tetrahydronaphthalene-2-carboxamide |
| I-541 | N-[3-[(dimethylamino)methyl]-5-(trifluoromethyl)phenyl]-7-[(7-oxo-5,6,7,8-tetrahydro-1,8-naphthyridin-4-yl)oxy]-1,2,3,4-tetrahydronaphthalene-2-carboxamide |

| | Chemical Name |
|---|---|
| I-542 | (2R)-7-({2-[(cyclopropylcarbonyl)amino]pyridin-4-yl}oxy)-N-[3-[(methylamino)-methyl]-5-(trifluoromethyl)phenyl]-1,2,3,4-tetrahydronaphthalene-2-carboxamide |
| I-543 | (3R)-N-{4-[(7-{[(3-tert-butylphenyl)amino]carbonyl}-5,6,7,8-tetrahydronaphthalen-2-yl)oxy]pyridin-2-yl}pyrrolidine-3-carboxamide |
| I-544 | N-[4-(aminomethyl)-3-(trifluoromethyl)phenyl]-7-({2-[(cyclopropylcarbonyl)-amino]pyridin-4-yl}oxy)-3,4-dihydroisoquinoline-2(1H)-carboxamide |
| I-545 | 7-({2-[(methoxyacetyl)amino]pyridin-4-yl}oxy)-N-[3-[(methylamino)methyl]-5-(trifluoromethyl)phenyl]-1,2,3,4-tetrahydronaphthalene-2-carboxamide |
| I-546 | 3-tert-butyl-N-[7-({2-[(cyclopropylcarbonyl)amino]pyridin-4-yl}oxy)-1,2,3,4-tetrahydronaphthalen-2-yl]-5-[(methylamino)methyl]benzamide |
| I-547 | N-[3-(aminomethyl)-5-(trifluoromethyl)phenyl]-7-{[2-(glycoloylamino)pyridin-4-yl]oxy}-1,2,3,4-tetrahydronaphthalene-2-carboxamide |
| I-548 | 7-({2-[(cyclopropylcarbonyl)amino]pyridin-4-yl}oxy)-N-[4-(pyrrolidin-1-ylmethyl)-3-(trifluoromethyl)phenyl]-3,4-dihydroisoquinoline-2(1H)-carboxamide |
| I-549 | 7-({2-[(cyclopropylcarbonyl)amino]pyridin-4-yl}oxy)-N-[3-(pyrrolidin-1-ylmethyl)-5-(trifluoromethyl)phenyl]-3,4-dihydroisoquinoline-2(1H)-carboxamide |
| I-550 | N-(4-{[7-({[3-(aminomethyl)-5-(trifluoromethyl)phenyl]amino}carbonyl)-5,6,7,8-tetrahydronaphthalen-2-yl]oxy}pyridin-2-yl)azetidine-3-carboxamide |
| I-551 | 7-({2-[(cyclopropylcarbonyl)amino]pyridin-4-yl}oxy)-N-[8-(trifluoromethyl)-1,2,3,4-tetrahydroisoquinolin-6-yl]-1,2,3,4-tetrahydronaphthalene-2-carboxamide |
| I-552 | N-(4-{[7-({[3-(aminomethyl)-5-(trifluoromethyl)phenyl]amino}carbonyl)-5,6,7,8-tetrahydronaphthalen-2-yl]oxy}pyridin-2-yl)piperidine-4-carboxamide |
| I-553 | 3-tert-butyl-N-[7-({2-[(cyclopropylcarbonyl)amino]pyridin-4-yl}oxy)-1,2,3,4-tetrahydronaphthalen-2-yl]-5-[(4-ethylpiperazin-1-yl)methyl]benzamide |
| I-554 | N-methyl-4-[(7-{[4-(trifluoromethoxy)benzoyl]amino}-5,6,7,8-tetrahydronaphthalen-2-yl)oxy]pyridine-2-carboxamide |
| I-555 | 4-({7-[(3-hydroxy-4-nitrobenzoyl)amino]-5,6,7,8-tetrahydronaphthalen-2-yl}-oxy)-N-methylpyridine-2-carboxamide |
| I-557 | 4-({7-[(3-hydroxy-4-methoxybenzoyl)amino]-5,6,7,8-tetrahydronaphthalen-2-yl}oxy)-N-methylpyridine-2-carboxamide |
| I-558 | N-methyl-4-[(7-{[(4-methyl-2-pyridin-2-yl-1,3-thiazol-5-yl)carbonyl]amino}-5,6,7,8-tetrahydronaphthalen-2-yl)oxy]pyridine-2-carboxamide |
| I-559 | 4-({7-[(3-fluorobenzoyl)amino]-5,6,7,8-tetrahydronaphthalen-2-yl}oxy)-N-methylpyridine-2-carboxamide |
| I-560 | 4-[(7-{[(5-chloro-1-benzofuran-2-yl)carbonyl]amino}-5,6,7,8-tetrahydronaphthalen-2-yl)oxy]-N-methylpyridine-2-carboxamide |
| I-561 | 4-({7-[(4-methoxy-3-methylbenzoyl)amino]-5,6,7,8-tetrahydronaphthalen-2-yl}-oxy)-N-methylpyridine-2-carboxamide |
| I-562 | 4-({7-[(4-bromobenzoyl)amino]-5,6,7,8-tetrahydronaphthalen-2-yl}oxy)-N-methylpyridine-2-carboxamide |
| I-563 | 4-[(7-{[4-(difluoromethoxy)benzoyl]amino}-5,6,7,8-tetrahydronaphthalen-2-yl)oxy]-N-methylpyridine-2-carboxamide |
| I-564 | 4-[(7-{[3-fluoro-5-(trifluoromethyl)benzoyl]amino}-5,6,7,8-tetrahydronaphthalen-2-yl)oxy]-N-methylpyridine-2-carboxamide |
| I-565 | 4-[(7-{[4-(1H-imidazol-1-yl)benzoyl]amino}-5,6,7,8-tetrahydronaphthalen-2-yl)oxy]-N-methylpyridine-2-carboxamide |
| I-566 | 4-[(7-{[4-fluoro-3-(trifluoromethyl)benzoyl]amino}-5,6,7,8-tetrahydronaphthalen-2-yl)oxy]-N-methylpyridine-2-carboxamide |
| I-567 | 4-({7-[(5-chloro-2-methoxybenzoyl)amino]-5,6,7,8-tetrahydronaphthalen-2-yl}-oxy)-N-methylpyridine-2-carboxamide |
| I-568 | 1-methyl-N-[7-({2-[(methylamino)carbonyl]pyridin-4-yl}oxy)-1,2,3,4-tetrahydronaphthalen-2-yl]-1H-indole-2-carboxamide |
| I-569 | methyl 4-({[7-({2-[(methylamino)carbonyl]pyridin-4-yl}oxy)-1,2,3,4-tetrahydronaphthalen-2-yl]amino}carbonyl)benzoate |
| I-570 | N-methyl-4-[(7-{[2-(1H-tetrazol-1-yl)isonicotinoyl]amino}-5,6,7,8-tetrahydronaphthalen-2-yl)oxy]pyridine-2-carboxamide |
| I-571 | N-methyl-4-({7-[(3,4,5-trimethoxybenzoyl)amino]-5,6,7,8-tetrahydronaphthalen-2-yl}oxy)pyridine-2-carboxamide |
| I-572 | 4-({7-[(1,3-benzodioxol-5-ylcarbonyl)amino]-5,6,7,8-tetrahydronaphthalen-2-yl}-oxy)-N-methylpyridine-2-carboxamide |
| I-574 | 4-[(7-{[3,5-bis(trifluoromethyl)benzoyl]amino}-5,6,7,8-tetrahydronaphthalen-2-yl)oxy]-N-methylpyridine-2-carboxamide |
| I-575 | 4-({7-[(3,5-difluorobenzoyl)amino]-5,6,7,8-tetrahydronaphthalen-2-yl}oxy)-N-methylpyridine-2-carboxamide |
| I-576 | 4-{[7-({[2,5-dimethyl-1-(pyridin-4-ylmethyl)-1H-pyrrol-3-yl]carbonyl}amino)-5,6,7,8-tetrahydronaphthalen-2-yl]oxy}-N-methylpyridine-2-carboxamide |
| I-577 | N-methyl-4-({7-[(4-methylbenzoyl)amino]-5,6,7,8-tetrahydronaphthalen-2-yl}-oxy)pyridine-2-carboxamide |
| I-578 | 4-({7-[(3-amino-4-methoxybenzoyl)amino]-5,6,7,8-tetrahydronaphthalen-2-yl}-oxy)-N-methylpyridine-2-carboxamide |
| I-581 | 4-[(7-{[(2-methoxypyridin-3-yl)carbonyl]amino}-5,6,7,8-tetrahydronaphthalen-2-yl)oxy]-N-methylpyridine-2-carboxamide |
| I-582 | 4-[(7-{[4-(dimethylamino)benzoyl]amino}-5,6,7,8-tetrahydronaphthalen-2-yl)-oxy]-N-methylpyridine-2-carboxamide |

| | Chemical Name |
|---|---|
| I-583 | N-[7-({2-[(methylamino)carbonyl]pyridin-4-yl}oxy)-1,2,3,4-tetrahydronaphthalen-2-yl]-1H-indole-5-carboxamide |
| I-584 | 4-({7-[(3-amino-4-hydroxybenzoyl)amino]-5,6,7,8-tetrahydronaphthalen-2-yl}-oxy)-N-methylpyridine-2-carboxamide |
| I-585 | N-methyl-4-[(7-{[3-(trifluoromethoxy)benzoyl]amino}-5,6,7,8-tetrahydronaphthalen-2-yl)oxy]pyridine-2-carboxamide |
| I-586 | 4-({7-[(3,5-dimethylbenzoyl)amino]-5,6,7,8-tetrahydronaphthalen-2-yl}oxy)-N-methylpyridine-2-carboxamide |
| I-587 | N-methyl-4-[(7-{[4-(trifluoromethyl)benzoyl]amino}-5,6,7,8-tetrahydronaphthalen-2-yl)oxy]pyridine-2-carboxamide |
| I-589 | N-methyl-4-({7-[(3-methylbenzoyl)amino]-5,6,7,8-tetrahydronaphthalen-2-yl}-oxy)pyridine-2-carboxamide |
| I-590 | 4-({7-[(4-isopropylbenzoyl)amino]-5,6,7,8-tetrahydronaphthalen-2-yl})-N-methylpyridine-2-carboxamide |
| I-591 | 4-({7-[(4-chlorobenzoyl)amino]-5,6,7,8-tetrahydronaphthalen-2-yl}oxy)-N-methylpyridine-2-carboxamide |
| I-592 | 4-({7-[(3-methoxybenzoyl)amino]-5,6,7,8-tetrahydronaphthalen-2-yl}oxy)-N-methylpyridine-2-carboxamide |
| I-593 | 4-({7-[(3-bromobenzoyl)amino]-5,6,7,8-tetrahydronaphthalen-2-yl}oxy)-N-methylpyridine-2-carboxamide |
| I-594 | 4-({7-[(3,5-dimethoxy-4-methylbenzoyl)amino]-5,6,7,8-tetrahydronaphthalen-2-yl}oxy)-N-methylpyridine-2-carboxamide |
| I-595 | N-methyl-4-[(7-{[3-(1H-tetrazol-1-yl)benzoyl]amino}-5,6,7,8-tetrahydronaphthalen-2-yl)oxy]pyridine-2-carboxamide |
| I-596 | 4-({7-[(4-benzylbenzoyl)amino]-5,6,7,8-tetrahydronaphthalen-2-yl}oxy)-N-methylpyridine-2-carboxamide |
| I-597 | 4-({7-[(4-ethylbenzoyl)amino]-5,6,7,8-tetrahydronaphthalen-2-yl}oxy)-N-methylpyridine-2-carboxamide |
| I-598 | N-[7-({2-[(methylamino)carbonyl]pyridin-4-yl}oxy)-1,2,3,4-tetrahydronaphthalen-2-yl]quinoline-8-carboxamide |
| I-599 | 4-[(7-{[4-(4-fluorophenoxy)benzoyl]amino}-5,6,7,8-tetrahydronaphthalen-2-yl)-oxy]-N-methylpyridine-2-carboxamide |
| I-600 | 4-({7-[(3-aminobenzoyl)amino]-5,6,7,8-tetrahydronaphthalen-2-yl}oxy)-N-methylpyridine-2-carboxamide |
| I-601 | N-methyl-4-({7-[(3,4,5-trifluorobenzoyl)amino]-5,6,7,8-tetrahydronaphthalen-2-yl}oxy)pyridine-2-carboxamide |
| I-602 | 4-[(7-{[(3-ethyl-1-methyl-1H-pyrazol-5-yl)carbonyl]amino}-5,6,7,8-tetrahydronaphthalen-2-yl)oxy]-N-methylpyridine-2-carboxamide |
| I-604 | N-methyl-4-[(7-{[3-(trifluoromethyl)benzoyl]amino}-5,6,7,8-tetrahydronaphthalen-2-yl)oxy]pyridine-2-carboxamide |
| I-605 | N-methyl-4-[(7-{[4-(methylsulfonyl)benzoyl]amino}-5,6,7,8-tetrahydronaphthalen-2-yl)oxy]pyridine-2-carboxamide |
| I-606 | N-methyl-4-[(7-{[2-(methylamino)benzoyl]amino}-5,6,7,8-tetrahydronaphthalen-2-yl)oxy]pyridine-2-carboxamide |
| I-607 | 4-({7-[(3-bromo-4-chlorobenzoyl)amino]-5,6,7,8-tetrahydronaphthalen-2-yl}-oxy)-N-methylpyridine-2-carboxamide |
| I-608 | 4-[(7-{[4-(benzyloxy)benzoyl]amino}-5,6,7,8-tetrahydronaphthalen-2-yl)oxy]-N-methylpyridine-2-carboxamide |
| I-609 | 4-({7-[(4-bromo-3-methylbenzoyl)amino]-5,6,7,8-tetrahydronaphthalen-2-yl}-oxy)-N-methylpyridine-2-carboxamide |
| I-610 | 4-[(7-{[2-chloro-5-(trifluoromethyl)benzoyl]amino}-5,6,7,8-tetrahydronaphthalen-2-yl)oxy]-N-methylpyridine-2-carboxamide |
| I-611 | 4-methoxy-N-[7-({2-[(methylamino)carbonyl]pyridin-4-yl}oxy)-1,2,3,4-tetrahydronaphthalen-2-yl]quinoline-2-carboxamide |
| I-612 | 4-({7-[(3-hydroxy-4-methylbenzoyl)amino]-5,6,7,8-tetrahydronaphthalen-2-yl}-oxy)-N-methylpyridine-2-carboxamide |
| I-613 | 4-[(7-{[3-(aminosulfonyl)-4-chlorobenzoyl]amino}-5,6,7,8-tetrahydronaphthalen-2-yl)oxy]-N-methylpyridine-2-carboxamide |
| I-615 | 4-({7-[(2-cyanobenzoyl)amino]-5,6,7,8-tetrahydronaphthalen-2-yl}oxy)-N-methylpyridine-2-carboxamide |
| I-616 | 4-({7-[(3-amino-4-chlorobenzoyl)amino]-5,6,7,8-tetrahydronaphthalen-2-yl}oxy)-N-methylpyridine-2-carboxamide |
| I-617 | 4-({7-[(4-benzoylbenzoyl)amino]-5,6,7,8-tetrahydronaphthalen-2-yl}oxy)-N-methylpyridine-2-carboxamide |
| I-618 | N-[7-({2-[(methylamino)carbonyl]pyridin-4-yl}oxy)-1,2,3,4-tetrahydronaphthalen-2-yl]quinoline-4-carboxamide |
| I-619 | 4-({7-[(4-ethoxybenzoyl)amino]-5,6,7,8-tetrahydronaphthalen-2-yl}oxy)-N-methylpyridine-2-carboxamide |
| I-620 | 4-({7-[(biphenyl-4-ylcarbonyl)amino]-5,6,7,8-tetrahydronaphthalen-2-yl}oxy)-N-methylpyridine-2-carboxamide |
| I-621 | N-methyl-4-[(7-{[4-(methylsulfanyl)-3-nitrobenzoyl]amino}-5,6,7,8-tetrahydronaphthalen-2-yl)oxy]pyridine-2-carboxamide |
| I-622 | 4-({7-[(4-fluorobenzoyl)amino]-5,6,7,8-tetrahydronaphthalen-2-yl}oxy)-N-methylpyridine-2-carboxamide |
| I-623 | 4-({7-[(3-cyanobenzoyl)amino]-5,6,7,8-tetrahydronaphthalen-2-yl}oxy)-N-methylpyridine-2-carboxamide |
| I-624 | 6-chloro-N-[7-({2-[(methylamino)carbonyl]pyridin-4-yl}oxy)-1,2,3,4-tetrahydronaphthalen-2-yl]imidazo[1,2-a]pyridine-2-carboxamide |

| | Chemical Name |
|---|---|
| I-625 | 4-({7-[(4-hydroxy-3-methoxybenzoyl)amino]-5,6,7,8-tetrahydronaphthalen-2-yl}oxy)-N-methylpyridine-2-carboxamide |
| I-626 | 4-({7-[(3-chloro-4-methoxybenzoyl)amino]-5,6,7,8-tetrahydronaphthalen-2-yl}-oxy)-N-methylpyridine-2-carboxamide |
| I-627 | 4-[(7-{[2-(3,5-dimethyl-1H-pyrazol-4-yl)benzoyl]amino}-5,6,7,8-tetrahydronaphthalen-2-yl)oxy]-N-methylpyridine-2-carboxamide |
| I-629 | N-methyl-4-[(7-{[(9-oxo-9H-fluoren-2-yl)carbonyl]amino}-5,6,7,8-tetrahydronaphthalen-2-yl)oxy]pyridine-2-carboxamide |
| I-630 | 4-({7-[(3,4-dichlorobenzoyl)amino]-5,6,7,8-tetrahydronaphthalen-2-yl}oxy)-N-methylpyridine-2-carboxamide |
| I-631 | N-methyl-4-({7-[(4-vinylbenzoyl)amino]-5,6,7,8-tetrahydronaphthalen-2-yl}-oxy)pyridine-2-carboxamide |
| I-632 | 4-({7-[(3,4-dihydroxybenzoyl)amino]-5,6,7,8-tetrahydronaphthalen-2-yl}oxy)-N-methylpyridine-2-carboxamide |
| I-633 | 4-({7-[(4-acetylbenzoyl)amino]-5,6,7,8-tetrahydronaphthalen-2-yl}oxy)-N-methylpyridine-2-carboxamide |
| I-634 | 4-({7-[(3,4-dimethoxybenzoyl)amino]-5,6,7,8-tetrahydronaphthalen-2-yl}oxy)-N-methylpyridine-2-carboxamide |
| I-635 | 4-({7-[(4-isobutylbenzoyl)amino]-5,6,7,8-tetrahydronaphthalen-2-yl}oxy)-N-methylpyridine-2-carboxamide |
| I-637 | 4-[(7-{[3-fluoro-4-(trifluoromethyl)benzoyl]amino}-5,6,7,8-tetrahydronaphthalen-2-yl)oxy]-N-methylpyridine-2-carboxamide |
| I-638 | N-methyl-4-({7-[(3-phenoxybenzoyl)amino]-5,6,7,8-tetrahydronaphthalen-2-yl}-oxy)pyridine-2-carboxamide |
| I-639 | 4-({7-[(3,5-dichlorobenzoyl)amino]-5,6,7,8-tetrahydronaphthalen-2-yl}oxy)-N-methylpyridine-2-carboxamide |
| I-640 | N-methyl-4-({7-[(4-phenoxybenzoyl)amino]-5,6,7,8-tetrahydronaphthalen-2-yl}-oxy)pyridine-2-carboxamide |
| I-641 | 4-({7-[(3-bromo-4-methylbenzoyl)amino]-5,6,7,8-tetrahydronaphthalen-2-yl}-oxy)-N-methylpyridine-2-carboxamide |
| I-642 | 4-({7-[(4-methoxybenzoyl)amino]-5,6,7,8-tetrahydronaphthalen-2-yl}oxy)-N-methylpyridine-2-carboxamide |
| I-644 | 4-({7-[(3,5-di-tert-butyl-4-hydroxybenzoyl)amino]-5,6,7,8-tetrahydronaphthalen-2-yl}oxy)-N-methylpyridine-2-carboxamide |
| I-645 | 3-({[7-({2-[(methylamino)carbonyl]pyridin-4-yl}oxy)-1,2,3,4-tetrahydronaphthalen-2-yl]amino}carbonyl)phenyl acetate |
| I-646 | 4-{[7-({4-[(benzylsulfonyl)amino]benzoyl}amino)-5,6,7,8-tetrahydronaphthalen-2-yl]oxy}-N-methylpyridine-2-carboxamide |
| I-647 | N-methyl-4-[(7-{[3-nitro-5-(trifluoromethyl)benzoyl]amino}-5,6,7,8-tetrahydronaphthalen-2-yl)oxy]pyridine-2-carboxamide |
| I-648 | 4-[(7-{[3,5-bis(acetylamino)benzoyl]amino}-5,6,7,8-tetrahydronaphthalen-2-yl)-oxy]-N-methylpyridine-2-carboxamide |
| I-649 | 4-({7-[(6-hydroxy-2-naphthoyl)amino]-5,6,7,8-tetrahydronaphthalen-2-yl}oxy)-N-methylpyridine-2-carboxamide |
| I-650 | N-methyl-4-[(7-{[4-(4-methylphenoxy)benzoyl]amino}-5,6,7,8-tetrahydronaphthalen-2-yl)oxy]pyridine-2-carboxamide |
| I-651 | 4-[(7-{[(3',4'-dichlorobiphenyl-4-yl)carbonyl]amino}-5,6,7,8-tetrahydronaphthalen-2-yl)oxy]-N-methylpyridine-2-carboxamide |
| I-652 | 4-({7-[(3-bromo-4-methoxybenzoyl)amino]-5,6,7,8-tetrahydronaphthalen-2-yl}-oxy)-N-methylpyridine-2-carboxamide |
| I-653 | N-[7-({2-[(methylamino)carbonyl]pyridin-4-yl}oxy)-1,2,3,4-tetrahydronaphthalen-2-yl]-1,3-benzothiazole-6-carboxamide |
| I-654 | 4-({7-[(3-ethoxy-4-methoxybenzoyl)amino]-5,6,7,8-tetrahydronaphthalen-2-yl}-oxy)-N-methylpyridine-2-carboxamide |
| I-655 | N-methyl-4-[(7-{[3-(1H-pyrazol-1-yl)benzoyl]amino}-5,6,7,8-tetrahydronaphthalen-2-yl)oxy]pyridine-2-carboxamide |
| I-656 | 4-[(7-{[3-(cyclopentyloxy)-4-methoxybenzoyl]amino}-5,6,7,8-tetrahydronaphthalen-2-yl)oxy]-N-methylpyridine-2-carboxamide |
| I-657 | 4-{[7-({4-[(2-hydroxyethyl)(methyl)amino]benzoyl}amino)-5,6,7,8-tetrahydronaphthalen-2-yl]oxy}-N-methylpyridine-2-carboxamide |
| I-658 | 4-[(7-{[4-(2,5-dimethoxybenzoyl)benzoyl]amino}-5,6,7,8-tetrahydronaphthalen-2-yl)oxy]-N-methylpyridine-2-carboxamide |
| I-659 | 4-[(7-{[(2'-fluorobiphenyl-3-yl)carbonyl]amino}-5,6,7,8-tetrahydronaphthalen-2-yl)oxy]-N-methylpyridine-2-carboxamide |
| I-660 | 4-[(7-{[(4'-fluorobiphenyl-3-yl)carbonyl]amino}-5,6,7,8-tetrahydronaphthalen-2-yl)oxy]-N-methylpyridine-2-carboxamide |
| I-661 | 1-methyl-N-[7-({2-[(methylamino)carbonyl]pyridin-4-yl}oxy)-1,2,3,4-tetrahydronaphthalen-2-yl]-1,2,3,4-tetrahydroquinoline-6-carboxamide |
| I-662 | 4-({7-[(3,4-dihydro-2H-1,5-benzodioxepin-7-ylcarbonyl)amino]-5,6,7,8-tetrahydronaphthalen-2-yl}oxy)-N-methylpyridine-2-carboxamide |
| I-663 | N-[7-({2-[(methylamino)carbonyl]pyridin-4-yl}oxy)-1,2,3,4-tetrahydronaphthalen-2-yl]-2,1,3-benzothiadiazole-5-carboxamide |
| I-664 | N-methyl-4-[(7-{[3-(2-methyl-1,3-thiazol-4-yl)benzoyl]amino}-5,6,7,8-tetrahydronaphthalen-2-yl)oxy]pyridine-2-carboxamide |
| I-665 | 4-({7-[(4-fluoro-3-methoxybenzoyl)amino]-5,6,7,8-tetrahydronaphthalen-2-yl}-oxy)-N-methylpyridine-2-carboxamide |
| I-666 | 4-({7-[(3-acetylbenzoyl)amino]-5,6,7,8-tetrahydronaphthalen-2-yl}oxy)-N-methylpyridine-2-carboxamide |

-continued

| | Chemical Name |
|---|---|
| I-667 | N-methyl-4-[(7-{[3-(methylsulfonyl)benzoyl]amino}-5,6,7,8-tetrahydronaphthalen-2-yl)oxy]pyridine-2-carboxamide |
| I-668 | 3-hydroxy-N-[7-({2-[(methylamino)carbonyl]pyridin-4-yl}oxy)-1,2,3,4-tetrahydronaphthalen-2-yl]quinoxaline-2-carboxamide |
| I-669 | 4-[(7-{[(2,6-dimethoxypyridin-3-yl)carbonyl]amino}-5,6,7,8-tetrahydronaphthalen-2-yl)oxy]-N-methylpyridine-2-carboxamide |
| I-670 | N-methyl-4-[(7-{[(2-phenoxypyridin-3-yl)carbonyl]amino}-5,6,7,8-tetrahydronaphthalen-2-yl)oxy]pyridine-2-carboxamide |
| I-672 | N-[7-({2-[(methylamino)carbonyl]pyridin-4-yl}oxy)-1,2,3,4-tetrahydronaphthalen-2-yl]quinoxaline-2-carboxamide |
| I-673 | 4-[(7-{[(6-hydroxypyridin-3-yl)carbonyl]amino}-5,6,7,8-tetrahydronaphthalen-2-yl)oxy]-N-methylpyridine-2-carboxamide |
| I-674 | 4-[(7-{[(2-chloropyridin-3-yl)carbonyl]amino}-5,6,7,8-tetrahydronaphthalen-2-yl)oxy]-N-methylpyridine-2-carboxamide |
| I-675 | 4-[(7-{[(5-bromopyridin-3-yl)carbonyl]amino}-5,6,7,8-tetrahydronaphthalen-2-yl)oxy]-N-methylpyridine-2-carboxamide |
| I-676 | N-methyl-4-[(7-{[(2-methylpyridin-3-yl)carbonyl]amino}-5,6,7,8-tetrahydronaphthalen-2-yl)oxy]pyridine-2-carboxamide |
| I-677 | 6-methoxy-N-[7-({2-[(methylamino)carbonyl]pyridin-4-yl}oxy)-1,2,3,4-tetrahydronaphthalen-2-yl]-2-phenylquinoline-4-carboxamide |
| I-678 | N-methyl-4-{[7-({[6-(1H-pyrazol-1-yl)pyridin-3-yl]carbonyl}amino)-5,6,7,8-tetrahydronaphthalen-2-yl]oxy}pyridine-2-carboxamide |
| I-679 | 4-chloro-1,3-dimethyl-N-[7-({2-[(methylamino)carbonyl]pyridin-4-yl}oxy)-1,2,3,4-tetrahydronaphthalen-2-yl]-1H-pyrazolo[3,4-b]pyridine-5-carboxamide |
| I-680 | N-methyl-4-{[7-({[6-(2,2,2-trifluoroethoxy)pyridin-3-yl]carbonyl}amino)-5,6,7,8-tetrahydronaphthalen-2-yl]oxy}pyridine-2-carboxamide |
| I-681 | N-methyl-4-{[7-({[2-(phenylsulfanyl)pyridin-3-yl]carbonyl}amino)-5,6,7,8-tetrahydronaphthalen-2-yl]oxy}pyridine-2-carboxamide |
| I-682 | N-methyl-4-{[7-({[5-(2-thienyl)pyridin-3-yl]carbonyl}amino)-5,6,7,8-tetrahydronaphthalen-2-yl]oxy}pyridine-2-carboxamide |
| I-683 | N-methyl-4-[(7-{[(6-morpholin-4-ylpyridin-3-yl)carbonyl]amino}-5,6,7,8-tetrahydronaphthalen-2-yl)oxy]pyridine-2-carboxamide |
| I-684 | N-methyl-4-{[7-({[2-(4-methylphenoxy)pyridin-3-yl]carbonyl}amino)-5,6,7,8-tetrahydronaphthalen-2-yl]oxy}pyridine-2-carboxamide |
| I-706 | 4-[(7-{[(7-ethoxy-1-benzofuran-2-yl)carbonyl]amino}-5,6,7,8-tetrahydronaphthalen-2-yl)oxy]-N-methylpyridine-2-carboxamide |
| I-707 | 4-[(7-{[(5-methoxy-1-benzofuran-2-yl)carbonyl]amino}-5,6,7,8-tetrahydronaphthalen-2-yl)oxy]-N-methylpyridine-2-carboxamide |
| I-708 | 4-({7-[(1-benzothien-2-ylcarbonyl)amino]-5,6,7,8-tetrahydronaphthalen-2-yl}oxy)-N-methylpyridine-2-carboxamide |
| I-709 | N-methyl-4-[(7-{[(5-methyl-1-phenyl-1H-pyrazol-4-yl)carbonyl]amino}-5,6,7,8-tetrahydronaphthalen-2-yl)oxy]pyridine-2-carboxamide |
| I-710 | 5-methoxy-N-[7-({2-[(methylamino)carbonyl]pyridin-4-yl}oxy)-1,2,3,4-tetrahydronaphthalen-2-yl]-1H-indole-2-carboxamide |
| I-711 | 4-{[7-({[3-(2-chloro-6-fluorophenyl)-5-methylisoxazol-4-yl]carbonyl}amino)-5,6,7,8-tetrahydronaphthalen-2-yl]oxy}-N-methylpyridine-2-carboxamide |
| I-712 | N-[7-({2-[(methylamino)carbonyl]pyridin-4-yl}oxy)-1,2,3,4-tetrahydronaphthalen-2-yl]-1H-indole-3-carboxamide |
| I-714 | N-[7-({2-[(methylamino)carbonyl]pyridin-4-yl}oxy)-1,2,3,4-tetrahydronaphthalen-2-yl]-1,3-benzothiazole-2-carboxamide |
| I-715 | N-methyl-4-[(7-{[(2-methyl-1,3-thiazol-4-yl)carbonyl]amino}-5,6,7,8-tetrahydronaphthalen-2-yl)oxy]pyridine-2-carboxamide |
| I-716 | N-methyl-4-[(7-{[(1-phenyl-1H-pyrazol-4-yl)carbonyl]amino}-5,6,7,8-tetrahydronaphthalen-2-yl)oxy]pyridine-2-carboxamide |
| I-717 | N-methyl-4-[(7-{[(2-phenyl-1,3-thiazol-4-yl)carbonyl]amino}-5,6,7,8-tetrahydronaphthalen-2-yl)oxy]pyridine-2-carboxamide |
| I-718 | 4-{[7-({[2-(4-chlorophenyl)-1,3-thiazol-4-yl]carbonyl}amino)-5,6,7,8-tetrahydronaphthalen-2-yl]oxy}-N-methylpyridine-2-carboxamide |
| I-719 | N-methyl-4-{[7-({[1-phenyl-5-(trifluoromethyl)-1H-pyrazol-4-yl]carbonyl}-amino)-5,6,7,8-tetrahydronaphthalen-2-yl]oxy}pyridine-2-carboxamide |
| I-720 | 4-{[7-({[5-chloro-1-methyl-3-(trifluoromethyl)-1H-pyrazol-4-yl]carbonyl}amino)-5,6,7,8-tetrahydronaphthalen-2-yl]oxy}-N-methylpyridine-2-carboxamide |
| I-721 | 5-methyl-N-[7-({2-[(methylamino)carbonyl]pyridin-4-yl}oxy)-1,2,3,4-tetrahydronaphthalen-2-yl]-1H-indazole-3-carboxamide |
| I-722 | N-methyl-4-[(7-{[(5-pyridin-2-yl-2-thienyl)carbonyl]amino}-5,6,7,8-tetrahydronaphthalen-2-yl)oxy]pyridine-2-carboxamide |
| I-723 | 4-({7-[(1-benzothien-3-ylcarbonyl)amino]-5,6,7,8-tetrahydronaphthalen-2-yl}oxy)-N-methylpyridine-2-carboxamide |
| I-724 | N-methyl-4-[(7-{[2-methyl-5-(morpholin-4-ylsulfonyl)-3-furoyl]amino}-5,6,7,8-tetrahydronaphthalen-2-yl)oxy]pyridine-2-carboxamide |
| I-725 | N-methyl-4-[(7-{[2-methyl-5-(piperidin-1-ylsulfonyl)-3-furoyl]amino}-5,6,7,8-tetrahydronaphthalen-2-yl)oxy]pyridine-2-carboxamide |
| I-726 | 4-({7-[(2,5-dimethyl-4-{[(2-thienylmethyl)amino]sulfonyl}-3-furoyl)amino]-5,6,7,8-tetrahydronaphthalen-2-yl}oxy)-N-methylpyridine-2-carboxamide |
| I-727 | 2,8-dimethyl-N-[7-({2-[(methylamino)carbonyl]pyridin-4-yl}oxy)-1,2,3,4-tetrahydronaphthalen-2-yl]imidazo[1,2-a]pyridine-3-carboxamide |
| I-728 | N-[7-({2-[(methylamino)carbonyl]pyridin-4-yl}oxy)-1,2,3,4-tetrahydronaphthalen-2-yl]-2-phenylimidazo[1,2-a]pyridine-3-carboxamide |

| | Chemical Name |
|---|---|
| I-729 | 5-chloro-N-[7-({2-[(methylamino)carbonyl]pyridin-4-yl}oxy)-1,2,3,4-tetrahydronaphthalen-2-yl]-1H-indole-2-carboxamide |
| I-730 | N-methyl-4-{[7-({5-[3-(trifluoromethyl)phenyl]-2-furoyl}amino)-5,6,7,8-tetrahydronaphthalen-2-yl]oxy}pyridine-2-carboxamide |
| I-733 | N-[7-({2-[(methylamino)carbonyl]pyridin-4-yl}oxy)-1,2,3,4-tetrahydronaphthalen-2-yl]quinoline-3-carboxamide |
| I-734 | N-methyl-4-({7-[(pyridin-3-ylcarbonyl)amino]-5,6,7,8-tetrahydronaphthalen-2-yl}oxy)pyridine-2-carboxamide |
| I-735 | 4-[(7-{[(2-hydroxypyridin-3-yl)carbonyl]amino}-5,6,7,8-tetrahydronaphthalen-2-yl)oxy]-N-methylpyridine-2-carboxamide |
| I-736 | 4-hydroxy-6-methoxy-N-[7-({2-[(methylamino)carbonyl]pyridin-4-yl}oxy)-1,2,3,4-tetrahydronaphthalen-2-yl]quinoline-3-carboxamide |
| I-737 | 1,3-dihydroxy-N-[7-({2-[(methylamino)carbonyl]pyridin-4-yl}oxy)-1,2,3,4-tetrahydronaphthalen-2-yl]acridine-9-carboxamide |
| I-738 | 2-(4-chlorophenyl)-N-[7-({2-[(methylamino)carbonyl]pyridin-4-yl}oxy)-1,2,3,4-tetrahydronaphthalen-2-yl]quinoline-4-carboxamide |
| I-740 | 7-({2-[(methylamino)carbonyl]pyridin-4-yl}oxy)-N-(3-methylphenyl)-3,4-dihydroisoquinoline-2(1H)-carboxamide |
| I-741 | N-(4-chlorophenyl)-7-({2-[(methylamino)carbonyl]pyridin-4-yl}oxy)-3,4-dihydroisoquinoline-2(1H)-carboxamide |
| I-742 | ethyl 4-({[7-({2-[(methylamino)carbonyl]pyridin-4-yl}oxy)-3,4-dihydroisoquinolin-2(1H)-yl]carbonyl}amino)benzoate |
| I-743 | 7-({2-[(methylamino)carbonyl]pyridin-4-yl}oxy)-N-1-naphthyl-3,4-dihydroisoquinoline-2(1H)-carboxamide |
| I-744 | N-(4-bromophenyl)-7-({2-[(methylamino)carbonyl]pyridin-4-yl}oxy)-3,4-dihydroisoquinoline-2(1H)-carboxamide |
| I-745 | N-(3-methoxyphenyl)-7-({2-[(methylamino)carbonyl]pyridin-4-yl}oxy)-3,4-dihydroisoquinoline-2(1H)-carboxamide |
| I-746 | N-(3,4-dichlorophenyl)-7-({2-[(methylamino)carbonyl]pyridin-4-yl}oxy)-3,4-dihydroisoquinoline-2(1H)-carboxamide |
| I-747 | N-(2,4-difluorophenyl)-7-({2-[(methylamino)carbonyl]pyridin-4-yl}oxy)-3,4-dihydroisoquinoline-2(1H)-carboxamide |
| I-748 | 7-({2-[(methylamino)carbonyl]pyridin-4-yl}oxy)-N-[4-(trifluoromethyl)phenyl]-3,4-dihydroisoquinoline-2(1H)-carboxamide |
| I-749 | N-(2,5-dichlorophenyl)-7-({2-[(methylamino)carbonyl]pyridin-4-yl}oxy)-3,4-dihydroisoquinoline-2(1H)-carboxamide |
| I-750 | N-(2,4-dimethoxyphenyl)-7-({2-[(methylamino)carbonyl]pyridin-4-yl}oxy)-3,4-dihydroisoquinoline-2(1H)-carboxamide |
| I-751 | N-(2,5-dimethoxyphenyl)-7-({2-[(methylamino)carbonyl]pyridin-4-yl}oxy)-3,4-dihydroisoquinoline-2(1H)-carboxamide |
| I-752 | N-(2-ethylphenyl)-7-({2-[(methylamino)carbonyl]pyridin-4-yl}oxy)-3,4-dihydroisoquinoline-2(1H)-carboxamide |
| I-753 | N-(2-chlorophenyl)-7-({2-[(methylamino)carbonyl]pyridin-4-yl}oxy)-3,4-dihydroisoquinoline-2(1H)-carboxamide |
| I-754 | N-(3-bromophenyl)-7-({2-[(methylamino)carbonyl]pyridin-4-yl}oxy)-3,4-dihydroisoquinoline-2(1H)-carboxamide |
| I-755 | N-(4-fluoro-3-nitrophenyl)-7-({2-[(methylamino)carbonyl]pyridin-4-yl}oxy)-3,4-dihydroisoquinoline-2(1H)-carboxamide |
| I-756 | 7-({2-[(methylamino)carbonyl]pyridin-4-yl}oxy)-N-[4-(trifluoromethoxy)phenyl]-3,4-dihydroisoquinoline-2(1H)-carboxamide |
| I-757 | N-[3,5-bis(trifluoromethyl)phenyl]-7-({2-[(methylamino)carbonyl]pyridin-4-yl}-oxy)-3,4-dihydroisoquinoline-2(1H)-carboxamide |
| I-758 | N-[2-chloro-5-(trifluoromethyl)phenyl]-7-({2-[(methylamino)carbonyl]pyridin-4-yl}oxy)-3,4-dihydroisoquinoline-2(1H)-carboxamide |
| I-759 | N-[4-chloro-2-(trifluoromethyl)phenyl]-7-({2-[(methylamino)carbonyl]pyridin-4-yl}oxy)-3,4-dihydroisoquinoline-2(1H)-carboxamide |
| I-760 | N-[4-chloro-3-(trifluoromethyl)phenyl]-7-({2-[(methylamino)carbonyl]pyridin-4-yl}oxy)-3,4-dihydroisoquinoline-2(1H)-carboxamide |
| I-761 | N-(2,5-difluorophenyl)-7-({2-[(methylamino)carbonyl]pyridin-4-yl}oxy)-3,4-dihydroisoquinoline-2(1H)-carboxamide |
| I-762 | 7-({2-[(methylamino)carbonyl]pyridin-4-yl}oxy)-N-[4-(methylsulfanyl)phenyl]-3,4-dihydroisoquinoline-2(1H)-carboxamide |
| I-763 | N-biphenyl-2-yl-7-({2-[(methylamino)carbonyl]pyridin-4-yl}oxy)-3,4-dihydroisoquinoline-2(1H)-carboxamide |
| I-764 | N-(4-acetylphenyl)-7-({2-[(methylamino)carbonyl]pyridin-4-yl}oxy)-3,4-dihydroisoquinoline-2(1H)-carboxamide |
| I-765 | N-(4-isopropylphenyl)-7-({2-[(methylamino)carbonyl]pyridin-4-yl}oxy)-3,4-dihydroisoquinoline-2(1H)-carboxamide |
| I-766 | 7-({2-[(methylamino)carbonyl]pyridin-4-yl}oxy)-N-(4-methyl-3-nitrophenyl)-3,4-dihydroisoquinoline-2(1H)-carboxamide |
| I-767 | N-(3-cyanophenyl)-7-({2-[(methylamino)carbonyl]pyridin-4-yl}oxy)-3,4-dihydroisoquinoline-2(1H)-carboxamide |
| I-768 | 7-({2-[(methylamino)carbonyl]pyridin-4-yl}oxy)-N-(3,4,5-trimethoxyphenyl)-3,4-dihydroisoquinoline-2(1H)-carboxamide |
| I-769 | ethyl 2-({[7-({2-[(methylamino)carbonyl]pyridin-4-yl}oxy)-3,4-dihydroisoquinolin-2(1H)-yl]carbonyl}amino)benzoate |
| I-770 | N-[4-fluoro-2-(trifluoromethyl)phenyl]-7-({2-[(methylamino)carbonyl]pyridin-4-yl}oxy)-3,4-dihydroisoquinoline-2(1H)-carboxamide |

-continued

| | Chemical Name |
|---|---|
| I-771 | N-(2-methoxy-4-nitrophenyl)-7-({2-[(methylamino)carbonyl]pyridin-4-yl}oxy)-3,4-dihydroisoquinoline-2(1H)-carboxamide |
| I-772 | N-(2-methoxy-5-nitrophenyl)-7-({2-[(methylamino)carbonyl]pyridin-4-yl}oxy)-3,4-dihydroisoquinoline-2(1H)-carboxamide |
| I-773 | N-(4-bromo-2-methylphenyl)-7-({2-[(methylamino)carbonyl]pyridin-4-yl}oxy)-3,4-dihydroisoquinoline-2(1H)-carboxamide |
| I-774 | dimethyl 5-({[7-({2-[(methylamino)carbonyl]pyridin-4-yl}oxy)-3,4-dihydroisoquinolin-2(1H)-yl]carbonyl}amino)isophthalate |
| I-775 | N-(5-fluoro-2-methylphenyl)-7-({2-[(methylamino)carbonyl]pyridin-4-yl}oxy)-3,4-dihydroisoquinoline-2(1H)-carboxamide |
| I-776 | N-(3,4-dimethylphenyl)-7-({2-[(methylamino)carbonyl]pyridin-4-yl}oxy)-3,4-dihydroisoquinoline-2(1H)-carboxamide |
| I-777 | N-(4-bromo-2,6-dimethylphenyl)-7-({2-[(methylamino)carbonyl]pyridin-4-yl}-oxy)-3,4-dihydroisoquinoline-2(1H)-carboxamide |
| I-778 | N-(3-iodophenyl)-7-({2-[(methylamino)carbonyl]pyridin-4-yl}oxy)-3,4-dihydroisoquinoline-2(1H)-carboxamide |
| I-779 | N-(2,4-dibromophenyl)-7-({2-[(methylamino)carbonyl]pyridin-4-yl}oxy)-3,4-dihydroisoquinoline-2(1H)-carboxamide |
| I-780 | methyl 3-({[7-({2-[(methylamino)carbonyl]pyridin-4-yl}oxy)-3,4-dihydroisoquinolin-2(1H)-yl]carbonyl}amino)benzoate |
| I-781 | N-(4-butylphenyl)-7-({2-[(methylamino)carbonyl]pyridin-4-yl}oxy)-3,4-dihydroisoquinoline-2(1H)-carboxamide |
| I-782 | N-[4-(difluoromethoxy)phenyl]-7-({2-[(methylamino)carbonyl]pyridin-4-yl}-oxy)-3,4-dihydroisoquinoline-2(1H)-carboxamide |
| I-783 | N-(2-iodophenyl)-7-({2-[(methylamino)carbonyl]pyridin-4-yl}oxy)-3,4-dihydroisoquinoline-2(1H)-carboxamide |
| I-784 | 7-({2-[(methylamino)carbonyl]pyridin-4-yl}oxy)-N-{4-[(trifluoromethyl)-sulfanyl]phenyl}-3,4-dihydroisoquinoline-2(1H)-carboxamide |
| I-785 | 7-({2-[(methylamino)carbonyl]pyridin-4-yl}oxy)-N-(2-phenoxyphenyl)-3,4-dihydroisoquinoline-2(1H)-carboxamide |
| I-786 | N-(4-cyanophenyl)-7-({2-[(methylamino)carbonyl]pyridin-4-yl}oxy)-3,4-dihydroisoquinoline-2(1H)-carboxamide |
| I-787 | N-(4-bromo-2-chlorophenyl)-7-({2-[(methylamino)carbonyl]pyridin-4-yl}oxy)-3,4-dihydroisoquinoline-2(1H)-carboxamide |

General Synthetic Methodology

The compounds of the present invention can be prepared by methods known to one of ordinary skill in the art and/or by reference to the schemes shown below and the synthetic examples that follow. Exemplary synthetic routes are set forth in Schemes 1 and 2 below, and in the Examples.

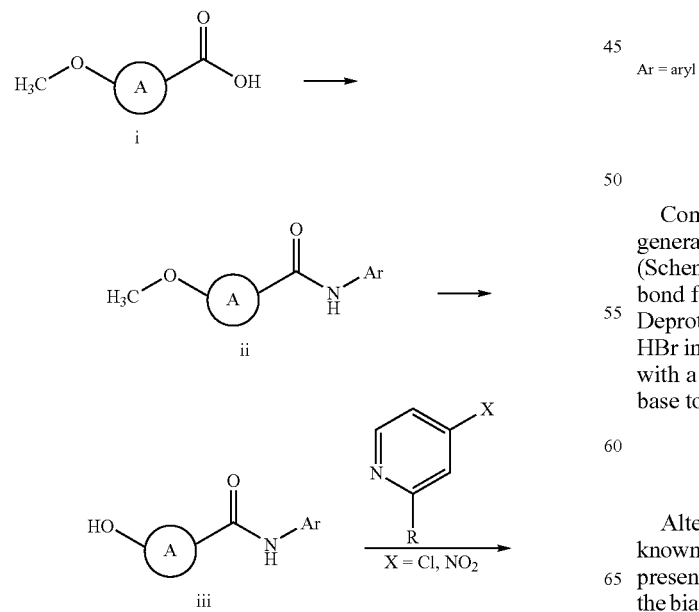

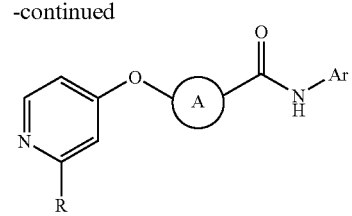

Ar = aryl

Compounds of formula (I) wherein $G^1$ is —O— can be generally prepared from a variety of known bicyclic acids i (Scheme 1). These acids are coupled under standard amide bond forming conditions with an aniline to provide amide ii. Deprotection of the methyl ether with boron tribromide or HBr in acetic acid provides phenol iii, which is then warmed with a 4-chloropyridine or 4-nitropyridine in the presence a base to provide the biaryl ether iv.

Alternatively, these compounds can be prepared from the known phenols v (Scheme 2). Warming of the phenol in the presence of a 4-chloropyridine or 4-nitropyridine provides the biaryl ether vi. The acid can then be converted to the amide vii under standard amide bond formation conditions.

Scheme 2

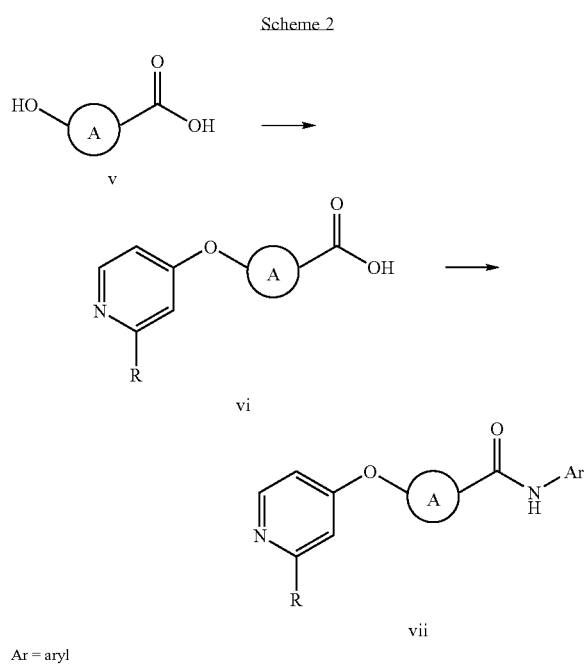

Ar = aryl

Scheme 3

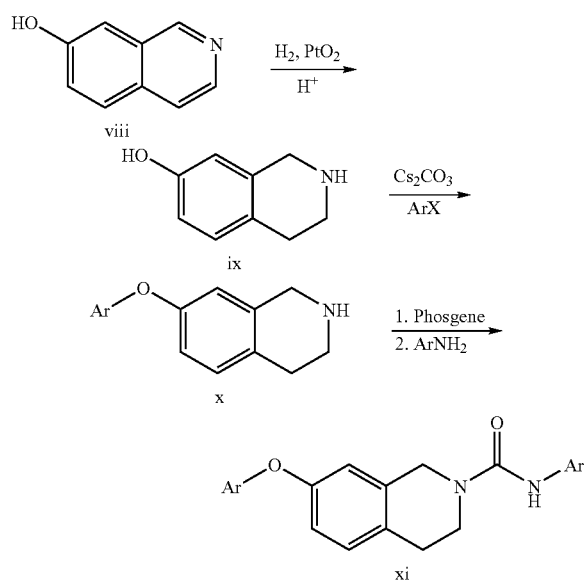

Compounds wherein ring A is tetrahydroisoquinoline can be prepared as shown in Scheme 3. Isoquinoline viii is reduced in the presence of platinum oxide and acid to provide tetrahydroisoquinoline ix (Ueno et al., *Bioorg. Med. Chem. Lett.* 15:185-189 (2005)). The phenol can then be coupled to an appropriate aromatic halide in the presence of base to provide x. Treatment with phosgene and an aniline then provides urea xi.

One of ordinary skill in the art will recognize that additional compounds of formula (I) may be prepared by methods analogous to those depicted in Schemes 1-3 by changing the starting materials or reagents.

Uses, Formulation, and Administration

As discussed above, the present invention provides compounds that are inhibitors of Raf kinases. The compounds can be assayed in vitro or in vivo for their ability to bind to and/or inhibit a Raf kinase. In vitro assays include assays to determine inhibition of the ability of the kinase to phosphorylate a substrate protein or peptide. Alternate in vitro assays quantitate the ability of the compound to bind to the kinase. Inhibitor binding may be measured by radiolabelling the inhibitor prior to binding, isolating the inhibitor/kinase complex and determining the amount of radiolabel bound. Alternatively, inhibitor binding may be determined by running a competition experiment in which new inhibitors are incubated with the kinase bound to a known radioligand. The compounds also can be assayed for their ability to affect cellular or physiological functions mediated by protein kinase activity. Assays for each of these activities are described in the Examples and/or are known in the art.

In another aspect, therefore, the invention provides a method for inhibiting Raf kinase activity in a cell, comprising contacting a cell in which inhibition of a Raf kinase is desired with a compound of formula (I). In some embodiments, the compound of formula (I) interacts with and reduces the activity of more than one Raf kinase enzyme in the cell. By way of example, when assayed against B-Raf and C-Raf, some compounds of formula (I) show inhibition of both enzymes.

In some embodiments, the compound of formula (I) inhibits one or more Raf kinase enzymes at a concentration that is lower than the concentration of the compound required for inhibition of other, unrelated, kinase enzymes. In some such embodiments, the concentration of the compound that is required for inhibition of a Raf kinase enzyme is lower, preferably at least 2-fold, 5-fold, 10-fold, or 50-fold lower, than the concentration of the compound required for inhibition of other, unrelated, kinase enzymes. In some other embodiments, in addition to inhibiting Raf kinase, the compound formula (I) also inhibits one or more other kinase enzymes, preferably other kinase enzymes involved in tumor cell proliferation.

The invention also provides a method for inhibiting cell proliferation, comprising contacting a cell in which such inhibition is desired with a compound of formula (I). The phrase "inhibiting cell proliferation" is used to denote the ability of a compound of formula (I) to inhibit cell number or cell growth in contacted cells as compared to cells not contacted with the inhibitor. An assessment of cell proliferation can be made by counting cells using a cell counter or by an assay of cell viability, e.g., an MTT or WST assay. Where the cells are in a solid growth (e.g., a solid tumor or organ), such an assessment of cell proliferation can be made by measuring the growth, e.g., with calipers, and comparing the size of the growth of contacted cells with non-contacted cells.

Preferably, the growth of cells contacted with the inhibitor is retarded by at least about 50% as compared to growth of non-contacted cells. In various embodiments, cell proliferation of contacted cells is inhibited by at least about 75%, at least about 90%, or at least about 95% as compared to non-contacted cells. In some embodiments, the phrase "inhibiting cell proliferation" includes a reduction in the number of contacted cells, as compare to non-contacted cells. Thus, a kinase inhibitor that inhibits cell proliferation in a contacted cell may induce the contacted cell to undergo growth retardation, to undergo growth arrest, to undergo programmed cell death (i.e., apoptosis), or to undergo necrotic cell death.

In another aspect, the invention provides a pharmaceutical composition comprising a compound of formula (I) as defined above, or a pharmaceutically acceptable salt thereof, and a pharmaceutically acceptable carrier.

If pharmaceutically acceptable salts of the compounds of the invention are utilized in these compositions, the salts preferably are derived from inorganic or organic acids and bases. For reviews of suitable salts, see, e.g., Berge et al, *J. Pharm. Sci.* 66:1-19 (1977) and Remington: The Science and Practice of Pharmacy, 20th Ed., ed. A. Gennaro, Lippincott Williams & Wilkins, 2000.

Nonlimiting examples of suitable acid addition salts include the following: acetate, adipate, alginate, aspartate, benzoate, benzene sulfonate, bisulfate, butyrate, citrate, camphorate, camphor sulfonate, cyclopentanepropionate, digluconate, dodecylsulfate, ethanesulfonate, formate, fumarate, lucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3phenyl-propionate, picrate, pivalate, propionate, succinate, tartrate, thiocyanate, tosylate and undecanoate.

Suitable base addition salts include, without limitation, ammonium salts, alkali metal salts, such as sodium and potassium salts, alkaline earth metal salts, such as calcium and magnesium salts, salts with organic bases, such as dicyclohexylamine salts, N-methyl-D-glucamine, and salts with amino acids such as arginine, lysine, and so forth.

Also, basic nitrogen-containing groups may be quaternized with such agents as lower alkyl halides, such as methyl, ethyl, propyl, and butyl chloride, bromides and iodides; dialkyl sulfates, such as dimethyl, diethyl, dibutyl and diamyl sulfates, long chain halides such as decyl, lauryl, myristyl and stearyl chlorides, bromides and iodides, aralkyl halides, such as benzyl and phenethyl bromides and others. Water or oil-soluble or dispersible products are thereby obtained.

The term "pharmaceutically acceptable carrier" is used herein to refer to a material that is compatible with a recipient subject, preferably a mammal, more preferably a human, and is suitable for delivering an active agent to the target site without terminating the activity of the agent. The toxicity or adverse effects, if any, associated with the carrier preferably are commensurate with a reasonable risk/benefit ratio for the intended use of the active agent.

The pharmaceutical compositions of the invention can be manufactured by methods well known in the art such as conventional granulating, mixing, dissolving, encapsulating, lyophilizing, or emulsifying processes, among others. Compositions may be produced in various forms, including granules, precipitates, or particulates, powders, including freeze dried, rotary dried or spray dried powders, amorphous powders, tablets, capsules, syrup, suppositories, injections, emulsions, elixirs, suspensions or solutions. Formulations may optionally contain stabilizers, pH modifiers, surfactants, bioavailability modifiers and combinations of these.

Pharmaceutical formulations may be prepared as liquid suspensions or solutions using a liquid, such as, but not limited to, an oil, water, an alcohol, and combinations of these. Pharmaceutically suitable surfactants, suspending agents, or emulsifying agents, may be added for oral or parenteral administration. Suspensions may include oils, such as but not limited to, peanut oil, sesame oil, cottonseed oil, corn oil and olive oil. Suspension preparation may also contain esters of fatty acids such as ethyl oleate, isopropyl myristate, fatty acid glycerides and acetylated fatty acid glycerides. Suspension formulations may include alcohols, such as, but not limited to, ethanol, isopropyl alcohol, hexadecyl alcohol, glycerol and propylene glycol. Ethers, such as but not limited to, poly(ethyleneglycol), petroleum hydrocarbons such as mineral oil and petrolatum; and water may also be used in suspension formulations.

Pharmaceutically acceptable carriers that may be used in these compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

According to a preferred embodiment, the compositions of this invention are formulated for pharmaceutical administration to a mammal, preferably a human being. Such pharmaceutical compositions of the present invention may be administered orally, parenterally, by inhalation spray, topically, rectally, nasally, buccally, vaginally or via an implanted reservoir. The term "parenteral," as used herein includes subcutaneous, intravenous, intramuscular, intra-articular, intra-synovial, intrastemal, intrathecal, intrahepatic, intralesional and intracranial injection or infusion techniques. Preferably, the compositions are administered orally, intravenously, or subcutaneously. The formulations of the invention may be designed to be short-acting, fast-releasing, or long-acting. Still further, compounds can be administered in a local rather than systemic means, such as administration (e.g., by injection) at a tumor site.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation. Compounds may be formulated for parenteral administration by injection such as by bolus injection or continuous infusion. A unit dosage form for injection may be in ampoules or in multi-dose containers.

The pharmaceutical compositions of this invention may be orally administered in any orally acceptable dosage form including, but not limited to, capsules, tablets, aqueous suspensions or solutions. When aqueous suspensions are required for oral use, the active ingredient is combined with emulsifying and suspending agents. If desired, certain sweetening, flavoring or coloring agents may also be added.

The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Alternatively, the pharmaceutical compositions of this invention may be, administered in the form of suppositories for rectal administration. These may be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract may be effected in a rectal suppository formulation (see above) or in a suitable enema formulation. Topically-transdermal patches may also be used. For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions may be formulated in a suitable lotion or- cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The pharmaceutical compositions of the invention preferably are formulated for administration to a patient having, or at risk. of developing or experiencing a recurrence of, a Raf kinase-mediated disorder. The term "patient", as used herein, means an animal, preferably a mammal, more preferably a human. Preferred pharmaceutical compositions of the invention are those formulated for oral, intravenous, or subcutaneous administration. However, any of the above dosage forms containing a therapeutically effective amount of a compound of the invention are well within the bounds of routine experimentation and therefore, well within the scope of the instant invention. In some embodiments, the pharmaceutical composition of the invention may further comprise another therapeutic agent. In some embodiments, such other therapeutic agent is one that is normally administered to patients with the disease or condition being treated.

By "therapeutically effective amount" is meant an amount sufficient to cause a detectable decrease in protein kinase activity or the severity of a Raf kinase-mediated disorder. The amount of Raf kinase inhibitor needed will depend on the effectiveness of the inhibitor for the given cell type and the length of time required to treat the disorder. It should also be understood that a specific dosage and treatment regimen for any particular patient will depend upon a variety of factors, including the activity of the specific compound employed, the age, body weight, general health, sex, and diet of the patient, time of administration, rate of excretion, drug combinations, the judgment of the treating physician, and the severity of the particular disease being treated. The amount of additional therapeutic agent present in a composition of this invention typically will be no more than the amount that would normally be administered in a composition comprising that therapeutic agent as the only active agent. Preferably, the amount of additional therapeutic agent will range from about 50% to about 100% of the amount normally present in a composition comprising that agent as the only therapeutically active agent.

In another aspect, the invention provides a method for treating a patient having, or at risk of developing or experiencing a recurrence of, a Raf kinase-mediated disorder. As used herein, the term "Raf kinase-mediated disorder" includes any disorder, disease or condition which is caused or characterized by an increase in Raf kinase expression or activity, or which requires Raf kinase activity. The term "Raf kinase-mediated disorder" also includes any disorder, disease or condition in which inhibition of Raf kinase activity is beneficial.

The Raf kinase inhibitors of the invention can be used to achieve a beneficial therapeutic or prophylactic effect, for example, in subjects with a proliferative disorder. Non-limiting examples of proliferative disorders include chronic inflammatory proliferative disorders, e.g., psoriasis and rheumatoid arthritis; proliferative ocular disorders, e.g., diabetic retinopathy; benign proliferative disorders, e.g., hemangiomas; and cancer. As used herein, the term "cancer" refers to a cellular disorder characterized by uncontrolled or disregulated cell proliferation, decreased cellular differentiation, inappropriate ability to invade surrounding tissue, and/or ability to establish new growth at ectopic sites. The term "cancer" includes, but is not limited to, solid tumors and bloodborne tumors. The term "cancer" encompasses diseases of skin, tissues, organs, bone, cartilage, blood, and vessels. The term "cancer" further encompasses primary and metastatic cancers.

Non-limiting examples of solid tumors that can be treated with the disclosed protein kinase inhibitors include pancreatic cancer; bladder cancer; colorectal cancer; breast cancer, including metastatic breast cancer; prostate cancer, including androgen-dependent and androgen-independent prostate cancer; renal cancer, including, e.g., metastatic renal cell carcinoma; hepatocellular cancer; lung cancer, including, e.g., non-small cell lung cancer (NSCLC), bronchioloalveolar carcinoma (BAC), and adenocarcinoma of the lung; ovarian cancer, including, e.g., progressive epithelial or primary peritoneal cancer; cervical cancer; gastric cancer; esophageal cancer; head and neck cancer, including, e.g., squamous cell carcinoma of the head and neck; skin cancer, including e.g., malignant melanoma; neuroendocrine cancer, including metastatic neuroendocrine tumors; brain tumors, including, e.g., glioma, anaplastic oligodendroglioma, adult glioblastoma multiforme, and adult anaplastic astrocytoma; bone cancer; soft tissue sarcoma; and thyroid carcinoma.

Non-limiting examples of hematologic malignancies that can be treated with the disclosed protein kinase inhibitors include acute myeloid leukemia (AML); chronic myelogenous leukemia (CML), including accelerated CML and CML blast phase (CML-BP); acute lymphoblastic leukemia (ALL); chronic lymphocytic leukemia (CLL); Hodgkin's disease (HD); non-Hodgkin's lymphoma (NHL), including follicular lymphoma and mantle cell lymphoma; B-cell lymphoma; T-cell lymphoma; multiple myeloma (MM); Waldenstrom's macroglobulinemia; myelodysplastic syndromes (MDS), including refractory anemia (RA), refractory anemia with ringed siderblasts (RARS), (refractory anemia with excess blasts (RAEB), and RAEB in transformation (RAEB-T); and myeloproliferative syndromes.

The compounds of formula (I) are particularly useful in the treatment of cancers or cell types characterized by aberrant activation of the Ras-Raf-MEK-ERK pathway, including, without limitation, those characterized by an activating Ras and/or Raf mutation. In some embodiments, the compound or composition of the invention is used to treat a patient having or at risk of developing or experiencing a recurrence in a cancer selected from the group consisting of melanoma, colon, lung, breast, ovarian, sarcoma and thyroid cancer. In certain embodiments, the cancer is a melanoma.

In some embodiments, the Raf kinase inhibitor of the invention is administered in conjunction with another therapeutic agent. In some embodiments, the other therapeutic agent is one that is normally administered to patients with the disease or condition being treated. The Raf kinase inhibitor of the invention may be administered with the other therapeutic agent in a single dosage form or as a separate dosage form. When administered as a separate dosage form, the other therapeutic agent may be administered prior to, at the same time as, or following administration of the protein kinase inhibitor of the invention.

In some embodiments, a Raf kinase inhibitor of formula (I) is administered in conjunction with an anticancer agent. As used herein, the term "anticancer agent" refers to any agent that is administered to a subject with cancer for purposes of treating the cancer. Nonlimiting examples anticancer agents include: radiotherapy; immunotherapy; DNA damaging chemotherapeutic agents; and chemotherapeutic agents that disrupt cell replication.

Non-limiting examples of DNA damaging chemotherapeutic agents include topoisomerase I inhibitors (e.g., irinotecan, topotecan, camptothecin and analogs or metabolites thereof, and doxorubicin); topoisomerase II inhibitors (e.g., etoposide, teniposide, and daunorubicin); alkylating agents (e.g., melphalan, chlorambucil, busulfan, thiotepa, ifosfamide, carmustine, lomustine, semustine, streptozocin, decarbazine, methotrexate, mitomycin C, and cyclophosphamide); DNA intercalators (e.g., cisplatin, oxaliplatin, and carboplatin); DNA intercalators and free radical generators such as bleomycin; and nucleoside mimetics (e.g., 5-fluorouracil, capecitibine, gemcitabine, fludarabine, cytarabine, mercaptopurine, thioguanine, pentostatin, and hydroxyurea).

Chemotherapeutic agents that disrupt cell replication include: paclitaxel, docetaxel, and related analogs; vincristine, vinblastin, and related analogs; thalidomide and related analogs (e.g., CC-5013 and CC-4047); protein tyrosine kinase inhibitors (e.g., imatinib mesylate and gefitinib); proteasome inhibitors (e.g., bortezomib); NF-κB inhibitors, including inhibitors of IKB kinase; antibodies which bind to proteins overexpressed in cancers and thereby downregulate cell replication (e.g., trastuzumab, rituximab, cetuximab, and bevacizumab); and other inhibitors of proteins or enzymes known to be upregulated, over-expressed or activated in cancers, the inhibition of which downregulates cell replication.

In order that this invention be more fully understood, the following preparative and testing examples are set forth. These examples illustrate how to make or test specific compounds, and are not to be construed as limiting the scope of the invention in any way.

EXAMPLES

Definitions

| | |
|---|---|
| AcOH | acetic acid |
| AcCN | acetonitrile |
| ATP | adenosine triphosphate |
| BCA | bicinchoninic acid |
| BSA | bovine serum albumin |
| BOC | tert-butoxycarbonyl |
| DABCO | 1,4-diazabicyclo[2.2.2]octane |
| DCM | dichloromethane |
| DIPEA | diisopropyl ethyl amine |
| DMA | dimethylacetamide |
| DMAP | 4-dimethylaminopyridine |
| DMEM | Dulbecco's Modified Eagle's medium |
| DMF | dimethylformamide |
| DTT | dithiothreitol |
| EDCI | 1-(3-dimethylaminopropyl)-3-ethylcarbodiimide |
| EDTA | ethylenediaminetetraacetic acid |
| EtOAc | ethyl acetate |
| $Et_2O$ | ethyl ether |
| FA | formic acid |
| FBS | fetal bovine serum |
| h | hours |
| HATU | O-(7-azabenzotriazol-1-yl)-N,N,N', N'-tetramethyluronium hexafluorophosphate |
| MeOH | methanol |
| min | minutes |
| MTT | methylthiazoletetrazolium |
| MWI | microwave irradiation |
| NMP | 1-methyl-2-pyrrolidinone |
| PBS | phosphate buffered saline |
| pTSA | p-toluenesulfonic acid |
| PKA | cAMP-dependent protein kinase |
| sec | seconds |
| rt | room temperature |
| TBTU | O-(1H-benzotriazol-1-yl)-N,N,N', N'-tetramethyluronium tetrafluoroborate |
| TEA | triethylamine |
| THF | tetrahydrofuran |
| TMB | 3,3•,5,5•-tetramethylbenzidine |
| WST | (4-[3-(4-iodophenyl)-2-(4-nitrophenyl)-2H-5-tetrazolio]-1,3-benzene disulfonate sodium salt) |
| m/z | mass to charge |
| MS | mass spectrum |
| LCMS | liquid chromatography mass spectrum |
| HRMS | high resolution mass spectrum |

Analytical LC-MS Methods

Spectra were run on a Phenominex Luna 5 μm C18 50×4.6 mm column on a Hewlett-Packard HP1100 at 2.5 ml/min for a 3 minute run using the following gradients:

Polar Formic Acid (PFA): Acetonitrile containing zero to 50 percent 0.1% formic acid in water.

Formic Acid (FA): Acetonitrile containing zero to 100 percent 0.1% formic acid in water.

Nonpolar Formic Acid (NFA) Acetonitrile containing 70 to 100 percent 0.1% formic acid in water.

Polar Ammonium Acetate (PAA): Acetonitrile containing zero to 50 percent 10 mM ammonium acetate in water.

Ammonium Acetate (AA): Acetonitrile containing zero to 100 percent 10 mM ammonium acetate in water.

Nonpolar Ammonium Acetate (NAA): Acetonitrile containing 70 to 100 percent 10 mM ammonium acetate in water.

Example 1

Preparation of Intermediates and Reagents 4-chloro-N-methylpyridine-2-carboxamide

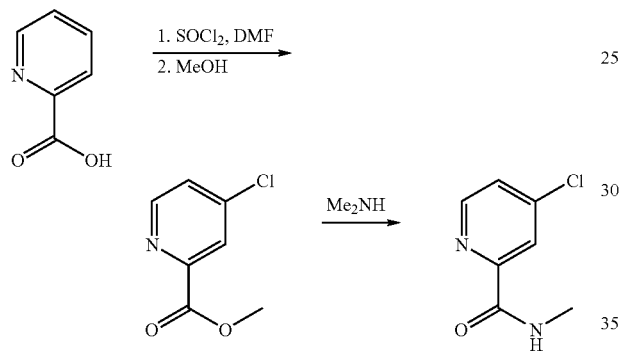

Step 1: Methyl 4-chloropyridine-2-carboxylate

Anhydrous DMF (3 mL) was slowly added to thionyl chloride (90 mL) at 40° C. under nitrogen. The solution was allowed to stir at 40° C. for 10 min, and pyridine 2-carboxylic acid (30.0 g, 243.7 mmol) was added portionwise over 10 min. The solution was heated at 72° C. for 16 h (a yellow precipitate formed). The mixture was cooled to rt, diluted with toluene (100 mL), and concentrated to small volume. This process was repeated two additional times before the mixture was concentrated to dryness. The dry yellow mixture was then cooled to 0° C., and MeOH (200 mL) added dropwise via addition funnel. The mixture was allowed to stir for 45 min and a white precipitate formed. Et$_2$O was added to the mixture and the white solid was filtered. Methyl 4-chloropyridine-2-carboxylate was collected in two crops (37.8 g, 91%). $^1$H NMR (300 MHz, d$_6$-DMSO) δ: 10.00 (br s, 1H), 8.68 (d, 1H), 8.08 (d, 1H), 7.82 (dd, 1H), and 3.88 (s, 3H).

Step 2: 4-chloro-N-methylpyridine-2-carboxamide

To a solution of methyl 4-chloropyridine-2-carboxylate (29.9 g, 174.9 mmol) in MeOH (15 mL) at 0° C. was added 2M methylamine in THF (437 mL, 874 nunol) dropwise. The reaction was allowed to stir at 0° C. for 3 h. The mixture was then concentrated and extracted with EtOAc (2×). The organic solutions were combined, washed with brine, dried over Na$_2$SO$_4$ and concentrated to give 4-chloro-N-methylpyridine-2-carboxamide (25 g, 84%). $^1$H NMR (300 MHz, d$_6$-DMSO) δ: 8.85 (br s, 1H), 8.61 (d, 1H), 8.00 (d, 1H), 7.74 (dd, 1H), 2.81 (d, 3H).

4-chloro-2-(4,5-dihydro-1H-imidazol-2-yl)pyridine

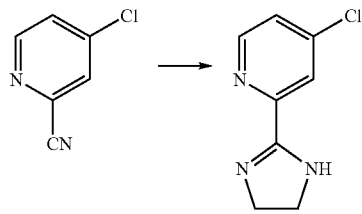

To a solution of 4-chloropyridine-2-carbonitrile (20.0 g, 121 nmuol, prepared as described by Sakamoto et al. *Chem. Pharm. Bull.* 1985, 33, 565-71) in MeOH (240 mL), was added sodium methoxide (0.655 g, 12.1 mmol). The reaction mixture was allowed to stir at rt under an atmosphere of argon for 2 h. Ethylene diamine (40.0 mL, 597 imol) was added and the mixture was allowed to stir at 50° C. for 20 h. The reaction mixture was allowed to cool to rt and then concentrated. The residue was dissolved in a mixture of water and DCM. The organic layer was separated, dried over MgSO$_4$, filtered and concentrated to give 4-chloro-2-(4,5-dihydro-1H-imidazol-2-yl)pyridine as a light brown solid (21.9 g, >99%). LCMS: (FA) ES$^+$ 182.1.

N-(4-nitropyridin-2-yl)acetamide

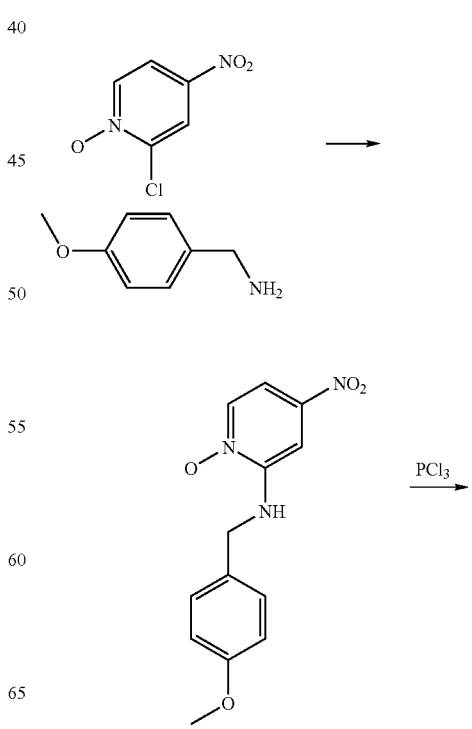

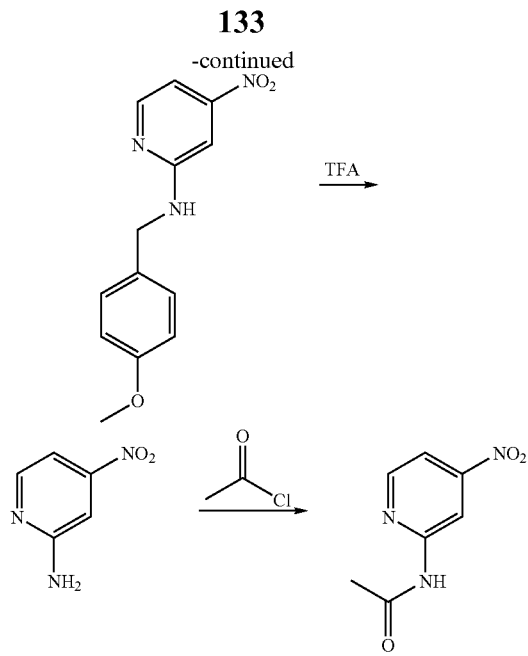

produced a light yellow solid that was isolated via filtration. The filtrate was allowed to stand overnight and a second crop of crystals was obtained. The combined batches of solids were dissolved in 1N NaOH (250 mL) and extracted with EtOAc (2×250 mL). The combined organic solutions were dried over $MgSO_4$, filtered and concentrated to give 2-amino-4-nitropyridine as an orange solid (10.2 g, 67%). LCMS: (FA) ES+ 140.1.

Step 4: N-(4-nitropyridin-2-yl)acetamide

To a solution of 2-amino-4-nitropyridine (3.0 g, 0.018 mol) in pyridine (40 mL) was added acetic anhydride (5.2 mL 0.055 mol). The reaction mixture was allowed to stir for 30 h at rt. Water was added to the solution and the resulting solid was collected and washed with water and dried under vacuum to give N-(4-nitropyridin-2-yl)acetamide as a brown solid (3.3 g, 99%). $^1$HNMR (300 MHz, $CDCl_3$) δ: 8.90 (s, 1H), 8.50 (d, 1H), 8.30 (br s, 1H), 7.8 (dd, 1H), 2.3 (s, 3H); LCMS: (FA) ES+ 182.2.

Compounds in the following table were prepared from the appropriate starting materials in a method analogous to that described for N-(4-nitropyridin-2-yl)acetamide and the corresponding intermediates:

| | |
|---|---|
| N-(4-nitropyridin-2-yl)cyclopropane-carboxamide | $^1$HNMR(300MHz, $CDCl_3$) δ: 8.90(s, 1H), 8.50(s, 1H), 8.50(br s, 1H), 7.7(dd, 1H), 1.6(m, 1H), 1.2(m, 2H), and 1.0(m, 2H); LCMS: (FA) ES+ 208.3. |
| 4-nitro-2-(1H-pyrazol-1-yl)pyridine 1-oxide | LCMS: (FA) ES+ 207.3. |
| 2-(1H-imidazol-1-yl)-4-nitropyridine 1-oxide | LCMS: (FA) ES+ 207.2. |

Step 1: N-(4-methoxybenzyl)-4-nitropyridin-2-amine 1-oxide

A mixture of 2-chloro-4-nitropyridine-1-oxide (75.00 g, 0.43 mol) and 1-(4-methoxyphenyl)methanamine (125.0 g, 0.91 mol) in ethanol (1 L) was heated at reflux for 5 h. The reaction was allowed to cool to rt and chilled in a freezer overnight. The resulting cold mixture was filtered. The solid was slurried in MeOH (100 mL) and filtered, to give N-(4-methoxybenzyl)-4-nitropyridin-2-amiine 1-oxide (51.62 g, 40% yield) as an orange solid. LCMS: (FA) ES+ 276.2.

Step 2: N-(4-methoxybenzyl)-4-nitropyridin-2-amine

To a 2 L 3 neck round bottom flask fitted with a mechanical stirrer, was added N-(4-methoxybenzyl)-4-nitropyridin-2-amine 1-oxide (38.72 g, 0.14 mol) and chloroform (580 mL). The reaction mixture was cooled to 0° C. and phosphorus trichloride (36.8 mL, 0.42 mol) was added dropwise. The reaction mixture was allowed to warm to rt and stir overnight. The reaction mixture was filtered and the resulting solid was slurried with hexanes and filtered (repeated several times) to afford N-(4-methoxybenzyl)-4-nitropyridin-2-amine (39.34 g, 102%) as a yellow solid. LCMS: (FA) ES+ 260.3.

Step 3: 4nitropyridin-2-amine

N-(4-methoxybenzyl)-4-nitropyridin-2-amine (27.8 g, 0.11 mol) and anisole (13 mL, 0.12 mol) were dissolved in trifluoroacetic acid (112 mL) and heated at 80° C. for 2 h. The reaction mixture was allowed to cool to rt and concentrated. Trituration of the resulting residue with EtOAc and hexanes 4-nitro-2-(1H-1,2,4triazol-1-yl)pyridine

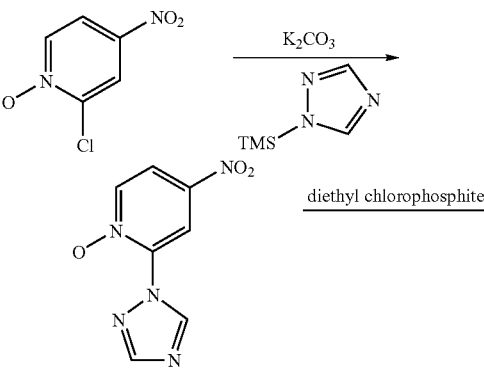

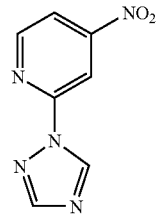

Step 1: 4-nitro-2-(1H-1,2,4-triazol-1-yl)pyridine 1-oxide

To a solution of 2-chloro-4-nitropyridine 1-oxide (2.00 g, 11.4 mmol) and 1-(trimethylsilyl)-1H-1,2,4-triazole (1.64 mL, 11.4 mmol) in DMF (40 mL), was added potassium carbonate (4.75 g, 34.4 mmol). The reaction mixture was allowed to stir at rt for 2 h. The DMF was evaporated and water was added. The precipitate was filtered and washed with water then hexane and dried under vacuum. The solid was purified by column to give 4-nitro-2-(1H-1,2,4-triazol-1-yl)pyridine 1-oxide (0.643 g, 27.1%) as a pale yellow solid. LCMS: (FA) ES+ 208.1, ES– 206.1.

Step 2: 4-nitro-2-(1H-1,2,4-triazol-1-yl)pyridine

To a solution of 4-nitro-2-(1H-1,2,4-triazol-1-yl)pyridine 1-oxide (0.643 g, 3.10 mmol) in CHCl₃ (30 mL) at 0° C. was added diethyl chlorophosphite (1.35 mL, 9.31 mmol). The reaction mixture was allowed to stir at rt for 72 h. Additional diethyl chlorophosphite (1.35 mL, 9.31 nmmol) was added and the reaction mixture was heated at 80° C. for 18 h. The reaction mixture was cooled to 0° C., basified by the addition of 1N NaOH solution and extracted with DCM. The organic solutions were combined, washed with brine, dried over Na₂SO₄, filtered and concentrated. The residue was purified by column chromatography. The product was triturated with hexane to provide 4-nitro-2-(1H-1,2,4triazol-1-yl)pyridine (0.192 g, 32.3%). LCMS: (FA) ES+ 192.3.

4-nitro-2,3'-bipyridine

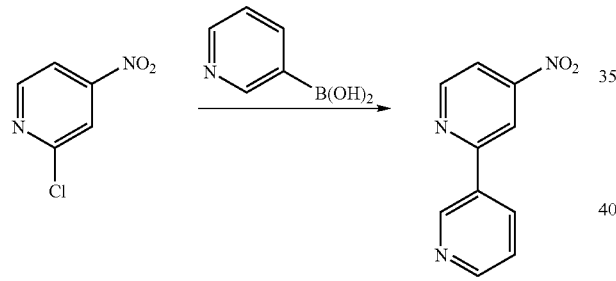

A mixture of 2-chloro-4nitropyridine (0.40 g, 2.56 mmol), pyridin-3-ylboronic acid (0.408, 3.32 mmol), tetrakis(triphenylphosphinepalladium(0) (0.18 g, 0.15 minol) and sodium carbonate (0.489 g, 4.6 mmol) in acetonitrile (9 mL) and water (9 mL) was heated at 80° C. overnight. Water was added and the mixture was extracted with EtOAc. The organic solutions were combined, washed with brine, dried over Na₂SO₄, filtered and concentrated. The residue was purified by column chromatography on basic alumina to give 4-nitro-2,3'-bipyridine (350 mg, 70%) as a pale yellow solid. LCMS: (FA) ES+ 202.1.

Compounds in the following table were prepared from the appropriate starting materials in a method analogous to that described for 4-nitro-2,3'-bipyridine:

| | |
|---|---|
| 2-(1-methyl-1H-pyrazol-4-yl)-4-nitropyridine | LCMS: (FA) ES+ 205.1 |
| 4-nitro-2,4'-bipyridine | LCMS: (FA) ES⁺ 202.1. |
| 5-(4-nitropyridin-2-yl)pyrimidine | ¹H NMR (400MHz, CD₃OD, HCl salt) δ: 9.53(s, 2H), 9.26(s, 1H), 9.06(d, 1H), 8.75-8.78(m, 1H), and 8.18(q, 1H) ppm. |
| 2-(3,5-dimethylisoxazol-4-yl)-4-nitropyridine | LCMS: (FA) ES⁺ 220.2 |

7-hydroxy-2-naphthoic acid

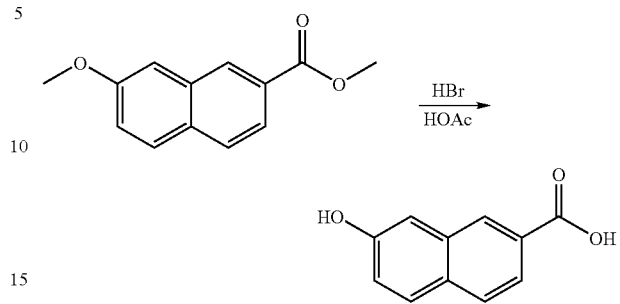

A suspension of methyl 7-methoxy-2-naphthoate (37.21 g, 172 mmol) in 48% aqueous HBr (195 mL, 1.72 mol) and AcOH (190 mL) was heated at 100° C. for 4 h. The mixture gradually went into solution and then precipitated. The reaction mixture was cooled to rt, and water was added. The solid was filtered and washed with water. The solid was dissolved in 1N NaOH and washed with Et₂O. The aqueous solution was acidified to pH 1 with concentrated HCl. The precipitate was filtered and washed with water, then dried under vacuum to give 7-hydroxy-2-naphthoic acid as an off-white solid (32.3 g, 99%). LCMS: (FA) ES⁻ 187.1.

7-hydroxy-1,2,3,4-tetrahydronaphthalene-2-carboxylic acid

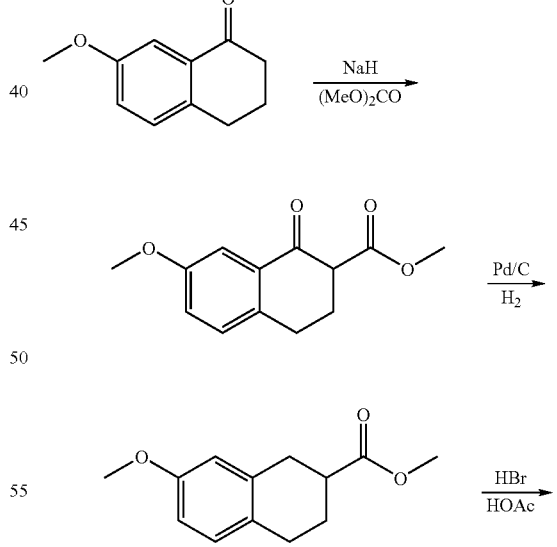

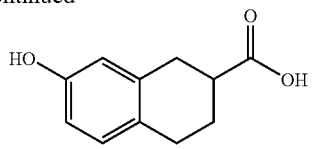

Step 1: Methyl 7-methoxy-1-oxo-1,2,3,4-tetrahydronaphthalene-2-carboxylate

To a suspension of sodium hydride (60% in mineral oil, 9.99 g, 250 nmuol) in THF (100 mL), was added dimethyl carbonate (21.0 mL, 249 mmol). The mixture was heated to 65° C. and a solution of 7-methoxy-1-tetralone (20.00 g, 114 nmuol) in THF (100 mL) was added. The reaction mixture was allowed to stir vigorously at 65° C. for 2 h. After this time the reaction became very vigorous, and gas was evolved. The heating bath was removed for 10 min then heating continued for an additional 1 h. AcOH (18.00 mL, 317 mmol) was added slowly, followed by water (100 mL). The mixture was extracted with $Et_2O$ (2×) and the organic solutions were combined, washed with water and saturated $NaHCO_3$ solution, dried over $Na_2SO_4$, filtered and evaporated. The residue was purified by filtration through a pad of silica to yield methyl 7-methoxy-1-oxo-1,2,3,4-tetrahydronaphthalene-2-carboxylate as an oil. (25.2 g, 95%). LCMS: (FA) $ES^+$ 235.0, $ES^-$ 233.0.

Step 2: Methyl 7-methoxy-1,2,3,4-tetrahydronaphthalene-2-carboxylate

A slurry of methyl 7-methoxy-1-oxo-1,2,3,4-tetrahydronaphthalene-2-carboxylate (6.0 g, 26 mmol) and 10% palladium on carbon (100 mg) in AcOH (120 mL), and concentrated sulfuric acid (780 µL) was allowed to stir under 30 psi of hydrogen for 2.5 h. The reaction mixture was diluted with chloroform, and filtered through Celite. The filtrate was washed with water (5×), dried over $Na_2SO_4$ and evaporated. The residue was purified by filtration through a pad of silica, to give methyl 7-methoxy-1,2,3,4-tetrahydro-naphthalene-2-carboxylate as an oil (4.03 g, 71%). $^1$H NMR (300 MHz, $CD_3OD$): δ 6.94 (d, 1H), 6.67-6.62 (m, 2H), 3.72 (s, 3H), 3.69 (s, 3H), 2.94-2.91 (m, 2H), 2.78-2.70 (m, 3H), and 2.18-2.09 (m, 1H), and 1.86-1.73 (m, 1H).

Step 3: 7-hydroxy-1,2,3,4-tetrahydronaphthalene-2-carboxylic acid 7-hydroxy-1,2,3,4-tetrahydronaphthalene-2-carboxylic acid was prepared from methyl 7-methoxy-1,2,3,4tetrahydronaphthalene-2-carboxylate in a manner similar to that described for 7-hydroxy-2-naphthoic acid.

6-Hydroxyquinoline-3-carboxylic acid

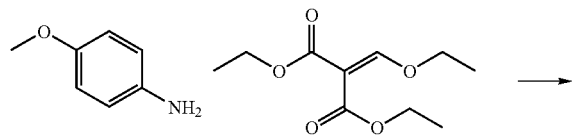

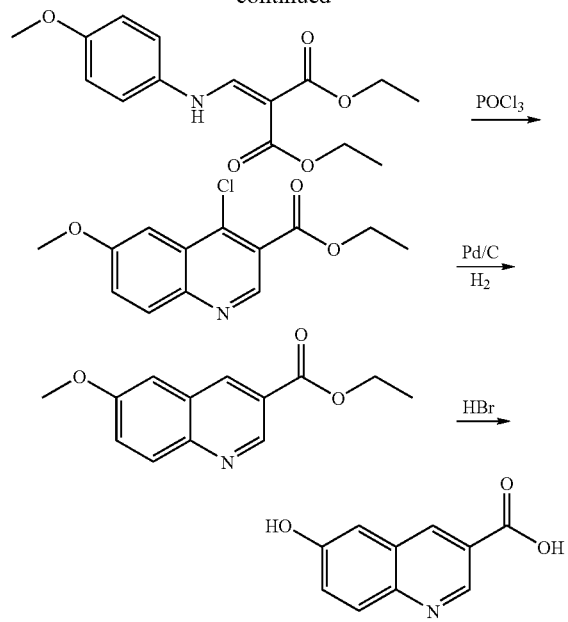

Step 1: diethyl {[(4-methoxyphenyl)amino]methylene}malonate

A mixture of 4methoxyaniline (28.3 g, 0.230 mol) in diethyl ethoxymethylene-malonate (46.0 mL, 0.230 mol) was allowed to stir at rt for 16 h. Removal of solvent gave diethyl ([(4-methoxyphenyl)aniino]methylenelmalonate. LCMS: (FA) $ES^+$ 294.2.

Step 2: ethyl 4-chloro-6-methoxyquinoline-3-carboxylate

Diethyl {[(4-methoxyphenyl)amino]methylene}malonate (63.5 g, 0.22 mol) was dissolved into $POCl_3$ (300 mL, 3.0 mol), and the reaction mixture was heated at reflux for 16 h. After removal of solvent, toluene was added and the mixture was concentrated to remove remaining $POCl_3$. The residue was diluted with DCM, washed with aqueous $Na_2CO_3$ and brine, dried over $Na_2SO_4$ and concentrated to give ethyl 4chloro-6methoxyquinoline-3-carboxylate (55.4 g, 96% yield) as a yellow solid which was used without further purification. LCMS: (FA) $ES^+$ 266.1.

Step 3: Ethyl 6-methoxyquinoline-3-carboxylate

Ethyl 4-chloro-6-methoxyquinoline-3-carboxylate (640 mg, 2.4 mmol) was dissolved in MeOH (30 mL). TEA (0.67 mL, 4.8 mmol) and 10% Pd on carbon (0.1 g) were added. The mixture was allowed to stir under an atmosphere of hydrogen (50 psi) for 20 h and was then filtered through Celite. Removal of solvents gave ethyl 6-methoxyquinoline-3-carboxylate, which was used without further purification. LCMS: (FA) $ES^+$ 232.0.

Step 4: 6-Hydroxyquinoline-3-carboxylic acid

Ethyl 6-methoxyquinoline-3-carboxylate (500 mg, 2.0 mmol) in 48% aq. HBr (5 mL) was subjected to MWI at 140° C. for 5 min. 6-Hydroxyquinoline-3-carboxylic acid precipitated from the reaction mixture and was collected by filtration. $^1$H NMR (300 MHz, CD$_3$OD): δ 9.50 (d, 1H), 9.36 (d, 1H), 8.18 (d, 1H), 7.83 (dd, 1H), and 7.64 (d, 1H). LCMS: (FA) ES$^+$ 190.1.

6-hydroxychromane-3-carboxylic acid

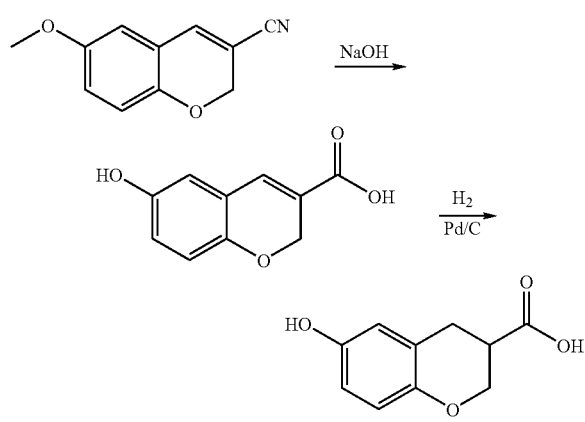

Step 1: 6-hydroxy-2H-chromene-3-carboxylic acid

A solution of 6-methoxy-2H-chromene-3-carbonitrile (50.0 g, 267 mmol) in 2.5M NaOH (750 mL) was heated at reflux overnight. The reaction mixture was allowed to cool to rt and then acidified with 1N HCl until a white precipitate formed. The solid was filtered, washed with 1N HCl, and dried under vacuum. The 6-hydroxy-2-H-chromene-3-carboxylic acid (53.7 g, 98%) was used without further purification.

Step 2: 6-hydroxychromane-3-carboxylic acid

A solution of 6-hydroxy-2H-chromene-3-carboxylic acid (2.00 g, 10.4 mmol) in MeOH (100 mL) was degassed. To this solution was added Pd/C (5 wt %, 1.32 g). The reaction mixture was allowed to stir at rt under an atmosphere of hydrogen for 3 h and then filtered through Celite. Concentration of the filtrate gave 6-hydroxychromane-3-carboxylic acid (1.52 g, 75%). LCMS: ES$^-$ 193.1.

2-(tert-Butoxycarbonyl)-6-hydroxy-1,2,3,4-tetrahydroisoquinoline-3-carboxylic acid

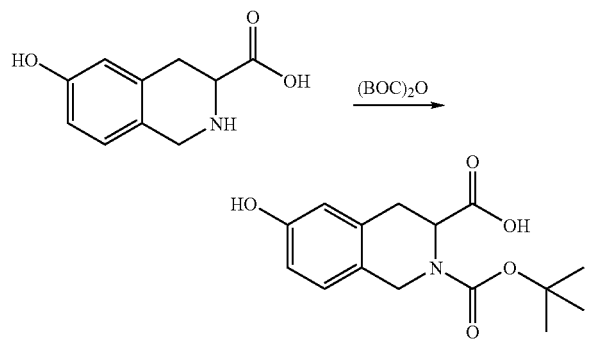

To a solution of 6-hydroxy-1,2,3,4-tetrahydroisoquinoline-3-carboxylic acid (prepared as described by Ornstein et al. in *J. Org. Chem.* 1991, 56, 4388-4392, 1.0 g, 5.2 mmol) in THF (25 mL) and water (25 mL) was added NaHCO$_3$ (870 mg, 10.4 mmol) and BOC anhydride (1.24 g, 5.7 mmol). The reaction was allowed to stir for 18 h. Water and DCM were added and the mixture was acidified to pH 4 by the addition of 1N HCl solution. The mixture was extracted with DCM (2×) and the combined organic solutions were dried over Na$_2$SO$_4$ and concentrated to give 2-(tert-Butoxycarbonyl)-6-hydroxy-1,2,3,4-tetrahydroisoquinoline-3-carboxylic acid as a white solid (1.35 g, 89%). $^1$H NMR (300 MHz, d$_6$-DMSO): δ 12.58 (s, 1H), 9.25 (s, 1H), 6.99-6.93 (m, 1H), 6.95-6.54 (m, 2H), 5.57-4.17 (m, 3H), 3.06-2.92 (m, 2H), 1.44 and 1.37 (s, 9H).

Methyl 6-hydroxyisoquinolne-3-carboxylate

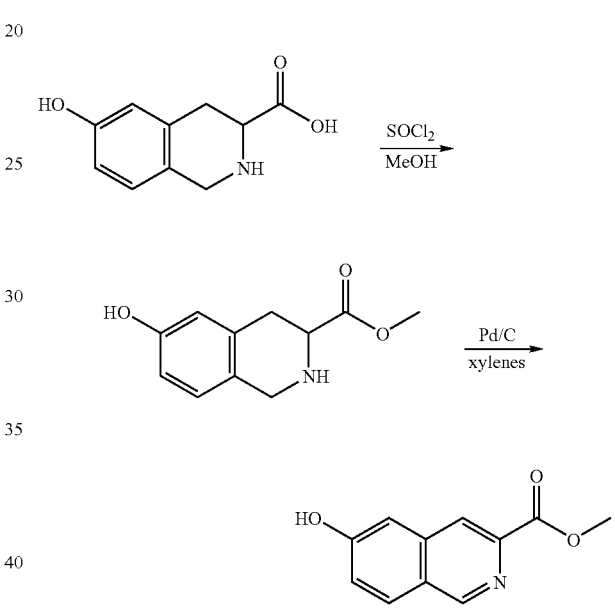

Step 1: methyl 6-hydroxy-1,2,3,4-tetrahydroisoquinoline-3-carboxylate

To a solution of 6-hydroxy-1,2,3,4-tetrahydroisoquinoline-3-carboxylic acid (1.0 g, 5.2 mmol) in MeOH (50 mL) was added thionyl chloride (0.56 mL, 7.8 mmol) slowly. The reaction was heated at reflux for 18 h and then cooled to rt. The solvent was evaporated. The residue was redissolved in DCM and saturated NaHCO$_3$ solution was added. The mixture was extracted with DCM (2×) and the combined organic solutions were dried over Na$_2$SO$_4$ and concentrated to give methyl 6-hydroxyisoquinoline-3-carboxylate as a white solid (0.72 g, 67%). LCMS: (FA) ES+ 208.2.

Step 2: methyl 6-hydroxyisoquinoline-3-carboxylate

To a solution of methyl 6-hydroxy-1,2,3,4-tetrahydroisoquinoline-3-carboxylate (0.72 g, 3.5 mmol) in xylenes (70 mL) was added 10% palladium on carbon (0.58 g). The mixture was heated at reflux for 18 h, and then cooled to rt. MeOH (5 mL) was added and the mixture was filtered through Celite. The solvents were evaporated and the residue was purified by column chromatography give methyl 6-hydroxyisoquinoline-3-carboxylate as yellow solid. (0.26 g, 36%). LCMS: (FA) ES+ 204.0, ES− 202.0.

7-[(2-aminopyridin-4-yl)oxy]-1,2,3,4-tetrahydronaphthalene-2-carboxylic acid

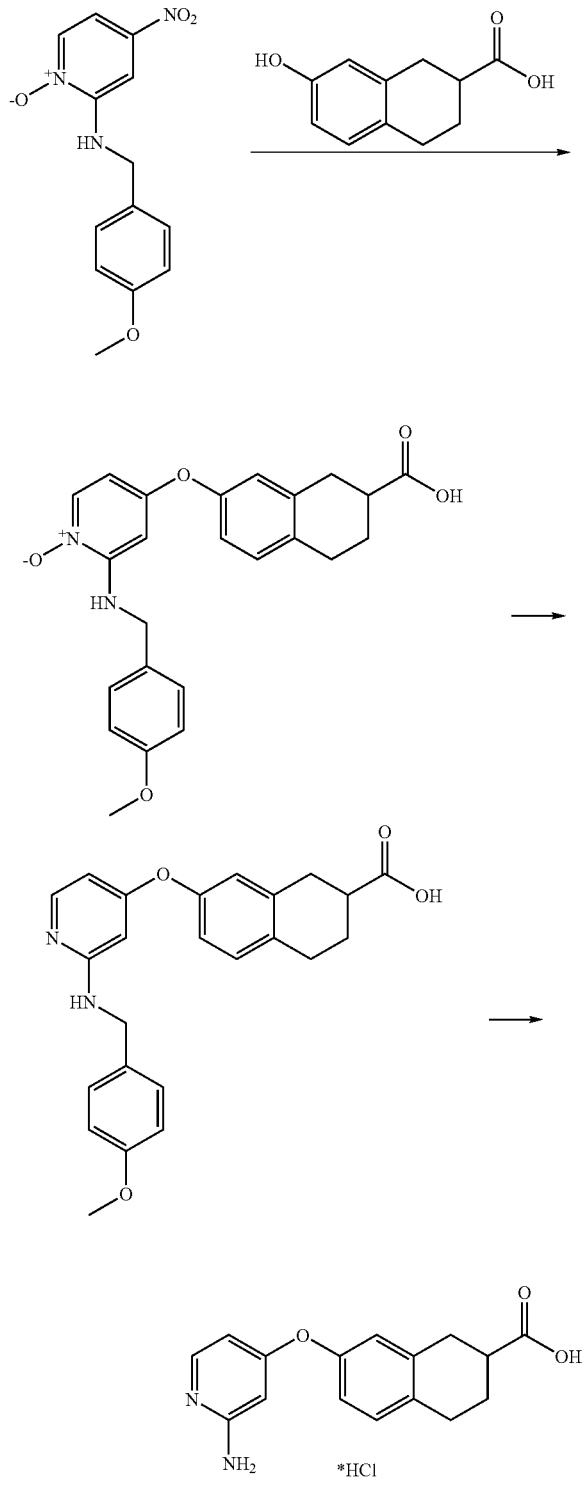

Step 1: 7-({2-[(4-methoxybenzyl)amino]-1-oxidopyridin-4yl}oxy)-1,2,3,4-tetrahydronaphthalene-2-carboxylic acid A mixture of N-(4-methoxybenzyl)-4-nitropyridin-2-amine 1-oxide (25.6 g, 0.0929 mol), 7-hydroxy-1,2,3,4-tetrahydronaphthalene-2-carboxylic acid (17 g, 0.088 mol) and cesium carbonate (92 g, 0.28 mol) in DMF (200 mL, 3 mol) was heated with stirring at 80° C. overnight. The reaction mixture was allowed to cool and then concentrated to small volume and 200 ml of water was added. The solution was acidified with conc. HCl to pH=4. The aqueous solution was removed and the remaining organic solution was washed with water (3×). The residue was treated with 1N NaOH (150 ml) and extracted with DCM (3×). The aqueous solution was acidified with conc. HCl. A precipitate formed and was filtered, washed with water (3×), and dried to give 7-({2-[(4-methoxybenzyl)amino]-1-oxidopyridin-4-yl}oxy)-1,2,3,4-tetrahydronaphthalene-2-carboxylic acid (33 g, 89%) as a brown solid. $^1$H NMR (d$_6$-DMSO, 400 MHz) δ: 12.40 (s, 1H); 8.03 (d, 1H); 7.80 (t, 1H); 7.20 (d, 2H); 7.12 (d, 1H); 6.82 (d, 2H); 6.76 (m, 2H); 6.20 (s, 1H); 6.10 (d, 1H); 4.30 (d, 1H); 3.70 (s, 3H); 2.80 (m, 4H); 2.65 (m, 1H); 2.08 (m, 1H); 1.74 (m, 1H) LCMS ES+ 421.1

Step 2: 7-({2-[(4-methoxybenzyl)amino]pyridin-4-yl}oxy)-1,2,3,4-tetrahydronaphthalene-2-carboxylic acid A mixture of 7-({2-[(4-methoxybenzyl)amino]-1-oxidopyridin-4-yl}oxy)-1,2,3,4-tetrahydronaphthalene-2-carboxylic acid (21.1 g, 0.0502 mol), cyclohexene (100 mL, 0.9 mol) and Pd (10% on Carbon, 4.5 g) in isopropyl alcohol (400 mL, 5 mol) was heated at 85° C. overnight. Additional catalyst (2.5 g) and cyclohexene (30 mL) were added. The mixture was heated at 90° C. overnight and then filtered. The filtrate was concentrated to give 7-({2-[(4-methoxybenzyl)amino]pyridin-4-yl}oxy)-1,2,3,4-tetrahydronaphthalene-2-carboxylic acid which was used in the next step without purification. LCMS ES+ 405.7

Step 3: 7-[(2-aminopyridin-4-yl)oxy]-1,2,3,4-tetrahydronaphthalene-2-carboxylic acid A solution of 7-({2-[(4-methoxybenzyl)amino]pyridin-4-yl}oxy)-1,2,3,4-tetrahydronaphthalene-2-carboxylic acid (21.5 g, 0.0532 mol), anisole (52 mL, 0.48 mol) and TFAA (100 mL, 2 mol) in DCM (400 mL) was stirred at 37° C. overnight. The solvent was removed by evaporation at 30° C. To the resulting mixture was added 1N NaOH (300 mL) and the solution was extracted with ether. The aqueous solution was acidified with conc. HCl to pH=3. The water layer was discarded, the residue was washed with water (3×). The solid was dried in vacuo overnight to give 7-[(2-aminopyridin-4-yl)oxy]-1,2,3,4-tetrahydronaphthalene-2-carboxylic acid (14.3 g). The combined yield for steps 2 and 3 was 94%. $^1$H NMR (DMSO-d6, 400 MHz) 7.83 (d, 1H); 7.30 (s, 2H); 7.20 (d, 1H); 6.98 d, 1H); 6.95 (dd, 1H); 6.46 (dd, 1H); 5.95 (d, 1H); 3.70 (s, 2H); 2.60-3.00 (m, 5H); 2.09 (m, 1H); 1.72 (m, 1H). LCMS ES+ 285.3.

Compounds in the following table were prepared from the appropriate starting materials in a method analogous to that described for 7-[(2-aminopyridin-4-yl)oxy]-1,2,3,4-tetrahydronaphthalene-2-carboxylic acid and the corresponding intermediates:

| | |
|---|---|
| 7-{[2-(1H-pyrazol-1-yl)pyridin-4-yl]oxy}-1,2,3,4-tetrahydro-naphthalene-2-carboxylic acid | LCMS: (FA) ES+ 336.3, ES– 334.3. |
| 7-{[2-(1H-imidazol-1-yl)pyridin-4-yl]oxy}-1,2,3,4-tetrahydro-naphthalene-2-carboxylic acid | LCMS: (FA) ES+ 336.4, ES– 334.4. |

3-(2-Pyrrolidin-1-ylethoxy)-5-(trifluoromethyl)aniline

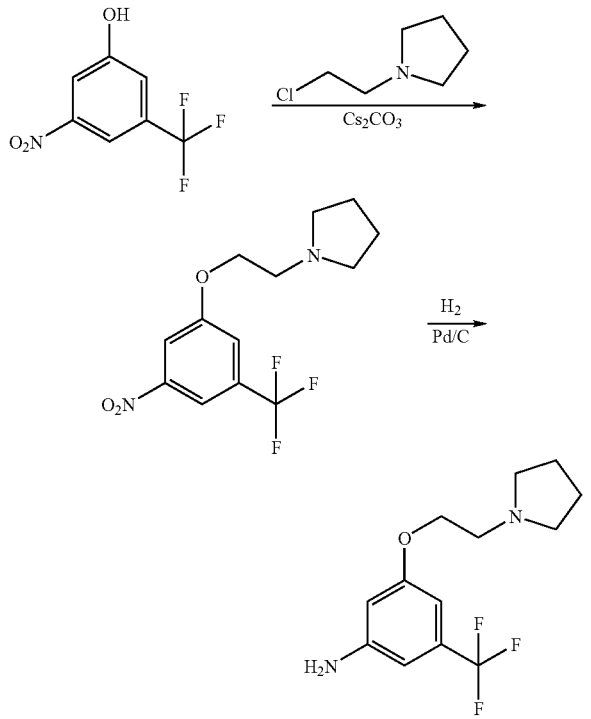

Step 1: 1-{2-[3-Nitro-5-(trifluoromethyl)phenoxy]ethyl}pyrrohdine

A mixture of 1-(2-chloroethyl)pyrrolidine (0.355 g, 2.66 mmol), 3-nitro-5-(trifluoromethyl)phenol (0.500 g, 2.41 nmmol), Cs$_2$CO$_3$ (2.36 g, 7.24 mmol), and DMF (18.69 mL) was allowed to stir at rt until reaction was judged to be complete. The mixture was diluted with EtOAc and washed with water (3×25 mL). The organic solution was dried over Na$_2$SO$_4$, filtered, and concentrated to give 3-(2-pyrrohidin-1-ylethoxy)-5-(trifluoromethyl)anlline as a brown oil (0.49 g, 63%). LCMS: (FA) ES+ 304.3.

Step 2: 3-(2-Pyrrolidin-1-ylethoxy)-5-(trifluoromethyl)aniline

A mixture of 1-{2-[3-nitro-5-(trifluoromethyl)phenoxy]ethyl}pyrrolidine (490 mg, 1.61 mmol), Pd/C (10 wt %, 49 mg), and EtOAc (15 mL) were allowed to stir under a hydrogen atmosphere until the reaction was judged to be complete. The mixture was filtered through Celite and concentrated to give 3-(2-pyrrolidin-1-ylethoxy)-5-(trifluoromethyl)anline as a brown solid (329 mg, 71% yield). LCMS: (FA) ES+ 275.2.

The preparation of 3-[2-(dimethylamino)ethoxy]-5-(trifluoromethyl)aniline was carried out by a similar procedure. LCMS: (FA) ES$^+$ 249.

tert-Butyl 4-[3-amino-5-(trifluoromethyl)phenoxy]piperidine-1-carboxylate

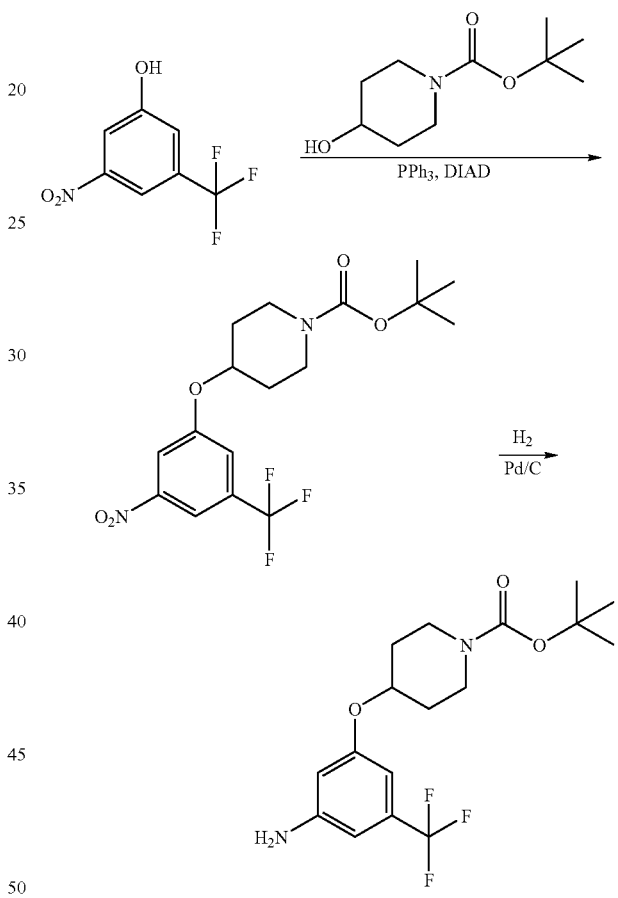

Step 1: tert-Butyl 4-(3-nitro-5-(trifluoromethyl)phenoxy) piperidine-1-carboxylate A solution of 3-nitro-5-(trifluoromethyl)phenol (0.583 g, 2.82 mmol), tert-butyl 4-hydroxypiperidine-1-carboxylate (0.850 g, 4.22 mmol), PPh3 (1.11 g, 4.22 mmol), DIAD (0.67 mL, 4.22 rnmol), and benzene (8.7 mL) was allowed to stir at rt until reaction was judged to be complete. The reaction mixture was concentrated. The resulting off-white solid was purified by column chromatography to give tert-butyl 4-(3-nitro-5-(trifluoromethyl) -phenoxy)piperidine-1-carboxylate (0.750 g, 66%). $^1$H NMR (400 MHz, CD$_3$OD) δ: 8.05-7.97 (m, 2H), 7.64 (s, 1H), 4.84-4.78 (m, 1H), 3.75-3.69 (m, 2H), 3.42-3.35 (m, 2H), 2.03-1.96 (m, 2H), 1.77-1.69 (m, 2H), and 1.46 (s, 9H).

Step 2: tert-Butyl 4-[3-amino-5-(trifluoromethyl) phenoxy]piperidine-1-carboxylate tert-Butyl 4-[3-amino-5-(trifluoromethyl)phenoxy]piperidine-1-carboxylate was prepared from tert-butyl 4-(3-nitro-5-(trifluoromethyl)phenoxy)piperidine-1-carboxylate using the procedure described above for the preparation of 3-(2-pyrrolidin-1-ylethoxy)-5-(trifluoromethyl)aniine. LCMS: (FA) ES+ 261.2.

2-{2-[3-amino-5-(trifluoromethyl)phenyl]ethyl}-1H-isoindole-1,3(2H)-dione

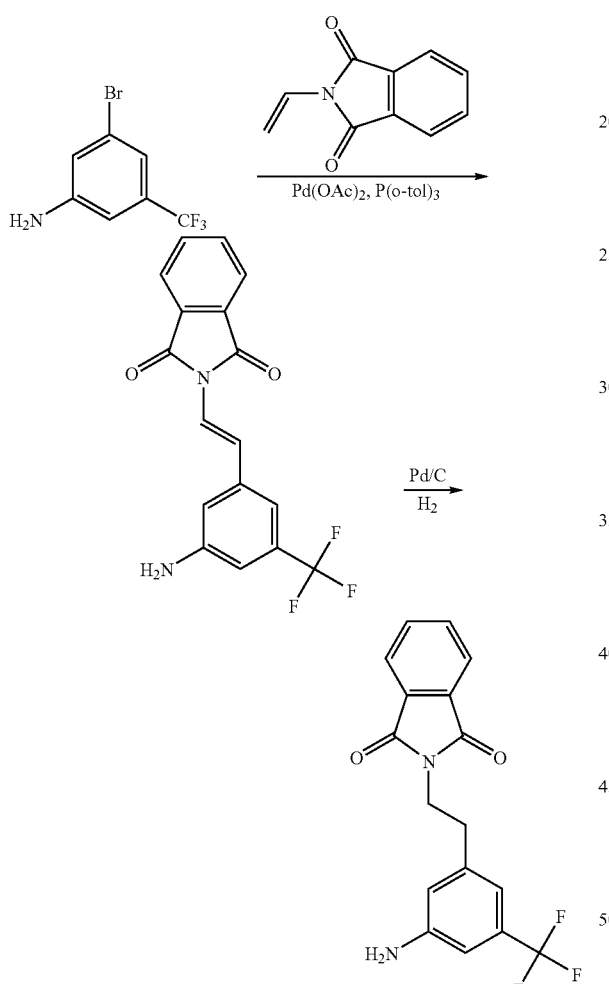

Step 1: 2-{(E)-2-[3-amino-5-(trifluoromethyl)phenyl]vinyl}-1H-isoindole-1,3(2H)-dione 3-Bromo-5-(trifluoromethyl)aniline (5.00 g, 0.0208 mol) was dissolved in AcCN (200 mL) and the solution was degassed with $N_2$. Pd(OAc)$_2$ (230 mg, 1.02 mmol), tris(2-methylphenyl)phosphine (630 mg, 2.07 mmol), and Et$_3$N (5.75 mL, 0.041 mol) were added and the bright orange solution was allowed to stir at rt for 1 h. To this solution was added 2-vinyl-1H-isoindole-1,3(2H)-dione (3.61 g, 0.021 mol) and the reaction mixture was degassed and heated at reflux for 16 h. The reaction was filtered through Celite. The filtrate was washed with water and brine, dried over Na$_2$SO$_4$, filtered and concentrated. The residue was purified by column chromatography to give 2-{(E)-2-[3-amino-5-(trifluoromethyl)phenyl]vinyl}-1H-isoindole-1,3(2H)-dione (1.99 g, 24% yield). LCMS: (FA) ES+ 334.

Step 2: 2-{2-[3-amino-5-(trifluoromethyl)phenyl]ethyl}-1H-isoindole-1,3(2)-dione A slurry of 2-{(E)-2-[3-amino-5-(trifluoromethyl)phenyl]vinyl}-1H-isoindole-1,3(2H)-dione (1.99 g, 5.98 nunol) and Pd/C (0.20 g, 10% by weight) in ETOH (123 mL) and THF (88 mL) was allowed to stir under 50 psi of hydrogen at rt until reaction was judged to be complete. The mixture was filtered through Celite and concentrated. The residue was purified by column chromatography to give 2-12-[3-amino-5-(trifluoromethyl)phenyl]ethyl)-1H-isoindole-1,3(2H)-dione (365 mg, 16% yield). LCMS: (FA) ES+ 335.

3-1(4-methylpiperazin-1-yl)methyll-5-(trifluoromethyl)anine

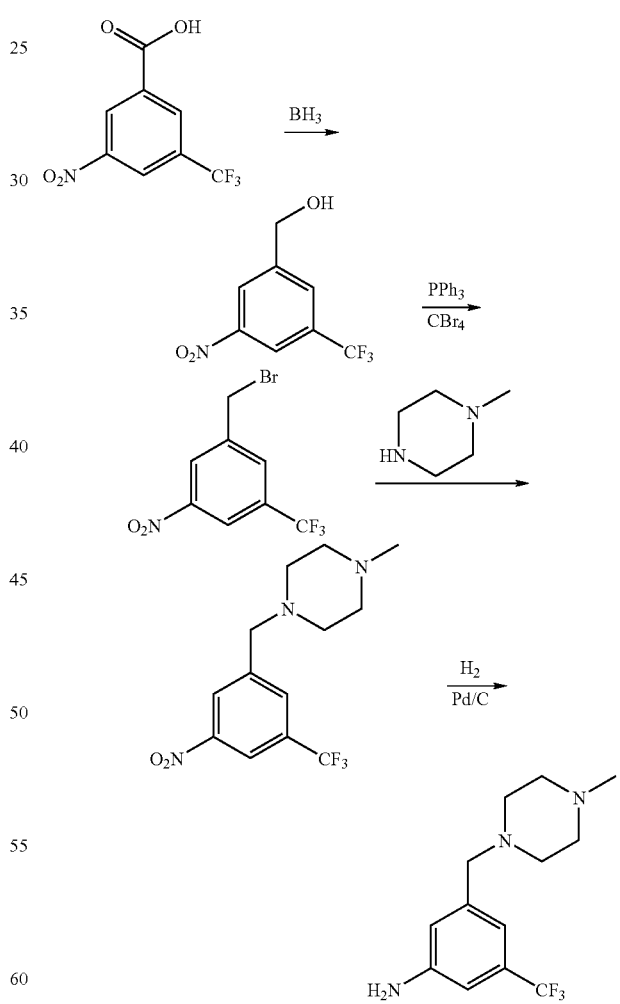

Step 1: [3-nitro-5-(trifluoromethyl)phenyl]methanol

To a solution of 3-nitro-5-(trifluoromethyl)benzoic acid (52.2 g, 0.222 mol) in THF (370 mL) at 0° C. was added BH$_3$ (1M in THF, 444 mL) slowly. The reaction mixture was allowed to stir and warm to rt. After 30 min, the reaction was quenched by the addition of sat. aq. NaHCO$_3$ at 0° C. and extracted with Et$_2$O. The organic solutions were combined, washed with brine, dried over MGSO$_4$, filtered and concentrated. The crude material (45.8 g, 93%) was used in the next step without purification.

Step 2: 1-(bromomethyl)-3-nitro-5-(trifluoromethyl)benzene

To a solution of [3-nitro-5-(trifluoromethyl)phenyl]methanol (13.15 g, 59.5 mmol) in DCM (200 mL) at 0° C. was added PPh$_3$ (18.7 g, 71.4 inmol) and CBr$_4$ (21.7 g, 65.4 mmol). The reaction mixture was allowed to stir and warm to rt overnight. The reaction mixture was poured directly onto a pad of silica and the eluant was concentrated to give 1-(bromomethyl)-3-nitro-5-(trifluoromethyl)benzene as a yellow oil (40 g, 689%).

Step 3: 1-methyl-4-[3-nitro-5-(trifluoromethyl)benzyl]piperazine

A mixture of 1-(bromomethyl)-3-itro-5-(trifluoromethyl)benzene (0.510 g. 1.80 mmol), TEA (0.30 mL, 2.15 minol) and 1-methylpiperazine (0.22 mL, 1.98 mmol) in DCM (10 mL) was allowed to stir at rt for 1 h and then quenched by the addition of sat. aq. NaHCO3. The solution was extracted with DCM and the organic solutions were combined, dried over MgSO4, filtered, and concentrated. The residue was purified by column chromatography to give 1-methyl-4-[3-nitro-5-(trifluoromethyl)benzyl]piperazine as a yellow oil (0.37 g, 68%). LCMS: ES$^+$ 304.0.

Step 4: 3-[(4-methylpiperazin-1-yl)methyl]-5-(trifluoromethyl)aniine

To a solution of 1-methyl-4-[3-nitro-5-(trifluoromethyl)benzyl]piperazine (0.35 g, 1.15 mmol) in EtOAc (15 mL) was added Pd (10% on C, 0.035 g). The reaction mixture was allowed to stir at rt under an atmosphere of hydrogen over night. The reaction mixture was filtered through Celite, washed with EtOAc, and concentrated to give 3-[(4-methylpiperazin-1-yl)methyl]-5-(trifluoromethyl)aniline (0.285 g, 90%) as a white solid which was used without further purification.

Compounds in the following table were prepared from the appropriate starting materials in a method analogous to that described for 3-[(4-methylpiperazin-1-yl)methyl]-5-(trifluoromethyl)aniline:

tert-butyl 4-{2-[2-amino-4-(trifluoromethyl)phenoxy]ethyl}piperazine-1-carboxylate

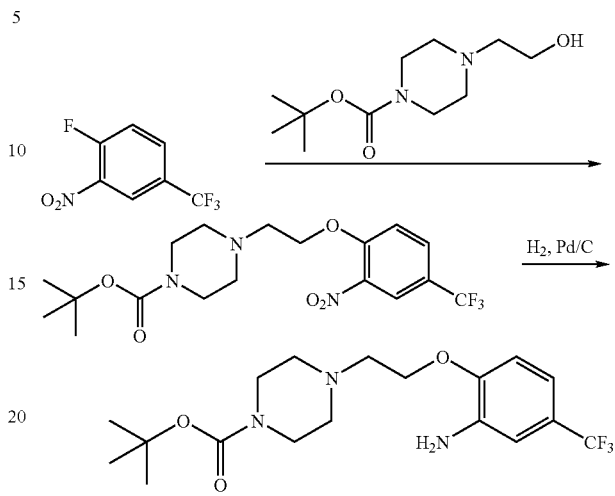

Step 1: tert-butyl 4-{2-[2-nitro-4-(trifluoromethyl)phenoxy]ethyl}piperazine-1-carboxylate Into a 1-neck round-bottom flask was added 4-fluoro-3-nitrobenzotrifluoride (1.62 mL, 0.012 mol), tert-butyl 4-(2-hydroxyethyl)piperazine-1-carboxylate (4.00 g, 0.017 mol), cesium carbonate (11.3 g, 0.035 mol), and DMF (100 mL). The reaction was allowed to stir and heat at 60° C. overnight. The reaction mixture was allowed to cool to rt and diluted with EtOAc and water. The organic solution was separated, washed with water and brine, and concentrated to yellow oil. The residue was purified by column chromatography to give tert-butyl 4-{2-[2-nitro-4-(trifluoromethyl)phenoxy]ethyl}piperazine-1-carboxylate (2.44 g, 48%) as a brown oil. LCMS: (AA) ES+420.1.

Step 2: tert-butyl 4-{2-[2-amino-4-(trifluoromethyl)phenoxy]ethyl}piperazine-1-carboxylate Into a 1-neck round-bottom flask was added tert-butyl 4-{2-[2-nitro-4-(trifluoromethyl)phenoxy]ethyl}piperazine-1-carboxylate (2.44 g, 0.0058 mol), 5% palladium/carbon (0.20 g), and EtOAc (74 mL). The mixture was allowed to stir under an atmosphere of hydrogen overnight and then filtered

| | |
|---|---|
| 3-(pyrrolidin-1-ylmethyl)-5-(trifluoromethyl)aniline | LCMS: ES$^+$ 245.3. |
| tert-butyl [3-amino-5-(trifluoromethyl)benzyl]methylcarbamate | LCMS: ES$^+$ 305.2. |
| tert-butyl [3-amino-5-(trifluoromethyl)benzyl](2-pyrrolidin-1-ylethyl)-carbamate | LCMS: ES$^+$ 388.3. |
| 3-[(diethylamino)methyl]-5-(trifluoromethyl)aniline | LCMS: ES$^+$ 347.3. |
| tert-butyl 4-[3-amino-5-(trifluoromethyl)benzyl]piperazine-1-carboxylate | LCMS: ES$^+$ 360.1. |
| 3-(morpholin-4-ylmethyl)-5-(trifluoromethyl)aniline | N/A |
| 4-[(4-methylpiperazin-1-yl)methyl]-3-(trifluoromethyl)aniline | LCMS: ES$^+$ 274.3. |
| tert-butyl 4-[4-amino-2-(trifluoromethyl)benzyl]piperazine-1-carboxylate | LCMS: ES$^+$ 360.3. |
| 4-(pyrrolidin-1-ylmethyl)-3-(trifluoromethyl)aniline | LCMS: ES$^+$ 245.1. |
| 3-[(4-ethylpiperazin-1-yl)methyl]-5-(trifluoromethyl)aniline | LCMS: ES$^+$ 288.1. |
| 3-(piperidin-1-ylmethyl)-5-(trifluoromethyl)aniline | N/A |
| tert-butyl [4-amino-2-(trifluoromethyl)benzyl]methylcarbamate | LCMS: ES$^+$ 305.5. |
| tert-butyl [3-amino-5-(trifluoromethyl)benzyl](2-methoxyethyl)-carbamate | N/A | through Celite. The filtrate was concentrated to give tert-butyl 4-{2-[2-amino-4-(trifluoromethyl)phenoxy]ethyl}piperazine-1-carboxylate (1.63 g, 68%) as a white solid. LCMS: (FA) ES+390.1.

tert-butyl {1-[3-amino-5-(trifluoromethyl)phenyl]-1-methylethyl}carbamate

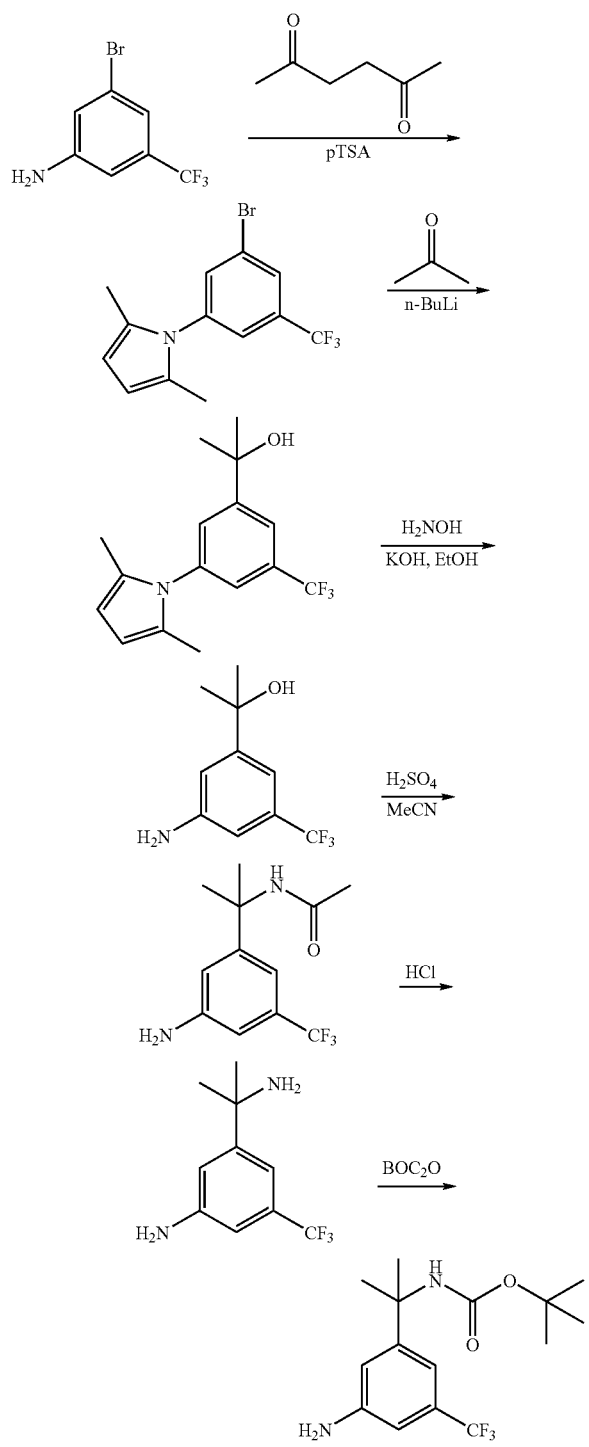

Step 1: 1-[3-bromo-5-(trifluoromethyl)phenyl]-2,5-dimethyl-1H-pyrrole

To a solution of 3-bromo-5-(trifluoromethyl)aniline (14.0 g, 58.3 mmol) in toluene (250 mL), was added hexane-2,5-dione (7.05 mL, 60.1 mmol) and pTSA (0.22 g, 1.20 mmol). The flask was fitted with a Dean Stark trap and reaction mixture was heated at reflux for 1 h. The mixture was allowed to cool to rt and concentrated. The residue was purified by filtration through a pad of silica to give 1-[3-bromo-5-(trifluoromethyl)phenyl]-2,5-dimethyl-1H-pyrrole as an orange solid (18.g g, 97.8%). $^1$H NMR (400 MHz, CDCl$_3$) δ: 7.81 (s, 1H), 7.58 (s, 1H), 7.44 (s, 1H), 5.92 (s, 2H), and 2.05 (s, 6H).

Step 2: 2-[3-(2,5-dimethyl-1H-pyrrol-1-yl)-5-(trifluoromethyl)phenyl]propan-2-ol To a solution of 1-[3-bromo-5-(trifluoromethyl)phenyl]-2,5-dimethyl-1H-pyrrole (4.98 g, 15.6 mmol) in THF (75 mL) at −78° C., was added a solution of 2.50M n-butyllithium in hexane dropwise. The reaction mixture was allowed to stir for 30 min and then acetone (1.49 mL, 20.4 mmol) was added dropwise. The reaction mixture was allowed to stir at −78° C. for 30 min, and then allowed to warm to rt. Saturated aq. NH$_4$Cl was added and the mixture was extracted with EtOAc (3×). The organic solutions were combined, washed with brine, dried over Na$_2$SO$_4$, filtered and concentrated. The residue was purified by column chromatography to give 2-[3-(2,5-dimethyl-1H-pyrrol-1-yl)-5-(trifluoromethyl)phenyl]propan-2-ol (2.29 g, 49.2%). LCMS: (FA) ES+ 298.2.

Step 3: 2-[3-amino-5-(trifluoromethyl)phenyl]propan-2-ol

To a solution of 2-[3-(2,5-dimethyl-1H-pyrrol-1-yl)-5-(trifluoromethyl)phenyl]-propan-2-ol (2.29 g, 7.70 mmol) in EtOH (70 mL) and water (41 mL), was added hydroxylamine hydrochloride (16.1 g, 23.1 mmol) and potassium hydroxide (8.64 g, 154 mmol). The reaction mixture was heated at 110° C. for 18 h, and then allowed to cool to rt. The solvents were evaporated and the residue was dissolved in water and extracted with EtOAc (2×). The organic solutions were combined, washed with brine, dried over Na$_2$SO$_4$, filtered and evaporated. The residue was triturated with Et$_2$O and the filtrate was evaporated to provide -[3-amino-5-(trifluoromethyl)phenyl]propan-2-ol (1.70 g, quant). $^1$H NMR (400 MHz,CDCl$_3$) δ: 7.08 (s, 1H), 6.99 (s, 1H), 6.79 (s, 1H), and 1.56 (s, 6H).

Step 4: N-{-[3amino-5-(trifluoromethyl)phenyl]-1-methylethyl}acetamide

To a solution of 2-[3-amino-5-(trifluoromethyl)phenyl]propan-2-ol (2.05 g, 9.35 mmol) in acetonitrile (110 mL), was added concentrated sulfuric acid (1.99 mL, 37.4 mol).The reaction was allowed to stir at rt for 72 h. Water was added and the pH was adjusted to 8 by the addition of saturated aq. Na$_2$CO$_3$. The mixture was extracted with EtOAc (2×) and the combined organic solutions were washed with water then brine, dried over Na$_2$SO$_4$, filtered and evaporated. The residue was triturated with DCM and the solid was collected. The filtrate was evaporated and further purified by column chromatography. The solid and column fractions were combined to give N-{1-[3-amino-5-(trifluoromethyl)phenyl]-1-methylethyl}acetamide (1.07 g, 44.0%). LCMS: (FA) ES+ 261.1.

Step 5: -(1-amino-1-methylethyl)-5-(trifluoromethyl) aniline

A solution of N-{1-[3-amino-5-(trifluoromethyl)phenyl]-1-methylethyl}acetamide (1.07 g, 4.11 mmol) in 6N HCl (20 mL) was heated at 110° C. for 18 h, then allowed to cool to rt and diluted with water. The mixture was washed with EtOAc and the aqueous solution was neutralized by the addition of 1N NaOH and washed again with EtOAc. The aqueous solution was further basified to pH 10-11 by addition of 1N NaOH and extracted with EtOAc (2×). The extracts were dried over $Na_2SO_4$, filtered and concentrated to give 3-(1-amino-1-methylethyl)-5-(trifluoromethyl)aniline as a brown oil (285 mg, 31.8%).

Step 6: tert-butyl {1-[3-amino-5-(trifluoromethyl)phenyl]-1-methylethyl}carbamate To a solution of 3-(1-amino-1-methylethyl)-5-(trifluoromethyl)aniline (285 mg, 1.31 mmol) in DCM (13 mL) at 0° C. was added di-tert-butyl dicarbonate (314 mg, 1.44 mmol). The reaction was allowed to warm slowly to rt and stirred for 18 h. Di-tert-butyl dicarbonate (140 mg, 0.65 mmol) was added and the reaction was stirred for an additional 18 h. The solvents were evaporated and the residue was purified by column chromatography to give tert-butyl {1-[3-amino-5-(trifluoromethyl)phenyl]-1-methylethyl}carbamate (218 mg, 52.4%). LCMS: (FA) ES+ 319.3, ES- 317.8.

3-(1,1-difluoroethyl)aniline

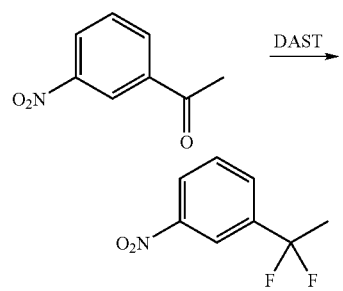

Step 1: 1-(1,1-difluoroethyl)-3-nitrobenzene

To a solution of 1-(3nitrophenyl)ethanone (4.13 g, 25.0 mmol) under an atmosphere of argon was added diethylaminosulfur trifluoride (DAST, 6.61 mL, 50.0 mmol). The reaction mixture was heated at 80° C. for 5 h. The reaction mixture was allowed to cool to rt, diluted with DCM (20 mL), washed with water, brine, dried over $Na_2SO_4$, filtered and concentrated. The residue was purified by column chromatography to give 1-(1,1-difluoroethyl)-3-nitrobenzene as a light yellow solid. $^1$H NMR (300 MHz, DMSO) δ 8.34 (dd, 1H), 8.31 (d, 1H), 8.03 (ddd, 1H), 7.79 (dd, 1H), 3.58 (t, 3H); LCMS: ES- 186.0-.

Step 2: 3-(1,1-difluoroethyl)aniline

To a solution of 1-(1,1-difluoroethyl)-3-nitrobenzene (2.75 g, 14.7 mmol) in AcOH (30 mL) was added zinc (10.0 g, 153 mmol). The reaction mixture was allowed to stir at rt overnight. The mixture was diluted with EtOAc (40 mL) and filtered through Celite. The filtrate was concentrated. The residue was diluted with DCM (20 mL), washed with saturated $NaHCO_3$ (20 mL) and brine, dried over $Na_2SO_4$, filtered and concentrated. The residue was purified by column chromatography to give 3-(1,1-difluoroethyl)benzenamine as light brown oil. $^1$H NMR (300 MHz, DMSO) δ 7.21 (dd, 1H), 6.89 (s, 1H), 6.80 (d, 1H), 6.79 (d, 1H), 186 (t, 3H); LCMS: ES+ 158.1.

3-amino-5-(trifluoromethyl)benzonitrile

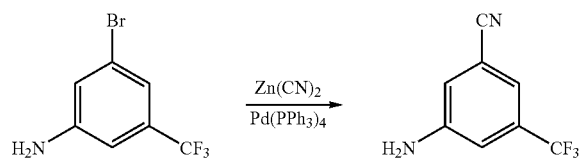

A solution of 3-bromo-5-(trifluoromethyl)aniline (1.00 mL, 7.07 mmol) was degassed with nitrogen. To this solution was added zinc cyanide (0.503 g, 4.28 mmol) and Pd(PPh$_3$)$_4$ (0.403 g, 0.35 mmol). The mixture was degassed a second time and then allowed to heat at 80° C. overnight. The reaction mixture was allowed to cool to rt and then diluted with EtOAc, washed with aq. ammonium hydroxide and LiCl, dried over MgSO$_4$, filtered, and concentrated. The residue was purified by column chromatography to give 3amino-5-(trifluoromethyl)benzonitrile (1.16 g, 88%). LCMS: ES+ 187.

3-amino-5-tert-butylbenzonitrile

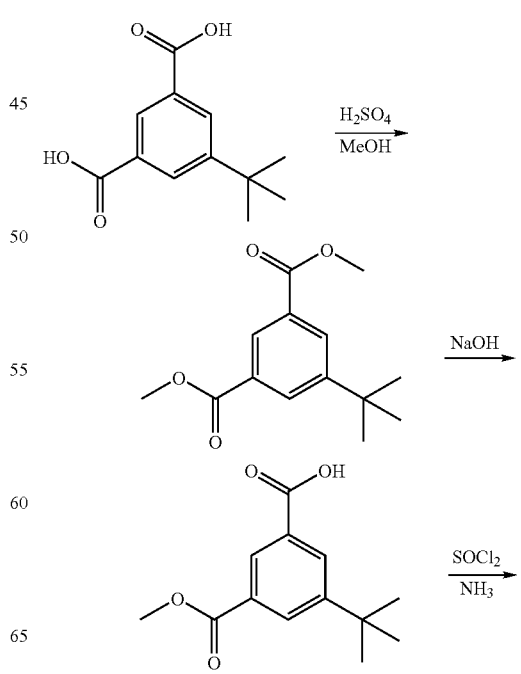

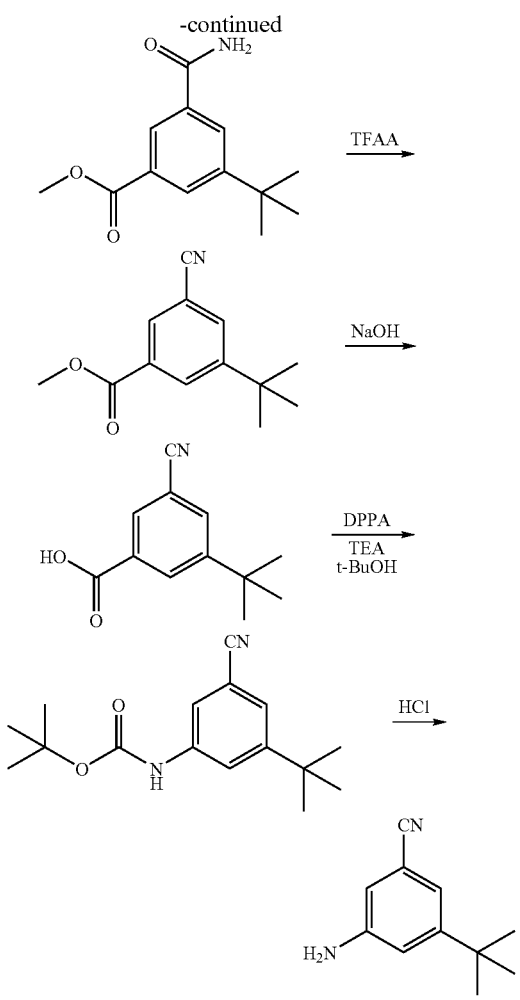

Step 1: dimethyl 5-tert-butylisophthalate

A solution of 5-tert-butylhsophthalic acid (100 g, 0.4 mol) in MeOH (800 mL) and sulfuric acid (80 ml) was allowed to heat at reflux overnight. The reaction mixture was allowed to cool to rt and a white solid precipitated. The solid was filtered, washed with MeOH, and dried under vacuum to give dimethyl 5-tert-butylisophthalate (93.4 g). The filtrate was evaporated, dissolved in EtOAc and washed with water. The organic solution was dried over MgSO$_4$, filtered, and concentrated to give a second crop of dimethyl 5-tert-butylisophthalate (18.8 g, total yield 100%). $^1$H NMR (400 MHz, CDCl$_3$) δ: 8.50 (s, 1H), 8.30 (s, 2H), 3.95 (s, 6H), and 1.32(s, 9H). LCMS ES+ 251.4.

Step 2: 3-tert-butyl-5-(methoxycarbonyl)benzoic acid

To a solution of dimethyl 5-tert-butylisophthalate (93.3 g, 0.373 mol) in MeOH (610 mL) was added a solution of sodium hydroxide (14.9 g, 0.373 mol) in water (41 mL) at 25° C. The mixture was allowed to stir at this temperature for 4 h and then concentrated. The residue was suspended in 1M H$_2$SO$_4$ and filtered. The solid was washed with water and dried under vacuum to give 3-tert-butyl-5-(methoxycarbonyl)benzoic acid (92 g) as a white solid which was used without purification. 1H NMR (400 MHz, d$_6$-DMSO) δ: 8.35 (s, 1H), 8.20 (m, 2H), 3.85 (s,3H), and 1.30 (s, 9H). LCMS: ES− 235.4.

Step 3: methyl 3-(aminocarbonyl)-5-tert-butylbenzoate

To a solution of 33-tert-butyl-5-(methoxycarbonyl)benzoic acid (16.6 g, 60% purity, 0.0422 mol) in toluene (300 mL) was added pyridine (6.8 mL, 0.084 mol). The reaction mixture was allowed to stir at rt under argon and thionyl chloride (7.7 mL, 0.10 mol) was added. After being allowed to stir for 2 h, the reaction mixture was concentrated. The residue was dissolved in THF (100 mL) and toluene (100 mL). Ammonia gas was bubbled through the solution for 5 min and the reaction mixture was allowed to stir at rt overnight. The solvent was removed and the residue was diluted with EtOAc (100ml). The solid was filtered and washed with EtOAc (100 ml) to give methyl 3-(aminocarbonyl)-5-tert-butylbenzoate (11.8 g, 80% purity, 95%). $^1$H NMR (400 MHz, d$_6$-DMSO) δ: 8.29 (t, 1H), 8.24 (s, 1H), 8.17 (t, 1H), 8.06 (t,1H), 7.49 (s, 1H), 3.86 (s,1H), and 1.32 (s,1H). LCMS ES+ 236.2

Step 4: methyl 3-tert-butyl-5-cyanobenzoate

To a solution of give methyl 3-(aminocarbonyl)-5-tert-butylbenzoate (11.8 g, 0.0451 mol) in THF (88) was added pyridine (5.5 mL, 0.068 mol) and TFAA (9.6 mL, 0.068 mol). The reaction mixture was allowed to stir at rt for 3 h and then quenched by the addition of aq sat NaHCO$_3$ and brine. The mixture was extracted with EtOAc. The organic solutions were combined and washed with sodium bicarbonate, brine, 1M HCl, water and brine. The solution was dried over MgSO$_4$, filtered, and concentrated to give methyl 3tert-butyl-5-cyanobenzoate (9.5 g, 70% pure, 68%). $^1$H NMR (400 MHz, d$_6$-DMSO) δ: 8.77 (s, 1H), 8.48 (s, 1H), 8.19 (m, 1H), 8.17 (m, 1H), 8.15 (1, m), 3.88 (s, 3H), and 1.31 (s, 9H). LCMS: ES+ 218.2

Step 5: 3-tert-butyl-5-cyanobenzoic acid

To a solution of methyl 3-tert-butyl-5-cyanobenzoate (8.8 g, 0.0360 mol) in MeOH (76 mL) was added a solution of NaOH (2.0 g, 0.050 mol) in water (15 mL). The mixture was allowed to stir at rt for 2.5 h and then acidified with 1N HCl. The mixture was concentrated to remove methanol and the residue was extracted with EtOAc. The organic solutions were combined, washed with 1NHCl and brine, dried over Na$_2$SO$_4$, filtered, and concentrated to a small volume. Hexane was added and the product precipitated. The solid was filtered, washed with hexanes and dried to give 3-tert-butyl-5-cyanobenzoic acid (9.1 g, 73%). $^1$H NMR (400 MHz, d$_6$-DMSO) δ: 8.19 (m, 1H), 8.13 (m, 1H), 8.10 (m, 1H), and 1.32 (s, 9H). LCMS: ES− 202.2.

Step 6: tert-butyl (3-tert-butyl-5-cyanophenyl)carbamate

To a suspension of 3-tert-butyl-5-cyanobenzoic acid (4.5 g, 0.022 mol) in THF (235 mL) at 0° C. was added TEA (11.1 mL, 0.0797 mol) and diphenylphosphonic azide (6.20 mL, 0.0288 mol). The reaction mixture was allowed to stir at 0° C. for 15 min then allowed to warm to rt. After 2 h, the solvents were evaporated and the residue was redissolved in EtOAc. The solution was washed with saturated NaHCO$_3$ solution and brine, dried over Na$_2$SO$_4$, filtered and concentrated. To the residue was added tert-butyl alcohol (108 mL, 1.13 mol). The reaction mixture was allowed to stir at 85° C. under an atmosphere of nitrogen for 3 h and then concentrated. The residue was purified by column chromatography to give tert-butyl (3-tert-butyl-5-cyanophenyl)carbamate (5.21 g, 86%) as a white solid. $^1$H NMR (400 MHz, d$_6$-DMSO) δ: 9.62(s, 1H), 7.75 (m, 1H), 7.41 (m,1 H), 7.32 (m,1H), 1.46 (s, 9H), and 1.23 (s, 9H). LCMS ES– 273.4

Step 7: 3-amino-5-tert-butylbenzonitrile

A solution of tert-butyl (3-tert-butyl-5-cyanophenyl)carbamate (4.29 g, 0.0133 mol) in 4M HCl in dioxane (18 mL) was allowed to stir at rt for 2 h. The reaction mixture was concentrated to give 3-amino-5-tert-butylbenzonitrile (4.33 g, 93%) which was used without further purification. 1H NMR (300 MHz, CD$_3$OD) δ: 7.99 (m, 1H), 7.72 (m, 1H), 7.56 (m, 1H), and 1.37(s, 9H). LCMS ES+ 175.1, ES– 173.1.

3-cyano-5-(trifluoromethyl)benzoic acid

Step 2: methyl 3-cyano-5-(trifluoromethyl)benzoate

A mixture of methyl 3-bromo-5-(trifluoromethyl)benzoate (5.10 g, 0.0180 mol), zinc cyanide (1.26 g, 0.0107 mol) and tetrakis(triphenylphosphine)palladium(0) (0.910 g, 0.000787 mol) in DMF (50 mL) was subjected to MWI for 20 min at 230° C. The solvent was evaporated and the residue was suspended in EtOAc. The organic solution was and washed with 1N HCl, water and brine, dried and concentrated. The residue was purified by column chromatography to give methyl 3-cyano-5-(trifluoromethyl)benzoate ($^{2.67}$ g, 64%) as white solid. $^1$H NMR (400 MHz, CDCl$_3$) δ: 8.50-8.52 (m, 2H), 8.09 (m, 1H), and 4.03 (s, 3H).

Step 3: 3-cyano-5-(trifluoromethyl)benzoic acid

A mixture of methyl 3-cyano-5-(trifluoromethyl)benzoate (2.67 g, 0.0105 mol) and lithium iodide (13 g, 0.070 mol) in pyridine (70 mL) was subjected to MWI for 30 min at 100° C. The mixture was concentrated and residue was extracted with EtOAc. The organic solutions were combined, washed with 1N HCl(, water and brine, dried over Na$_2$SO$_4$, filtered, and concentrated. The residue was redissolved in EtOAc, washed by 0.2N HCl and brine, dried and concentrated to give 3-cyano-5-(trifluoromethyl)benzoic acid (2.09 g. 92%). $^1$H NMR (400 MHz, d$_6$-DMSO) δ: 8.58 (s, 1H), 8.55 (s, 1H), and 8.39 (s, 1H). LCMS: ES– 214.2.

tert-butyl [4-amino-2-(trifluoromethyl)benzyl]carbamate

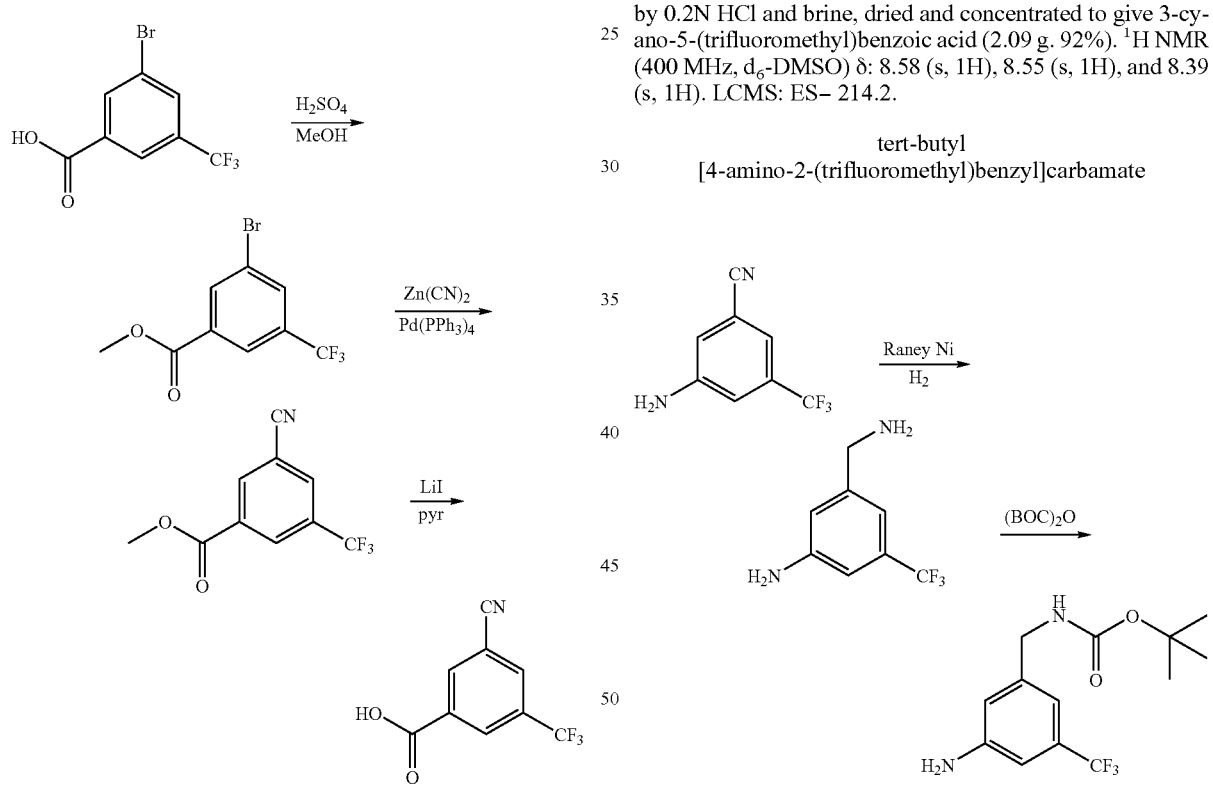

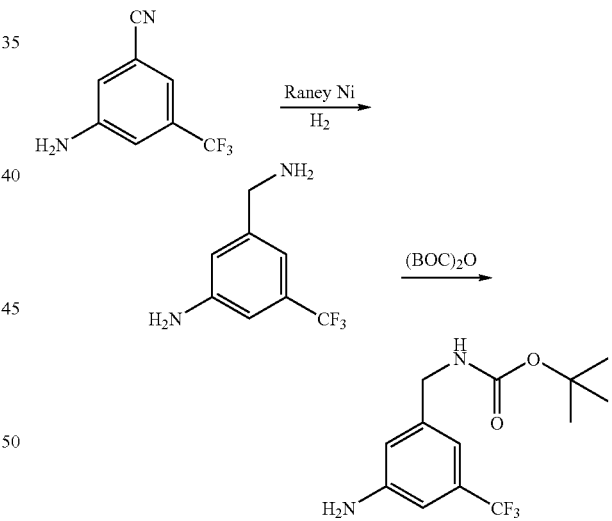

Step 1: methyl 3-bromo-5-(trifluoromethyl)benzoate

To a solution of 3-bromo-5-(trifluoromethyl)benzoic acid (12.43 g, 0.04620 mol) in MeOH (200 mL) was added H$_2$SO$_4$ (8 mL). The reaction mixture was heated at reflux overnight and then concentrated to small volume. The residue was extracted with EtOAc and washed with water, brine, aq. sat. NaHCO$_3$, and brine. The organic solution was concentrated to give methyl 3-bromo-5-(trifluoromethyl)benzoate (12.7 g, 92%). $^1$H NMR (300 MHz, CDCl$_3$) δ: 8.36 (s, 1H), 8.23 (s, 1H), 7.95 (s, 1H), and 3.97 (s, 3H).

Step 1: 4-(aminomethyl)-3-(trifluoromethyl)aniline

To a solution of 4-amino-2-(trifluoromethyl)benzonitrile (5.0 g, 26.7 mmol) in 7.0 M ammonia in MeOH (20.0 mL) was added Raney Nickel 2800 (50% slurry in water, 320 mg). The mixture was allowed to stir under an atmosphere of hydrogen for 18 h, then at 50 psi for 18 h. The mixture was diluted with DCM and filtered through Celite. The filtrate was evaporated and the residue was purified by column chromatography on silica to 4-(aminomethyl)-3-(trifluoro-methyl) aniline as an orange solid (3.43 g, 67%). LCMS: (FA) ES+ 187.1 ES– 185.2.

Step 2: tert-butyl [4-amino-2-(trifluoromethyl)benzyl]carbamate

To a solution of 4-(aminomethyl)-3-(trifluoromethyl) aniline (3.42 g, 18.0 mmol) in THF (90 mL), was added BOC anhydride (4.33 g, 19.8 mmol). The reaction was allowed to stir for 18 h. The solvents were evaporated and the residue was purified by column chromatography on silica to give tert-butyl [4-amino-2-(trifluoromethyl)benzyl]carbamate as yellow solid. (4.43 g, 85%). LCMS: (FA) ES+ 291.4.

Compounds in the following table were prepared from the appropriate starting materials in a method analogous to that described for tert-butyl [4-amino-2-(trifluoromethyl)-benzyl]carbamate:

| | |
|---|---|
| tert-butyl [4-amino-2-(trifluoromethyl)benzyl]carbamate | LCMS: ES+⁻ 291.3. |
| 3-{[(tert-butoxycarbonyl)amino]methyl}-5-tert-butylbenzoic acid | LCMS: ES−⁻ 306.5. |
| 3-{[(tert-butoxycarbonyl)amino]methyl}-5-(trifluoromethyl)benzoic acid | LCMS: ES−318.4. |

3-tert-butyl-5-(pyrrolidin-1-ylmethyl)aniline

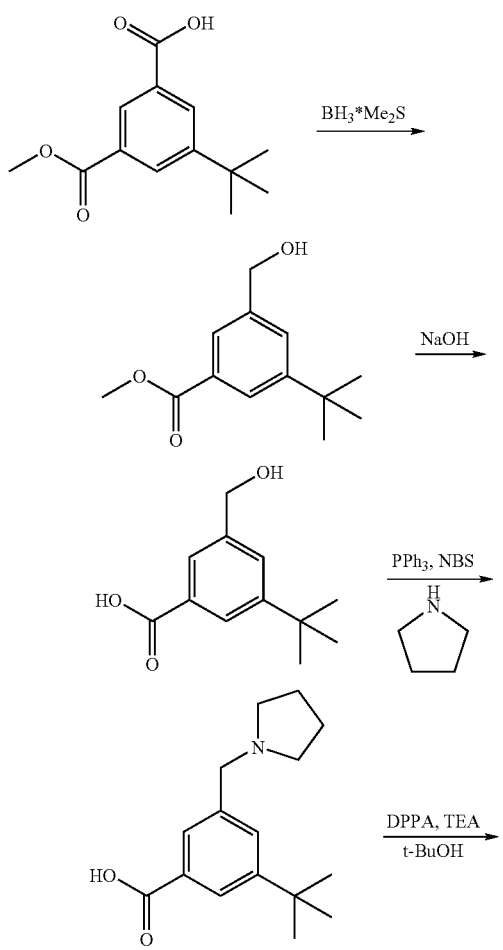

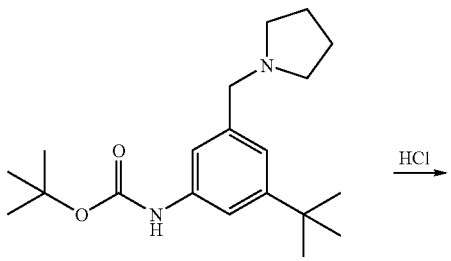

-continued

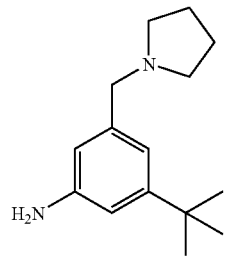

Step 1: methyl 3-tert-butyl-5-(hydroxymethyl)benzoate

To a solution of 3-tert-butyl-5-(methoxycarbonyl)benzoic acid (8.66 g, 0.0293 mol) in THF (60 mL) was slowly added borane-dimethyl sulfide complex (7.8 mL, 0.088 mol) over 20 min at rt. The reaction mixture was heated at 50° C. for 2 h. An additional amount of borane-dimethyl sulfide complex (7.8 mL, 0.088 mol) was added to reaction mixture and the heat increased to 80° C. The reaction mixture was allowed to stir for an additional 2 h. Unreacted borane was quenched by the addition of MeOH. Water was added and the mixture was extracted with EtOAc. The organic solutions were combined, washed with brine, dried over MgSO₄, filtered and concentrated. The residue was purified by column chromatography and triturated to give methyl 3-tert-butyl-5-(hydroxymethyl) benzoate (3.0 g, 46%) as a white solid. LCMS ES+ 223.

Step 2: 3-tert-butyl-5-(hydroxymethyl)benzoic acid

To a solution of methyl 3-tert-butyl-5-(hydroxymethyl) benzoate (3.0 g, 0.013 mol) in MeOH (20 mL) was added sodium hydroxide (0.54 g, 0.013 mol) in water (10 mL). The reaction mixture was allowed to stir at rt overnight and then concentrated. To the residue was added 1M HCl added (pH 5) and the resulting precipitate was collected by filtration to give 3-tert-butyl-5-(hydroxymethyl)benzoic acid (92%). LCMS ES−207.

Step 3: 3-tert-butyl-5-(pyrrolidin-1-ylmethyl)benzoic acid

To a solution of triphenylphosphine (1.2 g, 0.0048 mol) and 3-tert-butyl-5-(hydroxymethyl)benzoic acid (1.0 g, 0.0048 mol) in acetone (20 mL) at −18° C. was added N-bromosuccinimide (0.85 g, 0.0048 mol) portionwise over 2 minutes. After 5 minutes, pyrrolidine (0.96 mL, 0.012 mol) was added. The reaction mixture was heated at 80° C. overnight. EtOAc and water were added to the reaction mixture. The phases were separated and the organic solution was washed with 1M NaOH, 1M HCl, and brine, dried over MgSO$_4$, filtered and concentrated. The residue was purified by column chromatography to give 3-tert-butyl-5-(pyrrolidin-1-ylmethyl)benzoic acid (6%). LCMS ES+ 262, ES− 260.

Step 4: tert-butyl [3-tert-butyl-5-(pyrrolidin-1-ylmethyl)phenyl]carbamate 3-tert-butyl-5-(pyrrolidin-1-ylmethyl)benzoic acid (382 mg, 0.00146 mol) was stirred in THF (40 mL, 0.4 mol) at 0° C. for 15 minutes. To this cold solution was added diphenylphosphonic azide (0.41 mL, 0.0019 mol) and TEA (0.73 mL, 0.0053 mol). The reaction mixture was allowed to warm to rt and stir for 2 hours. The solvents were evaporated (low heat) and the residue was redissolved in EtOAc. The organic solution was washed with sat. NaHCO$_3$ solution and brine then dried over Na$_2$SO$_4$, filtered, and evaporated (low heat). tert-Butyl alcohol (35.8 mL, 0.374 mol) was added to the residue and the reaction mixture was heated overnight at 85° C. under an atmosphere of nitrogen. The mixture was concentrated and the residue taken up in EtOAc. The organic solution was washed with NaOH and brine, dried over MgSO$_4$, filtered and concentrated. The residue was purified by column chromatography using basic alumina to give tert-butyl [3-tert-butyl-5-(pyrrolidin-1-ylmethyl)phenyl]carbamate. LCMS ES+ 333.

Step 5: 3-tert-butyl-5-(pyrrolidin-1-ylmethyl)aniline tert-Butyl [3-tert-butyl-5-(pyrrolidin-1-ylmethyl)phenyl]carbamate (55 mg, 0.00016 mol) was allowed to stir in 1M Hydrochloric acid in Et$_2$O (10 mL) at rt for 5 h. The reaction mixture was concentrated to give 3-tert-butyl-5-(pyrrolidin-1-ylmethyl)aniline (100%) which was used without purification. LCMS ES+233.

3{[(4R)-2,2-dimethyl-1,3-dioxolan-4-yl]methoxy}-5-(trifluoromethyl)aniline

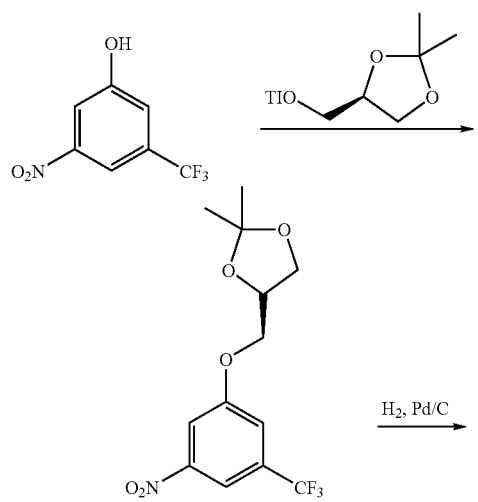

Step 1: (4R)-2,2-dimethyl-4-{[3-nitro-5-(trifluoromethyl)phenoxy]methyl}-1,3-dioxolane A slurry of 3-nitro-5-(trifluoromethyl)phenol (0.658 g, 3.17 mmol), cesium carbonate (3.10, 9.52 mmol) and [(4S)-2,2-dimethyl-1,3-dioxolan-4-yl]methyl trifluoromethanesulfonate (1.00 g, 3.49 mmol) in DMF (10 mL) was heated at 60° C. for 56 h. The reaction mixture was allowed to cool to rt and filtered. The filtrate was diluted with EtOAc and washed with water and brine, dried over Na$_2$SO$_4$, filtered and concentrated. The residue was purified by column chromatography to give (4R)-2,2-dimethyl-4-{[3-nitro-5-(trifluoromethyl)-phenoxy]methyl}-1,3-dioxolane (770 mg, 75%) of as pale yellow oil. $^1$H NMR (400 MHz,CDCl$_3$, HCl salt) δ: 8.10 (s, 1H), 7.94-7.97 (m, 1H), 7.51 (s, 1H), 4.49-4.56 (m, 1H), 4.09-4.23 (m, 3H), 3.92 (q, 1H), .1.45 (s, 3H), and 1.41 (s, 3H).

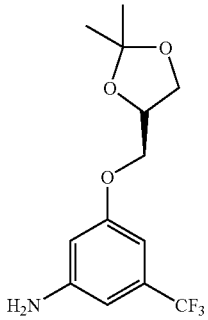

Step 2: 3-{[(4R)-2,2-dimethyl-1,3-dioxolan-4-yl]methoxy}-5-(trifluoromethyl)aniline (4R)-2,2-dimethyl-4-{[3-nitro-5-(trifluoromethyl)phenoxy]methyl}-1,3-dioxolane (0.7770 g, 2.4 mmol) was dissolved in EtOAc (30 mL) and Pd (77 mg, 10% on carbon) was added. The reaction mixture was allowed to stir at rt under an atmosphere of hydrogen for 6 h. The reaction mixture was filtered through a pad of Celite and washed with EtOAc. The solvents were evaporated to give 3-{[(4R)-2,2-dimethyl-1,3-dioxolan-4-yl]methoxy}-5-(trifluoromethyl)-aniline (700 mg, 100%) as a white solid. LCMS: (FA) ES$^+$291.9.

3-({[tert-butyl(dimethyl)silyl]oxy}methyl)-5-(trifluoromethyl)aniline

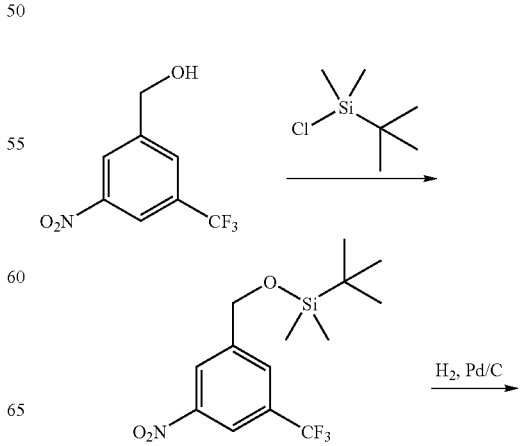

161
-continued

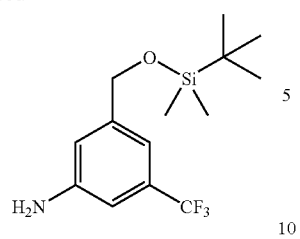

Step 1: tert-butyl(dimethyl){[3-nitro-5-(trifluoromethyl)benzyl]oxy}silane

To a solution of [3-nitro-5-(trifluoromethyl)phenyl]methanol (2.80 g, 12.7 mmol) in DCM (20 mL) was added DIPEA (6.62 mL, 38.00 mmol). The reaction mixture was cooled to 0° C. tert-Butyldimethylsilyl chloride (3.82 g, 25.3 mmol) was added dropwise and the reaction mixture was allowed to stir at rt over the weekend. The reaction mixture was diluted with DCM and washed with water and brine. The organic solution was dried over $Na_2SO_4$, filtered and concentrated. The residue was purified by column chromatography to give tert-butyl(dimethyl)-{[3-nitro-5-(trifluoromethyl)benzyl]oxy}silane (3.71 g, 87%) as a white solid. $^1$H NMR (400 MHz, CDCl$_3$, HCl salt) δ: 8.35-8.41 (m, 2H), 7.92 (s, 1H), 4.88 (s, 2H), 0.97 (s, 9H), and 0.15 (s, 6H).

Step 2: 3-({[tert-butyl(dimethyl)silyl]oxy}methyl)-5-(trifluoromethyl)aniline To a solution of tert-butyl(dimethyl){[3-nitro-5-(trifluoromethyl)benzyl]oxy}-silane (3.70 g, 11.00 mmol) in EtOAc (100 mL) was added Pd (300 mg, 10% on carbon). The reaction mixture was allowed to stir at rt overnight under an atmosphere of hydrogen. The reaction mixture was filtered through a pad of Celite and washed with EtOAc. The solvents were evaporated to give 3-({[tert-butyl(dimethyl)silyl]oxy}methyl)-5-(trifluoromethyl)aniline (3.32 g, 95. LCMS: (FA) ES$^+$ 306.2.

tert-butyl 2-[3-amino-5-(trifluoromethyl)phenyl]pyrrolidine-1-carboxylate

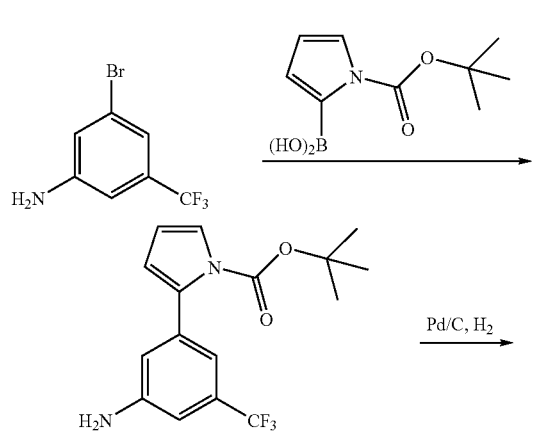

162
-continued

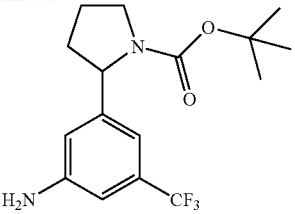

Step 1: tert-butyl 2-[3-amino-5-(trifluoromethyl)phenyl]-1H-pyrrole-1-carboxylate A mixture of 3-bromo-5-(trifluoromethyl)aniline (1.50 mL, 10.6 mmol), water (15.0 mL), 1,2 dimethoxyethane (75 mL), [1-(tert-butoxycarbonyl)-1H-pyrrol-2-yl]boronic acid (3.36 g, 15.9 mmol) and sodium carbonate (4.50 g, 42.4 mmol) was degassed with nitrogen for 5 min. Tetrakis(triphenylphosphine)palladium(0) (0.74 mg, 0.64 mmol) was added to the mixture and the slurry was heated at 80° C. for 3 h. Water was added and the mixture was extracted with EtOAc. The organic solutions were combined, dried over $Na_2SO_4$, filtered and concentrated. The residue was purified by column chromatography on basic alumina to give tert-butyl 2-[3-amino-5-(trifluoromethyl)phenyl]-1H-pyrrole-1-carboxylate (2.58 g, 74%). LCMS: (FA) ES$^+$ 327.3.

Step 2: tert-butyl 2-[3-amino-5-(trifluoromethyl)phenyl]pyrrolidine-1-carboxylate To a solution of tert-butyl 2-[3-amino-5-(trifluoromethyl)phenyl]-1H-pyrrole-1-carboxylate (1.99 g, 6.10 mmol) in EtOH (25 mL) was added Pd (200 mg, 10% on carbon). The reaction mixture was allowed to stir for 2 d under an atmosphere of hydrogen. The reaction mixture was filtered through a pad of Celite and washed with EtOAc. The solvents were evaporated to give tert-butyl 2-[3-amino-5-(trifluoromethyl)phenyl]pyrrolidine-1-carboxylate (1.81 g, 90%) as a white solid. LCMS: (FA) ES$^+$ 331.3.

3-({[tert-butyl(dimethyl)silyl]oxy}methyl)-5-(trifluoromethyl)aniline

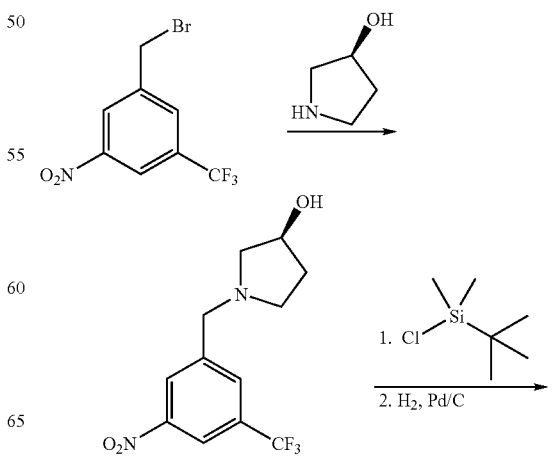

-continued

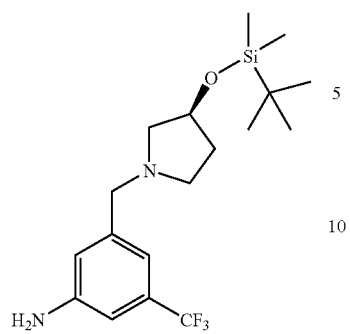

Step 1: (3S)-1-[3-nitro-5-(trifluoromethyl)benzyl]pyrrolidin-3-ol

To a solution of (S)-3-hydroxypyrrolidine (1.84 g, 21 mmol) in DCM (10 mL) at 0° C. was added a solution of 1-(bromomethyl)-3-nitro-5-(trifluoromethyl)benzene (2.00 g, 7 mmol) in DCM (10 mL) dropwise. After the addition, the reaction mixture was allowed to stir at rt for 2 h and then diluted with DCM and washed with brine. Removal of solvent gave (3S)-1-[3-nitro-5-(trifluoromethyl)benzyl]pyrrolidin-3-ol (2.25 g, 100% yield) as yellow oil. LCMS: (FA) ES+ 291.3.Step 2: 3-[((3S)-3-{[tert-butyl(dimethyl)silyl]oxy}pyrrolidin-1-yl)methyl]-5-(trifluoromethyl)aniline (3S)-1-[3-nitro-5-(trifluoromethyl)benzyl]pyrrolidin-3-ol was converted to 3-[((3S)-3-{[tert-butyl(dimethyl)silyl]oxy}pyrrolidin-1-yl)methyl]-5-(trifluoromethyl)aniline in a manner similar to that described above for 3-({[tert-butyl(dimethyl)silyl]oxy}methyl)-5-(trifluoromethyl)aniline. $^1$H NMR (300 MHz, CDCl$_3$) δ: 7.07 (d, 1H), 6.90 (s, 1H), 6.81 (s, 1H), 4.46 (br, 1H), 3.92 (m, 1H), 3.78 (m, 1H), 3.12 (br, 1H), 2.95 (br, 1H), 2.80 (m, 1H), 2.54 (m, 1H), 2.15 (m, 1H), 1.81 (m, 1H), 0.91 (s, 9H), and 0.05 (s, 6H). LCMS: (FA) ES+ 375.3.

3-(4methylpiperazin-1-yl)-5-(trifluoromethyl)aniline

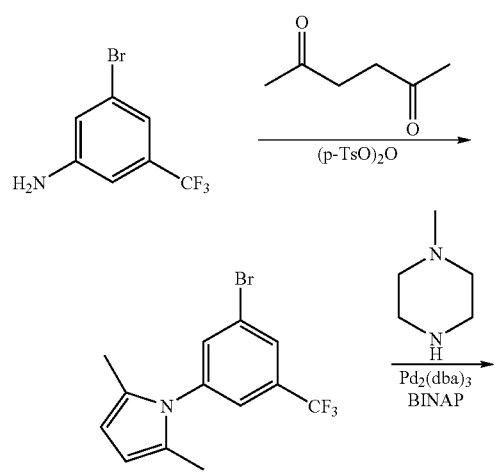

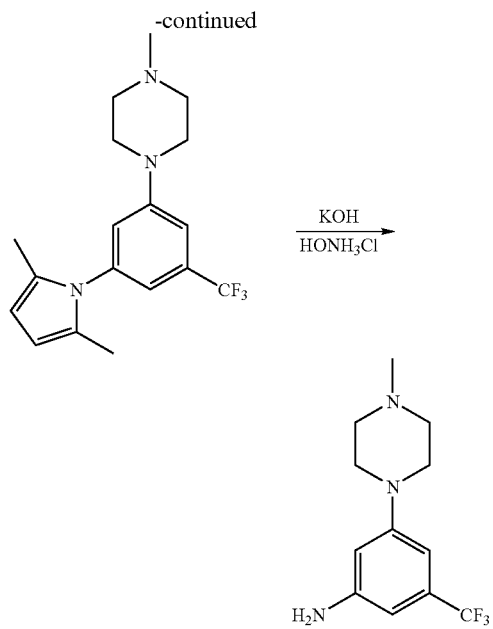

Step 1: 1-[3-bromo-5-(trifluoromethyl)phenyl]-2,5-dimethyl-1H-pyrrole

A solution of 3-bromo-5-(trifluoromethyl)aniline (14.00 g, 58 mmol), hexane-2,5-dione (7.05 mL, 60 mmol) and p-toluenesulfonic acid monohydrate (220 mg, 1.2 mmol) in toluene (250 mL) was heated under Dean-Stark conditions. After 1 h, the reaction mixture was concentrated. The residue was purified by column chromatography to give 1-[3-bromo-5-(trifluoromethyl)phenyl]-2,5-dimethyl-1H-pyrrole (18.15 g, 98%) as orange oil. LCMS: (FA) ES+ 318.1.

Step 2: 1-[3-(2,5-dimethyl-1H-pyrrol-1-yl)-5-(trifluoromethyl)phenyl]-4-methylpiperazine A mixture of 1-[3-bromo-5-(trifluoromethyl)phenyl]-2,5-dimethyl-1H-pyrrole (510 mg, 1.6 mmol), 1-methylpiperazine (210 µL, 1.9 mmol), Pd$_2$(dba)$_3$ (70 mg, 0.08 mmol), 2'-BINAP (100 mg, 0.2 mmol) and cesium carbonate (730 mg, 2.2 mmol) in toluene (5.1 mL) was subjected to MWI at 150° C. for 10 min. The reaction mixture was diluted with DCM and washed with brine. The residue was purified by column chromatography to give 1-[3-(2,5-dimethyl-1H-pyrrol-1-yl)-5-(trifluoromethyl)phenyl]-4methylpiperazine (172 mg, 32%) as a yellow solid. LCMS: (FA) ES+ 338.3.

Step 3: 3-(4-methylpiperazin-1-yl)-5-(trifluoromethyl)aniline

To a mixture of 1-[3-(2,5-dimethyl-1H-pyrrol-1-yl)-5-(trifluoromethyl)phenyl]-4-methylpiperazine (440 mg, 1.3 mmol) and potassium hydroxide (1.46 g, 26. mmol) in EtOH (10 mL) and water (3 mL) was added hydroxylamine hydrochloride (2.72 g, 39 mmol. The reaction mixture was heated at reflux overnight. The reaction mixture was then concentrated and the residue was dissolved in water and EtOAc. The reaction mixture was extracted with EtOAc. The organic solutions were combined, washed with brine, dried over Na$_2$SO$_4$ filtered and concentrated. The residue was purified by column chromatography to give 3-(4-methylpiperazin-1-yl)-5-(trifluoromethyl)aniline (247 mg, 73%) as a yellow oil. $^1$H NMR (300 MHz, CDCl$_3$) δ: 6.55 (d, 1H), 6.40 (d, 1H), 6.33 (d, 1H), 3.24 (t, 4H), 2.61 (t, 4H), and 2.38 (s, 3H). LCMS: (FA) ES+ 260.2.

BOC Deprotection

Note that in some of the examples described below, analogs were carried though with tert-butyl carbamate protected amines. In those cases, deprotection of the amine to give the final compound was carried out by dissolving the protected compound in an appropriate solvent (MeOH or DCM) and adding HCl (1 -4 N) in an appropriate solvent (Et$_2$O or dioxane). The final products were obtained after concentration of that solution.

Example 2

Preparation of N-[4-chloro-3-(trifluoromethyl)phenyl]-7-{[2-(4,5-dihydro-1H-imidazol-2-yl)pyridin-4-yl]oxy}-1,2,3,4-tetrahydronaphthalene-2-carboxamide (I-36)

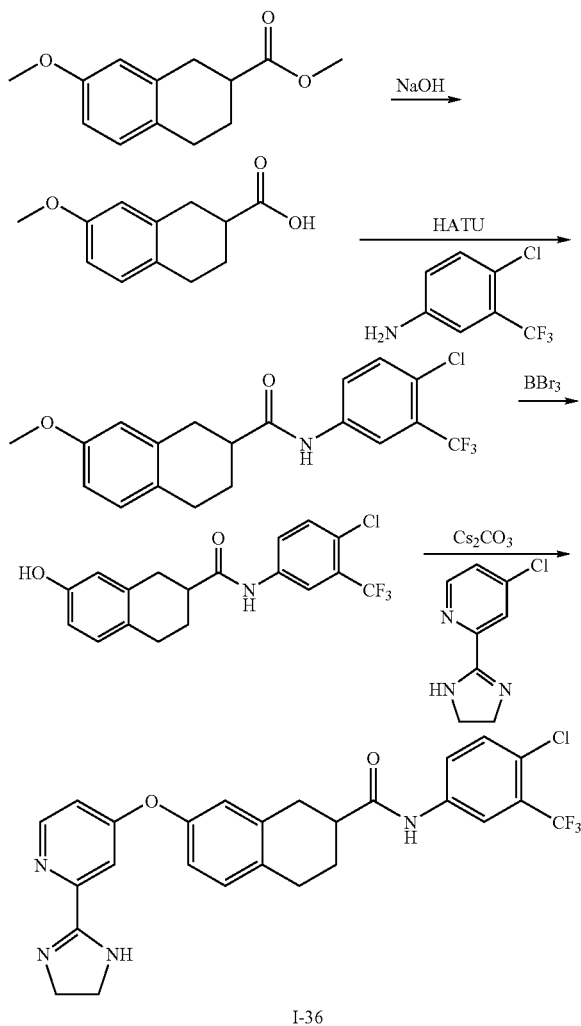

Step 1: 7-Methoxy-1,2,3,4-tetrahydronaphthalene-2-carboxylic acid

To a solution of methyl 7-methoxy-1,2,3,4-tetrahydronaphthalene-2-carboxylate (4.03 g, 18.3 mmol), in MeOH (180 mL), was added 1N NaOH solution (73.2 mL, 73.3 mmol). The reaction was allowed to stir for 3 h and then the solvents were evaporated until approximately 50 mL of water remained. The solution was washed with Et$_2$O and then the aqueous phase was acidified to pH 1 by the addition of 1N HCl solution. A precipitate formed and was filtered, washed with water and hexane, and dried under vacuum to give 7-methoxy-1,2,3,4tetrahydronaphthalene-2-carboxylic acid as a white solid (3.43 g, 91%).

Step 2: N-[4-Chloro-3-(trifluoromethyl)phenyl]-7-methoxy-1,2,3,4-tetrahydronaphthalene-2-carboxamide To a solution of 7-methoxy-1,2,3,4-tetrahydronaphthalene-2-carboxylic acid (250 mg, 1.21 mmol), and 4-chloro-3-(trifluoromethyl)aniline (260 mg, 1.33 mmol) in DMF (12.0 mL) was added DIPEA (1.06 mL, 6.07 mmol) and then HATU (508 mg, 1.34 mmol). The solution was allowed to stir at rt for 18 h. 1N HCl was added and the mixture was extracted with EtOAc. The organic solution was washed with saturated NaHCO$_3$ solution and brine, dried over Na$_2$SO$_4$, filtered and evaporated. The residue was purified by column chromatography to give N-[4-chloro-3-(trifluoromethyl)phenyl]-7-methoxy-1,2,3,4-tetrahydronaphthalene-2-carboxamide as a white solid (233 mg, 50%). LCMS: (FA) ES$^+$ 384.1, ES$^-$ 382.1.

Step 3: N-[4-Chloro-3-(trifluoromethyl)phenyl]-7-hydroxy-1,2,3,4-tetrahydronaphthalene-2-carboxamide To a solution of N-[4-chloro-3-(trifluoromethyl)phenyl]-7-methoxy-1,2,3,4-tetrahydronaphthalene-2-carboxamide (3.65 g mg, 9.53 mmol) in DCM (100 mL) at 0° C. was added a 1.0M solution of BBr$_3$ in DCM (14.3 mL) dropwise. The reaction mixture was allowed to warm to rt overnight. The reaction mixture was poured onto ice and extracted with EtOAc. The organic solution was dried over Na$_2$SO$_4$, filtered and evaporated. The residue was triturated with DCM to give N-[4-chloro-3-(trifluoromethyl)phenyl]-7-hydroxy-1,2,3,4-tetrahydronaphthalene-2-carboxamide as a beige solid (3.25 g, 92.4%). LCMS: (FA) ES$^+$ 370.2, ES$^-$ 368.1.

Step 4: N-[4-chloro-3-(trifluoromethyl)phenyl]-7-{[2-(4,5-dihydro-1H-imidazol-2-yl)-pyridin-4-yl]oxy}-1,2,3,4-tetrahydronaphthalene-2-carboxamide (I-36)

To a solution of N-[4-chloro-3-(trifluoromethyl)phenyl]-7-hydroxy-1,2,3,4-tetrahydronaphthalene-2-carboxamide (64 mg, 0.17 mmol) and 4-chloro-2-(4,5-dihydro-1H-imidazol-2-yl)pyridine (35 mg, 0.19 mmol) in DMF (1.70 mL) was added Cs$_2$CO$_3$ (170 mg, 0.52 mmol). The mixture was irradiated in a microwave for 200 sec at 200° C. Water was added, and the mixture was extracted with EtOAc. The organic solution was washed with water (3×) and brine, dried over Na$_2$SO$_4$, filtered and evaporated. The residue was purified by column chromatography. The product was dissolved in MeOH, and 2.0M HCl in Et$_2$O was added. The solvents were evaporated to give I-36 as a white solid (59 mg, 58%). $^1$H NMR (300 MHz, CD$_3$OD): δ 8.62 (d, 1H), 8.17 (d, 1H), 7.82-7.78 (m, 1H), 7.63 (d, 1H), 7.53 (d, 1H), 7.25 (d, 1H), 7.21-7.18 (m, 1H), 6.96-6.91 (m, 2H), 4.11 (s, 4H), 3.14-2.82 (m, 5H), 2.24-2.16 (m, 1H), and 2.01-2.90 (m, 1H). LCMS: (FA) ES$^+$ 516.2, ES$^-$ 513.2.

Compounds in the following table were prepared from the appropriate starting materials in a method analogous to that of Example 2:

| | |
|---|---|
| I-44 | $^1$H NMR(300MHz, CD$_3$OD): δ 8.635(d, 1H), 7.66-7.63(m, 2H), 7.43-7.40(m, 1H), 7.27-7.14(m, 4H), 6.97-6.91(m, 2H), 4.12(s, 4H), 3.15-2.83(m, 5H), 2.25-2.17(m, 1H), 2.04-1.92(m, 1H), and 1.32(s, 9H). LCMS: (FA) ES$^+$ 469.8, ES$^-$ 467.4. |
| I-1 | $^1$H NMR(400MHz, CD$_3$OD): δ 8.62(d, 1H), 7.62(d, 1H), 7.48-7.47(m, 1H), 7.40-7.36(m, 1H), 7.27-7.17(m, 3H), 7.00-6.90(m, 3H), 4.11(s, 4H), 3.13-2.79(m, 6H), 2.23-2.15(m, 1H), 2.00-1.89(m, 1H), and 1.24(d, 6H). LCMS: (FA) ES$^+$ 455.4, ES$^-$ 453.5. |
| I-20 | $^1$H NMR(400MHz, CD$_3$OD) δ: 8.62(d, 1H), 7.62(d, 1H), 7.65-7.55(br s, 1H), 7.51-7.49(m, 1H), 7.27-7.22(m, 1H), 7.22-7.18(m, 1H), 6.98-6.89(m, 3H), 4.11(s, 4H), 3.84(s, 3H), 3.13-2.81(m, 5H), 2.24-2.16(m, 1H), and 2.01-1.89(m, 1H). LCMS: (FA) ES+ 511.3, ES− 509.3. |
| I-8 | $^1$H NMR(300MHz, CD$_3$OD): δ 8.63(d, 1H), 8.18(s, 1H), 7.73(d, 2H), 7.64(d, 1H), 7.26(d, 1H), 7.22-7.19(m, 1H), 6.92-6.92(m, 2H), 4.12(s, 4H), 3.15-2.82(m, 5H), 2.26-2.17(m, 1H), and 2.02-1.90(m, 1H). LCMS: (FA) ES$^+$ 559.3/561.1 ES$^-$ 557.2/559.1. |
| I-2 | $^1$H NMR(300MHz, CD$_3$OD): δ 8.62(d, 1H), 8.08(s, 1H), 7.77(d, 1H), 7.63(d, 1H), 7.50(t, 1H), 7.37(d, 1H), 7.25(d, 1H), 7.21-7.29(m, 1H), 7.97-7.91(m, 2H), 4.11(s, 4H), 3.14-2.12(m, 5H), 2.25-2.17(m, 1H), and 2.02-1.91(m, 1H). LCMS: (FA) ES$^+$ 481.6, ES$^-$ 479.3 |
| I-25 | $^1$H NMR(400MHz, CD$_3$OD): δ 8.62(d, 1H), 7.62(d, 1H), 7.48-7.47(m, 1H), 7.40-7.36(m, 1H), 7.27-7.17(m, 3H), 7.00-6.90(m, 3H), 4.11(s, 4H), 3.13-2.79(m, 6H), 2.23-2.15(m, 1H), 2.00-1.89(m, 1H), and 1.24(d, 6H). LCMS: (FA) ES$^+$ 455.4, ES$^-$ 453.5. |
| I-21 | $^1$H NMR(300MHz, d$_6$-DMSO): δ 10.79(s, 2H), 10.68(s, 1H), 8.66(d, 1H), 8.23(d, 1H), 7.85-7.82(m, 2H), 7.63(d, 1H), 7.29(t, 1H), 7.18-7.15(m, 2H), 7.01(d, 1H), 3.99(s, 4H), 2.94-2.89(m, 2H), 2.81-2.74(m, 2H), 2.65-2.58(m, 2H), 2.15-2.08(m, 1H), and 2.83-2.67(m, 1H). LCMS: (FA) ES$^+$ 515.3, ES$^-$ 413.3. |
| I-46 | $^1$H NMR(300MHz, d$_6$-DMSO): δ 10.94(s, 1H), 10.80(s, 2H), 8.74(d, 1H), 8.65(s, 1H), 8.53(d, 1H), 8.23-8.17(m, 3H), 8.08(d, 1H), 7.96-7.94(m, 2H), 7.74(m, 1H), 7.58-7.74(m, 1H), 7.45-7.42(m, 1H), and 3.99(s, 4H). LCMS: (FA) ES$^+$ 511.2, ES$^-$ 509.3 |
| I-7 | $^1$H NMR(300MHz, d$_6$-DMSO) δ: 10.84(s, 2H), 10.42(s, 1H), 8.73(d, 1H), 8.61-8.60(m, 1H), 8.21-8.14(m, 2H), 8.09-8.06(m, 1H), 7.99-7.94(m, 2H), 7.82-7.81(m, 1H), 7.76-7.73(m, 1H), 7.53(dd, 1H), 7.41(dd, 1H), 7.28(t, 1H), 7.16-7.13(m, 1H), 3.98(s, 4H), and 1.29(s, 9H). LCMS: (FA) ES$^+$ 465.4, ES$^-$ 463.4. |
| I-6 | $^1$H NMR(300MHz, d$_6$-DMSO) δ: 10.96-10.90(m, 3H), 8.73(d, 1H), 8.68(s, 1H), 8.39-8.32(m, 1H), 8.22-8.05(m, 5H), 7.95-7.94(m, 1H), 7.64-7.53(m, 2H), 7.48-7.45(m, 1H), 7.40(dd, 1H), and 3.98(s, 4H). LCMS: (FA) ES$^+$ 603.1. |
| I-19 | $^1$H NMR(300MHz, d$_6$-DMSO) δ: 11.04-10.91(m, 3H), 8.73-8.68(m, 2H), 8.46-8.44(m, 1H), 8.22-8.03(m, 5H), 7.94-7.86(m, 2H), 7.55(dd, 1H), 7.39(dd, 1H), and 3.98(s, 4H). LCMS: (FA) ES$^+$ 555.2/557.2, ES$^-$ 553.2/555.2. |
| I-33 | $^1$H NMR(300MHz, d$_6$-DMSO) δ: 10.89-10.83(m, 3H), 8.73, 1H), 8.66(s, 1H), 8.19(t, 2H), 8.10-8.02(m, 2H), 7.95-7.92(m, 2H), 7.82(s, 1H), 7.57-7.53(m, 1H), 7.41-7.39(m, 1H), 6.99(s, 1H), 3.98(s, 4H), and 3.84(s, 3H). LCMS: (FA) ES$^+$ 507.3, ES$^-$ 505.3. |
| I-53 | $^1$H(400MHz, CD$_3$OD) δ: 8.69-8.67(m, 1H,), 8.544-8.54(m, 1H), 8.22(s, 1H), 8.14-8.08(m, 2H), 8.05-8.03(m, 1H), 8.00-7.97(m, 1H), 7.86(d, 1H), 7.73-7.72(m, 1H), 7.56(t, 1H), 7.48-7.43(m, 2H), 7.31-7.29(m, 1H), and 4.09(s, 4H). LCMS: (FA) ES$^+$ 477.2, ES$^-$ 475.3. |
| I-13 | $^1$H(300MHz, d$_6$-DMSO) δ: 10.94(s, 2H), 10.7(s, 1H), 8.73(d, 1H,), 8.66(s, 1H), 8.22-8.08(m, 5H), 7.96-7.95(m, 1H), 7.71-7.54(m, 3H), 7.40-7.37(m, 1H), and 3.98(s, 4H). LCMS: (FA) ES$^+$ 495.3, ES$^-$ 493.3. |
| I-14 | $^1$H NMR(300MHz, d$_6$-DMSO): δ 10.85(s, 2H), 10.61(s, 1H), 8.74(d, 1H), 8.61(s, 1H), 8.22-8.15(m, 2H), 8.08-8.04(m, 1H), 9.99-7.94(m, 2H), 7.60(br s, 1H), 7.57-7.52(m, 2H), 7.43-7.41(m, 1H), 6.80(br s, 1H), and 3.99(s, 4H). LCMS: (FA) ES$^+$ 492.5 |
| I-39 | $^1$H NMR(300MHz, d$_6$-DMSO): δ 10.95(s, 1H), 10.81(s, 2H), 8.74(d, 1H), 8.67(s, 1H), 8.52(br s, 3H), 8.35(s, 1H), 8.26-8.18(m, 3H), 8.10(d, 1H), 7.96(s, 2H), 7.78(d, 1H), 7.48-7.55(m, 1H), 7.44-7.41(m, 1H), 4.18-4.11(m, 2H), and 3.99(s, 4H). LCMS: (FA) ES$^+$ 506.3, ES$^-$ 504.4. |
| I-30 | $^1$H NMR(300MHz, d$_6$-DMSO) δ, 11.06(s, 1H), 9.36(d, 1H), 8.96(d, 1H), 8.58(d, 1H), 8.38(d, 1H), 8.25(d, 1H), 8.2(s, 1H), 8.15-8.11(m, 1H), 7.98(d, 1H), 7.81-7.75(m, 2H), 7.5(d, 1H), 7.29-7.26(m, 1H), and 3.59(s, 4H). LCMS: (FA) ES+ 512.2, ES− 510.2. |
| I-54 | $^1$H NMR(300MHz, d$_6$-DMSO): δ 11.91(s, 1H), 10.88(s, 2H), 8.71(d, 1H), 8.30(s, 1H), 8.22(br s, 1H), 8.03-7.97(m, 2H), 7.75(d, 1H), 7.45(d, 1H), 7.16-7.24(m, 3H), 4.50-4.40(m, 2H), 3.65-3.57(m, 1H), 3.34(s, 4H), and 3.05-3.20(m, 2H). LCMS: (FA) ES$^+$ 516.2, ES$^-$ 514.2. |
| I-52 | $^1$H NMR(400MHz, CD$_3$OD) δ: 8.66(d, 1H), 8.59(br s, 1H), 8.21-8.05(m, 3H), 7.97-7.89(m, 3H), 7.76(br s, 1H), 7.55-7.47(m, 2H), 7.11(br s, 1H), 4.49-4.43(m, 2H), 3.80-3.70(m, 4H), 3.29-3.22(m, 2H), 2.94(s, 3H), 2.27-2.16(m, 2H), and 2.14-2.02(m, 2H). LCMS: (FA) ES+ 579.2. |
| I-18 | $^1$H NMR(400MHz, d$_6$-DMSO; HCl salt) δ: 10.91-10.69(m, 2H), 8.74(d, 1H), 8.67(s, 1H), 8.23-8.15(m, 2H), 8.11-8.06(m, 1H), 7.99-7.89(m, 4H), 7.58-7.54(m, 1H), |

-continued

| | |
|---|---|
| | 7.43-7.39(m, 1H), 7.09(br s, 1H), 4.89-4.41(m, 2H), 3.99(s, 4H), 3.73-3.49(m, 4H), 3.19-3.053(m, 2H), and 2.09-1.82(m, 4H). LCMS: (FA) ES+ 590.2. |
| I-4 | $^1$H NMR(400MHz, d$_6$-DMSO) δ: 10.86(s, 1H), 10.77(s, 1H), 8.66(d, 1H), 7.92(s, 1H), 7.71(d, 2H), 7.28-7.24(m, 2H), 7.05-6.97(m, 3H), 4.42-4.38(m, 2H), 3.99(s, 4H), 3.61-3.53(m, 4H), 3.17-3.04(m, 2H), 2.98-2.79(m, 5H), and 2.16-1.75(m, 6H). LCMS: (FA) ES$^+$ 594.2. |
| I-43 | $^1$H NMR(400MHz, d$_6$-DMSO) δ 12.13(s, 1H), 8.86-8.81(m, 1H), 8.65-8.62(br s, 1H), 8.56(d, 1H), 8.21-8.14(m, 2H), 8.07-8.03(m, 1H), 7.93-7.91(m, 1H), 7.59-7.55(m, 1H), 7.51-7.48(m, 1H), 7.31-7.27(m, 1H), 6.47(s, 1H), 2.77(d, 3H), and 1.29(s, 9H). LCMS: (FA) ES$^+$ 446.6, ES$^-$ 443.2. |
| I-5 | $^1$H NMR(300MHz, d$_6$-DMSO) δ: 10.91(s, 1H), 8.91-8.79(m, 1H), 8.64-8.54(m, 2H), 8.41(br s, 1H), 8.23-8.13(m, 3H), 8.08-8.01(m, 1H), 7.92(br s, 1H), 7.78-7.68(m, 1H), 7.59-7.51(m, 1H), 7.51-7.46(m, 1H), 7.33-7.27(m, 1H), and 2.81-2.75(m, 3H). LCMS: (FA) ES+ 500.3. |
| I-37 | $^1$H NMR(300MHz, CD$_3$OD) δ: 8.61-8.56(m, 1H), 8.51(br s, 1H), 8.17-8.01(m, 3H), 7.88-7.83(m, 1H), 7.82-7.74(m, 2H), 7.62-7.55(m, 1H), 7.49-7.43(m, 1H), 7.35-7.21(m, 3H), 2.93(s, 3H), 1.35(s, 9H). LCMS: (FA) ES$^+$ 454.3. |
| I-15 | $^1$H NMR(400MHz, CDCl$_3$) δ: 12.51-12.42(br s, 1H), 9.91(s, 1H), 9.71(br s, 1H), 8.44(d, 1H), 8.04(s, 1H), 7.68(s, 1H), 7.56(s, 1H), 7.17-7.14(m, 1H), 6.84-6.73(m, 3H), 4.46(br s, 2H), 3.81-3.72(m, 3H), 3.48-3.42(m, 3H), 3.09-2.80(m, 8H), and 2.19-1.87(m, 6H). LCMS: (FA) ES+ 583.1. |
| I-26 | $^1$H NMR(400MHz, CD$_3$OD) δ: 8.64(d, 1H), 7.91(s, 1H), 7.45(dd, 1H), 7.29(d, 1H), 7.04(d, 1H), 7.01(d, 1H), 6.27(dd, 1H), 2.97-3.13(s, 2H), 2.96(s, 3H), 2.83-2.94(m, 3H), 2.16-2.24(m, 1H), 1.88-2.05(m, 1H), and 1.29(s, 9H). LCMS: (AA) ES+ 449.3, ES− 447.3. |
| I-24 | $^1$H NMR(400MHz, d$_6$-DMSO) δ: 10.63(s, 1H), 8.71(d, 1H), 8.41(d, 1H), 8.04(dd, 1H), 7.8(d, 1H), 7.66(d, 1H), 7.43(d, 1H), 7.36(dd, 1H), 7.19(d, 1H), 7.15(dd, 1H), 3.16(d, 2H), 3.01-3.10(m, 3H), 2.99(s, 3H), 2.29-2.36(m, 1H), and 1.96-2.07(m, 1H). LCMS: (AA) ES$^+$ 504.3/506.3, ES$^-$502.4/504.3. |
| I-23 | $^1$H NMR(400MHz, d$_6$-DMSO) δ: 9.98(s, 1H), 8.83(d, 1H), 8.51(d, 1H), 7.64(dd, 1H), 7.47-7.51(m, 1H), 7.4(d, 1H), 7.19-7.25(m, 2H), 7.14-7.18(m, 1H), 7.04-7.08(m, 1H), 7.02(d, 1H), 6.96(d, 1H), 2.94(d, 2H), 2.71-2.90(m, 6H), 2.06-2.12(m, 1H), 1.74-1.85(m, 1H), and 1.25(s, 9H). LCMS: (AA) ES+ 458.4, ES− 456.4. |
| I-48 | $^1$H NMR(400MHz, d$_6$-DMSO) δ: 10.89(s, 1H), 9.09(br s, 2H), 8.73(d, 1H), 8.69(br s, 1H), 8.22-8.09(m, 3H), 8.04-8.03(m, 1H), 7.96-7.89(m, 3H), 7.57-7.54(m, 1H), 7.42-7.39(m, 1H), 7.11(br s, 1H), 4.79-4.72(m, 1H), 3.99(s, 4H), 3.28-3.18(m, 2H), 3.13-3.03(m, 2H), 2.19-2.11(m, 2H), and 1.94-1.83(m, 2H). LCMS: (FA) ES$^+$ 576.4, ES$^-$ 574.4. |
| I-9 | $^1$H NMR(400MHz, d$_6$-DMSO) δ: 10.81(br s, 1H), 8.94(br s, 1H), 8.86-8.82(m, 1H), 8.61(br s, 1H), 8.56(d, 1H), 8.22-8.15(m, 2H), 8.07-8.03(m, 1H), 7.95-7.91(m, 1H), 7.88-7.82(m, 2H), 7.57-7.54(m, 1H), 7.49-7.45(m, 1H), 7.32-7.27(m, 1H), 7.11(br s, 1H), 4.81-4.73(m, 1H), 3.28-3.19(m, 2H), 3.13-3.04(m, 2H), 2.77(d, 3H), 2.19-2.08(m, 2H), and 1.93-1.83(m, 2H). LCMS: (FA) ES+ 566.3, ES− 563.2. |
| I-41 | $^1$H NMR(400MHz, CD$_3$OD) δ: 8.67(d, 1H), 7.96(s, 1H), 7.7(s, 1H), 7.61(s, 1H), 7.51(dd, 1H), 7.31(d, 1H), 7.02-7.09(m, 3H), 4.43(dd, 2H), 3.64(dd, 2H), 3.02-3.17(m, 3H), 2.99(s, 6H), 2.98(s, 3H), 2.88-2.96(m, 2H), 2.19-2.24(m, 1H), and 1.91-2.01(m, 1H). LCMS: (AA) ES+ 557.4, ES− 555.5. |
| I-31 | $^1$H NMR(400MHz, CD$_3$OD): δ 10.37(s, 1H), 8.61(d, 1H), 8.06(s, 1H), 7.98(s, 1H), 7.83(d, 1H), 7.53(s, 1H), 7.40-7.38(m, 1H), 7.30(d, 1H), 7.04-6.99(m, 2H), 4.19(s, 2H), 3.18-2.99(m, 3H), 2.97(s, 3H), 2.94-2.86(m, 2H), 2.28-2.19(m, 1H), and 2.03-1.90(m, 1H). LCMS: (FA) ES$^+$ 499.0. |
| I-50 | $^1$H NMR(300MHz, CD$_3$OD): δ 8.55-8.52(m, 2H), 8.26(d, 1H), 8.12(d, 1H), 7.93(d, 1H), 7.85(t, 1H), 7.69-64(m, 2H), 7.52(dd, 1H), 7.30(t, 1H), 7.23-7.19(m, 2H), 3.74(s, 4H), and 1.33(s, 9H). LCMS: (FA) ES$^+$ 467.2. |
| I-45 | $^1$H NMR(300MHz, CD$_3$OD): δ 8.60(d, 1H), 8.58(s, 1H), 8.44(d, 1H), 8.31(d, 1H), 8.16(d, 1H), 8.13(dd, 1H), 7.96(d, 1H), 7.67(d, 1H), 7.63-7.56(m, 2H), 7.25(dd, 1H), 3.77(s, 4H). LCMS: (FA) ES$^+$ 512.2. |
| I-12 | $^1$H NMR(400MHz, DMSO): δ 10.89(s, 2H), 10.11(s, 1H), 8.77(s, 1H), 7.95(s, 1H), 7.73(s, 1H), 7.61(s, 1H), 7.50(s, 1H), 7.32-7.04(m, 5H), 5.07(s, 2H), 4.00(s, 4H), and 1.27(s, 9H). LCMS: (FA) ES$^+$ 469.2, ES$^-$ 467.1. |
| I-10 | $^1$H NMR(400MHz, CD$_3$OD): δ 8.46(d, 1H), 8.17(s, 1H), 7.90(dd, 1H), 7.56-7.51(m, 2H), 7.37(s, 1H), 7.05-7.04(m, 3H), 6.97-6.95(d, 1H), 5.05(d, 2H), and 3.76(s, 4H). LCMS: (FA) ES$^+$ 515.2, ES$^-$ 513.2. |
| I-29 | $^1$H NMR(400MHz, CD$_3$OD) δ: 8.62(d, 1H), 7.86(d, 1H), 7.58(d, 2H), 7.39-7.43(m, 1H), 7.29(d, 1H), 7.24(d, 2H), 6.98-7.06(m, 2H), 3.65(s, 3H), 3.12-3.19(m, 2H), 3.04-3.12(m, 1H), 3.00-3.03(m, 1H), 2.87-2.98(m, 5H), 2.19(m, 1H), 1.97(m, 1H). LCMS: (AA) ES+ 445.1, ES− 443.1. |
| I-51 | $^1$H NMR(400MHz, CD$_3$OD) δ: 8.65(s, 1H), 8.93(s, 1H), 7.82(s, 1H), 7.54(d, 1H), 7.49(s, 1H), 7.39(dd, 1H), 7.31(d, 1H), 7.18(d, 1H), 7.06(s, 1H), 7.02(d, 1H), 4.08(s, 2H), 2.82-3.16(m, 8H), 2.17-2.24(m, 1H), and 1.88-2.00(m, 1H). LCMS: (AA) ES$^+$ 431.1, ES$^-$ 429.0. |
| I-42 | $^1$H NMR(400MHz, CD$_3$OD) δ: 8.51(d, 1H), 7.69(d, 2H), 7.62(s, 1H), 7.41(d, 2H), 7.24(d, 1H), 7.15(d, 1H), 6.95(s, 1H), 6.92(d, 1H), 4.07(s, 2H), 2.79-3.13(m, 8H), 2.21(d, 1H), and 1.88-1.99(m, 1H). LCMS: (AA) ES$^+$ 431.1, ES$^-$ 429.0. |
| I-32 | $^1$H NMR(400MHz, CD$_3$OD): δ 8.68(d, 1H), 8.60(s, 1H), 8.36(s, 1H), 8.21(d, 2H), 8.17-8.07(m, 2H), 7.98(s, 1H), 7.94(s, 1H), 7.70(d, 1H), 7.57-7.51(m, 2H), 4.30(s, 2H), and 2.95(s, 3H). LCMS: (FA) ES$^+$ 481.0. |
| I-35 | $^1$H NMR(300MHz, d$_6$-DMSO) δ: 11.31(s, 1H), 10.76(s, 1H), 9.57(s, 1H), 8.8(d, 1H), 8.74(s, 1H), 8.62(d, 1H), 8.5(d, 1H), 8.35-8.31(m, 1H), 8.12(d, 1H), 7.94(d, |

-continued

| | |
|---|---|
| | 1H), 7.78-7.73(m, 2H), 7.57-7.54(m, 1H), and 3.99(s, 4H). LCMS: (FA) ES+ 512.1, ES− 510.1. |
| I-299 | $^1$H NMR(400MHz, CD$_3$OD, HCl Salt) δ: 9.83(s, 2H), 8.87(d, 2H), 8.59(d, 1H), 8.51(d, 1H), 8.24(dd, 1H), 7.87(t, 1H), 7.74(d, 2H), 7.67(dd, 1H), 7.31(t, 1H), and 7.25(td, 1H). LCMS: (FA) ES+ 398.8, ES− 396.6. |
| I-351 | $^1$H NMR(300MHz, CD$_3$OD, HCl Salt) δ: 9.95(s, 1H), 9.87(s, 1H), 8.85(d, 2H), 8.60(d, 1H), 8.53(s, 1H), 8.25(d, 1H), 7.86(d, 2H), 7.72(d, 2H), 7.11(s, 1H), 4.47(s, 2H), 3.74(s, 4H), 3.30(m, 2H), and 2.12(m, 4H). LCMS: (FA) ES+ 523.7, ES− 521.7. |
| I-64 | $^1$H NMR(400MHz, d$_6$-DMSO, bis HCl salt) δ: 11.60(br s, 1H), 10.17(s, 1H), 8.97-9.03(m, 1H), 8.52(d, 1H), 8.50(d, 1H), 7.58(d, 1H), 7.44(dm, 1H), 7.18-7.26(m, 4H), 7.00-7.02(m, 1H), 6.94-6.99(m, 1H), 4.37-4.47(m, 2H), 3.48-3.67(m, 5H), 3.01-3.13(m, 2H), 2.83-2.97(m, 4H), 2.79(d, 3H), 2.07-2.18(m, 1H), 1.87-2.04(m, 4H), and 1.68-1.83(m, 1H). LCMS: (FA) ES+ 583.9, ES− 581.8. |
| I-290 | $^1$H NMR(400MHz, CD$_3$OD; CHOOH salt) δ: 9.34(s, 1H), 8.87(d, 1H), 8.64(d, 1H), 8.48(s, 1H), 8.23(d, 1H), 7.86(d, 1H), 7.79(dd, 1H), 7.72(dd, 1H), 7.67(dd, 1H), 7.60(d, 1H), 7.27-7.37(m, 2H), 7.21-7.25(m, 1H), 3.96(s, 4H), and 1.34(s, 9H). LCMS: (FA) ES+ 466.1, ES− 464.1. |
| I-340 | $^1$H NMR(300MHz, CD$_3$OD; HCl salt) δ: 8.58(d, 1H), 8.51(s, 1H), 8.02-8.16(m, 3H), 7.84(d, 1H), 7.81(s, 1H), 7.59(dd, 1H), 7.55(d, 1H), 7.46(dd, 1H), 7.32(dd, 1H), 7.20-7.26(m, 2H), and 1.37(s, 9H). LCMS: (FA) ES+ 422.0, ES− 420.1. |
| I-448 | LCMS: (FA) ES$^+$ 422.1. |
| I-451 | $^1$H NMR(400MHz, d$_6$-DMSO, HCl salt) δ: 10.85(br s, 1H), 10.72(s, 1H), 8.80-8.86(m, 1H), 8.51(d, 1H), 8.22-8.27(m, 1H), 8.07(d, 1H), 7.92-7.97(m, 1H), 7.39-7.42(m, 1H), 7.24(d, 1H), 7.16-7.20(m, 1H), 6.95-7.04(m, 2H), 4.42-4.47(m, 2H), 3.39-3.47(m, 2H), 2.75-3.13(m, 10H), and 1.72-2.17(m, 6H). LCMS: (FA) ES+ 553.2, ES− 551.2. |
| I-452 | $^1$H NMR(400MHz, d$_6$-DMSO, HCl salt) δ: 10.60(br s, 1H), 8.77-8.85(m, 1H), 8.50(d, 1H), 8.17(s, 1H), 7.87-7.92(m, 1H), 7.36-7.39(m, 1H), 7.24(d, 1H), 7.16-7.19(m, 1H), 6.95-7.04(m, 2H), 4.94-5.43(m, 5H), 3.40-3.56(m, 2H), 3.05-3.32(m, 3H), 2.66-2.99(m, 11H), 2.08-2.16(m, 1H), and 1.74-1.87(m, 1H). LCMS: (FA) ES+ 582.2, ES− 580.3. |
| I-424 | $^1$H NMR(400MHz, CD$_3$OD, HCl salt) δ: 8.63(d, 1H), 8.25(s, 1H), 7.93-8.04(m, 2H), 7.64(s, 1H), 7.16-7.30(m, 2H), 6.90-7.02(m, 2H), 4.42(br s, 2H), 4.12(s, 4H), 3.39-3.79(m, 8H), 2.82-3.11(m, 8H), 2.16-2.27(m, 1H), and 1.86-2.01(m, 1H). LCMS: (FA) ES+ 593.4. |
| I-427 | $^1$H NMR(400MHz, CD$_3$OD, HCl salt) δ: 8.62(d, 1H), 8.24-8.27(m, 1H), 7.97-8.02(m, 1H), 7.81(d, 1H), 7.62-7.66(m, 1H), 7.25(d, 1H), 7.17-7.21(m, 1H), 6.91-6.98(m, 2H), 4.54(s, 2H), 4.11(s, 4H), 3.56-3.65(m, 2H), 3.22-3.29(m, 2H), 2.85-3.14(m, 5H), 2.15-2.26(m, 3H), and 1.89-2.11(m, 3H). LCMS: (FA) ES+ 564.2, ES− 562.3. |

Example 3

Separation of enantiomers of I-36 (I-17 and I-34)

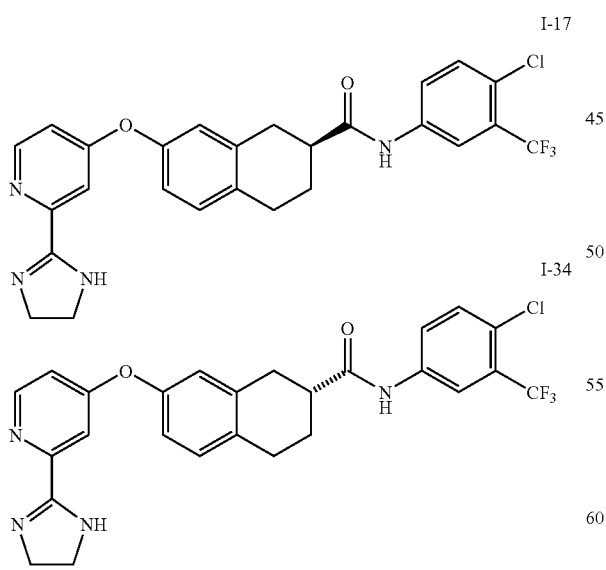

N-[4-chloro-3-(trifluoromethyl)phenyl]-7-{[2-(4,5-dihydro-1H-imidazol-2-yl)-yridine-4-yl]oxy}-1,2,3,4-tetrahydronaphthalene-2-carboxamide hydrochloride salt (I-36) (30 mg) was treated with saturated NaHCO$_3$ solution and extracted into EtOAc (3×). The combined organic solutions were dried over Na$_2$SO$_4$, filtered and evaporated. The enantiomers were separated by chiral HPLC (4.5×250 mm, 10 μm Chiralcel OD). Each enantiomer was dissolved in MeOH and 2.0M HCl-Et$_2$O was added. The solvents were evaporated to yield each of the single enantiomers I-17 and I-34.

The following single enantiomers were obtained from the appropriate starting materials in a method analogous to that of Example 3:

I-40 and I-38, I-313 and I-244, I-180 and I-201, I-386 and I-270, I-220 and I-323, I-311 and I-185.

Example 4

Preparation of 7-{[2-(acetylamino)pyridin-4-yl]oxy}-N-[4-chloro-3-(trifluoromethyl)phenyl]-2-naphthamide (I-88)

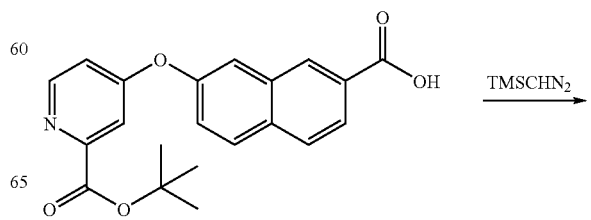

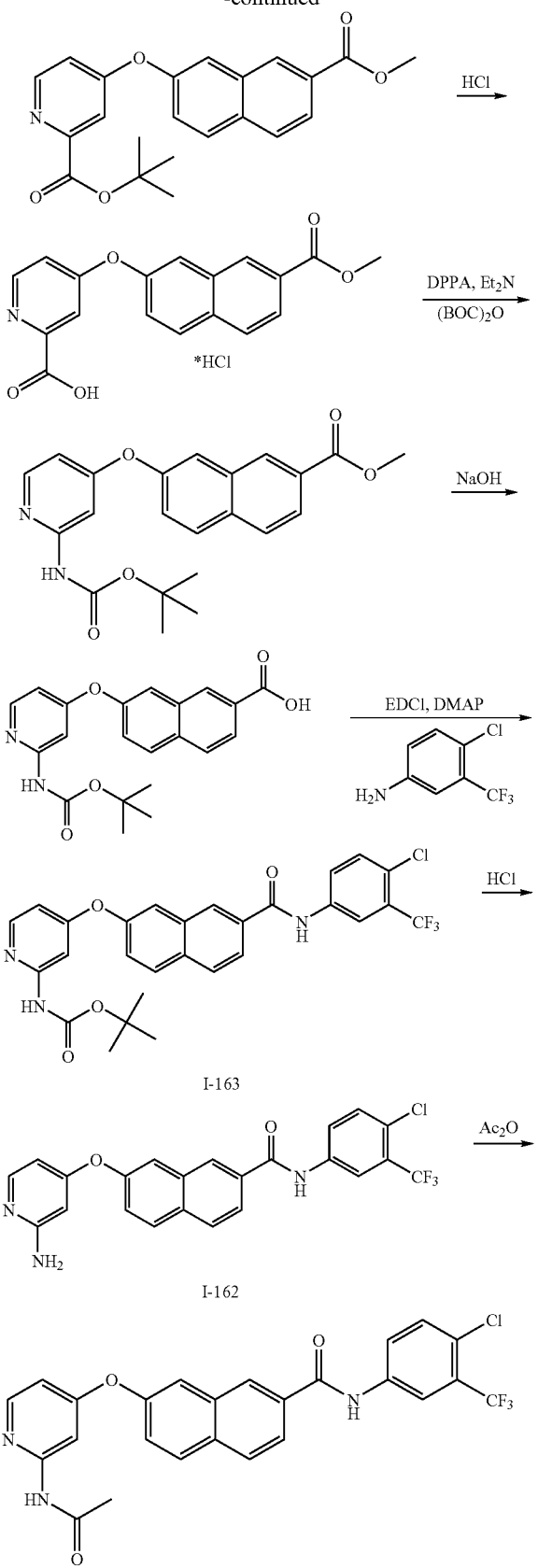

Step 1 tert-Butyl 4-{[7-(methoxycarbonyl)-2-naphthyl]oxy}pyridine-2-carboxylate To a solution of 7-{[2-(tert-butoxycarbonyl)pyridin-4-yl]oxy}-2-naphthoic acid (5.25 g, 14.3 mmol) in MeOH (50 mL) and toluene (50 mL), was added a solution of 2.0M trimethylsilyldiazomethane in hexane (14.3 mL, 28.7 mmol) dropwise. The reaction was allowed to stir for 5 h, after which time 2.0M trimethylsilyldiazomethane in hexane (7.17 mL, 14.3 mmol) was added. Stirring continued for an additional 1 h. The solvents were evaporated and the residue was dissolved in EtOAc and washed with saturated NaHCO₃ and brine. The organic solution was dried (Na₂SO₄), filtered and evaporated. The residue was purified by column chromatography to give tert-butyl 4-{[7-(methoxycarbonyl)-2-naphthyl]oxy}pyridine-2-carboxylate as an off-white solid (3.18 g, 58.4%). LCMS: (FA) ES⁺ 380.2.

Step 2 4-{[7-(Methoxycarbonyl)-2-naphthyl]oxy}pyridine-2-carboxylic acid

To tert-butyl 4-{[7-(methoxycarbonyl)-2-naphthyl]oxy}pyridine-2-carboxylate (2.98 g, 7.9 mmol) was added 4.0 M solution of HCl in dioxane (20 mL). The mixture was allowed to stir under nitrogen overnight. The solvents were evaporated to yield the title compound as the HCl salt (2.69 g, 95.2%). LCMS: (FA) ES⁺ 324.1.

Step 3 Methyl 7-({2-[(tert-butoxycarbonyl)amino]yridine-4-yl}oxy)-2-naphthoate To a suspension of 4-{[7-(methoxycarbonyl)-2-naphthyl]oxy}pyridine-2-carboxylic acid hydrochloride salt (2.49 g, 6.9 mmol) in THF (60.0 mL), was added TEA (3.47 mL, 24.9 mmol). The mixture was cooled to 0° C. and diphenylphosphonic azide (1.94 mL, 9.0 mmol) was added dropwise. The reaction mixture was allowed to stir at 0° C. for 15 min, then warmed to rt and allowed to stir for 2 h. The solvents were evaporated and the residue was taken up in EtOAc and washed with saturated NaHCO₃ solution and brine. The organic solution was dried (Na₂SO₄), filtered and evaporated. The residue was dissolved in 2-methylpropan-2-ol (30 mL) and heated at 85° C. for 1 h under nitrogen. The reaction mixture was cooled to rt and the precipitate was filtered and washed with MeOH to give methyl 7-({2-[(tert-butoxycarbonyl)amino]yridine-4-yl}oxy)-2-naphthoate as a white solid (1.95 g, 71.4%). LCMS: (FA) ES⁺ 395.2.

Step 4 7-({2-[(tert-Butoxycarbonyl)amino]pyridine-4-yl}oxy)-2-naphthoic acid To a solution of methyl 7-({2-[(tert-butoxycarbonyl)amino]pyridine-4-yl}oxy)-2-naphthoate (1.95 g, 4.9 mmol) in MeOH (100 mL), and THF (50 mL), was added 1N NaOH (19.8 mL, 19.8 mmol). The reaction mixture was heated at 70° C. for 4 h. The reaction mixture was cooled to rt and concentrated to remove the volatile solvents. The aqueous slurry was diluted with water (approx 400 mL) and acidified to pH 3 with 1N HCl solution. A precipitate formed and was filtered, washed with water and hexane and dried under vacuum to give 7-({2-[(tert-butoxycarbonyl)amino]yridine-4-yl}oxy)-2-naphthoic acid as a white solid (1.42 g, 91.4%). LCMS: (FA) ES⁺ 381.1, ES⁻ 379.1.

Step 5 tert-Butyl (4-{[7-({[4-chloro-3-(trifluoromethyl)phenyl]amino}carbonyl)-2-naphthyl]oxy}pyridin-2-yl)carbamate (I-163)

To a solution of 7-({2-[(tert-butoxycarbonyl)amino]pyridin-4-yl}oxy)-2-naphthoic acid (350 mg, 0.92 mmol) in DCM (9.0 mL), was added 4-chloro-3-(trifluoromethyl) aniline (198.0 mg, 1.0 mmol); EDCl (194 mg, 1.0 mmol) and DMAP (124 mg, 1.0 mmol). The mixture was allowed to stir for 18 h then diluted with EtOAc and washed with water and then brine. The organic phase was dried (Na$_2$SO$_4$) and evaporated, and the residue was triturated with DCM/EtOAc/MeOH to yield the title compound as a white solid (420 mg, 81.8%). LCMS: (FA) ES$^+$ 558.1, ES$^-$ 556.1.

Step 6 7-[(2-aminopyridin-4-yl)oxy]-N-[4-chloro-3-(trifluoromethyl)phenyl]-2-naphthamide (I-162)

A solution of tert-butyl (4-{[7-({[4-chloro-3-(trifluoromethyl)phenyl]-amino}carbonyl)-2-naphthyl]oxy}yridine-2-yl)carbamate (I-163) (420 mg, 0.75 mmol) in 4.0 M HCl in dioxane (10.0 mL) was allowed to stir under nitrogen for 18 h. The solvents were evaporated to yield (I-162) as the hydrochloride salt (389 mg, quant). LCMS: (FA) ES$^+$ 458.03, ES$^-$ 455.94.

Step 7: 7-{[2-(acetylamino)pyridin-4-yl]oxy}-N-[4-chloro-3-(trifluoromethyl)phenyl]-2-naphthamide (I-88)

To a solution of 7-[(2-aminopyridin-4-yl)oxy]-N-[4-chloro-3-(trifluoromethyl)-phenyl]-2-naphthamide hydrochloride (I-162) (200 mg, 0.40 mmol) in pyridine (4 mL), was added acetic anhydride (76.4 μL, 0.81 mmol). The mixture was allowed to stir for 16 h. Catalytic DMAP and acetic anhydride (76.4 μL, 0.81 mmol) were added and stirring continued for 3 h. Acetic anhydride (76.4 μL, 0.81 mmol) was added and stirring continued for an additional 72 h. Water was added and a precipitate formed, which was filtered and washed with water and hexane. The solid was purified by column chromatography. The product was dissolved in DCM and MeOH and 2M HCl in Et$_2$O was added. The solvents were evaporated to yield I-88 as the hydrochloride salt (113 mg, 52.1%). $^1$H NMR (300 MHz, d$_6$-DMSO): δ 11.1 (s, 1H), 10.92 (s, 2H), 8.62 (s, 1H), 8.42 (d, 1H), 8.27 (d, 1H), 8.20-8.16 (m, 3H), 8.05 (dd, 1H), 7.92 (d, 1H), 7.74 (d, 1H), 7.54 (dd, 1H), 7.43 (s, 1H), 6.95 (dd, 1H), and 2.07 (s, 3H). LCMS: (FA) ES$^+$ 500.2, ES$^-$ 498.1.

Compounds in the following table were prepared from the appropriate starting materials in a method analogous to that of Example 4:

Example 5

Preparation of 7-{[2-(acetylamino)pyridin-4-yl]oxy}-N-[4-(aminomethyl)-3-(trifluoromethyl)phenyl]-2-naphthamide (I-151)

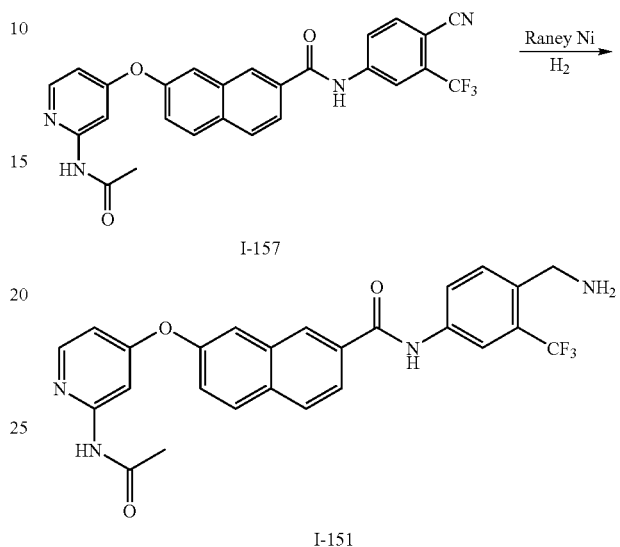

A slurry of 7-{[2-(acetylamino)pyridin-4-yl]oxy}-N-[4-cyano-3-(trifluoromethyl)-phenyl]-2-naphthamide (I-157) (163 mg, 0.33 mmol) and Raney Nickel (2800 slurry in water, 50% v/v, approx 8 mg) in THF (5 mL) and 7.0 M ammonia in MeOH (5 mL), was allowed to stir under an atmosphere of hydrogen for 18 h. After this time, additional Raney Nickel was added and hydrogenation continued for a further 18 h. The reaction mixture was filtered through Celite and washed with THF and MeOH. The filtrate was concentrated and purified by column chromatography. The product was dissolved in MeOH and 2M HCl in Et$_2$O was added. The solvents were evaporated to give 7-{[2-(acetylamino)pyridin-4-yl]oxy}-N-[4-(aminomethyl)-3-(trifluoromethyl)phenyl]-2-naphthamide (I-151) as an off-white solid (45 mg, 23%). $^1$H NMR I-160  $^1$H NMR(300MHz, d$_6$-DMSO) δ: 12.13(s, 1H), 11.04(s, 1H), 8.64(s, 1H), 8.27(d, 1H), 8.19-8.14(m, 2H), 8.05(dd, 1H), 7.90(d, 1H), 7.55(dd, 1H), 7.46(s, 1H), 6.93(dd, 1H), 6.47(s, 1H), 2.06(s, 3H), and 1.29(s, 9H). LCMS: (FA) ES$^+$ 445.6,, ES$^-$ 443.2.
I-159  LCMS: (FA) ES$^+$ 549.1.
I-158  LCMS: (FA) ES$^+$ 449.1, ES$^-$ 447.0.
I-157  LCMS: (FA) ES$^+$ 491.2, ES$^-$ 489.2.
I-235  LCMS: (FA) ES$^+$ 416.3, ES$^-$ 414.3.
I-140  $^1$H NMR(400MHz, d$_6$-DMSO, HCl salt) δ: 13.09(br s, 1H), 10.42(s, 1H), 8.61(s, 1H), 8.23(d, 1H), 8.17(d, 1H), 8.07-8.10(m, 1H), 8.01(d, 1H), 7.98(d, 1H), 7.81(t, 1H), 7.71-7.75(m, 2H), 7.55-7.58(m, 1H), 7.29(t, 1H), 7.14-7.17(m, 1H), 6.73-6.76(m, 1H), 6.12(d, 1H), and 1.29(s, 9H). LCMS: (FA) ES+ 412.1(M+1), ES– 410.1.
I-142  $^1$H NMR(400MHz, d$_6$-DMSO, HCl salt) δ: 13.36(br s, 1H), 10.89(s, 1H), 10.71(br s, 1H), 8.68(s, 1H), 8.24(d, 1H), 8.19(d, 1H), 8.09-8.11(m, 1H), 7.99-8.01(m, 2H), 7.90-7.94(m, 2H), 7.81(br s, 2H), 7.58-7.60(m, 1H), 7.10(s, 1H), 6.72-6.75(m, 1H), 6.15(d, 1H), 4.44(t, 2H), 3.58-3.63(m, 2H), 3.43-3.51(m, 2H), 3.08-3.16(m, 2H), 1.97-2.04(m, 2H), and 1.84-1.93(m, 2H). LCMS: (FA) ES+ 537.2.
I-139  $^1$H NMR(400MHz, d$_6$-DMSO, HCl salt) δ: 13.31(br s, 1H), 12.18(s, 1H), 8.68(s, 1H), 8.23(d, 1H), 8.18(d, 1H), 8.08-8.10(m, 1H), 8.01(d, 1H), 7.99(d, 1H), 7.79(br s, 2H), 7.58-7.61(m, 1H), 6.73-6.75(m, 1H), 6.47(s, 1H), 6.13(d, 1H), and 1.29(s, 9H). LCMS: (FA) ES+ 403.1, ES– 401.1.

(400 MHz, d$_6$-DMSO): δ 11.27 (s, 1H), 10.97 (s, 1H), 8.67 (s, 1H), 8.63 (br.s, 2H), 8.36 (d, 1H), 8.28 (d, 1H), 8.24-8.16 (m, 3H), 8.09-8.06 (m, 1H), 7.93 (d, 1H), 7.55 (dd, 1H), 7.45 (d, 1H), 6.96 (dd, 1H), 4.15-4.11 (m, 2H), and 2.08 (s, 3H). LCMS: (FA) ES$^+$ 495.4.

Compounds in the following table were prepared from the appropriate starting materials in a method analogous to that of Example 5:

| | |
|---|---|
| I-28 | $^1$H NMR(300MHz, d$_6$-DMSO) δ: 10.73(s, 1H), 8.87-8.85(s, 1H), 8.51(d, 1H), 8.21(s, 1H), 7.95-7.92(m, 1H), 7.72(d, 1H), 7.44(s, 1H), 7.25-7.23(m, 1H), 7.18-7.16(m, 1H), 7.02-6.95(m, 2H), 4.10-4.07(m, 2H), 2.97-2.82(m, 5H), 2.78(d, 3H), 2.17-2.11(m, 1H), and 1.84-1.72(m, 1H). LCMS: (FA) ES$^+$ 499.4, ES$^-$ 497.4. |
| I-331 | $^1$H NMR(400MHz, CD$_3$OD, HCl Salt) δ: 8.70(d, 1H), 7.64(t, 1H), 7.51(d, 1H), 7.43-7.39(m, 2H), 7.30(d, 1H), 7.23(t, 1H), 7.16-7.14(m, 1H), 7.05-6.99(m, 2H), 4.46(s, 2H), 3.15-2.82(m, 5H), 2.23-2.18(m, 1H), 2.01-1.91(m, 1H), and 1.31(s, 9H). LCMS: (FA) ES+ 431.1, ES− 430.4. |
| I-397 | $^1$H NMR(400MHz, CD3OD; 2×HCl salt) δ: 8.75(d, 1H), 8.56(s, 1H), 8.17(d, 1H), 8.10(d, 1H), 8.06(dd, 1H), 7.96(d, 1H), 7.80(dd, 1H), 7.63(m, 1H), 7.59(dd, 1H), 7.48-7.54(m, 2H), 7.29(dd, 1H), 7.21(dd, 1H), 4.49(d, 2H), and 1.34(s, 9H). LCMS: (FA) ES+ 426.1, ES− 424.1. |

Example 6

Preparation of N-[4-Chloro-3-(trifluoromethyl)phenyl]-6-{[2-(4,5-dihydro-1H-imidazol-2-yl)pyridin-4-yl]oxy}-2-methyl-1,2,3,4-tetrahydroisoquinoline-3-carboxamide (I-11)

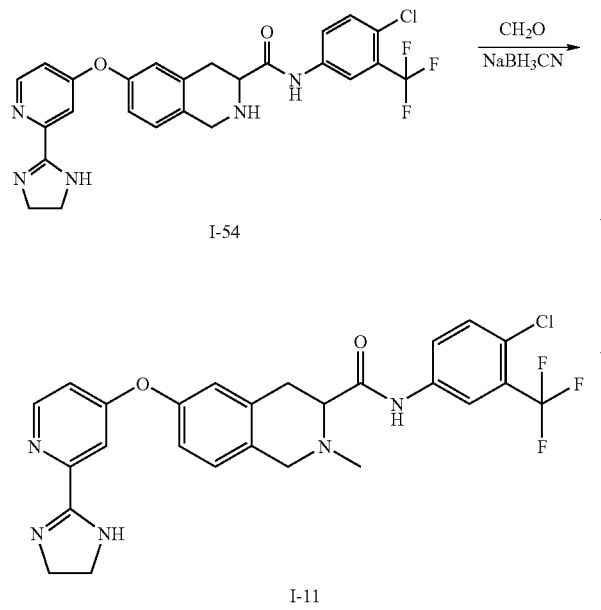

To a solution of N-[4-chloro-3-(trifluoromethyl)phenyl]-6-{[2-(4,5-dihydro-1H-imidazol-2-yl)pyridin-4-yl]oxy}-1,2,3,4-tetrahydroisoquinoline-3-carboxamide (I-54) (70.0 mg, 0.11 mmol), in acetonitrile (1.0 mL), was added formaldehyde (37% solution in water, 42 µL, 0.56 mmol) and sodium cyanoborohydride (28.8 mg, 0.46 mmol). A few drops of MeOH were added and the reaction was allowed to stir for 1 h. Saturated NaHCO$_3$ solution was added and the mixture was extracted with EtOAc (2×). The combined organic solutions were washed with brine, dried (Na$_2$SO$_4$), filtered and evaporated. The residue was purified by column chromatography and then further purified by HPLC (250 mm C18 column) eluting with acetonitrile containing 30% to 100% 10 mM ammonium acetate in water (20 min gradient), to give N-[4-chloro-3-(trifluoromethyl)phenyl]-6-{[2-(4,5-dihydro-1H-imidazol-2-yl)pyridin-4-yl]-oxy}-2-methyl-1,2,3,4-tetrahydroisoquinoline-3-carboxamide (I-11) as the diacetate salt (12 mg, 17%). $^1$H NMR (300 MHz, CD$_3$OD): δ 8.58 (d, 1H), 8.17 (d, 1H), 7.85-7.81 (m, 1H), 7.62 (d, 1H), 7.55 (d, 1H), 7.26 (d, 1H), 7.16-7.13 (m, 1H), 6.99-6.97 (m, 2H), 4.07 (d, 1H), 4.04 (s, 4H), 3.71 (d, 1H), 3.46-3.41 (m, 1H), 3.24-3.06 (m, 2H), 2.53 (s, 3H), and 1.91 (s, 6H). LCMS: (FA) ES$^+$ 530.3, ES$^-$ 528.2.

Example 7

Preparation of 4-{[7-({[3-amino-5-(trifluoromethyl)phenyl]amino}carbonyl)-2-naphthyl]oxy}-N-methylpyridine-2-carboxamide (I-55)

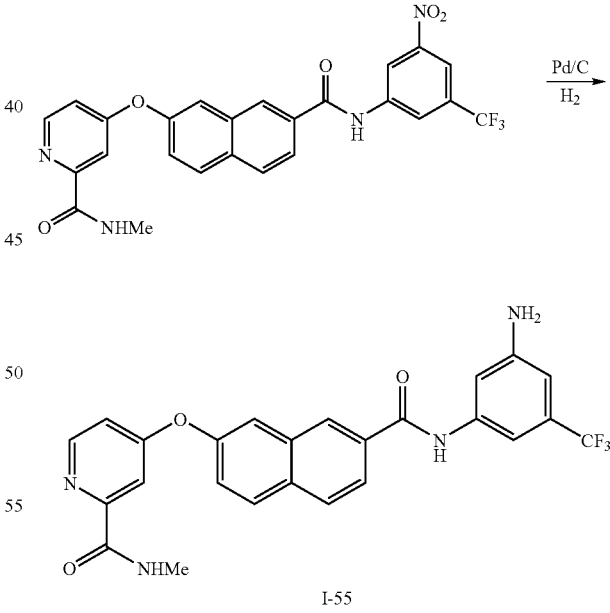

To a solution of N-methyl-4-{[7-({[3-nitro-5-(trifluoromethyl)phenyl]-amino}carbonyl)-2-naphthyl]oxy}pyridine-2-carboxamide (0.195 g, 0.382 mmol) in MeOH (10 mL) was added palladium (10% on carbon, 0.045 g). The reaction mixture was allowed to stir under an atmosphere of hydrogen at rt for 17 h. The reaction mixture was filtered over a pad of Celite and washed with MeOH. The filtrate was evaporated and the residue was purified by column chromatography, then further purified by HPLC eluting with 85% (95% water/5% FA):15% (99% AcCN:1% FA) to 20% (95% water/5% FA): 15% (99% AcCN:1% FA) (20 min gradient), to give 4-{[7-({[3-amino-5-(trifluoromethyl)phenyl]amino}carbonyl)-2-naphthyl]oxy}-N-methylpyridine-2-carboxamide (I-55) as the formate salt (34 mg, 19%). $^1$H NMR (400 MHz, $d_6$-DMSO): δ 10.11 (s, 1H), 8.83-8.79 (m, 1H), 8.56 (d, 1H), 8.53 (s, 1H), 8.18 (d, 1H), 8.14 (d, 1H), 8.00 (d, 1H), 7.91 (d, 1H), 7.55-7.52 (m, 1H), 7.45 (d, 1H), 7.38 (s, 1H), 7.28-7.26 (m, 2H), 6.50 (s, 1H), 5.66 (s, 2H), and 2.77 (d, 3H). LCMS: (FA) ES$^+$ 481.0. The HCl salt of the desired product was made by dissolving the residue in ETOH and adding 2M HCl in Et$_2$O and concentrating to give a white solid. $^1$H NMR (400 MHz, $d_6$-DMSO) δ: 10.86 (br s, 1H), 10.41 (br s, 1H), 8.87-8.82 (m, 1H), 8.62 (br s, 1H), 8.57 (d, 1H), 8.23-8.14 (m, 2H), 8.07-8.03 (m, 1H), 7.95-7.91 (m, 1H), 7.87 (br s, 1H), 7.58-7.54 (m, 1H), 7.49-7.46 (m, 1H), 7.31-7.28 (m, 1H), 7.09 (br s, 1H), 4.47-4.41 (m, 2H), 3.57-3.52 (m, 2H), 2.87-2.83 (m, 6H), and 2.79-2.77 (m, 3H). LCMS: (FA) ES$^+$ 553.2, ES$^-$ 551.4.

Compounds in the following table were prepared from the appropriate starting materials in a method analogous to that of Example 7:

| I-22 | $^1$H(300MHz, $d_6$-DMSO) δ: 10.3(s, 1H), 8.83-8.81(m, 1H), 8.50(d, 1H), 7.45-7.39(m, 3H), 7.23(d, 1H), 7.16(dd, 1H), 7.02-6.94(m, 2H), 6.81-6.78(m, 1H), 2.95-2.76(m, 8H), 2.14-2.05(m, 1H), and 1.86-1.75(m, 1H). LCMS: (FA) ES$^+$ 485.3, ES$^-$ 483.3 |
|---|---|

Example 8

Preparation of 4-{[7-({[3-(2-Aminoethyl)-5-(trifluoromethyl)phenyl]-amino}carbonyl)-5,6,7,8-tetrahydronaphthalen-2-yl]oxy}-N-methylpyridine-2-carboxamide (I-47)

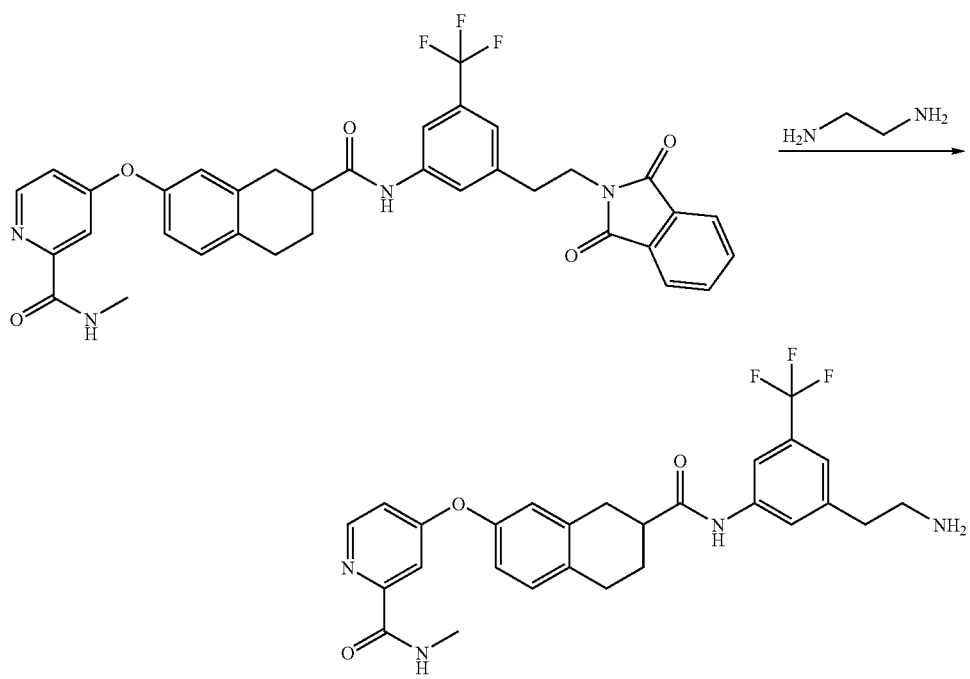

I-47

A solution of 4-{[7-({[3-[2-(1,3-dihydro-2H-isoindol-2-yl)ethyl]-5-(trifluoromethyl)phenyl]amino}carbonyl)-5,6,7,8-tetrahydronaphthalen-2-yl]oxy}-N-methylpyridine-2-carboxamide (0.158 g, 0.25 mmol) and ethane-1,2-diamine (2 mL) was allowed to stir at rt overnight. The reaction mixture was diluted with EtOAc and water. The solution was extracted with EtOAc. The combined organic solutions were washed with brine and concentrated to give a white solid. The residue was purified by column chromatography to give 4-{[7-({[3-(2-aminoethyl)-5-(trifluoromethyl)phenyl]-amino}carbonyl)-5,6,7,8-tetrahydronaphthalen-2-yl]oxy}-N-methylpyridine-2-carboxamide (I-47, 137 mg, 29%) as the formate salt. $^1$H NMR (300 MHz, CD$_3$OD): δ 8.44 (d, 1H), 8.42 (s, 1H), 7.91 (s, 1H), 7.78 (s, 1H), 7.51 (s, 1H), 7.34 (s, 1H), 7.24-7.21 (m, 1H), 7.07-7.04 (m, 1H), 6.92-6.89 (m, 1H), 3.24-3.19 (m, 2H), 3.10-2.78 (m, 9H), 2.56-2.13 (m, 1H), and 2.03-1.84 (m, 2H).

Example 9
Preparation of N-(3tert-Butylphenyl)-7-[(2-{5-[(4-methylpiperazin-1-yl)methyl]-1H-imidazol-2-yl}pyridin-4-yl)oxy]-1,2,3,4-tetrahydronaphthalene-2-carboxamide (I-156)
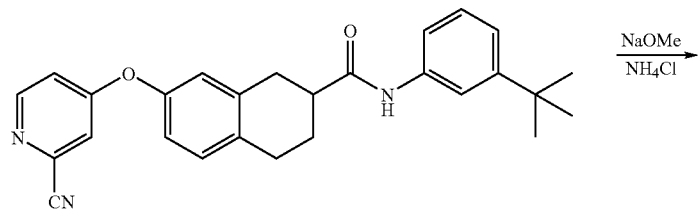
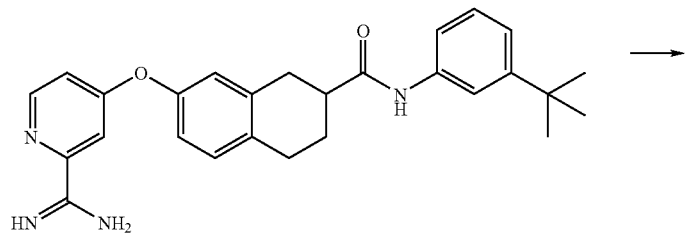
I-422
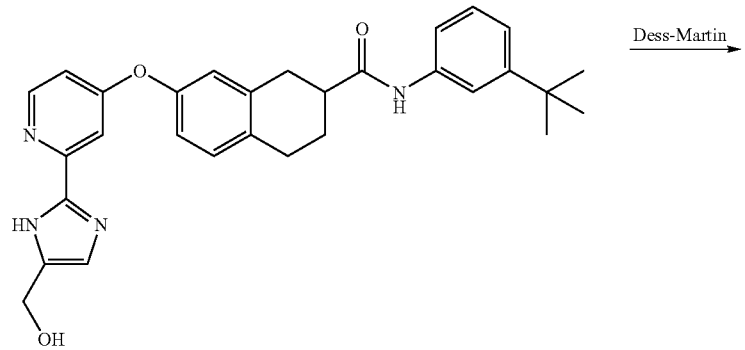
I-3
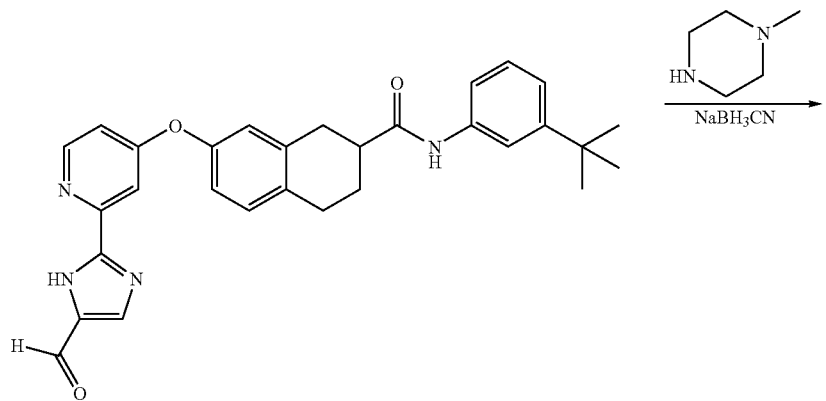

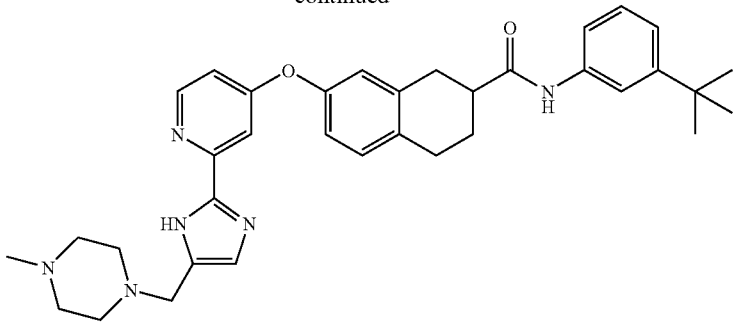

I-156

Step 1: 7-({2-[Amino(imino)methyl]pyridin-4-yl}oxy)-N-(3tert-butylphenyl)-1,2,3,4-tetrahydronaphthalene-2-carboxamide I-422

To a solution of N-(3-tert-butylphenyl)-7-[(2-cyanopyridin-4-yl)oxy]-1,2,3,4-tetrahydronaphthalene-2-carboxamide (1.5 g, 3.5 mmol) in MeOH (20 mL) was added sodium methoxide (28 mg, 0.52 mmol). The solution was allowed to stir at rt for 3 days and then ammonium chloride (0.28 g, 5.3 mmol) was added. The reaction mixture was allowed to stir overnight and then concentrated to give 7-({2-[amino(imino)methyl]pyridin-4-yl}oxy)-N-(3-tert-butylphenyl)-1,2,3,4-tetrahydronaphthalene-2-carboxamide I-422 as a white solid, which was directly used into the next step. LCMS: (FA) ES$^+$ 443.3.

Step 2: N-(3-tert-Butylphenyl)-7-({2-[4(hydroxymethyl)-1H-imidazol-2-yl]pyridin-4-yl}-oxy)-1,2,3,4-tetrahydronaphthalene-2-carboxamide (I-3)

A solution of 7-({2-[amino(imino)methyl]pyridin-4-yl}oxy)-N-(3-tert-butylphenyl)-1,2,3,4-tetrahydronaphthalene-2-carboxamide (208 mg, 0.470 mmol), 1,3-dihydroxyacetone dimer (250 mg, 1.4 mmol) and ammonium chloride (151 mg, 2.82 mmol) in ammonium hydroxide (4 mL) in 7M ammonia in MeOH (4 mL) was subjected to MWI at 120° C. for 5 min. The reaction mixture was poured into ice-water and extracted with DCM (10 mL×3). The combined organic solutions were washed with brine and dried over Na$_2$SO$_4$. The crude product was purified by reverse phase HPLC [20% water with acetonitrile (contained 0.1% FA) to 100% acetonitrile (contained 0.1% FA) over 25 mins]. The residue was dissolved in MeOH and 1N HCl in Et$_2$O was added. Concentration gave N-(3-tert-Butylphenyl)-7-({2-[4-(hydroxymethyl)-1H-imidazol-2-yl]pyridin-4-yl}oxy)-1,2,3,4-tetrahydronaphthalene-2-carboxamide (I-3) as a white solid. $^1$H NMR (400 MHz, CD$_3$OD): δ 8.64 (d, 1H), 7.67 (m, 1H), 7.55 (s, 1H), 7.43 (dd, 1H), 7.26 (d, 1H), 7.22 (d, 1H), 7.15 (m, 2H), 6.95 (m, 2H), 4.70 (s, 2H), 3.11-2.87 (m, 5H), 2.22 (m, 1H), 1.96 (m, 1H), and 1.31 (s, 9H). LCMS: (FA) ES$^+$ 497.3.

Step 3: N-(3-tert-butylphenyl)-7-{[2-(4-formyl-1H-imidazol-2-yl)pyridin-4-yl]oxy}-1,2,3,4-tetrahydronaphthalene-2-carboxamide To a suspension of N-(3-tert-butylphenyl)-7-({2-[4-(hydroxymethyl)-1H-imidazol-2-yl]pyridin-4-yl}oxy)-1,2,3,4-tetrahydronaphthalene-2-carboxamide (I-3) (1.24 g, 2.50 mmol) in DCM (10 mL) was added Dess-Martin periodinane (1.27 g, 3.00 mmol) at rt. The resulting suspension was allowed to stir at rt for 30 min, and then aqueous NaHCO$_3$/Na$_2$SO$_3$ solution (1:1) was added and the mixture was extracted with DCM (30 mL×3). The combined organic solutions were washed with brine, dried over Na$_2$SO$_4$, filtered and concentrated to give N-(3-tert-butylphenyl)-7-{[2-(4-formyl-1H-imidazol-2-yl)pyridin-4-yl]oxy}-1,2,3,4-tetrahydronaphthalene-2-carboxamide as a yellow foam which was used without further purification. LCMS: (FA) ES$^+$ 495.5.

Step 4: N-(3-tert-Butylphenyl)-7-[(2-{5-[(4-methylpiperazin-1-yl)methyl]-1H-imidazol-2-yl}pyridin-4-yl)oxy]-1,2,3,4-tetrahydronaphthalene-2-carboxamide (I-156)

To a solution of N-(3-tert-butylphenyl)-7-{[2-(4-formyl-1H-imidazol-2-yl)pyridin-4-yl]oxy}-1,2,3,4-tetrahydronaphthalene-2-carboxamide (156 mg, 0.315 mmol) in MeOH (3 mL) was added 1-methyl-piperazine (150 μL, 1.3 mmol) at rt. The reaction mixture was allowed to stir for 2 h, and then sodium cyanoborohydride (70 mg, 1.0 mmol) was added. The reaction mixture was allowed to stir overnight. DCM (10 mL) was added and the mixture was washed with brine. The organic solution was concentrated and the residue was purified by reverse phase HPLC [50% water with acetonitrile (contained 0.1% FA) to 100% acetonitrile (contained 0.1% FA) over 25 min]. The resulting solid was dissolved in MeOH. 1M HCl in Et$_2$O was added and the solution was concentrated to give the HCl salt of N-(3-tert-butylphenyl)-7-[(2-{5-[(4-methylpiperazin-1-yl)methyl]-1H-imidazol-2-yl}pyridin-4-yl)oxy]-1,2,3,4-tetrahydronaphthalene-2-carboxamide (I-156) as a white solid. $^1$H NMR (400 MHz, CD$_3$OD): δ 8.67 (d, 1H), 7.85 (d, 1H), 7.83 (s, 1H), 7.67 (m, 1H), 7.44 (dd, 1H), 7.39 (dd, 1H), 7.31 (d, 1H), 7.23 (t, 1H), 7.15 (d, 1H), 7.08 (s, 1H), 7.05 (d, 1H), 4.64 (s, 2H), 3.96 (m, 2H), 3.85 (m, 4H), 3.69 (m, 2H), 3.02-2.85 (m, 5H), 2.98 (s, 3H), 2.20 (m, 1H), 1.96 (m, 1H), and 1.31 (s, 9H). LCMS: (FA) ES$^+$ 579.3.

Compounds in the following table were prepared from the appropriate starting materials in a method analogous to that of Example 9:

| | |
|---|---|
| I-153 | ¹H NMR(400MHz, MeOD): δ 8.68(d, 1H), 8.53(s, 1H), 8.13(d, 1H), 8.07(d, 1H), 8.03(d, 1H), 7.85(s, 1H), 7.81(s, 1H), 7.75(d, 1H), 7.60(d, 1H), 7.53(s, 1H), 7.47(dd, 1H), 7.29(t, 1H), 7.22(m, 2H), 4.67(s, 2H), 3.35(s, 1H), and 1.34(s, 9H). LCMS: (FA) ES⁺ 493.5. |
| I-233 | ¹H NMR(400MHz, CD₃OD, HCl salt) δ: 9.76(s, 1H), 9.74(s, 1H), 8.79(d, 1H), 8.52(d, 1H, J=9.2Hz), 8.40(s, 1H), 8.20(d, 1H), 8.07(d, 1H), 7.86(s, 1H), 7.81(s, 1H), 7.67(d, 1H), 7.53(d, 1H), 7.34(t, 1H), 7.27(d, 1H), 4.42(s, 2H), 3.71-3.54(m, 8H), 2.97(s, 3H), and 1.35(s, 9H). LCMS: (FA) ES+ 576.2, ES− 574.2. |
| I-416 | ¹H NMR(400MHz, CD₃OD, HCl salt) δ: 8.71(d, 1H), 8.59(s, 1H), 8.17(d, 1H), 8.13(d, 1H), 8.08(dd, 1H), 7.95(br, 1H), 7.90(d, 1H), 7.54(s, 1H), 7.51(dd, 1H), 7.24(dd, 1H), 7.12(s, 1H), 4.68(s, 2H), 4.47(t, 2H), 3.73(m, 4H), 3.28(m, 2H), 2.22(m, 2H), and 2.08(m, 2H). LCMS: (FA) ES+ 618.6, ES− 616.3. |
| I-347 | ¹H NMR(400MHz, CD₃OD) δ: 8.49(s, 1H), 8.47(s, 1H), 7.98-8.11(m, 3H), 7.78(d, 2H), 7.56-7.59(m, 2H), 7.44(dd, 1H), 7.29(d, 1H), 7.21(ddd, 1H), 7.08(s, 1H), 7.01(dd, 1H), 3.65(dd, 4H), 3.54(s, 2H), 2.50(dd, 4H), and 1.34(s, 9H). LCMS: (FA) ES+ 466.1, ES− 464.1. |
| I-216 | ¹H NMR(400MHz, CD3OD; CHOOH) δ: 8.51(s, 1H), 8.47(d, 1H), 8.45(s, 1H), 7.97-7.08(m, 3H), 7.77(dd, 1H), 7.74(dd, 1H), 7.55-7.60(m, 2H), 7.40-7.43(dd, 1H), 7.28(dd, 1H), 7.20(ddd, 1H), 7.09(s, 1H), 7.00(dd, 1H), 3.56(s, 2H), 2.65(d, 6H), 2.43(s, 3H), and 1.32(s, 9H). LCMS: (FA) ES+ 562.9, ES− 560.4. |
| I-390 | ¹H NMR(400MHz, CD₃OD; HCOOH salt) δ: 8.51(d, 1H), 8.49(s, 1H), 841.00(s, 1H), 8.11(d, 1H), 8.10(d, 1H), 8.02(dd, 1H), 7.80(d, 1H), 7.79(dd, 1H), 7.58(d, 1H), 7.56(d, 1H), 7.46(dd, 1H), 7.30(dd, 1H), 7.20-7.24(m, 1H), 7.12(s, 1H), 7.04(dd, 1H), 3.77(s, 2H), 2.97(dd, 2H), 2.86(dd, 2H), and 1.35(s, 9H). LCMS: (FA) ES+ 535.6, ES− 533.8. |
| I-316 | ¹H NMR(400MHz, CD₃OD; 3×HCl salt) δ: 9.79(s, 1H), 9.77(s, 1H), 8.79(d, 1H), 8.53(d, 1H), 8.33(d, 1H), 8.19(d, 1H), 7.99(s, 1H), 7.86(s, 1H), 7.67(d, 1H), 7.57(s, 1H), 7.41(d, 1H), 7.32(dd, 1H), 7.25(d, 1H), 5.02(br. s, 5H), 4.70(s, 2H), and 1.35(s, 9H). LCMS: (FA) ES+ 494.6, ES− 492.2. |
| I-403 | ¹H NMR(400MHz, CD₃OD, HCl salt) δ: 8.63-8.61(m, 1H), 8.06-8.02(m, 2H), 7.68-7.66(m, 1H), 7.53(br s, 2H), 7.26(d, 1H), 7.12-7.01(q, 1H), 7.01-6.94(m, 2H), 4.69(s, 2H), 4.19(s, 2H), 3.15-2.88(m, 5H), 2.26-2.20(m, 1H), and 2.01-1.94(m, 1H). LCMS: (FA) ES+ 538.6, ES− 536.6. |
| I-189 | ¹H NMR(400MHz, CD₃OD, HCl salt) δ: 8.61(d, 1H), 8.09-8.04(m, 2H), 7.79-7.72(m, 2H), 7.53(s, 1H), 7.33-7.27(m, 2H), 7.09-7.01(m, 2H), 4.47(s, 2H), 4.19(s, 2H), 3.66-3.40(m, 2H), 3.16-2.91(m, 6H), and 2.27-1.93(m, 7H). LCMS: (FA) ES+ 591.4, ES− 589.7. |
| I-266 | ¹H NMR(400MHz, CD₃OD, HCl Salt) δ: 9.58(d, 1H), 9.36(d, 1H), 8.76(d, 1H), 8.40(d, 1H), 8.39(d, 1H), 8.24(dd, 1H), 8.14(d, 1H), 7.98(dd, 1H), 7.86(d, 1H), 7.73(d, 1H), 7.57(s, 1H), 7.33(dd, 1H), 4.70(s, 2H), and 4.32(s, 2H). LCMS: (FA) ES+ 535.1, ES− 533.1. |
| I-411 | ¹H NMR(400MHz, CD₃OD, HCl Salt) δ: 8.69(d, 1H), 8.61(s, 1H), 8.40(s, 1H), 8.20(d, 1H), 8.15(d, 1H), 8.11(d, 1H), 8.06(d, 1H), 7.90(s, 1H), 7.77(d, 1H), 7.74(d, 1H), 7.54(s, 1H), 7.50(d, 1H), 7.24(d, 1H), 4.68(s, 2H), and 4.31(s, 2H). LCMS: (FA) ES+ 534.4, ES− 532.0. |
| I-381 | ¹H NMR(400MHz, CD₃OD, HCl salt) δ: 8.70(d, 1H), 8.59(s, 1H), 8.38(d, 1H), 8.20(dd, 1H), 8.15(d, 1H), 8.12(d, 1H), 8.06(m, 1H), 7.90(d, 1H), 7.88(d, 1H), 7.72(d, 1H), 7.61(m, 1H), 7.50(dd, 1H), 7.29(dd, 1H), and 4.31(s, 2H). LCMS: (FA) ES+ 480.3, ES− 478.7. |
| I-369 | ¹H NMR(400MHz, d₆-DMSO, HCl salt) δ: 10.89(s, 1H), 8.67(s, 1H), 8.61(d, 1H), 8.24-8.15(m, 2H), 8.11-8.05(m, 2H), 7.98-7.92(m, 2H), 7.91(s, 1H), 7.65(br s, 1H), 7.61-7.55(m, 2H), 7.21-7.15(m, 1H), 7.10(s, 1H), 3.66-3.55(m, 1H), 3.39-3.29(m, 2H), 3.17-3.02(m, 4H), and 2.08-1.74(m, 8H). LCMS: (FA) ES+ 671.2, ES− 669.3. |
| I-339 | ¹H NMR(400MHz, d₆-DMSO, HCl salt) δ: 10.89(s, 1H), 10.78-10.68(br s, 1H), 8.67(s, 1H), 8.63(d, 1H), 8.24-8.16(m, 2H), 8.12-8.05(m, 1H), 7.98-7.92(m, 2H), 7.91(s, 1H), 7.62-7.55(m, 2H), 7.22-7.18(m, 1H), 7.10(s, 1H), 4.44(t, 2H), 3.66-3.43(m, 8H), 3.21-3.05(m, 6H), 2.74(s, 3H), and 2.02-2.01(m, 6H). LCMS: (FA) ES+ 700.2, ES− 698.1. |
| I-348 | ¹H NMR(400MHz, CD₃OD; HCl salt) δ: 8.63(d, 1H), 8.05(d, 2H), 7.76(d, 1H), 7.73(d, 1H), 7.53(s, 1H), 730.00(d, 1H), 7.27(dd, 1H), 7.05(d, 1H), 7.01(dd, 1H), 4.27(s, 2H), 4.20(s, 2H), 3.45-3.71(m, 8H), 3.02-3.71(m, 2H), 2.91-3.02(m, 6H), 2.21-2.27(m, 1H), and 1.92-2.01(m, 1H). LCMS: (FA) ES+ 620.7, ES− 618.1. |
| I-335 | LCMS: (FA) ES+ 440.7, ES− 438.2. |
| I-63 | LCMS: (FA) ES⁺ 439.6. |
| I-455 | ¹H NMR(400MHz, CD₃OD) δ: 8.68(d, 1H), 8.53(s, 1H), 8.13(d, 1H), 8.07(d, 1H), 8.03(d, 1H), 7.85(s, 1H), 7.81(s, 1H), 7.75(d, 1H), 7.60(d, 1H), 7.53(s, 1H), 7.47(dd, 1H), 7.29(t, 1H), 7.22(m, 2H), 4.67(s, 2H), 3.35(s, 1H), 1.34(s, 9H). LCMS: (FA) ES⁺ 493.5. |

Example 10

Preparation of N-(3-tert-butylphenyl)-7-[(2-{4-[(4-methylpiperazin-1-yl)carbonyl]-1H-imidazol-2-yl}pyridin-4-yl)oxy]-1,2,3,4-tetrahydronaphthalene-2-carboxamide (I-154)

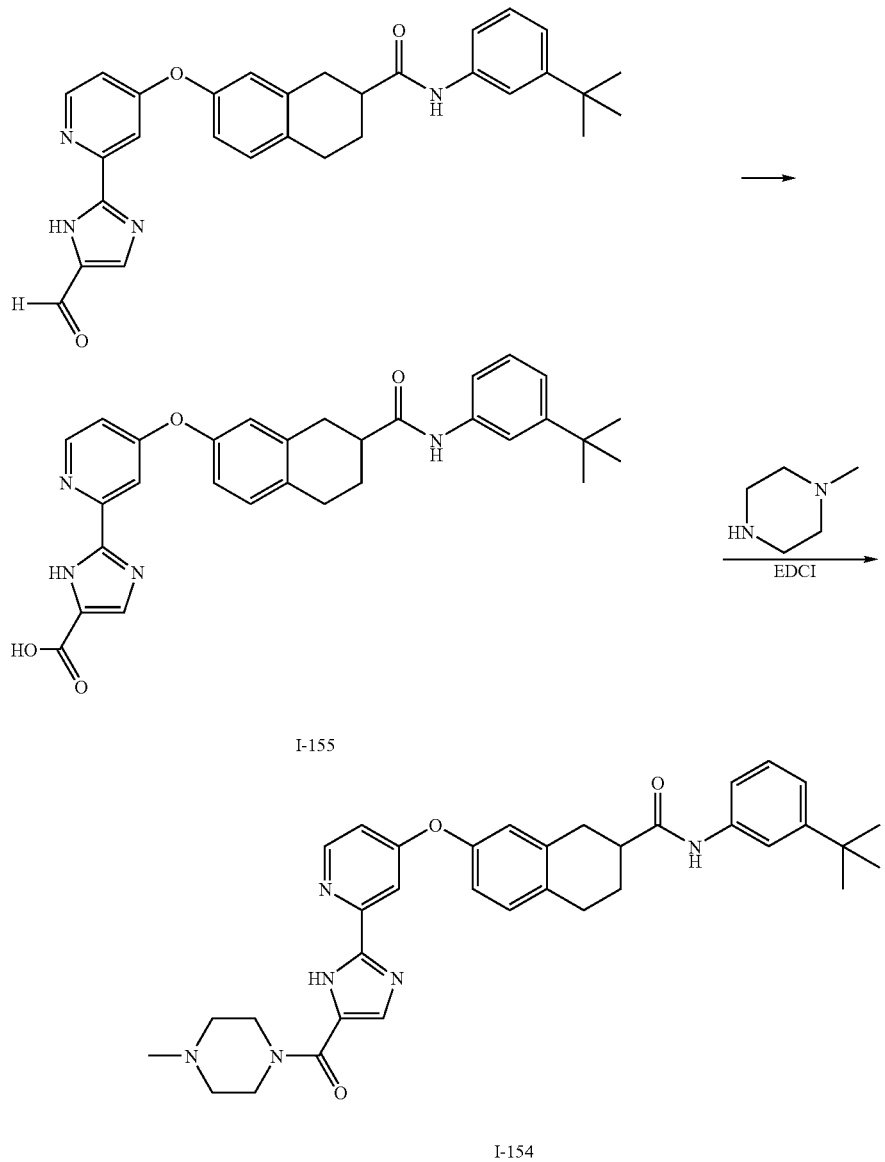

Step 1: 2-{4-[(7-{[(3-tert-Butylphenyl)amino]carbonyl}-5,6,7,8-tetrahydronaphthalen-2-yl)oxy]pyridin-2-yl}-1H-imidazole-4-carboxylic acid (I-155)

A suspension of N-(3-tert-butylphenyl)-7-{[2-(4-formyl-1H-imidazol-2-yl)pyridin-4-yl]oxy}-1,2,3,4-tetrahydronaphthalene-2-carboxamide (570 mg, 1.2 mmol) in 2-methyl-2-butene (3 mL), acetonitrile (6 mL) and tert-butyl alcohol (6 mL) was cooled to 0° C. To this cold reaction mixture was added a solution of sodium chlorite (646 mg, 5.71 mmol) and sodium dihydrogenphosphate (680 mg, 5.6 mmol) in water (3 mL). The yellow solution was allowed to stir at 0° C. overnight. The reaction was quenched by the addition of brine (3 mL) and extracted with EtOAc (15 mL×3). The combined organic solutions were washed with brine and dried over $Na_2SO_4$, filtered and concentrated to give 2-{4-[(7-{[(3-tert-butylphenyl)amino]carbonyl}-5,6,7,8-tetrahydronaphthalen-2-yl)oxy]pyridin-2-yl}-1H-imidazole-4carboxylic acid (I-155), which was used without further purification. LCMS: (FA) ES⁺ 511.2.

Step 2: N-(3-tert-butylphenyl)-7-[(2-{4-[(4-methylpiperazin-1-yl)carbonyl]-1H-imidazol-2-yl}pyridin-4-yl)oxy]-1,2,3,4-tetrahydronaphthalene-2-carboxamide (I-154)

A solution of 2-{4-[(7-{[(3-tert-butylphenyl)amino]carbonyl}-5,6,7,8-tetrahydronaphthalen-2-yl)oxy]pyridin-2-yl}-1H-imidazole-4-carboxylic acid (I-155) (178 mg, 0.349 mmol) and 1-methyl-piperazine (46 μL, 0.42 mmol) in DCM (0.9 mL) was cooled to 0° C. and then EDCI (87 mg, 0.45 mmol) was added. The reaction mixture was allowed to stir at rt for 16 h and then diluted with DCM and washed with brine. After removal of solvent, the crude product was purified by reverse phase HPLC [20% water with acetonitrile (contained 0.1% FA) to 100% acetonitrile (contained 0.1% FA) over 25 min]. The residue was dissolved in MeOH and 1M HCl in Et$_2$O was added to give N-(3-tert-butylphenyl)-7-[(2-{4-[(4-methylpiperazin-1-yl)-carbonyl]-1H-imidazol-2-yl}pyridin-4-yl)oxy]-1,2,3,4-tetrahydronaphthalene-2-carboxamide (I-154) as the HCl salt. $^1$H NMR (400 MHz, CD$_3$OD): δ 8.68 (d, 1H), 8.07 (s, 1H), 7.86 (d, 1H), 7.66 (t, 1H), 7.43 (m, 2H), 7.34 (d, 1H), 7.24 (t, 1H), 7.16 (d, 1H), 7.10 (s, 1H), 7.06 (d, 1H), 6.00-5.43 (br, 2H), 3.64 (m, 3H), 3.54 (m, 1H), 3.24-2.91 (m, 7H), 3.99 (s, 3H), 2.24 (m, 1H), 1.99 (m, 1H), and 1.32 (s, 9H). LCMS: (FA) ES$^+$ 593.3.

Compounds in the following table were prepared from the appropriate starting materials in a method analogous to that of Example 10:

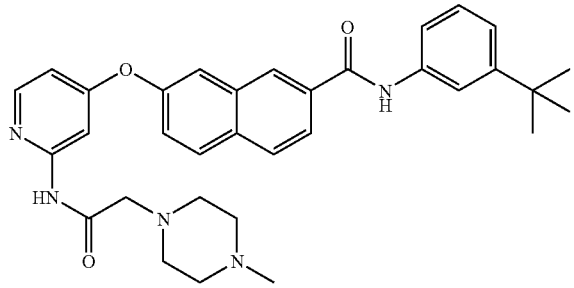

I-264

| | |
|---|---|
| I-392 | $^1$H NMR(400MHz, CD$_3$OD, HCl salt) δ: 9.80(s, 2H), 8.82(d, 1H), 8.56(s, 1H), 8.48(s, 1H), 8.25(m, 1H), 8.15(s, 1H), 8.08(s, 1H), 7.86(s, 1H), 7.67(d, 1H), 7.62(m, 1H), 7.33(t, 1H), 7.26(d, 1H), 3.64(m, 4H), 3.29(m, 4H), 2.97(s, 3H), and 1.35(s, 9H). LCMS: (FA) ES+ 590.5, ES− 588.4. |
| I-239 | $^1$H NMR(400MHz, CD$_3$OD) δ: 8.52(d, 1H), 8.47(s, 1H), 7.98-7.10(m, 3H), 7.78(dd, 2H), 7.74(s, 1H), 7.73(d, 1), 7.58(dd, 1H), 7.44(dd, 1H), 7.29(dd, 1H), 7.21(ddd, 1H), 7.04(dd, 1H), and 1.34(s, 9H). LCMS: (FA) ES+ 507.1 |
| I-377 | $^1$H NMR(400MHz, CD$_3$OD; HCOOH salt) δ: 8.49(d, 1H), 8.47(s, 1H), 8.42(s, 1H), 7.99-8.11(m, 3H), 7.75-7.80(m, 2H), 7.61-7.67(m, 2H), 7.58(d, 1H), 7.46(dd, 1H), 7.29(dd, 1H), 7.18-7.22(m, 1H), 7.01(dd, 1H), 3.89(s, 4H), 2.56(s, 4H), 2.39(s, 3H), and 1.34(s, 9H). MS: (FA) ES+ 589.8, ES− 587.4. |
| I-251 | $^1$H NMR(400MHz, CD$_3$OD, HCl) δ: 8.63(d, 1H), 8.04-8.02(m, 3H), 7.81(d, 1H), 7.53(s, 1H), 7.33(m, 2H), 7.07-7.02(m, 2H), 4.19(s, 2H), 3.66-3.56(m, 4H), 3.28-2.89(m, 12H), 2.28-2.21(m, 1H), and 2.03-1.91(m, 1H). |

Example 11

Preparation of N-(3-tert-butylphenyl)-7-[(2-{[(4-methylpiperazin-1-yl)acetyl]-amino}pyridin-4-yl)oxy]-2-naphthamide I-2640 ( )

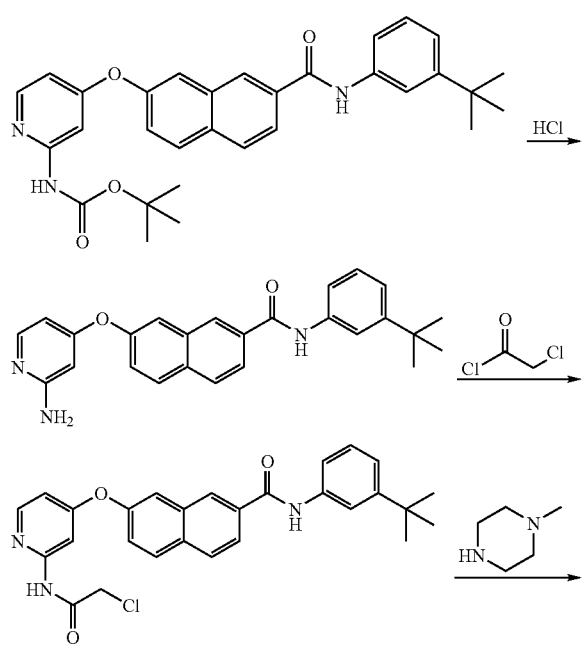

Step 1: 7-[(2-aminopyridin-4-yl)oxy]-N-(3-tert-butylphenyl)-2- naphthamide

A solution of [tert-butyl {4-[(7-{[(3-tert-butylphenyl)amino]carbonyl}-2-naphthyl)oxy]pyridin-2-yl}carbamate (1.05 g, 2.05 mmol;) in 4M HCl in 1,4-dioxane (40 mL) was allowed to stir under an atmosphere of nitrogen for 3 h. The solvents were evaporated to give 7-[(2-aminopyridin-4-yl)oxy]-N-(3-tert-butylphenyl)-2-naphthamide (977 mg, 98%).

Step 2: N-(3-tert-butylphenyl)-7-({2-[(chloroacetyl)amino]pyridin-4-yl}oxy)-2-naphthamide A solution of 7-[(2-aminopyridin-4-yl)oxy]-N-(3-tert-butylphenyl) -2-naphthamide•2[HCl] (100 mg, 0.206 mmol) and THF (5 mL) was cooled to 0° C. TEA (0.115 mL, 0.826 mmol) was added and the reaction mixture was allowed to stir for 15 min. Chloroacetyl chloride (0.018 mL, 0.227 mmol) was added slowly at 0° C. and the reaction mixture was allowed to stir for 1 hr. The solution was diluted with EtOAc and washed with water. The organic layer was dried over MgSO$_4$, filtered and concentrated. The residue was purified column chromatography to give N-(3-tert-butylphenyl)-7-({2-[(chloroacetyl)amino]-pyridin-4-yl}oxy)-2-naphthamide (65 mg, 64%) as a white solid.

Step 3: N-(3-tert-butylphenyl)-7-[(2-{[(4-methylpiperazin-1-yl)acetyl]amino}pyridin-4-yl)oxy]-2-naphthamide I-264 )

To a suspension of N-(3-tert-butylphenyl)-7-({2-[(chloroacetyl)amino]pyridin-4-yl}oxy)-2-naphthamide (65.0 mg, 0.133 mmol) and potassium carbonate (36.8 mg, 0.266 mmol) in DMF (2 mL) was added 1-methylpiperazine (0.177 mL, 0.160 mmol). The reaction mixture was allowed to stir at 60° C. for 2 h. and then concentrated. EtOAc and water were added and the organic and aqueous solutions were separated. The organic solution was washed with brine, dried over MgSO$_4$, filtered and concentrated. The residue was purified by column chromatography to give N-(3-tert-butylphenyl)-7-[(2-{[(4-methylpiperazin-1-yl)acetyl]-amino}pyridin-4-yl)oxy]-2-naphthamide I-264 ( ) (33 mg, 37%).

$^1$H NMR (400 MHz, d$_6$-DMSO; 3*HCl salt) δ: 11.61 (s, 1H), 11.18 (s, 1H), 10.44 (s, 1H), 8.59 (s, 1H), 8.32 (d, 1H), 8.14 (d, 2H), 8.05 (d, 1H), 7.90 (s, 1H), 7.82 (s, 1H), 7.74 (d, 1H), 7.63 (s, 1H), 7.50 (d, 1H), 7.23 (dd, 1H), 7.13 (d, 1H), 6.96 (d, 1H), 3.87-4.04 (m, 2H), 3.24-3.52 (m, 8H), 2.74 (s, 3H), and 1.28 (s, 9H).

LCMS: (FA) ES+ 552.2, ES− 550.3.

Compounds in the following table were prepared from the appropriate starting materials in a method analogous to that of Example 11:

| | |
|---|---|
| I-306 | $^1$H NMR(400MHz, d$_6$-DMSO; 2*HCl salt) δ: 11.28(s, 1H), 10.29(s, 1H), 8.60(s, 1H), 8.30(s, 1H), 8.16(d, 1H), 8.13(d, 1H), 8.05(d, 1H), 7.88(dd, 1H), 7.83(d, 1H), 7.74(dd, 1H), 7.61(dd, 1H), 7.50(br. s, 1H), 7.28(dd, 1H), 7.14(dd, 1H), 6.91(d, 1H), 5.49(dd, 1H), 4.23(br. s, 2H), 3.52(br. s, 2H), 3.03(br. s, 2H), 1.76-1.99(m, 4H), and 1.29(s, 9H). LCMS: (FA) ES+ 523.4, ES− 521.7. |
| I-394 | $^1$H NMR(400MHz, d$_6$-DMSO; 2*HCl salt) δ: 11.29(s, 1H), 10.51(s, 1H), 10.43(s, 1H), 8.59(s, 1H), 8.29(d, 1H), 8.15(dd, 2H), 8.04(d, 1H), 7.89(s, 1H), 7.82(s, 1H), 7.73(d, 1H), 7.60(d, 1H), 7.50(d, 1H), 7.28(dd, 1H), 7.14(d, 1H), 6.93(d, 1H), 4.18(s, 2H), 3.69-3.92(m, 4H), 3.17-3.42(m, 4H), and 1.29(s, 9H). LCMS: (FA) ES+ 539.3, ES− 537.1. |
| I-190 | $^1$H NMR(400MHz, d$_6$-DMSO: 3*HCl salt) δ: 11.31(s, 1H), 10.91(s, 1H), 10.46(s, 1H), 9.58(s, 1H), 8.59(s, 1H), 8.30(d, 1H), 8.16(d, 1H), 8.13(d, 1H), 8.04(d, 1H), 7.90(s, 1H), 7.85(s, 1H), 7.74(d, 1H), 7.59(s, 1H), 7.50(dd, 1H), 7.28(dd, 1H), 7.13(d, 1H), 6.92(d, 1H), 4.01(s, 2H), 3.38(s, 4H), 2.77(s, 6H), and 1.29(s, 9H). LCMS: (FA) ES+ 540.9, ES− 538.1. |
| I-419 | $^1$H NMR(400MHz, d$_6$-DMSO, HCl salt) δ: 11.43-11.29(m, 1H), 10.86-10.45(m, 1H), 10.13(s, 1H), 8.24(d, 1H, J=6.02Hz), 7.68-7.66(m, 1H), 7.59-7.50(m, 2H), 7.22-7.18(m, 2H), 7.07-7.04(m, 1H), 6.99-6.92(m, 2H), 6.79-6.77(m, 1H), 4.22(s, 2H), 3.93-3.79(m, 4H), 3.48-3.17(m, 4H), 2.95-2.76(m, 5H), 2.13-2.06(m, 1H), 1.80-1.73(m, 1H), and 1.25(s, 9H). LCMS: (FA) ES+ 543.9, ES− 541.4. |
| I-373 | $^1$H NMR(400MHz, d$_6$-DMSO, HCl salt) δ: 11.63-11.18(m, 1H), 10.99-10.30(m, 2H), 10.43(s, 1H), 8.24(d, 1H, J=5.77Hz), 7.61-7.52(m, 2H), 7.30-7.19(m, 3H), 6.99-6.92(m, 2H), 6.79-6.77(q, 1H), 4.23(s, 2H), 3.93-3.75(m, 4H), 3.45-3.23(m, 4H), 2.95-2.79(m, 5H), 2.11-2.05(m, 1H), 1.81-1.73(m, 1H), and 1.29(s, 9H). LCMS: (FA) ES+ 561.9, ES− 559.4. |
| I-353 | $^1$H NMR(400MHz, d$_6$-DMSO, HCl) δ: 10.10(s, 1H), 8.28(d, 1H), 7.66-7.49(m, 3H), 7.22-7.17(m, 2H), 7.07-6.84(m, 4H), 3.87(br s, 2H), 3.55-3.24(m, 8H), 2.95-2.75(m, 8H), 2.12-2.06(m, 1H), 1.80-1.73(m, 1H), and 1.25(s, 9H). |
| I-273 | $^1$H NMR(400MHz, d$_6$-DMSO, HCl) δ: 10.16(s, 1H), 8.24(d, 1H), 7.68-7.67(m, 1H), 7.53-7.50(m, 2H), 7.22-7.17(m, 2H), 7.06-6.92(m, 3H), 6.8-6.78(q, 1H), 4.26(s, 2H), 3.60(s, 2H), 3.122.77(m, 7H), 2.12-1.73(m, 6H), and 1.25(s, 9H). |
| I-393 | $^1$H NMR(400MHz, d$_6$-DMSO, HCl salt) δ: 11.02(br s, 1H), 10.59(s, 1H), 10.51(br s, 1H), 8.22(d, 1H), 7.67(d, 2H), 7.41(s, 1H), 7.24(d, 1H), 7.01-7.00(m, 2H), 6.98-6.95(m, 1H), 6.84-6.82(m, 1H), 4.39(t, 2H), 3.61-3.55(m, 4H), 3.14-3.06(m, 2H), 2.96-2.79(m, 6H), 2.74-2.67(m, 1H), 2.15-2.09(m, 1H), 2.03-2.97(m, 2H), 1.91-1.74(m, 3H), and 1.06(d, 6H). LCMS: (FA) ES$^+$ 611.3, ES$^-$ 609.2. |
| I-213 | $^1$H NMR(400MHz, d$_6$-DMSO, HCl salt) δ: 10.63(s, 1H), 10.53(br s, 1H), 8.27(d, 1H), 7.68(d, 2H), 7.46(s, 1H), 7.26(s, 1H), 7.04-6.94(m, 4H), 4.39(t, 2H), 3.60-3.56(m, 4H), 3.14-3.06(m, 2H), 2.97-2.95(m, 2H), 2.89-2.79(m, 3H), 2.14-2.09(m, 1H), 2.04-2.97(m, 2H), 1.94-1.75(m, 3H), and 1.21(s, 9H). LCMS: (FA) ES$^+$ 625.6, ES$^-$ 623.4. |
| I-384 | $^1$H NMR(300MHz, CD$_3$OD, HCl Salt) δ: 8.59(d, 1H), 7.66(s, 1H), 7.44-7.39(m, 2H), 7.30-7.20(m, 2H), 7.16-6.97(m, 4H), 4.58(s, 2H), 3.15-2.85(m, 5H), 2.57-2.47(m, 1H), 2.23-2.18(m, 1H), 2.00-1.90(m, 1H), 1.31(s, 9H), 1.08(s, 3H), and 1.05(s, 3H). LCMS: (FA) ES+ 500.5, ES− 498.5. |
| I-246 | $^1$H NMR(300MHz, CD$_3$OD, HCl Salt) δ: 8.56(d, 1H), 7.65(s, 1H), 7.43(d, 1H), 7.33-7.28(m, 3H), 7.22(t, 1H), 7.14(d, 1H), 7.02-6.97(m, 2H), 4.60(s, 2H), 3.15-2.82(m, 5H), 2.22-2.17(m, 1H), 2.01-1.89(m, 1H), and 1.30(s, 9H). LCMS: (FA) ES+ 473.0, ES− 470.2. |
| I-309 | $^1$H NMR(300MHz, CD$_3$OD, HCl Salt) δ: 8.61(d, 1H), 7.67(s, 1H), 7.47-7.45(m, 2H), 7.34-7.31(dd, 1H), 7.28(d, 1H), 7.22(t, 1H), 7.13(d, 1H), 7.02-6.98(m, 2H), 4.76(s, 3H), 3.99-3.83(m, 4H), 3.60-3.56(m, 2H), 3.14-3.03(m, 2H), 2.99-2.87(m, 4H), 2.21-2.16(m, 1H), 2.00-1.87(m, 1H), and 1.30(s, 9H). LCMS: (FA) ES+ 557.5, ES− 555.1. |
| I-387 | $^1$H NMR(300MHz, CD$_3$OD, HCl Salt) δ: 8.61(d, 1H), 7.67(s, 1H), 7.48-7.43(m, 2H), 7.34-7.32(dd, 1H), 7.28(d, 1H), 7.21(t, 1H), 7.13(d, 1H), 7.02-6.97(m, 2H), 4.75(s, 2H), 4.28(s, 2H), 3.75-3.67(m, 1H), 3.25-2.88(m, 7H), 2.21-1.88(m, 6H), and 1.29(s, 9H). LCMS: (FA) ES+ 541.8, ES− 539.5. |
| I-203 | $^1$H NMR(400MHz, CD$_3$OD, HCl Salt) δ: 8.58(s, 1H), 8.12(s, 1H), 8.01(s, 1H), 7.55(s, 1H), 7.33-7.29(m, 3H), 7.04-6.99(m, 2H), 4.62(s, 2H), 4.21(s, 2H), 3.14-2.96(m, 5H), 2.24-2.19(m, 1H), 2.04(s, 3H), and 2.00-1.92(m, 1H). LCMS: (FA) ES+ 513.1, ES− 511.1. |
| I-202 | $^1$H NMR(400MHz, CD$_3$OD, HCl Salt) δ: 8.59(d, 1H), 7.64(t, 1H), 7.45(d, 1H), 7.43-7.40(m, 1H), 7.34-7.29(m, 2H), 7.23(t, 1H), 7.17-7.14(m, 1H), 7.04(d, 1H), 7.00-6.98(dd, 1H), 4.73(s, 2H), 3.97(s, 2H), 3.47-340(m, 1H), |

-continued 3.14-2.83(m, 5H), 2.23-2.19(m, 1H), 2.01-1.90(m, 1H), 1.35(s, 3H), 1.33(s, 3H), and 1.31(s, 9H). LCMS: (FA) ES+ 530.0, ES- 527.4.

Example 12

Preparation of N-[3-(aminomethyl)-5-(trifluoromethyl)phenyl]-7-({2-[(cyclopropylcarbonyl)amino]pyridin-4-yl}oxy)-1,2,3,4-tetrahydronaphthalene-2-carboxamide I417 ( )

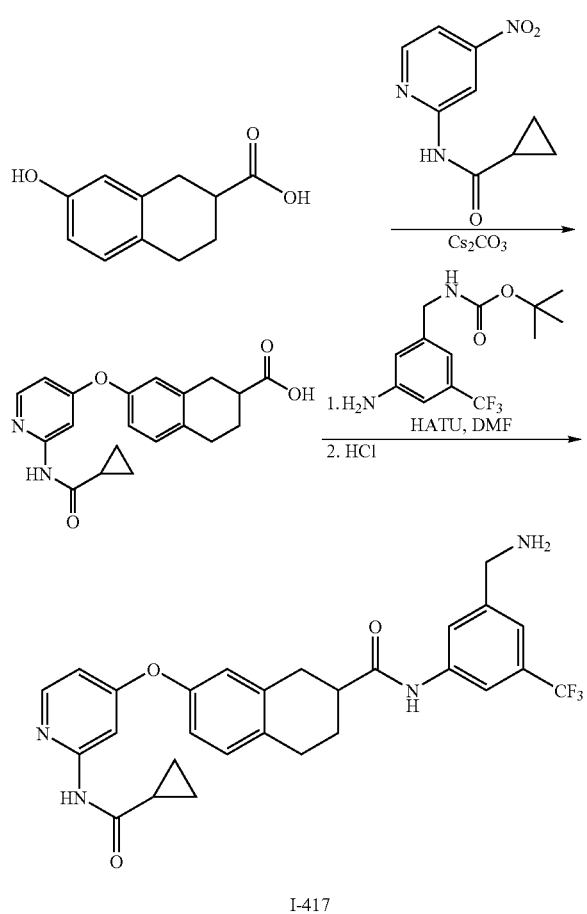

I-417

Step 1: 7-({2-[(cyclopropylcarbonyl)amino]pyridin-4-yl}oxy)-1,2,3,4-tetrahydronaphthalene-2-carboxylic acid A mixture of N-(4-nitropyridin-2-yl)cyclopropanecarboxamide (2.75 g, 13.3 mmol), 7-hydroxy-1,2,3,4-tetrahydronaphthalene-2-carboxylic acid (2.55 g, 13.3 mmol) and $Cs_2CO_3$.(13.0 g, 39.8 mmol) in DMF (40 mL) was heated at 80° C. for 18 h. The reaction mixture was cooled to rt and concentrated. The residue was acidified to approximately pH 3 by the addition of 1N HCl. The precipitate was filtered and washed with water then hexane and dried under vacuum to provide 7-({2-[(cyclopropylcarbonyl)amino]pyridin-4-yl}oxy)-1,2,3,4-tetrahydronaphthalene-2-carboxylic acid (4.08 g, 87.2%) as a beige solid. LCMS: (FA) ES+ 353.2, ES- 351.3.

Step 2: tert-butyl [3-({[7-({2-[(cyclopropylcarbonyl)amino]pyridin-4-yl}oxy)-1,2,3,4-tetrahydronaphthalen-2-yl]carbonyl}amino)-5-(trifluoromethyl)benzyl]carbamate To a solution of 7-({2-[(cyclopropylcarbonyl)amino]pyridin-4-yl}oxy)-1,2,3,4-tetrahydronaphthalene-2-carboxylic acid (3.03 g, 8.61 mmol) in DMF (75 mL), was added DIPEA (4.50 mL, 25.8 mmol) and HATU (4.91 g, 12.9 mmol). The reaction mixture was allowed to stir at rt for 30 min, and then tert-butyl [3-amino-5-(trifluoromethyl)benzyl]carbamate (2.50 g, 8.61 mmol) was added. The reaction mixture was allowed to stir for 18 h. Water was added and the precipitate was filtered, washed with water and hexane and dried under vacuum. The residue was purified by column chromatography to give tert-butyl [3-({[7-({2-[(cyclopropylcarbonyl)amino]pyridin-4-yl}oxy)-1,2,3,4-tetrahydronaphthalen-2-yl]carbonyl}-amino)-5-(trifluoromethyl)benzyl]carbamate (3.80 g, 70.6%) as a yellow solid. LCMS: (FA) ES+ 625.6, ES- 623.4.

Step 3: N-[3-(aminomethyl)-5-(trifluoromethyl)phenyl]-7-({2-[(cyclopropylcarbonyl)-amino]pyridin-4-yl}oxy)-1,2,3,4-tetrahydronaphthalene-2-carboxamide I-417

A solution of 4M HCl in dioxane (30 mL) was added to tert-butyl [3-({[7-({2-[(cyclopropylcarbonyl)amino]pyridin-4-yl}oxy)-1,2,3,4-tetrahydronaphthalen-2-yl]carbonyl}-amino)-5-(trifluoromethyl)benzyl]carbamate (3.80 g, 6.08 mmol). The suspension was allowed to stir for 2 h. The solvents were evaporated and the residue was purified by column chromatography to give N-[3-(aminomethyl)-5-(trifluoromethyl)phenyl]-7-({2-[(cyclopropylcarbonyl)amino]pyridin-4-yl}oxy)-1,2,3,4-tetrahydronaphthalene-2-carboxamide I-417 (2.60 g, 82%) as a white solid. The HCl salt was prepared by dissolving the solid in DCM and adding 2M HCl in $Et_2O$. The solvents were evaporated. $^1$H NMR (400 MHz, $d_6$-DMSO, HCl salt) δ: 11.62-11.77 (m, 1H), 10.77 (s, 1H), 8.43 (br s, 2H), 8.22 (d, 1H), 8.06 (s, 1H), 8.03 (s, 1H), 7.59 (s, 1H), 7.33 (s, 1H), 7.24 (d, 1H), 7.04-6.95 (m, 2H), 6.88-6.82 (m, 1H), 4.05-4.11 (m, 2H), 2.99-2.75 (m, 5H), 2.17-1.72 (m, 3H), and 0.91-0.80 (m, 4H). LCMS: (FA) ES+ 525.6, ES- 523.3.

Compounds in the following table were prepared from the appropriate starting materials in a method analogous to that of Example 12:

I-215 $^1$H NMR(400MHz, $d_6$-DMSO, HCl Salt) δ: 10.92(s, 1H), 8.81(s, 1H), 8.40(br s, 2H), 8.31(s, 1H), 8.26(d, 1H), 8.19-8.15(m, 3H), 8.05(d, 1H), 7.88(d, 1H), 7.67(s, 1H), 7.57-7.51(m, 2H), 6.87(dd, 1H), 4.14(q, 2H), and 2.05(s, 3H). LCMS: (FA) ES+ 492.9, ES- 495.0.

-continued

| | |
|---|---|
| I-198 | ¹H NMR(300MHz, d₆-DMSO, HCl Salt) δ: 11.02(s, 1H), 10.19(s, 1H), 8.20(d, 1H), 7.54(d, 1H), 7.35(s, 1H), 7.26-7.21(m, 3H), 6.99-6.93(m, 2H), 6.82-6.80(m, 1H), 2.95-2.67(m, 5H), 2.09(s, 4H), 1.79-1.68(m, 1H), and 1.29(s, 9H). LCMS: (FA) ES+ 476.7, ES- 474.8. |
| I-199 | ¹H NMR(400MHz, CD₃OD, HCl Salt) δ: 8.23(d, 1H), 7.71(s, 1H), 7.62(s, 1H), 7.33(d, 1H), 7.16(dd, 1H), 7.05(br, 2H), 7.02(d, 1H), 6.72(d, 1H), 4.43(s, 2H), 3.72(m, 4H), 3.30(m, 2H), 3.08-2.94(m, 6H), 2.21(m, 3H), 2.12(m, 2H), 1.97-1.82(m, 2H), and 1.13-1.06(m, 4H). LCMS: (FA) ES+ 609.6, ES- 607.3. |
| I-111 | ¹H NMR(400MHz, CD₃OD) δ: 8.08(d, 1H), 8.02(d, 1H), 7.77(dd, 1H), 7.66(d, 2H), 7.20(d, 1H), 6.82-6.86(m, 2H), 6.60(dd, 1H), 3.74(s, 2H), 2.70-3.09(m, 5H), 2.55(t, 4H), 2.12-2.20(m, 1H), 2.11(s, 3H), 1.83-1.97(m, 1H), 1.79(m, 4H). LCMS: (FA) ES+ 554, ES- 552. |
| I-281 | ¹H NMR(400MHz, CD₃OD) δ: 8.00(s, 1H), 7.64(m, 1H), 7.68(m, 3H), 7.24(m, 1H), 7.10(m, 2H), 6.78(m, 2H), 6.58(d, 1H), 5.22(d, 2H), 2.58-3.18(m, 5H), 2.10(s, 3H), 2.00-2.22(m, 1H), and 1.80-1.97(m, 1H). LCMS: (FA) ES+ 470.0, ES- 467.9. |
| I-303 | ¹H NMR(400MHz, d₆-DMSO) δ: 11.20(s, 1H), 10.22(s, 1H), 8.20(d, 1H), 7.70(m, 2H), 7.35(m, 2H), 7.22(m, 2H), 6.85-7.00(m, 3H), 2.65-2.92(m, 4H), 2.09(s, 3H), and 1.65-1.80(m, 1H). LCMS: (FA) ES+ 436.3, ES- 433.9. |
| I-333 | ¹H NMR(400MHz, CDCl₃) δ: 8.75(s, 1H), 8.25(s, 1H), 7.96(d, 1H), 7.77(d, 1H), 7.50(m, 2H), 7.20(m, 2H), 7.05(d, 1H), 6.78(d, 1H), 6.68(s, 1H), 6.64(d, 1H), 2.95(m, 1H), 2.79(m, 2H), 2.57(m, 2H), 2.07(s, 3H), 2.02(m, 2H), and 1.85(m, 2H). LCMS: (FA) ES+ 488.7, ES- 486.5. |
| I-208 | ¹H NMR(400MHz, CDCl₃) δ: 9.40(s, 1H), 8.95(s, 2H), 8.90(s, 1H), 8.05(d, 1H), 7.65(s, 1H), 7.02(d, 1H), 6.80(d, 1H), 6.74(s, 1H), 6.64(d, 1H), 2.70-3.00(m, 3H), 2.50(m, 2H), 2.16(s, 3H), 2.04(m, 1H), 1.90(m, 1H), and 1.38(s, 9H). LCMS: (FA) ES+ 460.4, ES- 458.0. |
| I-86 | ¹H NMR(400MHz, d₆-DMSO) δ: 9.50(s, 1H), 9.02(s, 1H), 8.05(d, 1H), 7.90(s, 1H), 7.80(d, 1H), 7.70(s, 1H), 7.37(d, 1H), 7.02(d, 1H), 6.79(d, 1H), 6.71(s, 1H), 6.65(d, 1H), 0.00(, H), 2.99(m, 1H), 2.72(m, 2H), 2.55(m, 2H), 2.15(s, 3H), 2.10(m, 1H), and 1.90(m, 1H). LCMS: (FA) ES+ 504.3, ES- 502.5. |
| I-232 | ¹H NMR(400MHz, d₆-DMSO) δ: 9.91(s, 1H), 8.22(d, 1H), 7.58(d, 2H), 7.31(m, 4H), 6.98-7.19(m, 5H), 6.63(d, 1H), 2.80-3.19(m, 5H), 2.22(s, 3H), 2.20(m, 1H), and 1.95(m, 1H). LCMS: (FA) ES+ 402.3, ES- 400.6. |
| I-146 | ¹H NMR(300MHz, CD₃OD) δ: 8.10(d, 1H), 7.67(m, 1H), 7.19(d, 1H), 6.88(m, 2H), 6.62(dd, 1H), 6.29(s, 1H), 2.93(m, 5H), 2.14(m, 1H), 2.11(s, 3H), 1.90(m, 1H), and 1.30(S, 9H). LCMS: (FA) ES+ 449.8, ES- 447.4. |
| I-217 | ¹H NMR(300MHz, CD₃OD) δ: 8.20(d, 1H), 8.15(s, 1H), 7.78(d, 1H), 7.50(t, 1H), 7.37(d, 1H), 7.26(d, 1H), 7.07(dd, 1H), 7.03(s, 1H), 6.99(dd, 1H), 6.60(s, 1H), 2.99(m, 5H), 2.22(s, 3H), 2.20(m, 1H), and 1.96(m, 1H). LCMS: (FA) ES+ 470.6, ES- 468.5. |
| I-211 | ¹H NMR(400MHz, CD₃OD) δ: 8.20(d, 1H), 7.64(s, 1H), 7.48(d, 1H), 7.39(dd, 1H), 7.18(d, 1H), 7.07(d, 1H), 6.79(m, 2H), 6.55(dd, 1H), 2.70(m, 5H), 2.26(s, 3H), 2.08(s, 3H), 2.09(m, 1H), and 1.84(m, 1H). LCMS: (FA) ES+ 450.4, ES- 448.5. |
| I-374 | ¹H NMR(300MHz, CDCl₃) δ: 9.03(s, 1H), 8.10(s, 1H), 7.72(s, 1H), 7.48(s, 1H), 7.33(d, 1H), 7.20(t, 1H), 7.07(d, 1H), 6.90(d, 1H), 6.82(dd, 1H), 6.76(s, 1H), 6.62(dd, 1H), 3.00(m, 1H), 2.85(m, 2H), 2.60(m, 4H), 2.16(s, 3H), 2.10(m, 1H), 1.97(m, 1H), and 1.20(t, 3H). LCMS: (FA) ES+ 430.3, ES- 428.0. |
| I-242 | ¹H NMR(400MHz, CDCl₃) δ: 8.50(s, 1H), 8.30(s, 1H), 8.10(m, 2H), 7.95(dd, 1H), 7.72(d, 1H), 7.65(s, 1H), 7.08(d, 1H), 6.82(dd, 1H), 6.76(s, 1H), 6.63(d, 1H), 3.02(m, 1H), 2.94(m, 2H), 2.73(m, 2H), 2.19(m, 1H), 2.15(s, 3H), and 2.00(m, 1H). LCMS: (FA) ES+ 495.3, ES- 493.2. |
| I-319 | ¹H NMR(400MHz, CDCl₃) δ: 9.19(s, 1H), 8.33(s, 1H), 8.50(d, 1H), 7.74(s, 1H), 7.37(t, 1H), 7.16(t, 1H), 7.43(d, 1H), 6.83(dd, 1H), 6.75(d, 1H), 6.63(m, 2H), 3.76(s, 3H), 3.03(m, 1H), 2.83(m, 2H), 2.59(m, 2H), 2.12(s, 3H), 2.08(m, 1H), and 1.91(m, 1H). LCMS: (FA) ES+ 432.4, ES- 430.5. |
| I-247 | ¹H NMR(300MHz, CDCl₃) δ: 9.38(s, 1H), 8.30(s, 1H), 8.08(d, 1H), 7.76(s, 1H), 7.57(s, 1H), 7.36(d, 1H), 7.19(t, 1H), 7.05(d, 1H), 6.95(d, 1H), 6.82(d, 1H), 6.75(s, 1H), 6.62(d, 1H), 3.03(m, 1H), 2.85(m, 3H), 2.60(m, 2H), 2.12(s, 3H), 2.10(m, 1H), 1.93(m, 1H), 1.23(d, 3H), and 1.21(d, 3H). LCMS: (FA) ES+ 444.8, ES- 442.2. |
| I-236 | ¹H NMR(300MHz, CDCl₃) δ: 8.90(s, 1H), 8.40(dd, 1H), 8.08(d, 1H), 7.79(s, 1H), 7.59(s, 1H), 7.15(d, 1H), 7.05(m, 2H), 6.84(m, 2H), 6.58(dd, 1H), 2.65-3.20(m, 5H), 2.23(m, 1H), 2.16(s, 3H), 2.00(m, 1H), and 1.30(s, 9H). LCMS: (FA) ES+ 476.4, ES- 474.5. |
| I-293 | ¹H NMR(400MHz, CDCl₃) δ: 8.98(s, 1H), 8.45(s, 1H), 8.08(d, 1H), 7.78(d, 2H), 7.72(dd, 1H), 7.32(s, 1H), 7.05(d, 1H), 6.92(dd, 1H), 6.74(d, 1H), 6.63(dd, 1H), 3.02(m, 1H), 2.84(m, 1H), 2.38-2.62(m, 3H), 2.10(m, 1H), 1.92(m, 1H), 1.56(m, 1H), 1.00(m, 2H), and 0.85(m, 2H). LCMS: (FA) ES+ 608.8, ES- 606.7. |
| I-269 | ¹H NMR(400MHz, d₆-DMSO, HCl salt) δ: 11.43(s, 1H), 10.72(s, 1H), 10.62(s, 1H), 8.21(d, 1H), 8.13(s, 1H), 8.07(s, 1H), 7.72(s, 1H), 7.38(s, 1H), 7.23(d, 1H), 7.00(d, 1H), 6.96(dd, 1H), 6.82(dd, 1H), 4.40(d, 2H), 3.36(m, 2H), 3.07(m, 1H), 2.80-2.97(m, 4H), 2.13(m, 1H), 1.78-2.05(m, 4H), and 0.82(m, 4H). LCMS: (FA) ES+ 579.2, ES- 577.4. |
| I-195 | ¹H NMR(400MHz, d₆-DMSO, HCl salt) δ: 11.51(s, 1H), 10.60(s, 1H), 8.22(d, 1H), 8.19(s, 1H), 8.10(s, 1H), 7.67(s, 1H), 7.32(s, 1H), 7.22(d, 1H), 7.03(d, 1H), 6.97(dd, 1H), 6.85(dd, 1H), 3.16(m, 2H), 2.82-2.96(m, 6H), 2.12(m, |

-continued

| | |
|---|---|
| | 1H), 1.95(m, 1H), 1.80(m, 1H), 1.22(t, 2H), and 0.84(m, 3H). LCMS: (FA) ES+ 622.4. |
| I-404 | ¹H NMR(300MHz, d₆-DMSO, HCl salt) δ: 11.23(br s, 1H), 10.74(s, 1H), 8.43(s, 2H), 8.23(d, 1H), 8.13-7.99(m, 2H), 7.58(s, 1H), 7.35(s, 1H), 7.28-7.22(m, 1H), 7.05-6.94(m, 2H), 6.87-6.80(m, 1H), 4.13-4.02(m, 2H), 2.98-2.79(m, 5H), 2.10(s, 4H), and 1.79(br s, 1H). LCMS: (FA) ES+ 499.7, ES− 497.4. |
| I-147 | ¹H NMR(400MHz, CD₃OD, HCl salt) δ: 8.33(br, 1H), 7.72(br, 1H), 7.68(br, 1H), 7.28(br, 1H), 7.16(br, 1H), 7.04(br, 3H), 6.80(br, 1H), 4.45(br, 2H), 3.75(br, 4H), 3.26-3.35(m, 2H), 3.06(br, 2H), 2.94(br, 3H), 2.28(s, 3H), 2.20(br, 3H), 2.09(br, 2H), and 1.90(br, 1H). LCMS: (FA) ES+ 583.4, ES− 581.6. |
| I-287 | ¹H NMR(400MHz, d₆-DMSO, HCl salt) δ: 11.65-10.72(m, 3H), 8.23(d, 1H), 8.14-8.07(m, 2H), 7.75(br s, 1H), 7.33-7.22(m, 2H), 7.03-6.94(m, 2H), 6.90-6.82(m, 1H), 4.44-4.38(m, 2H), 3.39-3.29(m, 2H), 3.09-2.77(m, 7H), and 2.17-1.75(m, 9H). LCMS: (FA) ES+ 553.6, ES− 551.3. |
| I-282 | ¹H NMR(300MHz, d₆-DMSO, HCl salt) δ: 11.36(br s, 1H), 10.81(s, 1H), 9.39(br s, 2H), 8.24-8.22(m, 2H), 7.97(d, 1H), 7.82(d, 1H), 7.28-7.23(m, 2H), 7.03-6.96(m, 2H), 6.89-6.87(m, 1H), 4.19(t, 2H), 2.97-2.82(m, 5H), 2.59(t, 3H), 2.16-2.11(m, 4H), and 1.86-1.74(m, 1H). LCMS: (FA) ES+ 513.1, ES− 510.9. |
| I-326 | ¹H NMR(300MHz, d₆-DMSO, HCl salt) δ: 11.09(br s, 1H), 10.72(s, 1H), 9.13(br s, 2H), 8.21(d, 1H), 8.07(br s, 2H), 7.63(s, 1H), 7.38(s, 1H), 7.23(d, 1H), 7.01-6.94(m, 2H), 6.83-6.79(m, 1H), 4.18(t, 2H), 2.98-2.82(m, 5H), 2.55(t, 3H), 2.16-2.09(m, 4H), and 1.88-1.74(m, 1H). LCMS: (FA) ES+ 513.2, ES− 511.0. |
| I-224 | ¹H NMR(400MHz, d₆-DMSO, HCl salt) δ: 11.36(s, 1H), 10.84(s, 1H), 10.63(s, 1H), 8.61(s, 1H), 8.26(d, 1H), 8.12-8.14(m, 2H), 8.06-8.02(m, 1H), 7.95-9.23(m, 1H), 7.90-7.86(m, 2H), 7.54-7.50(m, 2H), 7.09(s, 1H), 6.93-6.90(m, 1H), 4.47-4.42(m, 2H), 3.64-3.56(m, 4H), 3.16-3.09(m, 2H), 2.03-1.83(m, 5H), and 0.88-0.74(m, 4H). LCMS: (FA) ES+ 605.2. |
| I-219 | ¹H NMR(400MHz, d₆-DMSO, HCl salt) δ: 11.46-11.31(m, 1H), 10.85(s, 1H), 10.64-10.49(m, 1H), 8.23(d, 1H, J=6.27Hz), 8.14-8.09(m, 2H), 7.76(br s, 1H), 7.31-7.22(m, 2H), 7.04-6.86(m, 3H), 4.34-4.29(m, 2H), 3.31-3.24(m, 2H), 2.98-2.79(m, 7H), 2.17-2.08(m, 4H), 1.85-1.63(m, 6H), and 1.40-1.23(m, 1H). LCMS: (FA) ES+ 567.1, ES− 565.1. |
| I-375 | ¹H NMR(400MHz, d₆-DMSO, HCl salt) δ: 11.50-11.28(m, 2H), 10.84(s, 1H), 8.23(d, 1H, J=6.52Hz), 8.16-8.10(m, 2H), 7.78(s, 1H), 7.30-7.21(m, 2H), 7.07-6.85(m, 3H), 4.40(s, 2H), 3.98-3.71(m, 4H), 3.29-2.75(m, 9H), 2.18-2.04(m, 4H), and 1.87-1.73(m, 1H). LCMS: (FA) ES+ 569.1, ES− 567.1. |
| I-109 | ¹H NMR(400MHz, d₆-DMSO, HCl salt) δ: 7.43(d, 1H), 7.36(s, 1H), 7.09(s, 2H), 6.51(d, 1H), 6.39-6.35(m, 1H), 6.26-6.24(m, 1H), 6.23-6.18(m, 1H), 8.82(d, 1H), 3.39(br s, 2H), 2.91-2.53(m, 7H), 2.36-1.99(m, 11H), 1.46-1.39(m, 4H), and 1.19-1.08(m, 1H). LCMS: (FA) ES+ 582.1. |
| I-363 | ¹H NMR(300MHz, d₆-DMSO, HCl Salt) δ: 11.36(br s, 1H), 10.73(s, 1H), 8.42(br s, 3H), 8.21-8.26(m, 1H), 7.99-8.09(m, 1H), 7.59(s, 1H), 7.47(s, 1H), 7.14-7.27(m, 1H), 6.77-6.88(m, 1H), 4.04-4.12(m, 2H), 2.78-3.02(m, 6H), 2.04-2.15(m, 1H), 1.90-2.01(m, 1H), 1.71-1.88(m, 1H), and 0.78-0.88(m, 4H). LCMS: (FA) ES+ 543.3, ES− 541.4. |
| I-329 | ¹H NMR(400MHz, d₆-DMSO, HCl Salt) δ: 10.92(br s, 1H), 10.70(s, 1H), 8.34(br s, 3H), 8.16-8.23(m, 1H), 8.01-8.05(m, 2H), 7.59(s, 1H), 7.50(s, 1H), 7.15-7.25(m, 2H), 6.75-6.81(m, 1H), 4.06-4.14(m, 2H), 2.78-2.98(m, 4H), 2.03-2.15(m, 4H), and 1.73-1.84(m, 1H). LCMS: (FA) ES+ 517.4. |
| I-285 | ¹H NMR(400MHz, d₆-DMSO, HCl Salt) δ: 10.69(s, 1H), 8.89-8.79(m, 1H), 8.55-8.52(m, 1H), 8.47-8.35(m, 3H), 8.03(s, 2H), 7.59(s, 1H), 7.36(s, 1H), 7.30-7.20(m, 3H), 4.12-4.04(m, 2H), 2.99-2.82(m, 4H), 2.81-2.74(m, 3H), 2.16-2.07(m, 4H), and 1.86-1.75(m, 1H). LCMS: (FA) ES+ 517.4, ES− 515.5. |
| I-288 | ¹H NMR(300MHz, CD₃OD, HCl salt) δ: 8.61-8.56(m, 1H), 8.50(s, 1H), 8.17-7.99(m, 3H), 7.87-7.84(m, 1H), 7.81-7.73(m, 2H), 7.61-7.55(m, 1H), 7.50-7.44(m, 1H), 7.35-7.25(m, 2H), 7.25-7.20(m, 1H), 2.93(s, 3H), and 1.35(s, 9H). LCMS: (FA) ES+ 454.3. |
| I-87 | ¹H NMR(400MHz, CD₃OD; HCl salt) δ: 9.75(s, 1H), 8.23(d, 1H), 7.64(dd, 1H), 7.39-7.43(m, 1H), 7.30(d, 1H), 7.23(dd, 1H), 7.13-7.19(m, 2H), 7.04(d, 1H), 6.99(dd, 1H), 6.63(d, 1H), 2.79-3.16(m, 5H), 2.24(s, 3H), 2.17-2.23(m, 1H), 1.89-1.98(m, 1H), and 1.31s(s, 9H). LCMS: (FA) ES+ 458.6, ES− 456.6. |
| I-131 | ¹H NMR(400MHz, d₆-DMSO; HCl salt) δ: 11.43(s, 1H), 10.40(s, 1H), 8.57(s, 1H), 8.27(d, 1H), 8.17(d, 1H), 8.13(d, 1H), 8.04(dd, 1H), 7.91(d, 1H), 7.81(d, 1H), 7.73(dd, 1H), 7.51(dd, 1H), 7.43(d, 1H), 7.29(dd, 1H), 7.14(dd, 1H), 6.95(dd, 1H), 1.89-1.96(m, 1H), 1.29(s, 9H), and 0.77-0.85(m, 4H). LCMS: (FA) ES+ 480.8, ES− 478.2. |
| I-182 | ¹H NMR(400MHz, d₆-DMSO) δ: 8.45(dd, 1H), 8.21(s, 3H), 7.96(s, 1H), 7.81(s, 1H), 7.51(d, 1H), 7.39(s, 1H), 7.23(d, 1H), 7.05(dd, 1H), 6.88-6.94(m, 2H), 3.68(s, 2H), 3.21-3.30(m, 4H), 2.93-3.14(m, 5H), 2.92(s, 3H), 2.81(s, 3H), 2.68-2.83(m, 4H), 2.20(d, 1H), and 1.90-1.99(m, 1H). LCMS: (FA) ES+ 582.3, ES− 580.4. |
| I-379 | ¹H NMR(400MHz, CD₃OD, 3*HCOOH salt) δ: 10.67(s, 2H), 8.77-8.83(m, 1H), 8.50(d, 1H), 8.01(s, 1H), 8.05(s, 1H), 7.72(s, 1H), 7.36(s, 1H), 7.24(d, 1H), 7.16(dd, 1H), 7.02(d, 1H), 6.97(dd, 1H), 4.42(d, 2H), 3.36(s, 2H), 3.01-3.10(m, 2H), 2.96(d, 2H), 2.82-2.92(m, 3H), 2.77(d, 3H), 2.09-2.19(m, 1H), 1.96-2.16(m, 2H), and 1.78-1.89(m, 3H). LCMS: (FA) ES+ 553.3, ES− 551.4. |
| I-328 | LCMS: (FA) ES+ 557.2 |
| I-283 | LCMS: (FA) ES+ 696.4 |
| I-383 | ¹H NMR(400MHz, CD₃OD; HCOOH salt) δ: 8.51-8.85(m, 3H), 8.33(d, 1H), |

-continued 8.13(d, 1H), 8.11(d, 1H), 8.03(dd, 1H), 7.82(d, 1H), 7.57(d, 1H), 7.52(d, 1H), 7.51(d, 1H), 7.47(dd, 1H), 7.26(d, 1H), 4.33(dd, 2H), 2.89-2.97(m, 9H), and 2.67-2.72(m, 4H). LCMS: (FA) ES+ 594.9, ES− 592.3.

I-300 ¹H NMR(400MHz, CD₃OD: HCOOH salt) δ: 8.51(s, 1H), 8.46(d, 1H), 8.38(d, 1H), 7.49(d, 1H), 7.41(dd, 1H), 7.23(d, 1H), 7.20(d, 1H), 7.06(dd, 1H), 6.94(d, 1H), 6.91(dd, 1H), 4.29(dd, 2H), 3.14(dd, 4H), 2.92-3.10(m, 10H), 2.76(dd, 4H), 2.23(d, 1H), and 1.92-2.03(m, 1H). LCMS: (FA) ES+ 598.9, ES− 596.3.

I-402 ¹H NMR(400MHz, CD₃OD, HCl salt) δ: 8.68(d, 1H), 8.14(s, 1H), 8.10(s, 1H), 7.95(d, 1H), 7.55(d, 2H), 7.52(dd, 1H), 7.26(d, 1H), 7.19(dd, 1H), 7.04(d, 1H), 5.11(s, 2H), 4.21(s, 2H), and 2.97(s, 3H). LCMS: (FA) ES+ 499.9, ES− 497.3.

I-308 ¹H NMR(400MHz, CD₃OD; HCl salt) δ: 9.66(d, 1H), 9.49(s, 1H), 8.72(d, 1H), 8.43(d, 1H), 8.30(s, 1H), 8.21-8.24(m, 2H), 8.05(dd, 1H), 7.94(d, 1H), 7.65(s, 1H), 7.57(dd, 1H), 4.26(s, 2H), and 2.95(s, 3H). LCMS: (FA) ES+ 496.8, ES− 494.4.

I-371 ¹H NMR(400MHz, CD₃OD; HCl salt) δ: 10.37(s, 1H), 8.53(d, 1H), 8.14(s, 1H), 8.06(s, 1H), 7.67(d, 2H), 7.26(d, 1H), 7.24(dd, 1H), 6.98(d, 1H), 6.96(dd, 1H), 4.39(s, 2H), 3.57-3.65(m, 5H), 3.02-3.16(m, 3H), 2.85-3.01(m, 6H), 2.18-2.28(m, 1H), 2.15(br. s, 3H), and 1.95-2.02(m, 1H). LCMS: (FA) ES+ 596.3, ES− 594.3.

I-296 ¹H NMR(400MHz, CD₃OD; HCl salt) δ: 8.61(m, 1H), 8.09(d, 1H), 8.02(s, 1H), 7.84-7.89(m, 1H), 7.55(s, 1H), 7.38-7.45(m, 1H), 7.30(d, 1H), 7.05(s, 1H), 7.00(d, 1H), 4.26(s, 2H), 3.05-3.17(m, 2H), 2.87-3.03(m, 6H), 2.75(s, 3H), 2.24(d, 1H), and 1.92-2.04(m, 1H). LCMS: (FA) ES+ 513.2, ES− 511.2.

I-298 ¹H NMR(300MHz, d₆-DMSO; HCl salt) δ: 1.05(s, 1H), 8.78(dd, 1H), 8.52(d, 1H), 8.15(s, 1H), 7.74(s, 2H), 7.53(s, 1H), 7.39(d, 1H), 7.14-7.25(m, 3H), 7.00-7.05(m, 2H), 5.06(s, 2H), 4.30(dd, 2H), 3.29(dd, 2H), 3.02(dd, 4H), 2.78(d, 3H), and 1.80-1.88(m, 4H). LCMS: (FA) ES+ 583.9, ES− 581.2.

I-365 ¹H NMR(400MHz, d₆-DMSO: HCl salt) δ: 11.15(s, 1H), 10.87(s, 1H), 9.43(d, 1H), 9.08(d, 1H), 8.86(dd, 1H), 8.60(d, 1H), 8.28(d, 1H), 8.01(d, 1H), 7.90(d, 2H), 7.84(dd, 1H), 7.55(d, 1H), 7.34(dd, 1H), 7.13(s, 1H), 4.46(dd, 2H), 3.51-3.65(m, 4H), 3.06-3.15(m, 2H), 2.79(d, 3H), 1.95-2.06(m, 2H), and 1.81-1.93(m, 2H). LCMS: (FA) ES+ 580.7, ES− 578.2.

I-161 ¹H NMR(400MHz, d₆-DMSO: HCl salt) δ: 11.20(s, 1H), 9.44(d, 1H), 9.07(d, 1H), 8.83-8.88(m, 1H), 8.57-8.69(m, 4H), 8.35(d, 1H), 8.28(d, 1H), 8.22(d, 1H), 8.02(d, 1H), 7.80-7.86(m, 2H), 7.54(d, 1H), 7.34(dd, 1H), 4.16(d, 2H), and 2.79(d, 3H). LCMS: (FA) ES+ 496.2, ES− 494.2.

I-143 ¹H NMR(300MHz, CD₃OD; HCl salt) δ: 8.69(d, 1H), 8.27(s, 1H), 8.10(dd, 1H), 7.95(d, 1H), 7.68(d, 1H), 7.52(dd, 2H), 7.26(d, 1H), 7.19(d, 1H), 7.05(d, 1H), 5.12(s, 2H), 4.29(s, 2H), and 2.99(s, 3H). LCMS: (FA) ES+ 499.2, ES− 497.2.

I-382 ¹H NMR(400MHz, d₆-DMSO) δ: 10.56(s, 1H), 8.76(dd, 1H), 8.49(d, 1H), 8.09(d, 1H), 8.02(s, 1H), 7.72(dd, 1H), 7.36(d, 1H), 7.24(d, 1H), 7.15(dd, 1H), 7.02(d, 1H), 6.97(dd, 1H), 2.81-3.02(m, 5H), 2.77(d, 3H), 2.14-2.21(m, 1H), and 1.80-1.90(m, 1H). LCMS: (FA) ES+ 495.1, ES− 493.1.

I-204 ¹H NMR(400MHz, d₆-DMSO; 3*HCl salt) δ: 10.20(s, 1H), 9.49(s, 2H), 8.83-8.88(m, 1H), 8.51(d, 1H), 7.40-7.46(m, 2H), 7.22-7.25(d, 1H), 7.17(dd, 1H), 7.13(d, 1H), 7.01(s, 1H), 6.96(dd, 1H), 4.92(s, 4H), 4.20(s, 2H), 3.30(s, 2H), 2.89-2.96(m, 4H), 2.80-2.89(m, 3H), 2.77(d, 3H), 2.04-2.02(m, 1H), and 1.73-1.85(m, 1H). LCMS: (FA) ES+ 457.1, ES− 455.2.

I-209 ¹H NMR(400MHz, d₆-DMSO, HCl salt) δ: 11.19(br s, 1H), 10.42(s, 1H), 8.22(d, 1H), 8.05(s, 1H), 7.88(s, 1H), 7.45(s, 1H), 7.28(s, 1H), 7.24(d, 1H), 7.02-7.01(m, 1H), 6.98-6.96(m, 1H), 6.88-6.86(m, 1H), 2.96-2.77(m, 5H), 2.15-2.10(m, 4H), 1.85-1.74(m, 1H), and 1.43(s, 6H). LCMS: (FA) ES⁺ 528.6, ES⁻ 526.4.

I-197 ¹H NMR(400MHz, d₆-DMSO, HCl salt) δ: 11.14(br s, 1H), 10.72(s, 1H), 8.70(s, 3H), 8.22(d, 1H), 8.08(d, 2H), 7.67(s, 1H), 7.35(s, 1H), 7.24(d, 1H), 7.01-7.00(m, 1H), 6.98-6.95(m, 1H), 6.84-6.82(m, 1H), 2.97-2.82(m, 5H), 2.15-2.09(m, 4H), 1.86-1.75(m, 1H), and 1.65(s, 6H). LCMS: (FA) ES⁺ 527.2, ES⁻ 525.5.

I-181 ¹H NMR(400MHz, d₆-DMSO, HCl salt) δ: 11.45-12.00(m, 2H), 10:86(s, 1H), 8.06-8.31(m, 3H), 7.76(br s, 1H), 7.24-7.35(m, 2H), 6.90-7.10(m, 3H), 4.28-4.52(m, 2H), 3.05-3.74(m, 10H), 2.74-3.04(m, 5H), 2.07-2.24(m, 4H), 1.74-1.87(m, 1H), and 1.20-1.30(m, 3H). LCMS: (FA) ES+ 596.2, ES− 594.2.

I-410 ¹H NMR(400MHz, d₆-DMSO, HCl salt) δ: 11.45(br s, 1H), 10.88(s, 1H), 9.74(br s, 1H), 8.23(d, 1H), 8.16(s, 1H), 8.11(s, 1H), 7.80(s, 1H), 7.22-7.30(m, 2H), 6.96-7.04(m, 2H), 6.87-6.92(m, 1H), 4.39-4.47(m, 2H), 3.20-3.51(m, 8H), 2.76-2.99(m, 5H), 2.07-2.16(m, 4H), and 1.73-1.86(m, 1H). LCMS: (FA) ES+ 568.1, ES− 566.1.

I-91 ¹H NMR(400MHz, d₆-DMSO, HCl salt) δ: 11.40-11.56(m, 1H), 10.10(s, 1H), 8.24(d, 1H), 7.69-7.78(m, 1H), 7.55-7.63(m, 1H), 7.47(s, 1H), 7.07-7.37(m, 5H), 6.90-7.06(m, 2H), 5.04(s, 2H), 2.12(s, 3H), and 1.26(s, 9H). LCMS: (FA) ES+ 458.5, ES− 456.3.

I-376 ¹H NMR(400MHz, d₆-DMSO, HCl salt) δ: 10.89-11.09(m, 1H), 10.65(s, 1H), 8.20-8.26(m, 2H), 8.09(br s, 1H), 7.76(br s, 1H), 7.57(br s, 1H), 7.43-7.50(m, 1H), 7.11-7.22(m, 2H), 6.99-7.04(m, 1H), 6.78-6.84(m, 1H), 5.04-5.07(m, 2H), 4.41-4.46(m, 2H), 3.33-3.41(m, 2H), 3.01-3.12(m, 2H), 1.97-2.09(m, 5H), and 1.82-1.92(m, 2H). LCMS: (FA) ES+ 553.4, ES− 551.5.

I-301 ¹H NMR(400MHz, d₆-DMSO, HCl salt) δ: 10.66-10.79(m, 2H), 8.20-8.29(m, 2H), 8.10(br s, 1H), 7.77(br s, 1H), 7.58(br s, 1H), 7.42-7.47(m, 1H), 7.12-7.22(m, 2H), 6.97-7.05(m, 1H), 6.81-6.88(m, 1H), 5.03-5.11(m, 2H), 4.40-4.48(m,

| | |
|---|---|
| | 2H), 3.30-3.43(m, 2H), 3.01-3.13(m, 2H), 1.77-2.07(m, 5H), and 0.75-0.88(m, 4H). LCMS: (FA) ES+ 579.1, ES− 577.3. |
| I-346 | ¹H NMR(400MHz, d₆-DMSO, HCl salt) δ: 11.66-11.79(m, 1H), 10.08(s, 1H), 8.24(d, 1H), 7.69-7.73(m, 1H), 7.55-7.61(m, 1H), 7.46(br s, 1H), 7.30-7.34(m, 1H), 7.19-7.27(m, 2H), 7.09-7.16(m, 2H), 6.89-7.04(m, 2H), 5.04(s, 2H), 1.90-1.99(m, 1H), 1.26(s, 9H), and 0.82-0.92(m, 4H). LCMS: (FA) ES+ 484.7, ES− 482.0. |
| I-343 | ¹H NMR(400MHz, d₆-DMSO, HCl salt) δ: 10.25(s, 1H), 8.21-8.25(m, 1H), 7.84-7.91(m, 2H), 7.26-7.37(m, 2H), 6.96-7.15(m, 3H), 6.74(br s, 1H), 3.19-3.25(m, 2H), 2.82-3.15(m, 7H), 2.17-2.27(m, 4H), and 1.89-2.00(m, 1H). LCMS: (FA) ES+ 513.1, ES− 511.1. |
| I-389 | ¹H NMR(400MHz, CD₃OD, HCl salt) δ: 8.09(d, 1H), 7.93-7.92(m, 1H), 7.88-7.87(m, 1H), 7.65(s, 1H), 7.46(s, 1H), 7.18(d, 1H), 6.92-6.85(m, 2H), 6.63-6.60(dd, 1H), 3.29(s, 3H), 3.09-3.17(m, 5H), 2.21-2.16(m, 1H), 1.97-1.86(m, 1H), 1.33(s, 9H) LCMS: (FA) ES+ 483.0. |
| I-385 | ¹H NMR(400MHz, CD₃OD, HCl salt) δ: 10.06(s, 1H), 8.25(d, 1H), 7.66(d, 2H), 7.32-2.28(m, 2H), 7.17(d, 1H), 7.05(s, 1H), 7.01(d, 1H), 6.66(s, 1H), 4.06(s, 1H), 3.10-2.84(m, 5H), 2.24(s, 3H), 2.23-2.20(m, 1H), 1.96-1.88(m, 1H), 1.34(s, 9H) LCMS: (FA) ES+ 487.0, ES− 485.0. |
| I-243 | ¹H NMR(400MHz, d₆-DMSO, HCl salt) δ: 11.06(br s, 1H), 10.74(s, 1H), 9.94(br s, 1H), 9.01(br s, 1H), 8.20(d, 1H), 8.11(s, 1H), 8.05(s, 1H), 7.61(s, 1H), 7.39(br s, 1H), 7.23(d, 1H), 6.70(s, 1H), 6.93-6.98(m, 1H), 6.78-6.83(m, 1H), 4.56-4.65(m, 1H), 3.23-3.40(m, 2H), 2.78-2.99(m, 5H), 2.35-2.44(m, 1H), 1.98-2.16(m, 7H), and 1.74-1.86(m, 1H). LCMS: (FA) ES+ 539.3, ES− 537.4. |
| I-256 | ¹H NMR(400MHz, d₆-DMSO, HCl salt) δ: 11.68(br s, 1H), 10.83(s, 1H), 10.12(br s, 1H), 9.08(br s, 1H), 8.22(d, 1H8.14(s, 1H), 8.05(s, 1H), 7.63(s, 1H), 7.31(s, 1H), 7.24(d, 1H), 6.95-7.04(m, 2H), 6.84-6.92(m, 1H), 4.54-4.65(m, 1H), 3.22-3.40(m, 2H), 2.76-3.00(m, 5H), 2.34-2.43(m, 1H), 1.73-2.17(m, 6H), and 0.78-0.91(m, 4H). LCMS: (FA) ES+ 565.4, ES− 563.5. |
| I-414 | ¹H NMR(400MHz, d₆-DMSO, HCl salt) δ: 10.74-10.84(m, 1H), 8.06-8.24(m, 3H), 7.71-7.83(m, 1H), 7.36(s, 1H), 7.23(d, 1H, J=8.53Hz), 6.94-7.02(m, 2H), 6.82-6.87(m, 1H), 5.31-5.54(m, 2H), 4.43-4.54(m, 2H), 3.22-3.83(m, 4H), 2.76-2.99(m, 5H), 2.04-2.32(m, 3H), 1.92-2.02(m, 1H), 1.74-1.88(m, 1H), and 0.79-0.90(m, 4H). LCMS: (FA) ES+ 597.4, ES− 595.5. |
| I-255 | ¹H NMR(400MHz, CD₃OD, HCl salt) δ: 8.17(s, 1H), 8.10(d, 1H), 7.97(s, 1H), 7.65(br s, 1H), 7.58(s, 1H), 7.19(d, 1H), 6.87-6.92(m, 2H), 6.62-6.66(m, 1H), 4.39(s, 2H), 3.20(q, 4H), 2.80-3.11(m, 5H), 2.16-2.25(m, 1H), 2.12(s, 3H), 1.89-2.00(m, 1H), and 1.35(t, 6H). LCMS: (FA) ES+ 555.5. |
| I-307 | ¹H NMR(400MHz, d₆-DMSO, HCl salt) δ: 11.94(br s, 1H), 10.87(s, 1H), 9.34(s, 1H), 8.24(d, 1H), 8.11(s, 1H), 8.07(s, 1H), 7.66(s, 1H), 7.22-7.31(m, 2H), 6.97-7.05(m, 2H), 6.94-6.88(m, 1H), 4.13-4.20(m, 2H), 2.77-3.00(m, 5H), 2.53-2.57(m, 3H), 2.08-2.16(m, 1H), 1.94-2.01(m, 1H), 1.74-1.86(m, 1H), and 0.83-0.94(m, 4H). LCMS: (FA) ES+ 539.5, ES− 537.4. |
| I-360 | ¹H NMR(400MHz, d₆-DMSO, HCl salt) δ: 11.78(br s, 1H), 10.87(s, 1H), 10.60(br s, 1H), 8.23(d, 1H), 8.13(d, 2H), 7.80(s, 1H), 7.32(s, 1H), 7.24(d, 1H), 6.96-7.04(m, 2H), 6.86-6.91(m, 1H), 4.34-4.40(m, 2H), 2.76-3.10(m, 9H), 2.09-2.18(m, 1H), 1.94-2.00(m, 1H), 1.74-1.86(m, 1H), 1.24(t, 6H), and 0.82-0.93(m, 4H). LCMS: (FA) ES+ 581.3, ES− 579.4. |
| I-186 | ¹H NMR(400MHz, d₆-DMSO, HCl salt) δ: 11.15(br s, 1H), 10.95(br s, 1H), 10.63(s, 1H), 8.24-8.31(m, 1H), 8.20(d, 1H), 8.05-8.10(m, 1H), 7.71-7.83(m, 1H), 7.49-7.55(m, 2H), 7.11-7.19(m, 2H), 7.00(d, 1H), 6.74-6.79(m, 1H), 5.32-5.57(m, 1H), 5.05(s, 2H), 4.45-4.56(m, 2H), 3.23-3.58(m, 4H), 1.92-2.39(m, 3H), and 0.75-0.84(m, 4H). LCMS: (FA) ES+ 597.2, ES− 595.3. |
| I-279 | ¹H NMR(400MHz, d₆-DMSO, HCl salt) δ: 11.54(br s, 1H), 10.68(s, 1H), 8.10-8.25(m, 3H), 7.75(br s, 1H), 7.60(s, 1H), 7.41-7.46(m, 1H), 7.12-7.20(m, 2H), 7.01(d, 1H), 6.82-6.88(m, 1H), 5.05(s, 2H), 4.14-4.43(m, 2H), 3.04-3.67(m, 8H), 2.78(s, 3H), 1.93-2.01(m, 1H), and 0.77-0.89(m, 4H). LCMS: (FA) ES+ 608.5 |
| I-407 | ¹H NMR(400MHz, CD₃OD, HCl salt) δ: 8.20(d, 1H), 8.16(s, 1H), 8.07(s, 1H), 7.63(s, 1H), 7.28(d, 1H), 6.96-7.05(m, 3H), 6.91(br s, 1H), 5.38-5.55(m, 1H), 4.54(s, 2H), 3.39-3.80(m, 4H), 2.84-3.16(m, 5H), 2.15-2.71(m, 6H), and 1.89-2.03(m, 1H). LCMS: (FA) ES+ 571.3, ES− 569.4. |
| I-337 | ¹H NMR(400MHz, d₆-DMSO, HCl salt) δ: 11.87(br s, 1H), 10.78-11.00(m, 1H), 8.23(d, 1H), 8.09-8.21(m, 2H), 7.74-7.85(m, 1H), 7.30(s, 1H), 7.24(d, 1H), 6.96-7.06(m, 2H), 6.87-6.93(m, 1H), 5.32-5.55(m, 1H), 4.42-4.55(m, 2H), 3.20-3.86(m, 4H), 2.75-3.01(m, 5H), 2.06-2.36(m, 3H), 1.92-2.01(m, 1H), 1.73-1.86(m, 1H), and 0.81-0.94(m, 4H). LCMS: (FA) ES+ 597.5, ES− 595.6. |
| I-249 | ¹H NMR(400MHz, d₆-DMSO, HCl salt) δ: 8.22(d, 1H), 8.06-8.19(m, 2H), 7.68-7.79(m, 1H), 7.31-7.38(m, 1H), 7.24(d, 1H), 6.93-7.04(m, 2H), 6.83-6.89(m, 1H), 4.35-4.49(m, 3H), 3.37-3.54(m, 2H), 3.10-3.30(m, 2H), 2.78-3.01(m, 5H), 1.74-2.33(m, 5H), and 0.80-0.91(m, 4H). LCMS: (FA) ES+ 595.5, ES− 593.6. |

-continued

I-312 ¹H NMR(400MHz, CD₃OD, HCl salt) δ: 8.09-8.23(m, 2H), 7.99(s, 1H), 7.61(s, 1H), 7.52(s, 1H), 7.15-7.26(m, 1H), 6.88-6.96(m, 2H), 6.68-6.75(m, 1H), 5.35-5.56(m, 1H), 4.51(s, 2H), 3.40-3.71(m, 4H), 2.81-3.16(m, 5H), 2.10-2.57(m, 6H), and 1.87-2.01(m, 1H). LCMS: (FA) ES+ 571.4, ES− 569.4.

I-214 ¹H NMR(300MHz, d₆-DMSO) δ: 11.81(br s, 1H), 10.19(s, 1H), 8.154(d, 1H), 7.89(s, 1H), 7.68(s, 1H), 7.65(s, 1H), 7.62(d, 1H), 7.39(dd, 1H), 7.19(dd, 1H), 6.85(ddd, 1H), 6.61(dd, 1H), 2.96-2.88(m, 1H), 2.85-2.67(m, 2H), 2.18-2.02(m, 1H), 1.90(t, 3H), 1.94-1.86(m, 1H), 1.81-1.70(m, 1H), 1.21(br s, 1H), 0.85-0.80(m, 1H), and 0.76-0.70(m, 3H). LCMS: (FA) ES+ 492.2, ES− 490.3

I-250 ¹H NMR(400MHz, d₆-DMSO) δ: 1.51(br, 1H), 10.73(s, 1H), 9.11(s, 2H), 8.21(d, 1H), 8.09(s, 1H), 8.06(s, 1H), 7.65(s, 1H), 7.38(s, 1H), 7.23(d, 1H), 7.00(m, 1H), 6.95-6.98(m, 1H), 6.81-6.86(m, 1H), 4.16-4.21(m, 2H), 2.77-3.02(m, 6H), 2.68(s, 1H), 2.09-2.17(m, 1H), 1.92-2.00(m, 1H), 1.74-1.87(m, 1H), 1.21(t, 3H), and 0.76-0.84(m, 4H). LCMS: (FA) ES+ 553.4, ES− 551.5.

I-378 ¹H NMR(400MHz, d₆-DMSO) δ: 11.59(br s, 1H), 10.74(s, 1H), 9.23(br s, 2H), 8.21(d, 1H), 8.09(s, 1H), 8.06(s, 1H), 7.66(s, 1H), 7.37(s, 1H), 7.23(d, 1H), 7.00(m, 1H), 6.94-6.99(m, 1H), 6.81-6.85(m, 1H), 4.19-4.23(m, 4H), 3.59-3.62(m, 2H), 3.29(s, 3H), 3.08-3.14(m, 2H), 2.78-2.97(m, 5H), 2.09-2.16(m, 1H), 1.89-1.99(m, 1H), 1.74-1.85(m, 1H), and 0.80-0.89(m, 4H). LCMS: (FA) ES+ 583.4.

I-413 ¹H NMR(400MHz, d₆-DMSO) δ: 11.78(br s, 1H), 10.82(s, 1H), 9.14(s, 2H), 8.23(d, 1H), 8.11(s, 1H), 8.08(s, 1H), 7.71(s, 1H), 7.31(s, 1H), 7.24(d, 1H), 7.02-7.03(m, 1H), 6.96-6.99(m, 1H), 6.87-6.90(m, 1H), 4.16-4.21(m, 2H), 3.26-3.31(m, 1H), 2.77-2.98(m, 5H), 2.09-2.16(m, 1H), 1.93-1.99(m, 1H), 1.77-1.84(m, 1H), 1.29-1.32(m, 5H), and 0.83-0.92(m, 4H). LCMS: (FA) ES+ 567.4, ES− 565.5.

I-212 ¹H NMR(400MHz, CD₃OD, HCl salt) δ: 10.06(s, 1H), 8.21(d, 1H), 7.67(s, 1H), 7.59(s, 1H), 7.31(d, 1H), 7.28(s, 1H), 7.20(dd, 1H), 7.05(d, 1H), 7.00(dd, 1H), 6.74(d, 1H), 4.09(a, 2H), 2.82-3.15(m, 4H), 2.22(m, 2H), 1.89-2.00(m, 1H), 1.78-1.85(m, 1H), 1.35(s, 9H), and 1.02-1.14(m, 4'H). LCMS: (FA) ES+ 513.5, ES− 511.5.

I-223 ¹H NMR(300MHz, CD₃OD, HCOOH) δ: 8.11(d, 1H), 7.63(d, 1H), 7.58(d, 2H), 7.22(s, 1H), 7.16(d, 1H), 6.85-6.88(m, 2H), 6.62(d, 1H), 3.92(s, 2H), 2.86-3.10(m, 9H), 2.15-2.19(m, 1H), 1.93-1.96(m, 4H), 1.82-1.84(m, 1H), 1.33(s, 9H), and 0.83-0.92(m, 5H). LCMS: (FA) ES+ 613.0.

I-149 ¹H NMR(400MHz, d₆-DMSO, HCl salt) δ: 12.13(s, 1H), 11.04(br s, 1H), 8.64(s, 1H), 8.27(d, 1H), 8.14-8.19(m, 2H), 8.04-8.06(m, 1H), 7.89(d, 1H), 7.53-7.56(m, 1H), 7.46(s, 1H), 6.92-6.94(m, 1H), 6.47(s, 1H), 2.06(s, 3H), and 1.29(s, 9H). LCMS: (FA) ES+ 445.6, ES− 443.2.

I-152 ¹H NMR(400MHz, d₆-DMSO, HCl salt) δ: 11.06(br s, 1H), 10.85(s, 1H),
I-433 10.69(br s, 1H), 8.62(s, 1H), 8.27(d, 1H), 8.17(t, 2H), 8.04-8.06(m, 1H), 7.93(s, 1H), 7.88-7.90(m, 2H), 7.52-7.55(m, 1H), 7.51(s, 1H), 7.09(s, 1H), 6.90-6.92(m, 1H), 4.44(t, 2H), 3.58-3.62(m, 4H), 3.07-3.16(m, 2H), 2.06(s, 3H), 1.96-2.04(m, 2H), and 1.85-1.92(m, 2H). LCMS: (FA) ES+ 579.3, ES− 577.4.

I-304 ¹H NMR(400MHz, d₆-DMSO, HCl salt) δ: 10.64(s, 1H), 9.34(d, 1H), 8.38(d, 1H), 8.36(br s, 2H), 8.03(s, 2H), 7.85(d, 1H), 7.58(s, 1H), 7.41(d, 1H), 7.23(d, 1H), 7.07(6.99, 3H), 6.58-6.57(m, 1H), 4.09(q, 2H), 2.96-2.82(m, 5H), 2.15-2.09(m, 1H), and 1.86-1.76(m, 1H). LCMS: (FA) ES+ 524.3, ES− 522.4.

I-400 ¹H NMR(400MHz, d₆-DMSO, HCl salt) δ: 10.65(s, 1H), 8.59-8.58(m, 1H), 8.37(br s, 2H), 8.34(d, 1H), 8.03(s, 2H), 7.76-7.75(m, 1H), 7.58(s, 1H), 7.26-7.24(m, 2H), 7.06-7.05(m, 1H), 7.03-6.99(m, 1H), 6.96-6.94(m, 1H), 6.55-6.64(m, 1H), 4.09(q, 2H), 2.98-2.85(m, 5H), 2.16-2.10(m, 1H), and 1.88-1.78(m, 1H). LCMS: (FA) ES+ 508.3, ES− 506.4.

I-205 ¹H NMR(300MHz, d₆-DMSO, HCl salt) δ: 10.77(s, 1H), 9.73(s, 1H), 8.45(d, 2H), 8.39(s, 2H), 8.05(d, 2H), 7.79(s, 1H), 7.75(d, 1H), 7.59(s, 1H), 7.26(d, 1H), 7.04-6.98(m, 2H), 6.96-6.93(m, 1H), 4.10-4.07(m, 2H), 2.98-2.85(m, 5H), 2.17-2.09(m, 1H), and 1.88-1.74(m, 1H). LCMS: (FA) ES+ 508.3, ES− 506.3.

I-330 ¹H NMR(300MHz, d₆-DMSO, HCl salt) δ: 10.59(s, 1H), 9.35(s, 1H), 8.42(d, 1H), 8.34(br s, 2H), 8.25(s, 1H), 8.03(d, 2H), 7.57(s, 1H), 7.26(d, 1H), 7.20(d, 1H), 7.07-7.01(m, 3H), 4.11-4.07(m, 2H), 2.98-2.83(m, 5H), 2.17-2.09(m, 1H), and 1.87-1.76(m, 1H). LCMS: (FA) ES+ 509.2, ES− 507.3.

I-344 ¹H NMR(400MHz, d₆-DMSO, HCl salt) δ: 10.76(s, 1H), 10.67(br s, 1H), 8.66(s, 1H), 8.49(d, 1H), 8.34(s, 1H), 8.11(d, 2H), 7.72-7.67(m, 2H), 7.28(d, 1H), 7.09(s, 1H), 7.07-7.04(m, 1H), 6.95-6.92(m, 1H), 4.43-4.41(m, 2H), 3.92(s, 3H), 3.38-3.32(m, 2H), 3.10-2.84(m, 7H), 2.17-2.11(m, 1H), 2.04-1.98(m, 2H), and 1.91-1.79(m, 3H). LCMS: (FA) ES+ 576.5(M+1), ES− 574.5(M−1).

I-257 ¹H NMR(400MHz, d₆-DMSO, HCl salt) δ: 10.12(s, 1H), 9.44(s, 1H), 9.02(d, 1H), 8.90-8.96(m, 1H), 8.65(d, 1H), 8.00-8.07(m, 1H), 7.93-7.97(m, 1H), 7.65-7.69(m, 1H), 7.49-7.54(m, 1H), 7.17-7.27(m, 2H), 6.97-7.08(m, 4H), 2.76-3.00(m, 5H), 2.06-2.14(m, 1H), 1.73-1.84(m, 1H), and 1.25(s, 9H). LCMS: (FA) ES+ 478.3, ES− 476.4.

| | |
|---|---|
| I-294 | ¹H NMR(400MHz, d₆-DMSO, HCl salt) δ: 10.79(s, 1H), 9.42(s, 2H), 9.28(s, 1H), 8.63(d, 1H), 8.47(br s, 3H), 8.08(s, 1H), 8.03(s, 1H), 7.88(s, 1H), 7.60(s, 1H), 7.24(d, 1H), 6.98-7.05(m, 2H), 6.92-6.96(m, 1H), 4.04-4.11(m, 2H), 2.78-2.99(m, 5H), 2.08-2.16(m, 1H), and 1.75-1.87(m, 1H). LCMS: (FA) ES+ 520.4, ES− 518.4. |
| I-234 | ¹H NMR(400MHz, d₆-DMSO, HCl salt) δ: 11.32(br s, 1H), 10.76(s, 1H), 8.23(d, 1H), 8.11(s, 1H), 8.06(br s, 1H), 7.67-7.75(m, 1H), 7.29(s, 1H), 7.24(d, 1H), 6.95-7.03(m, 2H), 6.85-6.90(m, 1H), 4.09-4.48(m, 2H), 3.09-3.63(m, 8H), 2.72-2.99(m, 8H), 2.06-2.17(m, 4H), and 1.72-1.86(m, 1H). LCMS: (FA) ES+ 582.1, ES− 580.2. |
| I-184 | ¹H NMR(400MHz, d₆-DMSO, HCl salt) δ: 10.78(s, 1H), 8.59(d, 1H), 8.45(br s, 2H), 7.99-8.14(m, 2H), 7.60(s, 1H), 7.23-7.34(m, 2H), 6.94-7.11(m, 3H), 4.04-4.12(m, 2H), 2.76-3.02(m, 5H), 2.52(s, 3H), 2.32(s, 3H), 2.07-2.17(m, 1H), and 1.75-1.86(m, 1H). LCMS: (FA) ES+ 537.3, ES− 535.5. |
| I-183 | ¹H NMR(400MHz, d₆-DMSO, HCl salt) δ: 10.86(s, 1H), 8.95(d, 2H), 8.67(d, 1H), 8.44-8.61(m, 4H), 8.10(s, 1H), 8.00-8.07(m, 2H), 7.60(s, 1H), 7.24(d, 1H), 6.98-7.08(m, 3H), 4.03-4.12(m, 2H), 2.78-3.02(m, 5H), 2.08-2.18(m, 1H), and 1.74-1.87(m, 1H). LCMS: (FA) ES+ 519.5, ES− 517.4. |
| I-357 | ¹H NMR(400MHz, d₆-DMSO, HCl salt) δ: 10.83(s, 1H), 9.40(s, 1H), 8.85-8.94(m, 2H), 8.63(d, 1H), 8.47(br s, 2H), 8.09(s, 1H), 8.03(s, 1H), 7.86-7.97(m, 2H), 7.60(s, 1H), 7.24(d, 1H), 6.95-7.06(m, 3H), 4.02-4.12(m, 2H), 2.76-3.02(m, 5H), 2.07-2.16(m, 1H), and 1.74-1.88(m, 1H). LCMS: (FA) ES+ 519.3, ES− 517.4. |
| I-267 | ¹H NMR(400MHz, d₆-DMSO, HCl salt) δ: 8.49(br s, 2H), 8.23(d, 1H), 8.14(m, 1H), 8.08(m, 1H), 7.64(d, 2H), 7.35(m, 1H), 7.13-7.20(m, 2H), 7.00(d, 1H), 6.91(m, 1H), 5.05(s, 1H), 4.44(br s, 2H), 4.08(m, 2H), 3.64(s, 1H), 1.97(m, 1H), and 0.80-0.92(m, 4H). LCMS: (AA) ES+ 525.6, ES− 523.6. |
| I-398 | ¹H NMR(400MHz, CDCl₃) δ: 8.64(s, 1H), 8.08(t, 1H), 7.67-7.79(m, 3H), 7.49(s, 1H), 7.27(s, 1H), 6.79-6.96(m, 3H), 6.68(m, 1H), 6.62(m, 1H), 5.08(m, 1H), 4.90(s, 1H), 4.30(m, 2H), 1.55(m, 1H), 1.45(s, 9H), 1.01(m, 2H), 0.87(m, 2H). LCMS: (AA) ES+ 625.6, ES− 623.6. |
| I-447 | ¹H NMR(400MHz, d₆-DMSO, HCl salt) δ: 9.27(br s, 1H), 8.23(d, 1H), 8.18(m, 1H), 8.10(d, 1H), 7.68(d, 1H), 7.60(s, 1H), 7.38(m, 1H), 7.06-7.21(m, 3H), 7.01(d, 1H), 6.89(m, 1H), 5.05(s, 1H), 4.38(br s, 2H), 4.17(m, 2H), 2.54(m, 3H), 1.96(m, 1H), and 0.80-0.92(m, 4H). LCMS: (AA) ES+ 539.6, ES− 537.6. |
| I-429 | ¹H NMR(300MHz, CDCl₃) δ: 8.35(s, 1H), 8.09(t, 1H), 7.82(m, 1H), 7.71(dd, 2H), 7.56(d, 1H), 7.23(m, 1H), 6.83-6.98(m, 3H), 6.75(s, 1H), 6.62(s, 1H), 5.00(s, 1H), 4.43(s, 2H), 3.66(s, 1H), 2.86(s, 3H), 1.53(m, 1H), 1.47(s, 9H), 1.02(m, 2H), and 0.87(m, 2H). LCMS: (AA) ES+ 639.6, ES− 637.6. |
| I-456 | ¹H NMR(300MHz, CD₃OD, HCOOH salt) δ: 8.10(d, 1H), 7.61(br, 2H), 7.44(s, 1H), 7.18(d, 1H), 7.02(s, 1H), 6.88(s, 1H), 6.86(d, 1H), 6.65(dd, 1H), 3.50(br, 3H), 3.41(br, 4H), 2.94(s, 3H), 2.78-3.05(m, 6H), 2.17(m, 1H), 1.84(m, 2H), and 0.91(m, 4H). LCMS: (FA) ES+ 594.4, ES− 592.5. |
| I-434 | ¹H NMR(400MHz, d₆-DMSO, HCl salt) δ: 11.09(br s, 1H), 10.40(s, 1H), 8.57(s, 1H), 8.27(d, 1H), 8.13-8.19(m, 2H), 8.03-8.06(m, 1H), 7.91(d, 1H), 7.73(d, 1H), 7.50-7.53(m, 1H), 7.45(br s, 1H), 7.29(t, 1H), 7.15(d, 1H), 6.93-6.95(m, 1H), and 2.07(s, 3H). LCMS: (FA) ES+ 454.4, ES− 452.3. |

Example 13

Preparation of N-(3-tert-butylphenyl)-7-({2-[(methylsulfonyl)amino]pyridin-4-yl}-oxy)-1,2,3,4-tetrahydronaphthalene-2-carboxamide I-254 ( )

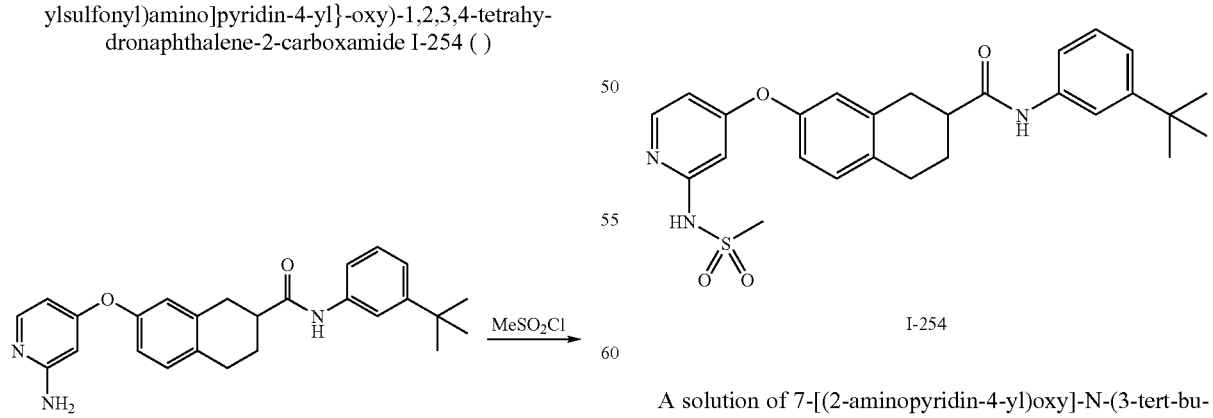

I-254

A solution of 7-[(2-aminopyridin-4-yl)oxy]-N-(3-tert-butylphenyl) -1,2,3,4-tetrahydronaphthalene-2-carboxamide (0.200 g, 0.481 mmol), THF (5.00 mL) and TEA (0.134 mL, 0.963 mmol) was allowed to stir under an atmosphere of nitrogen at 0° C. Methanesulfonyl chloride (0.558 mL, 0.721 mmol) in THF (0.2 mL) was added dropwise. The reaction was allowed to warm slowly to rt. After 3 h at rt, water was added and the product was extracted into EtOAc, the organic solutions were washed with water (2×) and brine, dried over $Na_2SO_4$, filtered and concentrated. The residue was purified by column chromatography to give N-(3-tert-butylphenyl)-7-({1-[(methylsulfonyl)amino]pyridin-4-yl}oxy)-1,2,3,4-tetrahydronaphthalene-2-carboxamide I-254 (54 mg, 21%) $^1$H NMR (400 MHz, $d_6$-DMSO; HCl salt) δ: 9.96 (s, 1H), 8.01 (d, 1H), 7.63 (dd, 2H), 7.49 (dd, 2H), 7.18-7.23 (m, 2H), 7.06 (d, 1H), 6.98 (d, 1H), 6.93 (dd, 1H), 6.53 (dd, 1H), 6.46 (d, 1H), 3.12 (s, 3H), 2.92 (d, 2H), 2.70-2.88 (m, 3H), 2.09 (d, 1H), 1.71-1.84 (m, 1H), and 1.26 (s, 9H). LCMS: (FA) ES+ 494.3, ES− 492.2.

Example 14

Preparation of ethyl (4-{[7-({[3-(aminomethyl)-5-(trifluoromethyl)phenyl]-amino}carbonyl)-5,6,7,8-tetrahydronaphthalen-2-yl]oxy}pyridin-2-yl)carbamate I-336 ( )

Step 1: tert-butyl [3-[({7-[(2-aminopyridin-4-yl)oxy]-1,2,3,4tetrahydronaphthalen-2-yl}-carbonyl)amino]-5-(trifluoromethyl)benzyl]carbamate To a solution of the hydrochloride salt of 7-[(2-aminopyridin-4-yl)oxy]-1,2,3,4-tetrahydronaphthalene-2-carboxylic acid (1.99 g), tert-butyl [3-amino-5-(trifluoromethyl)-benzyl]carbamate (1.98 g, 6.82 mmol), and DMAP (0.834 g, 6.82 mmol) in DMF (60 mL) was added EDCI (1.31 g, 6.82 mmol). The reaction mixture was allowed to stir at rt overnight under an atmosphere of nitrogen. The reaction mixture was diluted with water and extracted with EtOAc. The organic solutions were combined, washed with water and brine, dried over $Na_2SO_4$, filtered, and concentrated. The residue was purified by column chromatography to give tert-butyl [3-[({7-[(2-aminopyridin-4-yl)oxy]-1,2,3,4-tetrahydronaphthalen-2-yl}carbonyl)-amino]-5-(trifluoromethyl)benzyl]carbamate (2.45 g, 71%). LCMS: (FA) ES+ 557.9, ES+ 554.6.

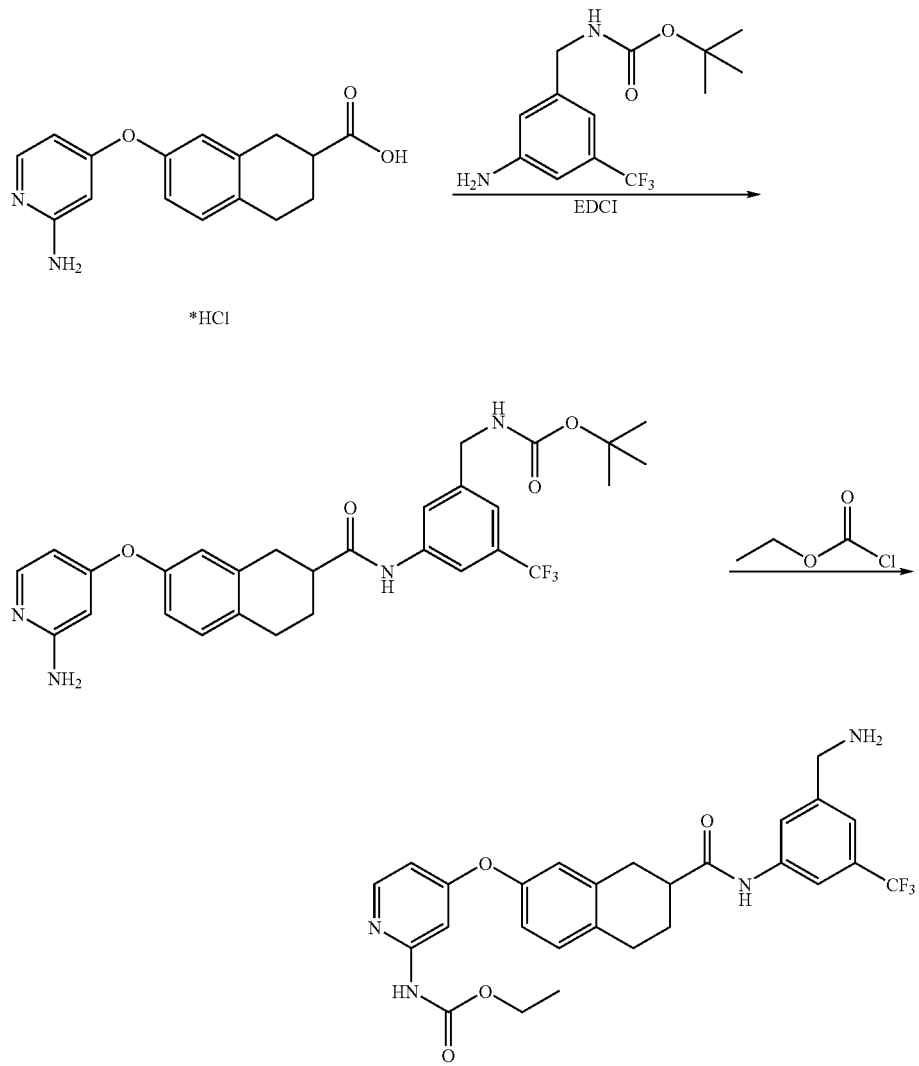

I-336

Step 2: Ethyl (4-{[7-({[3-(aminomethyl)-5-(trifluoromethyl)phenyl]amino}carbonyl)-5,6,7,8-tetrahydronaphthalen-2-yl]oxy}pyridin-2-yl)carbamate I-336

To a solution of 7-[(2-aminopyridin-4-yl)oxy]-N-(3-tert-butylphenyl)-1,2,3,4-tetrahydronaphthalene-2-carboxamide (0.456 g, 0.082 mmol) in pyridine (3 mL) at 0° C. was added ethyl chloroformate (0.102 mL, 1.06 mmol) in DCM (0.2 mL) dropwise. After 45 min, additional ethyl chloroformate (0.039 mL, 0.42 mmol) in DCM (0.2 mL) was added dropwise. After stirring for 1 hr, water was added and the solution was extracted with EtOAc. The organic solutions were combined, washed with water and brine, dried over $Na_2SO_4$, filtered, and concentrated. The residue was purified by column chromatography to give (264 mg, 52%). The material was treated with HCl to remove the protecting group and give ethyl (4-{[7-({[3-(aminomethyl)-5-(trifluoromethyl)phenyl]amino}carbonyl)-5,6,7,8-tetrahydronaphthalen-2-yl]oxy}pyridin-2-yl)carbamate I-336. $^1$H NMR (400 MHz, $d_6$-DMSO, HCl salt) δ: 10.70 (s, 1H), 10.67 (br s, 1H), 8.39 (br s, 3H), 8.18 (d, 1H), 8.04 (d, 2H), 7.59 (s, 1H), 7.24-7.21 (m, 2H), 7.00 (s, 1H), 6.97-6.95 (m, 1H), 6.77-6.75 (m, 1H), 4.13 (q, 2H), 4.11-4.06 (m, 2H), 2.96-2.82 (m, 5H), 2.15-2.09 (m, 1H), 1.85-1.75 (m, 1H), and 1.21 (t, 3H). LCMS: (FA) ES+ 529.7, ES− 526.9.

Compounds in the following table were prepared from the appropriate starting materials in a method analogous to that of Example 14:

| | |
|---|---|
| I-253 | $^1$H NMR(400MHz, $d_6$-DMSO; 2×HCl salt) δ: 10.89(s, 1H), 10.01(s, 1H), 8.20(d, 1H), 7.64(dd, 1H), 7.50(dd, 1H), 7.21(dd, 2H), 7.16(d, 1H), 7.06(ddd, 1H), 7.01(d, 1H), 6.96(d, 1H), 6.82(d, 1H), 3.70(s, 3H), 2.93(d, 2H), 2.73-2.89(m, 3H), 2.10(d, 1H), 1.72-1.83(m, 1H), and 1.26(s, 9H). LCMS: (FA) ES+ 474.3, ES− 472.3. |
| I-271 | $^1$H NMR(400MHz, $d_6$-DMSO, HCl salt) δ 13.23(br s, 1H), 10.79(s, 1H), 8.39(br s, 2H), 8.08(s, 1H), 8.02(s, 1H), 7.94(d, 1H), 7.82(br s, 2H), 7.59(s, 1H), 7.27(d, 1H), 7.05(s, 1H), 7.02(d, 1H), 6.64-6.61(m, 1H), 6.09-6.07(m, 1H), 4.09-4.06(m, 2H), 2.98-2.91(m, 5H), 2.15-2.09(m, 1H), and 1.85-1.77(m, 1H). LCMS: (FA) ES+ 457.5, ES− 455.5. |
| I-227 | 1H NMR(300MHz, CD3OD, HCl salt) δ: 8.30(d, 1H), 7.71(s, 1H), 7.68(s, 1H), 7.28(d, 1H), 7.12(d, 1H), 6.98-7.05(m, 3H), 6.76(s, 1H), 4.44(br, 2H), 3.89(s, 3H), 3.75(br, 4H), 3.30(m, 2H), 3.05(br, 2H), 2.95(br, 3H), 2.20(br, 3H), 2.08(br, 2H), and 1.92(m, 1H). LCMS: (FA) ES+ 599.3, ES− 597.6. |
| I-193 | $^1$H NMR(400MHz, $d_6$-DMSO, HCl salt) δ: 10.67(s, 1H), 10.64(br s, 1H), 8.36(br s, 3H), 8.17(d, 1H), 8.03(s, 2H), 7.58(s, 1H), 7.25(d, 1H), 7.23(d, 1H), 6.99(s, 1H), 6.97-6.94(m, 1H), 6.74-6.72(m, 1H), 4.09(q, 2H), 3.66(s, 3H), 2.97-2.82(m, 5H), 2.15-2.09(m, 1H), and 1.85-1.75(m, 1H). LCMS: (FA) ES+ 515.5, ES− 513.3. |
| I-241 | $^1$H NMR(400MHz, $d_6$-DMSO, HCl salt) δ: 10.86(br s, 1H), 10.72(br s, 2H), 8.64(s, 1H), 8.26(d, 1H), 8.18(t, 2H), 8.08-8.04(m, 1H), 7.95-7.87(m, 3H), 7.5-7.52(m, 1H), 7.32(s, 1H), 7.09(s, 1H), 6.91-6.86(m, 1H), 4.47-4.41(m, 2H), 3.65-3.56(m, 6H), 3.15-3.07(m, 2H), 2.08-1.95(m, 2H), and 1.96-1.84(m, 2H). LCMS: (FA) ES+ 595.1. |
| I-380 | $^1$H NMR(300MHz, $CD_3OD$, HCl Salt) δ: 8.56(d, 1H), 7.64(s, 1H), 7.43-7.40(m, 1H), 7.33-7.28(m, 3H), 7.22(t, 1H), 7.16-7.13(m, 1H), 7.04-6.98(m, 2H), 4.55(s, 2H), 3.68(s, 3H), 3.16-2.86(m, 5H), 2.25-2.18(m, 1H), 2.01-1.91(m, 1H), and 1.31(s, 9H). LCMS: (FA) ES+ 489.0, ES− 486.1. |
| I-192 | $^1$H NMR(400MHz, $CD_3OD$, HCl Salt) δ: 8.55(s, 1H), 8.04(s, 1H), 8.02(s, 1H), 7.53(s, 1H), 7.35-7.30(m, 3H), 7.05-6.99(m, 2H), 4.55(s, 2H), 4.19(s, 2H), 3.67(s, 3H), 3.16-2.87(m, 5H), 2.26-2.20(m, 1H), and 2.00-1.91(m, 1H). LCMS: (FA) ES+ 529.0, ES− 527.4. |
| I-372 | 1H NMR(400MHz, $d_6$-DMSO, HCl salt) δ: 10.74-10.98(m, 2H), 10.71(s, 1H), 8.24-8.26(m, 1H), 8.20(d, 1H), 8.11-8.14(m, 1H), 7.80(s, 1H), 7.61(s, 1H), 7.13-7.27(m, 3H), 7.00-7.04(m, 1H), 6.78-6.82(m, 1H), 5.05-5.07(m, 2H), 4.40-4.46(m, 2H), 3.67(s, 3H), 3.32-3.40(m, 2H), 3.00-3.10(m, 2H), and 1.82-2.06(m, 4H). LCMS: (FA) ES+ 569.3, ES− 567.6. |
| I-350 | $^1$H NMR(400MHz, $d_6$-DMSO, HCl salt) δ: 11.02-10.96(m, 1H), 10.10(s, 1H), 8.23(d, 1H, J=6.27Hz), 7.54-7.74(m, 1H), 7.54-7.61(m, 1H), 7.47(s, 1H), 7.18-7.27(m, 3H), 7.07-7.16(m, 2H), 7.00-7.03(m, 1H), 6.85-6.89(m, 1H), 5.04(s, 2H), 3.70(s, 3H), and 1.26(s, 9H). LCMS: (FA) ES+ 474.8, ES− 472.0. |
| I-240 | $^1$H NMR(400MHz, $d_6$-DMSO, HCl salt) δ: 10.79(s, 1H), 8.44(br s, 3H), 8.23(d, 1H), 8.07(s, 1H), 8.03(s, 1H), 7.59(s, 1H), 7.32(s, 1H), 7.25(d, 1H), 6.95-7.04(m, 2H), 6.86-6.91(m, 1H), 4.05-4.11(m, 2H), 3.29-3.38(m, 1H), 2.79-2.99(m, 5H), 2.06-2.24(m, 5H), and 1.73-1.98(m, 3H). LCMS: (FA) ES+ 539.5, ES− 537.6. |
| I-359 | $^1$H NMR(400MHz, $d_6$-DMSO, HCl salt) δ: 10.70-11.00(m, 2H), 8.23(d, 1H), 8.07-8.14(m, 2H), 7.76(s, 1H), 7.21-7.34(m, 2H), 6.95-7.05(m, 2H), 6.85-6.93(m, 1H), 4.41(d, 2H), 3.30-3.40(m, 2H), 2.78-3.10(m, 7H), 2.42(q, 2H), 2.09-2.17(m, 1H), 1.96-2.06(m, 3H), 1.75-1.92(m, 3H), and 1.04(t, 3H). LCMS: (FA) ES+ 567.8, ES− 565.7. |
| I-406 | $^1$H NMR(400MHz, $d_6$-DMSO, HCl salt) δ: 11.13(br s, 1H), 10.76(s, 1H), 9.12-9.21(m, 2H), 8.22(d, 1H), 8.07(s, 2H), 7.63(s, 1H), 7.35(br s, 1H), 7.24(d, 1H), 7.00-7.03(m, 1H), 6.95-6.99(m, 1H), 6.83-6.87(m, 1H), 4.15-4.20(m, 2H), 2.79-2.98(m, 5H), 2.53-2.57(m, 3H), 2.40(q, 2H), 2.09-2.16(m, 1H), 1.74-1.85(m, 1H), and 1.03(t, 3H). LCMS: (FA) ES+ 527.4, ES− 525.4. |

-continued

I-238 ¹H NMR(400MHz, d₆-DMSO, HCl salt) δ: 10.77(s, 1H), 8.42(br s, 3H), 8.23(d, 1H, J=6.52Hz), 8.07(s, 1H), 8.03(s, 1H), 7.59(s, 1H), 7.32(br s, 1H), 7.24(d, 1H, J=8.28Hz), 6.95-7.03(m, 2H), 6.86-6.89(m, 1H), 4.04-4.11(m, 2H), 2.78-3.00(m, 5H), 2.41(q, 2H), 2.07-2.17(m, 1H), 1.75-1.86(m, 1H), and 1.04(t, 3H). LCMS: (FA) ES+ 513.4, ES− 511.4.

Example 15

Preparation of N-(3-tert-butylphenyl)-7-[(2-{[(ethylamino)carbonyl]amino}-pyridin-4-yl)oxy]-1,2,3,4-tetrahydronaphthalene-2-carboxamide I-370 ( )

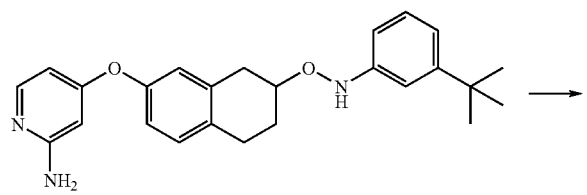

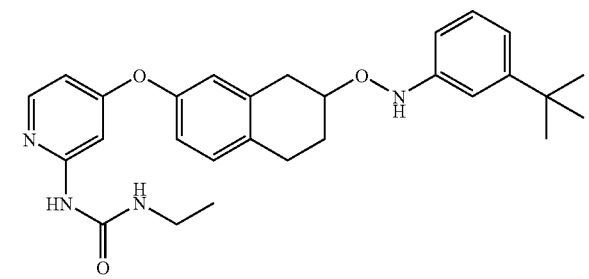

I-370

Example 16

Preparation of N-(3-tert-butylphenyl)-7-{[2-(1,4,5,6-tetrahydropyrimidin-2-yl)-pyridin-4-yl]oxy}-2-naphthamide I-245 ( )

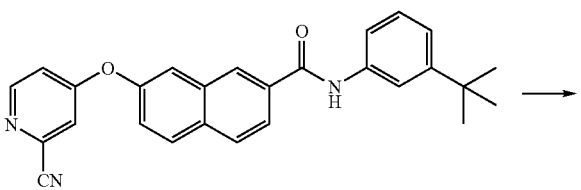

I-340

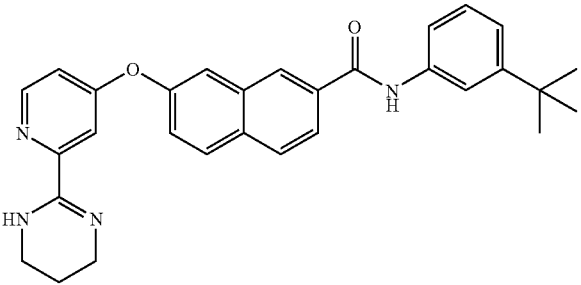

I-245

To a solution of 7-[(2-aminopyridin-4-yl)oxy]-N-(3-tert-butylphenyl)-1,2,3,4-tetrahydronaphthalene-2-carboxamide (0.183 g, 0.044 mmol) in THF (4.5 mL) under an atmosphere of nitrogen at 0° C. was added isocyanatoethane (0.035 mL, 0.44 mmol) in THF (0.2 mL) dropwise. The reaction mixture was allowed to warm to rt. After 3 h, additional isocyanatoethane (0.104 mL, 1.32 mmol) was added, and after 4 h isocyanatoethane (0.104 mL, 1.32 mmol) was added again. The reaction mixture was heated at 50° C. for 4 h and then diluted with water. The mixture was extracted with EtOAc. The organic solutions were combined, washed with water and brine, and dried over Na₂SO₄. The solution was filtered and concentrated. The residue was purified by column chromatography and then the product dissolved in DCM/MeOH. 2M HCl in Et₂O was added and the mixture was concentrated to give N-(3-tert-butylphenyl)-7-[(2-{[(ethylamino)carbonyl]amino}-pyridin-4-yl)oxy]-1,2,3,4-tetrahydronaphthalene-2-carboxamide I-370 as its HCl salt (143 mg, 62%). ¹H NMR (300 MHz, d₆-DMSO; HCl salt) δ: 10.02 (s, 1H), 8.16 (d, 1H), 7.65 (dd, 1H), 7.49 (d, 2H), 7.17-7.28 (m, 2H), 6.95-7.09 (m, 2H), 6.87 (d, 1H), 6.70 (s, 1H), 3.10-3.20 (, 2H), 2.72-2.97 (m, 5H), 2.09 (d, 1H), 1.71-1.81 (m, 1H), 1.26 (s, 9H), and 1.06 (dd, 3H). LCMS: (FA) ES⁺ 487.4, ES⁻ 485.3.

To a slurry of N-(3-tert-butylphenyl)-7-[(2-cyanopyridin-4-yl)oxy]-2-naphthamide I-340 (0.120 g, 0.285 mmol) in EtOH (6 mL) was added TEA (0.119 mL, 0.854 mmol). H2S was bubbled through the solution and then DCM was added to solubilize the mixture. The reaction mixture was allowed to stir at rt. When the reaction was complete, the mixture was diluted with EtOAc and poured into brine. The aqueous solution was extracted with EtOAc. The organic solutions were combined and loaded directly onto a silica gel column. The purified product was dissolved in MeOH and converted to the HCl salt by the addition of 1N HCl in Et2O. Concentration of the mixture gave N-(3-tert-butylphenyl)-7-{[2-(1,4,5,6-tetrahydropyrimidin-2-yl)pyridin-4-yl]oxy}-2-naphthamide I-245 ((0.104 g) as the HCl salt. ¹H NMR (400 MHz, CD₃OD; HCl salt) δ: 8.65 (d, 1H), 8.50 (s, 1H), 8.02-8.15 (m, 3H), 7.83 (d, 1H), 7.94 (dd, 1H), 7.70 (d, 1H), 7.57 (d, 1H), 7.45 (dd, 1H), 7.26-7.33 (m, 2H), 7.23 (d, 1H), 3.59 (dd, 4H), 2.05-2.12 (m, 2H), and 1.35 (s, 9H). LCMS: (FA) ES+ 479.2, ES− 477.2.

Compounds in the following table were prepared from the appropriate starting materials in a method analogous to that of Example 16:

| | |
|---|---|
| I-261 | $^1$H NMR(400MHz, CD$_3$OD: 2*COOH salt) δ: 8.60(d, 1H), 8.51(s, 2H), 8.40(s, 1H), 7.62(d, 1H), 7.41(dd, 1H), 7.22(dd, 2H), 7.17(dd, 1H), 6.96(d, 1H), 6.92(dd, 1H), 4.30(dd, 2H), 4.07(s, 4H), 3.16(dd, 4H), 2.99-3.14(m, 3H), 2.96(dd, 4H), 2.79(dd, 4H), 2.26(dd, 1H), and 1.91-2.03(m, 1H). LCMS: (FA) ES+ 609.7, ES− 608.0. |
| I-218 | $^1$H NMR(300MHz, d$_6$-DMSO, HCl salt) δ: 11.31(s, 1H), 11.11(s, 1H), 10.95(s, 1H), 9.18(s, 1H), 8.75(d, 1H), 8.35-8.27(m, 1H), 8.14-8.10(m, 1H), 8.06-8.03(m, 1H), 7.97-7.92(m, 2H), 7.87-7.82(m, 1H), 7.51-7.44(m, 1H), 7.12(s, 1H), 4.51-4.40(m, 3H), 3.65-3.52(m, 5H), 3.16-304(m, 2H), 2.06-1.83(m, 5H), and 1.33(d, 3H). LCMS: (FA) ES+ 605.1, ES− 603.4. |
| I-222 | $^1$H NMR(300MHz, d$_6$-DMSO, HCl salt) δ: 11.29(s, 1H), 10.94(s, 2H), 9.47(s, 1H), 9.15(s, 1H), 8.75(d, 1H), 8.29(d, 1H), 8.10-8.08(m, 1H), 8.04-8.03(m, 1H), 7.98-7.93(m, 2H), 7.87-7.82(m, 1H), 7.49-7.45(m, 1H), 4.49-4.43(m, 2H), 3.98(s, 4H), 3.67-3.53(m, 4H), 3.19-3.03(m, 2H), and 2.05-1.81(m, 4H). LCMS: (FA) ES+ 591.3, ES− 589.4. |
| I-396 | $^1$H NMR(400MHz, CD$_3$OD, HCl salt) δ: 9.66(s, 1H), 9.53(s, 1H), 8.78(d, 1H), 8.42(m, 2H), 8.25(dd, 1H), 8.19(s, 1H), 8.03(d, 1H), 7.88(d, 1H), 7.74(d, 1H), 7.45(dd, 1H), 4.32(s, 2H), and 4.13(s, 4H). LCMS: (FA) ES+ 507.5, ES− 505.8. |
| I-388 | $^1$H NMR(400MHz, CD$_3$OD, HCl salt) δ: 8.01(d, 1H), 7.79(d, 1H), 7.20(d, 1H), 6.81(d, 1H), 6.76(s, 1H), 6.65(s, 1H), 6.55(d, 1H), 6.39(dd, 1H), 6.27(d, 1H), 6.08(s, 1H), 5.86(dd, 1H), 2.71(s, 2H), and 2.57(s, 4H). MS: (FA) ES+ 507.5, ES− 505.7. |
| I-349 | $^1$H NMR(400MHz, CD$_3$OD) δ: 8.57(d, 1H), 8.53(s, 1H), 7.66(t, 1H), 7.62-7.50(m, 1H), 7.47-7.43(m, 1H), 7.39-7.36(m, 1H), 7.25(t, 1H), 7.20-7.16(m, 1H), 7.15-7.12(m, 1H), 7.10-7.08(m, 1H), 7.02-6.99(m, 1H), 6.98(s, 1H), 3.99(br s, 4H), 2.09-2.05(m, 3H), 1.33(s, 9H), and 1.28(s, 2H). LCMS: (FA) ES+ 471.3, ES− 469.0. |

Example 17

Preparation of N-(3-tert-butylphenyl)-7-({1-[imino(morpholin-4-yl)methyl]-pyridin-4-yl}oxy)-2-naphthamide I-990 ( )

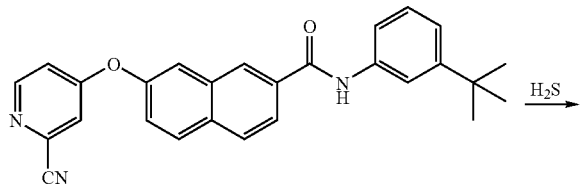

I-340

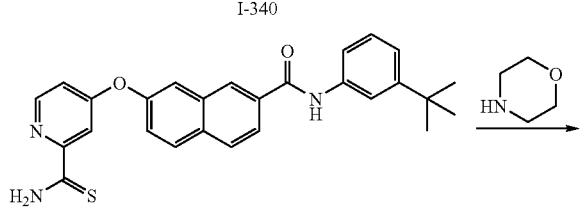

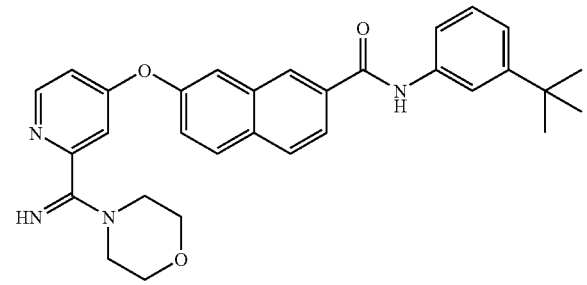

I-99

Step 1: 7-{[2-(aminocarbonothioyl)pyridin-4-yl]oxy}-N-(3-tert-butylphenyl)-2-naphthamide To a solution of N-(3-tert-butylphenyl)-7-[(2-cyanopyridin-4-yl)oxy]-2-naphthamide I-340 (1.37 g, 3.25 mmol) in DCM (20 mL) was added TEA (1.36 mL, 9.75 mmol). H$_2$S was bubbled into the reaction mixture. The vial was capped and the reaction mixture was allowed to stir at rt for 4 h. The solution was diluted with DCM and poured into brine. The solution was then extracted with EtOAc. The organic solutions were combined, dried over Na$_2$SO$_4$, filtered and concentrated to give a yellow solid which was sonicated with DCM, filtered and washed with hexanes to give 7-{[2-(aminocarbonothioyl)pyridin-4-yl]oxy}-N-(3-tert-butylphenyl)-2-naphthamide (1.13 g, 76%) as a light yellow solid which was used without further purification.

Step 2: N-(3-tert-butylphenyl)-7-({2-[imino(morpholin-4-yl)methyl]pyridin-4-yl}oxy)-2-naphthamide I-99)

Morpholine (2.00 mL, 22.9 mmol) and 7-{[2-(aminocarbonothioyl)pyridin-4-yl]-oxy}-N-(3-tert-butylphenyl)-2-naphthamide (0.155 g, 0. 34 mmol) were combined. The reaction mixture was allowed to stir at rt overnight in a sealed vial. And then heated at 60° C. for 6 h. The reaction mixture was diluted with EtOAc and poured into brine. The aqueous and organic solutions were separated and the aqueous solution was further extracted with EtOAc. The organic solutions were combined, dried over Na$_2$SO$_4$, and loaded onto a silica gel column. The product was collected from the column, concentrated, and redissolved in MeOH. To this solution was added 1M HCl in Et$_2$O. The solution was concentrated to give N-(3-tert-butylphenyl)-7-({2-[imino(morpholin-4-yl)methyl]pyridin-4-yl}oxy)-2-naphthamide I-99 (21 mg). $^1$H NMR (400 MHz, CD$_3$OD; 2*HCl salt) δ: 8.48 (d, 1H), 8.47 (s, 1H), 7.99-8.12 (m, 3H), 7.81 (dd, 2H), 7.58 (dd, 1H), 7.46 (dd, 1H), 7.31 (dd, 1H), 7.22 (ddd, 1H), 7.14 (d, 1H), 7.08 (d, 1H), 3.69 (dd, 4H), 3.31-3.33 (m, 4H), and 1.35 (s, 9H). LCMS: (FA) ES$^{30}$ 509.3, ES$^-$ 507.3.

Compounds in the following table were prepared from the appropriate starting materials in a method analogous to that of Example 17:

| | |
|---|---|
| I-93 | $^1$H NMR(400MHz, CD$_3$OD; 2*HCl salt) δ: 8.62(d, 1H), 8.52(s, 1H), 8.12(d, 1H), 8.07(d, 1H), 8.02(dd, 1H), 7.84(d, 1H), 7.80(s, 1H), 7.58(dd, 1H), 7.46(dd, 1H), 7.44(d, 1H), 7.29(dd, 1H), 7.22-7.24(m, 1H), 7.20-7.21(m, 1H), 3.61(dd, 4H), 1.96-2.02(m, 4H), and 1.34(s, 9H). LCMS: (FA) ES$^+$ 493.3, ES$^-$ 491.2. |
| I-317 | $^1$H NMR(300MHz, CD$_3$OD; 2*HCl salt) δ: 8.48(d, 1H), 8.45(s, 1H), 7.96-8.09(m, 3H), 7.79(dd, 1H), 7.43(d, 1H), 7.68(d, 1H), 7.58(dd, 1H), 7.42(dd, 1H), 7.29(d, 1H), 7.21(d, 1H), 7.08(dd, 2H), 3.29(dd, 2H), 1.34(s, 9H), and 1.24(dd, 3H). LCMS: (FA) ES+ 467.2, ES– 465.3. |
| I-354 | $^1$H NMR(300MHz, CD$_3$OD; 2*HCl salt) δ: 8.39-8.47(m, 1H), 7.39-8.03(m, 3H), 7.70(s, 1H), 7.68(dd, 2H), 7.55(dd, 1H), 7.39(d, 1H), 7.27(dd, 1H), 7.19(d, 1H), 7.03(d, 1H), 3.78-3.87(m, 1H), 1.32(s, 9H), and 1.19(d, 6H). LCMS: (FA) ES$^+$ 481.3, ES$^-$ 479.3. |
| I-260 | $^1$H NMR(300MHz, CD$_3$OD; 2*HCl salt) δ: 8.46(d, 1H), 8.40(s, 1H), 7.92-8.05(m, 3H), 7.76(dd, 1H), 7.69(d, 2H), 7.55(d, 1H), 7.36(dd, 1H), 7.25(dd, 1H), 7.17(ddd, 1H), 7.05(dd, 1H), 3.92(m, 1H), 1.96-2.07(m, 2H), 1.49-1.78(m, 6H), and 1.31(s, 9H). LCMS: (FA) ES+ 507.3, ES– 505.3. |
| I-265 | $^1$H NMR(400MHz, CD$_3$OD) δ 8.56(dd, 1H), 7.63(dd, 1H), 7.40(dd, 1H), 7.28(d, 1H), 7.23(dd, 2H), 7.09-7.17(m, 2H), 6.96(d, 1H), 6.93(dd, 1H), 3.79(dd, 2H), 3.57(dd, 3H), 3.05-3.13(m, 1H), 2.89-3.02(m, 3H), 2.78-2.89(m, 1H), 2.16-2.24(m, 1H), 1.89-2.01(m, 4H), and 1.31(s, 9H). LCMS: (FA) ES$^+$ 513.5. |
| I-280 | $^1$H NMR(300MHz, CD$_3$OD) δ: 8.58(d, 1H), 7.64(dd, 1H), 7.10(dd, 1H), 7.32(d, 1H), 7.24(d, 2H), 7.13-7.18(m, 2H), 6.90-6.98(m, 2H), 3.57(br. s, 3H), 2.77-3.15(m, 10H), 2.16-2.56(m, 1H), 1.88-2.01(m, 1H), and 1.31(s, 9H). |
| I-194 | $^1$H NMR(300MHz, CD$_3$OD) δ: 8.58(d, 1H), 8.51(br. s, 1H), 7.42(ddd, 1H), 7.33(d, 1H), 7.25(ddd, 2H), 7.12-7.19(m, 2H), 6.92-6.70(m, 2H), 3.53-3.67(m, 4H), 2.92-3.16(m, 4H), 2.71-2.91(m, 1H), 2.12-2.28(m, 3H), 1.91-2.06(m, 3H), and 1.32(s, 9H). LCMS: (FA) ES$^+$ 497.4. |
| I-178 | $^1$H NMR(300MHz, CD$_3$OD) δ: 3.57(d, 1H), 7.63(dd, 1H), 7.40(ddd, 1H), 7.30(d, 1H), 7.19-7.26(m, 2H), 7.12-7.17(m, 2H), 6.96(d, 1H), 6.94(dd, 1H), 3.58-3.63(m, 3H), 2.80-3.4(m, 7H), 2.59(dd, 3H), 2.35(s, 3H), 2.17-2.24(m, 1H), 1.94-2.00(m, 1H), and 1.31(s, 9H). LCMS: (FA) ES$^+$ 526.5. |
| I-450 | $^1$H NMR(400MHz, CD$_3$OD, HCl salt) δ: 8.60-8.65(m, 1H), 7.83(br s, 1H), 7.64(br s, 1H), 7.38-7.44(m, 1H), 7.21-7.27(m, 2H), 7.12-7.21(m, 2H), 6.90-6.99(m, 2H), 3.95-4.02(m, 2H), 3.52-3.59(m, 2H), 2.80-3.14(m, 11H), 2.15-2.24(m, 1H), 1.88-2.01(m, 1H), and 1.30(s, 9H). LCMS: (FA) ES+ 514.3, ES– 512.2 |

Example 18

Preparation of 4-{[7-({[3-({[(ethylamino)carbonyl]amino}methyl)-5-(trifluoromethyl)phenyl]amino}carbonyl)-5,6,7,8-tetrahydronaphthalen-2-yl]oxy}-N-methylpyridine-2-carboxamide I-420 ( )

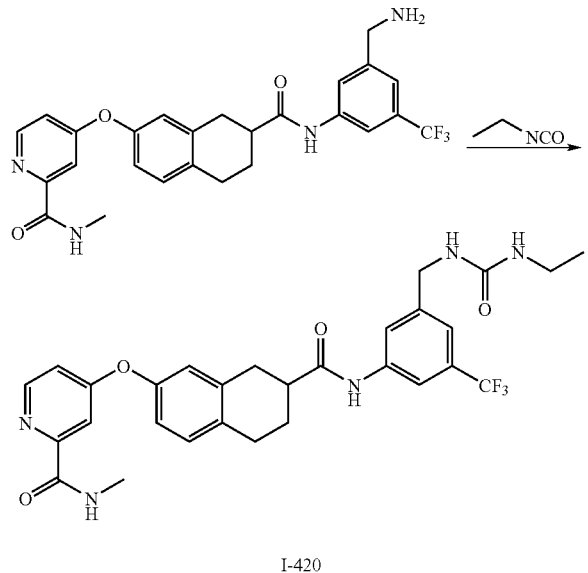

I-420

To a solution of 4-{[7-({[3-(aminomethyl)-5-(trifluoromethyl)phenyl]amino}-carbonyl)-5,6,7,8-tetrahydronaphtha-len-2-yl]oxy}-N-methylpyridine-2-carboxamide (0.411 g, 0.824 mmol) and TEA (0.23 mL, 1.65 mmol) in THF (10 mL) was added isocyanatoethane (0.10 mL, 1.26 mmol) in THF (5 mL) dropwise. The reaction mixture was allowed to stir at rt overnight. The reaction mixture was diluted with water and extracted with DCM. The organic solutions were combined, washed with brine, dried over MgSO$_4$, filtered, and concentrated. The residue was purified by column chromatography and then converted to the HCl salt of 4-{[7-({[3-({[(ethylamino)carbonyl]amino}methyl)-5-(trifluoromethyl)phenyl]amino}carbonyl)-5,6,7,8-tetrahydronaphthalen-2-yl]oxy}-N-methylpyridine-2-carboxamide I-420. $^1$H NMR (400 MHz, d$_6$-DMSO; HCl salt) δ: 10.42 (s, 1H), 8.84 (dd, 1H), 0.51 (dd, 1H), 8.03 (s, 1H), 7.68 (s, 1H), 7.41 (dd, 1H), 7.22-7.26 (m, 2H), 7.17 (dd, 1H), 7.01 (dd, 1H), 7.96 (dd, 1H), 4.23 (s, 2H), 3.01 (dd, 2H), 2.94 (dd, 2H), 2.80-2.90 (m, 3H), 2.77 (dd, 3H), 2.08-2.14 (m, 1H), 1.75-1.86 (m, 1H), and 0.98 (dd, 3H). LCMS: (FA) ES$^+$ 570.7, ES$^-$ 568.4.

Compounds in the following table were prepared from the appropriate starting materials in a method analogous to that of Example 18:

| | |
|---|---|
| I-314 | $^1$H NMR(400MHz, d$_6$-DMSO; HCl salt) δ: 10.39(s, 1H), 8.81(dd, 1H), 8.50(d, 1H), 8.01(s, 1H), 7.68(s, 1H), 7.39(d, 1H), 7.24(dd, 2H), 7.16(dd, 1H), 7.01(d, 1H), 6.97(dd, 1H), 4.23(s, 2H), 3.62-3.70(m, 1H), 2.94(d, 2H), 2.79-2.90(m, 3H), 2.77(d, 3H), 2.08-2.15(m, 1H), 1.75-1.86(m, 1H), and 1.02(d, 6H). LCMS: (FA) ES$^+$ 584.7, ES$^-$ 582.5. |

217

Example 19

Preparation of N-[3-(aminomethyl)-5-(trifluoromethyl)phenyl]-7-{[2-(pyrrolidin-1-ylcarbonyl)pyridin-4-yl]oxy}-1,2,3,4-tetrahydronaphthalene-2-carboxamide I-362 ( )

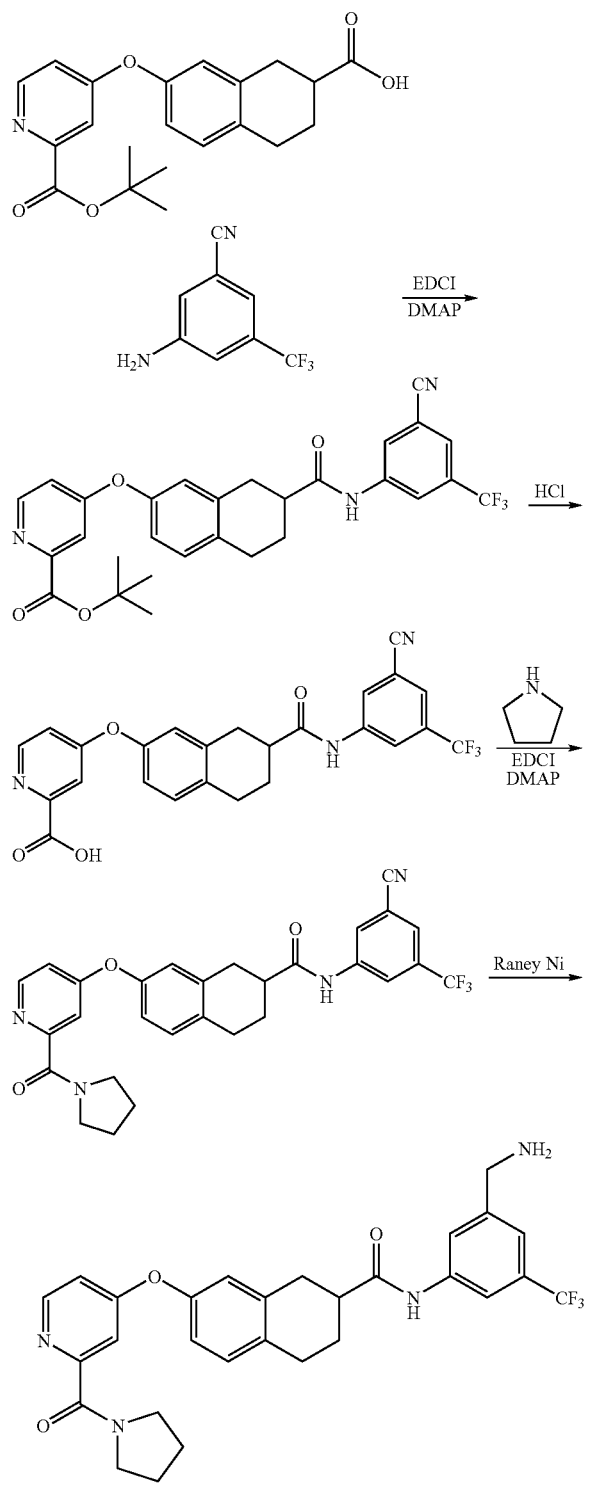

I-362

218

Step 1: tert-butyl 4-{[7-({[3-cyano-5-(trifluoromethyl)phenyl]amino}carbonyl)-5,6,7,8-tetrahydronaphthalen-2-yl]oxy}pyridine-2-carboxylate A solution of 7-{[2-(tert-butoxycarbonyl)pyridin-4-yl]oxy}-1,2,3,4-tetrahydronaphthalene-2-carboxylic acid (0.653 g, 1.77 mmol), 3-amino-5-(trifluoromethyl)-benzonitrile (0.362 g, 1.94 mmol), and DMAP (0.238 g, 1.94 mmol) in DCM (10 mL) was cooled to 0° C. To this solution was added EDCI (0.339 g, 1.77 mmol). The reaction mixture was allowed to stir and warm to rt overnight. The reaction mixture was diluted with EtOAc, washed with 1N HCl and sat. aq. NaHCO₃, and concentrated. The residue was purified by column chromatography to give tert-butyl 4-{[7-({[3-cyano-5-(trifluoromethyl)phenyl]-amino}carbonyl)-5,6,7,8-tetrahydronaphthalen-2-yl]oxy}pyridine-2-carboxylate (0.750 g, 79%). LCMS: (FA) ES$^+$ 538.6.

Step 2: 4-{[7-({[3-cyano-5-(trifluoromethyl)phenyl]amino}carbonyl)-5,6,7,8-tetrahydronaphthalen-2-yl]oxy}pyridine-2-carboxylic acid A solution of give tert-butyl 4-{[7-({[3-cyano-5-(trifluoromethyl)phenyl]-amino}carbonyl)-5,6,7,8-tetrahydronaphthalen-2-yl]oxy}pyridine-2-carboxylate (0.750 g, 1.40 mmol) in 2M HCl in dioxane (15 mL) was allowed to stir at rt overnight and then evaporated to give 4-{[7-({[3-cyano-5-(trifluoromethyl)phenyl]amino}carbonyl)-5,6,7,8-tetrahydronaphthalen-2-yl]oxy}pyridine-2-carboxylic acid (0.788 g), which was used without further purification.

Step 3: N-[3-cyano-5-(trifluoromethyl)phenyl]-7-{[2-(pyrrolidin-1-ylcarbonyl)pyridin-4-yl]oxy}-1,2,3,4-tetrahydronaphthalene-2-carboxamide To a mixture of -{[7-({[3-cyano-5-(trifluoromethyl)phenyl]amino}carbonyl)-5,6,7,8-tetrahydronaphthalen-2-yl]oxy}pyridine-2-carboxylic acid (0.385 g, 0.80 mmol), pyrrolidine (0.73 mL, 0.88 mmol) and DMAP (0.107 g, 0.88 mmol) in DCM (5 mL) at 0° C. was added EDCI (0.153 g, 0.80 mmol). The reaction mixture was allowed to stir and warm to rt overnight. The reaction mixture was loaded directly onto a silica gel column and purified by chromatography to give N-[3-cyano-5-(trifluoromethyl)phenyl]-7-{[2-(pyrrolidin-1-ylcarbonyl)-pyridin-4-yl]oxy}-1,2,3,4-tetrahydronaphthalene-2-carboxamide (0.310 g, 65%). LCMS: (FA) ES$^+$ 535.2.

Step 4: N-[3-(aminomethyl)-5-(trifluoromethyl)phenyl]-7-{[2-(pyrrolidin-1-ylcarbonyl)-pyridin-4-yl]oxy}-1,2,3,4-tetrahydronaphthalene-2-carboxamide ( )

A solution of N-[3-cyano-5-(trifluoromethyl)phenyl]-7-{[2-(pyrrolidin-1-ylcarbonyl)pyridin-4-yl]oxy}-1,2,3,4-tetrahydronaphthalene-2-carboxamide (0.310 g, 0.58 mmol) and Raney Ni (50% v/v in water, 2.0 mL) in 7M ammonia in MeOH (30 mL) was allowed to stir at rt under an atmosphere of hydrogen overnight. The reaction mixture was filtered over Celite, the Celite rinsed with MeOH, and the solution concentrated to give N-[3-(aminomethyl)-5-(trifluoromethyl)phenyl]-7-{[2-(pyrrolidin-1-ylcarbonyl)pyridin-4-yl]oxy}-1,2,3,4-tetrahydronaphthalene-2-carboxamide I-362 (0.205 g, 55%). $^1$H NMR (400 MHz, CD₃OD, HCl Salt) δ: 8.69 (d, 1H), 8.08 (s, 1H), 8.02 (s, 1H), 7.70 (d, 1H), 7.54 (s, 1H), 7.45-7.42 (dd, 1H), 7.31 (d, 2H), 7.09-7.03 (m, 2H), 4.20 (s, 2H), 3.65-3.59 (m, 4H), 3.15-2.91 (m, 5H), 2.25-2.21 (m, 1H), and 2.02-1.93 (m, 5H). LCMS: (FA) ES+ 539.8, ES– 537.5.

Compounds in the following table were prepared from the appropriate starting materials in a method analogous to that of Example 19:

---

I-229  ¹H NMR(400MHz, CD₃OD, HCl Salt) δ: 8.64(d, 1H), 8.07(s, 1H), 8.02-8.01(m, 1H), 7.54(s, 1H), 7.44-7.42(dd, 1H), 7.31(d, 1H), 7.06-7.00(m, 2H), 4.26-4.20(m, 1H), 4.12(s, 3H), 3.16-2.91(m, 5H), 2.26-2.21(m, 1H), 2.03-1.93(m, 1H), 1.28(s, 3H), and 1.27(s, 3H). LCMS: (FA) ES+ 527.9, ES– 525.4.

---

Example 20

Preparation of 6-{[2-(5-methyl-1H-imidazol-2-yl)pyridin-4-yl]oxy}-N-[3-(2-pyrrolidin-1-ylethoxy)-5-(trifluoromethyl)phenyl]quinoline-3-carboxamide I-409 ( )

To a solution of 6-{[2-(5-methyl-4,5-dihydro-1H-imidazol-2-yl)pyridin-4-yl]oxy}-N-[3-(2-pyrrolidin-1-ylethoxy)-5-(trifluoromethyl)phenyl]quinoline-3-carboxamide I-218 (0.500 g, 0.83 mmol) in DCM (20 mL) at 0° C. was added Dess-Martin periodinane (0.701 g, 1.65 mmol). The reaction mixture was allowed to stir at 0° C. overnight. Additional Dess-Martin periodinane (0.140 g, 0.32 mmol) was added and the reaction mixture was allowed to warm to rt until reaction was complete. Aq Na₂S₂O₃ was added and the reaction mixture was allowed to stir at rt for 10 min before the addition of sat. aq. NaHCO₃. The reaction mixture was extracted with DCM, concentrated, and purified by column chromatography to give 6-{[2-(5-methyl-1H-imidazol-2-yl)pyridin-4-yl]oxy}-N-[3-(2-pyrrolidin-1-ylethoxy)-5-(trifluoromethyl)phenyl]-quinoline-3-carboxamide I-409. ¹H NMR (300 MHz, d₆-DMSO, HCl salt) δ: 11.21 (s, 1H), 10.67-10.85 (br s, 1H), 9.45 (s, 1H), 9.11 (s, 1H), 8.71 (d, 1H), 8.29 (d, 1H), 8.13 (m, 1H), 8.04 (m, 1H), 7.94-7.91 (br s, 2H), 7.88-7.82 (m, 1H), 4.49-4.40 (m, 2H), 3.67-3.55 (m, 5H), 3.18-3.05 (m, 3H), 2.32 (s, 3H), and 2.08-1.84 (m, 5H). LCMS: (FA) ES+ 603.2, ES– 600.8.

Compounds in the following table were prepared from the appropriate starting materials in a method analogous to that of Example 20:

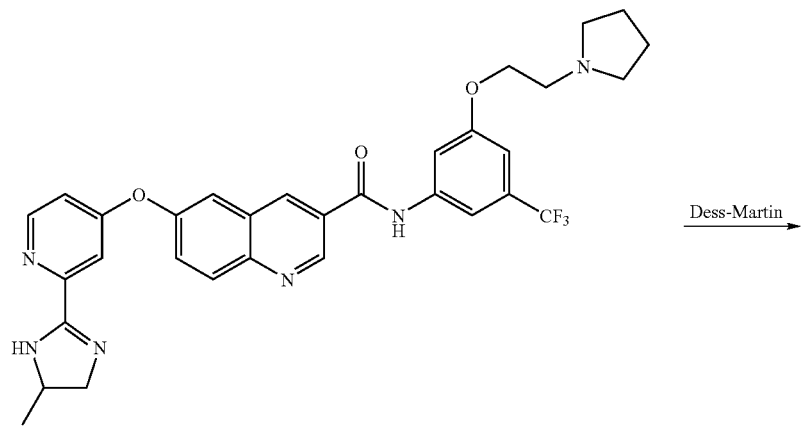

I-218

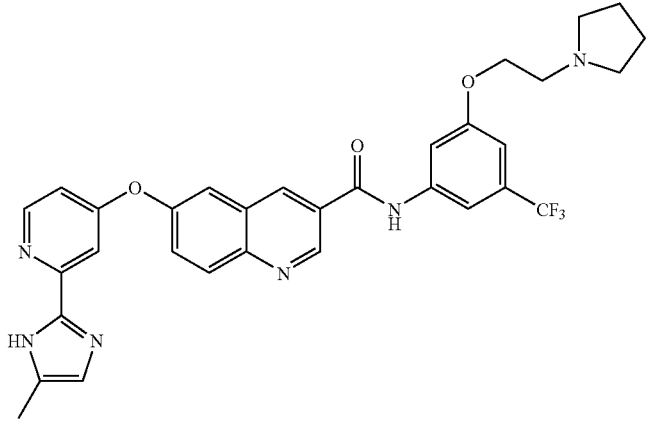

I-409

| | |
|---|---|
| I-341 | ¹H NMR(300MHz, d₆-DMSO, HCl salt) δ: 11.21(s, 1H), 10.93(br s, 1H), 9.46(s, 1H), 9.11(s, 1H), 8.76-8.70(m, 1H), 8.30(d, 1H), 8.20-8.10(m, 1H), 8.04(s, 1H), 7.92(s, 1H), 7.89-7.80(m, 3H), 7.39-7.29(m, 1H), 7.12(s, 1H), 4.51-4.42(m, 2H), 3.67-3.52(m, 4H), 3.20-3.05(m, 2H), 2.31(s, 1H), and 2.12-1.83(m, 4H). LCMS: (FA) ES+ 589.5, ES− 587.1. |
| I-315 | ¹H NMR(400MHz, CD₃OD, HCl salt) δ: 8.12(d, 1H, J=2.1Hz), 8.02(d, 1H), 7.20(d, 1H), 6.87(d, 1H), 6.85(d, 1H), 6.69(m, 1H), 6.67(s, 1H), 6.53(dd, 1H), 6.35(d, 1H), 6.17(d, 1H), 6.12(d, 2H), 5.80(dd, 1H), and 2.75(s, 2H). LCMS: (FA) ES+ 505.0, ES− 503.2. |
| I-418 | ¹H NMR(400MHz, CD₃OD, HCl salt) δ: 9.64(d, 1H), 9.51(s, 1H), 8.75(d, 1H), 8.40(d, 1H), 8.29(s, 1H), 8.23(s, 1H), 8.19(d, 1H), 8.04(dd, 1H), 7.88(d, 1H), 7.67(s, 2H), 7.63(s, 1H), 7.33(dd, 1H), and 4.25(s, 2H). LCMS: (FA) ES+ 505.1, ES− 503.0. |

Example 21

Preparation of N-[3-(aminomethyl)-5-(trifluoromethyl)phenyl]-7-{[2-(1,3-oxazol-5-yl)pyridin-4-yl]oxy}-1,2,3,4-tetrahydronaphthalene-2-carboxamide I-210

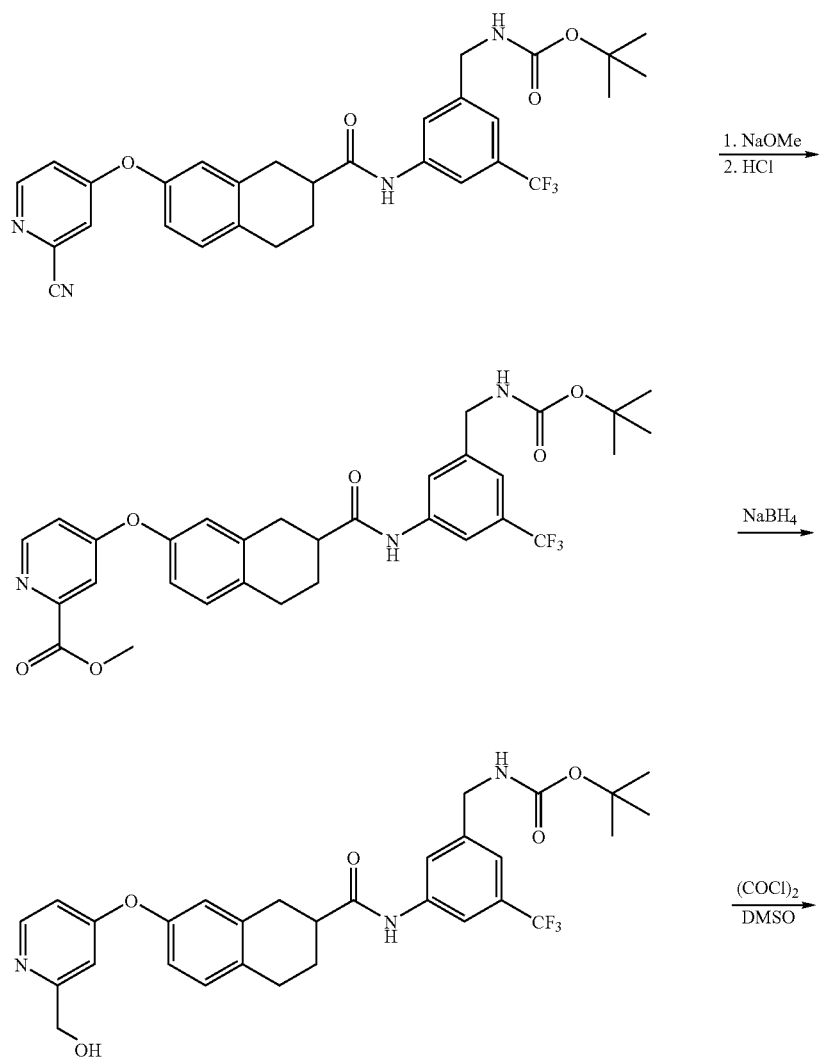

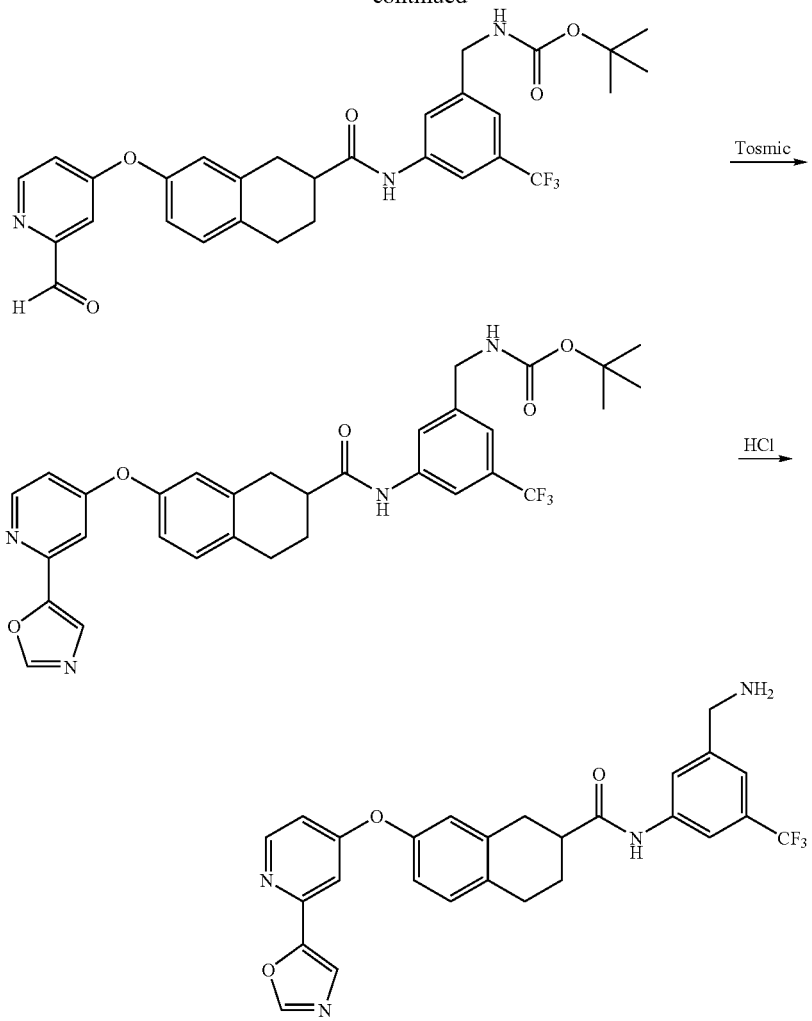

I-210

Step 1: methyl 4-{[7-({[3-{[(tert-butoxycarbonyl) amino]methyl}-5-(trifluoromethyl)phenyl]-amino}carbonyl)-5,6,7,8-tetrahydronaphthalen-2-yl]oxy}pyridine-2-carboxylate To a solution of tert-butyl [3-[({7-[(2-cyanopyridin-4-yl)oxy]-1,2,3,4-tetrahydronaphthalen-2-yl}carbonyl)amino]-5-(trifluoromethyl)benzyl]carbamate (2.00 g, 3.53 mmol) in MeOH (32 mL), was added a 25% solution of sodium methoxide in MeOH (0.402 mL, 1.76 mmol). The reaction mixture was heated at 65° C. for 90 min, then allowed to cool to rt. After the addition of 1N HCl solution (20.0 mL), the reaction mixture was allowed to stir at rt for 3 h. The mixture was basified by the addition of saturated NaHCO₃ and the MeOH was evaporated. The mixture was extracted with EtOAc and the organic solutions were combined, washed with brine, dried over Na₂SO₄, filtered and concentrated to give methyl 4-{[7-({[3-{[(tert-butoxycarbonyl)amino]methyl}-5-(trifluoromethyl)phenyl]-amino}carbonyl)-5,6,7,8-tetrahydronaphthalen-2-yl]oxy}pyridine-2-carboxylate (2.08 g, 98.3%). LCMS: (FA) ES+ 600.3, ES− 598.4.

Step 2: tert-butyl [3-{[(7-{[2-(hydroxymethyl)pyridin-4-yl]oxy}-1,2,3,4-tetrahydronaphthalen-2-yl)carbonyl]amino}-5-(trifluoromethyl)benzyl]carbamate To a solution of methyl 4-{[7-({[3-{[(tert-butoxycarbonyl)amino]methyl}-5-(trifluoromethyl)phenyl]amino}carbonyl)-5,6,7,8-tetrahydronaphthalen-2-yl]oxy}pyridine-2-carboxylate (1.03 g, 1.72 mmol) in MeOH (17 mL) at 0° C., was added sodium borohydride (0.39 g, 13.3 mmol) in small portions. The reaction mixture was allowed to warm slowly to rt and then allowed to stir for 18 h. Water was added and the precipitate which formed was filtered, washed with water and hexane and dried under vacuum to give tert-butyl [3-{[(7-{[2-(hydroxymethyl)pyridin-4-yl]oxy}-1,2,3,4-tetrahydronaphthalen-2-yl)carbonyl]amino}-5-(trifluoromethyl)benzyl]carbamate (913 mg, 93.0%) as a white solid. LCMS: (FA) ES+ 572.3, ES− 570.4.

Step 3: tert-butyl [3-[({7-[(2-formylpyridin-4-yl)oxy]-1,2,3,4-tetrahydronaphthalen-2-yl}-carbonyl)amino]-5-(trifluoromethyl)benzyl]carbamate To a solution of oxalyl chloride (0.086 mL, 1.02 mmol) in DCM (4 mL) at −78° C., was added a solution of DMSO (0.109 mL, 1.53 mmol) in DCM (1 mL) dropwise. The reaction mixture was allowed to stir at −78° C. for 30 min, and then a solution of tert-butyl [3-{[(7-{[2-(hydroxymethyl)pyridin-4-yl]oxy}-1,2,3,4-tetrahydronaphthalen-2-yl)carbonyl]amino}-5-(trifluoromethyl)benzyl]carbamate (292 mg, 0.51 mmol) in DCM (1 mL) was added dropwise. After 45 min. the reaction was incomplete. In a separate flask, oxalyl chloride (0.086 mL, 1.02 mmol) and DCM (4 mL) were cooled to −78° C., and a solution of DMSO (0.109 mL, 1.53 mmol) in DCM (1.00 mL) was added dropwise. The solution was stirred at −78° C. for 15 min, and then transferred via cannula to the reaction mixture and allowed to stir for 1 h. TEA (0.712 mL, 5.11 mmol) was added and the mixture was allowed to warm to rt. Water was added and the layers were separated. The organic solution was washed with brine, dried over Na₂SO₄, filtered and concentrated to give tert-butyl [3-[({7-[(2-formylpyridin-4-yl)oxy]-1,2,3,4-tetrahydronaphthalen-2-yl}carbonyl)amino]-5-(trifluoromethyl)benzyl]carbamate (285 mg, 97.9%). LCMS: (FA) ES+ 570.4.

Step 4: tert-butyl [3-{[(7-{[2-(1,3-oxazol-5-yl)pyridin-4-yl]oxy}-1,2,3,4-tetrahydronaphthalen-2-yl)carbonyl]amino}-5-(trifluoromethyl)benzyl]carbamate To a solution of tert-butyl [3-[({7-[(2-formylpyridin-4-yl)oxy]-1,2,3,4-tetrahydronaphthalen-2-yl}carbonyl)amino]-5-(trifluoromethyl)benzyl]carbamate (120 mg, 0.21 mmol) in MeOH (2 mL), was added potassium carbonate (116 mg, 0.84 mmol) and 1-[(isocyanomethyl)sulfonyl]-4-methylbenzene (45.2 mg, 0.23 mmol). The reaction mixture was heated at 70° C. for 30 min. and then allowed to cool to rt and the solvents were evaporated. The residue was dissolved in DCM, washed with water and brine, dried over Na₂SO₄, filtered and concentrated. The residue was purified by column chromatography to give tert-butyl [3-{[(7-{[2-(1,3-oxazol-5-yl)pyridin-4-yl]oxy}-1,2,3,4-tetrahydronaphthalen-2-yl)carbonyl]amino}-5-(trifluoromethyl)benzyl]carbamate (95.0 mg, 74.1%). LCMS: (FA) ES+ 609.3, ES− 607.4.

Step 5: N-[3-(aminomethyl)-5-(trifluoromethyl)phenyl]-7-{[2-(1,3-oxazol-5-yl)pyridin-4-yl]-oxy}-1,2,3,4-tetrahydronaphthalene-2-carboxamide I-210.

tert-butyl [3-{[(7-{[2-(1,3-oxazol-5-yl)pyridin-4-yl]oxy}-1,2,3,4-tetrahydronaphthalen-2-yl)carbonyl]amino}-5-(trifluoromethyl)benzyl]carbamate (95.0 mg, 0.16 mmol) was treated with a solution of 4M HCl in dioxane (2 mL) and the solution was allowed to stir for 1 h. The solvents were evaporated and the residue was purified by column chromatography to give N-[3-(aminomethyl)-5-(trifluoromethyl)phenyl]-7-{[2-(1,3-oxazol-5-yl)-pyridin-4-yl]oxy}-1,2,3,4-tetrahydronaphthalene-2-carboxamide carboxamide I-210. The HCl salt was prepared by dissolving the product in DCM and adding 2M HCl-Et₂O solution, followed by evaporation of the solvents. (35.0 mg, 38.6%). ¹H NMR (400 MHz, d₆-DMSO, HCl salt) δ: 10.64 (s, 1H), 8.52 (s, 1H), 8.50 (d, 1H), 8.34 (br s, 3H), 8.03 (s, 2H), 7.82 (s, 1H), 7.58 (s, 1H), 7.23-7.25 (m, 2H), 6.98-7.03 (m, 2H), 6.88-6.91 (m, 1H), 4.09 (q, 2H), 2.95-2.97 (m, 2H), 2.83-2.89 (m, 3H), 2.09-2.16 (m, 1H), and 1.76-1.85 (m, 1H). LCMS: (FA) ES+ 509.3, ES− 507.4.

Example 22

Preparation of 3-(aminomethyl)-N-[7-({2-[(cyclopropylcarbonyl)amino]pyridin-4-yl}oxy)-1,2,3,4-tetrahydronaphthalen-2-yl]-5-(trifluoromethyl)benzamide I-437

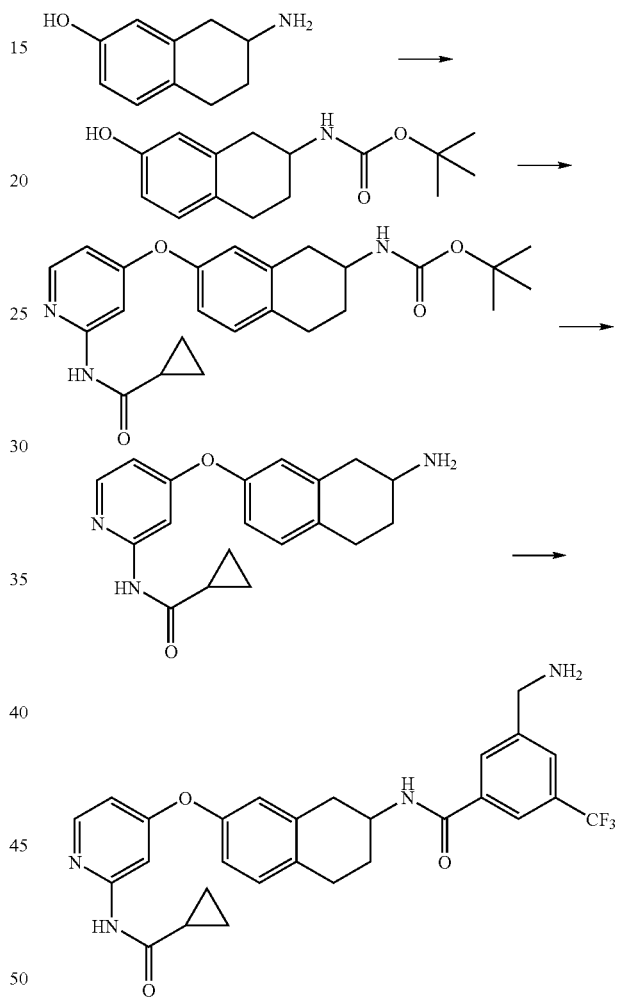

I-437

Step 1: tert-butyl (7-hydroxy-1,2,3,4-tetrahydronaphthalen-2-yl)carbamate

To a mixture of 7-amino-5,6,7,8-tetrahydronaphthalen-2-ol hydrochloric acid salt with 80% purity (3.78 g, 0.0104 mol) in DMF (12 mL, 0.15 mol) was added TEA (7.26 mL, 0.0521 mol) followed by di-tert-butyldicarbonate (2.96 g, 0.0135 mol) and reaction mixture was stirred at rt overnight. LCMS showed the completion of reaction. Water was added and the mixture was extracted with EtOAc. The organic layer was separated and washed with water, brine and then dried over magnesium sulfate. After evaporation, the crude product was purified flash chromatography to give tert-butyl (7-hydroxy-1,2,3,4-tetrahydronaphthalen-2-yl)carbamate (2.11 g, 76%). $^1$H NMR (400 MHz, CDCl$_3$) δ: 6.92 (d, 1H); 6.64 (dd, 1H); 6.54 (d, 1H); 4.65 (br, 1H); 3.92 (br, 1H); 3.00 (dd, 1H); 2.76 (t, 2H); 2.53 (dd, 1H); 2.00 (m, 1H); 1.70 (m, 1H); 1.46 (s, 9H). LCMS ES+ 264.3, ES− 262.4.

Step 2: tert-butyl [7-({2-[(cyclopropylcarbonyl)amino]pyridin-4-yl}oxy)-1,2,3,4-tetrahydronaphthalen-2-yl]carbamate A mixture of tert-butyl (7-hydroxy-1,2,3,4-tetrahydronaphthalen-2-yl)carbamate (2.07 g, 0.00707 mol), N-(4-nitropyridin-2-yl)cyclopropanecarboxamide (1.46 g, 0.00707 mol) and cesium carbonate (6.92 g, 0.0212 mol) in DMF was heated with stirring at 65° C. overnight. The reaction mixture was extracted with EtOAc. The organic solution was washed with water and brine, dried over MgSO$_4$, filtered, and concentrated. The residue was purified by column chromatography to tert-butyl [7-({2-[(cyclopropylcarbonyl)amino]pyridin-4-yl}oxy)-1,2,3,4-tetrahydronaphthalen-2-yl]carbamate. $^1$H NMR (CDCl$_3$, 300 MHz) δ: 9.18 (s, 1H); 8.02 (d, 1H); 7.82 (d, 1H); 7.32 (dd, 1H); 7.11 (d, 1H); 6.90 (d, 1H); 6.78 (s, 1H); 6.58 (dd, 1H); 4.60 (s, 1H); 4.1 (m, 1H); 3.96 (s, 1H); 3.10 (d, 1H); 2.86 (m, 2H); 2.61 (dd, 1H); 2.08 (m, 1H); 2.04 (m, 1H); 1.75 (m, 1H); 1.60 (m, 1H); 1.45 (s, 9H); 1.25 (m, 1H); 1.07 (m, 2H); 0.87 (m, 2H). LCMS ES+ 424.4; ES− 422.5.

Step 3: N-{4-[(7-amino-5,6,7,8-tetrahydronaphthalen-2-yl)oxy]pyridin-2-yl}-cyclopropanecarboxamide To tert-butyl [7-({2-[(cyclopropylcarbonyl)amino]pyridin-4-yl}oxy)-1,2,3,4-tetrahydronaphthalen-2-yl]carbamate (4.0 g, 0.0071 mol) was added HCl in dioxane (4M, 15 ml). After 2 h at rt, the solvent was removed. N-{4-[(7-amino-5,6,7,8-tetrahydronaphthalen-2-yl)oxy]pyridin-2-yl}cyclopropanecarboxamide was obtained as off white solid and was used without further purification (2.8 g). $^1$H NMR (d$_6$-DMSO, 400MHz, HCl salt) δ: 11.50 (s, 1H); 8.25 (s, 2H); 7.40 (s, 1H); 7.24 (d, 1H); 7.04 (d, 1H); 6.80 (dd, 1H); 6.82 (dd, 1H); 4.35 (s, 1H); 3.45 (s, 1H); 2.90 (dd, 1H); 2.85 (m, 3H); 2.14 (m, 1H); 1.95 (m, 1H); 1.77 (m, 1H); and 0.83 (m, 4H). LCMS ES+ 324.4, ES− 322.5

Step 4: 3-(aminomethyl)-N-[7-({2-[(cyclopropylcarbonyl)amino]pyridin-4-yl}-oxy)-1,2,3,4-tetrahydronaphthalen-2-yl]-5-(trifluoromethyl)benzamide I-437 To a mixture of N-{4-[(7-amino-5,6,7,8-tetrahydronaphthalen-2-yl)oxy]pyridin-2-yl}cyclopropanecarboxamide (160 mg, 0.00040 mol), 3-{[(tert-butoxycarbonyl)amino]methyl}-5-(trifluoromethyl)benzoic acid (130 mg, 0.00040 mol) and DIPEA (180 mg, 0.0014 mol) DMF (2 mL) was added N,N,N',N'-tetramethyl-O-(7-azabenzotriazol-1-yl)uronium hexafluorophosphate (210 mg, 0.00055 mol). The mixture was stirred at rt overnight. The mixture was extracted with EtOAc, washed with water and brine. The organic solutions were combined and the residue was purified by column chromatography. The resulting solid was dissolved in DCM. To this solution was added HCl in dioxane (2 ml). The solvent was removed to give 3-(aminomethyl)-N-[7-({2-[(cyclopropylcarbonyl)amino]pyridin-4-yl}oxy)-1,2,3,4-tetrahydronaphthalen-2-yl]-5-(trifluoromethyl)benzamide I-437 (152 mg, 93%). $^1$H NMR (CD$_3$OD, 400 MHz, HCl salt) δ: 8.37 (s, 1H); 8.27 (d, 1H); 8.23 (s, 1H); 8.04 (s, 1H); 7.32 (d, 2H); 7.16 (d, 1H); 7.10 (m, 2H); 6.81 (s, 1); 4.36 (m, 1H); 4.33 (s, 2H); 3.20 (m, 1H); 3.00 (m, 3H); 2.20 (d, 1H); 1.98 (m, 1H); 1.89 (m, 1H), and 1.08 (m, 4H). LCMS ES+ 525.5, ES− 523.5.

Compounds in the following table were prepared from the appropriate starting materials in a method analogous to that of Example 22:

| | |
|---|---|
| I-430 | $^1$H NMR(400MHz, d$_6$-DMSO, HCl salt) δ: 8.13(t, 1H), 8.00(d, 1H), 7.92(d, 2H), 7.76(t, 1H), 7.20(d, 1H), 6.85-6.92(m, 2H), 6.76(m, 1H), 4.53(m, 1H), 3.24(dd, 1H), 2.85-2.96(m, 3H), 2.00-2.20(m, 2H), 1.80(m, 1H), 1.35(s, 9H), 1.05-1.10(m, 2H), and 0.93-0.99(m, 2H). LCMS: (FA) ES+ 509.5, ES− 507.6. |
| I-441 | $^1$H NMR(400MHz, CD$_3$OD, HCl salt) δ: 8.37(s, 1H), 8.28(d, 1H), 8.22(s, 1H), 8.04(s, 1H), 7.32(d, 1H), 7.17(dd, 1H), 7.03(s, 1H), 7.01(m, 1H), 6.76(d, 1H), 4.33(s, 3H), 3.30(m, 1H), 3.07-3.24(m, 1H), 2.93-3.04(m, 3H), 2.26(s, 2H), 2.20(m, 1H), 1.91-2.03(m, 1H), and 1.02-1.14(m, 4'H). LCMS: (AA) ES+ 499.4, ES− 497.5. |
| I-432 | $^1$H NMR(400MHz, CDCl$_3$) δ: 9.59(s, 1H), 8.06(d, 1H), 8.04(s, 1H), 7.94(d, 1H), 7.74(s, 1H), 7.68(d, 1H), 7.49(t, 1H), 7.07(d, 1H), 6.99(d, 1H), 6.83(dd, 1H), 6.74(d, 1H), 6.57(dd, 1H), 4.44(m, 1H), 3.13(dd, 1H), 2.86(m, 2H), 2.75(m, 1H), 2.08-2.16(m, 4H), and 1.80-1.92(m, 1H). LCMS: (AA) ES+ 470.4, ES− 468.4. |
| I-421 | $^1$H NMR(400MHz, CDCl$_3$) δ: 9.10(s, 1H), 8.05(s, 1H), 7.70-7.76(m, 2H), 7.54(t, 1H), 7.01(d, 1H), 6.84(dd, 1H), 6.78(d, 1H), 6.61(dd, 1H), 6.54(d, 1H), 4.48(m, 1H), 3.18(dd, 1H), 2.90(m, 2H), 2.72-2.80(m, 1H), 2.01-2.09(m, 1H), 1.84-1.95(m, 1H), 1.56(m, 1H), 0.98-1.05(m, 2H), and 0.82-0.88(m, 2H). LCMS: (AA) ES+ 494.4, ES− 496.3. |
| I-428 | $^1$H NMR(400MHz, CDCl$_3$) δ: 9.16(s, 1H), 8.12(d, 1H), 8.07(d, 1H), 7.89(dd, 1H), 7.72(s, 1H), 7.53(d, 1H), 7.10(d, 1H), 6.85(dd, 1H), 6.80(d, 1H), 6.77(d, 1H), 6.60(dd, 1H), 4.45(m, 1H), 3.16(dd, 1H), 2.84-2.92(m, 2H), 2.72-2.80(m, 1H), 2.09-2.18(m, 4H), and 1.82-1.94(m, 1H). LCMS: (AA) ES+ 504.3, ES− 502.4. |
| I-443 | $^1$H NMR(400MHz, CDCl$_3$) δ: 9.61(s, 1H), 8.12(d, 1H), 8.07(d, 1H), 7.89(dd, 1H), 7.67(d, 1H), 7.50(d, 1H), 7.05(d, 2H), 6.82(d, 1H), 6.72(s, 1H), 6.60(m, 1H), 4.40(m, 1H), 3.06-3.15(m, 1H), 2.84(m, 2H), 2.69-2.78(m, 3H), 2.08(m, 1H), 1.84(m, 1H), 1.62(m, 1H), 0.98(m, 2H), and 0.83(m, 2H). LCMS: (AA) ES+ 530.4, ES− 528.5. |
| I-426 | $^1$H NMR(400MHz, d$_6$-DMSO, HCl salt) δ: 11.44(s, 1H), 8.57(d, 1H), 8.44(m, 2H), 8.23(d, 1H), 7.88(d, 2H), 7.72(m, 1H), 7.29(m, 1H), 7.25(d, 1H), 6.94-7.02(m, 2H), 6.90(dd, 1H), 4.20(m, 1H), 4.02-4.08(m, 2H), 3.02-3.10(m, 1H), 2.83-2.96(m, 3H), 2.12(s, 3H), 2.02-2.10(m, 1H), 1.78-1.89(m, 1H), 1.32(s, 9H), and 0.83(m, 2H). LCMS: (AA) ES+ 487.4, ES− 485.5. |

-continued

I-425 ¹H NMR(400MHz, d₆-DMSO, HCl salt) δ: 12.05(s, 1H), 8.59(d, 1H), 8.51(m, 2H), 8.24(d, 1H), 7.92(m, 1H), 7.86(m, 1H), 7.73(m, 1H), 7.30(d, 1H), 7.26(d, 1H), 6.97-7.03(m, 2H), 6.94(dd, 1H), 4.20(m, 1H), 4.05(m, 2H), 3.02-3.10(m, 1H), 2.84-2.95(m, 3H), 2.06(m, 1H), 1.98(m, 1H), 1.78-1.90(m, 1H), 1.32(s, 9H), and 0.84-0.95(m, 4H). LCMS: (AA) ES+ 513.5, ES− 511.6.

I-435 ¹H NMR(400MHz, d₆-DMSO, HCl salt) δ: 11.56(s, 1H), 8.45(d, 1H), 8.22(d, 1H), 7.86(m, 1H), 7.67(d, 1H), 7.54(d, 1H), 7.38(t, 1H), 7.28(m, 1H), 7.24(d, 1H), 6.95-7.01(m, 2H), 6.88(m, 1H), 4.18(m, 1H), 3.01-3.09(m, 1H), 2.78-2.95(m, 3H), 2.06(m, 1H), 1.86(m, 1H), 1.80(m, 1H), 1.30(s, 9H), and 0.80-0.90(m, 4H). LCMS: (AA) ES+ 484.4, ES− 482.4.

I-436 ¹H NMR(400MHz, d₆-DMSO, HCl salt) δ: 11.58(s, 1H), 8.48(d, 1H), 8.25(d, 1H), 7.87(s, 1H), 7.68(d, 1H), 7.55(d, 1H), 7.37(t, 1H), 7.26(d, 1H), 7.18(m, 1H), 7.02(m, 2H), 6.97(m, 1H), 4.19(m, 1H), 2.80-2.95(m, 3H), 2.14(s, 3H), 2.06(m, 1H), 1.82(m, 1H), and 1.30(s, 9H). LCMS: (AA) ES+ 458.4, ES− 456.5.

I-460 ¹H NMR(400MHz, d₆-DMSO, HCl salt) δ: 8.77(d, 1H), 8.49(d, 1H), 8.43(d, 1H), 7.85(s, 1H), 7.66(d, 1H), 7.53(d, 1H), 7.35-7.39(m, 2H), 7.22(d, 1H), 7.13(dd, 1H), 6.95-6.99(m, 2H), 4.19-4.20(m, 1H), 3.04-3.09(m, 1H), 2.82-2.92(m, 3H), 2.77(s, 3H), 2.04-2.06(m, 1H), 1.81-1.84(m, 1H), 1.30(s, 9H). LCMS: (FA) ES+ 458.0.

I-444 ¹H NMR(400MHz, d₆-DMSO) δ: 8.61(d, 1H), 8.25(s, 1H), 8.05(d, 1H), 7.85(s, 1H), 7.72(d, 1H), 7.40(dd, 1H), 7.30(d, 1H), 7.02(s, 2H), 4.27-4.36(m, 1H), 3.16-3.24(m, 1H), 3.00-3.05(m, 2H), 2.96(s, 3H), 2.84-2.92(m, 1H), 2.17-2.25(m, 1H), 1.88-1.95(m, 1H). LCMS: (FA) ES+ 504.0.

Example 23

Preparation of 4-chloro-N-(6-{[2-(4,5-dihydro-1H-imidazol-2-yl)pyridin-4-yl]-oxy}-3,4-dihydro-2H-chromen-3yl)-3-(trifluoromethyl)benzamide I-445

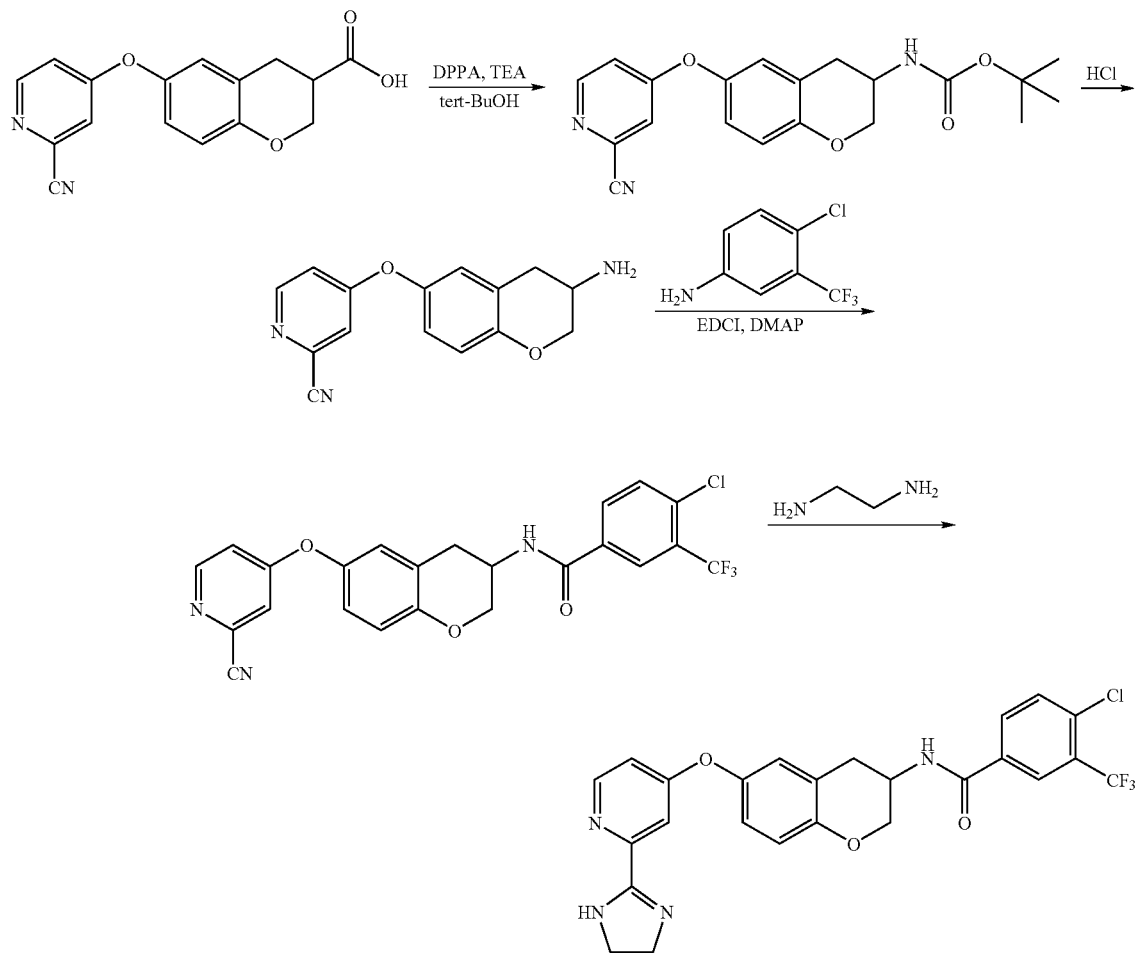

Step 1: tert-butyl {6-[(2-cyanopyridin-4-yl)oxy]-3,4-dihydro-2H-chromen-3-yl}carbamate To a solution of 6-[(2-cyanopyridin-4-yl)oxy]chromane-3-carboxylic acid (0.701 g, 2.37 mmol) in THF (25 mL) at 0° C. was added TEA (1.19 mL, 8.52 mmol) and then diphenylphosphonic azide (DPPA, 0.663 mL, 3.08 mmol). The reaction mixture was allowed to stir at 0° C. for 15 min and then at rt for 2 hr. The reaction mixture was concentrated at low temperature and the residue was dissolved in EtOAc, washed with sat. aq. NaHCO$_3$ and brine, dried over Na$_2$SO$_4$, filtered, concentrated at low temperature, and then dried under vacuum for 1 hr. The residue was redissolved in tert-butyl alcohol (12 mL) and heated at 90° C. overnight under an atmosphere of nitrogen. The reaction mixture was concentrated to give tert-butyl {6-[(2-cyanopyridin-4-yl)oxy]-3,4-dihydro-2H-chromen-3-yl}carbamate, which was used without further purification. LCMS: ES+ 368.4

Step 2: 4-[(3-amino-3,4-dihydro-2-H-chromen-6-yl)oxy]pyridine-2-carbonitrile A solution of tert-butyl {6-[(2-cyanopyridin-4-yl)oxy]-3,4-dihydro-2-H-chromen-3-yl}carbamate in 2M HCl in dioxane (8 mL) was allowed to stir at rt overnight. The reaction mixture was concentrated and the residue was purified by column chromatography to give 4-[(3-amino-3,4-dihydro-2H-chromen-6-yl)oxy]pyridine-2-carbonitrile (0.17 g, 12%).

Step 3: 4chloro-N-{6-[(2-cyanopyridin-4-yl)oxy]-3,4-dihydro-2H-chromen-3-yl}-3-(trifluoromethyl)benzamide A mixture of 4-[(3-amino-3,4-dihydro-2H-chromen-6-yl)oxy]pyridine-2-carbonitrile (0.17 g, 0.64 mmol), 4-chloro-3-(trifluoromethyl)aniline (0.157 g, 0.70 mmol), DMAP (0.086 g, 0.70 mmol), and EDCI (0.128 g, 0.67 mmol) in DCM (5 mL) was allowed to stir at rt overnight. The reaction mixture was loaded directly onto a silica gel column and purified by chromatography to give 4-chloro-N-{6-[(2-cyanopyridin-4-yl)oxy]-3,4-dihydro-2H-chromen-3yl}-3-(trifluoromethyl)benzamide (0.219 g, 73%). LCMS: ES+ 473.9, ES− 471.8.

Step 4: 4-chloro-N-(6-{[2-(4,5-dihydro-1H-imidazol-2-yl)pyridin-4-yl]oxy}-3,4-dihydro-2-H-chromen-3-yl)-3-(trifluoromethyl)benzamide I-445 To a solution of 4chloro-N-{6-[(2-cyanopyridin-4yl)oxy]-3,4-dihydro-2H-chromen-3-yl}-3-(trifluoromethyl)benzamide (0.219 g, 0.46 mmol) in ETOH (8 mL) was added TEA (0.193 mL, 1.39 mmol). Into the solution was bubbled H$_2$S. The reaction mixture was capped and allowed to stir at rt for 1 h and then diluted with EtOAc and poured into brine. The solution was extracted with EtOAc and the organic solutions were combined, dried over Na$_2$SO$_4$, filtered, and concentrated. The residue was redissolved in 1,2-diaminoethane and allowed to stir at rt for 1 hr. The reaction mixture was diluted with EtOAc and poured into brine. The solution was extracted with EtOAc and the organic solutions were combined, dried over Na$_2$SO$_{41}$, filtered, and concentrated. The residue was purified by column chromatography to give 4-chloro-N-(6-{[2-(4,5-dihydro-1H-imidazol-2-yl)pyridin-4-yl]oxy}-3,4-dihydro-2H-chromen-3-yl)-3-(trifluoromethyl)benzamide I-445, which was converted to the corresponding hydrochloride salt by dissolving in MeOH, adding 2N HCl in Et$_2$O, and concentrating. $^1$H NMR (400 MHz, d$_6$-DMSO, 2*HCl Salt) δ: 10.97 (s, 2H), 9.51 (br s, 1H), 9.06 (d, 1H), 8.65 (d, 1H), 8.35 (d, 1H), 8.26-8.23 (dd, 1H), 7.98 (d, 1H), 7.86 (d, 1H), 7.24-7.22 (dd, 1H), 7.05 (d, 1H), 6.70-6.92 (m, 2H), 4.42-4.34 (m, 1H), 4.26-4.23 (br dd, 1H), 4.06-4.01 (m, 1H), and 3.13-3.00 (m, 2H). LCMS: (FA) ES+ 519.1, ES− 514.9.

Compounds in the following table were prepared from the appropriate starting materials in a method analogous to that of Example 23:

| | |
|---|---|
| I-440 | $^1$H NMR(400MHz, CD$_3$OD) δ: 8.61(d, 1H), 8.41(d, 2H), 8.21(d, 1H), 7.94-8.01(m, 2H), 7.81(d, 1H), 7.74(dd, 1H), 7.64(d, 2H), 7.23-7.26(m, 2H), 4.00(s, 4H). LCMS: (FA) ES+ 511.0, ES− 509.0. |
| I-442 | $^1$H NMR(300MHz, d$_6$-DMSO) δ: 8.82(d, 1H), 8.44(s, 1H), 8.30(s, 1H), 8.21-8.08(m, 1H), 7.83(d, 1H), 7.29(d, 1H), 7.22(d, 1H), 7.07-6.90(m, 2H), 4.21-4.09(m, 1H), 3.62-3.55(m, 3H), 3.13-3.05(m, 1H), 2.85-2.78(m, 3H), 2.50-2.46(m, 1H), 2.08-2.00(m, 1H), and 1.84-1.76(m, 1H). |

Example 24

Preparation of N-(3-tert-butylphenyl)-7-{[2-(1-methyl-1H-tetrazol-5-yl)pyridin-4-yl]oxy}-1,2,3,4-tetrahydronaphthalene-2-carboxamide I-321 and N-(3-tert-butylphenyl)-7-{[2-(2-methyl-2H-tetrazol-5-yl)pyridin-4-yl]oxy}-1,2,3,4-tetrahydronaphthalene-2-carboxamide I-334

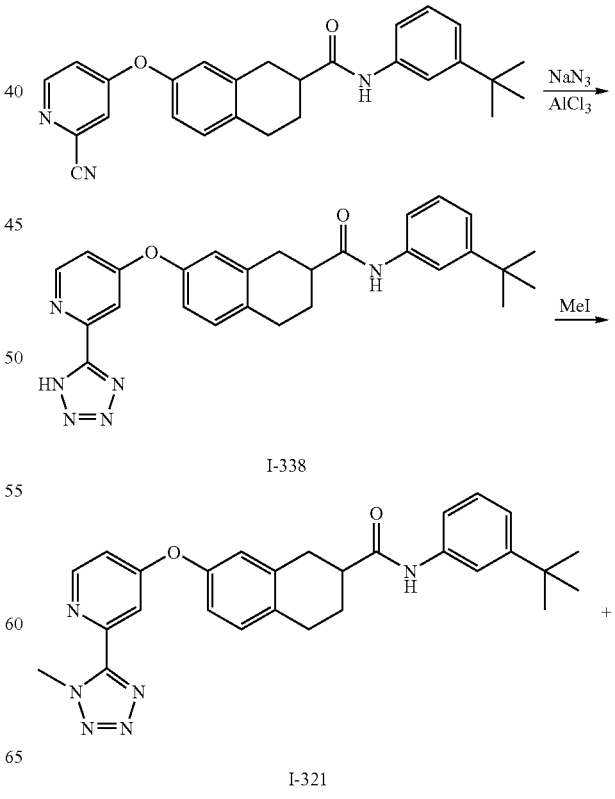

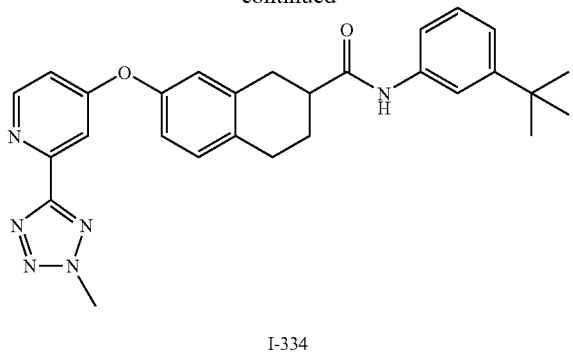

I-334

Step 1: N-(3-tert-butylphenyl)-7-{[2-(1H-tetrazol-5-yl)pyridin-4-yl]oxy}-1,2,3,4-tetrahydronaphthalene-2-carboxamide 1-338 A solution of N-(3-tert-butylphenyl)-7-[(2-cyanopyridin-4-yl)oxy]-1,2,3,4-tetrahydronaphthalene-2-carboxamide (1.00 g, 2.35 mmol), sodium azide (0.46 g, 0.70 mmol) and AlCl$_3$ (1M in nitrobenzene, 7 mL) in DMF (20 mL) was allowed to stir at reflux overnight. The reaction mixture was concentrated and triturated with Et$_2$O. The resulting solid was filtered, washed with Et$_2$O, and purified by column chromatography. The resulting solid was treated with HCl to give the hydrochloride salt of N-(3-tert-butylphenyl)-7-{[2-(1H-tetrazol-5-yl)pyridin-4-yl]oxy}-1,2,3,4-tetrahydronaphthalene-2-carboxamide (0.88 g, 80%) I-338. $^1$H NMR (400 MHz, CD$_3$OD, HCl salt) δ: 8.53 (d, 1H), 7.66 (d, 1H), 7.63-7.62 (t, 1H), 7.42 (d, 1H), 7.20-7.16 (m, 2H), 7.11-7.08 (m, 1H), 7.06-7.04 (dd, 1H), 6.90 (s, 1H), 6.88 (d, 1H), 3.08-2.87 (m, 5H), 2.17-2.13 (m, 1H), 1.93-1.85 (m, 1H), and 1.27 (s, 9H). LCMS: (FA) ES+ 469.0, ES− 467.0.

Step 2: N-(3-tert-butylphenyl)-7-{[2-(1-methyl-1H-tetrazol-5-yl)pyridin-4-yl]oxy}-1,2,3,4-tetrahydronaphthalene-2-carboxamide I-321 and N-(3-tert-butylphenyl)-7-{[2-(2-methyl-2H-tetrazol-5-yl)pyridin-4-yl]oxy}-1,2,3,4-tetrahydronaphthalene-2-carboxamide I-334

A suspension of N-(3-tert-butylphenyl)-7-{[2-(1H-tetrazol-5-yl)pyridin-4-yl]oxy}-1,2,3,4-tetrahydronaphthalene-2-carboxamide (0.075 g, 0.16 mmol), potassium carbonate (0.11 g, 0.80 mmol), and methyl iodide (0.019 mL, 0.30 mmol) in acetone (8 mL) was allowed to stir at 0° C. for 10 min. The reaction mixture was allowed to warm to rt, diluted with water, and extracted with EtOAc. The organic solution were combined and concentrated. The residue was purified by column chromatography to give N-(3-tert-butylphenyl)-7-{[2-(1-methyl-1H-tetrazol-5-yl)pyridin-4-yl]oxy}-1,2,3,4-tetrahydronaphthalene-2-carboxamide (9.3 mg) I-321 [$^1$H NMR (400 MHz, d$_6$-DMSO, HCOOH salt) δ: 9.94 (s, 1H), 8.67 (d, 1H), 7.63 (t, 1H), 7.57 (d, 1H), 7.49 (d, 1H), 7.27 (d, 1H), 7.18-7.22 (m, 2H), 7.04-7.07 (m, 2H), 6.99-7.02 (m, 1H), 3.31 (s, 3H), 2.73-2.96 (m, 5H), 2.08-2.12 (m, 1H), 1.79-1.83 (m, 1H), and 1.25 (s, 9H), LCMS: (FA) ES+ 484.0, ES− 482.0] and N-(3-tert-butylphenyl)-7-{[2-(2-methyl-2H-tetrazol-5-yl)pyridin-4-yl]oxy}-1,2,3,4-tetrahydronaphthalene-2-carboxamide (10.6 mg) I-334. [$^1$H NMR (400 MHz, d$_6$-DMSO, HCOOH salt) δ: 9.95 (s, 1H), 8.60 (d, 1H), 7.63 (t, 1H), 7.47-7.50 (m, 2H), 7.18-7.20 (m, 2H), 7.10 (dd, 1H), 7.05-7.07 (m, 2H), 6.98 (d, 1H), 3.31 (s, 3H), 2.74-2.95 (m, 5H), 2.07-2.12 (m, 1H), 1.77-1.82 (m, 1H), and 1.25 (s, 9H), LCMS: (FA) ES+ 484.0, ES− 482.0].

Compounds in the following table were prepared from the appropriate starting materials in a method analogous to that of Example 24:

| | |
|---|---|
| I-355 | $^1$H NMR(400MHz, d$_6$-DMSO, HCOOH salt) δ: 10.33(s, 1H), 8.46(s, 1H), 7.58(d, 2H), 7.30(s, 1H), 7.22(d, 1H), 6.94-7.00(m, 4H), 4.27-4.29(m, 2H), 3.37-3.41(m, 4H), 3.14-3.17(m, 4H), 2.76-2.97(m, 5H), 2.08-2.13(m, 1H), 1.84-1.89(m, 2H), 1.79-1.82(m, 1H). LCMS: (FA) ES+ 594.00. |

Example 25

Preparation of ethyl 5-{4-[(7-{[(3-tert-butylphenyl)amino]carbonyl}-5,6,7,8-tetrahydronaphthalen-2-yl)oxy]pyridin-2-yl}-1,3,4-oxadiazole-2-carboxylate I-310

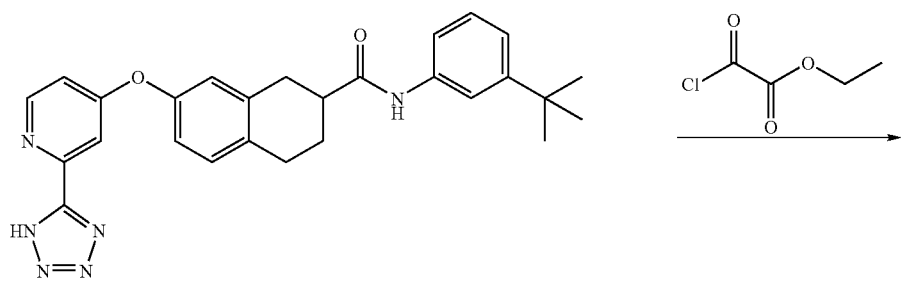

I-338

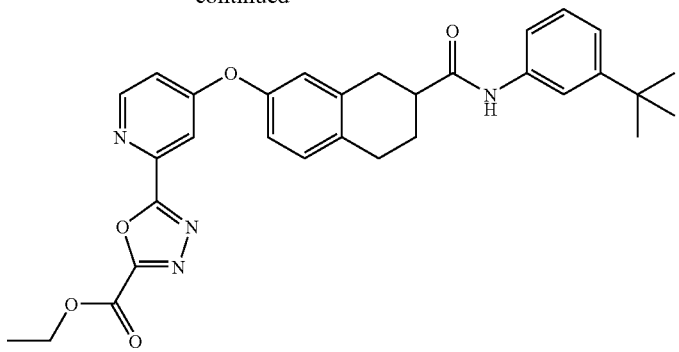

I-310

To a solution of N-(3-tert-butylphenyl)-7-{[2-(1H-tetrazol-5-yl)pyridin-4-yl]oxy}-1,2,3,4-tetrahydronaphthalene-2-carboxamide (0.65 g, 1.4 mL) and ethyl oxalyl chloride (0.15 mL, 1.4 mmol) in toluene (20 mL) was heated at reflux for 4 hr. The mixture was concentrated and the residue was purified by column chromatography to give ethyl 5-{4-[(7-{[(3-tert-butylphenyl)amino]carbonyl}-5,6,7,8-tetrahydronaphthalen-2-yl)oxy]pyridin-2-yl}-1,3,4-oxadiazole-2-carboxylate I-310 $^1$H NMR (400 MHz, d$_6$-DMSO, HCOOH salt) δ: 8.71 (d, 1H), 7.89 (d, 1H), 7.63 (t, 1H), 7.41 (d, 1H), 7.33 (dd, 1H), 7.28 (d, 1H), 7.22 (t, 1H), 7.13 (d, 1H), 6.98-7.04 (m, 2H), 4.53 (q, 2H), 2.80-3.15 (m, 5H), 2.17-2.19 (m, 1H), 1.94-1.96 (m, 1H), 1.44 (t, 3H), and 1.31 (s, 9H). LCMS: (FA) ES+ 541.0.

Example 26

Preparation of N-[3-(aminomethyl)-5-(trifluoromethyl)phenyl]-7-[(7-oxo-7,8-dihydro-1,8-naphthyridin-4-yl)oxy]-1,2,3,4-tetrahydronaphthalene-2-carboxamide I-187

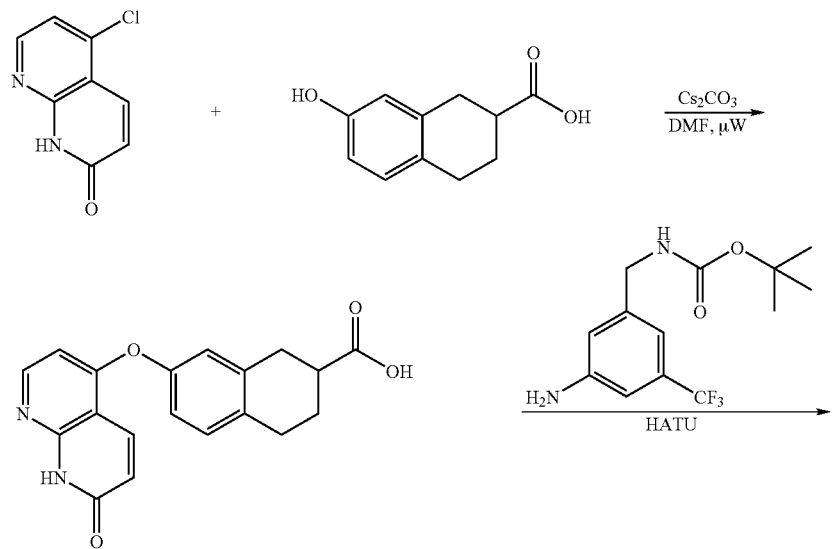

-continued

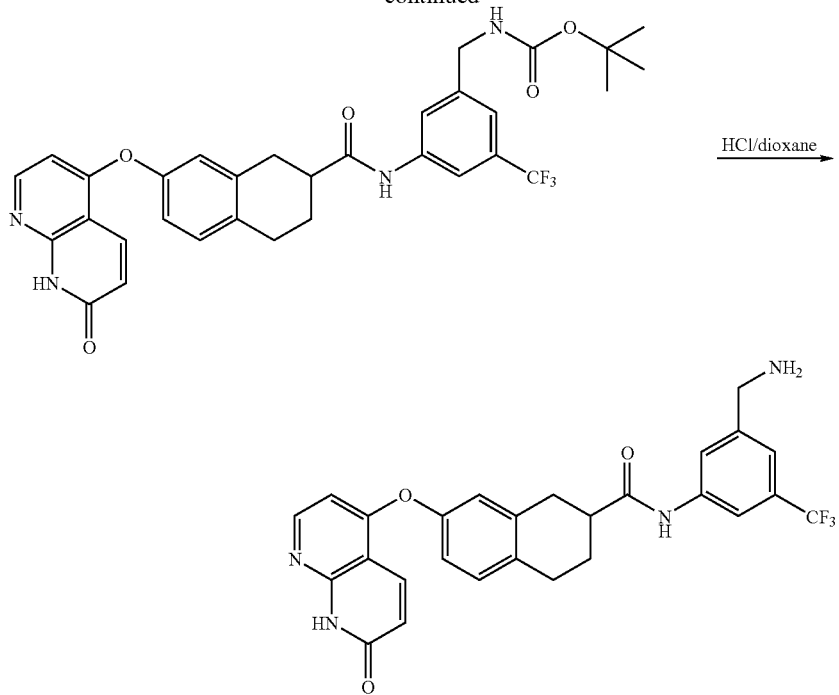

I-187

Step 1: 7-[(7-oxo-7,8-dihydro-1,8-naphthyridin-4-yl)oxy]-1,2,3,4-tetrahydronaphthalene-2-carboxylic acid A suspension of 5-chloro-1,8-naphthyridin-2(1H)-one (0.050 g, 0.00028 mol), 7-hydroxy-1,2,3,4-tetrahydronaphthalene-2-carboxylic acid (0.080 g, 0.00042 mol), and cesium carbonate (0.270 g, 0.000829 mol) in DMF (1 mL) was subjected to microwave heating (180° C.) for 15 min. The reaction mixture was dissolved in water and then acidified to pH of 2 with 1N HCl. The mixture was extracted with EtOAc (4×). The combined organic solutions were dried over MgSO$_4$, filtered, and concentrated. The residue was triturated with DCM and hexanes to produce 7-[(7-oxo-7,8-dihydro-1,8-naphthyridin-4-yl)oxy]-1,2,3,4-tetrahydronaphthalene-2-carboxylic acid as a white solid (0.066 g, 71%). LCMS: (FA) ES+ 337.3.

Step 2: tert-butyl [3-[({7-[(7-oxo-7,8-dihydro-1,8-naphthyridin-4-yl)oxy]-1,2,3,4-tetrahydronaphthalen-2-yl}carbonyl)amino]-5-(trifluoromethyl)benzyl]carbamate To a solution of 7-[(7-oxo-7,8-dihydro-1,8-naphthyridin-4-yl)oxy]-1,2,3,4-tetrahydronaphthalene-2-carboxylic acid (0.18 g, 0.00053 mol) in DMF (5.3 mL) was added diisopropylethylamine (0.11 mL, 0.00063 mol) and HATU (0.24 g, 0.00063 mol). The reaction mixture was allowed to stir at rt for 1 hr. tert-Butyl [3-amino-5-(trifluoromethyl)benzyl]-carbamate (0.15 g, 0.00053 mol) was added and the reaction mixture was allowed to stir for an additional 15 hr. Water was added to the reaction mixture and a solid precipitated. This solid was collected by filtration and purified by column chromatography to give tert-butyl [3-[({7-[(7-oxo-7,8-dihydro-1,8-naphthyridin-4-yl)oxy]-1,2,3,4-tetrahydronaphthalen-2-yl}carbonyl)amino]-5-(trifluoromethyl)benzyl]carbamate as a white solid (0.24 g, 75%). LCMS: (FA) ES+ 609.4.

Step 3: N-[3-(aminomethyl)-5-(trifluoromethyl)phenyl]-7-[(7-oxo-7,8-dihydro-1,8-naphthyridin-4-yl)oxy]-1,2,3,4-tetrahydronaphthalene-2-carboxamide I-187

A solution of HCl in dioxane (4.0 M, 1.0 mL) was added to a flask containing tert-butyl [3-[({7-[(7-oxo-7,8-dihydro-1,8-naphthyridin-4-yl)oxy]-1,2,3,4-tetrahydronaphthalen-2-yl}-carbonyl)amino]-5-(trifluoromethyl)benzyl]carbamate and the mixture was allowed to stir for 1 hr. The reaction mixture was concentrated to give the HCl salt of N-[3-(aminomethyl)-5-(trifluoromethyl)phenyl]-7-[(7-oxo-7,8-dihydro-1,8-naphthyridin-4-yl)oxy]-1,2,3,4-tetrahydronaphthalene-2-carboxamide I-187 (0.047 g, 98%) as a white solid. $^1$H NMR (400 MHz, d$_6$-DMSO) δ: 12.20 (s, 1H), 10.70 (s, 1H), 8.34-8.49 (m, 3H), 8.31 (d, 1H), 8.14 (d, 1H), 8.04 (d, 1H), 8.03 (s, 1H), 7.59 (s, 1H), 7.24 (d, 1H), 7.00-7.05 (m, 2H), 6.56 (d, 1H), 6.38 (d, 1H), 4.06-4.11 (m, 2H), 2.78-2.97 (m, 5H), 2.09-2.15 (m, 1H), and 1.76-1.86 (m, 1H). LCMS: (FA) ES+ 509.4.

Example 27

Preparation of N-[3-(aminomethyl)-5-(trifluoromethyl)phenyl]-7-[(7oxo-5,6,7,8-tetrahydro-1,8-naphthyridin-4-yl)oxy]-1,2,3,4-tetrahydronaphthalene-2-carboxamide I-191

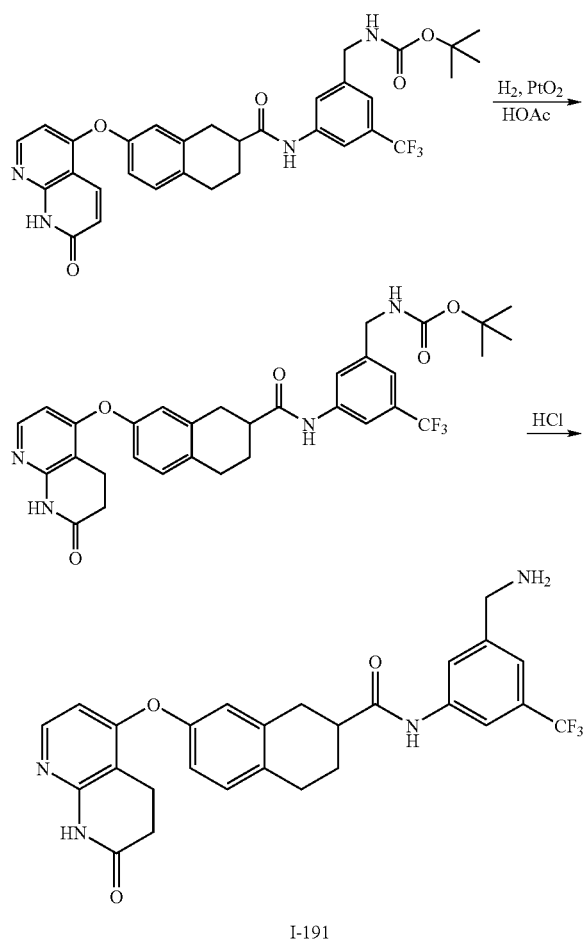

I-191

Step 1: tert-butyl [3-[({7-[(7-oxo-5,6,7,8-tetrahydro-1,8-naphthyridin-4-yl)oxy]-1,2,3,4-tetrahydronaphthalen-2-yl}carbonyl)amino]-5-(trifluoromethyl)benzyl]carbamate Platinum dioxide (1.9 mg, 0.0082 mmol) was added to a solution of tert-butyl [3-[({7-[(7-oxo-7,8-dihydro-1,8-naphthyridin-4-yl)oxy]-1,2,3,4-tetrahydronaphthalen-2-yl}-carbonyl)amino]-5-(trifluoromethyl)benzyl]carbamate (20 mg, 0.033 mmol) in AcOH (0.5 mL). The solution was allowed to stir under an atmosphere of hydrogen at rt. After 28 hr, an additional amount of platinum dioxide was added (1.9 mg, 0.0082 mmol) and the reaction continued to stir under an atmosphere of hydrogen for a total of 46 h. The reaction mixture was then filtered through Celite and the residue was purified by column chromatography to give tert-butyl [3-[({7-[(7-oxo-5,6,7,8-tetrahydro-1,8-naphthyridin-4-yl)oxy]-1,2,3,4tetrahydronaphthalen-2-yl}carbonyl)amino]-5-(trifluoromethyl)benzyl]carbamate (9.0 mg, 45%) as a white solid. LCMS: (FA) ES+ 611.4.

Step 2: N-[3-(aminomethyl)-5-(trifluoromethyl)phenyl]-7-[(7-oxo-5,6,7,8-tetrahydro-1,8-naphthyridin-4-yl)oxy]-1,2,3,4-tetrahydronaphthalene-2-carboxamide I-191

A solution of HCl in dioxane (4.0 M, 1.0 mL) was added to a flask containing tert-butyl [3-[({7-[(7-oxo-5,6,7,8-tetrahydro-1,8-naphthyridin-4-yl)oxy]-1,2,3,4-tetrahydronaphthalen-2-yl}carbonyl)amino]-5-(trifluoromethyl)benzyl]carbamate and the reaction mixture was allowed to stir for 1 hr. The mixture was concentrated to give the HCl salt of N-[3-(aminomethyl)-5-(trifluoromethyl)phenyl]-7-[(7-oxo-5,6,7,8-tetrahydro-1,8-naphthyridin-4-yl)-oxy]-1,2,3,4-tetrahydronaphthalene-2-carboxamide I-191 (.014 g, 79%) as a white solid. $^1$H NMR (300 MHz, $d_6$-DMSO) δ: 8.00-8.10 (m, 3H), 7.53 (s, 1H), 7.29 (d, 1H), 7.03 (s, 1H), 6.98 (d, 1H), 6.70 (d, 1H), 4.20 (s, 2H), 3.20 (t, 2H), 2.88-3.12 (m, 5H), 2.80 (t, 2H), 2.19-2.26 (m, 1H), and 1.90-2.00 (m, 1H). LCMS: (FA) ES+ 511.4.

Example 28

Preparation of 7-({2-[acetyl(methyl)amino]pyridin-4-yl}oxy)-N-(3-tert-butylphenyl)-1,2,3,4-tetrahydronaphthalene-2-carboxamide I-395

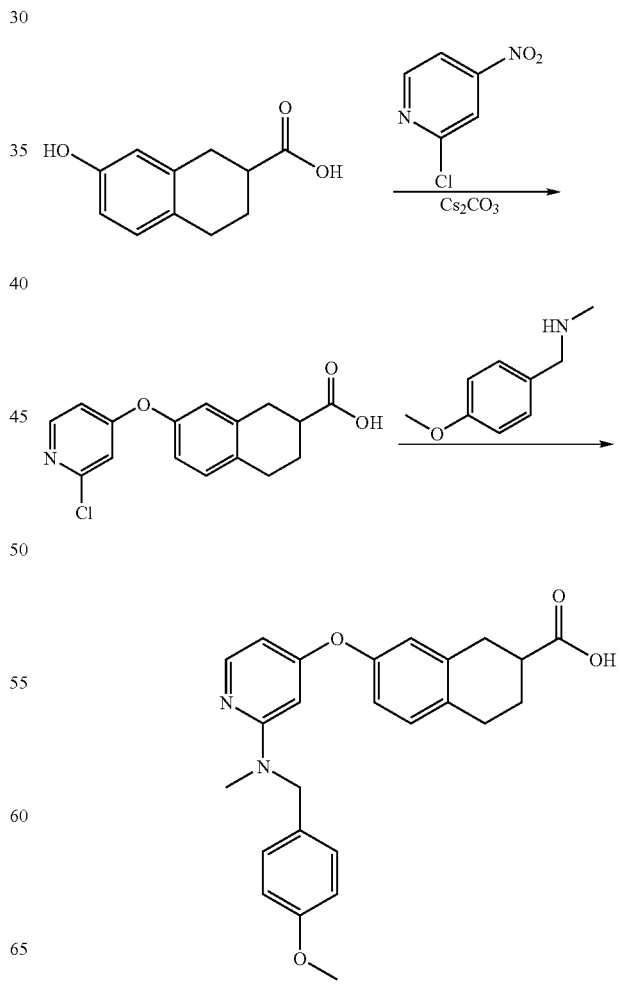

-continued

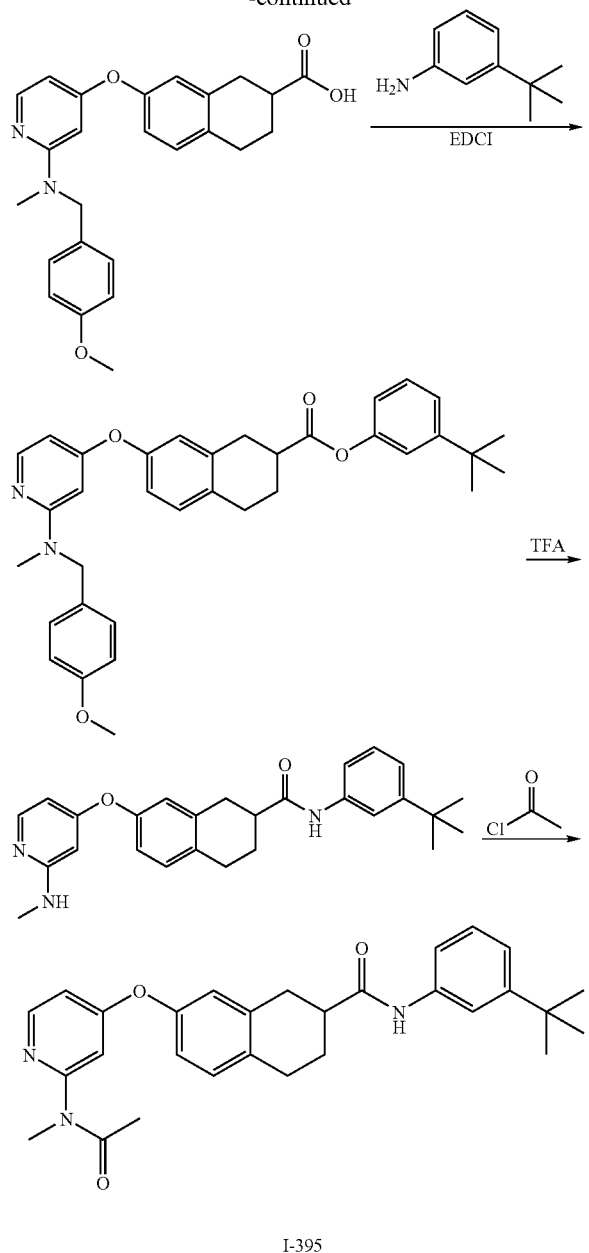

I-395

Step 1: 7-[(2-chloropyridin-4-yl)oxy]-1,2,3,4-tetrahydronaphthalene-2-carboxylic acid A mixture of 7-hydroxy-1,2,3,4-tetrahydronaphthalene-2-carboxylic acid (5.62 g, 29.2 mmol); 2-chloro-4-nitropyridine (5.10 g, 32.2 mmol) and cesium carbonate (28.6 g, 87.7 mmol) in DMF (150 mL) was heated at 50° C. for 5 hr. The reaction mixture was allowed to cool to rt and acidified to pH 3 by addition of 1N HCl. The mixture was extracted with EtOAc and the organic solutions were combined, washed with water, dried over $Na_2SO_4$ and evaporated. The residue was adsorbed onto silica and purified by filtration through a pad of silica. The product was then triturated with EtOAc to give 7-[(2-chloropyridin-4-yl)oxy]-1,2,3,4-tetrahydronaphthalene-2-carboxylic acid (4.62 g, 52.0%). LCMS: (FA) ES+ 304.1, ES− 302.1.

Step 2: 7-({1-[(4-methoxybenzyl)(methyl)amino]pyridin-4-yl}oxy)-1,2,3,4-tetrahydronaphthalene-2-carboxylic acid A solution of 7-[(2-chloropyridin-4-yl)oxy]-1,2,3,4-tetrahydronaphthalene-2-carboxylic acid (1.50 g, 4.94 mmol) and 1-(4-methoxyphenyl)-N-methylmethanamine (2.24 g, 14.8 mmol) in NMP (9 mL) was heated in a sealed tube at 150° C. for 40 hr. The reaction mixture was allowed to cool to rt and diluted with water and 1N HCl solution. The pH was adjusted to 4 by the addition of 1N NaOH solution. The mixture was extracted with EtOAc (3×) and the organic solutions were combined, washed with water and brine, dried over $Na_2SO_4$ and concentrated. The residue was purified by column chromatography to give 7-({2-[(4-methoxybenzyl)(methyl)amino]pyridin-4-yl}oxy)-1,2,3,4-tetrahydronaphthalene-2-carboxylic acid as an off-white solid (581 mg, 28.1%). LCMS: (FA) ES+ 419.2, ES− 417.2.

Step 3: N-(3-tert-butylphenyl)-7-({2-[(4-methoxybenzyl)(methyl)amino]pyridin-4-yl}-oxy)-1,2,3,4-tetrahydronaphthalene-2-carboxamide (I-179)

To a solution of 7-({1-[(4-methoxybenzyl)(methyl)amino]pyridin-4-yl}oxy)-1,2,3,4-tetrahydronaphthalene-2-carboxylic acid (581 mg, 1.39 mmol) and 3-tert-butylaniline (228 mg, 1.53 mmol) in DCM (13 mL), was added DMAP (186 mg, 1.53 mmol) and EDCI (293 mg, 1.53 mmol). The reaction mixture was allowed to stir for 18 hr, and then diluted with EtOAc and washed with water and brine. The organic solution was dried over $Na_2SO_4$ and concentrated. The residue was purified by column to give N-(3-tert-butylphenyl)-7-({2-[(4-methoxybenzyl)(methyl)amino]pyridin-4-yl}oxy)-1,2,3,4-tetrahydronaphthalene-2-carboxamide (I-179) as a white solid (491 mg, 64.3%). $^1H$ NMR (400 MHz, $d_6$-DMSO; HCl salt) δ: 9.98 (s, 1H), 7.97 (d, 1H), 7.64 (dd, 1H), 7.49 (d, 1H), 7.21 (dd, 1H), 7.20 (d, 1H), 7.12 (d, 2H), 7.07 (ddd, 1H), 6.96 (d, 1H), 6.87-6.92 (m, 3H), 6.37-6.49 (m, 2H), 4.69 (s, 2H), 3.72 (s, 3H), 3.17 (s, 3H), 2.72-2.99 (m, 5H), 2.03-2.99 (m, 1H), 1.73-1.84 (m, 1H), and 1.26 (s, 9H). LCMS: (FA) ES+ 550.3, ES− 448.4.

Step 4: N-(3-tert-butylphenyl)-7-{[2-(methylamino)pyridin-4-yl]oxy}-1,2,3,4-tetrahydronaphthalene-2-carboxamide A solution of N-(3-tert-butylphenyl)-7-({2-[(4-methoxybenzyl)(methyl)amino]-pyridin-4-yl}oxy)-1,2,3,4-tetrahydronaphthalene-2-carboxamide (454 mg, 0.83 mmol) in DCM (4 mL) and TFA (4 mL) was heated at 50° C. for 18 h. The reaction mixture was allowed to cool to rt and the solvents were evaporated. The residue was purified by column chromatography to give N-(3-tert-butylphenyl)-7-{[2-(methylamino)pyridin-4-yl]oxy}-1,2,3,4-tetrahydronaphthalene-2-carboxamide (337 mg, 94.9%). LCMS: (FA) ES+ 430.2.

Step 5: 7-({2-[acetyl(methyl)amino]pyridin-4-yl}oxy)-N-(3-tert-butylphenyl)-1,2,3,4-tetrahydronaphthalene-2-carboxamide I-395

To a solution of N-(3-tert-butylphenyl)-7-{[2-(methylamino)pyridin-4-yl]oxy}-1,2,3,4-tetrahydronaphthalene-2-carboxamide (337 mg, 0.78 mmol) in THF (8 mL) was added TEA (0.219 mL, 1.57 mmol). The reaction mixture was cooled to 0° C. and acetyl chloride (0.062 mL, 0.86 mmol) was added dropwise. The reaction mixture was allowed to stir at 0° C. for 5 hr. during which time further portions of TEA (0.219 mL, 1.57 mmol) and acetyl chloride (0.62 mL, 0.86 mmol) were added. Water was added and the mixture was extracted with EtOAc. The organic solutions were combined, washed with water and brine, dried over Na$_2$SO$_4$ and concentrated. The residue was purified by column chromatography. The product was further purified by HPLC (250 mm C18 column) eluting with 40% A/60% B to 100%/0% B (25 min gradient) (A=99/1 H$_2$O in AcCN, 0.1% FA, B=95/5 AcCN/H$_2$O, 0.1% FA). The product was dissolved in DCM and MeOH and 2M HCl-Et$_2$O solution was added. The solvents were evaporated to provide 7-({2-[acetyl(methyl)amino]pyridin-4-yl}oxy)-N-(3-tert-butylphenyl)-1,2,3,4-tetrahydronaphthalene-2-carboxamide I-395 as the HCl salt (22 mg, 5.4%). $^1$H NMR (300 MHz, d$_6$-DMSO, HCOOH Salt) δ: 9.94 (s, 1H), 8.31 (d, 1H), 7.63 (t, 1H), 7.50 (d, 1H), 7.24-7.18 (m, 2H), 7.10-7.05 (m, 2H), 6.76 (dd, 3H), 3.24 (s, 3H), 2.95-2.71 (m, 5H), 2.13-1.99 (m, 4H), 1.85-1.72 (m, 1H), and 1.26 (s, 9H). LCMS: (FA) ES+470.2, ES−472.9

Example 29

Preparation of N-(3-tert-butylphenyl)-7-{[2-(2-oxotetrahydropyrimidin-1(2H)-yl)-pyridin-4-yl]oxy}-1,2,3,4-tetrahydronaphthalene-2-carboxamide I-408

Step 1: N-(3-tert-butylphenyl)-7-{[2-({[(3-chloropropyl)amino]carbonyl}amino)pyridin-4-yl]oxy}-1,2,3,4-tetrahydronaphthalene-2-carboxamide To a solution of 7-[(2-aminopyridin-4-yl)oxy]-N-(3-tert-butylphenyl)-1,2,3,4-tetrahydronaphthalene-2-carboxamide (0.965 g, 2.32 mmol) in DCM (30 mL) was added 3-chloropropyl isocyanate (0.357 mL, 3.48 mmol). The reaction mixture was allowed to stir at rt for 64 hr. Additional 2-chloropropyl isocyanate (0.300 mL, 2.92 mmol) was added, and the reaction mixture was allowed to stir at rt for 24 h. The solvent was evaporated and the residue was purified by column chromatography to give N-(3-tert-butylphenyl)-7-{[2-({[(3-chloropropyl)amino]-carbonyl}amino)pyridin-4-yl]oxy}-1,2,3,4tetrahydronaphthalene-2-carboxamide (0.710 g; 1.33 mmol, 57%) as a white solid. LCMS: (FA) ES+536.6, ES−533.5.

Step 2: N-(3-tert-butylphenyl)-7-{[2-(2-oxotetrahydropyrimidin-1(2H)-yl)pyridin-4-yl]-oxy}-1,2,3,4-tetrahydronaphthalene-2-carboxamide I-408

To a solution of N-(3-tert-butylphenyl)-7-{[2-({[(3-chloropropyl)amino-]carbonyl}-amino)pyridin-4-yl]oxy}-1,2,3,4-tetrahydronaphthalene-2-carboxamide (0.71 g, 1.3 mmol) in tert-butyl alcohol (15 mL) was added potassium tert-bu-

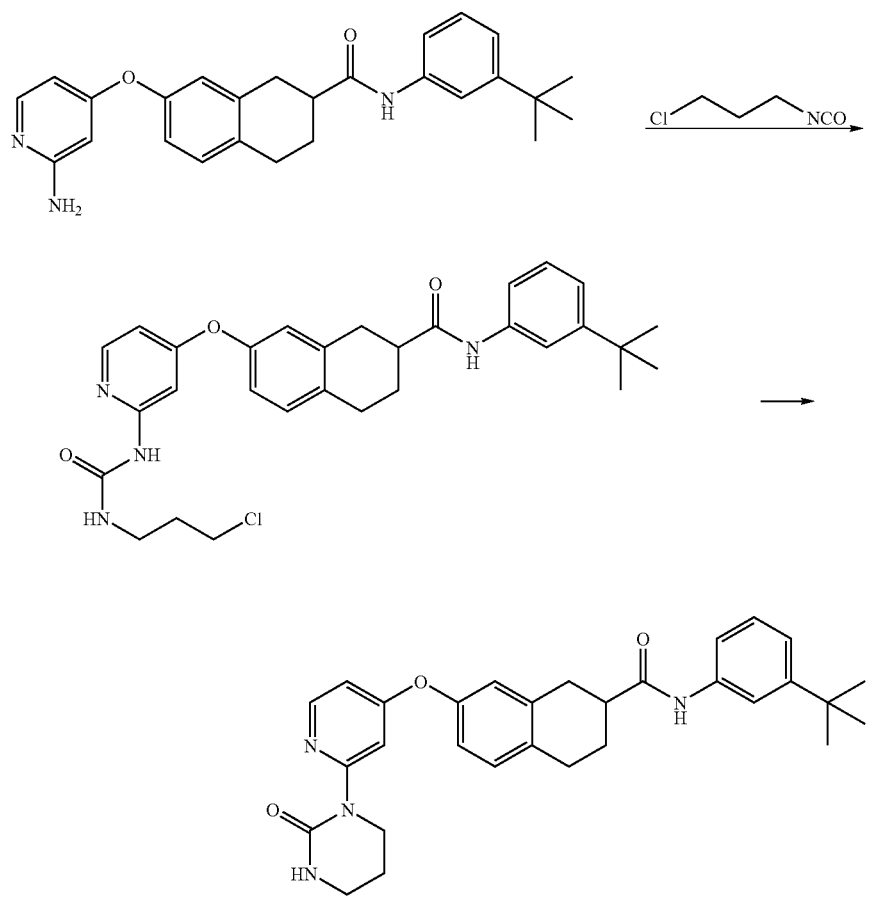

I-408 toxide (1M in THF, 4 mL). The reaction mixture was heated at 30° C. for 12 h and then acidified with 1N HCl and concentrated. The residue was redissolved in water and DCM and the aqueous solution was further extracted with DCM. The combined organic solutions were washed with brine, dried over MgSO$_4$, filtered and concentrated. The residue was purified by column chromatography. To a solution of the resulting product in MeOH, was added a 1N solution of HCl in Et$_2$O (2 mL). The solvent was evaporated to give N-(3-tert-butylphenyl)-7-{[2-(2-oxotetrahydropyrimidin-1(2H)-yl)-pyridin-4-yl]oxy}-1,2,3,4-tetrahydronaphthalene-2-carboxamide I-408 as the HCl salt (0.304 g, 46%). $^1$H NMR (400 MHz, d$_6$-DMSO, HCl salt) δ: 10.04 (s, 1H), 8.28 (d, 1H), 7.65 (t, 1H), 7.53-7.62 (br s, 1H), 7.48-7.53 (m, 1H), 7.29-7.32 (m, 1H), 7.17-7.26 (m, 2H), 7.04-7.08 (m, 1H), 7.00-7.04 (m, 1H), 6.94-6.99 (m, 1H), 6.77-6.82 (m, 1H), 3.81 (t, 2H), 3.21 (t, 2H), 2.74-2.97 (m, 5H), 2.05-2.13 (m, 1H), 1.95 (t, 2H), 1.70-1.83 (m, 1H), and 1.25 (s, 9H). LCMS: (FA) ES+499.7, ES-497.0.

Example 30

Preparation of N-(3-tert-butylphenyl)-7-{[2-(1H-pyrazol-3-yl)pyridin-4-yl]oxy}-1,2,3,4-tetrahydronaphthalene-2-carboxamide I-231

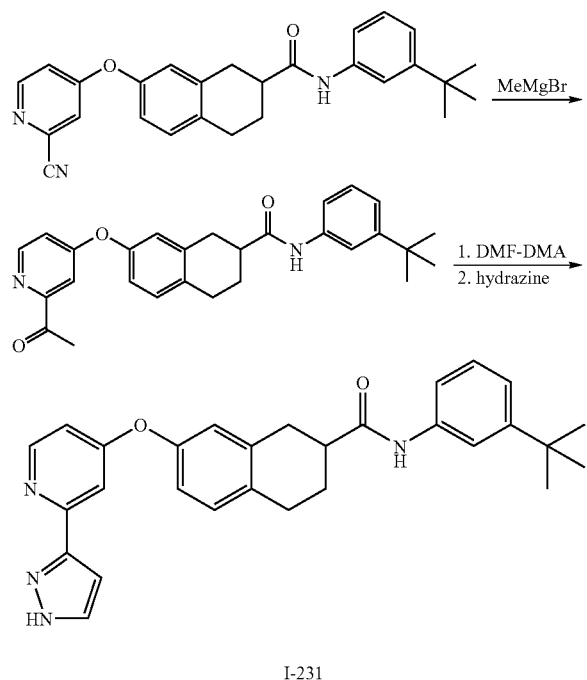

I-231

Step 1: 7-[(2-acetylpyridin-4-yl)oxy]-N-(3-tert-butylphenyl)-1,2,3,4-tetrahydronaphthalene-2-carboxamide To a stirred solution of N-(3-tert-butylphenyl)-7-[(2-cyanopyridin-4-yl)oxy]-1,2,3,4-tetrahydronaphthalene-2-carboxamide (1.164 g, 2.74 mmol) in THF (30 mL) at -12° C. was added methylmagnesium bromide (3M in Et$_2$O, 3.25 mL). The reaction mixture was allowed to warm to rt and then allowed to stir for 1 h. The reaction was quenched by the addition of water and the solution was extracted with EtOAc. The organic solutions were combined, washed with brine, dried over MgSO$_4$, filtered, and concentrated. The residue was purified by column chromatography to give 7-[(2-acetylpyridin-4-yl)oxy]-N-(3-tert-butylphenyl)-1,2,3,4-tetrahydronaphthalene-2-carboxamide (0.516 g, 43%). LCMS: (FA) ES+443.6, ES-441.3.

Step 2: N-(3-tert-butylphenyl)-7-{[2-(1H-pyrazol-3-yl)pyridin-4-yl]oxy}-1,2,3,4-tetrahydronaphthalene-2-carboxamide I-231

A solution of 7-[(2-acetylpyridin-4-yl)oxy]-N-(3-tert-butylphenyl)-1,2,3,4-tetrahydronaphthalene-2-carboxamide (0.516 g, 1.16 mmol) in 1,1-dimethoxy-N,N-dimethylmethanamine (20 mL) was allowed to stir at 115° C. for 12 h. The reaction mixture was concentrated. The residue was dissolved in ethanol (20 mL) and hydrazine hydrate (0.600 mL, 12.3 mmol) was added. The reaction mixture was allowed to stir at 90° C. for 1 h and then diluted with water. The solution was extracted with EtOAc and the combined organic solutions were washed with brine, dried over MgSO$_4$, filtered and concentrated. The residue was purified by column chromatography to give N-(3-tert-butylphenyl)-7-{[2-(1H-pyrazol-3-yl)-pyridin-4-yl]oxy}-1,2,3,4-tetrahydronaphthalene-2-carboxamide I-231 (0.184 g, 0.394 mmol, 34%) as a white solid. $^1$H NMR (400 MHz, d$_6$-DMSO, HCl salt) δ: 10.02 (s, 1H), 8.63-8.51 (m, 1H), 8.05-7.96 (m, 1H), 7.85-7.77 (m, 1H), 7.68-7.62 (m, 1H), 7.54-7.46 (m, 1H), 7.37-7.03 (m, 7H), 3.06-2.73 (m, 5H), 2.18-2.05 (m, 1H), 1.88-1.74 (m, 1H), and 1.25 (s, 9H). LCMS: (FA) ES+467.8, ES-465.5.

Example 31

Preparation of N-(3-tert-butylphenyl)-7-{[2-(1,3-oxazol-2-yl)pyridin-4-yl]oxy}-1,2,3,4-tetrahydronaphthalene-2-carboxamide I-325

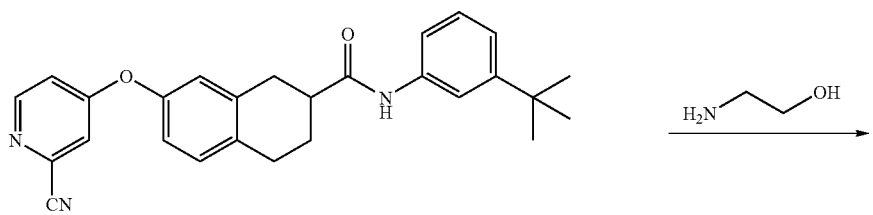

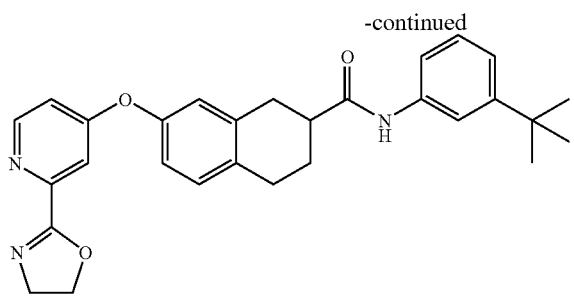

I-305

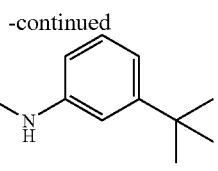
Nickel peroxide

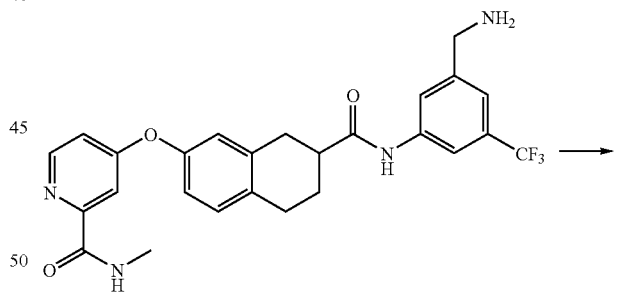

I-325

Step 1: N-(3-tert-butylphenyl)-7-{[2-(4,5-dihydro-1,oxazol-2-yl)pyridin-4-yl]oxy}-1,2,3,4-tetrahydronaphthalene-2-carboxamide I-305

To a solution of N-(3-tert-butylphenyl)-7-[(2-cyanopyridin-4-yl)oxy]-1,2,3,4-tetrahydronaphthalene-2-carboxamide (1.184 g, 2.78 mmol) in EtOH (30 mL) was added ethanolamine (1.00 mL, 16.6 mmol) and DIPEA (1.00 mL, 5.74 mmol). The reaction mixture was allowed to stir at 100° C. for 12 h. The mixture was concentrated and the residue was diluted with water and EtOAc. The solution was extracted with EtOAc and the organic solutions were combined, washed with brine, dried over MgSO$_4$, filtered and concentrated. The residue was purified by column chromatography to give N-(3-tert-butylphenyl)-7-{[2-(4,5-dihydro-1,3-oxazol-2-yl)pyridin-4-yl]oxy}-1,2,3,4-tetrahydronaphthalene-2-carboxamide I-305 (1.069 g, 82%) as a white solid. $^1$H NMR (400 MHz, d$_6$-DMSO, HCl salt) δ: 9.97 (s, 1H), 9.02 (t, 1H), 8.52 (d, 1H), 7.66-7.62 (m, 1H), 7.52-7.47 (m, 1H), 7.40-7.36 (m, 1H), 7.26-7.17 (m, 3H), 7.08-6.94 (m, 3H), 3.72 (t, 2H), 3.59 (q, 2H), 2.97-2.71 (m, 5H), 2.15-2.06 (m, 1H), 1.85-1.74 (m, 1H), and 1.25 (s, 9H). LCMS: (FA) ES+470.4, ES−468.2.

Step 2: N-(3-tert-butylphenyl)-7-{[2 -(1,3-oxazol-2-yl)pyridin-4-yl]oxy{-1,2,3,4-tetrahydronaphthalene-2-carboxamide I-325

To a solution of N-(3-tert-butylphenyl)-7-{[2-(4,5-dihydro-1,3oxazol-2-yl)pyridin-4-yl]oxy}-1,2,3,4-tetrahydronaphthalene-2-carboxamide (0.631 g, 1.34 mmol) in benzene (20 mL) was added nickel peroxide hydrate (1.461 g, 13.4 mmol). The reaction mixture was allowed to stir at 115° C. for 4 days. An additional amount of nickel peroxide (1.080 g) was added and stirring continued at 115° C. for 24 h. The mixture was filtered over a pad of Celite and the filtrate was concentrated. The residue was purified by column chromatography to give N-(3-tert-butylphenyl)-7-{[2-(1,3-oxazol-2-yl)pyridin-4-yl[oxy}-1,2,3,4-tetrahydronaphthalene-2-carboxamide I-325 (0.017 g, 0.036 mmol, 2.7%) as a white solid.

$^1$H NMR (400 MHz, d$_6$-DMSO, HCOOH salt) δ: 9.94 (br s, 1H), 8.56 (d, 1H), 8.28 (s, 1H), 7.63 (t, 1H), 7.51-7.47 (m, 1H), 7.44 (d, 1H), 7.41 (s, 1H), 7.26-7.18 (m, 2H), 7.11-7.03 (m, 3H), 7.02-6.97 (m, 1H), 2.97-2.63 (m, 5H), 2.15-2.03 (m, 1H), 1.88-1.73 (m, 1H), and 1.25 (s, 9H). LCMS: (FA) ES+468.1, ES−466.1.

Example 32

Preparation of methyl [3-({[7-({2-[(methylamino) carbonyl]pyridin-4-yl}oxy)-1,2,3,4-tetrahydronaphthalen-2-yl]carbonyl}amino)-5-(trifluoromethyl) benzyl]carbamate I-352

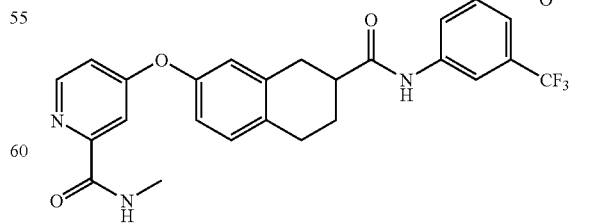

352

I-352

To a solution of 4-}[7-({[3-(aminomethyl)-5-(trifluoromethyl)phenyl]amino}-carbonyl)-5,6,7,8-tetrahydronaphthalen-2-yl]oxy}-N-methylpyridine-2-carboxamide (0.367 g, 0.736 mmol) in THF (10 mL) was added dimethyl dicarbonate (0.175 mL, 1.64 mmol) and TEA (0.257 mL, 1.84 mmol). The reaction mixture was allowed to stir at rt for 12 h. An additional amount of dimethyl dicarbonate (0.200 mL) was added and stirring continued for 24 h. The reaction mixture was diluted with water and DCM and extracted with DCM. The organic solutions were combined, washed with brine, dried over $MgSO_4$, filtered and concentrated. The residue was purified by column chromatography to methyl 3-({[7-({2-[(methylamino)carbonyl]-pyridin-4-yl}oxy)-1,2,3,4-tetrahydronaphthalen-2-yl[carbonyl}amino)-5-(trifluoromethyl)-benzyl]carbamate I-352 (0.139 g, 34%) as a white solid. $^1$H NMR (400 MHz, $d_6$-DMSO, HCl salt) δ: 10.40 (s, 1H), 8.82-8.76 (m, 1H), 8.50 (d, 1H), 8.05 (s, 1H), 7.79 (t, 1H), 7.68 (s, 1H), 7.37-7.36 (m, 1H), 7.28-7.22 (m, 2H), 7.17-7.14 (m, 1H), 7.03-7.00 (m, 1H), 6.99-6.95 (m, 1H), 4.22 (d, 2H), 3.56 (s, 3H), 2.98-2.79 (m, 5H), 2.77 (d, 3H), 2.17-2.08 (m, 1H), and 1.87-1.74 (m, 1H). LCMS: (FA) ES+557.3, ES−555.3.

Example 33

Preparation of 4-{[7-({[3-({[(dimethylamino)acetyl]amino}methyl)-5-(trifluoromethyl)phenyl]aminocarbonyl)-5,6,7,8-tetrahydronaphthalen-2-yl]-oxy}-N-methylpyridine-2-carboxamide I-284

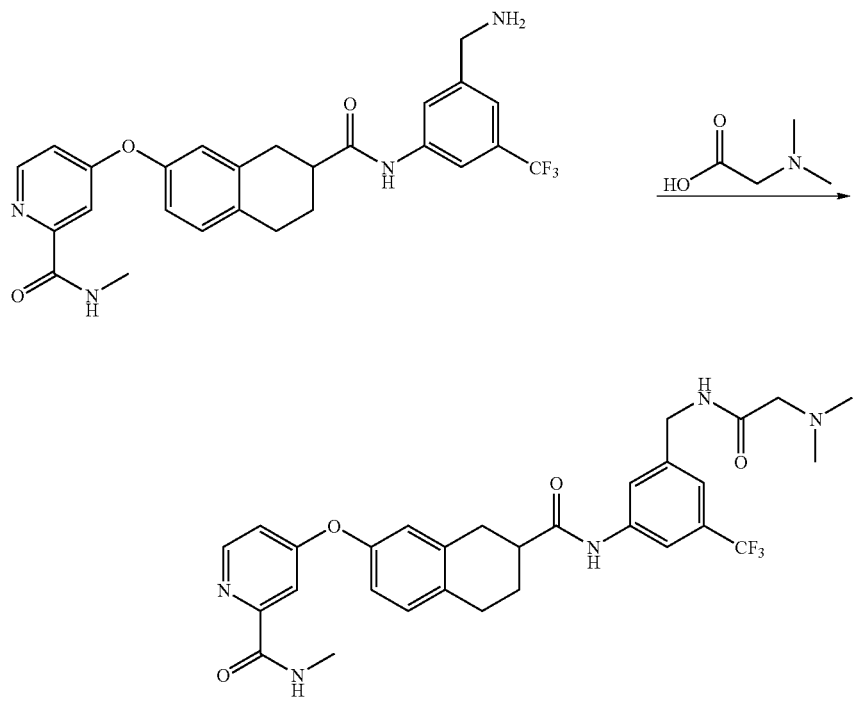

I-284

To a solution of 4-{[7-({[3-(aminomethyl)-5-(trifluoromethyl)phenyl]amino}-carbonyl)-5,6,7,8-tetrahydronaphthalen-2-yl[oxy}-N-methylpyridine-2-carboxamide (0.450 g, 0.903 mmol) in DMF (10 mL) was added N,N-dimethylglycine (0.115 g, 1.12 mmol), DMAP (0.132 g, 1.08 mmol), and EDCI (0.260 g, 1.35 mmol). The reaction mixture was allowed to stir at rt overnight and then diluted with water. The mixture was extracted with EtOAc and the combined organic solutions were washed with brine, dried over $MgSO_4$, filtered and concentrated. The residue was purified by column chromatography to give 4-{[7-({[3-({[(dimethylamino)acetyl]amino}methyl)-5-(trifluoromethyl)phenyl]amino}carbonyl)-5,6,7,8-tetrahydronaphthalen-2-yl]oxy}-N-methylpyridine-2-carboxamide I-284 (0.250 g, 47%) as a white solid. $^1$H NMR (400 MHz, $d_6$-DMSO, HCl salt) δ: 10.61 (s, 1H), 9.22 (t, 1H), 8.85-8.77 (m, 1H), 8.55-8.47 (m, 1H), 7.97 (s, 1H), 7.90 (s, 1H), 7.40-7.35 (m, 1H), 7.31 (s, 1H), 7.24 (d, 1H), 7.20-7.14 (m, 1H), 7.03-6.95 (m, 2H), 4.40 (d, 2H), 4.01 (d, 2H), 2.98-2.84 (m, 5H), 2.84-2.79 (m, 6H), 2.77 (d, 3H), 2.15-2.07 (m, 1H), and 1.87-1.75 (m, 1H). LCMS: (FA) ES+584.2, ES−582.2.

Example 34

Preparation of N-methyl-4-{[7-({[3-(methylamino)acetyl]amino}methyl)-5-(trifluoromethyl)phenyl]amino}carbonyl)-5,6,7,8-tetrahydronaphthalen-2-yl]-oxy}pyridine-2-carboxamide I-274

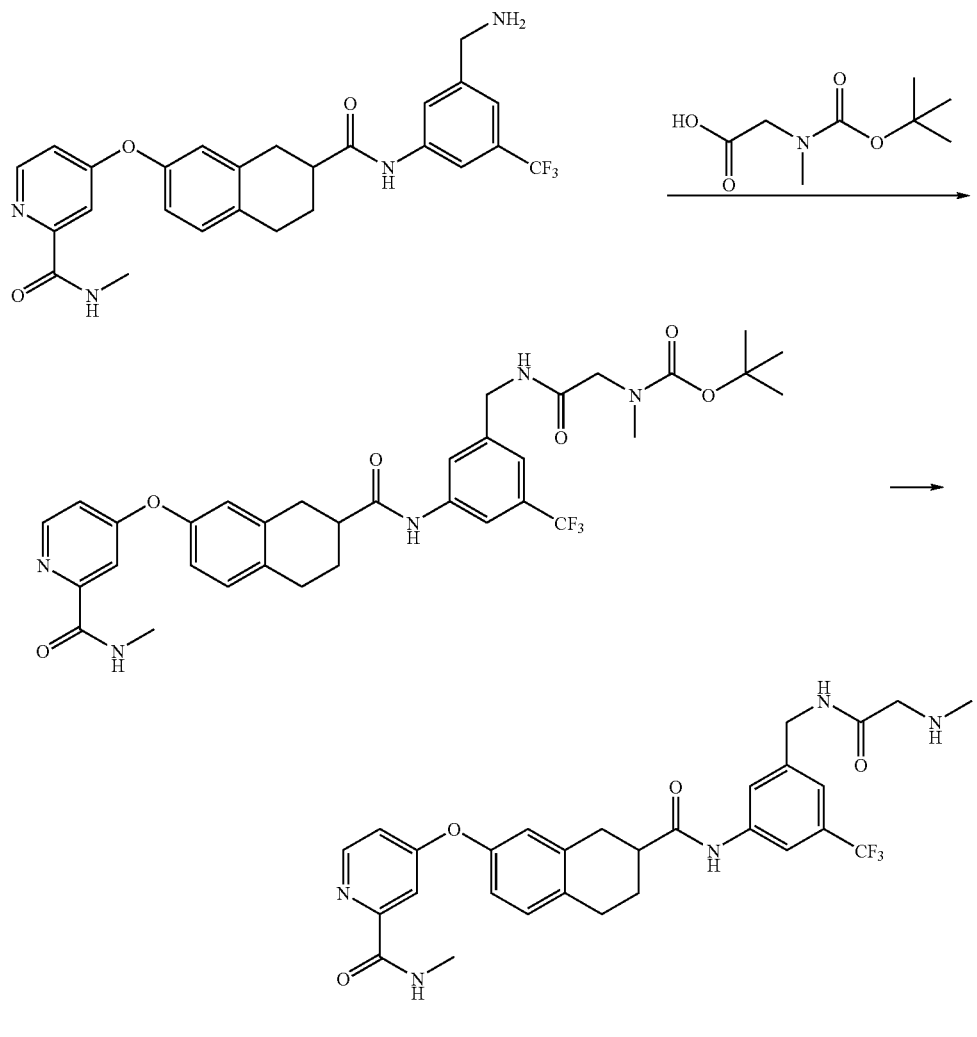

I-274

Step 1: tert-butyl methyl(2-{[3({[7-({2-[(methylamino)carbonyl]pyridin-4-yl}oxy)-1,2,3,4-tetrahydronaphthalen-2-yl]carbonyl}amino)-5-(trifluoromethyl)benzyl]amino}-2-oxoethyl)carbamate To a solution of 4-{[7-({[3-(aminomethyl)-5-(trifluoromethyl)phenyl]amino}-carbonyl)-5,6,7,8-tetrahydronaphthalen-2-yl]oxy}-N-methylpyridine-2-carboxamide (0.456 g,

Step 1: tert-butyl methyl(2-{[3-({[7-({2-[(methylamino)carbonyl]pyridin-4-yl}oxy)-1,2,3,4-tetrahydronaphthalen-2-yl]carbonyl}amino)-5-(trifluoromethyl)benzyl]amino}-2-oxoethyl)carbamate To a solution of 4-{[7-({[3-(aminomethyl)-5-(trifluoromethyl)phenyl]amino}-carbonyl)-5,6,7,8-tetrahydronaphthalen-2-yl[oxy}-N-methylpyridine-2-carboxamide (0.456 g, 0.915 mmol) in DMF (10 mL) was added [(tert-butoxycarbonyl)(methyl)amino]acetic acid (0.194 g, 1.02 mmol), DMAP (0.134 g, 1.10 mmol), and EDCI (0.263 g, 1.37 mmol). The reaction mixture was allowed to stir at rt, then diluted with water and EtOAc. The mixture was extracted with EtOAc and the combined organic solutions were washed with brine, dried over MgSO$_4$, filtered and concentrated to give tert-butyl methyl(2-{[3-({[7-({2-[(methylamino)-carbonyl]pyridin-4-yl}oxy)-1,2,3,4-tetrahydronaphthalen-2-yl]carbonyl}amino)-5-(trifluoromethyl)benzyl]amino}-2-oxoethyl)carbamate (1.048 g) in quantitative yield. LCMS: (FA) ES+670.2, ES−668.2.

Step 2: N-methyl-4-{[7-({[3-({[(methylamino)acetyl]amino}methyl)-5-(trifluoromethyl)-phenyl]amino}carbonyl)-5,6,7,8-tetrahydronaphthalen-2-yl]oxy}pyridine-2-carboxamide I-274

To a solution of tert-butyl methyl(2-{[3-({[7-({2-[(methylamino)carbonyl]pyridin-4-yl}oxy)-1,2,3,4-tetrahydronaphthalen-2-yl]carbonyl}amino)-5-(trifluoromethyl)benzyl]amino-2-oxoethyl)carbamate (1.048 g, 1.57 mmol) in MeOH (30 mL) was added concentrated HCl (2.00 mL, 65.3 mmol). The solution was allowed to stir at rt overnight. The residue was purified by column chromatography to give N-methyl-4-{[7-({[3-({[(methylamino)acetyl]amino}methyl)-5-(trifluoromethyl)phenyl]amino}carbonyl)-5,6,7,8-tetrahydronaphthalen-2-yl]oxy}pyridine-2-carboxamide I-274 (0.017 g, 2%) as a white solid. 1H NMR (400 MHz, d6-DMSO, HCl salt) δ: 10.52 (s, 1H), 9.05 (t, 1H), 8.88-8.76 (m, 2H), 8.50 (d, 1H), 7.98 (s, 1H), 7.86 (s, 1H), 7.38-7.34 (m, 1H), 7.31 (s, 1H), 7.24 (d, 1H), 7.20-7.14 (m, 1H), 7.03-6.94 (m, 2H), 4.39 (d, 2H), 3.77 (t, 2H), 2.99-2.79 (m, 5H), 2.77 (d, 3H), 2.56 (t, 3H), 2.16-2.07 (m, 1H), and 1.87-1.75 (m, 1H). LCMS: (FA) ES+h570.2, ES−568.3.

Example 35

Preparation of N-methyl-4-{[7-({[3-({[(methylamino)acetyl]amino}methyl)-5-(trifluoromethyl)phenyl]amino}carbonyl)-5,6,7,8-tetrahydronaphthalen-2-yl]-oxy}pyridine-2-carboxamide I-345

Step 1: 4-{[7-({[3-({[(1,3-dioxo-1,3-dihydro-2H-isoindol-2-yl)acetyl]amino}methyl)-5-(trifluoromethyl)phenyl]amino}carbonyl)-5,6,7,8-tetrahydronaphthalen-2-yl]-oxy}-N-methylpyridine-2-carboxamide To a solution of 4-{[7-({[3-(aminomethyl)-5-(trifluoromethyl)phenyl]amino}-carbonyl)-5,6,7,8-tetrahydronaphthalen-2-yl](oxy}-N-methylpyridine-2-carboxamide (0.463 g, 0.929 mmol) in DMF (11 mL) was added (1,3-dioxo-1,3-dihydro-2H-isoindol-2-yl)acetic acid (0.228 g, 1.11 mmol), DMAP (0.136 g, 1.11 mmol), and EDCI (0.267 g, 1.39 mmol). The reaction mixture was allowed to stir at rt overnight, and then diluted with water and EtOAc. The solution was extracted with EtOAc and the combined organic solutions were washed with brine, dried over MgSO$_4$, filtered and concentrated to give 4-{[7-({[3-({[(1,3dioxo-1,3-dihydro-2-H-isoindol-2-yl)acetyl]amino}methyl)-5-(trifluoromethyl)phenyl]amino}carbonyl)-5,6,7,8-tetrahydronaphthalen-2-

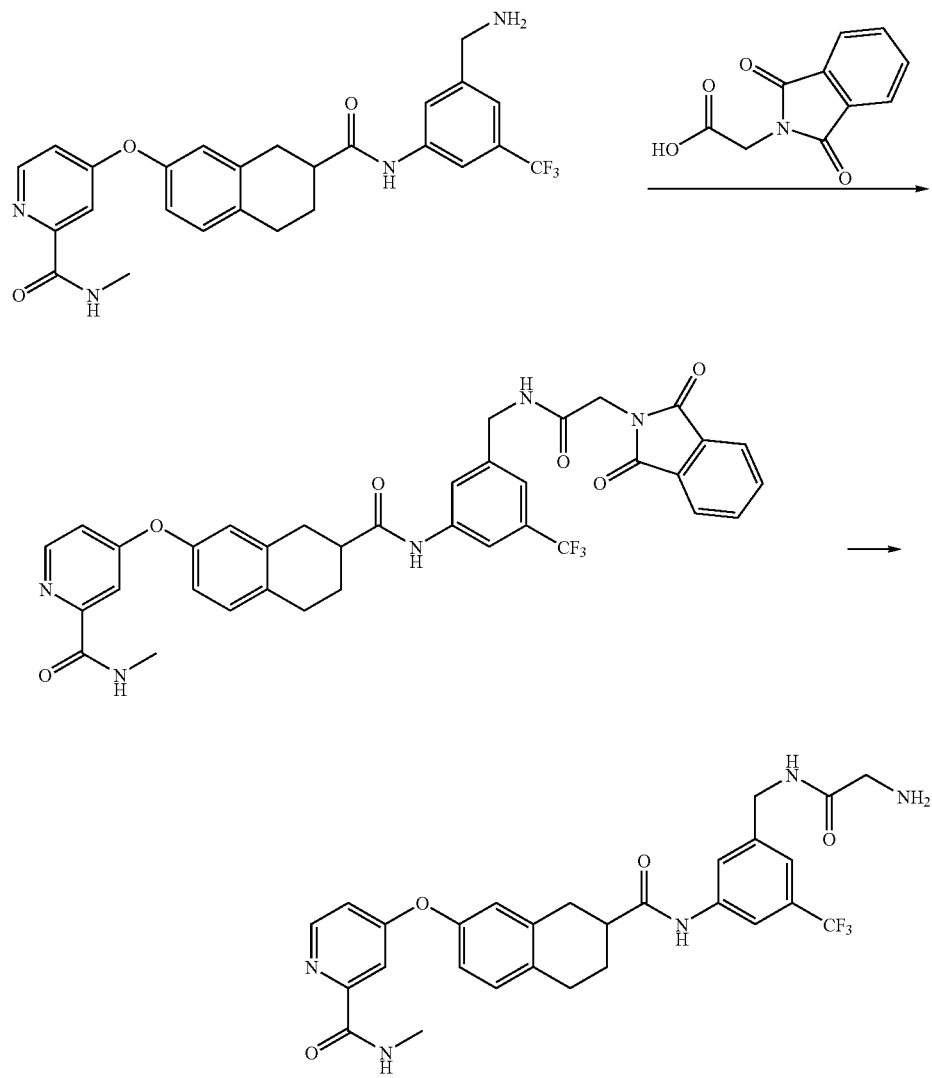

I-345 yl]oxy}-N-methylpyridine-2-carboxamide (0.819 grams) in quantitative yield. LCMS: (FA) ES+686.1, ES−684.1.

Step 2: N-methyl-4-{[7-({[3-({[(methylamino)acetyl]amino}methyl)-5-(trifluoromethyl)-phenyl]amino}carbonyl)-5,6,7,8-tetrahydronaphthalen-2-yl]oxy}pyridine-2-carboxamide I-345

To a solution of 4-{[7-({[3-({[(1,3dioxo-1,3-dihydro-2-H-isoindol-2-yl)acetyl]-amino}methyl)-5-(trifluoromethyl)phenyl]amino}carbonyl)-5,6,7,8-tetrahydronaphthalen-2-yl]-oxy}-N-methylpyridine-2-carboxamide (0.819 g, 1.19 mmol) in EtOH (20 mL) was added a 40% aqueous solution of methyl amine in water (5.00 mL, 44.8 mmol). The reaction mixture was allowed to stir at rt for 5 h and then concentrated. The residue was purified by column chromatography to give N-methyl-4-{[7-({[3-({[(methylamino)acetyl]amino}-methyl)-5-(trifluoromethyl)phenylamino}carbonyl)-5,6,7,8-tetrahydronaphthalen-2-yl]oxy}-pyridine-2-carboxamide I-345 (0.124 g, 19%) as a white solid. $^1$H NMR (400 MHz, d$_6$-DMSO, HCl salt) δ: 10.65 (s, 1H), 9.19-9.09 (br s, 1H), 8.85-8.77 (m, 1H), 8.50 (d, 1H), 8.17-8.02 (m, 2H), 7.66 (s, 1H), 7.41-7.36 (m, 1H), 7.28-7.21 (m, 1H), 7.19-7.14 (m, 1H), 7.04-6.94 (m, 2H), 4.22 (t, 2H), 3.83-3.76 (m, 2H), 3.67 (t, 2H), 3.03-2.81 (m, 5H), 2.77 (d, 3H), 2.17-2.08 (m, 1H), and 1.89-1.75 (m, 1H). LCMS: (FA) ES+543.2, ES−541.2.

Example 36

Preparation of 4-{[7-({[3-[(2-hydroxyethyl)amino]methyl}-5-(trifluoromethyl)-phenyl]amino}carbonyl)-5,6,7,8-tetrahydronaphthalen-2-yl]oxy}-N-methylpyridine-2-carboxamide I-276

To a solution of 4-{[7-({[3-(aminomethyl)-5-(trifluoromethyl)phenyl]amino}-carbonyl)-5,6,7,8-tetrahydronaphthalen-2-yl]oxy}-N-methylpyridine-2-carboxamide (0.459 g, 0.921 mmol) in DMF (10 mL) was added 2-bromoethanol (0.100 mL, 1.41 mmol) and TEA (0.300 mL, 2.15 mmol). The reaction mixture was allowed to stir at rt overnight, and then diluted with water. The mixture was extracted with EtOAc and the combined organic solutions were washed with 10% aqueous LiCl, dried over MgSO$_4$, filtered and concentrated. The residue was purified by column chromatography to give 4-{[7-({[3-{[(2-hydroxyethyl)amino]methyl}-5-(trifluoromethyl)phenyl]amino}carbonyl)-5,6,7,8-tetrahydronaphthalen-2-yl]oxy}-N-methylpyridine-2-carboxamide I-276 (0.352 g, 71%) as a white solid. $^1$H NMR (400 MHz, d$_6$-DMSO, HCl salt) δ: 10.65 (s, 1H), 9.19-9.09 (br s, 1H), 8.85-8.77 (m, 1H), 8.50 (d, 1H), 8.17-8.02 (m, 2H), 7.66 (s, 1H), 7.41-7.36 (m, 1H), 7.28-7.21 (m, 1H), 7.19-7.14 (m, 1H), 7.04-6.94 (m, 2H), 4.22 (t, 2H), 3.83-3.76 (m, 2H), 3.67 (t, 2H), 3.03-2.81 (m, 5H), 2.77 (d, 3H), 2.17-2.08 (m, 1H), and 1.89-1.75 (m, 1H). LCMS: (FA) ES+543.2, ES−541.2.

Compounds in the following table were prepared from the appropriate starting materials in a method analogous to that of Example 36:

| | |
|---|---|
| I-230 | $^1$H NMR(400MHz, d$_6$-DMSO, HCl salt) δ: 10.69(s, 1H), 9.25-9.17(br s, 1H), 8.86-8.79(m, 1H), 8.51(d, 1H), 8.47-8.38(br s, 2H), 8.10-8.01(m, 2H), 7.59(s, 1H), 7.40(s, 1H), 7.24(d, 1H), 7.20-7.15(m, 1H), 7.02(s, 1H), 7.01-6.94(m, 1H), 4.20(t, 1H), 4.12-4.04(m, 2H), 3.13-3.03(m, 1H), 3.02-2.81(m, 6H), 2.77(d, 3H), 2.55(t, 1H), 2.18-2.07(m, 1H), and 1.90-1.76(m, 1H). LCMS: (FA) ES+ 570.2, ES− 568.2. |

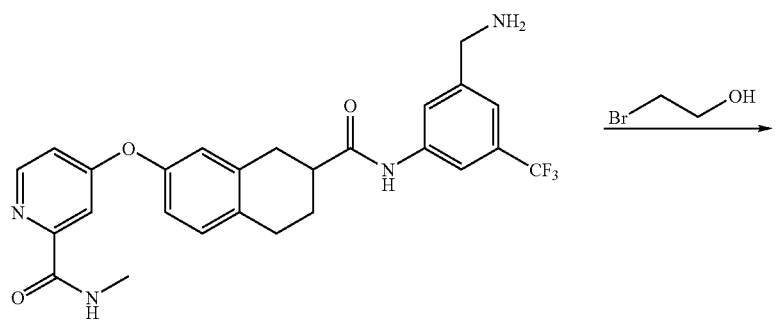

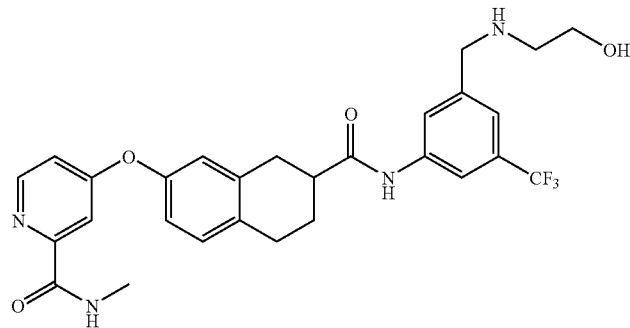

I-276

Example 37

Preparation of N-(3-tert-butylphenyl)-7-[(2-piperazin-1-ylpyridin-4-yl)oxy]-1,2,3,4-tetrahydronaphthalene-2-carboxamide I-278

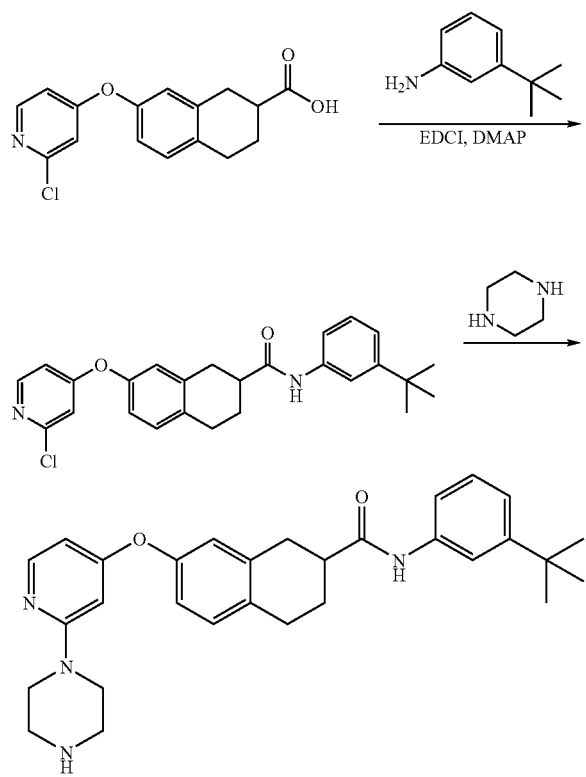

I-278

Step 1: N-(3-tert-butylphenyl)-7-[(2-chloropyridin-4-yl)oxy]-1,2,3,4-tetrahydronaphthalene-2-carboxamide A solution of 7-[(2-chloropyridin-4-yl)oxy]-1,2,3,4-tetrahydronaphthalene-2-carboxylic acid (1.07 g. 3.52 mmol), 3-tert-butylanline (0.58 mL, 3.9 mmol), DMAP (0.64 g, 5.3 mmol) and EDCI (1.0 g, 5.3 mmol) in DCM (20 mL) was allowed to stir at rt overnight. The reaction mixture was diluted with water and extracted with EtOAc. The organic solutions were combined, dried over $MgSO_4$, filtered and concentrated. The residue was purified by column chromatography to give N-(3-tert-butylphenyl)-7-[(2-chloropyridin-4-yl)oxy]-1,2,3,4-tetrahydronaphthalene-2-carboxamide as a white solid. LCMS: ES+435.

Step 2: N-(3-tert-butylphenyl)-7-[(2-piperazin-1-ylpyridin-4-yl)oxy]-1,2,3,4-tetrahydronaphthalene-2-carboxamide I-278

A solution of N-(3-tert-butylphenyl)-7-[(2-chloropyridin-4-yl)oxy]-1,2,3,4-tetrahydronaphthalene-2-carboxamide (0.265 g, 0.61 mmol) and piperazine (0.140 g, 1.6 mmol) in acetonitrile (10 mL) was allowed to stir and heated at reflux overnight. No product had formed so the mixture was subjected to MWI at 160° C. for 10 min, then at 180° C. for 20 min, then again at 180° C. for 20 min. The mixture was concentrated and the residue was purified by column chromatography to give N-(3-tert-butylphenyl)-7-[(2-piperazin-1-ylpyridin-4-yl)oxy]-1,2,3,4-tetrahydronaphthalene-2-carboxamide I-278 ) (96 mg, 33%). $^1$H NMR (400 MHz, $d_6$-DMSO, HCl salt) δ: 10.08 (s, 1H), 9.53 (s, 1H), 8.04 (d, 1H), 7.65 (s, 1H), 7.52 (d, 1H), 7.24-7.18 (m, 2H), 7.07 (d, 1H), 6.99 (s, 1H), 6.96 (d, 1H), 6.78 (s, 1H), 6.44 (d, 1H), 3.85 (s, 4H), 3.20 (s, 4H), 2.93-2.75 (m, 5H), 2.11-2.07 (m, 1H), 1.78-1.76 (m, 1H), 1.25 (s, 9H). LCMS: (FA) ES+485.0.

Compounds in the following table were prepared from the appropriate starting materials in a method analogous to that of Example 37:

| | |
|---|---|
| I-237 | $^1$H NMR(400MHz, $d_6$-DMSO, HCl salt) δ: 9.50(s, 1H), 7.21(d, 1H), 7.85(d, 2H), 6.44(d, 1H), 6.24(s, 1H), 6.15-6.19(m, 2H), 5.87-5.90(m, 2H), 3.60-3.63(m, 2H), 3.09-3.11(m, 4H), 2.89-2.94(m, 4H), 2.62-2.64(m, 4H), 2.42-2.47(m, 2H), 2.07-2.32(m, 5H), 1.08-1.43(m, 6H) LCMS: (FA) ES+ 610.00. |
| I-366 | $^1$H NMR(400MHz, $d_6$-DMSO, HCl salt) δ: 10.01(s, 1H), 7.93(d, 1H), 7.64(dd, 1H), 7.49(d, 1H), 7.17-7.27(m, 2H), 6.96-7.07(m, 3H), 6.48(d, 1H), 6.42(dd, 1H), 3.14(s, 6H), 2.92-2.98(m, 2H), 2.69-2.91(m, 3H), 2.04-2.14(m, 1H), 1.73-1.85(m, 1H), and 1.26(s, 9H). LCMS: (FA) ES+ 444.7, ES− 442.3. |
| I-415 | $^1$H NMR(400MHz, $d_6$-DMSO, HCl salt) δ: 10.88(s, 1H), 10.01(s, 1H), 8.04(d, 1H), 7.64(dd, 1H), 7.50(d, 1H), 7.18-7.23(m, 2H), 7.06(ddd, 1H), 6.95(d, 1H), 6.91(dd, 1H), 6.71(s, 1H), 6.34(d, 1H), 4.35(d, 2H), 3.46(d, 2H), 3.35(dd, 2H), 3.01-3.14(m, 2H), 2.88-2.98(m, 2H), 2.73-2.87(m, 6H), 2.09(d, 1H), 1.74-1.82(m, 1H), and 1.25(s, 9H). LCMS: (FA) ES+ 499.4, ES− 497.3. |
| I-367 | $^1$H NMR(400MHz, $d_6$-DMSO, HCl salt) δ: 9.86(s, 1H), 7.87(d, 1H), 7.64(dd, 1H), 7.42(ddd, 1H), 7.29-7.38(m, 3H), 7.23(dd, 1H), 7.18(d, 1H), 7.11-7.17(m, 3H), 6.85(d, 1H), 6.81(dd, 1H), 6.66(dd, 1H), 6.22(d, 1H), 4.70(s, 2H), 3.33(s, 3H), 2.76-3.09(m, 5H), 2.20(d, 1H), 1.88-2.00(m, 1H), and 1.31(s, 9H). LCMS: (FA) ES+ 521.0, ES− 518.6. |
| I-342 | $^1$H NMR(400MHz, $d_6$-DMSO; HCl salt) δ: 10.01(s, 1H), 8.39(br. s, 1H), 7.89(d, 1H), 7.64(s, 1H), 7.51(d, 1H), 7.26(d, 1H), 7.21(dd, 1H), 7.06(dd, 1H), 7.03(d, 1H), 6.98(dd, 1H), 6.59(d, 1H), 6.13(s, 1H), 2.89-2.97(m, 2H), 2.86(d, 4H), 2.72-2.84(m, 3H), 2.05-2.14(m, 1H), 1.70-1.84(m, 1H), and 1.26(s, 9H). LCMS: (FA) ES+ 430.1, ES− 428.4. |

Example 38

Preparation of N-[3-(aminomethyl)-5-(trifluoromethyl)phenyl]-7-({2-[5-(trifluoromethyl)-1H-imidazol-2-yl]pyridin-4-yl}oxy)-1,2,3,4-tetrahydronaphthalene-2-carboxamide I-332

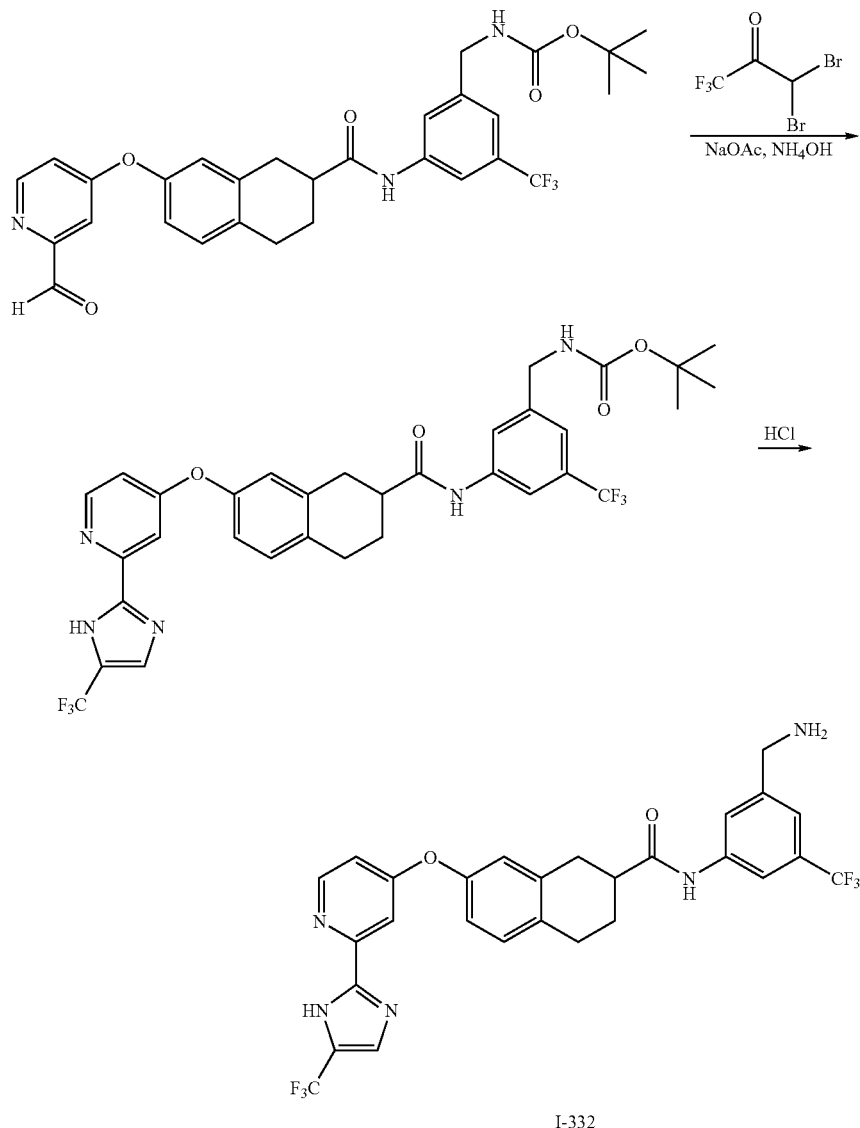

I-332

Step 1: tert-butyl [3-(trifluoromethyl)-5-({[7-({2-[5-(trifluoromethyl)-1H-imidazol-2-yl]-pyridin-4-yl}oxy)-1,2,3,4-tetrahydronaphthalen-2-yl]carbonyl}amino)-benzyl]-carbamate A solution of sodium acetate (93.6 mg, 1.14 mmol) and 3,3-dibromo-1,1,1-trifluoroacetone (80.3 mg, 0.69 mmol) in water (0.50 mL) was heated at 100° C. for 30 min. The solution was allowed to cool to rt and then added to a solution of tert-butyl [3-[({7-[(2-formylpyridin-4-yl)oxy]-1,2,3,4-tetrahydronaphthalen-2-yl}carbonyl)amino]-5-(trifluoromethyl)-benzyl]carbamate (130 mg, 0.23 mmol) in MeOH (2.00 mL) and ammonium hydroxide (0.50 mL). The reaction mixture was allowed to stir at rt for 90 min. and then additional MeOH was added to aid in dissolution. Stirring was continued for 7 h. The solvents were evaporated and the residue was triturated with DCM. The solid was removed. The filtrate was evaporated and the residue was purified by column chromatography to give tert-butyl [3-(trifluoromethyl)-5-({[7-({2-[5-(trifluoromethyl)-1H-imidazol-2-yl]pyridin-4-yl}oxy)-1,2,3,4-tetrahydronaphthalen-2-yl]carbonyl}amino)benzyl]carbamate (46.0 mg, 29.8%). LCMS: (FA) ES+676.3.

Step 2: N-3-(aminomethyl)-5-(trifluoromethyl)phenyl]-7-({2-[5-(trifluoromethyl)-1H-imidazol-2-yl]pyridin-4-yl}oxy)-1,2,3,4-tetrahydronaphthalene-2-carboxamide I-332 tert-Butyl [3-(trifluoromethyl)-5-({[7-({2-[5-(trifluoromethyl)-1H-imidazol-2-yl]-pyridin-4-yl}oxy)-1,2,3,4-tetrahydronaphthalen-2-yl]carbonyl}amino)benzyl]carbamate (45.0 mg, 0.07 mmol) was treated with a solution of 4.0M HCl in dioxane (12.0 mL) and stirred for 1 h. The solvents were evaporated to give N-[3-(aminomethyl)-5-(trifluoromethyl)phenyl]-7-({2-5-(trifluoromethyl)-1H-imidazol-2-yl]pyridin-4-yl}oxy)-1,2,3,4-tetrahydronaphthalene-2-carboxamide I-332 as the HCl salt (41.0 mg, 94.9%). $^1$H NMR (400 MHz, d$_6$-DMSO, HCl salt) δ: 10.58 (s, 1H), 8.54 (d, 1H), 8.31 (br s, 2H), 8.02 (d, 2H), 7.87 (s, 1H), 7.57 (s, 1H), 7.38 (d, 1H), 7.26 (d, 1H), 7.08-7.09 (m, 1H), 7.05 (d, 1H), 6.99-7.02 (m, 1H), 4.09 (q, 2H), 2.85-2.98 (m, 5H), 2.09-2.16 (m, 1H), and 1.79-1.89 (m, 1H). LCMS: (FA) ES+576.3, ES−574.4.

Compounds in the following table were prepared from the appropriate starting materials in a method analogous to that of Example 38:

| | |
|---|---|
| I-361 | $^1$H NMR(400MHz, d$_6$-DMSO, HCOOH salt) δ: 9.93(s, 1H), 8.53(d, 1H), 7.85(s, 1H), 7.63(t, 1H), 7.50-7.47(m, 1H), 7.37(d, 1H), 7.27-7.18(m, 2H), 7.08-7.03(m, 3H), 7.01-6.97(m, 1H), 2.98-2.64(m, 5H), 2.15-2.05(m, 1H), 1.87-1.72(m, 1H), and 1.25(s, 9H). LCMS: (FA) ES+ 535.1, ES− 533.0. |

Example 39

Preparation of N-(3-tert-butylphenyl)-7-({2-[(2-pyrrolidin-1-ylpropanoyl)-amino]pyridin-4-yl}oxy)-1,2,3,4-tetrahydronaphthalene-2-carboxamide I-275

Step 1: N-(3tert-butylphenyl)-7-{2-[(2-chloropropanyoyl)amino]pyridin-4}oxy)-1,2,3,4-tetrahydronaphthalene-2-carboxamide To a solution of 7-[(2-aminopyridin-4-yl)oxy]-N-(3-tert-butylphenyl)-1,2,3,4-tetrahydronaphthalene-2-carboxamide (1.50 g, 3.64 mmol) in THF (36 mL) at 0°, was added TEA (1.02 mL, 7.29 mmol) and then 2-chloropropanyoyl chloride (0.39 mL, 4.01 mmol) dropwise. The reaction was allowed to warm to rt and stir for 18 h. Water was added and the mixture was extracted with EtOAc (2×). The organic solutions were combined, washed with water, dried over Na$_2$SO$_4$ and concentrated. The residue was purified by column chromatography to give N-(3tert-butylphenyl)-7-({2-[(2-pyrrolidin-1-ylpropanyl)amino]pyridin-4yl}oxy)-1,2,3,4-tetrahydronaphthalene-2-carboxamide I-275 as a pale yellow solid (1.37 g, 74.9%).

Step 2: N-(3-tert-butylphenyl)-7-({2-[(2-pyrrolidin-1-ylpropanoyl)-amino]pyridin-4-yl}-oxy)-1,2,3,4tetrahydronaphthalene-2-carboxamide I-275

To a solution of N-(3tert-butylphenyl)-7-({2-[(2-chloropropanoyl)amino]pyridin-4yl}oxy)-1,2,3,4tetrahydronaphthalene-2-carboxamide (400 mg, 0.79 mmol) in DMF (8 mL) was added sodium iodide (131 mg, 0.88 mmol) and then pyrrolidine (0.67 mL, 7.97 mmol). The reaction mixture was allowed to stir at rt for 24 h. Water was added and the resulting precipitate was filtered, washed with water then hexane and

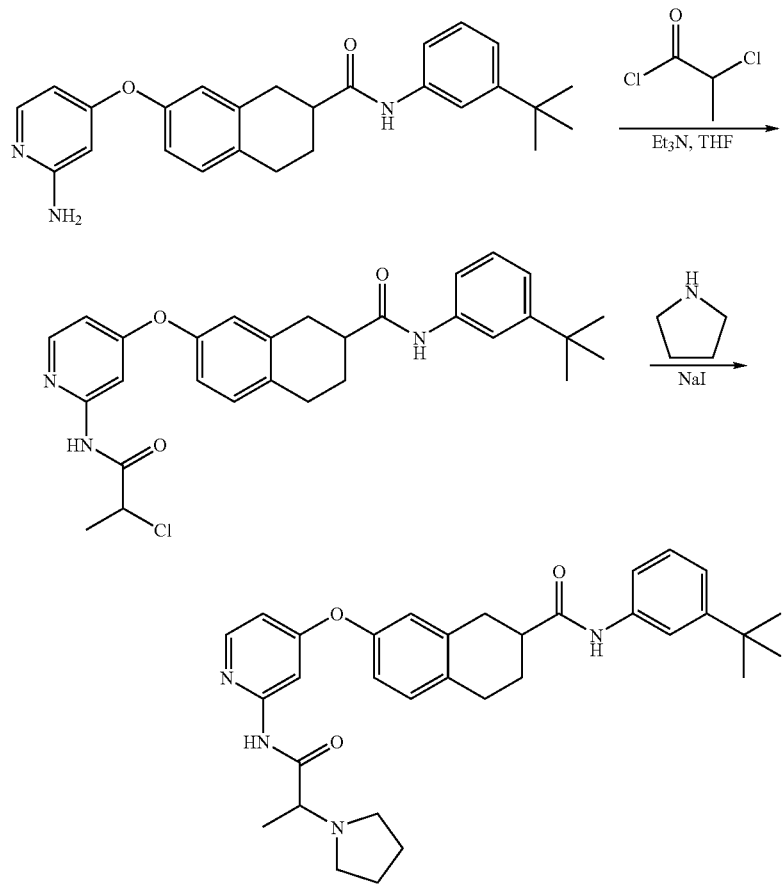

I-275 dried under vacuum. The HCl salt was prepared by dissolving the residue in MeOH/DCM and adding of 2.0M HCl-Et$_2$O solution, followed by evaporation. (424 mg, 87.3%). $^1$H NMR (400 MHz, d$_6$-DMSO) δ: 11.31 (s, 1H), 10.43 (br s, 1H), 10.05 (s, 1H), 8.24 (d, 1H), 7.65 (s, 2H), 7.50 (d, 1H), 7.23-7.19 (m, 2H), 7.05 (d, 1H), 6.98 (s, 1H), 6.95-6.92 (m, 1H), 6.77-6.74 (m, 1H), 4.17 (t, 1H), 3.47 (br s, 2H), 3.11-3.04 (m, 2H), 2.94-2.75 (m, 5H), 2.13-2.05 (m, 1H), 1.99-1.95 (m, 2H), 1.88-1.83 (m, 2H), 1.79-1.72 (m, 1H), 1.52 (d, 3H), and 1.25 (s, 9H). LCMS: (FA) ES+541.9, ES−539.1.

Compounds in the following table were prepared from the appropriate starting materials in a method analogous to that of Example 39:

| | |
|---|---|
| I-207 | $^1$H NMR(300MHz, d$_6$-DMSO, HCl Salt) δ: 11.35(s, 1H), 10.41(s, 1H), 10.33(br s, 1H), 8.58(s, 1H), 8.31(d, 1H), 8.15(t, 2H), 8.05(d, 1H), 7.90(s, 1H), 7.81(s, 1H), 7.73(d, 1H), 7.67(s, 1H), 7.53-7.50(m, 1H), 7.29(t, 1H), 7.14(d, 1H), 6.93-6.90(m, 1H), 4.20-4.12(m, 1H), 3.49-3.38(m, 2H), 3.11-3.00(m, 2H), 1.98-1.88(m, 2H), 1.85-1.77(m, 2H), 1.49(d, 3H), and 1.29(s, 9H). LCMS: (FA) ES+ 437.5, ES− 536.2. |
| I-289 | $^1$H NMR(300MHz, d$_6$-DMSO, HCl Salt) δ: 11.41(s, 1H), 10.87(br s, 1H), 10.43(s, 1H), 8.59(s, 1H), 8.32(d, 1H), 8.15(t, 2H), 8.06-8.03(m, 1H), 7.90(d, 1H), 7.82(s, 1H), 7.74(d, 1H), 7.67(s, 1H), 7.53-7.49(m, 1H), 7.29(t, 1H), 7.15(d, 1H), 6.95-6.92(m, 1H), 4.23-4.17(m, 1H), 3.95-3.68(m, 4H), 3.43-3.08(m, 4H), 1.50(d, 3H), and 1.29(s, 9H). LCMS: (FA) ES+ 553.8, ES− 551.9. |
| I-364 | $^1$H NMR(300MHz, d$_6$-DMSO, HCl Salt) δ: 11.11(s, 1H), 10.43(s, 1H), 8.60(s, 1H), 8.34(d, 1H), 8.20-8.13(m, 2H), 8.07-8.03(m, 1H), 7.92(d, 1H), 7.82(t, 1H), 7.76-7.70(m, 2H), 7.52(dd, 1H), 7.29(t, 1H), 7.15(d, 1H), 6.98(dd, 1H), 3.86(br s, 1H), 3.49-3.42(m, 2H), 3.34-3.15(m, 5H), 2.94(br s, 1H), 2.74(s, 3H), and 1.29(s, 12H). LCMS: (FA) ES+ 564.1, ES− 566.7. |

Example 40

Preparation of N-[3-(aminomethyl)-5-(trifluoromethyl)phenyl]-7-({2-[(cyclopropylcarbonyl)amino]pyridin-4-yl}oxy)-3,4-dihydroisoquinoline-2(1H)-carboxamide I-446

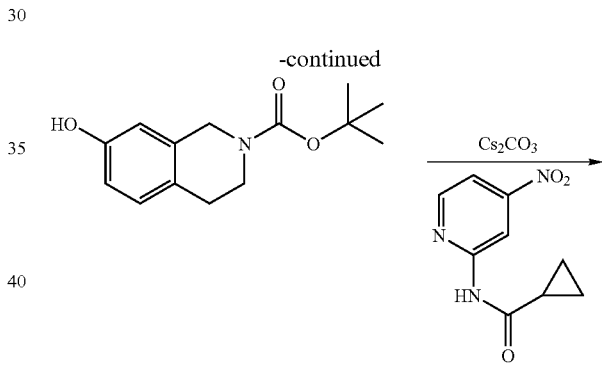

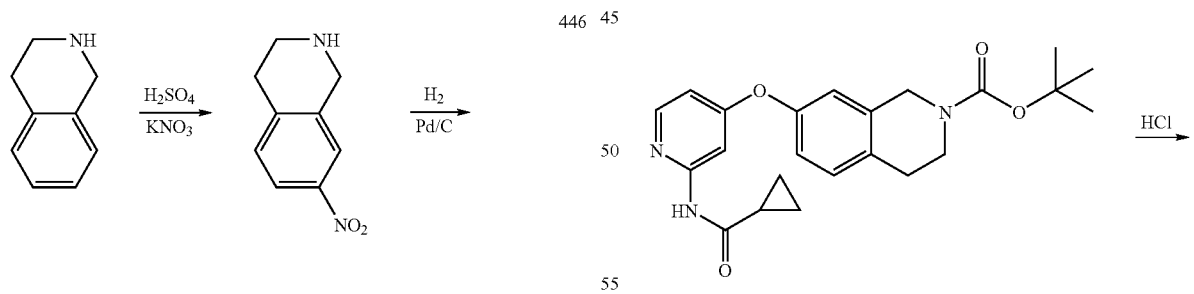

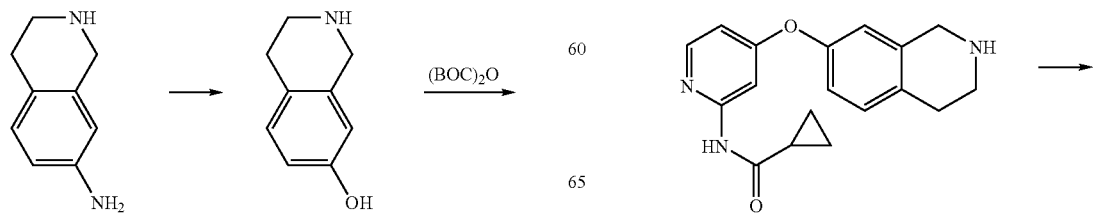

-continued

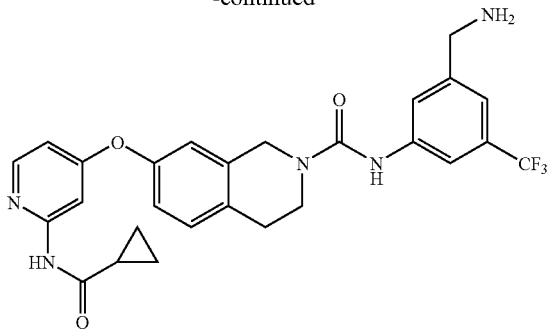

I-446

Step 1: 7-nitro-1,2,3,4-tetrahydroisoquinoline

Sulfuric acid (9.90 mL, 0.186 mol) was cooled to 0° C. To the cooled solution was added 1,2,3,4-Tetrahydroisoquinoline (2.5 mL, 020.0 mmol) dropwise via syringe. Potassium nitrate (2.16 g, 0.0214 mol) was then added in small portions over 4 min. The cooling bath was removed and the mixture was allowed to stir at rt for 12 h. Ice was added to the slurry and the mixture basified with NH$_4$OH (precipitate formed). The solution was extracted with chloroform, dried over Na$_2$SO$_4$, filtered, and concentrated to give a brown oil. The oil was dissolved in ethanol (14.8 mL, 0.254 mol) and to this solution was added HCl (2.47 mL, 0.0808 mol). Additional EtOH was added to transfer the precipitated solid for filtration. The white solid was dried under vacuum to yield the desired product without further purification (2.19 g, 51%)

Step 2: 1,2,3,4-tetrahydroisoquinolin-7-amine

A mixture of 7-nitro-1,2,3,4-tetrahydro-isoquinoline (38 g, 0.21 mol) and 10% Pd/C (5 g) in MeOH (400 mL) was stirred under an atmosphere of hydrogen at rt for 16 h and then filtered through Celite. Removal of solvent gave 1,2,3,4-tetrahydroisoquinolin-7-amine as a pink solid in quantitative yield. MS: 149.

Step 3: 1,2,3,4-tetrahydroisoquinolin-7-ol

A solution of 1,2,3,4-tetrahydro-isoquinolin-7-amine (4.5 g, 30 mmol) in sulfuric acid (6.5 mL, 120 mmol) and water (20 mL) was cooled to 0° C. To this cold solution was added a solution of sodium nitrite (2.51 g, 36 mmol) in water (20 mL) over 15 min. After the addition, the reaction mixture was heated at 120° C. for 2 h and then allowed to cool to rt. Solid Na$_2$CO$_3$ was added slowly to the reaction mixture until no gas generated. A small amount of water was added to dissolve the remaining Na$_2$CO$_3$ and a sticky brown glue was formed. The residue was dissolved in MeOH and filtered through Celite. The filtrate was concentrated to give 1,2,3,4-tetrahydroisoquinolin-7-ol as a brown solid (3.7 g, 82% crude yield), which was directly used in the next step without further purification. MS: 150.

Step 4: tert-butyl 7-hydroxy-3,4-dihydroisoquinoline-2(1H)-carboxylate

To a solution of 1,2,3,4-tetrahydroisoquinolin-7-ol (2.9 g, 19 mmol) in DMF (2.0 mL) and TEA (14 mL, 97 mmol) at −15° C. was added a solution of di-tert-butyldicarbonate (5.1 g, 23 mmol) in DMF (10 mL) dropwise. After the addition was complete, the reaction mixture was allowed to stir and warm to rt for 2 hr., and then concentrated. The residue was taken with EtOAc and washed with 0.5N aq. HCl and brine successively. Column chromatography (30% EtOAc/hexane) gave the product as a yellow solid (2.0 g, 41% yield). MS: 250. $^1$H NMR (300 MHz, CDCl$_3$) δ: 6.96 (d, 1H), 6.71 (dd, 1H), 6.66 (d, 1H), 4.50 (t, 2H), 3.61 (m, 2H), 2.73 (m, 2H), and 1.49 (s, 9H).

Step 5: tert-butyl 7-({2-[(cyclopropylcarbonyl)amino]pyridin-4-yl}oxy)-3,4-dihydroisoquinoline-2(1H)-carboxylate A solution of tert-butyl 7-hydroxy-3,4-dihydroisoquinoline-2(1H)-carboxylate (2.61 g, 0.011 mol), N-(4-nitropyridin-2-yl)cyclopropanecarboxamide (2.17 g, 0.011 mol) and cesium carbonate (10.2 g, 0.031 mol) in DMF (100 mL) was allowed to stir at 90° C. for 2 hr. The reaction mixture was allowed to cool to rt and was diluted with water until all of the cesium carbonate was dissolved. The solution was extracted with EtOAc. The organic solutions were combined, washed with water and brine, and concentrated. The residue was purified by column chromatography to give tert-butyl 7-({2-[(cyclopropylcarbonyl)amino]pyridin-4-yl}oxy)-3,4-dihydroisoquinoline-2(1H)-carboxylate (2.18 g, 49% yield) as a yellow oil. LCMS: (FA) ES+410.4.

Step 6: N-[4-(1,2,3,4-tetrahydroisoquinolin-7-yloxy)pyridin-2-yl]-cyclopropanecarboxamide A solution of tert-butyl 7-({2-[(cyclopropylcarbonyl)amino]pyridin-4-yl}oxy)-3,4-dihydroisoquinoline-2(1H)-carboxylate (2.22 g, 0.0051 mol) in 4M of HCl in 1,4-Dioxane (20 mL) was allowed to stir at rt for 30 min. The reaction mixture was concentrated to give N-[4-(1,2,3,4-tetrahydroisoquinolin-7-yloxy)pyridin-2-yl]cyclopropanecarboxamide. LCMS: (FA) ES+310.3.

Step 7: N-[3-(aminomethyl)-5-(trifluoromethyl)phenyl]-7-({2-[(cyclopropylcarbonyl)-amino]pyridin-4-yl}oxy)-3,4-dihydroisoquinoline-2(1H)-carboxamide I-446

A solution of tert-butyl [3-amino-5-(trifluoromethyl)benzyl]carbamate (206 mg, 7.11 mmol) in DCM (6 mL) was added to triphosgene (95.9 mg, 3.23 mmol) in DCM (4 mL) at 0° C. TEA (0.360 mL, 0.0026 mol) was added. After 30 min, N-[4-(1,2,3,4-tetrahydroisoquinolin-7-yloxy)pyridin-2-yl]cyclopropanecarboxamide (200 mg, 6.46 mmol) in DMF (6 mL) was added at 0° C. The solution was allowed to stir and warm to rt overnight. The reaction mixture was diluted with DCM, washed with water and brine and the organic solution was concentrated. The residue was purified by column chromatography to give the BOC protected material as a white solid (140 mg, 33%). LCMS: (FA) ES+626.4. This solid was dissolved in DCM and treated with 1N HCl in Et$_2$O. The solvents were evaporated to give N-[3-(aminomethyl)-5-(trifluoromethyl)phenyl]-7-({2-[(cyclopropylcarbonyl)amino]pyridin-4-yl}oxy)-3,4-dihydroisoquinoline-2(1H)-carboxamide I-446 (83 mg, 63%). ( ) $^1$H NMR (300 MHz, CD$_3$OD, HCl salt) δ: 8.20-8.30 (m, 1H), 7.89 (s, 1H), 7.81 (s, 1H), 7.30-7.48 (m, 2H), 7.11-7.18 (m, 3H), 6.73-6.08 (m, 1H), 4.74-4.84 (m, 2H), 4.18 (s, 2H), 3.79-3.99 (m, 2H), 3.00-3.06 (m, 2H), 2.76-2.84 (m, 1H), 1.78-1.84 (m, 1H), and 1.00-1.13 (m, 4H). LCMS: (FA) ES+526.4, ES−524.5.

Compounds in the following table were prepared from the appropriate starting materials in a method analogous to that of Example 40:

| | |
|---|---|
| I-259 | $^1$H NMR(400MHz, $d_6$-DMSO, HCl Salt) δ: 11.13(br s, 1H), 9.07(s, 1H), 8.20(d, 1H), 8.10-8.05(m, 1H), 7.86-7.81(m, 1H), 7.60-7.55(m, 1H), 7.47(s, 1H), 7.30(d, 1H), 7.07-7.00(m, 2H), 6.78-6.72(m, 1H), 4.66(s, 2H), 3.77-3.67(m, 3H), 2.99-2.84(m, 2H), 1.97-1.90(m, 1H), and 0.84-0.74(m, 3H). LCMS: (FA) ES+ 531.2. |
| I-164 | $^1$H NMR(400MHz, $d_6$-DMSO, HCl Salt) δ: 10.93(s, 1H), 9.08(s, 1H), 8.24-8.18(m, 1H), 8.07(s, 1H), 7.88-7.80(m, 1H), 7.61-7.55(m, 1H), 7.41(br s, 1H), 7.35-7.30(m, 1H), 7.11-7.00(m, 2H), 6.82-6.76(m, 1H), 4.66(s, 2H), 3.81-3.65(m, 2H), 2.96-2.85(m, 2H), and 2.07(s, 3H). LCMS: (FA) ES+ 505.2, ES− 503.3. |
| I-172 | $^1$H NMR(400MHz, $d_6$-DMSO) δ: 9.05(s, 1H), 8.50(d, 1H), 8.18(s, 1H), 8.06(d, 1H), 7.82(dd, 1H), 7.57(d, 1H), 7.38-7.40(m, 1H), 7.32(d, 1H), 7.14(dd, 1H), 7.07(d, 1H), 7.04(dd, 1H), 4.67(s, 2H), 3.75(dd, 2H), 3.60(s, 4H), and 2.90(dd, 2H). LCMS: (FA) ES+ 513.9, ES− 516.5. |
| I-405 | $^1$H NMR(300MHz, $CD_3OD$, HCl Salt) δ: 8.20-8.26(m, 1H), 7.91(br s, 1H), 7.83(br s, 1H), 7.46(br s, 1H), 7.41(d, 1H), 7.09-7.09(m, 3H), 6.72-6.79(m, 1H), 4.78(s, 1H), 4.24(s, 2H), 3.78-3.89(m, 2H), 3.00-3.07(m, 2H), 2.75(m, 4H), 1.75-1.83(m, 1H), and 0.99-1.12(m, 4H). LCMS: (FA) ES$^+$ 540.4. |
| I-431 | $^1$H NMR(300MHz, $CD_3OD$, HCl Salt) δ: 8.20-8.26(m, 1H), 7.28-7.89(m, 2H), 7.07-7.24(m, 6H), 6.65-6.75(m, 1H), 4.72-4.85(m, 2H), 3.76-3.90(m, 2H), 3.00-3.08(m, 1.5H), 2.71-2.81(m, 0.5H), 1.75-1.84(m, 1H), 1.29-1.35(m, 9H), and 1.00-1.15(m, 4H). LCMS: (FA) ES+ 485.4. |
| I-446 | $^1$H NMR(300MHz, $CD_3OD$, HCl Salt) δ: 8.20-8.30(m, 1H), 7.89(s, 1H), 7.81(s, 1H), 7.30-7.48(m, 2H), 7.11-7.18(m, 3H), 6.73-6.08(m, 1H), 4.74-4.84(m, 2H), 4.18(s, 2H), 3.79-3.99(m, 2H), 3.00-3.06(m, 2H), 2.76-2.84(m, 1H), 1.78-1.84(m, 1H), and 1.00-1.13(m, 4H). LCMS: (FA) ES+526.4, ES− 524.5. |
| I-459 | $^1$H NMR(300MHz, $CD_3OD$, HCl Salt) δ: 8.19-8.26(m, 1H), 7.37-7.45(m, 3H), 7.19(m, 1H), 7.06-7.14(m, 3H), 6.77-6.86(m, 1H), 4.74-4.83(m, 2H), 4.06(m, 2H), 3.71-3.85(m, 2H), 2.98-3.06(m, 1.5H), 2.75(m, 0.5H), 1.76-1.83(m, 1H), 1.29-1.35(m, 9H), and 0.99-1.12(m, 4H). LCMS: (FA) ES+ 514.5. |

Example 41

Preparation of tert-butyl [3-{[(7-{[2-(1H-pyrazol-4yl)pyridin-4-yl]oxy}-1,2,3,4-tetrahydronaphthalen-2-yl)carbonyl]amino}-5-(trifluoromethyl)benzyl] carbamate I-252

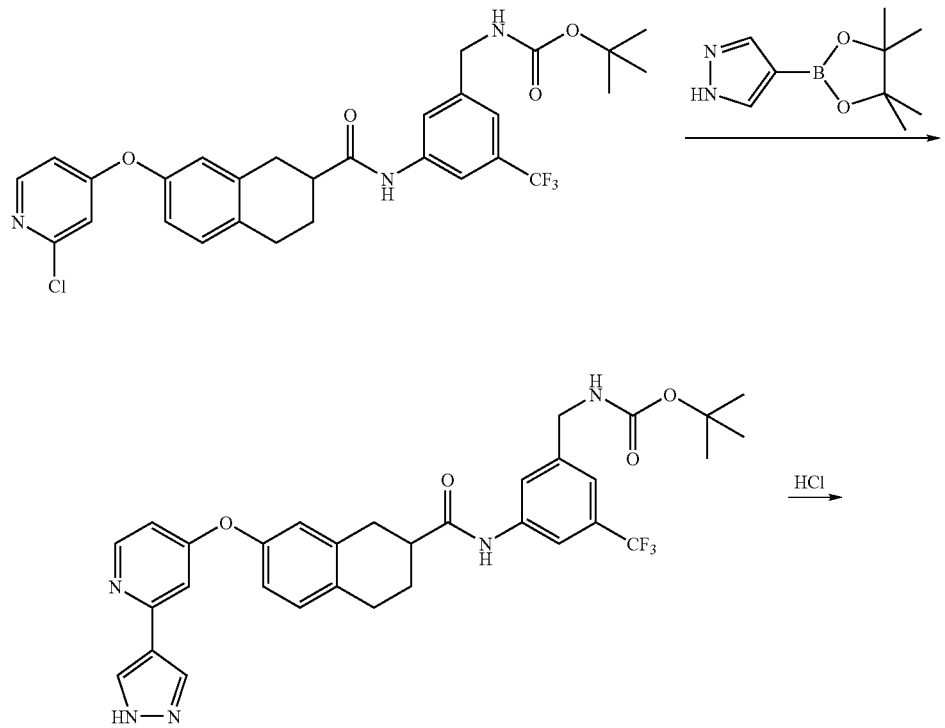

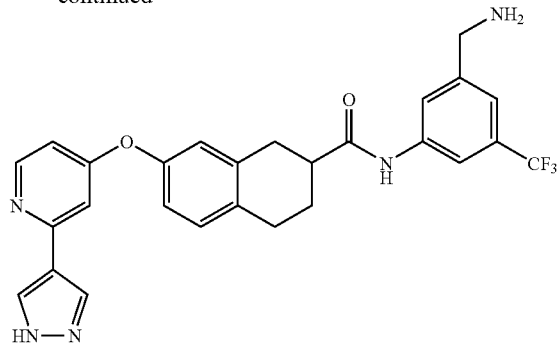

I-252

Step 1: tert-butyl [3-{[(7-{[2-(1H-pyrazol-4-yl)pyridin-4-yl]oxy}-1,2,3,4-tetrahydronaphthalen-2-yl)carbonyl]amino}-5-(trifluoromethyl)benzyl]carbamate A mixture of tert-butyl 3-[({7-[(2-chloropyridin-4-yl)oxy]-1,2,3,4-tetrahydronaphthalen-2-yl}carbonyl)amino]-5-(trifluoromethyl)benzyl]carbamate (0.500 g, 0.86 mmol), 4-(4,4,5,5-tetramethyl-1,3,2-dioxaborolan-2-yl)-1H-pyrazole (0.253 g, 1.3 mmol) and sodium carbonate (0.368 g, 3.47 mmol) in water (1 mL) and 1,2 dimethoxyethane (5 mL) was degassed it with nitrogen gas for 5 min. Tetrakis(triphenylphosphine)palladium(0) (0.0.06 g, 0.05 mmol) was added the mixture was subjected to MWI at 120° C. for 1 h. Water was added and the mixture was extracted with EtOAc. The organic solutions were combined, washed with brine, dried over $Na_2SO_4$, filtered and concentrated. The residue was purified by column chromatography to give tert-butyl 3-{[(7-{[2-(1H-pyrazol-4-yl)pyridin-4-yl]oxy}-1,2,3,4-tetrahydronaphthalen-2-yl)carbonyl]amino}-5-(trifluoromethyl)benzyl]carbamate. LCMS: (FA) ES$^+$608.3.

Step 2: N-[3-(aminomethyl)-5-(trifluoromethyl)phenyl]-7-{[2-(1H-pyrazol-4-yl)pyridin-4-yl]oxy}-1,2,3,4tetrahydronaphthalene-2-carboxamide I-252

A mixture of tert-butyl [3-{[(7-{[2-(1H-pyrazol-4-yl)pyridin-4-yl]oxy}-1,2,3,4-tetrahydronaphthalen-2-yl)carbonyl]amino}-5-(trifluoromethyl)benzyl]carbamate (0.238 g, 0.39 mmol) and 4M of HCl in dioxane (4 mL) was allowed to stir at rt for 1 h. The solvents were evaporated to give N-[3-(aminomethyl)-5-(trifluoromethyl)phenyl]-7-{[2-(1H-pyrazol-4-yl)-pyridin-4-yl]oxy}-1,2,3,4-tetrahydronaphthalene-2-carboxamide I-252. $^1$H NMR (400 MHz, d$_6$-DMSO, HCl salt) δ: 10.83 (s, 1H), 8.71 (br s, 2H), 8.36-8.56 (m, 4H), 8.09 (s, 1H), 8.03 (s, 1H), 7.89 (s, 1H), 7.60 (s, 1H), 7.29 (d, 1H), 7.04-7.13 (m, 2H), 6.93-6.97 (m, 1H), 4.05-4.12 (m, 2H), 2.79-3.01 (m, 5H), 2.09-2.17 (m, 1H), and 1.76-1.88 (m, 1H). LCMS: (FA) ES+508.3, ES–506.4.

Example 42

Preparation of 7-{[2-(acetylamino)pyridin-4-yl]oxy}-N-[3-{[(2R)-2,3-dihydroxypropyl]oxy}-5-(trifluoromethyl)phenyl]-1,2,3,4-tetrahydronaphthalene-2-carboxamide I-412

I-412

A mixture of 7-{[2-(acetylamino)pyridin-4-yl]oxy}-N-[3-{[(4S)-2,2-dimethyl-1,3-dioxolan-4-yl]methoxy}-5-(trifluoromethyl)phenyl]-1,2,3,4-tetrahydronaphthalene-2-carboxamide (100 mg, 0.16 mmol) and pTSA (28 mg, .16 mmol) in MeOH (7 mL) and water (1 mL) was allowed to stir at rt overnight and then at 70° C. Water was added and the mixture was extracted with EtOAc. The organic solutions were combined, washed with sat. aq. NaHCO$_3$ and brine, dried over Na$_2$SO$_4$, filtered and concentrated. The residue was purified by column chromatography to give 7-{[2-(acetylamino)pyridin-4-yl]oxy}-N-3-{[(2R)-2,3-dihydroxypropyl]-oxy}-5-(trifluoromethyl)phenyl]-1,2,3,4-tetrahydronaphthalene-2-carboxamide (I-412) (80 mg, 68%) as a white solid. $^1$H NMR (400 MHz, d$_6$-DMSO, HCl salt) δ: 10.52 (s, 1H), 8.24 (d, 1H), 7.66 (br s, 1H), 7.56 (br s, 1H), 7.29-7.17 (m, 2H), 7.06-6.86 (m, 4H), 4.07-3.75 (m, 3H), 3.46-3.40 (m, 2H), 3.00-2.74 (m, 5H), 2.19-2.05 (m, 4H), and 1.89-1.71 (m, 1H). LCMS: (FA) ES+560.1, ES−558.0.

Example 43:

Preparation of (2S)-2,3-dihydroxypropyl {4-[(7-{[(3tert-butylphenyl)-amino]carbonyl}-5,6,7,8-tetrahydronaphthalen-2-yl)oxy]pyridin-2-yl}carbamate (I-272)

Step 1: N-(3-tert-butylphenyl)-7-[(2-isocyanatopyridin-4-yl)oxy]-1,2,3,4-tetrahydronaphthalene-2-carboxamide A solution of triphosgene (304 mg, 1.02 mmol) in THF (15 mL) was cooled to 0° C. To this solution was added TEA (0.74 mL, 5.32 mmol). A solution of 7-[(2-aminopyridin-4-yl)oxy]-N-(3-tert-butylphenyl)-1,2,3,4-tetrahydronaphthalene-2-carboxamide (850 mg, 2.04 mmol) in THF (6 mL) was added dropwise to the reaction mixture over the 20 min. The reaction mixture was allowed to stir at 0° C. and then to warm to rt and stir for 1 h. The reaction mixture was filtered and the

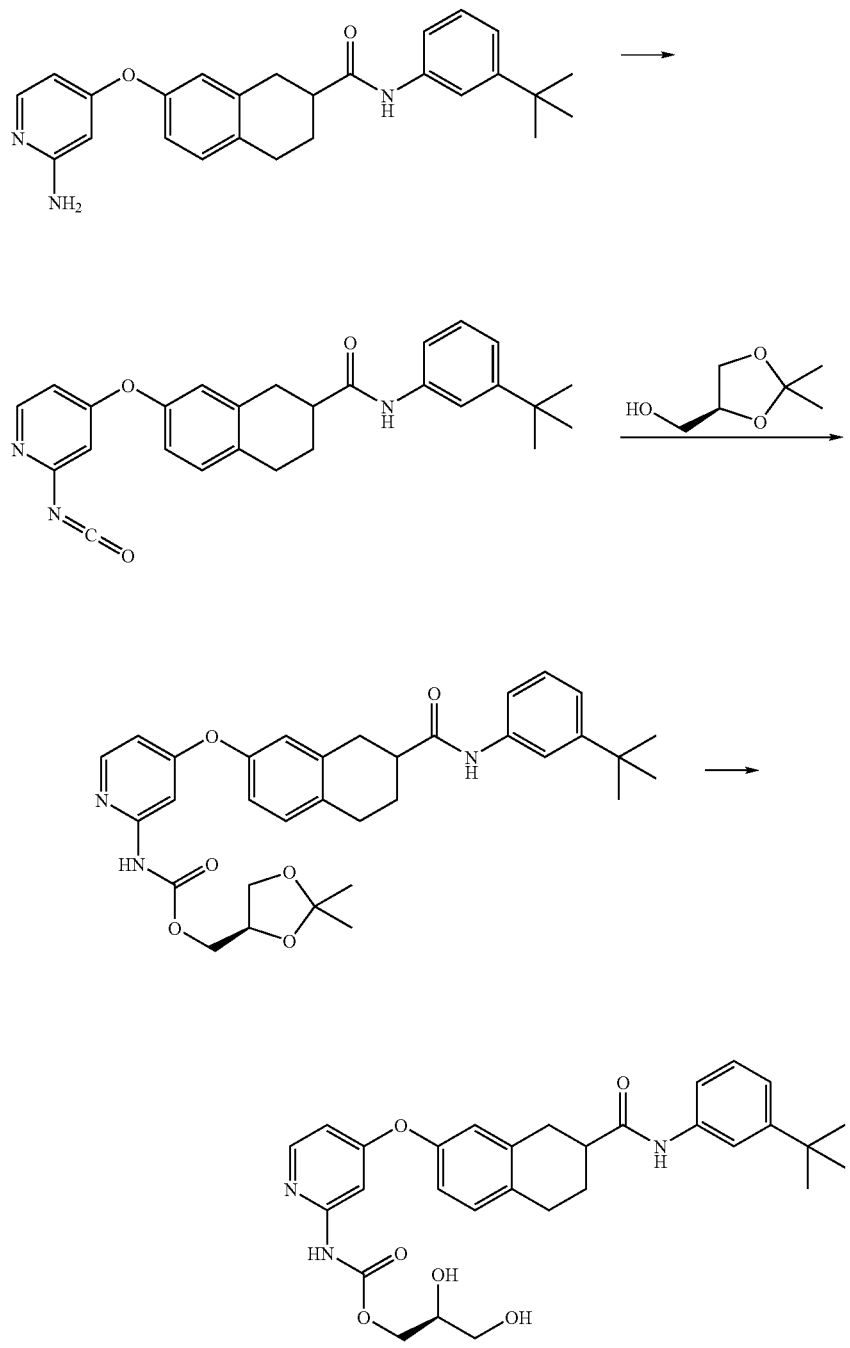

filtrate was evaporated. The residue was purified by column chromatography to give N-(3-tert-butylphenyl)-7-[(2-isocyanatopyridin-4-yl)oxy]-1,2,3,4-tetrahydronaphthalene-2-carboxamide (510 mg, 56%) as yellow solid. LCMS: (FA) ES+442.5.

Step 2: [(4R)-2,2-dimethyl-1,3-dioxolan-4-yl]methyl {4-[(7-{[(3-tert-butylphenyl)-amino]carbonyl}-5,6,7,8-tetrahydronaphthalen-2-yl)oxy]pyridin-2-yl}carbamate A solution of N-(3-tert-butylphenyl)-7-[(2-isocyanatopyridin-4-yl)oxy]-1,2,3,4-tetrahydronaphthalene-2-carboxamide (250 mg, 0.56 mmol), [(4S)-2,2-dimethyl-1,3-dioxolan-4-yl]methanol (150 mg, 1.13 mmol) and pyridine (0.091 mL, chromatography to give (2S)-2,3-dihydroxypropyl {4-[(7-{[(3-tert-butylphenyl)amino]carbonyl}-5,6,7,8-tetrahydronaphthalen-2-yl)oxy]pyridin-2-yl}carbamate (I-272) (150 mg, 55%) as a white solid. $^1$H NMR (400 MHz, CD$_3$OD, HCl salt) δ: 9.86 (s, 1H), 8.21 (d, 1H), 7.65-7.62 (m; 1H), 7.43-7.38 (m, 1H), 7.31-7.20 (m, 2H), 7.17-7.14 (m, 1H), 7.11-7.06 (m, 1H), 7.04-6.97 (m, 2H), 6.70-6.67 (m, 1H), 4.40-4.25 (qq, 2H), 3.91-3.85 (m, 1H), 3.60-3.56 (m, 2H), 3.15-2.79 (m, 5H), 2.24-2.16 (m, 1H), 1.99-1.88 (m, 1H), and 1.31 (s, 9H). LCMS: (FA) ES+534.3, ES−532.6.

Compounds in the following table were prepared from the appropriate starting materials in a method analogous to that of Example 43:

| | |
|---|---|
| I-277 | $^1$H NMR(400MHz, CD$_3$OD, HCl salt) δ: 9.85(s, 1H), 8.21(d, 1H, J=7.27Hz), 7.65-7.61(m, 1H), 7.43-7.37(m, 1H), 7.31-7.27(m, 1H), 7.26-7.21(m, 1H), 7.18-7.14(m, 1H), 7.10-6.97(m, 3H), 6.74-6.68(m, 1H), 4.41-4.24(m, 2H), 3.91-3.83(m, 1H), 3.62-3.56(m, 2H), 3.15-2.79(m, 5H), 2.24-2.13(m, 1H), 2.00-1.89(m, 1H), and 1.31(s, 9H). LCMS: (FA) ES+ 534.3, ES− 532.6. |
| I-322 | $^1$H NMR(400MHz, d$_6$-DMSO, HCl salt) δ: 10.79(br s, 1H), 10.53(s, 1H), 10.39(s, 1H), 8.57(s, 1H), 8.23(d, 1H), 8.15(t, 2H), 8.05-8.02(m, 1H), 7.87(d, 1H), 7.81(t, 1H), 7.74-7.72(m, 1H), 7.51-7.48(m, 1H), 7.38(d, 1H), 7.29(t, 1H), 7.16-7.13(m, 1H), 6.84-6.82(m, 1H), 4.41(t, 2H), 3.95-3.90(m, 2H), 3.78-3.72(m, 2H), 3.49-3.45(m, 2H), 3.38(br s, 2H), 3.15(br s, 2H), and 1.29(s, 9H). LCMS: (FA) ES+ 569.8, ES− 567.6. |
| I-196 | $^1$H NMR(300MHz, d$_6$-DMSO, HCl Salt) δ: 10.63(s, 1H), 10.41(s, 1H), 8.58(s, 1H), 8.25(d, 1H), 8.15(t, 2H), 8.04(dd, 1H), 7.89(d, 1H), 7.81(t, 1H), 7.74(d, 1H), 7.51(dd, 1H), 7.36(d, 1H), 7.29(t, 1H), 7.15(d, 1H), 7.86(dd, 1H), 4.37(t, 2H), 3.59-3.50(m, 2H), 3.43-3.38(m, 2H), 3.07-2.95(m, 2H), 1.99-1.81(m, 4H), and 1.29(s, 9H). LCMS: (FA) ES+ 551.0, ES− 553.9. |
| I-401 | $^1$H NMR(400MHz, d$_6$-DMSO, HCl salt) δ: 10.07(s, 1H), 8.21(d, 1H), 7.68-7.71(m, 1H), 7.57-7.61(m, 1H), 7.45(s, 1H), 7.20-7.27(m, 2H), 7.10-7.18(m, 3H), 7.00-7.03(m, 1H), 6.83-6.88(m, 1H), 5.04(br s, 2H), 4.12-4.18(m, 1H), 4.00-4.05(m, 1H), 3.64-3.70(m, 1H), 3.34-3.40(m, 2H), and 1.26(s, 9H). LCMS: (FA) ES+ 534.4, ES− 532.0. |

1.13 mmol) in THF (10 mL) was allowed to stir at rt. After 2 h, additional pyridine (0.14 mL) and [(4S)-2,2-dimethyl-1,3-dioxolan-4-yl]methanol (0.220 mg) were added. The reaction mixture was heated at 70° C. overnight and then another portion of pyridine (0.10 mL) and [(4S)-2,2-dimethyl-1,3-dioxolan-4-yl]methanol (0.150 mg g) were added. Heating continued for an additional 2 h and then the reaction mixture was subjected to MWI at 135° C. for 5 min. The reaction mixture was diluted with EtOAc and washed with water and brine, dried over Na$_2$SO$_4$, filtered and concentrated. The residue was purified by column chromatography to give [(4R)-2,2-dimethyl-1,3-dioxolan-4-yl]methyl {4-[(7-{[(3-tert-butylphenyl)amino]carbonyl}-5,6,7,8-tetrahydronaphthalen-2-yl)-oxy]pyridin-2-yl}carbamate (290 mg, 89%) as a white solid. LCMS: (FA) ES+574.4.

Step 3: (2S)-2,3-dihydroxypropyl {4-[(7-{[(3-tert-butylphenyl)amino]carbonyl}-5,6,7,8-tetrahydronaphthalen-2-yl)oxy]pyridin-2-yl}carbamate (I-272)

A mixture of [(4R)-2,2-dimethyl-1,3-dioxolan-4-yl]methyl {4-[(7-{[(3-tert-butylphenyl)amino]carbonyl}-5,6,7,8-tetrahydronaphthalen-2-yl)oxy]pyridin-2-yl}carbamate (290 mg, 0.50 mmol) and pTSA (87 mg, 0.50 mmol) in MeOH (10 mL) and water (1 mL) were heated at 70° C. for 56 h. The reaction mixture was concentrated; diluted with water, and extracted with EtOAc. The organic solutions were combined, washed with sat. aq. NaHCO$_3$ and brine, dried over Na$_2$SO$_4$, filtered and concentrated. The residue was purified by column Example 44

Preparation of 7-({2-[(cyclopropylcarbonyl)amino]pyridin-4-yl}oxy)-N-[3-(hydroxymethyl)-5-(trifluoromethyl)phenyl]-1,2,3,4-tetrahydronaphthalene-2-carboxamide I-206

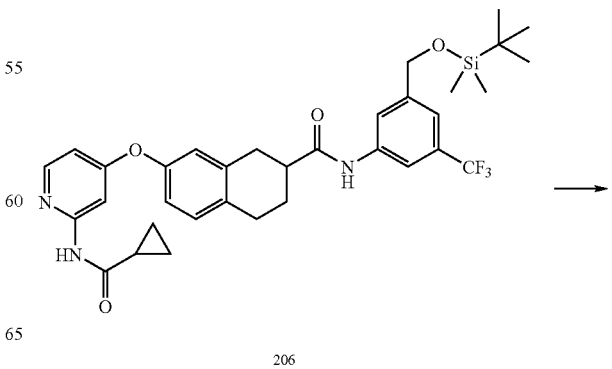

206

275
-continued

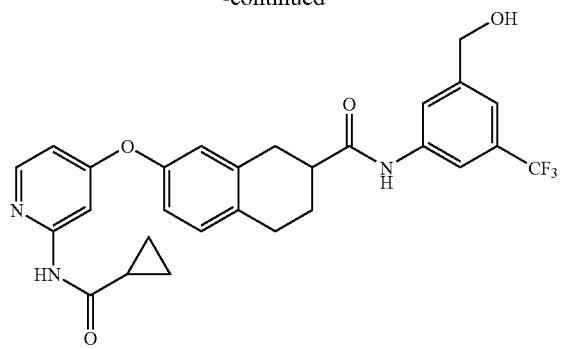

I-206

To a solution of N-[3-({[tert-butyl(dimethyl)silyl]oxy}methyl)-5-(trifluoromethyl)-phenyl]-7-({2-[(cyclopropylcarbonyl)amino]pyridin-4-yl}oxy)-1,2,3,4-tetrahydronaphthalene-2-carboxamide (0.250 g, 0.39 mol) in THF (5 mL) at 0° C. was added 1.0 M tetra-n-butylammonium fluoride in THF (0.43 mL). The reaction mixture was allowed to stir at 0° C. for 1 h and then at rt overnight. Water was added and the reaction mixture was extracted with EtOAc. The organic solutions were combined, dried over $Na_2SO_4$, filtered and concentrated. The residue was purified by column chromatography to give 7-({2-[(cyclopropylcarbonyl)amino]pyridin-4-yl}-oxy)-N-3(hydroxymethyl)-5-(trifluoromethyl)phenyl]-1,2,3,4-tetrahydronaphthalene-2-carboxamide I-206 (199 mg, 88%) as a white solid. $^1$H NMR (400 MHz, $d_6$-DMSO, HCl salt) δ: 11.48 (br s, 1H), 10.46 (s, 1H), 8.21 (d, 1H), 8.02 (s, 1H), 7.79 (s, 1H), 7.35 (br s, 1H), 7.31 (s, 1H), 7.22 (d, 1H), 6.93-7.02 (m, 2H), 6.81-6.86 (m, 1H), 4.54 (s, 2H), 2.76-2.97 (m, 5H), 2.07-2.15 (m, 1H), 1.90-1.98 (m, 1H), 1.73-1.85 (m, 1H), and 0.81-0.89 (m, 4H). LCMS: (FA) ES+526.4, ES−524.5.

Compounds in the following table were prepared from the appropriate starting materials in a method analogous to that of Example 44:

276
Example 45

Preparation of 4-({7-[(3-fluoro4methoxybenzoyl)amino]-5,6,7,8-tetrahydronaphthalen-2-yl}oxy)-N-methylpyridine-2-carboxamide

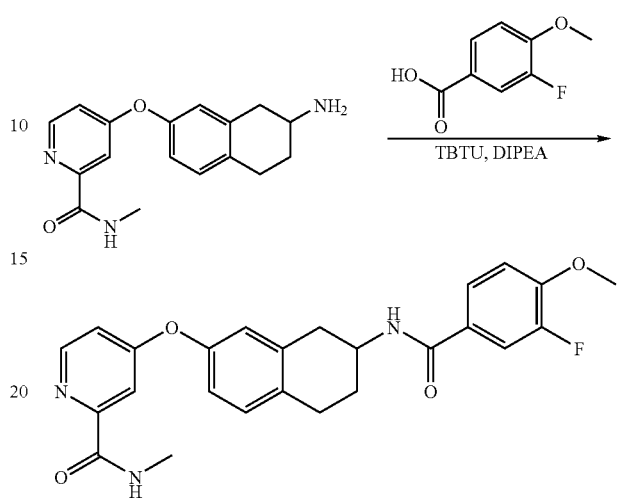

To a stirred solution of 4-[(7-amino-5,6,7,8-tetrahydronaphthalen-2-yl)oxy]-N-methylpyridine-2-carboxamide (25 mg) in DMA (1 mL) were added 3-fluoro-4-methoxybenzoic acid (16 mg, 0.094 mmol), DIPEA (26 μL), and a solution of TBTU (41 mg, 0.128 mmol) in DMA:NMP (1:1 v/v, 1 mL). The reaction mixture was allowed to stir at rt for 24 h. Water was added and the mixture was extracted with DCM. The organic solution was concentrated and purified by reverse phase HPLC to give 4-({7-[(3-fluoro-4-methoxybenzoyl)amino]-5,6,7,8-tetrahydronaphthalen-2-yl}oxy)-N-methylpyridine-2-carboxamide (26.5 mg, 70%). LCMS: (AA) ES+450.5.

Compounds in the following table were prepared from the appropriate starting materials in a method analogous to that of Example 45:

---

| | |
|---|---|
| I-286 | $^1$H NMR(400MHz, $d_6$-DMSO, HCl salt) δ: 11.05(br s, 1H), 10.44(s, 1H), 8.20(d, 1H), 8.02(s, 1H), 7.79(s, 1H), 7.35(br s, 1H), 7.31(s, 1H), 7.22(d, 1H), 6.99-7.02(m, 1H), 6.93-6.97(m, 1H), 6.79-6.83(m, 1H), 4.54(s, 2H), 2.76-2.97(m, 5H), 2.07-2.16(m, 4H), and 1.73-1.85(m, 1H). LCMS: (FA) ES+ 500.3, ES− 498.4. |
| I-226 | $^1$H NMR(300MHz, $CD_3OD$) δ: 8.08(d, 1H), 7.96(s, 1H), 7.80(s, 1H), 7.63(d, 1H), 7.42(s, 1H), 7.14(d, 1H), 6.86(br, 2H), 6.62(dd, 1H), 3.88(s, 2H), 3.68(t, 2H), 2.98(m, 2H), 2.91(m, 2H), 2.77(m, 2H), 2.17(m, 1H), 1.80-2.01(m, 1H), 1.27(br, 2H), 0.91(m, 2H), and 0.84(m, 2H). LCMS: (FA) ES+ 569.4, ES− 567.5. |
| I-399 | $^1$H NMR(400MHz, $d_6$-DMSO, HCl salt) δ: 10.94(br s, 1H), 10.55-10.84(m, 2H), 8.00-8.23(m, 3H), 7.67-7.77(m, 1H), 7.44(br s, 1H), 7.22(d, 1H), 6.93-7.03(m, 2H), 6.77(br s, 1H), 4.35-4.51(m, 3H), 3.10-3.31(m, 3H), 2.77-3.02(m, 5H), 2.21-2.33(m, 1H), and 1.74-2.16(m, 7H). LCMS: (FA) ES+ 569.3, ES− 567.4. |

| Compound | LCMS: (AA) ES+ |
|---|---|
| I-633 | 444.3 |
| I-624 | 476.3 |
| I-595 | 470.3 |
| I-635 | 458.3 |
| I-594 | 476.3 |
| I-621 | 493.3 |
| I-558 | 500.3 |

| Compound | LCMS: (AA) ES+ |
|---|---|
| I-555 | 463.3 |
| I-620 | 478.3 |
| I-591 | 436.3 |
| I-622 | 420.3 |
| I-592 | 432.3 |
| I-627 | 496.3 |
| I-562 | 482.2 |
| I-590 | 444.3 |
| I-607 | 514.2 |
| I-571 | 492.3 |
| I-619 | 446.3 |
| I-589 | 416.3 |
| I-576 | 510.4 |
| I-565 | 468.3 |
| I-560 | 476.2 |
| I-631 | 428.3 |
| I-611 | 483.3 |
| I-564 | 488.3 |
| I-626 | 466.3 |
| I-639 | 470.2 |
| I-599 | 512.2 |
| I-642 | 432.3 |
| I-641 | 494.2 |
| I-597 | 430.3 |
| I-569 | 460.3 |
| I-606 | 431.3 |
| I-600 | 417.3 |
| I-638 | 494.2 |
| I-582 | 445.3 |
| I-567 | 466.2 |
| I-630 | 470.2 |
| I-610 | 504.2 |
| I-557 | 448.3 |
| I-568 | 455.3 |
| I-583 | 441.3 |
| I-604 | 470.3 |
| I-602 | 434.4 |
| I-593 | 480.2 |
| I-634 | 462.3 |
| I-581 | 433.3 |
| I-596 | 492.3 |
| I-554 | 486.3 |
| I-608 | 508.3 |
| I-598 | 453.3 |
| I-574 | 538.2 |
| I-644 | 530.2 |
| I-645 | 460.2 |
| I-646 | 571.2 |
| I-647 | 515.2 |
| I-648 | 516.3 |
| I-649 | 468.3 |
| I-650 | 508.3 |
| I-651 | 546.2 |
| I-652 | 512.2 |
| I-653 | 459.3 |
| I-654 | 476.3 |
| I-655 | 468.3 |
| I-656 | 516.4 |
| I-657 | 475.4 |
| I-658 | 566.3 |
| I-659 | 496.3 |
| I-660 | 496.3 |
| I-661 | 471.4 |
| I-662 | 474.3 |
| I-663 | 460.3 |
| I-664 | 499.3 |
| I-665 | 450.3 |
| I-666 | 444.3 |
| I-667 | 480.3 |
| I-668 | 470.3 |
| I-669 | 463.3 |
| I-670 | 495.3 |
| I-672 | 454.3 |
| I-673 | 419.3 |
| I-674 | 437.3 |
| I-675 | 481.2 |
| I-676 | 417.4 |
| I-677 | 559.4 |
| I-678 | 469.3 |
| I-679 | 505.3 |
| I-680 | 501.3 |
| I-681 | 511.3 |
| I-682 | 485.3 |
| I-683 | 488.4 |
| I-684 | 509.4 |
| I-706 | 486.3 |
| I-707 | 472.3 |
| I-708 | 458.3 |
| I-709 | 482.3 |
| I-710 | 471.4 |
| I-711 | 535.3 |
| I-712 | 441.3 |
| I-714 | 459.3 |
| I-715 | 423.3 |
| I-716 | 468.3 |
| I-717 | 485.3 |
| I-718 | 519.3 |
| I-719 | 536.3 |
| I-720 | 508.2 |
| I-721 | 456.3 |
| I-722 | 485.3 |
| I-724 | 555.3 |
| I-725 | 553.3 |
| I-726 | 595.3 |
| I-727 | 470.4 |
| I-728 | 518.4 |
| I-729 | 475.3 |
| I-730 | 536.3 |
| I-732 | 522.3 |
| I-733 | 453.4 |
| I-734 | 403.4 |
| I-735 | 419.4 |
| I-736 | 499.4 |
| I-737 | 563.3 |

Example 46

Preparation of N-(3-fluoro-4-methylphenyl)-7-({2-[(methylamino)carbonyl]-pyridin-4-yl}oxy)-3,4-dihydroisoquinoline-2(1H)-carboxamide

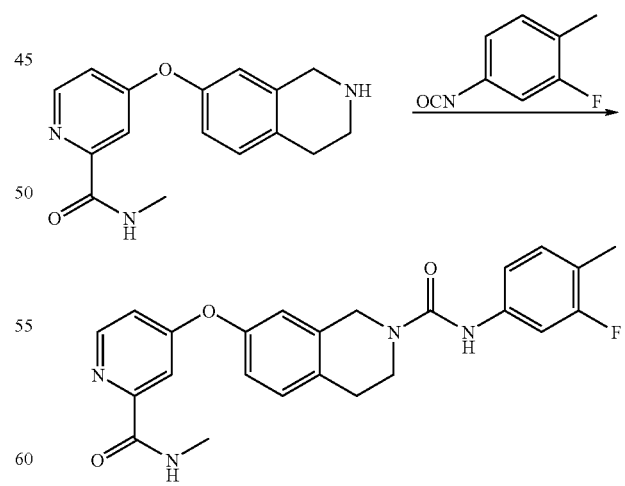

To a solution of N-methyl-4-(1,2,3,4-tetrahydroisoquinolin-7-yloxy)pyridine-2-carboxamide (34 mg, 0.12 mmol) in DMF (1 mL) was added to 2-fluoro-4isocyanato-1-methylbenzene (21.8 mg, 0.144 mmol). The reaction mixture was allowed to stir for 24 h. Water added and the resulting solid was separated and purified by reverse phase HPLC to N-(3-fluoro-4-methylphenyl)-7-({2-[(methylamino)carbonyl]-pyridin-4-yl}oxy)-3,4-dihydroisoquinoline-2(1H)-carboxamide (32 mg, 61%). LCMS: (AA) ES+) 435.5.

Compounds in the following table were prepared from the appropriate starting materials in a method analogous to that of Example 46:

| Compound | LCMS: (AA) ES+ |
|---|---|
| I-740 | 417.5 |
| I-741 | 437.4 |
| I-742 | 475.5 |
| I-743 | 453.5 |
| I-744 | 481.4 |
| I-745 | 433.5 |
| I-746 | 471.4 |
| I-747 | 439.5 |
| I-748 | 471.5 |
| I-749 | 471.4 |
| I-750 | 463.5 |
| I-751 | 463.5 |
| I-752 | 431.6 |
| I-753 | 437.9 |
| I-754 | 481.4 |
| I-755 | 466.5 |
| I-756 | 488.0 |
| I-757 | 539.5 |
| I-758 | 505.9 |
| I-759 | 505.5 |
| I-760 | 505.5 |
| I-761 | 439.5 |
| I-762 | 449.5 |
| I-763 | 479.6 |
| I-764 | 445.5 |
| I-765 | 444.6 |
| I-766 | 462.5 |
| I-767 | 428.5 |
| I-768 | 493.6 |
| I-769 | 475.6 |
| I-770 | 489.5 |
| I-771 | 478.5 |
| I-772 | 478.5 |
| I-773 | 495.5 |
| I-774 | 519.5 |
| I-775 | 435.5 |
| I-776 | 431.6 |
| I-777 | 511.5 |
| I-778 | 529.4 |
| I-779 | 559.4 |
| I-780 | 461.6 |
| I-781 | 459.6 |
| I-782 | 469.5 |
| I-783 | 529.4 |
| I-784 | 503.5 |
| I-785 | 495.6 |
| I-786 | 428.6 |
| I-787 | 515.4 |

Example 47

Expression and Purification of Raf Kinase Enzymes

Wild-Type B-Raf

Enzymatically active wild-type B-Raf was purchased from Upstate (cat# 14-530).

V599E B-Raf

Enzymatically active mutant B-Raf(V599E) was purchased from Upstate (cat# 14-557).

Wild Type C-Raf

Enzymatically active C-Raf was purchased from Upstate (cat# 14-352).

Example 48

Raf Kinase Enzyme Assays

B-Raf Flash Plate® Assay

Enzyme mix (15 μL), containing 50 mM HEPES pH 7.5, 0.025% Brij 35, 10 mM DTT, 4 nM B-Raf (V599E or Wild Type), was added to the wells of an assay plate and incubated for 20 minutes. Substrate mix (15 μL), containing 50 mM HEPES pH 7.5, 0.025% Brij 35, 10 mM MnCl$_2$, 2 μM Peptide 118 (Biotin-DRGFPRARYRARTTNYNSSRSRFYSGFN-SRPRGRVYRGRAR-ATSWYSPY-NH$_2$, New England Peptide), 1 μM ATP, 0.2 mg/mL BSA, $^{33}$P ATP 0.5 μCi/reaction was then added. Final reagent concentrations in the reaction mixture were 50 mM HEPES pH 7.5, 0.025% Brij 35, 5 mM DTT, 5 mM MnCl$_2$, 1 μM Peptide 118, 0.5 μM ATP, 0.1 mg/mL BSA, 2 nM B-Raf Wild Type, and $^{33}$P ATP 0.5 μCi/reaction. The reaction mixture, with or without Raf kinase inhibitor, was incubated for 60 minutes, and then stopped by the addition of 50 μL of 100 mM EDTA. The stopped reaction mixture (65 μL) was transferred to a Flash Plate® (Perkin Elmer) and incubated for 2 hours. The wells were washed three times with 0.02% Tween-20. Plates were read on a TopCount analyzer.

Compounds I-1 to I-15, I-17 to I-55, I-63, I-64, I-77, I-83, I-86, I-87, I-88, I-89, I-91, I-93, I-99, I-107, I-111, I-128, I-129, I-131, I-139, I-140, I-141, I-142, I-143, I-146, I-147, I-149, I-151, I-152, I-153, I-154, I-155, I-156, I-157, I-158, I-160, I-161, I-162, I-164, I-172, I-178, I-179, I-180, I-181, I-182, I-183, I-184, I-185, I-186, I-187, I-189, I-190, I-191, I-192, I-193, I-194, I-195, I-196, I-197, I-198, I-199, I-201, I-202, I-203, I-204, I-205, I-206, I-207, I-208, I-209, I-210, I-211, I-212, I-213, I-214, I-215, I-216, I-217, I-218, I-219, I-220, I-222, I-223, I-224, I-226, I-227, I-229, I-230, I-231, I-232, I-233, I-234, I-235, I-236, I-237, I-238, I-239, I-240, I-241, I-242, I-243, I-244, I-245, I-246, I-247, I-249, I-250, I-251, I-252, I-253, I-254, I-255, I-256, I-257, I-259, I-260, I-261, I-264, I-265, I-266, I-267, I-269, I-270, I-271, I-272, I-273, I-274, I-275, I-276, I-277, I-278, I-279, I-280, I-281, I-282, I-283, I-284, I-285, I-286, I-287, I-288, I-289, I-290, I-293, I-296, I-298, I-299, I-300, I-301, I-303, I-304, I-305, I-306, I-307, I-308, I-309, I-310, I-311, I-312, I-313, I-314, I-315, I-316, I-317, I-319, I-321, I-322, I-323, I-325, I-326, I-328, I-329, I-330, I-331, I-332, I-333, I-334, I-335, I-336, I-337, I-338, I-339, I-340, I-341, I-342, I-343, I-344, I-345, I-346, I-347, I-348, I-349, I-350, I-351, I-352, I-353, I-354, I-355, I-357, I-359, I-360, I-361, I-362, I-363, I-364, I-365, I-366, I-367, I-369, I-370, I-371, I-372, I-373, I-374, I-375, I-376, I-377, I-378, I-379, I-380, I-381, I-382, I-383, I-384, I-385, I-386, I-387, I-388, I-389, I-390, I-392, I-393, I-394, I-395, I-396, I-397, I-398, I-399, I-400, I-401, I-402, I-403, I-404, I-405, I-406, I-407, I-408, I-409, I-410, I-411, I-412, I-413, I-414, I-415, I-416, I-417, I-418, I-419, I-420, I-421, I-422, I-424, I-425, I-426, I-427, I-428, I-429, I-430, I-431, I-432, I-433, I-434, I-435, I-436, I-437, I-440, I-441, I-442, I-443, I-444, I-445, I-446, I-447, I-448, I-451, I-452, I-455, I-456, I-459, and I-460, inhibited the enzyme with IC$_{50}$ values less than or equal to 1 μM in this assay.

Compounds I-1, I-2, I-6, I-8, I-20, I-22, I-26, I-27, I-29, I-35, I-42, I-45, I-50, I-51, I-86, I-184, I-205, I-229, I-231, I-232, I-261, I-300, I-304, I-325, I-330, I-362, I-366, and I-400, exhibited IC$_{50}$ values in this assay less than 200 μnM, but greater than 50 nM.

Compounds I-3 to I-5, I-7, I-9, I-10, I-12 to I-15, I-17 to I-19, I-23 to I-25, I-28, I-30 to I-34, I-36 to I41, I-43, I-44, I-46 to I-49, I-52, I-53, I-55, I-63, I-64, I-77, I-87, I-88, I-91, I-93, I-99, I-111, I-131, I-139, I-140, I-142, I-143, I-146, I-147, I-149, I-151, I-152, I-153, I-154, I-155, I-156, I-157, I-158, I-160, I-161, I-162, I-164, I-172, I-178, I-180, I-181, I-182, I-183, I-185, I-186, I-187, I-189, I-190, I-191, I-192, I-193, I-194, I-195, I-196, I-197, I-198, I-199, I-201, I-202, I-203, I-204, I-206, I-207, I-208, I-209, I-210, I-211, I-212, I-213, I-214, I-215, I-216, I-217, I-218, I-219, I-220, I-222, I-223, I-224, I-226, I-227, I-230, I-233, I-234, I-235, I-236, I-237, I-238, I-239, I-240, I-241, I-242, I-243, I-244, I-245, I-246, I-247, I-249, I-250, I-251, I-252, I-253, I-254, I-255, I-256, I-257, I-259, I-260, I-264, I-265, I-266, I-267, I-269, I-270, I-271, I-272, I-273, I-274, I-275, I-276, I-277, I-279, I-280, I-281, I-282, I-283, I-284, I-285, I-286, I-287, I-288, I-289, I-290, I-293, I-296, I-298, I-299, I-301, I-303, I-305, I-306, I-307, I-308, I-309, I-310, I-311, I-312, I-313, I-314, I-315, I-316, I-317, I-319, I-321, I-322, I-323, I-326, I-329, I-331, I-332, I-333, I-334, I-335, I-336, I-337, I-338, I-339, I-340, I-341, I-342, I-343, I-344, I-345, I-346, I-347, I-348, I-350, I-351, I-352, I-353, I-354, I-355, I-357, I-359, I-360, I-361, I-363, I-364, I-365, I-369, I-370, I-371, I-372, I-374, I-375, I-376, I-377, I-378, I-379, I-380, I-381, I-382, I-383, I-384, I-385, I-386, I-387, I-388, I-389, I-390, I-392, I-393, I-394, I-395, I-396, I-397, I-398, I-399, I-401, I-402, I-403, I-404, I-405, I-406, I-407, I-408, I-409, I-410, I-411, I-412, I-413, I-414, I-416, I-417, I-418, I-419, I-420, I-421, I-422, I-424, I-425, I-426, I-427, I-428, I-429, I-430, I-431, I-432, I-433, I-434, I-435, I-436, I-437, I-440, I-441, I-442, I-443, I-444, I-445, I-446, I-447, I-448, I-451, I-452, I-455, I-456, I-459, and I-460 exhibited $IC_{50}$ values in this assay less than 50 nM.

C-Raf Flash Plate® Assay

Enzyme mix (15 µL), containing 50 mM HEPES pH 7.5, 0.025% Brij 35, 10 mM DTT, 20 nM C-Raf (Wild Type), was added to the wells of an assay plate and incubated for 20 minutes. Substrate mix (15 µL), containing 50 mM HEPES pH 7.5, 0.025% Brij 35, 10 mM MnCl$_2$, 4 µM Peptide 118, 1 µM ATP, 0.1 mg/mL BSA, $^{33}$P ATP 0.5 µCi/reaction was then added. Final reagent concentrations in the reaction mixture were 50 mM HEPES pH 7.5, 0.025% Brij 35, 5 mM DTT, 5 mM MnCl$_2$, 2 µM Peptide 118, 1.0 µM ATP, 0.1 mg/mL BSA, 10 nM C-Raf Wild Type, and $^{33}$P ATP 0.5 µCi/reaction. The reaction mixture was incubated for 40 minutes, and then stopped by the addition of 50 µL of 100 mM EDTA. The stopped reaction mixture (65 µL) was transferred to a Flash Plate® (Perkin Elmer) and incubated for 2 hours. The wells were washed three times with 0.02% Tween-20. Plates were read on a TopCount analyzer.

Example 49

Raf Kinase Cellular Assays

Phospho-ERK ELISA Assay

Inhibition of Raf kinase activity in whole cell systems can be assessed by determining the decrease in phosphorylation of Raf kinase substrates. Any known Raf kinase substrate can be used to measure inhibition of Raf kinase activity in a whole cell system.

In a specific example, A375 cells were seeded in a 96-well cell culture plate (12×10$^3$ cells/100 µL/well) and incubated overnight at 37° C. Medium was removed, and cells were incubated with Raf kinase inhibitors for 3 hours at 37° C. Medium was removed, and cells were fixed with 4% paraformaldehyde for 15 minutes at room temperature. Methanol was added for 15 min. Cells were removed and blocked with 10% sheep serum and 1% BSA in PBS overnight at 4° C. Cells were incubated with anti-p44/42MAPK antibody (1:100, Cell Signaling Technologies, #9101L) (20 µL/well) for one hour at room temperature. After washing with PBS three times, cells were stained with anti-rabbit horseradish peroxidase-linked antibody from donkey (1:100, Amersham Bioscience #NA934V) for 1 hour at room temperature. Cells were washed three times with 0.5% Tween-20 in PBS and twice with PBS. 3,3', 5,5'-Tetramethylbenzidine (TMB) liquid substrate system (Sigma, #T8665) (50 µL/well) was added, and cells were incubated for 30-45 minutes at room temperature. Optical density was read at 650 nm. Cells were then washed 3-5 times with PBS to remove color solution. Results were normalized for the protein content in each well using a BCA protein assay kit (Pierce).

Compounds I-1 to I-15, I-17 to I-55, I-63, I-64, I-77, I-86, I-87, I-88, I-91, I-93, I-99, I-111, I-129, I-131, I-134, I-138, I-139, I-140, I-142, I-147, I-149, I-153, I-154, I-155, I-156, I-157, I-158, I-161, I-162, I-164, I-172, I-178, I-180, I-181, I-182, I-183, I-185, I-186, I-187, I-189, I-190, I-191, I-192, I-193, I-194, I-196, I-197, I-198, I-199, I-201, I-202, I-203, I-205, I-206, I-207, I-209, I-210, I-212, I-215, I-216, I-218, I-219, I-220, I-222, I-223, I-224, I-226, I-227, I-229, I-230, I-231, I-233, I-234, I-235, I-236, I-238, I-239, I-240, I-241, I-242, I-243, I-244, I-245, I-246, I-249, I-250, I-251, I-252, I-253, I-254, I-255, I-256, I-259, I-260, I-261, I-264, I-265, I-266, I-267, I-269, I-270, I-271, I-272, I-273, I-274, I-276, I-277, I-278, I-278, I-279, I-281, I-282, I-284, I-285, I-287, I-288, I-290, I-296, I-298, I-299, I-300, I-301, I-303, I-306, I-307, I-308, I-311, I-312, I-313, I-315, I-316, I-317, I-322, I-323, I-326, I-329, I-331, I-332, I-333, I-335, I-336, I-337, I-339, I-340, I-341, I-343, I-344, I-345, I-346, I-347, I-348, I-349, I-350, I-351, I-352, I-353, I-354, I-357, I-359, I-360, I-362, I-363, I-364, I-365, I-369, I-370, I-371, I-372, I-373, I-375, I-376, I-377, I-378, I-379, I-381, I-382, I-383, I-385, I-386, I-387, I-388, I-389, I-390, I-392, I-393, I-394, I-396, I-397, I-399, I-402, I-403, I-404, I-405, I-406, I-407, I-409, I-410, I-411, I-412, I-413, I-414, I-415, I-416, I-417, I-418, I-419, I-420, I-422, I-139, I-424, I-425, I-426, I-427, I-430, I-433, I-434, I-437, I-440, I-441, I-442, I-444, I-445, I-448, I-452, I-455, I-140, and I-460 inhibited the formation of phospho-ERK with $IC_{50}$ values less than or equal to 25 µM in this assay.

Compounds I-1, I-4, I-9, I-10, I-13, I-15, I-18, I-20, I-22, I-24, I-26, I-27, I-31, I-32, I-34, I-41, I-47, I-49, I-52, I-53, I-64, I-77, I-86, I-111, I-134, I-139, I-140, I-172, I-178, I-182, I-183, I-189, I-202, I-207, I-218, I-222, I-230, I-231, I-239, I-240, I-241, I-242, I-252, I-259, I-260, I-265, I-266, I-274, I-276, I-278, I-278, I-285, I-296, I-298, I-300, I-308, I-312, I-317, I-323, I-333, I-336, I-345, I-348, I-352, I-354, I-357, I-364, I-365, I-369, I-370, I-371, I-373, I-375, I-379, I-382, I-383, I-387, I-393, I-396, I-397, I-402, I-403, I-409, I-412, I-424, I-427, I-442, I-445, and I-452 exhibited $IC_{50}$ values in this assay less than 5 µM, but greater than 1 µM.

Compounds I-2, I-3, I-5 to I-8, I-12, I-14, I-17, I-19, I-25, I-30, I-33, I-36 to I-40, I-43, I-44, I-55, I-63, I-87, I-88, I-91, I-131, I-139, I-147, I-149, I-151, I-153, I-154, I-156, I-157, I-164, I-180, I-181, I-185, I-186, I-187, I-190, I-191, I-193, I-196, I-197, I-198, I-199, I-201, I-206, I-209, I-212, I-215, I-216, I-219, I-220, I-223, I-224, I-226, I-227, I-233, I-234, I-236, I-238, I-243, I-245, I-249, I-250, I-251, I-253, I-255, I-256, I-264, I-267, I-269, I-270, I-272, I-273, I-277, I-279, I-282, I-284, I-287, I-288, I-290, I-301, I-306, I-307, I-311, I-313, I-315, I-316, I-322, I-326, I-329, I-332, I-335, I-337, I-339, I-341, I-343, I-346, I-347, I-350, I-353, I-359, I-360, I-363, I-372, I-376, I-377, I-378, I-385, I-386, I-388, I-389, I-390, I-392, I-394, I-399, I-404, I-405, I-406, I-407, I-410, I-411, I-413, I-414, I-416, I-417, I-418, I-419, I-422, I-425, I-426, I-430, I-433, I-434, I-437, I-440, I-441, and I-455 exhibited $IC_{50}$ values in this assay less than 1 µM.

Example 50

Anti-proliferation Assays

WST Assay

A375 cells (4000) in 100 µL of 1% FBS-DMEM were seeded into wells of a 96-well cell culture plate and incubated overnight at 37° C. Test compounds were added to the wells and the plates were incubated for 48 hours at 37° C. Test compound solution was added (100 µL/well in 1% FBS DMEM), and the plates were incubated at 37° C. for 48 hours. WST-1 reagent (Roche #1644807, 10 µL) was added to each well and incubated for four hours at 37° C. as described by the manufacturer. The optical density for each well was read at 450 nm and 600 nm. A well containing medium only was used as a control.

Example 51

In Vivo Assays

In Vivo Tumor Efficacy Model

Raf kinase inhibitors are tested for their ability to inhibit tumor growth in standard xenograft tumor models.

For example, HCT-116 cells ($1 \times 10^6$) in 100 µL of phosphate buffered saline are aseptically injected into the subcutaneous space in the right dorsal flank of female CD-1 nude mice (age 5-8 weeks, Charles River) using a 23-ga needle. Beginning at day 7 after inoculation, tumors are measured twice weekly using a vernier caliper. Tumor volumes are calculated using standard procedures ($0.5 \times \text{length} \times \text{width}^2$). When the tumors reach a volume of approximately 200 mm³, nice are injected i.v. in the tail vein with test compound (100 µL) at various doses and schedules. All control groups receive vehicle alone. Tumor size and body weight are measured twice a week, and the study is terminated when the control tumors reach approximately 2000 mm. Analogous procedures are followed for melanoma (A375 or A2058 cells), colon (HT-29 or HCT-116 cells), and lung (H460 cells) tumor models.

While the foregoing invention has been described in some detail for purposes of clarity and understanding, these particular embodiments are to be considered as illustrative and not restrictive. It will be appreciated by one skilled in the art from a reading of this disclosure that various changes in form and detail can be made without departing from the true scope of the invention, which is to be defined by the appended claims rather than by the specific embodiments.

The patent and scientific literature referred to herein establishes knowledge that is available to those with skill in the art. Unless otherwise defined, all technical and scientific terms used herein have the same meaning as commonly understood by one of ordinary skill in the art to which this invention belongs. The issued patents, applications, and references that are cited herein are hereby incorporated by reference to the same extent as if each was specifically and individually indicated to be incorporated by reference. In the case of inconsistencies, the present disclosure, including definitions, will control.

What is claimed is:

1. A compound of formula (I-A):

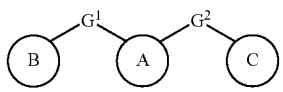

(I-A)

or a pharmaceutically acceptable salt thereof;

wherein:

$G^1$ is —O—;
$G^2$ is —C(O)—NH or —NH—C(O);
Ring A is

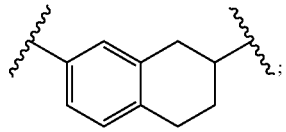

Ring B has the formula:

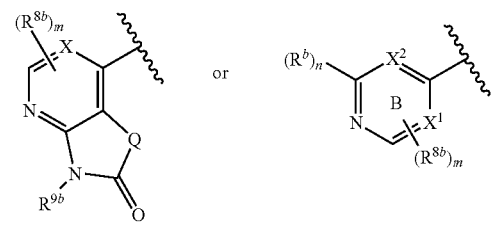

X is CH;
$X^1$ and $X^2$ are each CH;
Q is —C($R^{10}$)($R^{11}$)—C($R^{10}$)($R^{11}$)— or —C($R^{11}$)=C($R^{11}$)—;
$R^{9b}$ is hydrogen;
$R^{10}$ is hydrogen;
$R^{11}$ is hydrogen;
$R^b$ is selected from the group consisting of Ring D, —$R^{1b}$, —$R^{2b}$, -$T^1$—$R^{1b}$, -$T^1$—$R^{2b}$, —$V^1$-$T^1$—$R^{1b}$, —$V^1$-$T^1$—$R^{2b}$;
  wherein Ring D is selected from the group consisting of imidazolyl, oxazolyl, isoxazolyl, pyrazolyl, triazolyl, tetrazolyl, oxadiazolyl, imidazolinyl, oxazolinyl, piperazinyl, pyridyl, and pyrimidinyl;
  each substitutable unsaturated ring carbon atom in Ring D is unsubstituted or is substituted with —$R^d$;
  each substitutable ring nitrogen atom in Ring D is unsubstituted or is substituted with $C_{1-4}$ aliphatic;
  each $R^d$ independently is $C_{1-4}$ aliphatic optionally substituted with halo, —OH, pyrrolyl, or piperazinyl, —$R^{1d}$, —$R^{2d}$, -$T^3$—$R^{1d}$, or -$T^3$—$R^{2d}$;
  $T^3$ is a $C_{1-4}$ alkylene chain;
  each $R^{1d}$ independently is piperazinyl optionally substituted with $C_{1-4}$ aliphatic;
  each $R^{2d}$ independently is —N ($R^4$)$_2$, —$CO_2R^5$ or —C(O)N($R^4$)$_2$;
  $T^1$ is a $C_{1-6}$ alkylene chain, wherein the alkylene chain optionally is interrupted by —N($R^4$)C(O)—;
  $V^1$ is —N($R^4$)—, —N($R^4$)C(O)—, —N($R^4$)$CO_2$—, or —C(=N$R^4$)—N($R^4$);
  $R^{1b}$ is phenyl, pyrrolidinyl, piperazinyl, or morpholinyl, optionally substituted with $C_{1-4}$ aliphatic or —$OCH_3$;
  each $R^{2b}$ independently is —$OR^5$, —N($R^4$)$_2$, —$NR^4$C(O)$R^5$, —$NR^4$C(O)N($R^4$)$_2$, —$NR^4CO_2R^6$, —N($R^4$)$SO_2R^6$, —C(O)N($R^4$)$_2$ or —C(=N$R^4$)—N($R^4$)$_2$;
Ring C is phenyl;
Ring C is substituted on its substitutable ring carbon atoms with 0-2 $R^c$ and 0-2 $R^{8c}$;
  each $R^c$ independently is halo, —$NO_2$, —CN, —C($R^5$)=C($R^5$)$_2$, —$OR^5$, —$SR^6$, —$SO_2R^6$, —$SO_2N(R^4)_2$, —N($R^4$)$_2$, —C(O)$R^5$, or phenyl, pyrazolyl, pyrrolidinyl, or tetrazolyl;

each $R^{8c}$ independently is selected from the group consisting of $C_{1-4}$ aliphatic, $C_{1-4}$ fluoroaliphatic, —O($C_{1-4}$ aliphatic), —O($C_{1-4}$ fluoroaliphatic), and halo;

each $R^4$ independently is hydrogen or an aliphatic optionally substituted with —N(CH$_3$)$_2$ or —OR$_5$; or two $R^4$ on the same nitrogen atom, taken together with the nitrogen atom, form a piperazinyl, pyrrolidinyl, or morpholinyl ring, optionally substituted with $C_{1-4}$ aliphatic;

each $R^5$ independently is hydrogen, phenyl, or an aliphatic optionally substituted with halo —OH, —N(CH$_3$)$_2$ or pyrrolidinyl;

each $R^6$ independently is an aliphatic;

n is 0 or 1; and m is 0.

2. The compound of claim 1, wherein:

$R^b$ is selected from the group consisting of —N(R$^{4x}$)(R$^{4z}$) —C(O)—N(R$^{4x}$)(R$^{4z}$), —N(R$^{4x}$)C(O)R$^5$, —N(R$^{4x}$)C(O)—OR$^{5x}$, —N(R$^{4x}$)C(O)—N(R$^{4x}$)(R$^{4z}$), —N(R$^{4x}$)SO$_2$R$^{6x}$, and —C(=NR$^{4x}$)N(R$^{4x}$)(R$^{4z}$);

$R^{4x}$ is hydrogen or $C_{1-4}$ aliphatic;

$R^{4z}$ is hydrogen or $C_{1-4}$ aliphatic or $R^{4x}$ and $R^{4z}$, taken together with the nitrogen atom to which they are attached, form piperazinyl or morpholinyl optionally substituted with $C_{1-4}$ aliphatic; and $R^{5x}$ is $C_{1-4}$ aliphatic;

$R^{6x}$ is $C_{1-4}$ aliphatic.

3. The compound of claim 2, wherein $R^b$ is —NHC(O)R$^{5x}$, —NHC(O)OR$^{5x}$, —C(=NH)N(R$^{4x}$)(R$^{4z}$), or —C(O)N(R$^{4x}$)(R$^{4z}$).

4. The compound of claim 3, wherein $R^b$ is —N(R$^{4x}$)(R$^{4z}$) and $R^{4z}$ is hydrogen, $C_{1-4}$ aliphatic, benzyl optionally substituted with —OCH$_3$.

5. The compound of claim 1, wherein $X^1$ and $X^2$ are each CH and $V^1$ is —NH—C(O)—, or —C(=NH)NH—.

6. The compound of claim 1 having the formula (III-A) or (III-B):

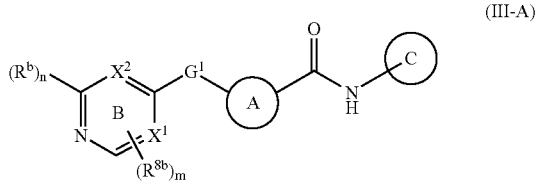

(III-A)

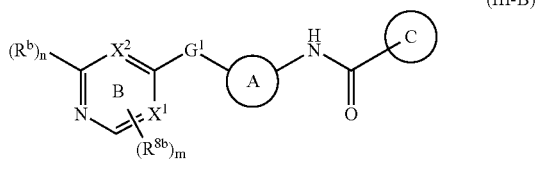

(III-B)

or a pharmaceutically acceptable salt thereof, wherein:

$X^1$ and $X^2$ are each CH;

$R^b$ is selected from the group consisting of:

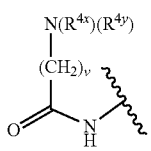 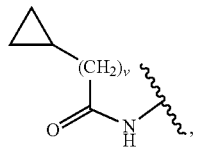 and

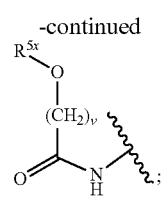

$R^{4x}$ is hydrogen or $C_{1-4}$ aliphatic;

$R^{4y}$ is hydrogen or $C_{1-4}$ aliphatic; or $R^{4x}$ and $R^{4y}$, taken together with the nitrogen atom to which they are attached, form a morpholinyl, pyrrolidinyl or piperazinyl ring;

$R^{5x}$ is $C_{1-4}$ aliphatic optionally substituted with —OH;

v is 0 or 1.

7. The compound of claim 1, having the formula (III-A) or (III-B):

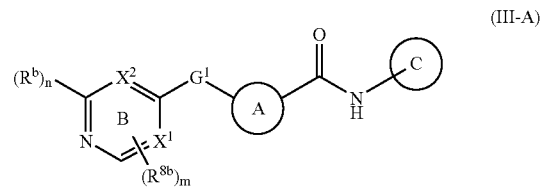

(III-A)

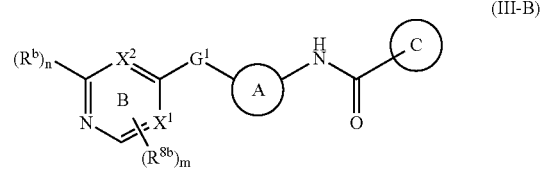

(III-B)

or a pharmaceutically acceptable salt thereof;

wherein:

$X^1$ and $X^2$ are each CH;

$R^b$ is -T$^1$—R$^{1b}$ or -T$^1$—R$^{2b}$;

T$^1$ is a $C_{1-6}$ alkylene chain wherein the alkylene chain optionally is interrupted by —N(R$^4$)—C(O);

$R^{1b}$ is phenyl pyrrolidinyl, or morpholinyl;

$R^{2b}$ is —OR$^5$, —N(R$^4$)$_2$, —NR$^4$C(O)R$^5$, —NR$^4$C(O)N(R$^4$)$_2$, —C(O)N(R$^4$)$_2$, —N(R$^4$)—CO$_2$R$^5$, or —C(=NR$^4$)—N(R$^4$)$_2$;

m is 0; and n is 0 or 1.

8. The compound of claim 7, wherein:

$R^b$ is —(CH$_2$)$_q$—R$^{2y}$;

$R^{2y}$ is —N(R$^{4x}$)(R$^{4z}$), —NR$^{4x}$C(O)R$^{5x}$, or —N(R$^{4x}$)—CO$_2$R$^{5x}$;

$R^{4x}$ is hydrogen;

$R^{4z}$ is hydrogen; or $R^{5x}$ is $C_{1-4}$ aliphatic; and q is 1.

9. The compound of claim 1, having the formula (IV-A) or (IV-B):

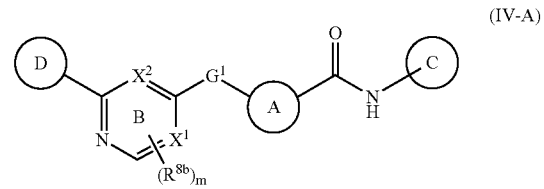

(IV-A)

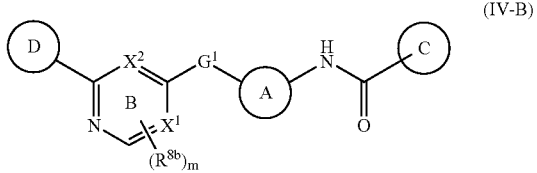

(IV-B)

or a pharmaceutically acceptable salt thereof;
wherein:
X$^1$ and X$^2$ are each CH;
Ring D is selected from the group consisting of imidazolyl, oxazolyl, isoxazolyl, pyrazolyl, triazolyl, tetrazolyl, oxadiazolyl, imidazolinyl, oxazolinyl, piperazinyl, pyridyl, and pyrimidinyl;
each substitutable unsaturated ring carbon atom in Ring D is unsubstituted or is substituted with —R$^d$;
each substitutable ring nitrogen atom in Ring D is unsubstituted or is substituted with C$_{1-4}$ aliphatic;
each R$^d$ independently is;
C$_{1-4}$ aliphatic optionally substituted with halo, —OH, pyrrolyl, or piperazinyl, —R$^{1d}$, —R$^{2d}$, -T$^3$—R$^{1d}$, -T$^3$—R$^{2d}$;
T$^3$ is a C$_{1-4}$ alkylene chain;
each R$^{1d}$ independently is piperazinyl optionally substituted with C$_{1-4}$ aliphatic;
each R$^{2d}$ independently is —N(R$^4$)$_2$, —CO$_2$R$^5$ or —C(O)N(R$^4$)$_2$; and
m is 0.

10. The compound of claim 9, wherein Ring D is selected from the group consisting of:

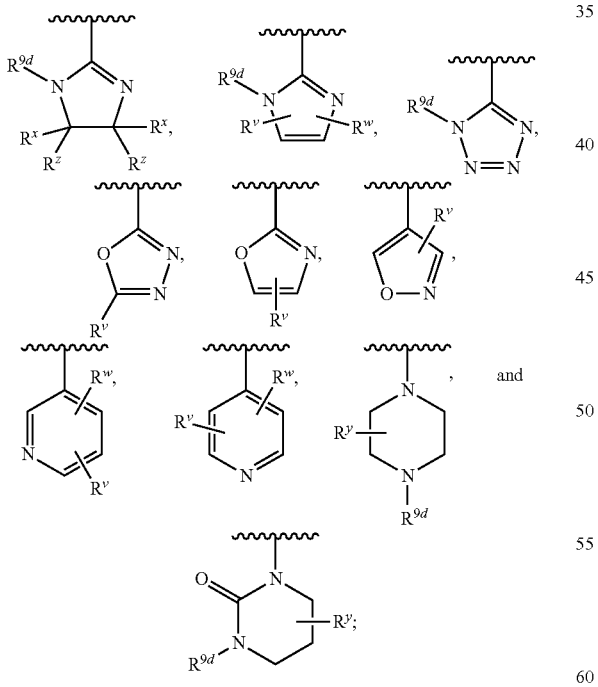

R$^v$ is hydrogen, C$_{1-4}$ aliphatic, C$_{1-4}$ fluoroaliphatic, —CO$_2$R$^5$, —C(O)N(R$^4$)$_2$, -T$^3$—OR$^5$, -T$^3$—N(R$^4$)$_2$;
each R$^w$ independently is hydrogen, C$_{1-4}$ aliphatic, —CO$_2$R$^5$, —C(O)N(R$^4$)$_2$, or -T$^3$—N(R$^4$)$_2$;
R$^x$ is hydrogen;
R$^y$ is hydrogen;

R$^z$ is hydrogen; and
T$^3$ is a C$_{1-4}$ alkylene chain; and
R$^{9d}$ is hydrogen or a C$_{1-4}$ aliphatic.

11. The compound of claim 10, wherein Ring D is selected from the group consisting of:

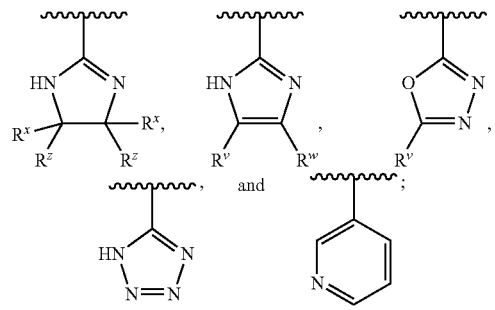

R$^v$ is hydrogen, C$_{1-4}$ aliphatic optionally substituted with —OH, C$_{1-4}$ fluoroaliphatic, or —(CH$_2$)$_p$—CO$_2$R$^{5x}$;
each R$^w$ independently is hydrogen, C$_{1-4}$ aliphatic, —(CH$_2$)$_p$—N(R$^{4x}$)(R$^{4z}$), —(CH$_2$)$_p$—CO$_2$R$^{5x}$, or —(CH$_2$)$_p$—C(O)N(R$^{4x}$)(R$^{4z}$);
each R$^x$ independently is hydrogen or C$_{1-4}$ aliphatic;
each R$^z$ independently is hydrogen or C$_{1-4}$ aliphatic;
R$^{4x}$ and R$^{4z}$, taken together with the nitrogen atom to which they are attached, form a piperazinyl or pyrrolidinyl ring, optionally substituted with C$_{1-4}$ aliphatic;
each R$^{5x}$ is C$_{1-4}$ aliphatic; and
p is 0 or 1.

12. The compound of claim 11, wherein:
X$^1$ and X$^2$ are each CH; and
Ring D is selected from the group consisting of:

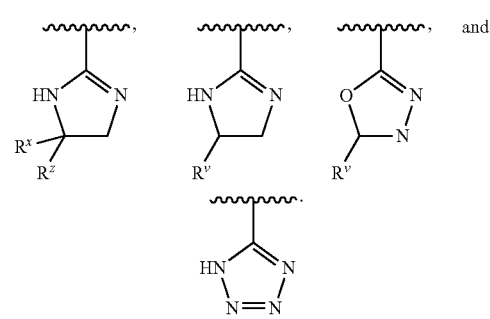

13. The compound of claim 1, wherein:
Ring C is phenyl which is substituted with 0-2 R$^c$ and 0-1 R$^{8c}$;
each R$^c$ independently is selected from the group consisting of C$_{1-4}$ aliphatic,
C$_{1-4}$ fluoroaliphatic, halo, —R$^{1c}$, —R$^{2c}$ and -T$^2$—R$^{2c}$;
T$^2$ is a C$_{1-4}$ alkylene chain optionally substituted with one or two groups independently selected from —F, C$_{1-4}$ aliphatic, and C$_{1-4}$ fluoroaliphatic;
each R$^{1c}$ independently is pyrrolidinyl, piperazinyl, pyrazolyl, imidazolyl, or tetrazolyl, optionally substituted with C$_{1-4}$ aliphatic;
each R$^{2c}$ independently is —CN, —C(R$^5$)=C(R$^5$)$_2$, —OR$^5$, —SR$^6$, —N(R$^4$)$_2$, —NR$^4$C(O)R$^5$, —NR$^4$C(O)N(R$^4$)$_2$, —NR$^4$CO$_2$R$^6$, —CO$_2$R$^5$, or —C(O)N(R$^4$)$_2$; and each $R^{8c}$ independently is selected from the group consisting of $C_{1-4}$ aliphatic, $C_{1-4}$ fluoroaliphatic, —O($C_{1-4}$ aliphatic), and halo.

14. The compound of claim 13, wherein:
each $R^c$ independently is halo, —CN, —C($R^{5x}$)=C($R^{5x}$)($R^{5y}$), —O$R^{5y}$, —S$R^{6x}$, or —N($R^{4x}$)($R^{4y}$); or $R^c$ is a $C_{1-4}$ aliphatic or $C_{1-4}$ fluoroaliphatic optionally substituted with —N($R^{4x}$)($R^{4y}$); or $R^c$ is pyrrolidinyl, piperazinyl, pyrazolyl, imidazolyl, or tetrazolyl, optionally substituted with $C_{1-4}$ aliphatic;
$R^{4x}$ is hydrogen or $C_{1-4}$ aliphatic;
$R^{4y}$ is hydrogen or a $C_{1-4}$ aliphatic optionally substituted with one or two substituents —O$R^{5x}$; or
$R^{4x}$ and $R^{4y}$, taken together with the nitrogen atom to which they are attached, form a pyrrolidinyl or piperazinyl, optionally substituted with $C_{1-4}$ aliphatic;
$R^{5x}$ is $C_{1-4}$ aliphatic;
each $R^{5y}$ independently is hydrogen, phenyl a $C_{1-4}$ aliphatic or $C_{1-4}$ fluoroaliphatic; and
$R^{6x}$ is $C_{1-4}$ aliphatic.

15. The compound of claim 14, wherein Ring C is selected from the group consisting of:

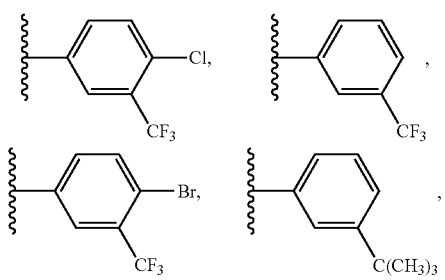

each $R^c$ independently is halo, —CN, —C($R^{5x}$)=C($R^{5x}$)($R^{5y}$), —O$R^{5y}$, —S$R^{6x}$, —N($R^{4x}$)($R^{4y}$), —CO$_2R^{5x}$; or $R^c$ is a $C_{1-4}$ aliphatic or $C_{1-4}$ fluoroaliphatic optionally substituted with one or two substituents independently selected from the group consisting of —O$R^{5x}$ or —N($R^{4x}$)($R^{4y}$); or $R^c$ is a piperazinyl ring optionally substituted with $C_{1-4}$ aliphatic; and
$R^{8c}$ is $C_{1-4}$ aliphatic, $C_{1-4}$ fluoroaliphatic, —O($C_{1-4}$ aliphatic), —O($C_{1-4}$ fluoroaliphatic), or halo.

16. The compound of claim 15, wherein Ring C is selected from the group consisting of:

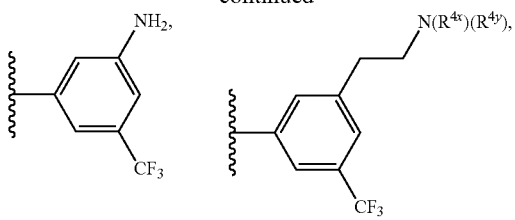
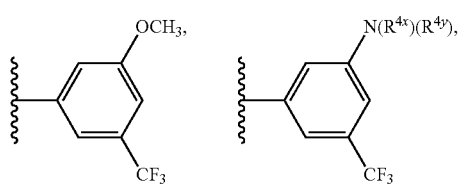
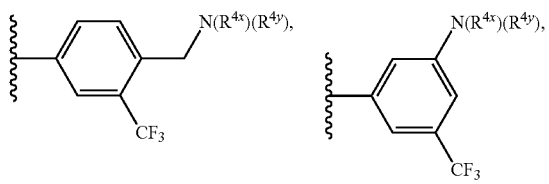
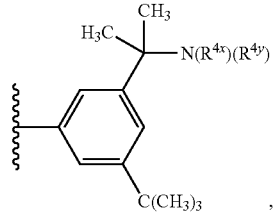
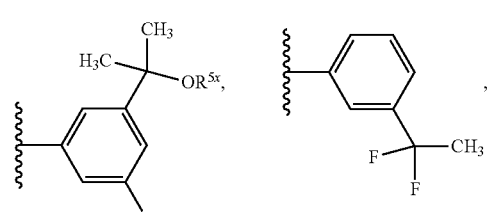
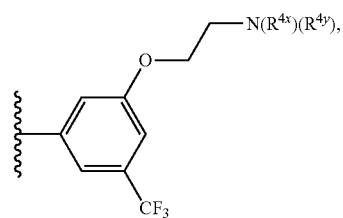
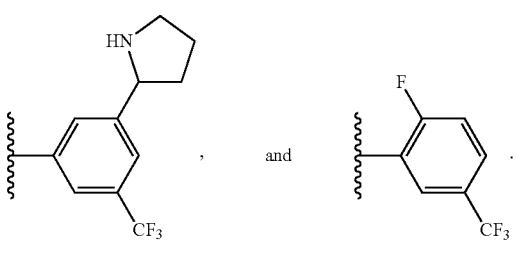

17. The compound of claim 1, having the formula (V-A) or (V-B):

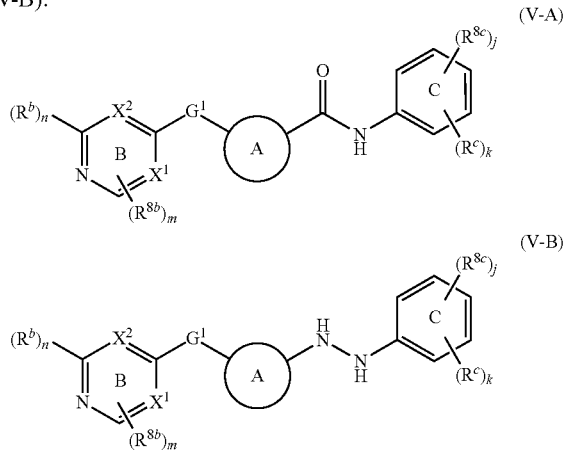

or a pharmaceutically acceptable salt thereof;
wherein:
$G^1$ is —O—;
$X^1$ and $X^2$ are each CH;
Ring A is

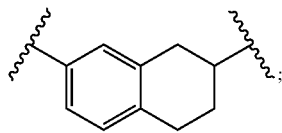

$R^b$ is selected from the group consisting of —$R^{2b}$, -$T^1$—$R^{2b}$, —$V^1$-$T^1$—$R^{1b}$, —$V^1$-$T^1$—$R^{2b}$;
$T^1$ is a $C_{1-6}$ alkylene chain
$V^1$ is —N($R^4$)—, —N($R^4$)C(O)—, —C(=N$R^4$)—($R^4$);
$R^{1b}$ is phenyl, pyrrolidinyl, morpholinyl, piperazinyl, optionally substituted with $C_{1-4}$ aliphatic or —OCH$_3$;
$R^{2b}$ is —O$R^5$, —N($R^4$)$_2$, —N$R^4$C(O)$R^5$, —N$R^4$C(O)N($R^4$)$_2$, —N($R^4$)—CO$_2R^5$, —N($R^4$)—SO$_2R^6$, or —C(=N$R^4$)—N($R^4$)$_2$; or
j is 0 or 1;
k is 0 or 1;
each $R^c$ independently is halo, —CN, —C($R^{5x}$)=C($R^{5x}$)($R^{5y}$), O$R^{5y}$, —S$R^{6x}$, —N($R^{4x}$)($R^{4y}$), or —CO$_2R^{5x}$; or $R^c$ a $C_{1-4}$ aliphatic or $C_{1-4}$ fluoroaliphatic optionally substituted with one or two substituents independently selected from the group consisting of —O$R^{5x}$ or —N($R^{4x}$)($R^{4y}$); or $R^c$ is an imidazolyl or tetrazolyl or piperazinyl;
$R^{4x}$ is hydrogen or $C_{1-4}$ alkyl;
$R^{4y}$ is hydrogen or a $C_{1-4}$ alkyl optionally substituted with one or two substituents independently selected from the group consisting of —O$R^{5x}$ or —C(O)N($R^{4x}$)$_2$; or
$R^{4x}$ and $R^{4y}$, taken together with the nitrogen atom to which they are attached, form a piperazinyl or morpholinyl optionally substituted with $C_{1-4}$ aliphatic;
each $R^{5x}$ independently is hydrogen or $C_{1-4}$ alkyl;
each $R^{5y}$ independently is hydrogen, a phenyl optionally substituted with halo, or a $C_{1-4}$ alkyl or $C_{1-4}$ fluoroalkyl optionally substituted with one or two substituents independently selected from the group consisting of —O$R^{5x}$ or —N($R^{4x}$)$_2$; and
$R^{6x}$ is $C_{1-4}$ alkyl.

18. The compound of claim 1 selected from the following compounds:
7-{[2-(4,5-dihydro-1H-imidazol-2-yl)pyridin-4-yl]oxy}-N-[2-fluoro-5-(trifluoromethyl)phenyl]-1,2,3,4-tetrahydronaphthalene-2-carboxamide;
7-{[2-(4,5-dihydro-1H-imidazol-2-yl)pyridin-4-yl]oxy}-N-[3-(trifluoromethyl)-phenyl]-1,2,3,4-tetrahydronaphthalene-2-carboxamide;
N-(3-tert-butylphenyl)-7-({2-[4-(hydroxymethyl)-1H-imidazol-2-yl]pyridin-4-yl}-oxy)    -1,2,3,4-tetrahydronaphthalene-2-carboxamide;
7{[2-(4,5-dihydro-1H-imidazol-2-yl) pyridin-4-yl]oxy}-N-[3-(2-pyrrolidin-1-ylethoxy)    -5-(trifluoromethyl)phenyl]-1,2,3,4-tetrahydronaphthalene-2-carboxamide;
N-[4-bromo-3-(trifluoromethyl)phenyl]-7-{[2-(4,5-dihydro-1H-imidazol-2-yl)  -pyridin-4-yl]oxy}-1,2,3,4-tetrahydronaphthalene-2-carboxamide;
N-methyl-4-{[7-({[3-(2-pyrrolidin-1-ylethoxy)-5-(trifluoromethyl)phenyl]-amino}carbonyl)-5,6,7,8-tetrahydronaphthalen-2-yl]oxy}pyridine-2-carboxamide;
(2S)-N-[4-chloro-3-(trifluoromethyl)phenyl]-7-}[2-(4,5-dihydro-1H-imidazol-2-yl)  -pyridin-4-yl]oxy)-1,2,3,4-tetrahydronaphthalene-2-carboxamide;
7-{[2-(4,5-dihydro-1H-imidazol-2-yl)pyridin-4-yl]oxy}-N-[3-methoxy-5-(trifluoromethyl)phenyl]-1,2,3,4-tetrahydronaphthalene-2-carboxamide;
N-[4-chloro-3-(trifluoromethyl)phenyl]-8-{[2-(4,5-dihydro-1H-imidazol-2-yl)  -pyridin-4-yl]oxy}-1,2,3,4-tetrahydronaphthalene-2-carboxamide;
4-{[7-({[3-amino-5-(trifluoromethyl)phenyl]amino}carbonyl)-5,6,7,8-tetrahydronaphthalen-2-yl]oxy}-N-methylpyridine-2-carboxamide;
4-[(7-{[(3-tert-butylphenyl)amino]carbonyl}-5,6,7,8-tetrahydronaphthalen-2-yl)oxy]-N-methylpyridine-2-carboxamide;
4-{[7-({[4-chloro-3-(trifluoromethyl)phenyl]amino}carbonyl)-5,6,7,8-tetrahydronaphthalen-2-yl]oxy}-N-methylpyridine-2-carboxamide;
7-{[2-(4,5-dihydro-1H-imidazol-2-yl)pyridin-4-yl]oxy}-N-(3-isopropylphenyl) -1,2,3,4-tetrahydronaphthalene-2-carboxamide;
4-{[7-({[4-(aminomethyl)-3-(trifluoromethyl)phenyl]amino}carbonyl)-5,6,7,8-tetrahydronaphthalen-2-yl]oxy}-N-methylpyridine-2-carboxamide;
4-{[7-({[4-(2-aminoethyl)phenyl]amino}carbonyl)-5,6,7,8-tetrahydronaphthalen-2-yl]oxy}-N-methylpyridine-2-carboxamide;
4-{[7-({[3-(aminomethyl)-5-(trifluoromethyl)phenyl]amino}carbonyl)-5,6,7,8-tetrahydronaphthalen-2-yl]oxy}-N-methylpyridine-2-carboxamide;
(2R)-N-[4-chloro-3-(trifluoromethyl)phenyl]-7-{[2-(4,5-dihydro-1H-imidazol-2-yl) -pyridin-4-yl]oxy}-1,2,3,4-tetrahydronaphthalene-2-carboxamide;
N-[4-chloro-3-(trifluoromethyl)phenyl]-7-{[2-(4,5-dihydro-1H-imidazol-2-yl) -pyridin-4-yl]oxy}-1,2,3,4-tetrahydronaphthalene-2-carboxamide;
(2R)-N-(3-tert-butylphenyl)-7-{[2-(4,5-dihydro-1H-imidazol-2-yl)pyridin-4-yl]oxy}-1,2,3,4-tetrahydronaphthalene-2-carboxamide;
(2S)-N-(3-tert-butylphenyl)-7-{[2-(4,5-dihydro-1H-imidazol-2-yl)pyridin-4-yl]oxy}-1,2,3,4-tetrahydronaphthalene-2-carboxamide;
4-{[7-({[3-[2-(dimethylamino)ethoxy]-5-(trifluoromethyl)phenyl]amino}carbonyl)    -5,6,7,8-tetrahydronaphthalen-2-yl]oxy}-N-methylpyridine-2-carboxamide;

4-{[7-({[4-(aminomethyl)phenyl]amino}carbonyl)-5,6,7,8-tetrahydronaphthalen-2-yl]oxy}-N-methylpyridine-2-carboxamide;

N-(3-tert-butylphenyl)-7-{[2-(4,5-dihydro-1H-imidazol-2-yl)pyridin-4-yl]oxy}-1,2,3,4-tetrahydronaphthalene-2-carboxamide;

4-{[7-({[3-(2-aminoethyl)-5-(trifluoromethyl)phenyl]amino}carbonyl)-5,6,7,8-tetrahydronaphthalen-2-yl]oxy}-N-methylpyridine-2-carboxamide;

4-{[7-({[3-(aminomethyl)phenyl]amino}carbonyl)-5,6,7,8-tetrahydronaphthalen-2-yl]oxy}-N-methylpyridine-2-carboxamide;

N-methyl-4-{[7-({[2-(2-pyrrolidin-1-ylethoxy)-5-(trifluoromethyl)phenyl]-amino}carbonyl)-5,6,7,8-tetrahydronaphthalen-2-yl]oxy}pyridine-2-carboxamide;

N-(3-tert-butylphenyl)-7-({2-[{[2-(dimethylamino)ethyl]amino}(imino)methyl]-pyridin4-yl]oxy)-1,2,3,4-tetrahydronaphthalene-2-carboxamide;

7-({2-[amino(imino)methyl]pyridin-4-yl}oxy)-N-(3-tert-butylphenyl)-1,2,3,4-tetrahydronaphthalene-2-carboxamide;

7-{[2-(acetylamino)pyridin-4-yl]oxy}-N-[4-chloro-3-(trifluoromethyl)phenyl]-1,2,3,4-tetrahydronaphthalene-2-carboxamide;

7-{[2-(acetylamino)pyridin-4-yl]oxy}-N-(3-tert-butylphenyl)-1,2,3,4-tetrahydronaphthalene-2-carboxamide;

7-{[2-(4,5-dihydro-1H-imidazol-2-yl)pyridin-4-yl]oxy}-N-[4-(pyrrolidin-1-ylmethyl)-3-(trifluoromethyl)phenyl]-1,2,3,4-tetrahydronaphthalene-2-carboxamide;

7-{[2-(acetylamino)pyridin-4-yl]oxy}-N-[4-[(4-methylpiperazin-1-yl)methyl]-3-(trifluoromethyl)phenyl]-1,2,3,4-tetrahydronaphthalene-2-carboxamide;

7-{[2-(acetylamino)pyridin-4-yl]oxy}-N-[4-(pyrrolidin-1-ylmethyl)-3-(trifluoromethyl)phenyl]-1,2,3,4-tetrahydronaphthalene-2-carboxamide;

N-methyl-4-{[7-({[4-[(4-methylpiperazin-1-yl)methyl]-3-(trifluoromethyl)phenyl]-amino}carbonyl)-5,6,7,8-tetrahydronaphthalen-2-yl]oxy}pyridine-2-carboxamide;

N-methyl-4-{[7-({[4-(pyrrolidin-1-ylmethyl)-3-(trifluoromethyl)phenyl]-amino}carbonyl)-5,6,7,8-tetrahydronaphthalen-2-yl]oxy}pyridine-2-carboxamide;

7-{[2-(acetylamino)pyridin-4-yl]oxy}-N-[3-(2-pyrrolidin-1-ylethoxy)-5-(trifluoromethyl)phenyl]-1,2,3,4-tetrahydronaphthalene-2-carboxamide;

N-(3-tert-butylphenyl)-7-[(2-{4-[(4-methylpiperazin-1-yl)carbonyl]-1H-imidazol-2-yl}pyridin-4-yl)oxy]-1,2,3,4-tetrahydronaphthalene-2-carboxamide;

2-{4-[(7-{[(3-tert-butylphenyl)amino]carbonyl}-5,6,7,8-tetrahydronaphthalen-2-yl)-oxy]pyridin-2-yl}-1H-imidazole-4-carboxylic acid;

N-(3-tert-butylphenyl)-7-[(2-{4-[(4-methylpiperazin-1-yl)methyl]-imidazol-2-yl}-pyridin-4-yl)oxy]-1,2,3,4-tetrahydronaphthalene-2-carboxamide;

N-(3-tert-butylphenyl)-7-({2-[imino(4-methylpiperazin-1-yl)methyl]pyridin-4-yl)-oxy)-1,2,3,4-tetrahydronaphthalene-2-carboxamide;

N-(3-tert-butylphenyl)-7-({2-[(4-methoxybenzyl)(methyl)amino]pyridin-4-yl}oxy)-1,2,3,4-tetrahydronaphthalene-2-carboxamide;

(2S)-7-{[2-(acetylamino)pyridin-4-yl]oxy}-N-[3-(aminomethyl)-5-(trifluoromethyl)-phenyl]-1,2,3,4-tetrahydronaphthalene-2-carboxamide;

N-methyl-4-{[7-({[3-[(4-methylpiperazin-1-yl)methyl]-5-(trifluoromethyl)phenyl]-amino}carbonyl)-5,6,7,8-tetrahydronaphthalen-2-yl]oxy}pyridine-2-carboxamide;

N-[3-(aminomethyl)-5-(trifluoromethyl)phenyl]-7-(2,4'-bipyridin-4-yloxy)-1,2,3,4-tetrahydronaphthalene-2-carboxamide;

N-[3-(aminomethyl)-5-(trifluoromethyl)phenyl]-7-{[2-(3,5-dimethylisoxazol-4-yl)-pyridin-4-yl]oxy}-1,2,3,4-tetrahydronaphthalene-2-carboxamide;

(2R)-7-{[2-(acetylamino)pyridin-4-yl]oxy}-N-[3-(pyrrolidin-1-ylmethyl)-5-(trifluoromethyl)phenyl]-1,2,3,4-tetrahydronaphthalene-2-carboxamide;

N-[3-(aminomethyl)-5-(trifluoromethyl)phenyl]-7-[(7-oxo-7,8-dihydro-1,8-naphthyridin-4-yl)oxy]-1,2,3,4-tetrahydronaphthalene-2-carboxamide;

N-[3-(aminomethyl)-5-(trifluoromethyl)phenyl]-7-({2-[4-(pyrrolidin-1-ylmethyl)-1H-imidazol-2-yl]pyridin-4-yl}oxy)-1,2,3,4-tetrahydronaphthalene-2-carboxamide;

N-[3-(aminomethyl)-5-(trifluoromethyl)phenyl]-7-[(7-oxo-5,6,7,8-tetrahydro-1,8-naphthyridin-4-yl)oxy]-1,2,3,4-tetrahydronaphthalene-2-carboxamide;

methyl [(4-{[7-({[3-(aminomethyl)-5-(trifluoromethyl)phenyl]amino}carbonyl)-5,6,7,8-tetrahydronaphthalen-2-yl]oxy}pyridin-2-yl)methyl]carbamate;

methyl (4-{[7-({[3-(aminomethyl)-5-(trifluoromethyl)phenyl]amino}carbonyl)-5,6,7,8-tetrahydronaphthalen-2-yl]oxy}pyridin-2-yl)carbamate;

N-(3-tert-butylphenyl)-7-({2-[imino(pyrrolidin-1-yl)methyl]pyridin-4-yl}oxy)-1,2,3,4-tetrahydronaphthalene-2-carboxamide;

7-({2-[(cyclopropylcarbonyl)amino]pyridin-4-yl}oxy)-N-[3-[(4-ethylpiperazin-1-yl)-methyl]-5-(trifluoromethyl)phenyl]-1,2,3,4-tetrahydronaphthalene-2-carboxamide;

7-{[2-(acetylamino)pyridin-4-yl]oxy}-N-[3-(1-amino-1-methylethyl)-5-(trifluoromethyl)phenyl]-1,2,3,4-tetrahydronaphthalene-2-carboxamide;

7-{[2-(acetylamino)pyridin-4-yl]oxy}-N-(3-tert-butyl-4-fluorophenyl)-1,2,3,4-tetrahydronaphthalene-2-carboxamide;

7-({2-[(cyclopropylcarbonyl)amino]pyridin-4-yl}oxy)-N-[3-(2-pyrrolidin-1-ylethoxy)-5-(trifluoromethyl)phenyl]-1,2,3,4-tetrahydronaphthalene-2-carboxamide;

(2R)-7-{[2-(acetylamino)pyridin-4-yl]oxy}-N-[3-(aminomethyl)-5-(trifluoromethyl)-phenyl]-1,2,3,4-tetrahydronaphthalene-2-carboxamide;

N-(3-tert-butylphenyl)-7-{[2-({[isopropylamino)acetyl]amino}methyl)pyridin-4-yl]-oxy}-1,2,3,4-tetrahydronaphthalene-2-carboxamide;

7-({2-[(acetylamino)methyl]pyridin-4-yl}oxy)-N-[3-(aminomethyl)-5-(trifluoromethyl)phenyl]-1,2,3,4-tetrahydronaphthalene-2-carboxamide;

N-[3-(aminomethyl)-5-(trifluoromethyl)phenyl]-7-{[2-(1H-imidazol-1-yl)pyridin-4-yl]oxy}-1,2,3,4-tetrahydronaphthalene-2-carboxamide;

7-({2-[(cyclopropylcarbonyl)amino]pyridin-4-yl}oxy)-N-[3-(hydroxymethyl)-5-(trifluoromethyl)phenyl]-1,2,3,4-tetrahydronaphthalene-2-carboxamide;

7-{[2-(acetylamino)pyridin-4-yl]oxy}-N-[3-(1-hydroxy-1-methylethyl)-5-(trifluoromethyl)phenyl]-1,2,3,4-tetrahydronaphthalene-2-carboxamide;

N-[3-(aminomethyl)-5-(trifluoromethyl)phenyl]-7-{[2-(1,3-oxazol-5-yl)pyridin-4-yl]-oxy}-1,2,3,4-tetrahydronaphthalene-2-carboxamide;

7-{[2-(acetylamino)pyridin-4-yl]oxy}-N-(4-chloro-3-methylphenyl)-1,2,3,4-tetrahydronaphthalene-2-carboxamide;

N-[3-(aminomethyl)-5-tert-butylphenyl]-7-({2-[(cyclopropylcarbonyl) -amino]pyridin-4-yl}oxy)-1,2,3,4-tetrahydronaphthalene-2-carboxamide;

7-({2-[(2,2-dimethylpropanoyl)amino]pyridin-4-yl}oxy)-N-[3-(2-pyrrolidin-1-ylethoxy)-5-(trifluoromethyl)phenyl]-1,2,3,4-tetrahydronaphthalene-2-carboxamide;

7-({2-[(cyclopropylcarbonyl)amino]pyridin-4-yl}oxy)-N-[3-(1,1-difluoroethyl) -phenyl]-1,2,3,4-tetrahydronaphthalene-2-carboxamide;

7-{[2-(acetylamino)pyridin-4-yl]oxy}-N-[3-(trifluoromethyl)phenyl]-1,2,3,4-tetrahydronaphthalene-2-carboxamide;

7-{[2-(acetylamino)pyridin-4-yl]oxy}-N-[3-(piperidin-1-ylmethyl)-5-(trifluoromethyl)phenyl]-1,2,3,4-tetrahydronaphthalene-2-carboxamide;

methyl (4-{[(7S)-7-({[3-(aminomethyl)-5-(trifluoromethyl)phenyl]amino}carbonyl) -5,6,7,8-tetrahydronaphthalen-2-yl]oxy}pyridin-2-yl)carbamate;

N-[3-tert-butyl-5-(pyrrolidin-1-ylmethyl)phenyl]-7-({2-[(cyclopropylcarbonyl) -amino]pyridin-4-yl}oxy)-1,2,3,4-tetrahydronaphthalene-2-carboxamide;

7-({2-[(cyclopropylcarbonyl)amino]pyridin-4-yl}oxy)-N-[3-{[(2-hydroxyethyl) -amino]methyl}-5-(trifluoromethyl)phenyl]-1,2,3,4-tetrahydronaphthalene-2-carboxamide;

methyl (4-{[7-({[3-(2-pyrrolidin-1-ylethoxy)-5-(trifluoromethyl)phenyl]-amino}carbonyl)-5,6,7,8-tetrahydronaphthalen-2-yl]oxy}pyridin-2-yl)carbamate;

4-{[7-({[3-(aminomethyl)-5-(trifluoromethyl)phenyl]amino}carbonyl)-5,6,7,8-tetrahydronaphthalen-2-yl]oxy}-N-isopropylpyridine-2-carboxamide;

4-{[7-({3-{[(3-amino-3-oxopropyl)amino]methyl}-5-(trifluoromethyl)phenyl]-amino}carbonyl)-5,6,7,8-tetrahydronaphthalen-2-yl]oxy}-N-methylpyridine-2-carboxamide;

N-(3-tert-butylphenyl)-74[2-(1H-pyrazol-3-yl)pyridin-4-yl]oxy}-1,2,3,4-tetrahydronaphthalene-2-carboxamide;

7-{[2-(acetylamino)pyridin-4-yl]oxy}-N-phenyl-1,2,3,4-tetrahydronaphthalene-2-carboxamide;

7-{[2-(acetylamino)pyridin-4-yl]oxy}-N-[3-[(4-methylpiperazin-1-yl)methyl]-5-(trifluoromethyl)phenyl]-1,2,3,4-tetrahydronaphthalene-2-carboxamide;

7-[(2-aminopyridin-4-yl)oxy]-N-(3-tert-butylphenyl)-1,2,3,4-tetrahydronaphthalene -2-carboxamide;

7-{[2-(acetylamino)pyridin-4-yl]oxy}-N-(5-tert-butyl-2-fluorophenyl)-1,2,3,4-tetrahydronaphthalene-2-carboxamide;

7-[(2-piperazin-1-ylpyridin-4-yl)oxy]-N-[3-(2-pyrrolidin-1-ylethoxy)-5-(trifluoromethyl)phenyl]-1,2,3,4-tetrahydronaphthalene-2-carboxamide;

N-[3-(aminomethyl)-5-(trifluoromethyl)phenyl]-7-{[2-(propionylamino)pyridin-4-yl]oxy}-1,2,3,4-tetrahydronaphthalene-2-carboxamide;

N-[3-(aminomethyl)-5-(trifluoromethyl)phenyl]-7-({2-[(cyclobutylcarbonyl) -amino]pyridin-4-yl}oxy)-1,2,3,4-tetrahydronaphthalene-2-carboxamide;

7-{[2-(acetylamino)pyridin-4-yl]oxy}-N-[4-cyano-3-(trifluoromethyl)phenyl]-1,2,3,4-tetrahydronaphthalene-2-carboxamide;

7-{[2-(acetylamino)pyridin-4-yl]oxy}-N-[3-pyrrolidin-2-yl-5-(trifluoromethyl) -phenyl]-1,2,3,4-tetrahydronaphthalene-2-carboxamide;

4-{[(7R)-7-({[3-(aminomethyl)-5-(trifluoromethyl)phenyl]amino}carbonyl)-5,6,7,8-tetrahydronaphthalen-2-yl]oxy}-N-methylpyridine-2-carboxamide;

7-({2-[(acetylamino)methyl]pyridin-4-yl}oxy)-N-(3-tert-butylphenyl)-1,2,3,4-tetrahydronaphthalene-2-carboxamide;

7-{[2-(acetylamino)pyridin-4-yl]oxy}-N-(3-isopropylphenyl)-1,2,3,4-tetrahydronaphthalene-2-carboxamide;

7-({2-[(cyclopropylcarbonyl)amino]pyridin-4-yl}oxy)-N-P-{[(3S)-3-hydroxypyrrolidin-1-yl]methyl}-5-(trifluoromethyl)phenyl]-1,2,3,4-tetrahydronaphthalene-2-carboxamide;

7-({2-[(cyclopropylcarbonyl)amino]pyridin-4-yl}oxy)-N-[3-[(ethylamino)methyl]-5-(trifluoromethyl)phenyl]-1,2,3,4-tetrahydronaphthalene-2-carboxamide;

N-[3-(aminomethyl)-5-(trifluoromethyl)phenyl]-7-[(2-{4-[(4-methylpiperazin-1-yl) -carbonyl]-1H-imidazol-2-yl}pyridin-4-yl)oxy]-1,2,3,4-tetrahydronaphthalene-2-carboxamide;

N[3-(aminomethyl)-5-(trifluoromethyl)phenyl]-7-{[2-(1H-pyrazol-4-yl)pyridin-4-yl]oxy}-1,2,3,4-tetrahydronaphthalene-2-carboxamide;

methyl {4-[(7-{[(3-tert-butylphenyl)amino]carbonyl}-5,6,7,8-tetrahydronaphthalen-2-yl)oxy]pyridin-2-yl}carbamate;

N-(3-tert-butylphenyl)-7-({2-[(methylsulfonyl)amino]pyridin-4-yl}oxy)-1,2,3,4-tetrahydronaphthalene-2-carboxamide;

7-{[2-(acetylamino)pyridin-4-yl]oxy}-N-[3-[(diethylamino)methyl]-5-(trifluoromethyl)phenyl]-1,2,3,4-tetrahydronaphthalene-2-carboxamide;

7-({2-[(cyclopropylcarbonyl)amino]pyridin-4-yl}oxy)-N-[3-pyrrolidin-2-yl-5-(trifluoromethyl)phenyl]-1,2,3,4-tetrahydronaphthalene-2-carboxamide;

7-(2,3'-bipyridin-4-yloxy)-N-(3-tert-butylphenyl)-1,2,3,4-tetrahydronaphthalene-2-carboxamide;

7-{[2-(4,5-dihydro-1H-imidazol-2-yl)pyridin-4-yl]oxy}-N-[2-(2-piperazin-1-ylethoxy)-5-(trifluoromethyl)phenyl]-1,2,3,4-tetrahydronaphthalene-2-carboxamide;

N-(3-tert-butylphenyl)-7-({2-[imino(morpholin-4-yl)methyl]pyridin-4-yl}oxy) -1,2,3,4-tetrahydronaphthalene-2-carboxamide;

7-({2-[(cyclopropylcarbonyl)amino]pyridin-4-yl}oxy)-N-[3-(pyrrolidin-1-ylmethyl) -5-(trifluoromethyl)phenyl]-1,2,3,4-tetrahydronaphthalene-2-carboxamide;

(2R)-N-[3-(aminomethyl)-5-(trifluoromethyl)phenyl]-7-({2-[(cyclopropylcarbonyl) -amino]pyridin-4-yl}oxy)-1,2,3,4-tetrahydronaphthalene-2-carboxamide;

N-[3-(aminomethyl)-5-(trifluoromethyl)phenyl[-7-[(2-aminopyridin-4-yl)oxy]-1,2,3,4-tetrahydronaphthalene-2-carboxamide;

(2S)-2,3-dihydroxypropyl {4-[(7-{[(3-tert-butylphenyl)amino]carbonyl}-5,6,7,8-tetrahydronaphthalen-2-yl)oxy]pyridin-2-yl}carbamate;

N-(3-tert-butylphenyl)-7-({2-[(pyrrolidin-1-ylacetyl)amino]pyridin-4-yl}oxy)-1,2,3,4-tetrahydronaphthalene-2-carboxamide;

N-methyl-4-{[7-({[3-({[(methylamino)acetyl]amino}methyl)-5-(trifluoromethyl) -phenyl]amino}carbonyl)-5,6,7,8-tetrahydronaphthalen-2-yl]oxy}pyridine-2-carboxamide;

N-(3-tert-butylphenyl)-7-({2-[(2-pyrrolidin-1-ylpropanoyl)amino]pyridin-4-yl}oxy) -1,2,3,4-tetrahydronaphthalene-2-carboxamide;

4-{[7-({[3-{[(2-hydroxyethyl)amino]methyl}-5-(trifluoromethyl)phenyl]-amino}carbonyl)-5,6,7,8-tetrahydronaphthalen-2-yl]oxy)-N-methylpyridine-2-carboxamide;

(2R)-2,3-dihydroxypropyl {4-[(7-{[(3-tert-butylphenyl) amino]carbonyl}-5,6,7,8-tetrahydronaphthalen-2-yl)oxy]pyridin-2-yl}carbamate;

N-(3-tert-butylphenyl)-7-[(2-piperazin-1-ylpyridin-4-yl)oxy]-1,2,3,4-tetrahydronaphthalene-2-carboxamide;

N-(3-tert-butylphenyl)-7-({2-[imino(piperazin-1-yl)methyl]pyridin-4-yl}oxy)-1,2,3,4-tetrahydronaphthalene-2-carboxamide;

7-{[2-(acetylamino)pyridin-4-yl]oxy}-N-[4-(trifluoromethyl)phenyl]-1,2,3,4-tetrahydronaphthalene-2-carboxamide;

7-{[2-(acetylamino)pyridin-4-yl]oxy}-N-[4-(methylamino)methyl]-3-(trifluoromethyl)phenyl]-1,2,3,4-tetrahydronaphthalene-2-carboxamide;

tert-butyl [3-({[7-({2-[(methylamino)carbonyl]pyridin-4-yl}oxy)-1,2,3,4-tetrahydronaphthalen-2-yl]carbonyl}amino)-5-(trifluoromethyl)benzyl](2-pyrrolidin-1-ylethyl)carbamate;

4-{[7-({[3-({[(dimethylamino)acetyl]amino}methyl)-5-(trifluoromethyl)phenyl]-amino}carbonyl)-5,6,7,8-tetrahydronaphthalen-2-yl]oxy}-N-methylpyridine-2-carboxamide;

4-{[7-({[3-(aminomethyl)-5-(trifluoromethyl)phenyl]amino}carbonyl)-3-fluoro-5,6,7,8-tetrahydronaphthalen-2-yl]oxy}-N-methylpyridine-2-carboxamide;

7-{[2-(acetylamino)pyridin-4-yl]oxy)-N-[3-(hydroxymethyl)-5-(trifluoromethyl)-phenyl]-1,2,3,4-tetrahydronaphthalene-2-carboxamide;

7-{[2-(acetylamino)pyridin-4-yl]oxy}-N-[3-(pyrrolidin-1-ylmethyl)-5-(trifluoromethyl)phenyl]-1,2,3,4-tetrahydronaphthalene-2-carboxamide;

7-({2-[(cyclopropylcarbonyl)amino]pyridin-4-yl}oxy)-N-[3-[(4-methylpiperazin-1-yl)methyl]-5-(trifluoromethyl)phenyl]-1,2,3,4-tetrahydronaphthalene-2-carboxamide;

N-[3-(aminomethyl)-5-(trifluoromethyl)phenyl]-7-[(2-pyridin-5-ylpyridin-4-yl)-oxy]-1,2,3,4-tetrahydronaphthalene-2-carboxamide;

N-methyl-4-{[7-({[3-[(methylamino)methyl]-5-(trifluoromethyl)phenyl]-amino}carbonyl)-5,6,7,8-tetrahydronaphthalen-2-yl]oxy}pyridine-2-carboxamide;

N-methyl-4-{[7-({[2-(2-piperazin-1-ylethoxy)-5-(trifluoromethyl)phenyl]-amino}carbonyl)-5,6,7,8-tetrahydronaphthalen-2-yl]oxy}pyridine-2-carboxamide;

7-{[2-(acetylamino)pyridin-4-yl]oxy}-N-(4-chlorophenyl)-1,2,3,4-tetrahydronaphthalene-2-carboxamide;

N[3-(aminomethyl)-5-(trifluoromethyl)phenyl]-7-{[1-oxido-2-(1H-pyrazol-1-yl)-pyridin-4-yl]oxy}-1,2,3,4-tetrahydronaphthalene-2-carboxamide;

N-(3-tert-butylphenyl)-7-{[2-(4,5-dihydro-1,3-oxazol-2-yl)pyridin-4-yl]oxy}-1,2,3,4-tetrahydronaphthalene-2-carboxamide;

7-({2-[(cyclopropylcarbonyl)amino]pyridin-4-yl}oxy)-N-[3-[(methylamino)methyl]-5-(trifluoromethyl)phenyl]-1,2,3,4-tetrahydronaphthalene-2-carboxamide;

N-(3-tert-butylphenyl)-7-[(2-{[(morpholin-4-ylacetyl)amino]methyl}pyridin-4-yl)-oxy]-1,2,3,4-tetrahydronaphthalene-2-carboxamide;

ethyl 5-{4-[(7-{[(3-tert-butylphenyl)amino]carbonyl}-5,6,7,8-tetrahydronaphthalen-2-yl)oxy]pyridin-2-yl}-1,3,4-oxadiazole-2-carboxylate;

(2S)-7-{[2-(acetylamino)pyridin-4-yl]oxy}-N-[3(pyrrolidin-1-ylmethyl)-5-(trifluoromethyl)phenyl]-1,2,3,4-tetrahydronaphthalene-2-carboxamide;

7-{[2-(acetylamino)pyridin-4-yl]oxy}-N-[3-{[(3S)-3-fluoropyrrolidin-1-yl]methyl}-5-(trifluoromethyl)phenyl]-1,2,3,4-tetrahydronaphthalene-2-carboxamide;

4-{[7S)-7-({[3-(aminomethyl)-5-(trifluoromethyl)phenyl]amino}carbonyl)-5,6,7,8-tetrahydronaphthalen-2-yl]oxy}-N-methylpyridine-2-carboxamide;

4-{[7-({[3-({[(isopropylamino)carbonyl]amino}methyl)-5-(trifluoromethyl)phenyl]-amino}carbonyl)-5,6,7,8-tetrahydronaphthalen-2-yl]oxy}-N-methylpyridine-2-carboxamide;

7-{[2-(acetylamino)pyridin-4-yl]oxy}-N-(3-methoxyphenyl)-1,2,3,4-tetrahydronaphthalene-2-carboxamide;

N-(3-tert-butylphenyl)-7-{[2-(1-methyl-1H-tetrazol-5-yl)pyridin-4-yl]oxy}-1,2,3,4-tetrahydronaphthalene-2-carboxamide;

methyl (4-{[(7R)-7-({[3-(aminomethyl)-5-(trifluoromethyl)phenyl]amino}carbonyl)-5,6,7,8-tetrahydronaphthalen-2-yl]oxy}pyridin-2-yl)carbamate;

N-(3-tert-butylphenyl)-7-{[2-(1,3-oxazol-2-yl)pyridin-4-yl]oxy}-1,2,3,4-tetrahydronaphthalene-2-carboxamide;

7-{[2-(acetylamino)pyridin-4-yl]oxy}-N-[3-[(methylamino)methyl]-5-(trifluoromethyl)phenyl]-1,2,3,4-tetrahydronaphthalene-2-carboxamide;

tert-butyl methyl[3-({[7-({2-[(methylamino)carbonyl]pyridin-4-yl}oxy)-1,2,3,4-tetrahydronaphthalen-2-yl]carbonyl}amino)-5-(trifluoromethyl)benzyl]-carbamate;

N-[3-(aminomethyl)-5-(trifluoromethyl)phenyl]-7-{[2-(1H-1,2,4-triazol-1-yl)pyridin-4-yl]oxy}-1,2,3,4-tetrahydronaphthalene-2-carboxamide;

7-{[2-(aminomethyl)pyridin-4-yl]oxy}-N-(3-tert-butylphenyl)-1,2,3,4-tetrahydronaphthalene-2-carboxamide;

N-[3-(aminomethyl)-5-(trifluoromethyl)phenyl]-7-({2-[5-(trifluoromethyl)-1H-imidazol-2-yl]pyridin-4-yl}oxy)-1,2,3,4-tetrahydronaphthalene-2-carboxamide;

7-{[2-(acetylamino)pyridin-4-yl]oxy)-N-[2-fluoro-5-(trifluoromethyl)phenyl]-1,2,3,4-tetrahydronaphthalene-2-carboxamide;

N-(3-tert-butylphenyl)-7-{[2-(2-methyl-2H-tetrazol-5-yl)pyridin-4-yl]oxy}-1,2,3,4-tetrahydronaphthalene-2-carboxamide;

ethyl (4-{[7-({[3-(aminomethyl)-5-(trifluoromethyl)phenyl]amino}carbonyl)-5,6,7,8-tetrahydronaphthalen-2-yl]oxy}pyridin-2-yl)carbamate;

7-({2-[(cyclopropylcarbonyl)amino]pyridin-4-yl}oxy)-N-[3-{[(3R)-3-fluoropyrrolidin-1-yl]methyl}-5-(trifluoromethyl)phenyl]-1,2,3,4-tetrahydronaphthalene-2-carboxamide;

N-(3-tert-butylphenyl)-7-{[2-(1H-tetrazol-5-yl)pyridin-4-yl]oxy}-1,2,3,4-tetrahydronaphthalene-2-carboxamide;

N-(3-tert-butylphenyl)-7-{[2-(methylamino)pyridin-4-yl]oxy}-1,2,3,4-tetrahydronaphthalene-2-carboxamide;

7-{[2-(acetylamino)pyridin-4-yl]oxy}-N-[3-(2-aminoethyl)-5-(trifluoromethyl)-phenyl]-1,2,3,4-tetrahydronaphthalene-2-carboxamide;

7-{[2-(1-methyl-1H-pyrazol-4-yl)pyridin-4-yl]oxy}-N-[3-(pyrrolidin-1-ylmethyl)-5-(trifluoromethyl)phenyl]-1,2,3,4-tetrahydronaphthalene-2-carboxamide;

4-{[7-({[3-{[(aminoacetyl)amino]methyl}-5-(trifluoromethyl)phenyl]-amino}carbonyl)-5,6,7,8-tetrahydronaphthalen-2-yl]oxy}-N-methylpyridine-2-carboxamide;

N-[3-(aminomethyl)-5-(trifluoromethyl)phenyl]-7-[(2-{4-[(4-methylpiperazin-1-yl)-methyl]-1H-imidazol-2-yl}pyridin-4-yl)oxy]-1,2,3,4-tetrahydronaphthalene-2-carboxamide;

methyl [3-({[7-({2-[(methylamino)carbonyl]pyridin-4-yl}oxy)-1,2,3,4-tetrahydronaphthalen-2-yl]carbonyl}amino)-5-(trifluoromethyl)benzyl]-carbamate;

N-(3-tert-butylphenyl)-7-[(2-{[(4-methylpiperazin-1-yl)acetyl]amino}pyridin-4-yl)-oxy]-1,2,3,4-tetrahydronaphthalene-2-carboxamide;

N-[3-(2-pyrrolidin-1-ylethoxy)-5-(trifluoromethyl)phenyl]-7-{[2-(2H-tetrazol-5-yl)-pyridin-4-yl]oxy}-1,2,3,4-tetrahydronaphthalene-2-carboxamide;

N-[3-(aminomethyl)-5-(trifluoromethyl)phenyl]-7-(2,3'-bipyridin-4-yloxy)-1,2,3,4-tetrahydronaphthalene-2-carboxamide;

7-{[2-(propionylamino)pyridin-4-yl]oxy}-N-[3-(pyrrolidin-1-ylmethyl)-5-(trifluoromethyl)phenyl]-1,2,3,4-tetrahydronaphthalene-2-carboxamide;

7-({2-[(cyclopropylcarbonyl)amino]pyridin-4-yl}oxy)-N-[3-(diethylamino)methyl]-5-(trifluoromethyl)phenyl]-1,2,3,4-tetrahydronaphthalene-2-carboxamide;

N-(3-tert-butylphenyl)-7-({2-[5-(trifluoromethyl)-1H-imidazol-2-yl]pyridin-4-yl}-oxy)-1,2,3,4-tetrahydronaphthalene-2-carboxamide;

N-[3-(aminomethyl)-5-(trifluoromethyl)phenyl]-7-{[2-(pyrrolidin-1-ylcarbonyl)-pyridin-4-yl]oxy}-1,2,3,4-tetrahydronaphthalene-2-carboxamide;

N-[3-(aminomethyl)-5-(trifluoromethyl)phenyl]-7-({2-[(cyclopropylcarbonyl)-amino]pyridin-4-yl}oxy)-6-fluoro-1,2,3,4-tetrahydronaphthalene-2-carboxamide;

N-(3-tert-butylphenyl)-7-{[2-(dimethylamino)pyridin-4-yl]oxy}-1,2,3,4-tetrahydronaphthalene-2-carboxamide;

7-({2-[benzyl(methyl)amino]pyridin-4-yl}oxy)-N-(3-tert-butylphenyl)-1,2,3,4-tetrahydronaphthalene-2-carboxamide;

N-(3-tert-butylphenyl)-7-[(2-{[(ethylamino)carbonyl]amino}pyridin-4-yl)oxy]-1,2,3,4-tetrahydronaphthalene-2-carboxamide;

N-methyl-4-{[7-({[3-{[(2-pyrrolidin-1-ylethyl)amino]methyl}-5-(trifluoromethyl)-phenyl]amino}carbonyl)-5,6,7,8-tetrahydronaphthalen-2-yl]oxy}pyridine-2-carboxamide;

N-(3-tert-butyl-4-fluorophenyl)-7-({2-[(morpholin-4-ylacetyl)amino]pyridin-4-yl}-oxy)-1,2,3,4-tetrahydronaphthalene-2-carboxamide;

7-{[2-(acetylamino)pyridin-4-yl]oxy}-N-(3-ethylphenyl)-1,2,3,4-tetrahydronaphthalene-2-carboxamide;

7-{[2-(acetylamino)pyridin-4-yl]oxy}-N-[3-(morpholin-4-ylmethyl)-5-(trifluoromethyl)phenyl]-1,2,3,4-tetrahydronaphthalene-2-carboxamide;

7-({2-[(cyclopropylcarbonyl)amino]pyridin-4-yl}oxy)-N-[3-{[(2-methoxyethyl)-amino]methyl}-5-(trifluoromethyl)phenyl]-1,2,3,4-tetrahydronaphthalene-2-carboxamide;

N-methyl-4-{[7-({[3-(pyrrolidin-1-ylmethyl)-5-(trifluoromethyl)phenyl]-amino}carbonyl)-5,6,7,8-tetrahydronaphthalen-2-yl]oxy}pyridine-2-carboxamide;

methyl ({4-[(7-{[(3-tert-butylphenyl)amino]carbonyl}-5,6,7,8-tetrahydronaphthalen-2-yl)oxy]pyridin-2-yl}methyl)carbamate;

4-{[7-({[2-cyano-5-(trifluoromethyl)phenyl]amino}carbonyl)-5,6,7,8-tetrahydronaphthalen-2-yl]oxy}-N-methylpyridine-2-carboxamide;

N-(3-tert-butylphenyl)-7-({2-[(isobutyrylamino)methyl]pyridin-4-yl}oxy)-1,2,3,4-tetrahydronaphthalene-2-carboxamide;

7-{[2-(acetylamino)pyridin-4-yl]oxy}-N-[3-(aminomethyl)-5-tert-butylphenyl]-1,2,3,4-tetrahydronaphthalene-2-carboxamide;

(2S)-N-[3-(aminomethyl)-5-(trifluoromethyl)phenyl]-7-({2-[(cyclopropylcarbonyl)-amino]pyridin-4-yl}oxy)-1,2,3,4-tetrahydronaphthalene-2-carboxamide;

N-(3-tert-butylphenyl)-7-[(2-{[(pyrrolidin-1-ylacetyl)amino]methyl}pyridin-4-yl)-oxy]-1,2,3,4-tetrahydronaphthalene-2-carboxamide;

7-{[2-(acetylamino)pyridin-4-yl]oxy}-N-(3-tert-butyl-5-cyanophenyl)-1,2,3,4-tetrahydronaphthalene-2-carboxamide;

7-{[2-(isobutyrylamino)pyridin-4-yl]oxy}-N-[3-(2-pyrrolidin-1-ylethoxy)-5-(trifluoromethyl)phenyl]-1,2,3,4-tetrahydronaphthalene-2-carboxamide;

7-({2-[acetyl(methyl)amino]pyridin-4-yl}oxy)-N-(3-tert-butylphenyl)-1,2,3,4-tetrahydronaphthalene-2-carboxamide;

7-{[2-(acetylamino)pyridin-4-yl]oxy}-N-[3-{[(3R)-3-hydroxypyrrolidin-1-yl]methyl}-5-(trifluoromethyl)phenyl]-1,2,3,4-tetrahydronaphthalene-2-carboxamide;

N[3-(aminomethyl)-5-(trifluoromethyl)phenyl]-7-{[2-(1H-pyrazol-1-yl)pyridin-4-yl]oxy}-1,2,3,4-tetrahydronaphthalene-2-carboxamide;

N-[3-(aminomethyl)-5-(trifluoromethyl)phenyl]-7-({[2-(hydroxymethyl)-1H-imidazol-2-yl]pyridin-4-yl]oxy)-1,2,3,4-tetrahydronaphthalene-2-carboxamide;

7-{[2-(acetylamino)pyridin-4-yl]oxy}-N-[3-(aminomethyl)-5-(trifluoromethyl)-phenyl]-1,2,3,4-tetrahydronaphthalene-2-carboxamide;

N-[3-[(methylamino)methyl]-5-(trifluoromethyl)phenyl]-7-{[2-(propionylamino)-pyridin-4-yl]oxy}-1,2,3,4-tetrahydronaphthalene-2-carboxamide;

7-{[2-(acetylamino)pyridin-4-yl]oxy}-N-[3-{[3R)-3-fluoropyrrolidin-1-yl]methyl}-5-(trifluoromethyl)phenyl]-1,2,3,4-tetrahydronaphthalene-2-carboxamide;

N-(3-tert-butylphenyl)-7-{[2-(2-oxotetrahydropyrimidin-1(2H)-yl)pyridin-4-yl]oxy}-1,2,3,4-tetrahydronaphthalene-2-carboxamide;

7-{[2-(acetylamino)pyridin-4-yl]oxy}-N-[3-(piperazin-1-ylmethyl)-5-(trifluoromethyl)phenyl]-1,2,3,4-tetrahydronaphthalene-2-carboxamide;

7-{[2-(acetylamino)pyridin-4-yl]oxy}-N-[3-{[(2R)-2,3-dihydroxypropyl]oxy}-5-(trifluoromethyl)phenyl]-1,2,3,4-tetrahydronaphthalene-2-carboxamide;

7-({[2-[(cyclopropylcarbonyl)amino]pyridin-4-yl}oxy)-N-[3-[(isopropylamino)-methyl]-5-(trifluoromethyl)phenyl]-1,2,3,4-tetrahydronaphthalene-2-carboxamide;

7-({2-[(cyclopropylcarbonyl)amino]pyridin-4-yl}oxy)-N-[3-{[(3S)-3-fluoropyrrolidin-1-yl]methyl}-5-(trifluoromethyl)phenyl]-1,2,3,4-tetrahydronaphthalene-2-carboxamide;

N-(3-tert-butylphenyl)-7-{[2-(4-methylpiperazin-1-yl)pyridin-4-yl]oxy}-1,2,3,4-tetrahydronaphthalene-2-carboxamide;

N-[3-(aminomethyl)-5-(trifluoromethyl)phenyl]-7-({[2-[(cyclopropylcarbonyl)-amino]pyridin-4-yl}oxy)-1,2,3,4-tetrahydronaphthalene-2-carboxamide;

N-(3-tert-butylphenyl)-7-({2-(morpholin-4-ylacetyl)amino]pyridin-4-yl}oxy)-1,2,3,4-tetrahydronaphthalene-2-carboxamide;

4-{[7-({[3-(ethylamino)carbonyl]amino}methyl)-5-(trifluoromethyl)phenyl]-amino}carbonyl)-5,6,7,8-tetrahydronaphthalen-2-yl]oxy)-N-methylpyridine-2-carboxamide;

N-[7-({2-[(cyclopropylcarbonyl)amino]pyridin-4-yl}oxy)-1,2,3,4-tetrahydronaphthalen-2-yl]-3-(trifluoromethyl)benzamide;

7-({2-[amino (imino)methyl]pyridin-4-yl}oxy)-N-(3-tert-butylphenyl) -1,2,3,4-tetrahydronaphthalene-2-carboxamide;

7-{[2-(4,5-dihydro-1H-imidazol-2-yl)pyridin-4-yl]oxy}-N-[4-[(4-methylpiperazin-1-yl)methyl]-3-(trifluoromethyl)phenyl]-1,2,3,4-tetrahydronaphthalene-2-carboxamide;

3-(aminomethyl)-5-tert-butyl-N-[7-({2-[(cyclopropylcarbonyl)amino]pyridin -4yl}-oxy)-1,2,3,4-tetrahydronaphthalen-2-yl]benzamide;

N-(7-{[2-(acetylamino)pyridin-4-yl]oxy}-1,2,3,4-tetrahydronaphthalen-2-yl)-3-(aminomethyl)-5-tert-butylbenzamide;

7-{[2-(4,5-dihydro-1H-imidazol-2-yl)pyridin-4-yl]oxy}-N-[4-(pyrrolidin-1-ylmethyl) -3-(trifluoromethyl)phenyl1-1,2,3,4-tetrahydronaphthalene-2-carboxamide;

N-(7-{[2-(acetylamino)pyridin-4-yl]oxy}-1,2,3,4-tetrahydronaphthalen-2-yl)-4-chloro-3-(trifluoromethyl)benzamide;

3-tert-butyl-5-cyano-N-[7-({[2-[(cyclopropylcarbonyl)amino]pyridin-4-yl}oxy) -1,2,3,4-tetrahydronaphthalen-2-yl]benzamide;

N-(7-{[2-(acetylamino)pyridin-4-yl]oxy}-1,2,3,4-tetrahydronaphthalen-2-yl)-3-(trifluoromethyl)benzamide;

3-tert-butyl-N-[7-({2-[(cyclopropylcarbonyl)amino]pyridin-4-yl}oxy)-1,2,3,4-tetrahydronaphthalen-2-yl]benzamide;

N-(7-{[2-(acetylamino)pyridin-4-yl]oxy}-1,2,3,4-tetrahydronaphthalen-2-yl)-3-tert -butylbenzamide;

3-(aminomethyl)-N-[7-({2-[(cyclopropylcarbonyl)amino]pyridin-4-yl}oxy)-1,2,3,4-tetrahydronaphthalen-2-yl]-5-(trifluoromethyl)benzamide;

N-(7-{[2-(acetylamino)pyridin-4-yl]oxy}-1,2,3,4-tetrahydronaphthalen-2-yl)-3-(aminomethyl)-5-(trifluoromethyl)benzamide;

4-chloro-N-(7-{[2-(4,5-dihydro-1H-imidazol-2-yl)pyridin-4-yl]oxy}-1,2,3,4-tetrahydronaphthalen-2-yl)-3-(trifluoromethyl)benzamide;

4-chloro-N-[7-({2-[(cyclopropylcarbonyl)amino]pyridin-4-yl}oxy)-1,2,3,4-tetrahydronaphthalen-2-yl]-3-(trifluoromethyl)benzamide;

4-[(7-{[4-chloro-3-(trifluoromethyl)benzoyl]amino}-5,6,7,8-tetrahydronaphthalen-2-yl)oxy]-N-methylpyridine-2-carboxamide;

N-methyl-4-{[7-({[4-(pyrrolidin-1-ylmethyl)-3-(trifluoromethyl)phenyl]-amino}carbonyl)-5,6,7,8-tetrahydronaphthalen-2-yl]oxy}pyridine-2-carboxamide;

N-methyl-4-{[7-({[4-[(4-methylpiperazin-1-yl)methyl]-3-(trifluoromethyl)phenyl]-amino}carbonyl)-5,6,7,8-tetrahydronaphthalen-2-yl]oxy}pyridine-2-carboxamide;

7-({[2-[(cyclopropylcarbonyl)amino]pyridin-4-yl}oxy)-N-[3-(4-methylpiperazin-1-yl) -5-(trifluoromethyl)phenyl]-1,2,3,4-tetrahydronaphthalene-2-carboxamide;

4-({7-[(3-tert-butylbenzoyl)amino]-5,6,7,8-tetrahydronaphthalen-2-yl)oxy)-N -methylpyridine-2-carboxamide;

N-methyl-4-[(7-{[4-(trifluoromethoxy)benzoyl]amino}-5,6,7,8-tetrahydronaphthalen-2-yl)oxy]pyridine-2-carboxamide;

4-({7-[(3-hydroxy-4-nitrobenzoyl)amino]-5,6,7,8-tetrahydronaphthalen-2-yl}oxy)-N -methylpyridine-2-carboxamide;

({7-[(3-hydroxy-4-methoxybenzoyl)amino]-5,6,7,8-tetrahydronaphthalen-2-yl}-oxy)-N-methylpyridine-2-carboxamide;

4-({7-[(3-fluorobenzoyl)amino]-5,6,7,8-tetrahydronaphthalen-2-yl}oxy)-N -methylpyridine-2-carboxamide;

4-({7-(4-methoxy-3-methylbenzoyl)amino]1-5,6,7,8-tetrahydronaphthalen-2-yl}oxy) -N-methylpyridine-2-carboxamide;

4-({7-[(4-bromobenzoyl)amino]-5,6,7,8-tetrahydronaphthalen-2-yl}oxy)-N -methylpyridine-2-carboxamide;

4-[(7-{[4-(difluoromethoxy)benzoyl]amino}-5,6,7,8-tetrahydronaphthalen-2-yl)oxy]-N-methylpyridine-2-carboxamide;

4-[(7-{[3-fluoro-5-(trifluoromethyl)benzoyl]amino}-5,6,7,8-tetrahydronaphthalen-2-yl)oxy]-N-methylpyridine-2-carboxamide;

4-[(7-{[4-(1H-imidazol-1-yl)benzoyl]amino}-5,6,7,8-tetrahydronaphthalen-2-yl)oxy]-N-methylpyridine-2-carboxamide;

4-[(7-{[4-fluoro-3-(trifluoromethyl)benzoyl]amino}-5,6,7,8-tetrahydronaphthalen-2-yl)oxy}-N-methylpyridine-2-carboxamide;

4-({7-[(5-chloro-2-methoxybenzoyl)amino]-5,6,7,8-tetrahydronaphthalen-2-yl}oxy) -N-methylpyridine-2-carboxamide;

methyl 4-({[7-({[2-[(methylamino)carbonyl]pyridin-4-yl}oxy)-1,2,3,4-tetrahydronaphthalen-2-yl] amino}carbonyl)benzoate;

N-methyl-4-({7-[(3,4,5-trimethoxybenzoyl)amino]-5,6,7,8-tetrahydronaphthalen-2-yl}oxy)pyridine-2-carboxamide;

4-[7-[3,5-bis(trifluoromethyl)benzoyl]amino}-5,6,7,8-tetrahydronaphthalen-2-yl) -oxy]-N-methylpyridine-2-carboxamide;

4-({7-[(3,5-difluorobenzoyl)amino]-5,6,7,8-tetrahydronaphthalen-2-yl}oxy)-N -methylpyridine-2-carboxamide;

N-methyl-4-({7-[(4-methylbenzoyl)amino]-5,6,7,8-tetrahydronaphthalen-2-yl}-oxy)pyridine-2-carboxamide;

4-({7-[(3-amino-4-methoxybenzoyl)amino]-5,6,7,8-tetrahydronaphthalen-2-yl}oxy) -N-methylpyridine-2-carboxamide;

4-[(7-{[4-(dimethylamino)benzoyl]amino}-5,6,7,8-tetrahydronaphthalen-2-yl)oxy]-N-methylpyridine-2-carboxamide;

4-({7-(3-amino-4-hydroxybenzoyl)amino]-5,6,7,8-tetrahydronaphthalen-2-yl}oxy) -N-methylpyridine-2-carboxamide;

N-methyl-4-[(7-{[3-(trifluoromethoxy)benzoyl]amino}-5,6,7,8-tetrahydronaphthalen-2-yl)oxy]pyridine-2-carboxamide;

4-({7-[(3,5-dimethylbenzoyl)amino]-5,6,7,8-tetrahydronaphthalen-2-yl}oxy)-N -methylpyridine-2-carboxamide;

N-methyl-4-[(7-{[4-(trifluoromethyl)benzoyl]amino}-5,6,7,8-tetrahydronaphthalen -2-yl)oxy]pyridine-2-carboxamide;

N-methyl-4-({7-[(3-methylbenzoyl)amino]-5,6,7,8-tetrahydronaphthalen-2-yl) -oxy)pyridine-2-carboxamide;

4-({7-[(4-isopropylbenzoyl)amino]-5,6,7,8-tetrahydronaphthalen-2-yl}oxy)-N-methylpyridine-2-carboxamide;

4-({7-[(4-chlorobenzoyl)amino]-5,6,7,8-tetrahydronaphthalen-2-yl}oxy)-N-methylpyridine-2-carboxamide;

4-({7-[(3-methoxybenzoyl)amino]-5,6,7,8-tetrahydronaphthalen-2-yl}oxy)-N-methylpyridine-2-carboxamide;

4-({7-[(3-bromobenzoyl)amino]-5,6,7,8-tetrahydronaphthalen-2-yl}oxy)-N-methylpyridine-2-carboxamide;

4-({7-[(3,5-dimethoxy-4-methylbenzoyl)amino]-5,6,7,8-tetrahydronaphthalen-2-yl}-oxy)-N-methylpyridine-2-carboxamide;

N-methyl-4-[(7-{[3-(1H-tetrazol-1-yl)benzoyl]amino}-5,6,7,8-tetrahydronaphthalen-2-yl)oxy]pyridine-2-carboxamide;

4-({7-[(4-benzylbenzoy)amino]-5,6,7,8-tetrahydronaphthalen-2-yl}oxy)-N-methylpyridine-2-carboxamide;

4-({7-[(4-ethylbenzoyl)amino]-5,6,7,8-tetrahydronaphthalen-2-yl}oxy)-N-methylpyridine-2-carboxamide;

4-[(7-{[4-(4-fluorophenoxy)benzoyl]amino}-5,6,7,8-tetrahydronaphthalen-2-yl)oxy]-N-methylpyridine-2-carboxamide;

4-({7-[(3-aminobenzoyl)amino]-5,6,7,8-tetrahydronaphthalen-2-yl}oxy)-N-methylpyridine-2-carboxamide;

N-methyl-4-({7-[(3,4,5-trifluorobenzoyl)amino]-5,6,7,8-tetrahydronaphthalen-2-yl}oxy)]pyridine-2-carboxamide;

N-methyl-4-[(7-{[3-(trifluoromethyl)benzoyl]amino}-5,6,7,8-tetrahydronaphthalen-2-yl)oxy]pyridine-2-carboxamide;

N-methyl-4-[(7-{[4-(methylsulfonyl)benzoyl]amino}-5,6,7,8-tetrahydronaphthalen-2-yl)oxy]pyridine-2-carboxamide;

N-methyl-4-[(7-{[2-(methylamino)benzoyl]amino}-5,6,7,8-tetrahydronaphthalen-2-yl)oxy]pyridine-2-carboxamide;

4-({7-[(3-bromo-4-chlorobenzoyl)amino]-5,6,7,8-tetrahydronaphthalen-2-yl}oxy)-N-methylpyridine-2-carboxamide;

4-[(7-{[4-(benzyloxy)benzoyl]amino}-5,6,7,8-tetrahydronaphthalen-2-yl)oxy]-N-methylpyridine-2-carboxamide;

4-({7-[(4-bromo-3-methylbenzoyl)amino]-5,6,7,8-tetrahydronaphthalen-2-yl}oxy)-N-methylpyridine-2-carboxamide;

4-[(7-{[2-chloro-5-(trifluoromethyl)benzoyl]amino}-5,6,7,8-tetrahydronaphthalen-2-yl)oxy}-N-methylpyridine-2-carboxamide;

4-({7-[(3-hydroxy-4-methylbenzoyl)amino]-5,6,7,8-tetrahydronaphthalen-2-yl}oxy)-N-methylpyridine-2-carboxamide;

4-[(7-{[3-(aminosulfonyl)-4-chlorobenzoyl]amino}-5,6,7,8-tetrahydronaphthalen-2-yl)oxy]-N-methylpyridine-2-carboxamide;

4-({7-[(2-cyanobenzoyl)amino]-5,6,7,8-tetrahydronaphthalen-2-yl}oxy)-N-methylpyridine-2-carboxamide;

4-({7-[(3-amino-4-chlorobenzoyl)amino]-5,6,7,8-tetrahydronaphthalen-2-yl}oxy)-N-methylpyridine-2-carboxamide;

4-({7-[(4-benzoylbenzoyl)amino]-5,6,7,8-tetrahydronaphthalen-2-yl}oxy)-N-methylpyridine-2-carboxamide;

4-({7-[(4-ethoxybenzoyl)amino]-5,6,7,8-tetrahydronaphthalen-2-yl}oxy)-N-methylpyridine-2-carboxamide;

4-({7-[(biphenyl-4-ylcarbonyl)amino]-5,6,7,8-tetrahydronaphthalen-2-yl}oxy)-N-methylpyridine-2-carboxamide;

N-methyl-4-[(7-{[4-(methylsulfanyl)-3-nitrobenzoyl]amino}-5,6,7,8-tetrahydronaphthalen-2-yl)oxy]pyridine-2-carboxamide;

4-({7-[(4-fluorobenzoyl)amino]-5,6,7,8-tetrahydronaphthalen-2-yl}oxy)-N-methylpyridine-2-carboxamide;

4-({7-[(3-cyanobenzoyl)amino]-5,6,7,8-tetrahydronaphthalen-2-yl}oxy)-N-methylpyridine-2-carboxamide;

4-({7-[(4-hydroxy-3-methoxybenzoyl)amino]-5,6,7,8-tetrahydronaphthalen-2-yl}-oxy)-N-methylpyridine-2-carboxamide;

4-({7-[(3-chloro-4-methoxybenzoyl)amino]-5,6,7,8-tetrahydronaphthalen-2-yl}oxy)-N-methylpyridine-2-carboxamide;

4-[(7-{[2-(3,5-dimethyl-1H-pyrazol-4-yl)benzoyl]amino}-5,6,7,8-tetrahydronaphthalen-2-yl)oxy}-N-methylpyridine-2-carboxamide;

4-({7-[(3,4-dichlorobenzoyl)amino]-5,6,7,8-tetrahydronaphthalen-2-yl}oxy)-N-methylpyridine-2-carboxamide;

N-methyl-4-({7-[(4-vinylbenzoyl)amino]-5,6,7,8-tetrahydronaphthalen-2-yl}-oxy)pyridine-2-carboxamide;

4-({7-[(3,4-dihydroxybenzoyl)amino]-5,6,7,8-tetrahydronaphthalen-2-yl}oxy)-N-methylpyridine-2-carboxamide;

4-({7-[(4-acetylbenzoyl)amino]-5,6,7,8-tetrahydronaphthalen-2-yl}oxy)-N-methylpyridine-2-carboxamide;

4-({7-[(3,4-dimethoxybenzoyl)amino]-5,6,7,8-tetrahydronaphthalen-2-yl}oxy)-N-methylpyridine-2-carboxamide;

4-({7-[(4-isobutylbenzoyl)amino]-5,6,7,8-tetrahydronaphthalen-2-yl}oxy)-N-methylpyridine-2-carboxamide;

4-[(7-{[3-fluoro-4-(trifluoromethyl)benzoyl]amino}-5,6,7,8-tetrahydronaphthalen-2-yl)oxy}-N-methylpyridine-2-carboxamide;

N-methyl-4-({7-[(3-phenoxybenzoyl)amino]-5,6,7,8-tetrahydronaphthalen-2-yl}-oxy)pyridine-2-carboxamide;

4-({7-[(3,5-dichlorobenzoyl)amino]-5,6,7,8-tetrahydronaphthalen-2-yl}oxy)-N-methylpyridine-2-carboxamide;

N-methyl-4-({7-[(4-phenoxybenzoyl)amino]-5,6,7,8-tetrahydronaphthalen-2-yl}-oxy)pyridine-2-carboxamide;

4-({7-[(3-bromo-4-methylbenzoyl)amino]-5,6,7,8-tetrahydronaphthalen-2-yl}oxy)-N-methylpyridine-2-carboxamide; and 4-({7-[(4-methoxybenzoyl)amino]-5,6,7,8-tetrahydronaphthalen-2-yl}oxy)-N-methylpyridine-2-carboxamide.

19. A pharmaceutical composition comprising a compound according to claim 1 and a pharmaceutically acceptable carrier.

* * * * *